US010300126B2

(12) United States Patent
Fang et al.

(10) Patent No.: US 10,300,126 B2
(45) Date of Patent: May 28, 2019

(54) PORCINE REPRODUCTIVE AND RESPIRATORY SYNDROME VACCINE VIRUS

(71) Applicant: Elanco US Inc., Indianapolis, IN (US)

(72) Inventors: Ying Fang, Manhattan, KS (US); Stephen Qitu Wu, Fishers, IN (US)

(73) Assignee: Elanco US Inc., Greenfield, IN (US)

( * ) Notice: Subject to any disclaimer, the term of this patent is extended or adjusted under 35 U.S.C. 154(b) by 0 days.

(21) Appl. No.: 16/151,450

(22) Filed: Oct. 4, 2018

(65) Prior Publication Data

US 2019/0022208 A1 Jan. 24, 2019

Related U.S. Application Data

(62) Division of application No. 15/429,206, filed on Feb. 10, 2017, now Pat. No. 10,155,035.

(60) Provisional application No. 62/296,658, filed on Feb. 18, 2016.

(51) Int. Cl.
*A61K 39/12* (2006.01)
*C12N 7/00* (2006.01)
*A61K 39/00* (2006.01)

(52) U.S. Cl.
CPC ................ *A61K 39/12* (2013.01); *C12N 7/00* (2013.01); *A61K 2039/5254* (2013.01); *A61K 2039/552* (2013.01); *C12N 2770/10021* (2013.01); *C12N 2770/10034* (2013.01); *C12N 2770/10064* (2013.01)

(58) Field of Classification Search
None
See application file for complete search history.

(56) References Cited

U.S. PATENT DOCUMENTS

2017/0239343 A1 8/2017 Fang et al.

FOREIGN PATENT DOCUMENTS

WO 2015140774 A1 9/2015

OTHER PUBLICATIONS

Wang, Yue, Yajie Liang, Jun Han, Kelly M. Burkhart Eric M. Vaughn, Michael B. Roof, and Kay S. Faaberg. "Attenuation of porcine reproductive and respiratory syndrome virus strain MN184 using chimeric construction with vaccine sequence." *Virology* 371, No. 2 (2008): 418-429.

An, Tong-Qing, Zhi-Jun Tian, Yan-Jun Zhou, Yan Xiao, Jin-Mei Peng, Jin Chen, Yi-Feng Jiang, Xiao-Fang Hao, and Guang-Zhi Tong. "Comparative genomic analysis of five pairs of virulent parental/attenuated vaccine strains of PRRSV." Veterinary microbiology 149, No. 1-2 (2011): 104-112.

Lawson, Steven, Joan Lunney, Federico Zuckermann, Fernando Osorio, Eric Nelson, Craig Welbon, Travis Clement et al., "Development of an 8-plex Luminex assay to detect swine cytokines for vaccine development: assessment of immunity after porcine reproductive and respiratory syndrome virus (PRRSV) vaccination." *Vaccine* 28, No. 32 (2010): 5356-5364.

Park, Changhoon, Hwi Won Seo, Kiwon Han, Ikjae Kang, and Chanhee Chae. "Evaluation of the efficacy of a new modified live porcine reproductive and respiratory syndrome virus (PRRSV) vaccine (Fostera PRRS) against heterologous PRRSV challenge." *Veterinary microbiology* 172, No. 3 (2014): 432-442.

Geidhof, Marc F., Merijn Vanhee, Wander Van Breedam, Jan Van Doorsselaere, Uladzimir U. Karniychuk, and Hans J. Nauwynck. "Comparison of the efficacy of autogenous inactivated Porcine Reproductive and Respiratory Syndrome Virus (PRRSV) vaccines with that of commercial vaccines against homologous and heterologous challenges," *BMC veterinary research* 8, No. 1 (2012): 182.

Kim, Hyunii, Hye Kwon Kim, Jung Ho Jung, Yoo Jung Choi, Jiho Kim, Chang Gyu Um, Su Bin Hyun et al. "The assessment of efficacy of porcine reproductive respiratory syndrome virus inactivated vaccine based on the viral quantity and inactivation methods." *Virology journal* 8, No. 1 (2011): 323.

Leng, Xue, Zhenguang Li, Minggi Xia, Yanliang He, and Hua Wu. "Evaluation of the efficacy of an attenuated live vaccine against highly pathogenic porcine reproductive and respiratory syndrome virus in young pigs." *Clinical and Vaccine Immunology* 19, No. 8 (2012): 1199-1206.

Graham, Patrick L., and Peggy Anne Hawkins, "MJ PRRS vaccine: Field efficacy,".

Li, Xiangdong, Amy Galliher-Beckley, Jerome C. Nietfeld, Kay S. Faaberg, and Jishu Shi. "Montanide TM Gel01 ST adjuvant enhances PRRS modified live vaccine efficacy by regulating porcine humoral and cellular immune responses," World Journal of Vaccines, No. 3 (2013): 1-9.

Sun, Zhi, Yanhua Li, Russell Ransburgh, Eric J. Snijder, and Ying Fang. "Nonstructural protein 2 of porcine reproductive and respiratory syndrome virus inhibits the antiviral function of interferon-stimulated gene 15." *Journal of virology* 86, No. 7 (2012): 3839-3850.

Vu, Hiep Lx, Asit K. Pattnaik, and Fernando A. Osorio. "Strategies to broaden the cross-protective efficacy of vaccines against porcine reproductive and respiratory syndrome virus." Veterinary microbiology 206 (2017): 29-34.

Tian, Zhi-Jun, Tong-Qing An, Yan-Jun Zhou, Jin-Mei Peng, Shou-Ping Hu, Tian-Chao Wei, Yi-Feng Jiang, Yan Xiao, and Guang-Zhi Tong. "An attenuated live vaccine based on highly pathogenic porcine reproductive and respiratory syndrome virus (HP-PRRSV) protects piglets against HP-PRRS." Veterinary microbiology 138, No. 1-2 (2009): 34-40.

*Primary Examiner* — Shanon A. Foley
(74) *Attorney, Agent, or Firm* — David L. Pflugh

(57) ABSTRACT

The present invention relates to modified, live Porcine Reproductive and Respiratory Syndrome viruses. Viruses were genetically analyzed and selected based on phylogenetic grouping for modification by repeated passage in tissue culture. The modified, live viruses were assessed for the ability to provide protective immunity to heterologous viruses. The modified, live viruses are useful in vaccines, particularly in vaccines which can treat infection of swine by multiple heterologous viruses.

13 Claims, 5 Drawing Sheets

Figure 1:
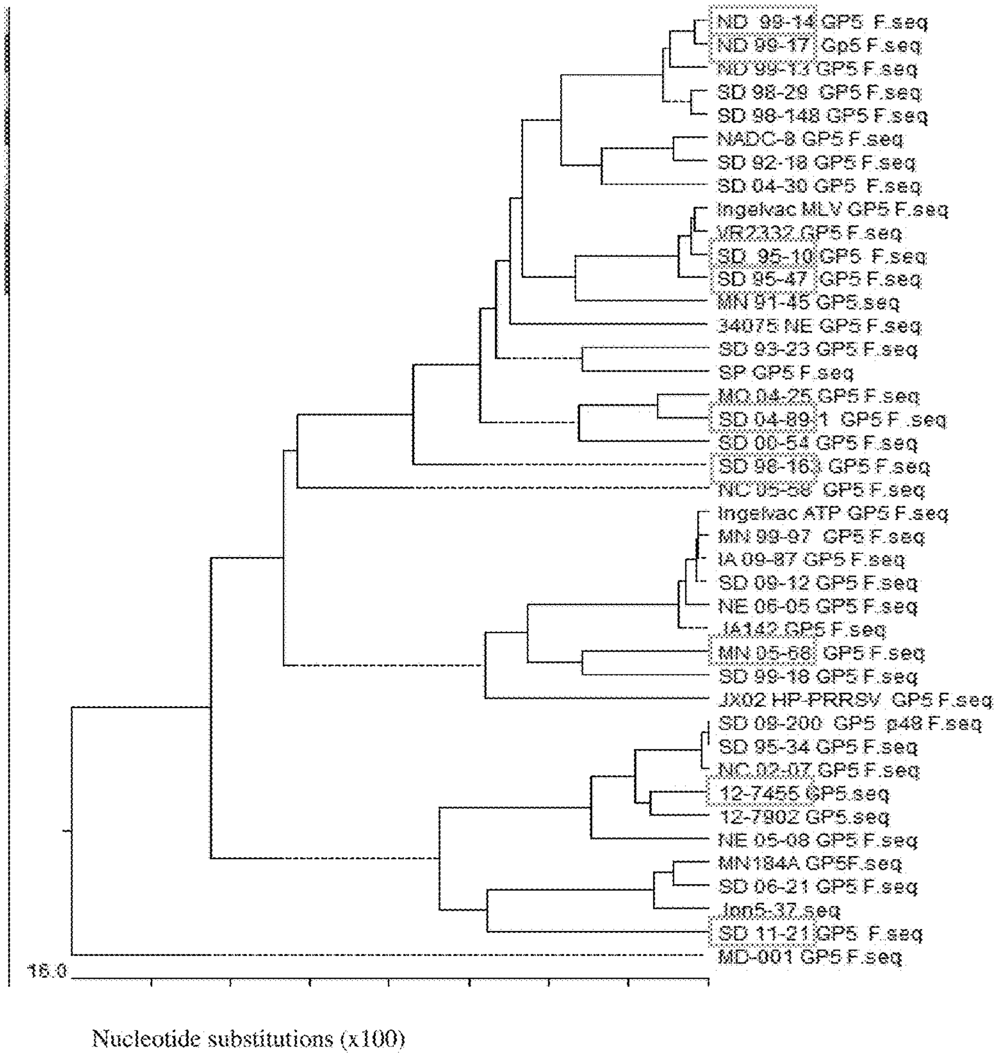

Specification includes a Sequence Listing.

PORCINE REPRODUCTIVE AND RESPIRATORY SYNDROME VACCINE VIRUS

The present application is a divisional application of U.S. Patent Application Ser. No. 15/429,206 filed Feb. 10, 2017, which claims benefit of priority to U.S. Patent Application Ser. No. 62/296,658, filed Feb. 18, 2016, which is hereby incorporated by reference in its entirety.

The present invention relates to modified, live Porcine Reproductive and Respiratory Syndrome viruses. The modified, live viruses are useful in vaccines, particularly in vaccines which provide protection against heterologous viruses.

Porcine Reproductive and Respiratory Syndrome (PRRS), originally called Mystery Swine Disease, was first described in Europe but has now spread worldwide. PRRS causes late-stage abortions, stillbirths, and infertility in breeding age sows, and respiratory disease, decreased growth performance, and even death in nursery and growing/finishing pigs. PRRS causes economic losses of over $600 million each year in the US alone.

Symptoms of PRRS virus infection in adult porcine animals include, without limitation, reduced appetite, lethargy, fever, and behavioral changes such as loss of balance, circling, and falling to one side. Pregnant sows may prematurely farrow, abort fetuses, or deliver mummified or stillborn piglets, and up to 10% of pregnant sows may die from PRRS virus infection. Infected piglets have a high preweaning mortality rate, are often weak, and can have edema around the eyes. PRRS virus infection in weaned nursery or grow/finish pigs can cause, without limitation, a failure to thrive, respiratory distress, labored or rapid breathing, blotchy reddening of the skin, and rough hair coats.

The PRRS virus is an enveloped virus with an approximately 15 kb, linear, positive-stranded, single-stranded RNA genome, and the virus has been classified to the family Arteriviridae. To date at least nine open reading frames have been identified in the genome. PRRS viruses are divided into two general subtypes. The European subtype, Type 1 PRRS viruses, is exemplified by the Lelystad strain, while the Type 2 North American PRRS viruses are exemplified by the strain VR-2332.

The two subtypes can have as little as about 60% sequence identity in their genomes, and even within subtypes individual strains can vary up to about 20% in the identity of their genomes. This variability has complicated the development of vaccines to effectively treat and/or prevent PRRS. Modified, live virus (MLV) variants of the PRRS virus can generate immunity against challenge with PRRS viruses, but the vaccine is most effective when the challenge is with a PRRS virus genetically homologous to the MLV. The MLV vaccines have been less effective against challenge with heterologous viruses. Further, MLV have shown some reversion to virulence, such that the vaccine virus causes disease in vaccinated animals. Vaccines containing inactivated (i.e. killed) PRRS viruses have better safety profiles, but efficacy against heterologous challenge has been limited.

Because current PRRS vaccines do not show sufficient safety and efficacy to reduce the economic impact of PRRS virus infection, new and improved vaccines are needed. Preferably, those vaccines would be both safe and efficacious. If the vaccines comprise attenuated MLV, those attenuated MLV should not demonstrate reversion to virulence in order to be considered safe to use in the field. For example, by adapting a PRRS strain to growth in tissue culture cells for at least 80 passages, or preferably at least 100 passages, the MLV should not demonstrate reversion to virulence. To be efficacious, a vaccine virus strain should be able to elicit protective immunity in a porcine animal against a range of phylogenetically diverse wild type PRRS strains. Preferably, a new PRRS vaccine virus strain would be able to elicit protective immunity in a porcine animal against at least three phylogenetically diverse wild type PRRS strains.

The present invention provides for a modified, live Porcine Reproductive and Respiratory Syndrome (PRRS) vaccine virus strain, wherein the consensus complementary DNA sequence of said PRRS strain is at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. As a person of ordinary skill will appreciate, due to the high mutation rate of the PRRS virus, a modified, live PRRS strain might comprise a multiplicity of subpopulations, each having a homologous but not identical genome.

The present invention provides for a modified, live Porcine Reproductive and Respiratory Syndrome (PRRS) virus strain, wherein the PRRS virus strain is a ND 99-14 strain or a SD 11-21 strain. The PRRS virus strain should be passaged preferably at least 80 times, or more preferably 84 times, in tissue culture cells. Most preferably, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Most preferably, modified, live PRRS virus strains passaged 100 times have a low probability of reverting to wild-type virulence.

The present invention provides for an immunogenic composition comprising a modified, live PRRS virus strain having a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. As a person of ordinary skill will appreciate, due to the high mutation rate of the PRRS virus, a modified, live PRRS strain might comprise a multiplicity of subpopulations, each having a homologous but not identical genome.

The present invention provides for an immunogenic composition comprising a modified, live PRRS virus strain, wherein said PRRS virus strain is ND 99-14 or SD 11-21. The ND 99-14 strain or the SD 11-21 strain may be passaged at least 80 times, or preferably even 84 times, in tissue culture cells. Most preferably, the ND 99-14 strain or the SD 11-21 strain may be passaged 100 times in tissue culture cells. The immunogenic composition may further comprise a pharmaceutically-acceptable excipient, stabilizer, solubilizer, or diluent. The immunogenic composition may also comprise a further antigen from a different virus or from a bacterial strain or from a parasite.

The present invention provides for a vaccine comprising a modified, live PRRS virus strain, wherein the consensus complementary DNA sequence of said PRRS strain is at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. The vaccine may further comprise an adjuvant. The vaccine may further comprise a pharmaceutically-acceptable excipient, stabilizer, solubilizer, or diluent. The vaccine may comprise a further antigen from a different virus or from a bacterial strain or from a parasite.

The present invention provides for a vaccine for use in treating or preventing Porcine Reproductive and Respiratory Syndrome in a porcine animal. As PRRS is caused by a PRRS virus, the present invention provides a vaccine for use in treating a PRRS virus infection. The present invention also provides for a vaccine for use in treating a porcine animal for a symptom caused by a PRRS virus infection. The infection may be from a wild-type virulent strain of a PRRS virus. A symptom may be, without limitation, reduced appetite, lethargy, fever, behavioral changes such as loss of balance, circling, and falling to one side, premature farrowing, abortion, stillbirths, edema, a failure to thrive, cough, respiratory distress, labored or rapid breathing, blotchy reddening of the skin, rough hair coats, lung lesions, viral shedding, and mortality. The present invention provides for a vaccine for use in therapy of a porcine animal. The present invention also provides for a vaccine for use in therapy of PRRS in a porcine animal. Preferably, the vaccine comprises a modified, live PRRS strain having a consensus complementary DNA sequence that is at least 90%, at least 95%, or at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the vaccine comprises a modified, live PRRS strain which is ND 99-14 or SD 11-21. The vaccine may further comprise an adjuvant. The vaccine may further comprise a pharmaceutically-acceptable excipient, stabilizer, solubilizer, or diluent. The vaccine may comprise a further antigen from a different virus or from a bacterial strain or from a parasite.

The present invention provides for a vaccine comprising a modified, live PRRS virus strain for use in the treatment or prevention of Porcine Reproductive and Respiratory Syndrome in a porcine animal. The present invention also provides for a vaccine comprising a modified, live PRRS virus strain for use in the treatment or prevention of a symptom caused by a PRRS virus infection in a porcine animal. A symptom may be, without limitation, reduced appetite, lethargy, fever, behavioral changes such as loss of balance, circling, and falling to one side, premature farrowing, abortion, stillbirths, edema, a failure to thrive, cough, respiratory distress, labored or rapid breathing, blotchy reddening of the skin, rough hair coats, lung lesions, viral shedding, and mortality. The present invention provides for a vaccine comprising a modified, live PRRS virus strain for use in therapy of a porcine animal. The present invention also provides for a vaccine comprising a modified, live PRRS virus strain for use in therapy of PRRS in a porcine animal. The infection may be from a wild-type virulent strain of a PRRS virus heterologous to the modified, live PRRS virus in the vaccine. Preferably, the vaccine comprises a modified, live PRRS strain having a consensus complementary DNA sequence that is at least 90%, at least 95%, or at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the vaccine comprises a modified, live PRRS strain which is ND 99-14 or SD 11-21. The vaccine may further comprise an adjuvant. The vaccine may further comprise a pharmaceutically-acceptable excipient, stabilizer, solubilizer, or diluent. The vaccine may comprise a further antigen from a different virus or from a bacterial strain or from a parasite.

The present invention provides for a method of treating or preventing a symptom of Porcine Reproductive and Respiratory Syndrome in a porcine animal, comprising administering to said porcine animal an immunogenic composition comprising a modified, live PRRS virus strain. The present invention also provides for a method of treating or preventing Porcine Reproductive and Respiratory Syndrome in a porcine animal, comprising administering to said porcine animal an immunogenic composition comprising a modified, live PRRS virus strain. Preferably, the modified, live PRRS virus strain for use in the method would have a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live PRRS virus strain for use in the method would have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the modified, live PRRS virus strain for use in the method would have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. The immunogenic composition may further comprise a pharmaceutically-acceptable excipient, stabilizer, solubilizer, or diluent. The immunogenic composition may comprise a further antigen from a different virus or from a bacterium or from a parasite.

The present invention provides for a method of treating or preventing Porcine Reproductive and Respiratory Syndrome in a porcine animal, comprising administering to said porcine animal an immunogenic composition comprising a modified, live Porcine Reproductive and Respiratory Syndrome (PRRS) virus strain, wherein the said PRRS virus strain is ND 99-14 or SD 11-21. The ND 99-14 strain or the SD 11-21 strain for use in the method may be passaged at least 80 times, or preferably even 84 times, in tissue culture cells. Most preferably, the ND 99-14 strain or the SD 11-21 strain for use in the method is passaged 100 times in tissue culture cells. The immunogenic composition may further comprise a pharmaceutically-acceptable excipient, stabilizer, solubilizer, or diluent. The immunogenic composition may comprise a further antigen from a different virus or from a bacterial strain or from a parasite.

The present invention provides for a method of treating or preventing a symptom caused by a PRRS virus infection in a porcine animal, comprising administering to said porcine animal an immunogenic composition comprising a modified, live Porcine Reproductive and Respiratory Syndrome (PRRS) virus strain, wherein the consensus complementary DNA sequence of said PRRS strain is preferably at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain for use in the method could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the modified, live strain for use in the method could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. The immunogenic composition may further comprise a pharmaceutically-acceptable excipient, stabilizer, solubilizer, or diluent. The immunogenic composition may also comprise a further antigen from a different virus or from a bacteria strain or from a parasite.

The present invention provides for a method of treating or treating a symptom caused by a PRRS virus infection in a porcine animal, comprising administering to said porcine animal an immunogenic composition comprising a modified, live Porcine Reproductive and Respiratory Syndrome (PRRS) virus strain, wherein the said PRRS virus strain is ND 99-14 or SD 11-21. The ND 99-14 strain or the SD 11-21 strain for use in the method may be passaged at least 80 times, or preferably even 84 times, in tissue culture cells. Most preferably, the ND 99-14 strain or the SD 11-21 strain for use in the method may be passaged 100 times in tissue culture cells. The immunogenic composition may further comprise a pharmaceutically-acceptable excipient, stabilizer, solubilizer, or diluent. The immunogenic composition may also comprise a further antigen from a different virus or from a bacteria strain or from a parasite. The PRRS virus infection may be an infection by a virulent PRRS virus heterologous to the modified, live PRRS virus strain in the immunogenic composition. Two PRRS virus strains are considered to be heterologous if a genomic consensus sequence of each virus strain maps to a different phylogenetic group. Two PRRS virus strains are considered to be heterologous if a complementary DNA consensus sequence of each virus strain maps to a different phylogenetic group.

The present invention provides for the use of a modified, live PRRS virus strain in the manufacture of a medicament for treating or preventing a symptom of PRRS, wherein the modified, live PRRS virus comprises a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13.

The present invention provides for the use of a modified, live PRRS virus strain comprising a ND 99-14 strain or a SD 11-21 strain in the manufacture of a medicament for treating or preventing a symptom of PRRS. The modified, live PRRS virus strain should be passaged at least 80 times, or preferably even 84 times, in tissue culture cells. Further, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 100 times have a low probability of reverting to wild-type virulence.

The present invention provides for the use of an immunogenic composition comprising a modified, live PRRS virus strain in the manufacture of a medicament for treating a PRRS virus infection, wherein the modified, live PRRS virus strain comprises a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13.

The present invention provides for the use of an immunogenic composition comprising a modified, live PRRS virus strain comprising a ND 99-14 strain or a SD 11-21 strain in the manufacture of a medicament for treating a PRRS virus infection. The PRRS virus strain should be passaged at least 80 times, or preferably even 84 times, in tissue culture cells. Further, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 100 times have a low probability of reverting to wild-type virulence.

The present invention provides for the use of an immunogenic composition comprising a modified, live PRRS virus strain in the manufacture of a medicament for protecting a porcine animal from a PRRS virus infection, wherein the modified, live PRRS virus strain comprises a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13.

The present invention provides for the use of an immunogenic composition comprising a modified, live PRRS virus strain comprising a ND 99-14 strain or a SD 11-21 strain in the manufacture of a medicament for protecting a porcine animal from a PRRS virus infection. The PRRS virus strain should be passaged at least 80 times, or preferably even 84 times, in tissue culture cells. Further, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 100 times have a low probability of reverting to wild-type virulence.

FIG. 1. Phylogenetic analysis of type 2 PRRSV ORF5 nucleotide sequences.

Figure 2:
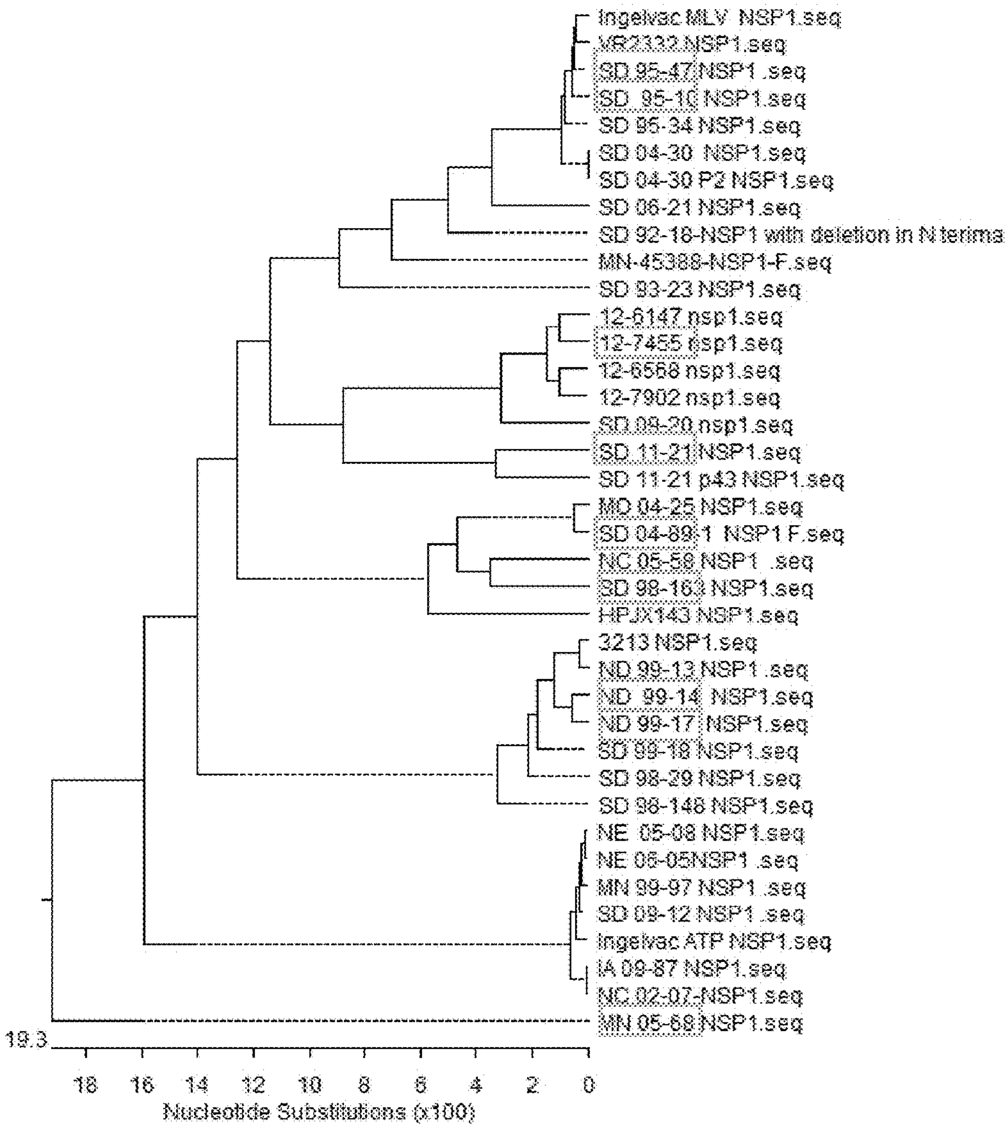

FIG. 2. Phylogenetic analysis of type 2 PRRSV nsp1 nucleotide sequences.

Figure 3:
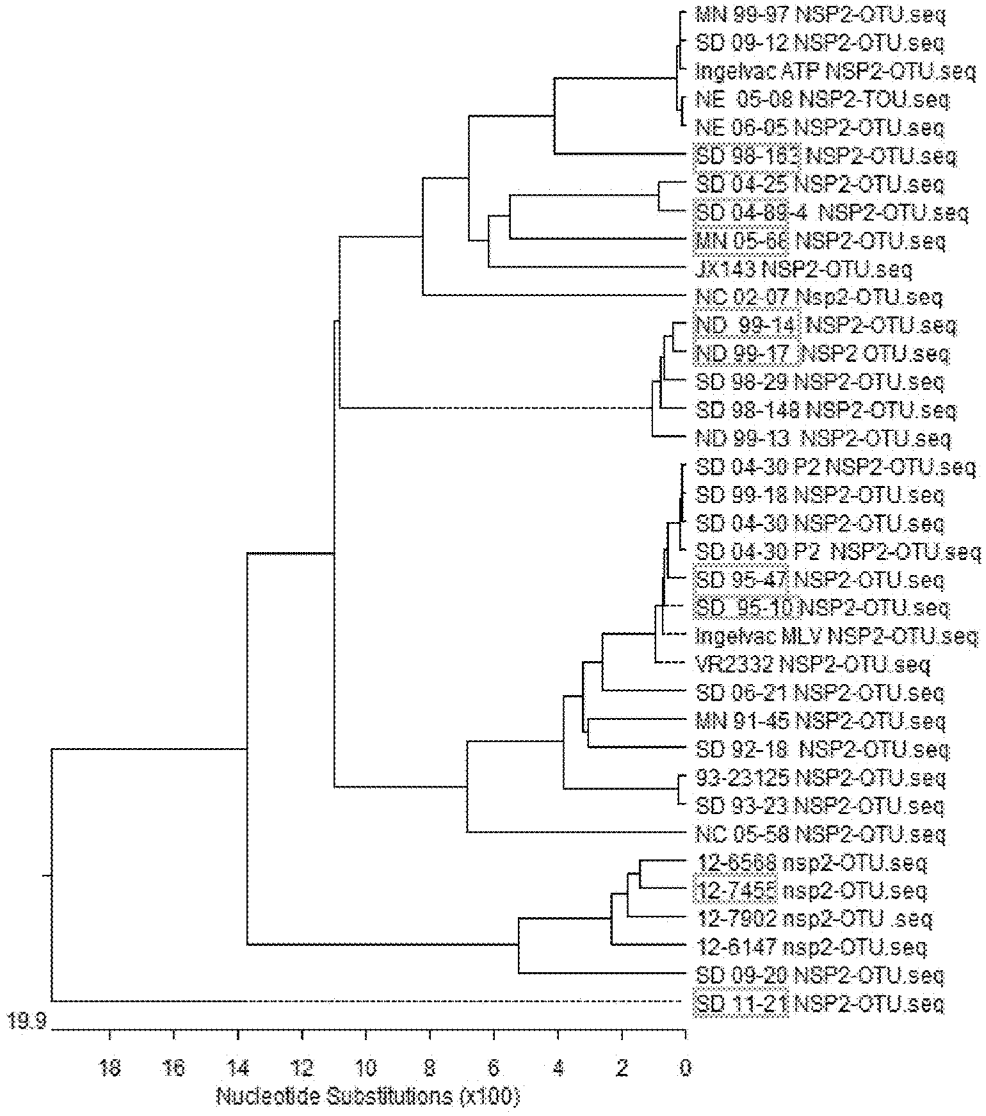

FIG. 3. Phylogenetic analysis of type 2 PRRSV nsp2 OTU domain nucleotide sequences.

Figure 4:
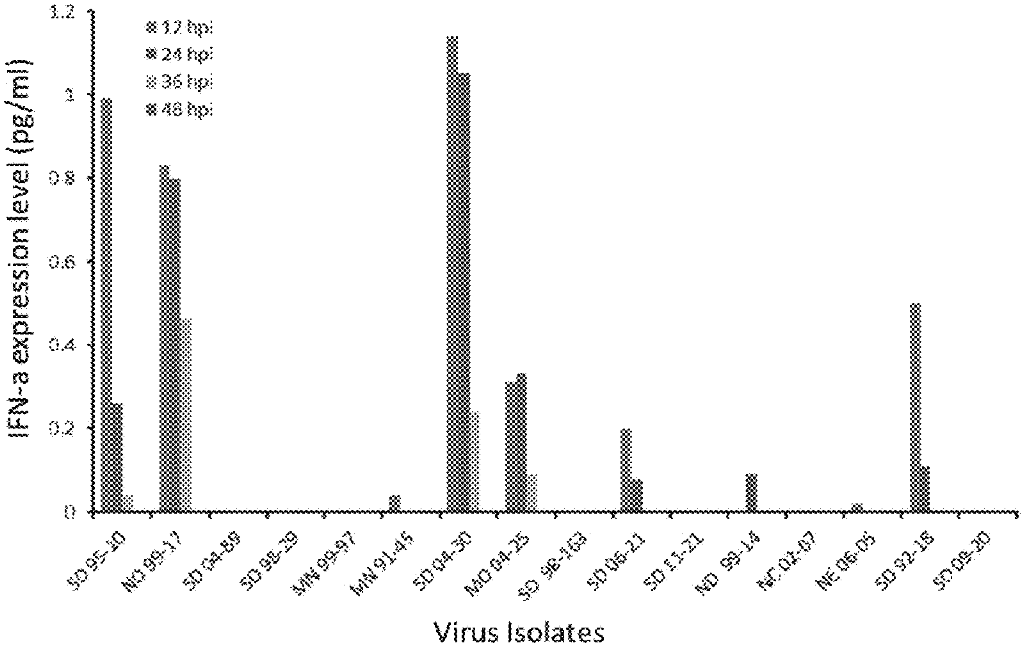

FIG. 4. Variation of different PRRSV field isolates on the stimulation of IFN-alpha (IFN-$\alpha$) expression.

Figure 5:
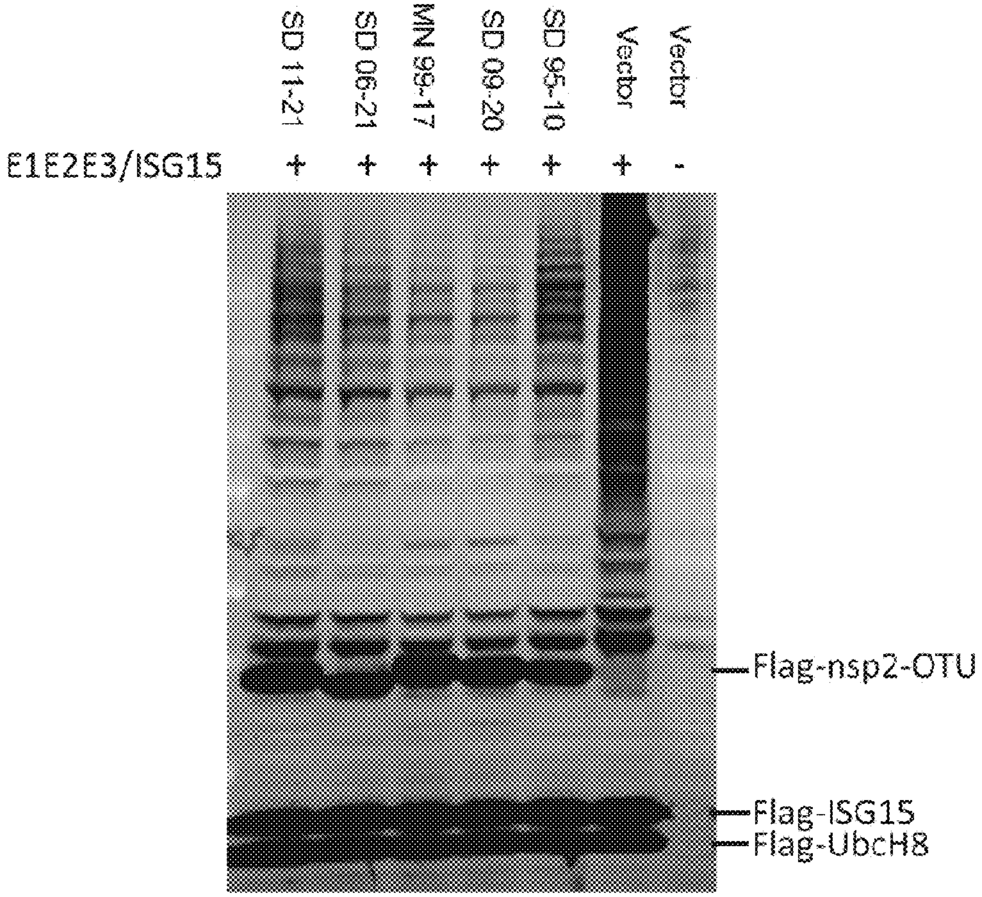

FIG. 5. DeISGylation assay with different field PRRSV isolates.

As used in the following discussion, the terms “a” or “an” should be understood to encompass one or more, unless otherwise specified.

As used herein, the term “virus” could mean either the species of virus, or, interchangeably, an individual infectious unit which may contain nucleic acids, proteins, and a lipid membrane. An individual infectious unit is also called a “viral particle” or a “virion”, the latter terms being synonymous.

As used herein, a “strain” or “isolate” a virus means a collection of genetically homologous virions. Two viruses would be considered “homologous” if those viruses map to the same phylogenetic clade. Two viruses would be considered “heterologous” if those viruses map to different phylogenetic clades. As the PRRS virus has a high mutation rate, it will be appreciated that a single PRRS strain comprises individual virions with related but variable genetic sequences. Thus, subpopulations of strains exist within each PRRS strain, and the genetic sequence of a PRRS strain is a consensus sequence such that the genetic sequence of an individual member of the PRRS strain may not be identical to the consensus sequence for that strain. A “consensus” sequence is a nucleic acid sequence in which each nucleic acid residue at a given position is present in >50% of the polynucleotides in a PRRS virus strain or isolate.

“Percent identity” can be determined by calculating the number of identical nucleotides or amino acids at the same positions in a nucleic acid or protein. Calculation of percent identity includes determination of the optimal alignment between two or more sequences. Alignment can take into account insertions and deletions (i.e. “gaps”) in each of the sequences to be tested, such as, without limitation, in the non-coding regions of nucleic acids and truncations or extensions of polypeptide sequences. Computer programs and algorithms such as the Basic Local Alignment Search Tool (BLAST) may be used to determine the percent identity. BLAST one of the many resources provided by the U.S. National Center for Biotechnology Information. Because the genetic code is degenerate, and more than one codon can encode a given amino acid, coding regions of nucleic acids are considered identical if the nucleic acids encode identical polypeptides. Thus, percent identity could also be calculated based on the polypeptide encoded by the nucleic acid. Percent identity could be calculated based on full length consensus genomic sequences or on a fraction of the genomic sequence, such as for example without limitation on individual open reading frames (ORFs).

As used herein, the term “modified, live virus” applies to any individual viral particle (i.e. a “virion”) or to a multiplicity of viral particles whose genetic sequence has been altered from the genetic sequence of a naturally-occurring wild type virus. Alterations include, without limitation, genetic mutations such as insertions and deletions of nucleotides and transitions and transversions which change one nucleotide for another nucleotide. Alterations can be accomplished by adapting a wild-type virus to replication in a tissue culture system, and continuing to passage a virus in a tissue culture system, whereby the virus accumulates genetic mutations. Alterations can also be accomplished using molecular techniques. Attenuated viruses form a subset of modified, live viruses.

As used herein, the term “attenuated” or “attenuation” means the ability of virus to cause or exacerbate clinical disease has been reduced or eliminated. An attenuated virus can still infect a host cell, either in vitro or in vivo, and that infection may result in subclinical effects in the host organism, but that infection does not result in one or more clinical disease symptoms.

In contrast, as used herein, “inactivated” viruses mean viruses which can no longer replicate in a host cell. Inactivated viruses are considered to be killed or dead viruses. Inactivation can be accomplished by a variety of methods, including but not limited to chemical alteration of viral proteins, to chemical or physical alterations in the structure of a virion, or to chemical or physical alterations in viral nucleic acids.

An “antigen” is any molecule capable of being specifically detected by the immune system of an organism. Typically a viral antigen is a viral protein encoded by the viral genome or derived from products of the viral genome. The presence of viral antigens can be specifically detected by the surface antigen receptors of both host T lymphocytes and host B lymphocytes and by antibody molecules synthesized by host cells.

“Immunogenicity” refers to the ability of an antigen to elicit an immune response, said immune response comprising both antigen-specific responses and non-antigen-specific responses or innate immune responses. “Protective immunity” is an immune response which can reduce or prevent clinical symptoms when an immunized animal is challenged or exposed to a pathogenic virus strain. As one skilled in the art would appreciate, protective immunity may decline with time or increased age of the immunized animal. Protective immunity as used herein should be effective for at least four months, but preferably at least six months, from the latest date of immunization. Protective immunity may be elicited with a single dose of a vaccine. A second or further dose may be used to increase or prolong the protective immune response. For example, increasing the protective immune response in a breeding sow may result in an increased level of maternally derived antibody in piglets.

In contrast to an antigen, an “adjuvant” is a non-specific stimulator of an immune response. An adjuvant could stimulate the innate immune response by binding and activating a pattern recognition receptor (PRR). Such stimulators of PRRs could be, for example, viral or bacterial nucleic acids, lipids from bacteria or parasites, or bacterial proteins or toxins, or any artificially-constructed mimic of such molecules. Adjuvants also include, without limitation: inorganic compounds that aggregate antigens to facilitate recognition by B lymphocytes or uptake by phagocytes, such as alum, aluminum hydroxide, aluminum phosphate, calcium phosphate hydroxide or ammonium sulfate; oils; and detergents. Adjuvants could also be host mediators of immune signaling, such as, without limitation, cytokines, lymphokines, chemokines, interferons, anaphylatoxins, growth factors, differentiation factors, and adhesion molecules.

As used herein, an "immunogenic composition" is a composition that elicits an immune response when administered to an animal. An immunogenic composition comprises at least one antigen and at least one pharmaceutically-acceptable excipient, stabilizer, solubilizer, or diluent. A description of pharmaceutically-acceptable excipients, stabilizers, solubilizers, or diluents can be found, for example, in "Remington: The Science and Practice of Pharmacy," Lloyd V. Allen, ed., Pharmaceutical Press, London, UK, $22^{nd}$ edition, 2012. The antigen can be a whole virus, bacterium, or other pathogen, either live or inactivated. The antigen can also be isolated, purified, or partially purified antigenic molecule from a virus, bacterium, or other pathogen. The antigen can be a polypeptide, a polysaccharide, a nucleic acid, or a lipid.

As used herein, a "vaccine" is an immunogenic composition which confers protection from, resistance to, prevention of, or treatment for a disease symptom when administered to an animal, wherein said symptom is caused by a pathogenic organism, for example a virus. A PRRS vaccine may include, without limitation, viral antigens or intact virions, either live or inactivated, in composition with pharmaceutically-acceptable adjuvants, excipients, stabilizers, solubilizers, or diluents.

As used herein, the terms "treating", "to treat", or "treatment", include without limitation restraining, slowing, stopping, reducing, ameliorating, or reversing the progression or severity of an existing symptom, disorder, condition, or disease. A treatment may be applied or administered therapeutically.

As used herein, the terms "preventing", "to prevent", or "prevention", include without limitation decreasing, reducing, or ameliorating the risk of a symptom, disorder, condition, or disease, and protecting an animal from a symptom, disorder, condition, or disease. A prevention may be applied or administered prophylactically.

As used herein, "administering to an animal" includes but is not limited to cutaneous, subcutaneous, intramuscular, mucosal, submucosal, transdermal, oral or intranasal administration. Administration could include injection or topical administration.

The following experimental examples are illustrative of modified, live PRRS viruses. The following experimental examples are also illustrative of immunogenic compositions comprising modified, live PRRS viruses. The following experimental examples are also illustrative of using modified, live PRRS viruses to treat porcine animals for symptoms of PRRS. It will be appreciated that other embodiments and uses will be apparent to those skilled in the art and that the invention is not limited to these specific illustrative examples or preferred embodiments.

EXAMPLE 1

We intend to develop a broadly protective MLV vaccine for PRRS. Unique regions in vaccine viruses are identified for genetic marker and differential diagnostic test development. Specific objectives are: 1) to establish the candidate PRRS vaccine strains; 2) to identify the unique marker region in candidate vaccine virus and develop differential diagnostic reagents and tests for differentiation of the vaccinated animals from wild-type virus infected animals; and 3) to perform in vivo evaluation of the safety and efficacy of candidate vaccines and assess the differential ability of companion diagnostic assays.

We have generated nine candidate vaccine viruses. Detailed characterization of these candidate viruses is presented below.

Virus is initially isolated by growth in porcine alveolar macrophages, obtained from the lungs of conventionally raised 3- to 9-week-old pigs. The lungs are excised and washed three or four times with phosphate-buffered saline, pH 7.2. Cells are centrifuged for 10 min at 800×g at 4° C. Supernatant fluid is decanted, and cells are washed in phosphate-buffered saline and re-pelleted two times. Cells are resuspended in RPMI 1640 medium supplemented with 10% irradiated fetal bovine serum and appropriate levels of antibiotics. Macrophages are seeded at $10^6$ cells/ml to 24-well plates and allowed to adhere for 7 h. Non-adherent cells are decanted, and wells are refilled with 10% fetal bovine serum and RPMI medium. Field swine serum samples confirmed to be PRRSV positive by RT-PCR are used to inoculate the macrophages at 72 h post culture of the macrophages. At 48 h post inoculation, infection is confirmed by a direct fluorescent antibody test using monoclonal antibody (mAb) against the PRRSV nucleocapsid protein.

Each virus isolate is then plaque-purified. Confluent cell monolayers are infected with viruses at a multiplicity of infection (MOI) of 0.1. After 2 h, cell culture supernatant is removed and an agar overlay is applied. Plaques are detected after 5 days at 37° C. At least 10 single plagues from each virus isolate are picked and expanded in cultured cells.

Subsequent passage of the virus is performed by infecting cells with plaque-purified viruses at an MOI of 0.1. After 3 days, the culture supernatant is layered onto a 0.5 M sucrose cushion and centrifuged at 100,000×g for 14 h. Virus pellets are washed with PBS and could be stored at −80° C.

To determine the genomic sequence of each virus isolate, RNA is extracted from the sucrose cushion purified viruses using a QiaAmp viral RNA kit (Qiagen). The full-length genome sequences are determined using next generation sequencing at the Purdue University Genomic Core Facility.

The nucleotide sequences are aligned using the CLUSTAL W multiple sequence alignment program. The neighbor-joining distance analysis is performed on the resulting distance matrix using the Molecular Evolutionary Genetics Analysis (MEGA4) software available from the Center for Evolutionary Medicine and Informatics (Tempe, Ariz., USA). The bootstrap option is carried out with NJBOOT from 5000 replicates to assess the robustness of interior branches of the phylogenetic tree.

A total of 32 PRRSV field isolates have been evaluated for their potential as vaccine candidates. Initially, three of the most hyper-variable regions of the virus (nsp1, nsp2 and ORF6) have been sequenced for phylogenetic analysis. FIGS. 1-3 show the result of phylogeny trees constructed by neighbor-joint method based on the sequences of nsp1, nsp2 ovarian tumor (OTU) domain, or ORF6. Nine isolates (highlighted in boxes) representing each major cluster in the phylogenetic tree have been selected for further characterization. In all three phylogeny trees, isolates ND99-14 and ND99-17 locate in a separate clade from clades containing current commercial PRRSV vaccine strains. These two viruses also have ability to stimulate interferon (IFN)-α production (see FIG. 4). Isolates SD95-10 and SD95-47 are grouped in a same clade as the VR2332 and INGELVAC® PRRS MLV strains which was derived from VR2332. Isolates 12-7455 and SD11-21 represent a clade of more recent field stains. In nsp1 and nsp2 OTU domain phylogeny trees, SD04-89 and SD98-163 are grouped in a clade with the Chinese highly pathogenic stain JX143 and INGELVAC® PRRS ATP strain, which was derived from the JA142 strain. In ORF5 and nsp2 OTU domain phylogeny trees, MN05-68 is grouped in a clade with the JX143 and INGELVAC® PRRS ATP strains.

One of the criteria for vaccine development is that the candidate virus should have the ability to stimulate the host immune responses. Previous studies have shown that PRRSV suppresses the host cellular innate immune response and nsp2 is one of the innate antagonists to suppress the expression of interferon (IFN) and interferon stimulated genes (ISGs). To assess whether virus strains can induce interferon alpha (IFN-α), swine macrophages are either infected with different field isolates at an MOI of 1, or were mock infected. At 24 hour post infection, cell-culture supernatant was harvested for the quantification of IFN-α expression using fluorescent microsphere immunoassay as described previously (Lawson et al., Vaccine 28: 5356-64 (2010)). The quantity of IFN-α was determined using mean fluorescent intensity values, and the result was compared with the mean values from mock-infected control cells.

The in vitro delSGylation assay has been performed to select viruses that have weak ability to suppress the ISG expression. The delSGylation assay is conducted as described previously (Sun et al., *J. Virology* 86(7): 3839-50 (2012)). Briefly, HeLa cells are co-transfected with plasmid DNA expressing conjugation enzymes E1/E2/E3, FLAG-tagged ISG15 and PRRSV PLP2 (aa386-578). The empty vector plasmid is included as a control. At 6 h post-transfection, cells are stimulated with 1,000 U/ml of IFN-α. Cells are harvested at 24 h post-stimulation and analyzed by immunoblotting. The membrane is probed with anti-FLAG antibody to detect the expression of free and conjugated forms of ISG15. The expression of PRRSV PLP2 is detected using an nsp2-specific monoclonal antibody. As shown in FIG. 5, isolates SD95-10 and SD11-21 have less effect on the ISGylation of cellular proteins, suggesting these two isolates would have potential being used for future vaccine development. We further tested the ability of viruses to stimulate IFN-α expression. The SD04-30 and M004-25 were documented previously to be able to enhance IFN-α production. Using these two isolates as controls, IFN-α expression levels are measured in PRRSV-infected swine alveolar macrophages. As we expected, the SD04-30 and M004-25 stimulate significant amount of IFN-α expression (FIG. 4). In contrast, isolates SD95-21, ND99-17, SD06-21 and SD92-18 stimulate a level of IFN-α compatible to that of SD04-30 and M004-25. The isolates MN91-45, ND99-14 and NE06-05 show weak stimulation of IFN-α expression.

Based on the immune assay result and phylogeny analysis, nine Type 2 isolates are initially selected for continued passage in cultured non-swine cells for 80 passages. In addition to these nine type 2 viruses, SD03-15 (type 1 strain), SD02-11 (type 1 strain) and SD02-10 (mix of type 1 and type 2 viruses) are also included in further analysis. A total of nine passage-80 (P80) viruses are selected for plaque purification two times in cell culture, and passage-82 (P82) viruses are further purified through sucrose cushion and stored as virus stock. The virus titers are determined during the passage of each candidate vaccine virus, which were ranged between 4.5-7 logs of fluorescent focus unit (FFU)/ml. Virus isolates with titer lower than 5 logs of FFU/ml are excluded from further study. Full-length genome sequences for eleven candidate virus isolates were initially determined on Feb. 11, 2013, and the final products of nine candidate vaccine viruses (P83) purified by plaque purification and sucrose cushion were sequenced again and documented on Dec. 22, 2013.

The cDNA consensus sequences for nine PRRS virus isolates at passage 83 (P83) were deposited in GenBank genetic sequence database, an annotated collection of all publicly available nucleic acid sequences. The GenBank database is maintained by the National Center for Biotechnology Information (NCBI), part of the United States National Institutes of Health (NIH). GenBank is part of the International Nucleotide Sequence Database Collaboration.

The cDNA consensus sequence of PRRS strain SD 95-10 at P83 has been assigned GenBank Accession number KU131565 (SEQ. ID. NO:1). The cDNA consensus sequence designated SEQ. ID. NO:1 is:

```
  1 ATGACGTATA GGTGTTGGCT CTATGCCATG ACATTTGTAT AGTCAGGAGC TGCGACCATT
 61 GGTACAGCCC AAAACTTGCT GCACGGAAAC GCCCTTCCGT GACAGCCCTC TTCAGGGGAG
121 TTTAGGGGTC TATCCCTAGC ACCTTGCTTC CGGAGTTGCA CTGCTTTACG GTCTCTCCAA
181 CCCTTTAACC ATGTCTGGGA TACTTGATCG GTGCACGTGT ACCCCCAATG CCAGGGTGTT
241 CATGGCGGAG GGCCAAGTCT ACTGCACACG ATGTCTCAGT GCACGGTCTC TCCTTCCTCT
301 GAATCTCCAA GTTCCCGAGC TTGGAGTGCT GGGCCTATTT TACAGGCCCG AAGAGCCGCT
361 CCGGTGGACG TTGCCACGTG CATTCCCCAC TGTCGAGTGC TCCCCCGCCG GGGCTTGCTG
421 GCTTTCTGCG ATCTTCCCAA TTGCACGAAT GACCAGTGGA AACCTGAACT TTCAACAAAG
481 AATGGTGCGG GTCGCTGCCG AGATTTACAG AGCCGGCCAG CTCACCCCTG CAGTCTTGAA
541 GGCTCTACAA GTTTATGAAC GGGGTTGCCG CTGGTACCCC ATTGTCGGAC CTGTCCCTGG
601 AGTGGCCGTT TTCGCCAACT CCCTACATGT GAGTGACAAA CCTTTTCCGG GAGCAACTCA
661 TGTGTTAACC AATCTACCGC TCCCGCAGAG GCCCAAGCCT GAAGACTTTT GCCCTTTTGA
721 GTGTGCTATG GCTGACATCT ATGACATCGG TCATGACGCC GTCATGTATG TGGCCGGAGA
```

-continued

```
781 GAAAGTCTCC TGGGCCCCTC GTGGCGGGGA TGAAGTGAAA TTTGAAAATG TTCCCAAGGA
841 GTTGAAGTTG ATTGCGAACC GACTCCACAT CTCCTTCCCG CCCCACCACG TAGTGGACAT
901 GTCCAAGTTT ACCTTCATAG CCCCCGGGAG TGGTGTCTCC ATGCGGGTTG AGTGCCAACA
961 CGGCTGCCTC CCCGCTGATA CTGTTCCTGA AGGAAACTGC TGGTGGCGCT TGTTCGACTC
1021 GCTCCCGCCG GAAGTCCAGC ACAAAGAAAT TCGCTATGCT AACCAATTTG GTTATCAAAC
1081 CAAGCATGGT GTCTCTGGCA AGTACCTACA GCGGAGGCTG CAAGTTAACG GTCTCCGAGC
1141 AGTGACCGAC GTACATGGAC CTATCGTCAT ACAGTACTTC TCTGTTAAGG AGAGTTGGAT
1201 CCGCCACTTC AGGCTGGCGG AAGAACCTAG CCTCCCTGGG TTCGAAGACC TCCTCAGAAT
1261 TAGGGTTGAG CCCAATACAT CACCACTGGC TGGCGAGGAT GGGAAGATCT TCCGGTTTGG
1321 CAGTCACAAG TGGTACGGTG CTGGAAGGAG AGCAAGGAAA GCACGTTCTG GTGCGACCAC
1381 CATGGTCGCT CATCGCGCTT TGTCCGCTCG TGAAACCCAG CAGGCAAAGA AGGACGAGGG
1441 TGCCGACGCT AACAAGGCTG AGCATCTCAA GCACTACTCT CCGCCCGCCG AAGGGAACTG
1501 TGGTTGGCAC TGTATTTCCG CCATCGCCAA CCGGATGATA AATTCCAAAT TTGAAACTAC
1561 CCTTCCCGAA AGAGTAAGGC CTCTGGATGA CTGGGCTACT GACGAGGATC TTGTGAATAC
1621 CATCCAAATC CTCAGGCTCC CCGCGGCCTT GGATAGGAAC GGTGCTTGTA GTAGCGCCAA
1681 GTACGTGCTT AAGCTGGAAG GTGTGCATTG GACTGTCTCT GTGACCCCTG GGATGTCCCC
1741 TTCCTTGCTC CCCCTTGAAT GTGTTCAGGG CTGTTGCGAG CATAAGGGCG GTTTTGGCTC
1801 CCCAGATGCG GTCGAAGTTT CCGGATTTGA CCCTGCCTGC CTTGACCGAC TGGCTGAGGT
1861 AATGCACTTG CCTAGCAGTG CCATCCCAGC CGCTCTGGCC GAAATGTCCG GCGACTCCAA
1921 TCGTCCGGCT TCCCCGGTCA ACACTGTGTG GACTGTTTCG CAATTCTATG CCCGTCATAC
1981 AGGAGGAAAT CATCCTGACC AGGTGTGCTT AGAGCAGATC ATTAATCTCT GTCAGGTTAT
2041 TGAGGTTTGT TGCTGCCATC AAAACAAAAC CAACCGGGCC ACCCCGGAAG AGGTCGCGGC
2101 AAAGATTGAT CAGTACCTCC GTGGTGCAAC AAATCTTGAA GAATGCTTGA CCAGGCTTGA
2161 GAGGGTTTGC CCGCCGAGCG CTGCGGACAC CTCCTTTGAT TGGAATGTTG TGCTCCCTGG
2221 GGTTGAGGCT GCAACTCAGA CAACCAAACA GCCCCACGTC AACCAGTGCT GCGCTCTGGT
2281 TCCTGTCGTG ACTCAAGAGC CTTTGGACAA AGACTCGGTC CCTCTGACCG CCTTCTCGCT
2341 GTCCAATTGC TACTACCCTG CACAAGGTGA AGAGGTTCGT CACCGTGAGA GACTAAACTC
2401 CGTACTCTCG AAGTTGGAGG GGGCTGTTCG TGAGGAATAT GGGCTCACGC CAACTGAACC
2461 TGGCCTGCAA CCCGCACTAC CGAACGGGCT CGACGAACTT AAAGACCGGA TGGAGGAGGA
2521 TCTGCTGAAA CTAGTCAACG CTCAGGCAAC TTCAGAAATG ATGGCCTGGG CAGCCGAGCA
2581 GATTGATTTA AAAGCTTGGG TCAAAAACTA CCCACGGTGG ACACCGCCAC CCCCTCCACC
2641 AAGAGCTCAG CCTCGGAAAA CGAAGTCTGT TAAGAGCTTG CCAGGGAACA AGCCTATCCC
2701 TGCTCCACGC AGGAAGGTCA GATCTGATTT GACTGTTAAT GGCCCCCTTG ATCTTTCGAC
2761 ACCATCCGAG CCGATGACAC CCCTGAGTGA GCCTGCACTT ATGCCCGCGT TGCAACATAT
2821 TTCTAGGCCA GTGACATCTT TGAGTGAGCC GGTCCCAGTT CCTGCACCGC GTAGAGCTGT
2881 GTCCCGACCG GTGACGCCCT TGAGTGGGCC AACTTTTGAG TTTGCGCCGC GACACAAATT
2941 TCAGCAGGTG GGAGAAGTGA ATCTGGCGGC AACAACGCTG ACGCACCAGG ACGAACCTCT
3001 AGATTTGTCT GCATCCTCAC AGACTGAATA TGAGGCTTCT CCCCTAGTAC CACCGCAGAA
3061 CATGGGTATC CTGGGGGTGG GGGGGCAAGA GGCTGAAGAA GTTCTGAGTG AAATCTCGGA
3121 TATACTGAGT GACATTAACC CTGCACCTGT GTCATTAAGC AGCTCCCTGT CAAGTGTTAA
```

-continued

3181 GATCACACGC CCAAAATACT CAGCTCAAGC CATCATTGAC TCGGGCGGGC CCTGCAGTGG

3241 GCATCTCCGA AGGGAAAAAG AAGCATGCCT CAGCGTCATG CGTGAGGCTT GTGATGCGGC

3301 TAAACTTAGC GACCCTGCCA CGCAGGAATG GCTTTCTCGC ATGTGGGATA GGGTTGACAT

3361 GCTGACCTGG CGCAATAAGT CTGCTTACCA GGCGTTTCGC ATCTTGGATG GCAGGTTTGA

3421 GTTTCTCCCA AAGATGATAC TCGAGACACC GCCGCCCTAT CCGTGTGGGT TTGTGATGCT

3481 GCCTCACACG CCTGCACCTT CCGTGAGTGC AGAGAGTGAC CTTACCATTG GTTCAGTCGC

3541 CACTGAAGAT GTTCCACGCA TCCTCGGGAA AATAGAAAAC GCCGGCGAGG TGCCCAACCA

3601 GGGGCTCTCG GCATCCTCCG GGGAAGAACC GATGTATGAC CAACCTGCCA AAGACTCCCG

3661 GATGTCGTCG CGGGGGTTTG ACGAGAGCAT AACGGCTCCG TCCGTAGGTA CAGGTGGCGC

3721 TGACTTACTC ACTGATTTGC CACCTTCAGG TGGTGTGGAT GTGGACGGGG GGGGGCCGTT

3781 ACGGACGGTA AGAAAGAAAA TTGAAAGGCT CTTCGACCAA TTTAGCCGTC AGGTTTTTAA

3841 CCTCGTCTCC CATCTCCCTG TTTTCTTCTC ACACCTCTTC AAACCTGACA GTGGTTATTC

3901 TCCGGGTGAT TGGGGTTTTG CAGCTTTCAC TCTACTTTGC CTCTTTTTGT GTTATAGCTA

3961 CCCATTCTTT GGCTTCGCTC CCCTCTTGGG TGTATTTTCT GGGTCTTCTC GGAGGGTGCG

4021 CATGGGGGTT TTTGGCTGCT GGTTGGCTTT TGCTGTTGGC CTGTTCAAGC CTGTGTCCGA

4081 CCCAGTCGGC ACTGCTTGTG AATTTGACTC GCCAGAGTGT AGGAACGTCC TTCATTCTTT

4141 TGAGCTTCTC AAACCTTGGG ACCCTGTTCG CAGCCTTGTT GTGGGCCCCG CAGGTCTCGG

4201 TCTTGCCATT CTTGGCAGGT TACTGGGCGG GGCACGCTAC ATCTGGCATT TTTTGCTTAG

4261 GCTTGGCATT GTTGCAGATT GTGTCTTGGC TGGAGCTTAT GTGCTTTCTC AAGGTAGGTG

4321 TAAAAAGTGC TGGGGATCTT GTATAAGAAC TGCTCCTAAT GAAATCGCCT TCAACGTGTT

4381 CCCTTTCACG CGTGCGACCA GGTCGTCACT CATCGACCTG TGCGACCGGT TTCGTGCGCC

4441 AAAAGGCATG GACCCTGTTT TCCTCGCTAC TGGGTGGCGC GGGTGCTGGA CCGGTCAAAG

4501 TCCCATTGAG CAACCCTCTG AAAAACCCAT CGCGTTCGCC CAGTTGGATG AAAAGAGGAT

4561 CACGGCTAGA ACTGTGGTCG CTCAGCCTTA TGATCCTAAC CAAGCCGTAA AGTGCTTGCG

4621 GGTGCTACAG GCGGGTGGGG CGATGGTGGC CGAGGCAGTC CCAAAAGTGG TCAAGGTTTC

4681 CGCTATTCCA TTCCGAGCCC CCTTTTTTCC CACCGGAGTG AAGGTTGATC CTGAGTGCAG

4741 GATCGTGGTC GACCCCGACA CTTTTACTAC AGCTCTCCGG TCTGGTTACT CCACCACAAA

4801 CCTCGTCCTT GGTGTGGGGG ACTTTGCCCA ATTGAATGGA TTGAAAATCA GGCAAATTTC

4861 CAAGCCTTCG GGAGGAGGCC CACACCTCAT TGCTGCCCTG CATGTTGCGT GCTCTATGGC

4921 GTTGCACATG CTTGCTGGGG TTTATGTAAC TGCAGTGGGG TCTTGCGGTA CCGGCACCAA

4981 CGATCCGTGG TGCACTAACC CATTCGCCGT CCCTGGCTAC GGACCTGGCT CTCTCTGCAC

5041 GTCCAGATTG TGCATCTCCC AACATGGCCT CACCCTGCCC TTGACAGCAC TTGTGGCAGG

5101 ATTCGGTCTT CAGGAAATTG CCTTAGTCGT TTTGATTTTC GTTTCCATCG GAGGCATGGC

5161 TCATAGGTTG AGTTGTAAGG CTGACATGCT GTGCATCTTA CTTGCAATCG CCAGCTATGT

5221 TTGGGTACCC CTTACCTGGT TGCTCTGTGT GTTTCCTTGC TGGTTGCGCT GGTTCACTTT

5281 GCACCCTCTC ACCATCCTAT GGTTGGTGTT TTTCCTGATT TCTGTAAATA TGCCTTCGGG

5341 AATCTTGGCC ATGGTGTTAT TGGTTGCTCT TTGGCTTTTA GGCCGTTATA CTAATGTTGT

5401 TGGTCTTGTT ACCCCCTATG ATATTCACCA TTACACCAGT GGCCCCCGCG GTGTAGCCGC

5461 CTTGGCCACC GCACCAGATG GGACTTACTT GGCCGCTGTC CGCCGCGCTG CGTTGACTGG

5521 CCGCACCGTG CTGTTTACCC CGTCTCAGCT TGGGTCCCTT CTTGAGGGCG CTTTCAGGAC

5581 TCGAAAGCCC TCATTGAACA CCGTCAATGT GGTCGGGTCC TCCATGGGCT CTGGCGGAGT

-continued

5641 GTTCACTATC GACGGGAAAA TCAAGTGCGT GACTGCCGCA CATGTCCTTA CGGGTAATTC

5701 AGCCAGGGTT TCCGGGGTCG GCTTCAATCA AATGCTTGAC TTTAATGTAA AGGGGGACTT

5761 CGCCATAGCT GATTGCCCGA ATTGGCAAGG GGCTGCTCCC AAGACCCAAT TCTGCGAGGA

5821 TGGATGGACT GGTCGTGCCT ATTGGCTGAC ATCCTCTGGT GTCGAACCCG GTATCATTGG

5881 GAATGGATTT GCCTTCTGCT TCACCGCGTG CGGCGATTCT GGATCCCCAG TGATTACCGA

5941 AGCCGGTGAG CTTGTCGGCG TTCACACAGG ATCGAACAAA CAAGGAGGAG GCATTGTCAC

6001 GCGCCCCTCG GGCCAGTTTT GTAATGTGGC GCCCATCAAG CTGAGCGAAT TGAGTGAATT

6061 CTTCGCTGGA CCTAAGGTCC CGCTCGGTGA TGTGAAGGTT GGCAGCCACA TAATTAAAGA

6121 CATATGCGAG GTACCTTCAG ACCTTTGCGC CTTGCTTGCT GCCAAACCCG AACTGGAAGG

6181 AGGCCTCTCT ACCGTCCAAC TTCTGTGTGT GTTTTTCCTC CTGTGGAGAA TGATGGGGCA

6241 TGCCTGGACG CCCTTGGTTG CTGTGGGGTT TTTTATCTTG AATGAGGTCC TCCCAGCTGT

6301 CCTGGTCCGG AGTGTTTTCT CCTTTGGAAT GTTTGTGCTA TCTTGGCTCA CGCCATGGTC

6361 TGCGCAAGTT CTGATGATCA GGCTTCTAAC AGCAGCTCTT AACAGGAACA GATTTTCACT

6421 CGCCTTTTAC AGCCTTGGTG CAGCGACCGG TTTTGTCGCA GATCTGGCGA CAACTCAAGG

6481 GCATCCGTTG CAGGCAGTAA TGAATTTAAG TACCTATGCC TTCCTGCCTC GGATGATGGT

6541 TGTGACATCA CCAGTCCCAG TGATTGCGTG TGGTGTTGTG CACCTCCTTG CCATAATTTT

6601 GTACTTGTTC AAGTACCGTT GCCTGCACAA TGTCCTTGTT GGCGACGGAG CGTTCTCTGC

6661 GGCTTTTTTC TTGCGATACT TTGCCGAGGG AAAGTTGAGA GAAGGGGTGT CGCAGTCCTG

6721 CGGGATGAAT CACGAGTCAC TGACTGGAGC CCTCGCTATG AGACTCAATG ACGAGGACTT

6781 GGACTTCCTT ACGAAATGGA CTGATTTTAA GTGCTTTGTT TCTGCTTCCA ATATGAGGAA

6841 TGCAGCGGGC CAATTCATCG AGGCAGCCTA TGCTAAAGCA CTTAGAATAG AACTTGCCCA

6901 GTTGGTGCAG GTCGACAAGG TTCGAGGTGT TTTGGCCAAA CTTGAAGCTT TTGCTGATAC

6961 TGTGGCACCC CAACTCTCGC CCGGTGACAT TGTCGTTGCT CTTGGCCATA CGCCTGTTGG

7021 TAGTATCTTC GACCTAAAGG TTGGTAGCAC CAAGCATACT CTCCAAGCCA TTGAGACCAG

7081 AGTCCTTGCC GGGTCCAAGA TGACCGTGGC GCGCGTCGTT GACCCAACCC CCACGCCCCC

7141 ACCCGCACCC GTGCCTATCC CCCTCCCGCC AAAAATTCTG GAGAATGGTC CCAACGCCTG

7201 GGGGGATGAG GACCGTTTGA ATAAGAAGAA GAGGCGCAGG ATGGAAGCCG TTGGCATCTT

7261 TGTTATGGGC GGGAAGAAGT ACCAGAAATT TTGGGACAAG AGCTCCGGTG ATGTGTTTTA

7321 CGAGGAAGTC CATGATAACA CAGATGCATG GGAGTGCTTC AGAGTTGACA ACCCTGCCGA

7381 CTTTGACCCT GAGAAGGGAA CTCTGTGTGG GCATACCACC ATTGAAAATA AGGCTTACAA

7441 TGTCTACGTC TCCCCATCTG GCAGGAAGTT TCTAGTCCCT GTCAACCCAG AGAGTGGAAA

7501 AGCCCAATGG GAAGCTGCAA GGCTTTCCGT GGAGCAGGCC CTTGGCATGA TGAATGTCAA

7561 CGGTGAACTG ACAGCCAAAG AACTGGAGAA ACTGAAAAGA ATAATTGACA AACTCCAGGA

7621 CCTGACTAAG GAGCAGTGTT TAAACTGCTA GCCGCCAGCG GCTTGACCCG CTGTGGTCGC

7681 GGCGGCTTAG TTGTTACTGA GACAGCGGTA AAAATAGTCA AATTTCACAA CCGGACCTTC

7741 ACCCTAGGAC CCGTAAACTT AAAAGTGGCC AGTGAGGTTG AGCTAAAAGA CGCGGTCGAG

7801 CATAACCAAC ACCCGGTTGC AAGACCGGTT GATGGCGGTG TTGTGCTCCT GCGCTCCGCA

7861 GTTCCTTCGC TTATAGACGT CTTGATCTCC GGCGCTGATG CATCTCCTAA GTTACTCGCC

7921 CGCCACGGGC CGGGAAACAC TGGGATCGAT GGCACGCTTT GGGACTTTGA GGCCGAGGCC

7981 ACTAGAGAGG AAATTGCACT CAGTGCGCAA ATAATACAGG CTTGTGACAT TAGGCGCGGC

-continued

```
8041 GACGCGCCCG AAATTGGTCT TCCTTATAAG CTGTACCCTG TTAGGGGCAA CCCTGAGCGG
8101 GTAAAAGGAG TTTTACAGAA CACAAGGTTT GGAGACATAC CTTACAAAAC CCCCAGTGAC
8161 ACTGGAAGCC CAGTACACGC GGCTGCCTGC CTCACGCCCA ATGCCACTCC GGTGACTGAT
8221 GGGCGCTCCG TCTTGGCTAC GACTATGCCC TCCGGTTTTG AGTTGTATGT ACCGACCATT
8281 CCAGCGTCTG TCCTTGATTA TCTTGATTCT AGGCCTGACT GCCCTAAACA GTTGACAGAG
8341 CACGGTTGTG AGGATGCCGC ATTGAGAGAC CTCTCCAAGT ATGACTTGTC CACCCAAGGT
8401 TTTGTTTTGC CTGGAGTTCT TCGCCTTGTG CGGAAGTACC TGTTTGCCCA TGTGGGTAAG
8461 TGCCCGTCCG TTCATCGGCC TTCCACTTAC CCTGCCAAGA ATTCTATGGC TGGAATAAAT
8521 GGGAACAGGT TTCCAACCAA GGACATTCAG AGCGTCCCTG AAATCGACGT TCTGTGCGCA
8581 CAGGCCGTGC GAGAGAACTG GCAAACTGTC ACCCCTTGTA CCCTCAAGAA ACAGTATTGT
8641 GGGAAGAAGA AGACTAGGAC AATACTCGGC ACCAATAACT TCATTGCGTT GGCCCACCGA
8701 GCAGCGTTGA GTGGTGTCAC CCAGGGCTTC ATGAAAAAGG CGTTTAACTC GCCCATCGCC
8761 CTCGGGAAAA ACAAATTTAA GGAGCTGCAG ACTCCGGTCT TAGGCAGGTG CCTTGAAGCT
8821 GATCTTGCAT CCTGCGATCG ATCCACACCA GCAATTGTTC GCTGGTTTGC CGCCAATCTT
8881 CTTTATGAAC TTGCCTGTGC TGAGGAGCAT CTGCCATCGT ACGTGCTGAA CTGCTGCCAC
8941 GACTTACTGG TCACGCAGTC CGGCGCGGTG ACTAAGAGAG GTGGCCTGTC GTCTGGCGAC
9001 CCGATTACTT CTGTGTCAAA CACCATTTAC AGCTTGGTGA TATATGCACA GCACATGGTG
9061 CTCAGTTACT TTAAAAGTGG TCACCCTCAT GGCCTTCTGT TTCTGCAAGA CCAGCTGAAG
9121 TTTGAGGACA TGCTCAAGGT TCAACCCCTG ATCGTCTATT CGGACGACCT CGTGCTGTAT
9181 GCCGAGTCTC CCACCATGCC AAACTACCAC TGGTGGGTGG AACATCTGAA TCTTATGCTG
9241 GGTTTTCAGA CGGACCCAAG GAAGACAGCC ATAACAGATT CGCCATCATT TCTAGGCTGT
9301 AGGATAATAA ATGGACGCCA ACTAGTCCCC AACCGTGACA GGATCCTCGC GGCCCTCGCT
9361 TACCATATGA AGGCAAGCAA TGTTTCTGAA TACTACGCCT CGGCGGCTGC AATACTCATG
9421 GACAGCTGTG CTTGTTTAGA GTATGATCCT GAATGGTTTG AAGAGCTCGT GGTTGGGATG
9481 GCGCAGTGCG CCCGCAAGGA CGGCTATAGT TTCCCTGGCC CGCCGTTCTT CTTGTCCATG
9541 TGGGAAAAAC TCAGGTCCAA TCATGAAGGG AAGAAGTCCA GAATGTGCGG GTACTGCGGG
9601 GCCCCGGCTC CGTACGCCAC TGCCTGTGGC CTCGACGTCT GTGTTTATCA CACCCACTTT
9661 CACCAGCATT GTCCAGTCAT AATCTGGTGT GGCCATCCGG CTGGTTCTGG TTCTTGCAGT
9721 GAGTGCAAAC CCCCCTTAGG GAAAGGCACA AGCCCTCTAG ATGAGGTGTT AGAACAAGTC
9781 CCGTACAAGC CTCCACGGAC TGTAATCATG CATGTGGAGC AGGGTCTCAC CCCTCTTGAC
9841 CCAGGTAGAT ACCAGACTCG CCGCGGATTA GTCTCCGTTA GGCGTGGCAT CAGGGGAAAT
9901 GAAGTTGACC TACCAGACGG TGATTATGCT AGTACCGCCC TGCTCCCCAC TTGTAAAGAG
9961 ATCAACATGG TCGCTGTCGC CTCTAACGTG TTGCGCAGCA GGTTCATCAT CGGTCCGCCT
10021 GGTGCTGGGA AAACATACTG GCTCCTTCAA CAGGTCCAAG ATGGTGATGT CATTTACACG
10081 CCGACTCACC AGACCATGCT CGACATGATT AGGGCTTTGG GGACGTGCCG GTTCAACGTC
10141 CCGGCAGGTA CAACGCTGCA ATTCCCCGCC CCCTCCCGTA CCGGCCCGTG GGTTCGCATC
10201 CTAGCCGGCG GTTGGTGTCC TGGTAAGAAT TCCTTCCTGG ATGAAGCAGC GTATTGCAAT
10261 CACCTTGATG TCTTGAGGCT TCTTAGCAAA ACTACCCTTA CCTGCCTAGG AGACTTCAAA
10321 CAACTCCACC CGGTGGGTTT TGACTCTCAT TGCTATGTTT TTGACATCAT GCCTCAGACC
10381 CAACTGAAGA CCATCTGGAG GTTTGGACAG AACATCTGTG ATGCCATCCA ACCAGATTAC
10441 AGGGACAAAC TTGTATCCAT GGTCAACACA ACCCGTGTAA CCTACGTGGA AAGACCTGTC
```

-continued

10501 AATTATGGGC AAGTCCTCAC CCCTTACCAC AGGGACCGAG AGGACGGCGC CATCACAATT

10561 GACTCCAGTC AAGGCGCCAC ATTTGATGTG GTTACACTGC ATCTGCCCAC TAAAGACTCA

10621 CTCAACAGGC AAAGAGCCCT TGTTGCTATC ACCAGGGCAA GACATGCTAT CTTTGTGTAT

10681 GACCCACACA GGCAACTGCA GAGCATGTTT GATCTTCCTG CGAAAGGCAC ACCCGTCAAC

10741 CTCGCTGTGC ACCGTGACGA GCAGCTGATC GTACTAGATA GAAATAACAA AGAATGCACG

10801 GTTGCTCAGG CTCTAGGCAA TGGGGATAAA TTCAGGGCCA CAGACAAGCG CGTTGTAGAT

10861 TCTCTCTGCG CCATTTGTGC AGATCTGGAA GGGTCGAGCT CTCCGCTCCC CAAGGTCGCA

10921 CACAACTTGG GGTTTTATTT CTCACCTGAT TTGACACAGT TTGCTAAACT CCCGGTAGAA

10981 CTTGCACCCC ACTGGCCCGT GGTGACAACC CAGAACAATG AAAAGTGGCC AGACCGGCTG

11041 GTTGCCAGTC TTCGCCCTGT CCATAAGTAT AGCCGTGCGT GCATCGGTGC CGGCTACATG

11101 GTGGGCCCCT CAGTGTTTCT AGGCACCCCT GGGGTTGTGT CATACTATCT CACAAAATTT

11161 GTCAAGGGCG AGGCTCAAAT GCTTCCGGAG ACAGTTTTCA GCACCGGCCG AATTGAGGTA

11221 GATTGCCGGG AGTATCTTGA TGACCGGGAA CGAGAAATTG CTGAGTCCCT CCCCCATGCC

11281 TTCATTGGCG ACGTCAAAGG CACTACCGTT GGAGGATGTC ACCATGTCAC CTCCAAATAC

11341 CTTCCGCGCT TCCTTCCCAA GGAATCAGTC GCGGTAGTCG GGGTTTCAAG CCCCGGGAAA

11401 GCCGCAAAAG CAGTTTGCAC ATTAACAGAT GTGTACCTCC CAGACCTTGA GGCTTACCTC

11461 CACCCAGAGA CCCAGTCCAG GTGCTGGAAA ATGATGTTGG ACTTCAAGGA AGTTCGACTG

11521 ATGGTCTGGA AAGACAAGAC GGCCTATTTT CAACTTGAAG GCCGCCATTT CACCTGGTAT

11581 CAGCTTGCGA GCTATGCCTC GTACATCCGA GTTCCTGTTA ACTCTACGGT GTATTTGGAC

11641 CCATGCATGG GCCCTGCCCT TTGCAATAGA AGGGTTGTCG GGTCCACCCA TTGGGGAGCT

11701 GACCTCGCAG TCACTCCTTA TGATTATGGT GCCAAGATCA TTTTGTCTAG TGCATACCAT

11761 GGTGAAATGC CTCCTGGGTA CAAAATCCTA GCGTGTGCGG AGTTCTCGCT TGATGATCCA

11821 GTGAGGTACA AGCACACCTG GGGATTTGAA TCGGATACAG CGTATCTGTA CGAGTTCACC

11881 GGAAACGGTG AGGACTGGGA GGATTACAAT GATGCGTTTC GTGCGCGCCA GAAAGGGAAA

11941 ATTTATAAGG CCACTGCCAC CAGCATGAGG TTTCATTTTC CCCCGGGCCC TGTCATTGAA

12001 CCAACTTTGG GCCTGAACTG AAATGAAATG GGGGCTATGC AAAGCCTTTT CTACAAAATT

12061 GGCCAACTTT TTGTGGATGC TTTCACGGAG TTTTTGGTGT CCATTGTTGA TATCATCATA

12121 TTTCTGGCCA TTTTGTTTGG CTTCACCATC GCCGGCTGGC TGGTGGTCTT CTGCATCCGA

12181 TTGGTTTGCT CCGCGGTACT CCGTGCGCGC CCTACCGTTC ACCCTGAGCA ATTACAGAAG

12241 ATCTTATGAG GCCTTTCTTT CTCAGTGCCA GGTGGACATT CCCACCTGGG GAACCAAACA

12301 TCCCTTGGGG ATGCTTTGGC ACCATAAGGT GTCAACCCTG ATTGATGAAA TGGTGTCGCG

12361 TCGAATGTAC CGCATCATGG AAAAAGCAGG ACAGGCTGCC TGGAAACAGG TGGTGAGCGA

12421 GGCCACGCTG TCTCGTATTA GTGGTTTGGA TGTGGTGGCT CATTTTCAGC ATCTTGCTGC

12481 CATTGAAGCC GAGAACTGTA AATATTTGGC CTCTCGGCTG CCCATGCTAC ACAACCTGCG

12541 CATGACAGGG TCAAATGTAA CCTTAGTGTA TAATAGCACT TTGAATCAGG TGTTCGCTAT

12601 CTTTCCAACC CCTGGTTCCC GGCCAAAGCT TCATGATTTT CAGCAATGGC TAATAGCTGT

12661 ACATTCCTCT ATATTTTCCT CCGTTGCGGC TTCTTGTACT CTTTTTGTTG TGCTGTGGTT

12721 GCGAATCCCA ATTCTACGTA CTGTTTTTGG TTTCCACTGG TTAGGGGCAA TTTCTCTTTC

12781 GAACTCACAG TGAATTACAC GGTGTGCCCA CCTTGCCTCA CCCGACAAGC AGCCGCTGAG

12841 ATCTATGAAC CCGGCAGGTC TCTTTGGTGC AGGATAGGGA ATGACCGATG TAGTGAGAGC

-continued

12901 GATCATGACG AACTAGGGTT CATGGTTCCG TCTGGCCTCT CCAGCGAAGG CCACTTGACC

12961 AGTGTTTACG CTTGGTTGGC GTTTCTGTCC TTCAGCTACA CGGCCCAGTT CCATCCCGAG

13021 ATATTTGGGA TAGGGAATGT GAGTAAAGTT TATGTTGACA TCAAGCACCA ATTAATCTGC

13081 GCCGTTCATG ACGGGCAGAA CACCACCTTG CCTCGCCATG ACAATATTTC AGCCGTATTT

13141 CAGACCTATT ATCAACATCA GGTCGACGGC GGCAACTGGT TTCACCTAGA ATGGCTGCGT

13201 CCCTTCTTTT CCTCTTGGTT GGTTTTAAAT GTTTCGTGGT TTCTCAGGCG TTCGCCTGCA

13261 AGCCATGTTT CAGTTCGAGT CTTTCGGACA TCAAGACCAA CACTACCGCA GCATCAGGCT

13321 TTGTCGTCCT CCAGGACATC AGCTGCCTTA GGCATGGCGA CTCGTCCTCT CAGACGATTC

13381 GCAAAAGCTC TCAGTGCCGC ACGGCGATAG GGACGCCCGT GTACATCACC ATGACAGCCA

13441 ATGTCACAGA TGAGAATTAT TTGCATTCTT CTGATCTCCT CATGCTTTCT TCTTGCCTTT

13501 TCTATGCTTC TGAGATGAGT GAAAAGGGAT TCAAGGTGGT GTTTGGCAAT GTGTCAGGCA

13561 TCGTGGCTGT GTGTGTCAAC TTTACCAGCT ACGTCCAACA CGTCAAGGAG TTCACCCAAC

13621 GCTCCTTGGT AGTCGATCAT GTGCGGCTGC TTCACTTCAT GACACCTGAG ACCATGAGGT

13681 GGGCAACCGT TTTAGCCTGT CTTTTTGCCA TCTTGCTGGC AATTTGAATG TTCAAGTATG

13741 TTGGGGAAAT GCTTGACCGC GGGCTGTTGC TCGCGATTGC CTTTTTTGTG GTGTATCGTG

13801 CCGTTCTGTT TTGCTGTGAT CGTCGACGCC AACAGCAACA GCAGCTCTCA TTTCCAGTTG

13861 ATTTATAACT TGACGTTATG CGAGCTGAAT GGCACAGATT GGCTGGTTGA TAAATTTGAT

13921 TGGGCAGTGG AGACTTTTGT CATTTTTCCC GTGTTGACTC ACATTGTTTC TTATGGTGCA

13981 CTCACCACCA GCCATTTCCT TGACACAGTT GGTCTGGTTA CTGTATCCGC CGCCGGGTTT

14041 TGTCACGGGC GGTATGTCTT GAGTAGCATC TACGCGGTCT GTGCCCTGGC TGCGTTGGTT

14101 TGCTTTGTCA TCAGATTTGC GAAGAACTGC ATGTCCTGGC GCTACTCATG TACTAGATAC

14161 ACCAACTTCC TTCTAGACAC TAAGGGCAGA CTCTATCGTT GGCGGTCGCC TGTCATCATA

14221 GAGAAAAGGG GCAAGGTTGA GGTCGAAGGC CATCTGATCG ACCTCAAAAA AGTTGTGCTT

14281 GATGGTTCCG CGGCAACCCC TTTAACCAGA ATTTCAGCGG AACAATGGTG TCGTCCCTAG

14341 ACGACTTTTG CAATGATAGC ACAGCTCCAC GGAAGGTGCT CTTGGCGTTT TCTATCACCT

14401 ACACGCCAGT GATGATATAT GCTCTAAAGG TAAGTCGCGG CCGACTGTTG GGGCTTCTGC

14461 ACCTTTTGAT TTTTCTGAAC TGTGCCTTTA CCTTCGGGTA CATGACATTC ACGCACTTTC

14521 AGAGCACAAA TAGGGTCGCG CTCACTATGG GAGCAGTAGT CGCACTCCTT TGGGGGGTGT

14581 ACTCAGCCAT AGAAACCTGG AAATTCATCA CCTCCAGATG CCGTTTGTGC TTGCTAGGCC

14641 GCAAGTACAT TTTGGCCCCT GCCCACCACG TCGAAAGTGC CGCGGGCTTT CATCCGATTG

14701 CGGCAAATGA TAACCACGCA TTTGTCGTCC GGCGTCCCGG CTCCACTACG GTCAACGGCA

14761 CATTGGTGCC CGGGTTGAAA AGCCTCGTGT TGGGTGGCAG AAAAGCTGTT AAACAGGGAG

14821 TGGTAAACCT TGTCAAATAT GCCAAATAAC AACGGCAAGC AGCAAAAGAA AAAGAAGGGG

14881 AATGGCCAGC CAGTCAATCA GCTGTGCCAG ATGCTGGGTA AGATCATCGC CCAGCAAAAC

14941 CAGTCCAGAG GTAAGGGACC GGGGAAGAAA AATAAGAAGA AAAACCCGGA GAAGCCCCAT

15001 TTTCCTCTAG CGACCGAAGA TGACGTCAGG CATCACTTTA CCCCTAGTGA GCGGCAATTG

15061 TGTCTGTCGT CGATCCAGAC TGCCTTTAAC CAGGGCGCTG GAACTTGCAC CCTGTCAGAC

15121 TCAGGGAGGA TAAGTTACAC TGTGGAGTTT AGTTTGCCGA CGCATCATAC TGTGCGCCTG

15181 ATTCGCGCCA CAGCATCAAC CTCAGCATGA TGGGCTGGCA TTCTTGAAGC ACCACAGTGT

15241 TAGGATTGGA AGAATGTGTG GTGAATGGCA CTGATTGACA CTGTGCCTCT AAGTCACCTA

-continued

15301 TTCAATTAGG GCGACCGTGT GGGGGTAAAG TTTAATTGGC GAGAACCATG CGGCCGCAAT

15361 TAAAAAAAAA AAAAAAAAAA AAAAAA

The cDNA consensus sequence of PRRS strain SD 95-47 at P83 has been assigned GenBank Accession number KU131564 (SEQ. ID. NO:2). The cDNA consensus sequence designated SEQ. ID. NO:2 is:

1 TATGTACGTA TAGGTGTTGG CTCTATGCCT TTGGCATTTG TATTGTCAGG AGCTGTGACC

61 ATTGGCACAG CCCAAAACTT GCTACACAGA AACACCCTTC TGTGATAGCC TCCTTCAGGG

121 GAGCTTAGGG TTTGTCCCTA GCACCTTGCT TCCGGAGTTG CACTGCTTTA CGGTCTCTCC

181 ACCCCTTTAA CCATGTCTGG GATACTTGAT CGGTGCACGT GTACCCCCAA TGCCAGGGTG

241 TTTATGGCGG AGGGCCAAGT CTACTGCACA CGATGCCTCA GTGCACGGTC TCTCCTTCCC

301 CTGAACCTCC AAGTTTCTGA GCTCGGGGTG CTAGGCCTAT TCTACAGGCC CGAAGAGCCA

361 CTCCGGTGGA CGTTGCCACG TGCATTCCCC ACTGTTGAGT GCTCCCCCGC CGGGGCCTGC

421 TGGCTTTCTG CAATCTTTCC AATCGCACGA ATGACCAGTG GAAACCTGAA CTTCCAACAA

481 AGAATGGTAC GGGTCGCAGC TGAGCTTTAC AGAGCCGGCC AGCTCACCCC TGCAGTCTTG

541 AAGGCTCTAC AAGTTTATGA ACGGGGTTGC CGCTGGTACC CCATTGTTGG ACCTGTCCCT

601 GGAGTGGCCG TTTTCGCCAA TTCCCTACAT GTGAGTGATA AACCTTTCCC GGGAGCAACT

661 CACGTGTTGA CCAACCTGCC GCTCCCGCAG AGACCCAAGC CTGAAGACTT TTGCCCCTTT

721 GAGTGTGCTA TGGCTACTGT CTATGACATT GGTCATGACG CCGTCATGTA TGTGGCCGAA

781 AGGAAAATCT CCTGGGCCCC TCGTGGCGAG GATGAAGTGA AATTTGAAGC TGTCCCCGGG

841 GAGTTGAAGT TGATTGCGAA CCGGCTCCGC ACCTCCTTCC CGCCCCACCA CACAGTGGAC

901 ATGTCTAAGT TCGCCTTCAC AGCCCCTGGG TGTGGTGTTT CTATGCGGGT CGAATGCCAA

961 CACGGCTGCC TTCCCGCTGA CACTGTCCCT GAAGGCAACT GCTGGTGGAG CTTGTTTGAC

1021 TTGCTTCCAC TGGAAGTTCA GAACAAAGAA ATTCGCCATG CTAACCAATT TGGCTACCAG

1081 ACCAAGCATG GTGTCTCTGG CAAATACCTA CAGCGTAGGC TGCAAGTTAA TGGTCTCCGA

1141 GCAGTAACTG ACCTAAACGG ACCTATCGTC GTACAGTACT TCTCCGTTAA GGAGAGTTGG

1201 ATCCGCCATT TGAAACTGGC GGGAGAACCC AGCTACTCTG GGTTTGAGGA CCTCCTCAGA

1261 ATAAGGGTTG AGCCTAACAC GTCGCCATTG GCTGACAAGG AAGAAAAAAT TTTCCGGTTT

1321 GGCAGTCACA AGTGGTACGG CGCTGGAAAG AGAGCAAGAA AAGCGCGCTC TTGTGCGACT

1381 GCTACAGTCG CTGGCCGCGC TTTGTCCGTT TGTGAAACCC GGCAGGCCAA GGAGCACGAG

1441 GTTGCCGGCG CCAACAAGGC TGAGCACCTC AAACACTACT CCCCGCCTGC CGAAGGGAAT

1501 TGTGGTTGGC ACTGCATTTC CGCCATCGCC AACCGGATGG TGAATTCCAA ATTTGAAACC

1561 ACCCTTCCCG AAAGAGTGAG ACCTTCAGAT GACTGGGCTA CTGACGAGGA TCTTGTGAAT

1621 GCCATCCAAA TCCTCAGACT CCCTGCGGCC TTAGACAGGA ACGGTGCTTG TACTAGCGCC

1681 AAGTACGTAC TTAAGCTGGA AGGTGAGCAT TGGACTGTCA CTGTGACCCC TGGGATGTCC

1741 CCTTCTTTGC TCCCTCTTGA ATGTGTTCAG GGCTGTTGTG GGCACAAGGG CGGTCTTGGT

1801 ACCCCAGATG CAGTCGAGGT CTCCGGATTT GACCCTGCCT GCCTTGACCG GCTGGCTGAG

1861 GTGATGCACC TGCCTAGCAG TGCTATCCCA GCCGCTCTGG CCGAAATGTC TGGCGATTCC

1921 GATCGTTCGG CTTCTCCGGT CACCACCGTG TGGACTGTTT CGCAGTTCTT TGCCCGTCAC

1981 AGCGGAGGGA ATCACCCTGA CCAAGTGCGC TTAGGGAAAA TTATCAGTCT TTGTCAGGTG

2041 ATTGAGGACT GCTGCTGTTC CCAGAACAAA ACCAACCGGG TCACCCCGGA GGAGGTCGCA

-continued

2101 GCAAAGATTG ACCTGTACCT CCGTGGTGCA ACAAATCTTG AAGAATGCTT GGCCAGGCTT

2161 GAGAAAGCGC GCCCGCCGCG CGTAATCGAC ACCTTCTTTG ATTGGGATGT TGTGCTCCCT

2221 GGGGTTGAGG CGGCAACCCA GACGATCAAG CTGCCCCAGG TCAACCAGTG TCGTGCTCTG

2281 GTCCCTGTTG TGACTCAAAA GTCCTTGGAC AACAACTCGG TCCCCCTGAC CGCCTTTTCA

2341 CTGGCTAACT ACTACTACCG TGCGCAAGGT GACGAAGTTC GTCACCGTGA AAGACTAACC

2401 GCCGTGCTCT CCAAGTTGGA AAAGGTTGTT CGAGAAGAAT ATGGGCTCAT GCCAACCGAG

2461 CCTGGTCCAC GGCCCACACT GCCACGCGGG CTCGACGAAC TCAAAGACCA GATGGAGGAG

2521 GACTTGCTGA AACTGGCTAA CGCCCAGACG ACTTCGGACA TGATGGCCTG GGCAGTCGAG

2581 CAGGTTGACT TAAAAACTTG GGTCAAGAAC TACCCGCGGT GGACACCACC ACCCCCTCCG

2641 CCAAAAGTTC AGCCTCGAAA AACGAAGCCT GTCAAGAGCT TGCCGGAGAG AAAGCCTGTC

2701 CCCGCCCCGC GCAGGAAGGT TGGGTCCGAT TGTGGCAGCC CGGTTTCATT AGGCGGCGAT

2761 GTCCCTAACA GTTGGGAAGA TTTGGCTGTT AGTAGCCCCT TTGATCTCCC GACCTCACCT

2821 GAGCCGGCAA CACCTTCAAG TGAGCTGGTG ATTGTGTCCT CACCGCAATG CATCTTCAGG

2881 CCGGCGACAC CCTTGAGTGA GCCGGCTCCA ATTCCCGCAC CTCGCGGAAC TGTGTCTCGA

2941 CCGGTGACAC CCTTGAGTGA GCCGATCCCT GTGCCCGCAC CGCGGCGTAA GTTTCAGCAG

3001 GTGAAAAGAT TGAGTTCGGC GGCGGCAATC CCACCGTACC AGAACGAGCC CCTGGATTTG

3061 TCTGCTTCCT CACAGACTGA ATATGAGGCC TCTCCCCCAG CACCGCCGCA GAGCGGGGGC

3121 GTTCTGGGAG TAGAGGGGCA TGAAGCTGAG GAAACCCCGA GTGAAATCTC GGACATGTCG

3181 GGTAACATTA AACCTGCGTC CGTGTCATCA AGCAGCTCCT TGTCCAGCGT GAGAATCACA

3241 CGCCCAAAAT ACTCAGCTCA AGCCATCATC GACTCGGGCG GGCCCTGCAG TGGGCATCTC

3301 CAAGAGGTAA AGGAAACATG CCTTAGTGTC ATGCGCGAGG CATGTGATGC GACTAAGCTT

3361 GATGACCCTG CTACGCAGGA ATGGCTTTCT CGCATGTGGG ATCGGGTGGA CATGCTGACT

3421 TGGCGCAATA CGTCTGCTTA CCAGGCGATT TGCACCTTAG ATGGCAGGTT AAAGTTCCTC

3481 CCAAAAATGA TACTCGAGAC ACCGCCGCCC TATCCGTGTG AGTTTGTGAT GATGCCTCAC

3541 ACGCCTGCAC CTTCCGTAGG TGCGGAGAGC GACCTTACCA TTGGCTCAGT TGCTACTGAA

3601 GATGTTCCAC GCATCCTCGA GAAAATAGAA AATGTCGGCG AGATGGCCAA CCAGGGACCC

3661 TTGGCCTTCT CCGAGGATAA ACCGGTAGAT GACCAACTTG TCAACGACCC CCGGATACCG

3721 TCGCGGAGGC CTGACGAGAG CACATCAGCT CCGTCCGCAG GCACAGGTGG CGCCGGCTCT

3781 TTTACCGATT TGCCGCCTTC AGATGGCGCG GATGCGGACG GGGGGGGGCC GTTTCGGACG

3841 GTAAAAAGAA AAGCTGAAAG GCTCTTTGAC CAACTGAGCC GTCAGGTTTT TGACCTCGTC

3901 TCCCATCTCC CTGTTTTCTT CTCACGCCTT TTCTACCCTG GCGGTGGTTA TTCTCCGGGT

3961 GATTGGGGTT TTGCAGCTTT TACTCTATTG TGCCTCTTTT TATGTTACAG TTACCCAGCC

4021 TTTGGTATTG CTCCCCTCTT GGGTGTGTTT TCTGGGTCTT CTCGGCGCGT TCGAATGGGG

4081 GTTTTTGGCT GCTGGTTGGC TTTTGCTGTT GGTCTGTTCA AGCCTGTGTC CGACCCAGTC

4141 GGCGCTGCTT GTGAGTTTGA CTCGCCAGAG TGTAGAAACA TCCTTCATTC TTTTGAGCTT

4201 CTCAAACCTT GGGACCCTGT TCGCAGCCTT GTTGTGGGCC CCGTCGGTCT CGGTCTTGCC

4261 ATTCTTGGCA GGCTACTGGG CGGGGCACGC TGTATCTGGC ACTTTTTGCT TAGGCTTGGC

4321 ATTGTTGCAG ACTGTATCTT GGCTGGAGCT TACGTGCTTT CTCAAGGTAG GTGTAAAAAG

4381 TGCTGGGGAT CTTGTATAAG AACTGCTCCT AATGAGGTCG CTTTTAACGT GTTTCCTTTC

4441 ACACGTGCGA CCAGGTCGTC ACTTATCGAC CTGTGCGATC GGTTTTGTGC ACCAAAAGGA

4501 ATGGACCCCA TTTTTCTCGC CACTGGGTGG CGCGGGTGCT GGGCCGGCCG AAGCCCCATT

-continued

4561 GAGCAACCCT CTGAAAAACC CATCGCGTTT GCCCAATTGG ATGAAAAGAA GATTACGGCT

4621 AGGACTGTGG TCGCCCAGCC TTATGACCCC AACCAAGCCG TAAAGTGCTT GCGGGTGTTG

4681 CAGGCGGGTG GGGCGATGGT GGCTGAGGCG GTCCCAAAAG TGGTCAAGGT TTCCGCTGTT

4741 CCATTCCGAG CCCCCTTCTT TCCCACTGGA GTGAAAGTTG ATCCTGATTG CAGGGTCGTG

4801 GTTGACCCTG ATACTTTCAC TGCAGCTCTC CGGTCTGGCT ACTCCACCAC AAACCTCGTC

4861 CTTGGTGTAG GGGACTTTGC CCAGCTGAAT GGATTAAAAA TCAGGCAAAT TTCCAAGCCT

4921 TCAGGGGGAG GCCCACATCT CATGGCTGCC CTGCATGTTG CCTGCTCGAT GGCTCTGCAC

4981 ATGCTTGCTG GGATCTATGT GACTGCGGTG GGTTCTTGCG GCACCGGCAC CAACGACCCG

5041 TGGTGCGCTA ACCCGTTTGC CGTCCCTGGC TACGGACCTG GCTCTCTCTG CACGTCCAGA

5101 TTGTGCATTT CCCAACACGG CCTTACCCTG CCCTTGACAG CACTTGTGGC GGGATTCGGT

5161 ATTCAAGAAA TTGCCTTAGT CGTTTTGATT TTTGTTTCCA TCGGAGGCAT GGCTCATAGG

5221 TTGAGCTGTA AGGCTGACAT GCTGTTTGTT TTGCTTGCAA TCGCCAGCTA TGTTTGGGTA

5281 CCTCTTACCT GGTTGCTTTG TGTGTTTCCT TGCTGGTTGC GCTGTTTTTC TTTGCACCCC

5341 CTCACCGTCC TATGGTTGGT GTTTTTCTTG ATTTCTGTGA ATATGCCTTC AGGAATCTTG

5401 GCCATGGTGT TGTTGGTTTC TCTTTGGCTT CTTGGTCGTT ATACTAATGT TGCTGGCCTT

5461 GTCACCCCCT ACGACATTCA CCATTACACC AGCGGCCCCC GCGGTGTTGC CGCCTTGGCT

5521 ACCGCTCCAG ATGGGACCTA CTTGGCCGCT GTCCGCCGCG CTGCGTTGAC TGGCCGCACC

5581 ATGCTGTTTA CCCCGTCCCA GCTTGGGTCT CTTCTTGAGG GTGCTTTCAG AACTCGAAAG

5641 CCCTCACTGA ACACCGTCAA TGTGATCGGG TCCTCCATGG GCTCTGGCGG GGTGTTTACC

5701 ATCGACGGGA AAGTCAAGTG CGTAACTGCC GCACATGTCC TTACGGGCAA TTCAGCTCGG

5761 GTTTCCGGGG TCGGCTTCAA TCAAATGCTT GACTTTGACG TAAAGGGAGA TTTTGCTATA

5821 GCTGATTGCC CGAATTGGCA AGGGGCTGCC CCCAAGACCC AATTCTGCAC GGATGGATGG

5881 ACTGGCCGTG CCTATTGGCT AACATCCTCT GGCGTCGAAC CCGGCGTCAT TGGAAAAGGA

5941 TTCGCCTTCT GCTTCACCGC ATGTGGCGAT TCCGGGTCCC CAGTGATCAC CGAGGCCGGT

6001 GAGCTTGTCG GCGTTCACAC GGGATCGAAT AAACAAGGGG GGGGCATTGT TACGCGCCCC

6061 TCAGGCCAGT TTTGTAATGT GGCACCCATC AAGCTAAGCG AATTAAGTGA ATTCTTTGCT

6121 GGGCCTAAGG TCCCGCTCGG TGATGTGAAG GTCGGCAGCC ACATAATTAT AGACATAAGC

6181 GAGGTGCCTT CAGATCTTTG TGCCTTGCTT GCTGCCAAAC CTGAACTGGA AGGAGGCCTC

6241 TCCACCGTCC AACTTCTTTG TGTGTTTTTT CTCCTGTGGA GAATGATGGG ACATGCCTGG

6301 ACGCCCTTGG TTGCTGTGAG TTTCTTTATT CTGAATGAGG TTCTCCCTGC CGTCCTGGTC

6361 CGGAGTGTTT TCTCCTTTGG AATGTTTGTG CTATCCTGGC TCACGCCATG GTCTGCGCAA

6421 GTTCTGATGA TCAGGCTTCT GACAGCAGCT CTTAACAGGA ACAGATGGTC ACTTGCCTTT

6481 TTCAGCCTCG GTGCAGTGAC CGGTTTTGTC GCAGATCTTG CGGCCACTCA GGGGCATCCG

6541 TTGCAGGCAG TGATGAATTT GAGCACCTAT GCATTCCTGC CTCGGATGAT GGTTGTGACC

6601 TCACCAGTCC CAGTGATCAC GTGTGGTGTC GTGCACCTAC TTGCCATCAT TTTGTACTTG

6661 TTTAAGTACC GTGGCCTGCA CCATATCCTT GTTGGCGATG GAGTGTTCTC TGCGGCTTTC

6721 TTCTTGAGAT ACTTTGCCGA GGGAAAGTTG AGGGAAGGGG TGTCGCAATC CTGCGGAATG

6781 AATCATGAGT CTCTGACTGG TGCCCTCGCT ATGAGACTCA ATGACGAGGA CTTGGATTTC

6841 CTTATGAAAT GGACTGATTT TAAGTGCTTT GTTTCTGCGT CCAACATGAG GAATGCAGCG

6901 GGTCAATTTA TCGAGGCTGC CTATGCTAAA GCACTTAGAG TAGAACTGGC CCAGTTGGTG

-continued

6961 CAGGTTGATA AAGTTCGAGG TACTTTGGCC AAACTTGAAG CTTTTGCTGA TACCGTGGCA

7021 CCTCAACTCT CGCCCGGTGA CATTGTTGTC GCTCTCGGCC ACACGCCTGT TGGCAGTATC

7081 TTCGACCTAA AGGTTGGTAG CACCAAGCAT ACCCTCCAAG CCATTGAGAC CAGAGTCCTT

7141 GCTGGGTCCA AAATGACCGT GGCGCGCGTC GTCGACCCGA CCCCCACGCC CCCGCCCGCA

7201 CCCGTGCCCA TCCCCCTCCC ACCGAAAGTT CTGGAGAATG GCCCCAACGC TTGGGGGGAT

7261 GAGGACCGTT TGAATAAGAA GAAGAGGCGC AGGATGGAAG CCCTCGGCAT CTATGTTATG

7321 GGCGGGAAAA AGTACCAGAA ATTTTGGGAC AAGAATTCCG GTGATGTGTT TTATGAGGAG

7381 GTCCATAATA ACACAGATGA TTGGGAGTGT CTCAGAGTTG GCGACCCTGC CGACTTTGAC

7441 CCTGAGAAGG GAACTCTGTG TGGACATGTC ACCATTGAAA ACAAGGCTTA CCATGTTTAC

7501 ACCTCCCCAT CTGGTAAGAA GTTCTTGGTC CCCGTCAACC CAGAGAATGG AAGAGTTCAA

7561 TGGGAAGCTG CAAAGCTTTC CGTGGAGCAG GCCCTAGGTA TGATGAATGT CGACGGCGAA

7621 CTGACTGCCA AAGAACTGGA GAAACTGAAA AGAATAATTG ACAAACTCCA GGGCCTGACT

7681 AAGGAGCAGT GTTTAAACTG CTAGCCGCTA GCGACTTGAC CCGCTGTGGT CGCGGCGGCT

7741 TGGTTGTTAC TGAAACAGCG GTAAAAATAG TCAAATTTCA CAACCGGACC TTCACCCTGG

7801 GACCTGTGAA TTTAAAAGTG GCCAGTGAGG TTGAGCTAAA AGACGCGGTT GAGCACAACC

7861 AACACCCGGT TGCGAGACCG ATCGATGGTG GAGTTGTGCT CCTGCGTTCC GCGGTTCCTT

7921 CGCTTATAGA CGTCTTGATC TCCGGTGCTG ATGCATCTCC CAAGTTACTT GCCCATCACG

7981 GGCCGGGAAA CACTGGGATC GATGGCACGC TCTGGGATTT TGAGTCCGAA GCCACTAAAG

8041 AGGAAGTCGC ACTCAGTGCG CAAATAATAC AGGCTTGTGA CATTAGGCGC GGCGACGCTC

8101 CTGAAATTGG TCTCCCTTAC AAGCTGTACC CTGTTAGGGG TAACCCTGAG CGGGTGAAAG

8161 GAGTTCTGCA GAATACAAGG TTTGGAGACA TACCTTACAA AACCCCCAGT GACACTGGAA

8221 GCCCAGTGCA CGCGGCTGCC TGCCTTACGC CCAACGCCAC TCCGGTGACT GATGGGCGCT

8281 CCGTCTTGGC CACGACCATG CCCCCCGGGT TTGAGTTATA TGTACCGACC ATACCTGCGT

8341 CTGTCCTTGA TTACCTTGAC TCTAGGCCTG ACTGCCCTAA ACAGCTGACA GAGCACGGCT

8401 GCGAAGATGC CGCACTGAAA GACCTCTCCA AATATGACTT GTCCACCCAA GGCTTTGTTT

8461 TACCTGGAGT TCTTCGCCTT GTGCGGAAAT ACCTGTTTGC CCATGTAGGT AAGTGCCCAC

8521 CCGTTCATCG GCCTTCTACT TACCCTGCTA AGAATTCTAT GGCTGGAATA AATGGGAATA

8581 GGTTCCCAAC CAAGGACATT CAGAGCGTCC CTGAAATCGA CGTTCTGTGC GCACAGGCTG

8641 TGCGAGAAAA CTGGCAAACT GTCACCCCTT GCACTCTTAA GAAACAGTAT TGCGGGAAGA

8701 AGAAGACTAG GACCATACTC GGCACCAATA ACTTCATCGC ACTAGCCCAC CGAGCAGTGT

8761 TGAGTGGTGT TACCCAGGGC TTCATGAAAA AGGCGTTTAA CTCGCCCATC GCCCTCGGAA

8821 AGAACAAGTT TAAGGAGCTA CAGACTCCGG TCCTGGGCAG GTGCCTTGAA GCTGATCTCG

8881 CATCCTGCGA TCGATCCACG CCTGCAATTG TCCGCTGGTT TGCCGCCAAC CTTCTTTATG

8941 AACTTGCCTG TGCTGAAGAG CATCTACCGT CGTACGTGCT GAACTGCTGC CACGACTTAC

9001 TGGTCACGCA GTCCGGCGCA GTGACTAAGA GAGGTGGCCT GTCGTCTGGC GACCCGATCA

9061 CCTCTGTGTC TAACACCATT TATAGTTTGG TGATCTATGC ACAGCATATG GTGCTTAGTT

9121 ACTTCAAAAG TGGTCACCCC CATGGCCTTC TGTTCTTACA AGACCAGCTA AAGTTTGAGG

9181 ACATGCTCAA GGTTCAACCC CTGATCGTCT ATTCGGACGA CCTCGTGCTG TATGCCGAGT

9241 CTCCCACCAT GCCAAACTAT CACTGGTGGG TTGAACATCT GAATTTGATG CTGGGGTTTC

9301 AGACGGACCC AAAGAAGACA GCAATAACAG ACTCGCCATC ATTTCTAGGC TGTAGAATAA

9361 TAAATGGGCG CCAGCTAGTC CCCAACCGTG ACAGGATCCT CGCGGCCCTC GCCTATCACA

-continued

9421 TGAAGGCGAG TAATGTTTCT GAATACTATG CCTCAGCGGC TGCAATACTC ATGGACAGCT
9481 GTGCTTGTTT GGAGTATGAT CCTGAATGGT TTGAAGAACT TGTAGTTGGA ATAGCGCAGT
9541 GCGCCCGCAA GGACGGCTAC AGCTTTCCCG GCACGCCGTT CTTCATGTCC ATGTGGGAAA
9601 AACTCAGGTC CAATTATGAG GGGAAGAAGT CGAGAGTGTG CGGGTACTGC GGGGCCCCGG
9661 CCCCGTACGC TACTGCCTGT GGCCTCGACG TCTGCATTTA CCACACCCAC TTCCACCAGC
9721 ATTGTCCAGT CACAATCTGG TGTGGCCATC CAGCGGGTTC TGGTTCTTGT AGTGAGTGCA
9781 AATCCCCTGT AGGGAAAGGC ACAAGCCCTT TAGACGAGGT GCTGGAACAA GTCCCGTATA
9841 AGCCCCCACG GACCGTTATC ATGCATGTGG AGCAGGGTCT CACCCCCCTT GATCCAGGTA
9901 GATACCAAAC TCGCCGCGGA CTGGTCTCTG TCAGGCGTGG AATTAGGGGA AATGAAGTTG
9961 AACTACCAGA CGGTGATTAT GCTAGCACCG CCTTGCTCCC TACCTGCAAA GAGATCAACA
10021 TGGTCGCTGT CGCTTCCAAT GTATTGCGCA GCAGGTTCAT CATCGGCCCA CCCGGTGCTG
10081 GGAAAACATA CTGGCTCCTT CAACAGGTCC AGGATGGTGA TGTTATTTAC ACACCAACTC
10141 ACCAGACCAT GCTTGACATG ATTAGGGCTT TGGGGACGTG CCGGTTCAAC GTCCCGGCAG
10201 GCACAACGCT GCAATTCCCC GTCCCCTCCC GCACCGGTCC GTGGGTTCGC ATCCTAGCCG
10261 GCGGTTGGTG TCCTGGCAAG AATTCCTTCC TAGATGAAGC AGCGTATTGC AACCACCTTG
10321 ATGTTTTGAG GCTTCTCAGT AAAACTACCC TCACCTGTCT AGGAGACTTC AAGCAACTCC
10381 ACCCAGTGGG TTTTGATTCT CATTGCTATG TTTTTGACAT CATGCCTCAA ACTCAACTGA
10441 AGACCATCTG GAGGTTTGGA CAGAATATCT GTGATGCCAT TCAGCCAGAT TACAGGGACA
10501 AACTCATGTC CATGGTCAAC ACAACCCGTG TGACCTACGT GGAAAAACCT GTCAGGTATG
10561 GGCAGGTCCT CACCCCCTAC CACAGGGACC GAGAGGACGA CGCCATCACT ATTGACTCCA
10621 GTCAAGGCGC CACATTCGAT GTGGTTACGT TGCATTTGCC CACTAAAGAT TCACTCAACA
10681 GGCAAAGAGC CCTTGTTGCC ATCACCAGGG CAAGACACGC TATCTTTGCG TATGACCCAC
10741 ACAGGCAGCT GCAGGGCTTA TTTGATCTTC CTGCAAAAGG CACACCCGTC AACCTCGCAG
10801 TGCACCGCGA CGGGCAGCTG ATCGTGCTGG ATAGAAATAA CAAAGAATGC ACGGTTGCTC
10861 AGGCTCTAGG CAACGGGGAT AAATTTAGGG CCACAGATAA GCGTGTTGTA GATTCTCTCC
10921 GCGCCATTTG TGCTGATCTA GAAGGGTCGA GCTCTCCGCT CCCCAAGGTC GCACACAACT
10981 TGGGATTTTA TTTCTCACCT GATTTAACAC AGTTTGCTAA ACTCCCAGTA GAACTTGCAC
11041 CTCACTGGCC CGTGGTGACA ACCCAGAACA ATGAAAAGTG GCCAGATCGG CTGGTTGCCA
11101 GCCTTCGCCC TATCCATAAA TACAGCCGCG CGTGCATCGG TGCCGGCTAT ATGGTGGGCC
11161 CTTCGGTGTT TCTAGGCACT CCTGGGGTCG TGTCATACTA TCTCACAAAA TTTGTTAAGG
11221 GCGAGGCTCA ATTGCTTCCA GAGACGGTTT TCAGCACCGG CCGAATTGAG GTAGACTGCC
11281 GGGAATATCT TGATGATCGG GAGCGAGAAG TTGCTGCGTC CCTCCCACAC GCTTTCATTG
11341 GCGACGTCAA AGGCACTACC GTTGGAGGAT GTCATCATGT CACCTCCAGA TACCTCCCGC
11401 GCGTCCTTCC CAAGGAATCA GTTGCGGTAG TCGGGGTTTC AAGCCCCGGA AAAGCCGCGA
11461 AAGCATTGTG CACACTGACA GATGTGTACC TCCCAGATCT TGAAGCCTAT CTCCACCCGG
11521 AGACCCAGTC CAAGTGCTGG AAAATGATGT TGGACTTCAA AGAAGTTCGA CTAATGGTCT
11581 GGAAAGACAA AACAGCCTAT TTCCAACTTG AAGGTCGCTA TTTCACCTGG TATCAGCTTG
11641 CCAGCTATGC CTCGTACATC CGTGTTCCTG TCAACTCTAC GGTGTACTTG GACCCCTGCA
11701 TGGGCCCCGC CCTTTGCAAC AGGAGAGTCG TCGGGTCCAC CCATTGGGGG GCTGACCTCG
11761 CGGTCACCCC TTATGATTAC GGCGCTAAAA TTATCCTGTC TAGCGCGTAC CATGGTGAAA

-continued

11821 TGCCCCCCGG ATACAAAATT CTGGCGTGCG CGGAGTTCTC GTTGGATGAC CCAGTTAAGT

11881 ACAAACATAC CTGGGGGTTT GAATCGGATA CAGCGTATCT GTATGAGTTC ACCGGAAACG

11941 GTGAGGACTG GGAGGATTAC AATGATGCGT TTCGTGCGCG CCAGGAAGGG AAAATTTACA

12001 AGGCCACTGC CACCAGCTTG AAGTTTCATT TTCCCCCGGG CCCTGTCATT GAACCAACTT

12061 TAGGCCTGAA TTGAAATGAA ATGGGGTCCA TGCAAAGCCT TTTTCACAAA ATTGGCCAAC

12121 TTTTTGTGGA TGCTTTCACG GAGTTCTTGG TGTCCATTGT TGATATCATC ATATTTTTGG

12181 CCATTTTGTT TGGCTTCACC ATCGCCGGTT GGCTGGTGGT CTTTTGCATC AGATTGGTTT

12241 GCTCCGCGAT ACTCCGTACG CGCTCTGCCA TTCACTCTGA GCAATTACAG AAGATCTTAT

12301 GAGGCCTTTC TTTCCCAGTG CCAAGTGGAC ATTCCCACCT GGGGAACTAA ACATCCTTTG

12361 GGGATTCTCT GGCACCATAA GGTGTCAACC CTGATTGATG AAATGGTGTC GCGTCGAATG

12421 TACCGCATCA TGGAAAAATC AGGGCAGGCT GCCTGGAAAC AGGTGGTGAG CGAGGCTACG

12481 CTGTCTCGCA TTAGTAGTTT GGATGTGGTG GCTCATTTTC AGCATCTAGC CGCCATTGAA

12541 GCCGAGACCT GTAAATATTT GGCCTCCCGG CTGCCCATGC TACACAACCT GCGCATGACA

12601 GGTTCAAATG TAACCATAGT GTATAATAGC ACTTTGAATC AGGTGTTTGC TATTTTTCCA

12661 ACCTCTGGTT CCCGGCCAAA GCTTCATGAT TTTCAGCAAT GGTTAATAGC TGTACATTCC

12721 TCCATATTTT CCTCTGTTGC AGCTTCTTGT ACTCTTTTTG TTGTGCTGTG GTTGCGTGTT

12781 CCAATACTAC GTACTGTTTT TGGTTTCCGC TGGTTAGGGG CAATTTTTCT TTCGAACTCA

12841 CAGTGAATTA CACGGTGTGT CCACCTTGCC TCACCCGGCA AGCAGCCGCA GAGATCTACG

12901 AACCCGGTAG GTCTCTTTGG TGCAGGATAG GGTATGACCG ATGTGAGGAG GATGATCATG

12961 ACGAGCTAGG GTTTATGGTA CCGCCTGGCC TCTCCAGCGA AGGCCACTTG ACTAGTGTTT

13021 ACGCCTGGTT GGCGTTCTTG TCCTTCAGCT ACACGGCCCA GTTCCATCCC GAGATATTCG

13081 GGATAGGGAA TGTGAGTCGA GTTTATGTTG ACATCAAACA TCAACTCATC TGCGCCGAAC

13141 ATGACGGGCA GAACACCACC TTGCCTCGTC ATGACAACAT TTCAGCCGTG TTTCAGACCT

13201 ATTACCAACA TCAAGTCGAT GGCGGCAATT GGTTTCACCT AGAATGGCTT CGTCCCTTCT

13261 TTTCCTCGTG GCTGGTTTTA AATGTCTCTT GGTTTCTCAG GCGTTCGCCT GCAAACCATG

13321 TTTCAGTTCG AGTCTCGCAG ATATTGAGAC CAACACCACC GCAGCGGCAA GCTTTGCTGT

13381 CCTCCAAGAC ATCAGTTGCC TTAGGCATCG CGACTCGGCC TCTGAGGCGA TTCGCAAAAT

13441 CCCTCAGTGC CGTACGGCGA TAGGGACACC CGTGTATATT ACTATCACAG CCAATGTGAC

13501 AGATGAGAAT TATTTACATT CTTCTGATCT CCTCATGCTT TCTTCTTGCC TTTTCTATGC

13561 TTCTGAGATG AGTGAAAAGG GATTTAAGGT GGTATTTGGC AATGTGTCAG GCATCGTGGC

13621 TGTGTGTGTC AATTTTACCA GCTACGTCCA ACATGTCAAG GAGTTCACCC AACGCTCCCT

13681 GGTGGTCGAC CATGTGCGGT TGCTCCATTT CATGACACCT GAGACCATGA GGTGGGCAAC

13741 TGTTTTAGCC TGTCTTGTTG CCATTCTGTT GGCAATTTGA ATGTTTAAGT ATGTTGGAGA

13801 AATGCTTGAC CGCGGGCTGT TGCTCGCAAT TGCTTTCTTT GTGGTGTATC GTGCCGTTCT

13861 GTTTTGCTGT GCTCGCCAAC GCCAGCAGCG ACAGCAGCTC CCATCTACAG CTGATTTACA

13921 ACTTGACGCT ATGTGAGCTG AATGGCACAG ATTGGCTAGC TGACAAATTT GATTGGGCAG

13981 CGGAGAGTTT TGTCATCTTT CCCGTTTTGA CTCACATTGT CTCCTATGGT GCCCTCACTA

14041 CTAGCCATTT CCTTGACACG GTCGCTTTAG CCACTGTGTC TACCGCCGGG TTTGTTCACG

14101 GGCGGTATGT CCTAAGTAGC ATCTACGCGG TCTGTGCCCT GGCTGCGTTG ACTTGCTTCG

14161 TCATTAGGTT TGCAAAGAAT TGCATGTCCT GGCGCTACGC GTGTACCAGA TATACCAACT

14221 TTCTTCTGGA CACTAAGGGC AGACTCTATC GTTGGCGGTC GCCTGTCATC ATAGAGAAAA

-continued

```
14281 GGGGCAAAGT TGAGGTCGAA GGTCATCTGA TCGACCTCAA AAGAGTTGTG CTTGATGGTT
14341 CCGTGGCAAC CCCTATAACC AGAGTTTCAG CGGAACAATG GGGTCGTCCT TAGATGACTT
14401 CTGTCATGAT AGCACGGCTC CAGAAAAGGT GCTTTTGGCG TTTTCTATTA CCTACACGCC
14461 AGTGATGATA TATGCCCTAA AGGTGAGTCG CGGCCGACTG CTAGGGCTTC TGCACCTTTT
14521 GATCTTCCTG AATTGTGCTT TCACCTTCGG GTACATGACT TTCGCGCACT TTCAGAGTAC
14581 AAATAAGGTC GCGCTCACTA TGGGAGCAGT AGTTGCACTC CTTTGGGGGG TGTACTCAGC
14641 CATAGAAACC TGGAAATTCA TCACCTCCAG ATGCCGTTTG TGCTTGCTAG GCCGCAAGTA
14701 CATTCTGGCC CCTGCCCACC ACGTTGAAAG TGCCGCAGGC TTTCATCCGA TTGCGGCAAA
14761 TGATAACCAC GCATTTGTCG TCCGGCGTCC CGGCTCCACT ACGGTCAACG GCACATTGGT
14821 GCCCGGGTTA AAAAGCCTCG TGTTGGGTGG CAGAAAAGCT GTTAAACAGG GAGTGGTAAA
14881 CCTTGTCAAA TATGCCAAAT AACAACGGCA AGCAGCAGAA GAGAAAGAAG GGGGATGGCC
14941 AGCCAGTCAA TCAGCTGTGC CAGATGCTGG GTAAGATCAT CGCTCAGCAA AACCAGTCCA
15001 GAGGCAAGGG ACCGGGAAAG AAAAATAAGA AGAAAAACCC GGAGAAGCCC CATTTTCCTC
15061 TAGCGACTGA AGATGATGTC AGACATCACT TTACCCCTAG TGAGCGGCAA TTGTGTCTGT
15121 CGTCAATCCA GACCGCCTTT AATCAAGGCG CTGGGACTTG CACCCTGTCA GATTCAGGGA
15181 GGATAAGTTA CACTGTGGAG TTTAGTTTGC CTACGCATCA TACTGTGCGC CTGATCCGCG
15241 TCACAGCATC ACCCTCAGCA TGATGGGCTG GCATTCTTGA GACATCTCAG TGTTTGAATT
15301 GGAAGAATGT GTGGTGAATG GCACTGATTG ACATTGTGCC TCTAAGTCAC CTATTCAATT
15361 AGGGCGACCG TGTGGGGGTG AGATTTAATT GGCGAGAACC ATGCGGCCGA AATTAAAAAA
15421 AAAAAAAAAA AAAAAAAAAA AAAA
```

The cDNA consensus sequence of PRRS strain SD 98-163 at P83 has been assigned GenBank Accession number KU131563 (SEQ. ID. NO:3). The cDNA consensus sequence designated SEQ. ID. NO: 3 is:

```
  1 ATGACGTATA GGTGTTGGCT CTATGCCACG GCATTTGTAT TGTCAGGAGC TGTGACCATT
 61 GGCACAGCCC AAAACTTGCT GCACGGAAAA CGCCCTTCCG TGACAGCCTT CTTCAGGGGA
121 GCTTAGGGGT CTGTCCCTAA CACCTTGCTT CTGGAGTTGC ACTGCTTTAC GGTCTCTCCA
181 ACCCTTTAAC CATGTCTGGG ATACTTGATC GGTGCACGTG CACCCCCAAT GCCAGGGTGT
241 TTATGGCGGA GGGCCAAGTC TACTGCACAC GATGTCTCAG TGCACGGTCT CTCCTTCCTC
301 TGAATCTCCA AGTTTCTGAG CTTGGAGTGC TGGGCCTATT TTATAGGCCC GAAGAGCCAC
361 TCCGGTGGAC GTTGCCACGT GCATACCCCA CTGTCGAGTG CTCCCCCGCC GGGGCCTGCT
421 GGCTTTCTGC GATCTTTCCA ATTGCACGAA TGACCAGTGG GAACCTGAAC TTTCAACAAA
481 GAATGGTGCG GGTCGCAGCT GAGATTTACA GAGTCGGTCA GCTCACCCCC ACAGTCTTGA
541 AGAATCTACA AGTTTATGAA CGGGGTTGCC GCTGGTACCC CATTGTCGGA CCTGTCCCTG
601 GAGTGGCCGT TTTCGCCAAT TCCCTACATG TGAGTGACAA ACCTTTTCCG GGAGCAACTC
661 ATGTGTTAAC TAATCTACCG CTCCCGCAGA GGCCCAAGCC TGAAGACTTT TGTCCTTTTG
721 AGTGTGCTAT GGCTGACATC TATGACATTG GTCATGACGC CGTCATGTAT GTGGCCGGAG
781 GGAAAGTCTC CTGGGCCCCT CGTGGCGGGG ATGAAGGGAA ATTTGAAACT GTCCCCGAGG
841 AGTTGAAGTT AATTGCGAAC CGACTTCACA TCTCCTTCCC GCCCCACCAC GTAGTGGACA
901 TATCTAAGTT TGCCTTTATA GCCCCCGGGA GTGGTGTCTC CATGCGGGTT GAGTGCCAAC
961 ATGGCTGCCT CCCCGCTGAT ACTGTTCCTG GAGGGAACTG CTGGTGGCGC TTGTTCGACT
```

-continued

```
1021 CGCTCCCACC GGAAGTTCAG AATAAAGAAA TTCGCTATGC TAACCAATTT GGTTATCAAA
1081 CCAAGCATGG TGTCTCTGGC AAGTACCTAC AGCGGAGGCT GCAAGTTAAT GGTCTCCGAG
1141 CAGTGACTGA TACAAGTGGG CCTATCGTCG TACAGTATTT CTCTGTTAAG GAGAGTTGGA
1201 TCCGCCACTT AAGGCTGGCG GAAGAACCTA GCCTCCCTGG GTTTGAGGAC CTCCTCAGAA
1261 TAAGGGTTGA GCCCAATACG TCACCATTGG TTGGCAAGGA TGTGAAAATC TTCCGGTTTG
1321 GCAATCACAA ATGGTACGGC GCTGGAAAGA GAGCAAGGAA ATCACGCTCT GGTGCGACTG
1381 CCACGGTCGC TCACCGCGCT TTACCCGTTC GTGAAACCCT GCAGGCTAAG AGGCGCGAGG
1441 TTGCCAGCGC CAACAGGGCT GAGCATATCA AGCACTATTA TCCGCCAGCC GACGGAAACT
1501 GTGGTTGGCA CTGCATTTCC GCTATTGTCA ACCGGATGGT GAATTCTAAA TTTGAAACTG
1561 CTCTTCCCGA GAGAGCGAGA CCTTCTGATG ACTGGGCTAC TGACGAGGAC CTTGTGAATA
1621 CCATCCAAAT CCTCAGACTC CCTGCGGCCT TGGACAGGGA CGGTGCTTGT GTTAGCGCCA
1681 AGTACGTGCT TAAACTAGAA GGCGAGCATT GGACTGTCTC TGTGACCCCT GGGATGTCCC
1741 CTTCTTTGCT CCCCCTTGAA TGTGTTCAGG GCTGTTGTGA ACATAAGAAC GGCCTTGGTC
1801 CCCCAGATGC GGTCGAAAGT TTTGGATTTG ACCCTGCCTG CCTTGACCGA CTGGCTGAGG
1861 TAATGCACTT GCCTAGTAGT GTCATCCCAG CTGCTCTGGC CGAAATGTCC GGTGACCCCA
1921 ATTGTCCGGC ATCCCCGGTC ACCACTGTGT GGACTGTTTC ACAATTCTTT GCCCGCCACA
1981 GAGGAGGAGA GCACCCTGAT CAGGTGCGCT TAGGAAAGAT CATCAGCCTT TGTCAAGTTG
2041 TTGAGGAATG CTGTTGCCAT CAGAATAAAA CCAACCGGGC CACCCCGGAA GAGGTCGCGG
2101 CAAAGATTAA TCAGTACCTC CATGGTGCAA CAAGTCTTGA AGACTGCTTG ACTAGGCTTG
2161 AGAGGGCTTG CCCGCCGAGT GCTGCGGACA CCTTCTTTGA TTGGAACGTT GTGCTCCCTG
2221 GGGTTGAGGC TGCAACTCCG CCACCCCCTC CACCAAGAGT TCAGCCTCGA AAAACAAAGT
2281 CTGTCAAGAG CTTGCCGGGA AACAATCCTG TCCCCGCTCC ACGCAGGAAG GTTAGATCTG
2341 ACTGTGGCAG CCCGATTTTG ACGGGCGACA ATGATCTTTC GACGCCATCC GAGCCGATGA
2401 CATCTCTGAA TGAGCCTGCG CTTATGCCTG CGTTGCAATG TATCTCTAGG CCAGTGACAT
2461 CTTTGAGTGT GCCGGCCCCA GTTCCTGCAC CGCGTAGAGC TGTGTCCCGA CCGGTGACGC
2521 CCTTGAGTGA GCCAGTTTTT TTGTCTGCAC CGCGACACAA ATTTCAGCAG GTGAAAGAAG
2581 CGAATCTGGT GGCAACAACG CTGATGTGCC AGGACGAACC TCTAGATTTG TCTGCATCCT
2641 CACAGACTGA ATATGAAGCT TCCCCCCCAG CACCACTGCA GAACATGGGT ATTCTGGAGG
2701 TGGGGGGACA AGAAGCTGTG GAAGTTCTGA GTGAAATCTC GGATACACTG AATGACACCA
2761 ACCCTGCACC TGTGTCATCA AGCAGCTCCC TGTCAAGTGT TAAGATCACA CGCCCAAAAT
2821 ACTCAGCTCA AGCCATCATT GATTCGGGCG GGCCCTGCAG TGGGCACCTC CGAAGGGGAA
2881 AAGAAGCATG CCTCAGCCTC ATGCGTGAGG CTTGTGATGC GGCTAAGCTT AGTGACCCTG
2941 CCACGCAAGA ATGGCTTTCT CGCATGTGGG ATAGGGTTGA CATGCTGACC TGGCGCAACA
3001 CGTCTGCCTA CCAGGCGTTT CGCATCTTAG ATGGTAGGTT TGAGTTTCTC CCAAAGATGA
3061 TACTCGAGAC ACCGCCGCCC TACCCGTGTG GGTTTGTGAT GCTGCCTCAC ACGCCTGCAC
3121 CTTCCGTGAG TGCAGAGAGC GACCTTACCA TTGGTTCAGT CGCCACTGAA GATGTTCCAC
3181 GCATTCTCGG GAAAATAGAA AACGCCGGCG AGACGCCCAA CCAGGGGCTC TTGGCACCCT
3241 TCGGGGAAGA ACCGGTGTGC GACCAACCTG TCAAAGACTC CCGGATGTTG TCGCGGGGGT
3301 TTGACGAGAG CACGACGGCT CCGTCCGCAG GTACAGGTGG CGCTGACTTA CCCACTGATT
3361 TGCCACCTTC AGATGGTGTG GATGCGGACG GGGTGGGGCT GTTACGGACG GTAAGAAAGA
3421 AAGCTGAAAG GCTCTTCGAC CAATTGAGCC GTCAGGTTTT TAACCTCGTC TCCCATCTCC
```

-continued

```
3481 CTGTTTTCTT CTCACACCTC TTCAAATCTG ACAGTGGTTA TTCTCCGGGT GATTGGGGTT
3541 TTGCAGCTTT TACTTTATTT TGCCTCTTTT TATGTTACAG CTACCCATTC TTCGGTTTCG
3601 CTCCCCTCTT GGGTGTGTTT TCTGGGTCTT CTCGGCGCGT GCGCATGGGG GTTTTTGGCT
3661 GCTGGTTGGC TTTTGCTGTT GGCCTGTTCA AGCCTGTGTC CGACCCAGTC GGCACTGCTT
3721 GTGAGTTTGA CTCGCCAGAG TGTAGGAACG TCCTTCATTC TTTTGAGCTT CTCAAACCTT
3781 GGGACCCTGT CCGCAGCCTT GTTGTGGGCC CCGTCGGTCT CGGTCTTGCC ATTCTTGGCA
3841 GGTTACTGGG CGGGGCACGC TACATCTGGC ATTTTTTCCT TAGGCTTGGC ATTGTTGCAG
3901 ATTGCTTCTT GGCTGGAGCT TATGTGCTTT CTCAAGGTAG GTGTAAAAAA TGCTGGGGAT
3961 CTTGTGTAAG AACTGCTCCT AATGAAATCG CCTTCAACGT GTTCCCTTTT ACGCGTGCGA
4021 CCAGGTCGTC ACTCATCGAC CTGTGCGATC GGTTTTGTGC GCCAAAAGGC ATGGACCCCA
4081 TTTTCCTCGC TACTGGGTGG CGTGGGTGCT GGACCGGCCG GAGTCCCATT GAGCAACCCT
4141 CTGAAAAACC TATCGCGTTC GCCCAGTTGG ATGAGAAGAG GATTACGGCT AGAACTGTGG
4201 TCGTTCAGCC TTATGATCCT AACCAAGCCG TAAAGTGCTT GCGGGTGTTA CAGGCGGGTG
4261 GGGCGATGGT GGCCGAGGCA GTCCCAAAAG TGGTCAAGGT TTCCGCCATT CCATTCCGAG
4321 CTCCCTTTTT TCCCACCGGA GTGAAGGTTG ATCCTGAGTG CAGGATCGTG GTCGACCCCG
4381 ACACTTTTAC TACAGCTCTC CGGTCTGGTT ACTCCACCAC AAACCTCGTC CTTGGTGTGG
4441 GGGACTTTGC CCAACTGAAT GGATTAAAAA TCAGGCAAAT TTCCAAGTCT TCGGGGGGAG
4501 GCCCACACCT CATTGCTGCC CTGCATGTTG CTTGCTCGAT GGCGTTGCAC ATGCTTGCTG
4561 GGGTTTATGT AACTGCAGTG GGGTCTTGCG GTACCGGCAC CAATGATCCG TGGTGCACTA
4621 ACCCATTCGC CGTCCCTGGC TACGGACCTG GCTCTCTCTG CACGTCCAGA TTGTGCATCT
4681 CCCAACATGG CCTTACCCTG CCCTTGACAG CACTTGTGGC AGGATTCGGT CTTCAGGAAA
4741 TTGCCTTAGT CGTTTTGATT TTTGTTTCCA TCGGAGGCAT GGCTCATAGG TTGAGTTGCA
4801 AGGCTGATAT GCTGTGCGTC TTACTTGCAA TCGCAAGCTA TGTTTGGGTA CCCCTTACCT
4861 GGTTGCTCTG TGTGTTTCCT TGCTGGTTGC GCTGGTTCTC TTTGCACCCT CTCACCATCC
4921 TATGGTTGGT GTTTTTCTTA ATTTCCGTAA ATATGCCTTC GGGAATCTTG GCCGTGGTGT
4981 TATTGGTTGC TCTTTGGCTT CTAGGCCGTT ATACTAATGT TGTTGGTCTT GTTACCCCCT
5041 ATGATATTCA TCATCACACC AGTGGCCCCC GCGGTGTTGC CGCCTTGGCT ACCGCACCGG
5101 ATGGGACTTA TTTGGCCGCT GTCCGCCGCG CTGCGTTGAC TGGCCGCACC GTGTTGTTTA
5161 CCCCGTCCCA GCTTGGGTCC CTCCTTGAGG GCGCTTTCAG AACTCGAAAG CCCTCACTGA
5221 ACACCGTCAA TGTGGTCGGG TCCTCTATGG GCTCTGGCGG AGTGTTCACT ATCGATGGGA
5281 AAATTAAGTG CGTGACTGCC GCACATGTCC TTACGGGTAA TTCAGCTAGG GTTTCCGGGG
5341 TTGGCTTCAA TCAAATGCTT GACTTTGATG TAAAAGGGGA CTTCGCCATA GCTGATTGCC
5401 CGAATTGGCA AGGGGCTGCT CCTAAGACCC AATTCTGCGA GGATGGGTGG ACTGGCCGTG
5461 CCTATTGGCT GACATCCTCT GGTGTCGAAC CCGGCGTCAT TGGGAATGGA TTCGCCTTCT
5521 GCTTCACCGC GTGCGGCGAT TCTGGGTCCC CAGTGATCAC CGAAGCCGGT GAGCTTGTCG
5581 GCGTTCACAC AGGATCAAAT AAACAAGGAG GAGGCATTGT TACGCGCCCC TCAGGCCAGT
5641 TTTGTAATGT GGCACCCATC AAGCTGAGCG AATTAAGTGA GTTCTTTGCT GGACCTAAGG
5701 TCCCGCTCGG TGATGTGAAG GTTGGCAGCC ACATAATTAA AGATATATGC GAGGTACCTT
5761 CAGACCTTTG CGCCTTGCTT GCCGCCAAAC CCGAATTGGA AGGAGGCCTC TCCACCGTCC
5821 AACTTTTATG TGTGTTTTTC CTCCTGTGGA GAATGATGGG ACATGCCTGG ACACCCTTGG
```

-continued

5881 TTGCTGTGGG TTTTTTTATC TTGAATGAAG TCCTCCCAGC TGTCCTGGTC CGGAGTGTTT

5941 TCTCCTTTGG AATGTTTGTG CTATCTTGGC TCACACCATG GTCTGCGCAA GTTCTGATGA

6001 TCAGGCTTCT AACAGCAGCT CTCAACAGGA ACAGATTGTC ACTCGCCTTT TACAGCCTTG

6061 GTGCGGCGAC CGGCTTTGTC GCAGATCTGG CGGCAACTCA AGGGCATCCG TTGCAAGCAG

6121 TAATGAATTT AAGTACCTAT GCCTTCCTGC CTCGGATGAT GGTTGTGACC TCACCAGTCC

6181 CAGTTATTGC GTGTGGTGTC GTGCACCTCC TTGCCATAAT TTTGTACTTG TTTAAGTACC

6241 GCTGCCTGCA CAATGTTCTT GTTGGCGATG GAGCGTTCTC TGCGGCTTTC TTTTTGCGAT

6301 ACTTTGCCGA GGGGAAATTG AGGGAAGGGG TGTCGCAATC CTGCGGGATG AATCATGAGT

6361 CGCTGACTGG TGCCCTCGCT ATGAGACTCA ATGACGAGGA CTTGGATTTC CTTACGAAAT

6421 GGACTGATTT TAAGTGCTTT GTTTCTGCGT CCAACATGAG GAATGCGGCG GGCCAGTTCA

6481 TCGAGGCTGC CTATGCAAAA GCACTTAGAA TTGAACTTGC CCAGTTGGTG CAGGTTGATA

6541 AGGTTCGAGG TACTATGGCC AAACTTGAAG CTTTTGCTGA TACCGTGGCA CCCCAACTCT

6601 CGCCCGGTGA CATTGTTGTT GCTCTTGGCC ATACACCTGT TGGCGGTATC TTCGACCTAA

6661 AGGTTGGTAG CACCAAGCAC ACCCTCCAAT CCATTGAGAC CAGAGTCCTT GCCGGGTCCA

6721 AAATGACCGT GGCGCGTGTC GTTGACCCAA CCCCCACACC CCCACCCGCA CCCGTGCCCA

6781 TCCCCCTCCC ACCGAAAGTT CTGGAGAATG GTCCTAACGC CTGGGGGGAT GAGGATCGTT

6841 TGAACAAGAA GAAGAGGCGC AGGATGGAAG CCGTCGGCAT CTTTGTTATG GGTGGAAAGA

6901 AATACCAGAA ATTTTGGGAC AAGAATTCCG GTGATGTGTT TTATGAGGAG GTCCATGATA

6961 ACACAGACGC GTGGGAGTGC CTCAGAGTTG ACAACCCTGC CGACTTTGAC CCTGAGAAGG

7021 GAACTCTGTG TGGGCATACT ACCATTGAAG GTAAGGCTTA CAATGTCTAC GCCTCCCCAT

7081 CTGGCAAGAA GTTTCTGGTC CCCGTCAACC CAGAGAGTGG AAGAGCCCAA TGGGAAGCTG

7141 CAAAGCTTTC CGTGGAGCAG GCCCTTGGCA TGATGAATGT CGACGGTGAG CTGACAGCCA

7201 AAGAACTGGA GAAACTGAAA AGAATAATTG ACAAACTCCA GGGTCTGACT AAGGAGCAGT

7261 GTTTAAACTG TTAGCCGCCA GCGGCTTGAC CCGCTGTGGT CGCGGCGGCT TGGTTGTTAC

7321 TGAGACAGCG GTAAAAATAG TCAAATTTCA CAACCGGACC TTCACCCTAG GACCTGTGAA

7381 CTTAAAAGTG GCCAGTGAGG TTGAGCTAAA AGACGCGGTC GAGCACAACC AACACCCGGT

7441 TGCAAGACCG GTTGATGGTG GCGTTGTACT CCTGCGCCCC GCAGTTCCTT CGCTTGTAGA

7501 TGTCTTGATC TCTGGCGCTG ATGCATCCCC TAAGTTACTC GCCCGCCATG GGCCGGGAAA

7561 CACTGGGATC GATGGCACGC TTTGGGATTT TGAGACCGAA GCCACCAAAG AGGAAATTAC

7621 ACTTAGTGCG CAAATAATAC AGGCTTGTGA CATTAGGCGC GGCGACGCAC CTGAAATTGG

7681 TCTCCCTTAT AAGCTGCACC CTGTTAGGGG CAACCCTGAG CGGATAAAAG GAGTTTTACA

7741 GAATACAAGG TTTGGGGACA TACCTTACAA AACCCCCAGT GACACTGGCA GCCCAGTGCA

7801 TGCGGCTGCC TGCCTCACGC CCAATGCCAC TCCGGTGACC GATGGGCGCT CCGTCTTGGC

7861 TACGACTATG CCCTCCGGTT TTGAGTTGTA TATACCGACC ATTCCATCGT CTGTCCTTGA

7921 TTATCTTGAT TCTAGGCCTG ACTGCCCCAA ACAGTTAACA GAGCACGGCT GTGAGGATGC

7981 CGCATTGAGA GACCTCTCCA AGTATGACTT GTCCACCCAA GGCTTTGTTT TGCCTGGAGT

8041 TCTTCGCCTA GTGCGTAAGT ACCTGTTTGC TCATGTGGGT AAGTGCCCGC CCGTTCATCG

8101 GCCTTCCACT TATCCTGCCA AGAACTCTAT GGCTGGAATA AATGGGAACA GGTTTCCAAC

8161 CAAGGACATT CAGAGCATCC CTGAAATCGA CGTTCTGTGC GCACAGGCTG TGCGAGAAAA

8221 CTGGCAAACT GTTACCCCTT GCACCCTCAA GAAACAATAT TGTGGGAAGA AGAAGACTAG

8281 GACAATACTC GGCACCAATA ACTTCGTTGC GTTGGCCCAC CGGGCAGCGT TGAGTGGTGT

-continued

8341 CACCCAGGGC TTTATGAAAA AGGCGTTTAA CTCGCCCATT GCCCTCGGGA AAAACAAATT
8401 TAAAGAGCTA CAGACTCCGG TCTTAGGCAG GTGCCTTGAA GCTGATCTTG CATCCTGCGA
8461 TCGGTCCACA CCTGCAATTG TCCGCTGGTT TGCCGCCAAT CTTCTTTATG AACTTGCCTG
8521 TACTGAAGAA CATCTACCGT CGTACGTGCT GAACTGCTGC CACGACCTAC TGGTCACGCA
8581 GTCCGGCGCG GTGACTAAGA GAGGTGGCCT GTCGTCTGGC GACCCGATTA CCTCTGTGTC
8641 AAACACCATT TACAGCTTAG TGATATATGC ACAGCACATG GTGCTCAGTT ACTTTAAAAG
8701 TGGTCACCCT CACGGCCTTC TGTTTCTGCA AGACCAGCTA AAGTTTGAGG ACATGCTCAA
8761 GGTTCAACCC CTGATCGTCT ATTCGGACGA CCTCGTGCTG TATGCCGAGT CTCCCACCAT
8821 GCCAAACTAC CACTGGTGGG TTGAACATCT GAATCTTATG TTGGGTTTTC AAACGGACCC
8881 AAGGAAGACA GCCATAACAG ACTCACCATC TTTTCTAGGC TGTAGAATAA TAAATGGGCG
8941 CCAGCTAGTC CCCCACCGTG ACAGGATTCT CGCGGCCCTT GCCTACCATA TGAAAGCAAG
9001 CAATGTTTCT GAATATTACG CCTCGGCGGC TGCAATACTC ATGGACAGCT GTGCTTGTTT
9061 AGAGTATGAT CCTGAATGGT TTGAAGAGCT CGTGGTTGGG ATGGCGCAGT GCGCCCGCAA
9121 GGACGGCTAC AGTTTTCCTG GCCCGCCGTT CTTCTTGTCC ATGTGGGAAA AACTCAGGTC
9181 CAACCACGAG GGAAAGAAGT CCAGAATGTG CGGGTACTGC GGGGCCCCGG CTCCGTACGC
9241 CACTGCCTGT GGCCTCGATG TCTGTGTTTA CCACACCCAC TTCCACCAGC ATTGTCCAGT
9301 CATAATCTGG TGTGGCCATC CGGCGGGTTC TGGTTCTTGT AGTGAGTGCA AACCCCCCCT
9361 AGGGAAAGGC ACAAGCCCTC TGGATGAGGT GTTGGAACAA GTCCCGTACA AGCCTCCGCG
9421 GACTGTAATC ATGCATGTGG AGCAGGGTCT CACCCCTCTT GACCCAGGTA GATACCAAAC
9481 TCGCCGCGGA TTAGTCTCCG TTAGGCGTGG CATCAGGGGA AATGAAGTTG ACCTACCAGA
9541 CGGTGATTAT GCCAGTACCG CCCTGCTCCC TACTTGTAAA GAGATCAACA TGGTCGCTGT
9601 CGCCTCTAAT GTGTTGCGCA GCAGGTTCAT CATCGGTCCG CCCGGTGCTG GGAAAACATA
9661 CTGGCTCCTT CAACAGGTCC AGGATGGTGA TGTCATTTAC ACACCAACTC ACCAGACCAT
9721 GCTTGACATG ATTAGGGCTT TGGGGGCGTG CCGGTTCAAC GTCCCAGCAG GCACAACGCT
9781 GCAATTCCCT GCCCCCTCCC ATACCGGCCC GTGGGTTCGC ATCCTAGCCG GCGGTTGGTG
9841 TCCTGGTAAG AATTCCTTCC TGGATGAAGC AGCGTATTGT AATCACCTTG ATGTCTTGAG
9901 GCTCCTTAGC AAAACTACCC TCACCTGTCT AGGAGATTTC AAACAACTCC ACCCAGTGGG
9961 TTTTGATTCT CATTGCTATG TTTTTGACAT TATGCCTCAG ACTCAACTGA AGACCATCTG
10021 GAGATTTGGA CAGAATATCT GCGATGCCAT TCAGCCAGAT TACAGGGACA AACTTGTATC
10081 CATGGTCAAC ACAACCCGTG TAACCTACTT GGAAAAACCT GTCAAGTATG GGCAAGTCCT
10141 CACCCCTTAC CACAGGGACC GAGAGGACGG CGCCATCACA ATTGACTCTA GTCAAGGCGC
10201 CACATTTGAT GTGGTTACAC TGTATTTGCC CACTAAAGAT TCACTCAACA GGCAAAGAGC
10261 CCTTGTTGCT ATCACCAGGG CAAGACATGC TATCTTTGTG TATGACCCAC ACAGGCAACT
10321 GCAGAGCATG TTTGATCTTC CCGCGAAAGG CACACCCGTC AACCTCGCTG TGCACCGTGA
10381 CGAGCAGCTG ATCGTACTAG ATAGAAACAA CAAAGAATGC TCGGTTGCTC AGGCTCTAGG
10441 CAATGGGGAT AAATTCAGGG CCACAGACAA GCGCGTTGTA GATTCTCTCC GCGCCATTTG
10501 TGCAGATCTT GAAGGGTCGA GCTCCCCGCT TCCCAAGGTC GCACACAACT TGGGATTTTA
10561 TTTCTCGCCT GATTTGACAC AGTTTGCCAA ACTCCCGGTA GAACTTGCAC CCCACTGGCC
10621 CGTGGTGACA ACACAGAACA ATGAAAAGTG GCCAGACCGG TTGGTTGCTA GCCTTCGCCC
10681 TGTCCATAAG TATAGCCGCG CGTGCATCGG TGCCGGCTAC ATGGTGGGCC CCTCAGTGTT

-continued

10741 TCTAGGCACC CCTGGGGTTG TGTCATACTA TCTCACAAAA TTTGTCAGGG GCGAGGCTCA

10801 AATGCTTCCG GAGACAGTCT TCAGCACCGG CCGAATTGAG GTAGATTGCC GGGAGTACCT

10861 TGATGACCGG GAGCGAGAAA TTGCTGAGTC CCTCCCCCAT GCTTTCATTG GTGACGTCAA

10921 AGGTACTACC GTTGGAGGAT GTCACCATGT CACCTCCAAA TACCTTCCGC GCTTCCTTCC

10981 CAAGGAATCA GTCGCGGTAG TCGGGGTTTC AAGCCCCGGG AAAGCCGCAA AAGCAGTTTG

11041 CACATTAACA GATGTGTATC TCCCAGACCT TGAAGCTTAC CTCCACCCAG AGACCCAGTC

11101 CAAGTGCTGG AAAATGATGT TGGACTTCAA GGAAGTTCGA CTGATGGTCT GGAAAGGCAA

11161 GACGGCCTAT TTTCAACTTG AAGGCCGCCA TTTCACCTGG TATCAGCTTG CAAGCTACGC

11221 CTCGTACATC CGAGTACCTG TTAATTCTAC GGTGTATTTG GACCCCTGCA TGGGCCCTGC

11281 CCTTTGCAAC AGAAGAGTTG TCGGGTCCAC CCATTGGGGA GCCGACCTCG CAGTCACCCC

11341 TTATGATTAC GGTGCCAAAG TCATTCTGTC TAGTGCATAC CATGGTGAAA TGCCTCCTGG

11401 GTACAAAATC CTGGCGTGCG CGGAGTTCTC GCTTGACGAT CCAGTTAGGT ACAAACGCAC

11461 CTGGGGGTTT GAATCGGATA CAGCGTATCT GTATGAGTTC ACCGGAAACG GTGAGGACTG

11521 GGAAGACTAC AATGATGCGT TTCGTGCGCG CCAGAAAGGG AAAATTTATA AGGCCACTGC

11581 CACCAGCATG AGGTTTCATT TTCCCCCGGG CCCTGTTATT GAACCAACTT TAGGCCTGAA

11641 TTGAGATGAA ATGGGGTCTA TGCAAAGCCT CTTTAACAAA ATTGGCCAAC TTTTTGTGGA

11701 TGCTTTCACG GAATTTTTGG TGTCCATTGT TGATATCATC ATATTTTTGG CCATTTTGTT

11761 TGGCTTCACC ATCGCAGGTT GGCTGGTGGT CTTCTGCATC AGATTGGTTT GCTCCGCGGT

11821 ACTCCGTGCG CGCCCTGCCA TTCACCCTGA GCAATTACAG AAGATCCTAT GAGGCCTTTC

11881 TTTCTCAGTG CCGGGTGGAC ATTCCCACCT GGGGAACTAA ACATCCTTTG GGGATATTGT

11941 GGCACCATAA GGTGTCAACC CTGATTGATG AAATGGTGTC GCGTCGAATG TACCGCACCA

12001 TGGAAAAAGC AGGACAGGCT GCCTGGAAAC AGGTGGTGAG CGAGGCCACG TTGTCTCGC

12061 TTAGTGGTTT GGATGTGGTG GCTCATTTTC AGCATCTTGC CGCCATTGAA GCCGAGACCT

12121 GTAAATATTT GGTTTCTCGG CTGCCCATGC TACACAACCT GCGCATGACA GGGTCAAATG

12181 TAACCATAGT GTATAATAGC ACTTTAAATC AGGTGTTTGC CATTTTTCCA ACCCCTGGTT

12241 CCCGGCCAAG GCCTCATGAT TTTCAGCAAT GGCTAATAGC TGTGCATTCC TCCATATTTT

12301 CCTCTGTTGC GGCTTCTTGT ACTCTTTTTG TTGTGCTGTG GTTGCGGATC CCAATGCTAC

12361 GTACTGTTTT TGGTTTCCAC TGGTCAGGGG CAATTTTTCT TTCGAACTCA CGGTGAATTA

12421 CACGGTGTGC CCACCTTGCC TCACCCGGCA AGCAGCCGCT GAGATCTACG AATCCGGCAG

12481 GTCTCTTTGG TGCAGGATAG GGCATGACCG ATGTAGTGAG GACGATCACG ACGAACTAGG

12541 GTTCATGGTT CCGCCTGGCC TCTCCAGCGA AGGCCACTTA ACCAGTGTTT ATGCCTGGTT

12601 GGCGTTCCTG TCTTTCAGCT ACACGGCCCA ATTCCATCCC GAGATATTTG GGATAGGGAA

12661 TGTGAGTAAA GTTTATGTTG ACGTCAAGCA CCAATTCATC TGCGCCGTTC ATGACGGACA

12721 AAACACCACC TTGCCCCGCC ATGACAACAT TTCAGCCGTA TTTCAGACCT ACTATCAACA

12781 TCAGGTCGAC GGCGGCAATT GGTTCCACCT AGAATGGCTG CGTCCCTTCT TTTCCTCTTG

12841 GTTAGTTTTA AATGTTTCGT GGTTTCTCAG GCGTTCGCCT GCAAGCCATG TTTCAGTTCA

12901 AGTCTTTCAG ACATCAAAAC CAACACCACT GCAGCATCAG GCTTCGTTGT CCTCCAGGAC

12961 ATCAGCTGCC TTAGGTATGG CGACTCGTCC TCTCCGACGA TTCGCAAAAG CTCTCAATGC

13021 CGCACGGCGA TAGGGACACC CGTGTATATT ACCATCACAG CCAATGTGTC AGACGAGAAT

13081 TACTTACATT CTTCAGATCT CCTCATGCTT TCTTCTTGCC TTTTCTATGC CTCTGAGATG

13141 AGTGAAAAGG GGTTCAAGGT GATATTTGGC AATGTTTCAG GCATTGTGGC TGTGTGTGTC

-continued

13201 AACTTTACCA GCTACGTCCA ACATGTTAGG GAGTTCACCC AACGCTCTCT GGCGGTCGAT

13261 CATGTGCGGC TGCTTCATTT CATGACACCT GAGACCATGA GGTGGGCAAC CGTTTTAGCC

13321 TGTCTTGTTG CCATCCTTTT GGCAATTTGA ATGTTTAAGT ATGTTGGGGA AATGCTTGAC

13381 CGCGGGCTAT TGCTCGCGAT TGCCTTTTTT GTGGTGTATC GTGCCGTTCT GTTTTGCTGT

13441 GATCGTCAAC GCCAGCAGCA ACAGCAGCTC TCATTTTCAG TCGATTTATA ACTTGACGCT

13501 ATGTGAGCTG AATGGCACAG ATTGGCTGGC TGGTAAATTT GATTGGGCAG TGGAGACTTT

13561 TGTTATCTTT CCCGTGTTGA CTCACATTGT TTCCTATGGT GCACTTACCA CCAGCCATTT

13621 CCTTGACACA GTTGGTCTGG TTATTGTGTC CACCGCCGGG TTTTATCATG GGCGGTATGT

13681 CTTGAGTAGC GTCTACGCAG TCTGTGCCCT GGCTGCGTTG ATTCGCTTTG TCATTAGATT

13741 TGCGAAGAAC TGCATGTCCT GGCGCTACTC ATGTACCAGA TATACCAACT TCCTTCTAGA

13801 TACCAAGGGC AAACTCTATC GTTGGCGGTC GCCTGTTATC ATAGAGAAAG GGGGTAAGGT

13861 TGAGGTCGAA GGTCACCTGA TCGACCTCAA AAGAGTTGTG CTTGATGGTT CCGTGGCAAC

13921 TCCTTTAACC AGAGTTTCAG CTGAACAATG GGGTCGTCCC TAGACGACTT TTGCAATGAT

13981 AGCACGGCTC CGCAAAAGGT GCTTCTGGCG TTTTCCATTA CCTACACGCC AGTGATGATA

14041 TATGCTCTGA AGGTAAGTCG CGGCCGCCTG CTAGGGCTTC TGCACCTTTT AATCTTTCTG

14101 AATTGTGCTT TCACCTTCGG GTACATGACA TTCGCGAACT TTCAGAGCAC AAACAGGGTT

14161 GCGCTCACTA TGGGAGCAGT AGTTGCACTT CTTTGGGGGG TGTACTCAGC CATAGAAACC

14221 TGGAAATTCA TCACCTCCAG ATGCCGTTTG TGCTTGCTAG GCCGCAGGTA CATTCTGGCC

14281 CCTGCCCACC ACGTCGAAAG TGTCGCAGGC TTTCATCCGA TTGCGGCAAG TGATAACCAC

14341 GCATTTGTCG TCCGGCGTCC CGGCTCCACT ACGGTTAACG GCACATTGGT GCCCGGGTTG

14401 AAAAGCCTCG TGTTGGGTGG CAGAAAAGCT GTTAAACAGG GAGTGGTAAA CCTTGTCAAA

14461 TATGCCAAAT AACAATGGCA GGCAGCAAAA AAGAAATAAG GGGGACGGCC AGCCAGTCAA

14521 TCAGCTGTGT CAGATGCTGG GTAAGATCAT CGCCCAGCAA AATCAGTCCA GAGGCAGGGG

14581 ACCGGGGAAG AAAAATAAAA AGAAAAACCC GGAGAAGCCC CATTTTCCTC TAGCGACCGA

14641 AGATGACGTC AGGCATCACT TCACCCCTAG TGAGCGGCAA TTGTGTCTGT CGTCGATCCA

14701 GACTGCCTTT AACCAGGGCG CTGGAACTTG TACCCTGTCA GATTCAGGGA GGATAAGTTA

14761 CACTGTGGAG TTTAGTTTGC CGACGCATCA CACTGTGCGC CTGATTCGCG CCACAGCATC

14821 ACCCTCAGCG TGATGGGCTG GCATTCTTGA AGCACCTCAG TGTTAGAATT GGAAGAATGT

14881 GTGGTGGATG GCACTGATTG ACACTGTGCC TCTAAGTCAC CTATTCAATT AGGGCGACCG

14941 TGTGGGGGTA AAGTTTAATT GGCGAGAACC ATGCGGCCGA AATTAAAAAA AAAAAAAAAA

15001 AAAAAAAAAA AAA

The cDNA consensus sequence of PRRS strain ND 99-14 at P83 has been assigned GenBank Accession number KU131562 (SEQ. ID. NO:4). The cDNA consensus sequence designated SEQ. ID. NO:4 is:

1 ATGACGTATA GTTGTTGGCT CTATGTCGTG ACATTTGTAT AGTCAGGAGC TGCGACCATT

61 GGTACAGCCC AAAACTTGCT GCGCGGGAAC GCCCTTCCGT GACAGCCTTC TTCAGGGGAG

121 TTTAGGGGTC TATCCCTAGC ACCTTGCTTC CGGAGTTGCA CTGCTTTACG GTCTCTCCAC

181 CCCTTTAACC ATGTCTGGGA TACTTGATCG GTGCACGTGT ACCCCCAATG CCAGGGTGTT

241 TGTGGCGGAG GGCCAAGTCT ACTGCACACG ATGTCTCAGT GCACGGTCTC TCCTTCCTTT

301 GAATCTCCAA GTTTCTGAGC TTGGGGTGCT GGGCTTATTT TATAGGCCCG AAGAGCCGCT

-continued

```
361  CCGGTGGACG TTGCCACGTG CATTCCCCAC TGTCGAGTGC TCCCCCGCCG GGGCCTGCTG
421  GCTTTCTGCG ATTTTTCCAA TTGCACGAAT GACCAGTGGA AACCTGAACT TTCAACAAAG
481  AATAGTGCGG GTCGCAGCTG AGCTCTACAG AGCCGGTCAG CTCACCCCCG TAGTCTTGAA
541  GAATCTACAG GTTTATGAAC GGGGTTGCCG TTGGTACCCC ATCGTTGGAC CTGTTCCTGG
601  AGTGGCTGTT TATGCCAATT CCTTACACGT GAGTGACAAA CCTTTCCCGG GAGCAACTCA
661  TGTGTTAACC AACCTACCGC TCCCGCAGAG GCCCAAGCCT GAAGACTTTT GCCCCTTTGA
721  GTGTGCTATG GCTGACGTCT ATGACATTGG TCATGACGCT GTCATGTATG TGGCCGGAGG
781  GAGAGTCTCC TGGGCCCCTC GTGGCGGGGA CAAAGGAAAA TTTGAAATAG TTCCCAAGGA
841  GTTGAAGTTG ATTGCGAATC GACTCCACAT TTCCTTCCCG CCCCACCACG CAGTGGACAT
901  GTCCAAGTTT GCCTTTATAA GCCCTGGGAG TGGTGTTTCC ATGCGGGTCG AGTACCAACA
961  TGGCTGTCTC CCCGCTGATA CTGTCCCTGA AGGAAACTGT TGGTGGCGCT TGTTTGACTT
1021 GCTTCCACCG GAAGTTCAGA ACAAAGAGAT TCGCCATGCT AACCAACTCG GCTATCAGAC
1081 CAAGCATGGT GTCGCTGGCA AGTACCTACA GCGGAGGCTG CAAGTTAATG GACTCCGAGC
1141 AGTAACTGAC GCGAATGGAC CTATCGTCAT ACAGTATTTT TGTGATAGGG AAAGCTGGAT
1201 CCGCCACTTA AGACTGGTAG AAGAACCTAG CCTCCCTGGG TTTGAGGACC TCCTCAGAAT
1261 AAGAGTTGAG CCCAATACGT TGCCATTGGT TGGCGAGGAT GAGAAAATCT TCCGATTTGG
1321 CAATCACAAA TGGTACGGTG CTGGAAAGAG GGCAAGGAAA GCACGCTTTG GTGCGGCTGC
1381 CACGGTCGCT CACCGCGCTT TGCCCGCTCA CGAAACCCAG CAGGCCAAGA AGCACGAAGT
1441 TACCAGCGCC AACAGGGCTG AGCATCTCGA GCACTATTCC CCGCCTACCG ACGGGAACTG
1501 TGGTTGGCAC TGCGTTTCCG CCATTGTCAA CCGGATTGTG AATTCCAAAT TTGAAACCAC
1561 CCTTCCCGAG AGAGTGAGAC CTTTAGATGA CTGGGCTACT GACGAGGATC TTGTGAATAC
1621 TATCCAAATC CTCAGGCTCC CTGCGGCCTT GGACAGGAAC GGTGCTTGTG TCGGCGCCAA
1681 GTACGTGCTC AAGCTGGAAG GTGTGCACTG GACAGTCTCT GTGGCCCCTG GGATGACCCC
1741 TTCTCTGCTC CCCCTTGAAT GTGTTCAGGG CTGTTGTGAG CATAAGAGCG GTCTTGGTCC
1801 CCCAGATGTG GCTGAAGTTT CCGGATTTGA CCCTGCCTGC CTTAACCGAC TGGCTGAGGT
1861 AATGCACTTG CCTAGTTGTG TCATCCCAGC TGCTCTGGCT GAAATGTCCG ACGACCCCAA
1921 TCGCCCGGCT TCCCCAGTCA CCACTGTGTG GACTATTTCG CAATTCTTTG CCCATTATAG
1981 AGGAGGAGAG CACCCTGATC AGGTGTGCTT AGGGAAAATC ATCAGCCTTT GTCAGGTGAT
2041 TGAGGAATGC TGTTGTTCCC AGAACAAAAC CAACCGGGCC ACCCCGGAAG AGGTCGCGGC
2101 AAAAATTGAC CAGTACCTCC GTGATGCAGC AAGCCTTGGA GAATGCTTAG CCAAGCTTGA
2161 GAGGGCTCGC CCGCCGAGCG CGATGGACAC CTCCTTTGAT TGGAATGTTG TGCTTCCTGG
2221 GGTTGAGGCG GCGAACCAGA CGACCAAACA GCTCCATGTC AACCAGCACC GTGCTCCGGT
2281 TCCTGCCATG ACTCAGGAGC CTTTGGACAA AGACTCGGTC CCTTTGACCG CCTTCTCGCT
2341 GTCTAATTGC TACTACCCTG CACAAGGTGA CGAGGTTCGT CACCGTGAGA GGCTGATCTC
2401 CGTGCTCTCT AAGTTGGAGG AGGTTGTTCG TGAGGAATAT GGGCTCACGC CAACTGGATC
2461 TGGCCCGCGA CCCGCACTGC CGAACGGGCT CGACGAGCTC AAAGACCAGA TGGAAGAGGA
2521 TCTGTTGAAA CTGGTCAACG CCCAGGCAAC TTCAGAAATG ATGGCCCGGG CAGCTGAGCA
2581 GGTTGATCTA AAAGTTTGGG TCAAAAATTA CCCACGGTGG ACACCGCCAC CCCCTCCACC
2641 AAGAGTTCAG CCTCGAAAAA CAAAGTCTGC TAAGAGCCTG CCAGAGAACA AGCCTGTCCC
2701 TGCTCCGCGC AGGAAAGTCA GATCTGATTG TGGCAGCCCG ACTTTGAGGG GCAACAATGT
2761 TCCTAACGGT TGGGAAGACT TGGCCGTTGG TGGTCCTCTT GATCTTTCGA CACCATCCGA
```

-continued

```
2821 GCCGATGACA CCTCTGAGTG AGCCTGCACT TATGCCCGTG TTGCAACATA TTTCTGGACC
2881 AGTGACGCCT TTGAGCGTGC CGGCCCCTAT TCCTGCACCG CGTAAAGCTG TGTCCCGACC
2941 GATGGCGCCC TCGAGTGAGC CAATTTTTGT GTCTGCACCG CGGCAAAAAT TTCAGCAGGT
3001 GGAAGAAGCA AATCTGGCGG CAACAACGCT GACATACCAG GACGAACCTA TAGATCTGTC
3061 AGCATCCTCA CAGACTGAAT ATGAGGCTCC TTCCCTAGCA CCACTGCAGA ACATAGGTAC
3121 TCTGGAGGTG GGGGGGCAAG AAGCTGAGGA AATTCTGAGT GAAACCTCGG ATATACCGAA
3181 TGACATCAAC CCTGTGCCTG TATCATCAAG CAGCTCCTTG TCAAGCGTTA AGATCACACG
3241 CCCAAGACAC TCAGCTCAAG CCATCATCGA CTCGGGCGGG CCCTGCAGTG GGCATCTCCA
3301 AAGGGAGAAA GAAGCGTGCC TCCGCATCAT GCGTGAGGCT TGTGATGCGA CTAAGCTTAG
3361 TGACCCTGCC ACGCAGGAAT GGCTTTCTCG CATGTGGGAT AGGGTGGACA TGCTGACTTG
3421 GCGCAACACG TCTGCTTTCC AGGCGTTTCG CATCTTAGAC GGCAGGCTTG AGTTTCTTCC
3481 AAAGATGATA CTCGAGACGC CGCCGCCCTA CCCGTGTGGG TTTGTGATGC TGCCTCACAC
3541 CCCTGCACCT TCCGTGAGTG CAGAGAGCGA CCTTACCATC GGTTCAGTCG CCACTGAAGA
3601 TATTCCACGC ATCCTCGGGA AAATAGAAAA CACCAGTGAG ATGATCAACC AGGGACCCTT
3661 GGCATCCTCT GAGGAAAAAC CGGCATACAA CCAACCCGCT AAGGACTCCC TGATATCGTC
3721 GCGGGGGTTT GACGAGAGCA CAGCAGCTCC GTCCGCAGGT ACGGGTGGCG CCGGCTTGTT
3781 TACTGATTTG CCACCTTCAG ACGGTGTAGA TGCGGACGGG GGGGGGCCGC TGCAGACGGT
3841 GAAAAAGAAC GCTGAAAGGC TCCTCGACCG ATTGAGCCGT CAGGTTTTTA ACCTCGTCTC
3901 CCATCTCCCT GTTTTCCTCT CACACCTCTT CAAATCTGAC AGTGGTTATT CTCCGGGTGA
3961 TTGGGGTTTT GCAGCTTTTA CTCTATTTTG CCTCTTTTTA TGTTACAGCT ACCCATTCTT
4021 TGGTTTCGCT CCCCTTTTGG GTGTGTTTTC TGGGTCTTCT CGGCGCGTGC GCATGGGGGT
4081 TTTTGGCTGC TGGTTGGCTT TTGCTGTTGG TTTGTTCAAG CCTGTGTCCG ACCCAGTCGG
4141 CACTGCTTGT GAGTTTGATT CGCCAGAGTG TAGGAATGTC CTTCATTCTT TTGAGCTTCT
4201 CAAACCTTGG GACCCTGTTC GCAGCCTTGT TGTGGGCCCC GTCGGTCTCG GTCTTGCCAT
4261 TCTTGGCAGG TTACTGGGCG GGGCACGCTA CATCTGGCAT TTTCTGCTTA GGCTTGGCAT
4321 TGTTACAGAC TGTATCCTGG CTGGAGCTTA TGTGCTTTCT CAAGGTAGGT GTAAAAAGTG
4381 CTGGGGATCT TGCATAAGAA CAGCTCCTAA TGAGATTGCC TTTAACGTGT TCCCTTTTAC
4441 ACGTGCGACT AGGTCGTCAC TCATCGACCT GTGCAATCGG TTTTGTGCGC CAAAGGGCAT
4501 GGACCCTATT CTCCTCGCCA CTGGGTGGCG TGGGTGCTGG ACCGGCCGAA GCCCCATTGA
4561 ACAACCCTCT GAAAAACCCA TCGCGTTTGC CCAGTTGGAC GAAAAGAGGA TTACGGCCAG
4621 GACCGTGGTC GCCCAGCCTT ATGACCCCAA CCAAGCCGTA AAGTGCTTGC GGGTGTTACA
4681 GGCGGGCGGG GCGATGGTGG CTGAGGCAGT CCCAAAAGTG GTCAAAGTTT CCGCTATTCC
4741 ATTCCGAGCC CCCTTTTTTC CCACCGGAGT GAAAGTTGAC CCTGAGTGTA GGATCGTGGT
4801 TGACCCCGAC ACTTTTACTA CAGCCCTCCG GTCCGGCTAT TCCACCACAA ACCTCGTTCT
4861 TGGTGTGGGG GACTTTGCCC AGCTGAATGG ATTAAAAATC AGGCAAATTT CCAAGCCTTC
4921 GGGAGGAGGC CCGCACCTCA TTGCTGCCCT ACATGTTGCC TGCTCGATGG CGTTGCACAT
4981 GCTTGCTGGG GTTTATGTAA CTGCAGTGGG GTCTTGCGGT ACCGGCACCA ACGATCCGTG
5041 GTGCACCAAC CCGTTTGCCG TCCCTGGCTA CGGGCCTGGT ACTCTTTGCA CGTCCAGATT
5101 GTGCATCTCC CAACATGGCC TTACCCTGCC CTTGACAGCA CTTGTGGCAG GATTCGGTCT
5161 TCAGGAAATT GCCTTGGTTG TTTTGATTTT CGTTTCCATC GGAGGCATGG CTCACAGGTT
```

-continued

5221 GAGTTGCAAG GCTGACATGC TGTGCGTTTT ACTTGCAATC GCCAGCTATG TTTGGGTGCC

5281 CCTTACCTGG TTTCTTTGTG TGTTTCCTTG CTGGTTGCGC TGGTTCTCTT TGCATCCCCT

5341 CACCATCCTA TGGTTGGTGT TTTTCTTGAT TTCTGTAAAT GTGCCTTCGG GAATCTTGGC

5401 TGTGGTGTTG TTAGTTTCTC TTTGGCTCTT AGGTCGTTAC ACTAATGTTG CTGGTCTTGT

5461 CACCCCATAT GACATTCATC ATCACACCAG TGGCCCCCGA GGTGTTGCCG CCTTGGCTAC

5521 TGCACCGGAT GGGACCTACT TGGCCGCCGT TCGCCGTGCT GCGTTGACCG GTCGTACCAT

5581 GCTGTTTACC CCGTCTCAGC TTGGGTCCCT TCTTGAGGGT GCTTTCAGAA CTCAAAAGCC

5641 CTCACTGAAC ACCGTCAATG TGGTCGGATC CTCTATGGGC TCCGGCGGGG TGTTCACCAT

5701 CGACGGGAAA ATTAAGTGCG TAACAGCCGC ACATGTCCTT ACGGGTAATT CAGCTAGGGT

5761 TTCCGGGGTC GGCTTCAACC AAATGCTTGA TTTTGATGTG AAAGGGGACT TCGCCATAGC

5821 TGATTGCCCG AATTGGCAAG GAGCTGCCCC CAAGACCCAA TTCTGCGAGG ATGGATGGAC

5881 TGGCCGTGCC TATTGGCTGA CATCCTCTGG AGTCGAACCC GGTGTCATTG GGAATGGATT

5941 CGCCTTCTGC TTCACCGCGT GCGGCGATTC TGGATCCCCG GTGATTACCG AAGCCGGTGA

6001 GCTTGTCGGC GTTCACACAG GATCAAACAA ACAAGGAGGA GGCATAGTCA CACGCCCCTC

6061 AGGCCAGTTT TGTAATGTGG CGCCCATCAA GCTGAGCGAA TTGAGTGAAT TCTTCGCTGG

6121 ACCTAAGGTC CCGCTCGGTG ATGTGAAGAT TGGCAGCCAC ATAATTAAAG ACGTATGCGA

6181 GGTACCTTCA GATCTTTGCG CCTTGCTCGC TGCCAAACCC GAACTGGAAG GAGGCCTCTC

6241 CACCGTCCAA CTTCTGTGTG TGTTTTTCCT CCTGTGGAGA ATGATGGGAC ATGCCTGGAC

6301 GCCCTTGGTT GCTGTGGGGT TTTTTATCTT GAATGAGGTT CTCCCAGCTG TCCTGGTCCG

6361 GAGTGTCTTC TCCTTTGGTA TGTTTGTGCT ATCTTGGCTT ACACCATGGT CTGCGCAAGT

6421 CCTGATGATC AGGCTTCTAA CAGCAGCTCT TAACAGGAAC AGGGGGTCAC TCGCCTTCTA

6481 CAGCCTCGGT GCAGTGACCG GATTTATCGC AGATCTTGCA GCAACTCAGG GGCATCCGCT

6541 GCAGGCAGTG ATGAACTTAA GCACCTATGC CTTCCTGCCT CGGATGATGG TTGTGACCTC

6601 ACCAGTCCCA GTGCTTGCTT GTGGTGTTGT GCACCTCCTT GCCATAATTT TGTACCTGTT

6661 TAAGCACCGT TGCCTGCATT ATGTCCTTGT TGGCGATGGA GTGTTCTCTA AAGCCTTCTT

6721 CTTGCGATAC TTTGCCGAAG GGAAGTTGAG GGAAGGGGTG TCGCAGTCCT GCGGGATGAA

6781 TCACGAGTCA CTGACTGGTG CCCTCGCTAT GAGACTCAAT GACGAAGACT TGGACTTCCT

6841 TACGAAATGG ACTGATTTTA AGTGCTTTGT TTCTGCGTCC AACATGAGGA ATGCAGCGGG

6901 CCAATTCATC GAGGCTGCCT ATGCAAAAGC ACTTAGAATT GAGCTTGCCC AGTTAGTACA

6961 GGTTGATAAG GTTCGAGGTA CTTTGGCCAA ACTTGAAGCC TTTGCTGATA CCGTGGCACC

7021 CCAGCTCTCG CCCGGTGACA TTGTTGTTGC TCTTGGCCAC ACGCCTGTTG GCAGTATCTT

7081 CGACCTAAAG GTTGGCAGTA CCAAGCATAC CCTCCAGGCC ATTGAGACCA GAGTCCTTGC

7141 CGGGTCCAAA ATGACCGTGG CGCGTGTCGT TGATCCAACC CCCACGCCCC CACCCGCACC

7201 CGTGCCCATC CCCCTCCCAC CGAAAGTCCT GGAGAACGGC CCCAACGCCT GGGGGGATGA

7261 GGACCGGTTG AATAAGAGGA AGAGACGCAG GATGGAAGCC GTCGGCATCT TTGTTATGGG

7321 TGGGAAGAAG TACCAAAAAT TTTGGGACAA GAATTCCGGT GATGTGTTTT ACGAGGAGGT

7381 CCATGATAAC ACAGATGCGT GGGAGTGCCT CAGAGTTGGT GACCCTGCCG ACTTTGACCC

7441 TGAGAAGGGA ACTCTGTGTG GGCATACTAC CATTGAAGAC AAGGCTTATA ATGTCTACAC

7501 CTCCCCATCT GGCAGGAAGT TCCTGGTCCC CGTCAACCCA GAGAGCGGAA GAGCCCAATG

7561 GGAAGCTGCA AAGCTTTCCG TAGAGCAGGC CCTTAGCATG ATGAATGTCG ACGGTGAGCT

7621 GACAGCCAAA GAACTGGAGA AACTGAAAAG AATAATTGAC AAACTCCAGG GCCTAACTAA

-continued

7681 GGAGCAGTGT TTAAACTGCT AGCCGCCAGC GGCTTGACCC GCTGTGGTCG CGGCGGCTTG

7741 GTTGTTACTG AGACAGCGGT GAAAATAGTT AAATTTCACA ACCGGACCTT CACCCTAGGA

7801 CCTGTGAATT TAAAAGTGGC CAGTGAGGTT GAGCTAAAAG ACGCAGTCGA GCATAACCAA

7861 CACCCGGTTG CAAGACCGGT TGATGGTGGT GTTGTGCTCC TGCGCTCCGC AGTTCCTTCG

7921 CTTATAGACG TCTTGATCTC TGGCGCTGAT GCATCTCCTA AGTTACTCGC CCACCACGGG

7981 CCGGGAAACA CTGGGATCGA TGGTTCGCTT TGGGATTTTG AGGCCGAGGC CACCAAAGAG

8041 GAAATTGCAC TCAGTGCGCA AATAATACAG GCTTGTGACA TTAGGCGCGG CGACGCACCC

8101 GAAATTGGTC TTCCTTATAA GCTGCACCCT GTTAGGGGCA ACCCTGAGCG GGTAAAAGGG

8161 GTTTTACAGA ATACAAGGTT TGGAGACATA CCTTATAAAA CCCCCAGTGA CACTGGGAGC

8221 CCAGTGCACG CGGCTGCCTG CCTCACGCCC AATGCCACTC CGGTGACTGA CGGTCGTTCC

8281 GTCTTGGCTA CGACCATGCC CTCCGGTTTT GAGTTGTATG TACCGACCAT TCCAGCGTCT

8341 GTCCTTGATT ATCTTGATTC CAGGCCTGAT TGCCCCAAAC AGTTGACAGA GCACGGCTGT

8401 GAGGATGCCG CATTAAGAGA CCTCTCCAAG TATGACTTGT CCACCCAAGG CTTTGTCTTG

8461 CCTGGAGTTC TTCGCCTTGT GCGTAAGTAC CTGTTTGCTC ATGTGGGTAA GTGCCCGCCT

8521 ATTCATCGGC CTTCCACTTA CCCTGCCAAG AATTCCATGG CTGGAATAAA TGGGAACAGG

8581 TTTCCAACCA AGGACATTCA GAGCGTCCCT GAAATCGACG TTTTGTGCGC ACAGGCCGTG

8641 CGAGAAAACT GGCAAACTGT TACTCCTTGT ACCCTCAAGA AGCAGTATTG CGGGAAGAAG

8701 AAGACTAGGA CAATACTCGG CACTAATAAC TTCATTGCGC TGGCCCACCG GGCAGCATTG

8761 AGTGGTGTCA CCCAGGGCTT CATGAAAAAA GCGTTTAACT CGCCCATCGC ACTCGGGAAA

8821 AACAAATTCA AGGAGCTGCA GACTCCGGTC TTGGGCAGAT GTCTTGAAGC TGACCTTGCA

8881 TCCTGTGACC GATCCACACC CGCAATTGTC CGCTGGTTTG CCGCCAATCT TCTTTATGAA

8941 CTTGCCTGTG CTGAGGAGCA TATACCATCG TACGTGTTGA ACTGCTGCCA CGACTTACTG

9001 GTCACGCAGT CCGGCGCGGT GACTAAGAGA GGTGGCCTAT CGTCTGGCGA CCCGATTACT

9061 TCTGTATCAA ACACCATTTA CAGCTTGGTG ATATATGCAC AGCACATGGT ACTCAGTTAT

9121 TTTAAAAGTG GTCACCCCCA TGGCCTTCTG TTTCTACAAG ACCAGCTAAA GTTTGAGGAC

9181 ATGCTCAAGG TTCAGCCCCT GATCGTCTAT TCGGACGACC TCGTGCTGTA CGCCGAGTCT

9241 CCCACCATGC CAAACTACCA CTGGTGGGTT GAACATCTGA ACCTGATGCT GGGTTTTCAG

9301 ACGGACCCAA AGAAGACAGC TATAACAGAC TCGCCATCAT TTTTGGGTTG TAGGATAATA

9361 AATGGACGCC AGTTAGTCCC CAACCGTGAC AGGATCCTCG CGGCCCTCGC CTACCATATG

9421 AAGGCAAACA ATGTTTCTGA ATACTACGCC TCGGCGGCTG CAATACTCAT GGACAGTTGT

9481 GCTTGTTTGG AGTACGATCC TGAGTGGTTT GAAGAGCTCG TGGTTGGGAT GGCGCAGTGC

9541 GCCCGCAAGG ACGGCTACAG TTTTCCTGGC CCGCCGTTCT TCTTGTCCAT GTGGGAAAAA

9601 CTCAGGTCCA ATCATGAGGG GAAGAAGTCT AGAATGTGCG GGTACTGTGG GGCCCCAGCT

9661 CCGTATGCCA CTGCCTGTGG CCTTGATGTT TGTATTTATC ACACCCACTT CCACCAGCAT

9721 TGTCCAGTCA TAATCTGGTG TGGCCATCCG GCGGGTTCTG GCTCTTGTAG TGAGTGCAAA

9781 CCCCCCCTAG GGAAAGGCAC AAGCCCTCTA GATGTGGTGT TAGAACAAGT CCCGTACAAG

9841 CCTCCACGAA CTGTAATCAT GCATGTGGAG CAGGGTCTCA CCCCTCTTGA CCCAGGCAGA

9901 TACCAGACTC GCCGCGGATT AGTCTCCGTT AGGCGTGGCA TCAGGGGAAA CGAAATCGAC

9961 CTACCAGACG GTGATTATGC TAGTACCGCC TTGCTCCCCA CTTGTAAAGA TATCAACATG

10021 GTCGCTGTCG CTTCCAATGT GTTGCGCAGC AGGTTCATCA TCGGTCCACC CGGTGCTGGT

-continued

10081 AAAACATACT GGCTCCTTCA ACAGGTCCAG GATGGTGATG TCATTTACAC GCCAACTCAT

10141 CAGACCATGC TTGACATGAT CAAGGCTTTG GGGACGTGCC GGTTCAACGC CCCAGCAGGC

10201 ACAACGCTGC AATTCCCTGC TCCCTCCCGT ACCGGCCCGT GGGTTCGCAT CCTGGCCGGC

10261 GGTTGGTGTC CTGGCAAGAA TTCCTTCCTG GATGAAGCAG CGTATTGTAA TCACCTTGAT

10321 GTCTTGAGGC TTCTTAGCAA AACTACCCTC ACCTGTCTGG GAGATTTCAA ACAACTCCAC

10381 CCAGTGGGTT TTGATTCTCA TTGCTATGTT TTTGACATCA TGCCTCAGAC TCAACTGAAG

10441 ACCATCTGGA GGTTTGGACA GAATATCTGT GATGCCATTC AGCCAGATTA CAGGGACAAA

10501 CTTGTGTCCA TGGTCAACAC AACCCGTGTA ACCTACGTGG AAAGACCTGT CAAGCATGGG

10561 CAGGTCCTCA CCCCTTACCA CAGGGACCGA GAGGACGGCG CCATCACAAT TGACTCCAGT

10621 CAAGGCGCCA CATTTGATGT GGTTACATTG CATTTGCCCA CTAAAGATTC ACTCAACAGG

10681 CAAAGAGCCC TTGTTGCTAT CACCAGGGCG AGACATGCTA TCTTTGTGTA TGACCCACAT

10741 AGGCAACTGC AGAGCATGTT TGATCTTCCT GCAAAAGGCA CACCCGTCAA CCTTGCCGTG

10801 CACCGTGACG AGCAGCTGAT CGTACTAGAT AGAAATAACA AAGAGTGCAC GGTTGCTCAG

10861 GCTCTAGGCA ATGGGGACAA ATTCAGGGCC ACAGACAAGC GCGTTGTAGA TTCTCTCCGC

10921 GCCATTTGTG CAGATCTTGA AGGGTCGAGC TCCCCGCTCC CCAAGGTCGC ACATAACTTG

10981 GGATTTTATT TCTCACCTGA TTTGACACAG TTTGCTAAAC TCCCGGCAGA ACTTGCACCC

11041 CACTGGCCCG TGGTGACAAC CCAGAACAAT GAAAAGTGGC CAGACAGGCT GGTTGCCAGC

11101 CTCCGCCCTA TCCATAAATA TAGCCGCGCA TGCATTGGAG CCGGCTATAT GGTGGGCCCT

11161 TCGGTGTTTC TAGGCACCCC TGGGGTTGTG TCATACTATC TCACAAAATT TGTTAAGGGG

11221 GAGGCTCAGG TGCTTCCGGA GACAGTCTTC AGCACCGGCC GAATTGAGGT AGATTGCCGG

11281 GAGTATCTTG ATGATCGGGA ACGAGAAGTT GCTGAGTCCC TCCCACATGC CTTCATTGGC

11341 GACGTCAAAG GCACTACCGT TGGGGGATGT CACCATGTCA CCTCTAAATA CCTTCCGCGC

11401 TTCCTTCCTA AGGAATCAGT TGCGGTGGTT GGGGTTTCGA GCCCCGGGAA AGCCGCAAAA

11461 GCAGTCTGCA CATTAACAGA TGTGTATCTC CCAGACCTTG AAGTTTACCT CCACCCAGAG

11521 ACCCAATCCA AGTGCTGGAA AATAATGTTG GACTTCAAGG AAGTCCGACT GATGGTCTGG

11581 AAAGACAAAA CGGCCTATTT TCAACTTGAA GGCCGCCATT TCACCTGGTA TCAGCTTGCA

11641 AGCTATGCCT CGTACATCCG AGTTCCTGTT AACTCTACGG TGTATTTGGA CCCCTGCATG

11701 GGCCCTGCCC TTTGCAACAG AAGAGTTGTC GGGTCCACTC ATTGGGGGGC TGACCTCGCA

11761 GTCACCCCTT ATGATTATGG TGCCAAAATC ATTCTGTCTA GTGCATACCA TGGTGAAATG

11821 CCTCCTGGGT ACAAAATCCT GGCGTGCGCG GAGTTCTCGC TTGACGACCC AGTGAGGTAC

11881 AAACACACCT GGGGGTTTGA ATCGGACACA GCGTATCTGT ACGAGTTCAC CGGAAACGGT

11941 GAGGACTGGG AGGATTACAA TGACGCATTT CGTGCGCGCC AGAAAGGGAA AATTTATAAG

12001 GCCACTGCCA CCAGCATGAG GTTTCATTTT CCCCCGGGCC CCATCATTGA ACCAACTTTA

12061 GGCCTGAACT GAAATGAGAT GGGGGCTATG CAAAGCCTTT TCTACAAAAT TGGCCAACTT

12121 TTTGTGGATG CTTTCACGGA ATTTTTGGTG TCCATTGTTG ATATCATCAT ATTTTTGGCC

12181 ATTTTGTTTG GCTTCACCAT CGCCGGTTGG CTGGTGGTCT TCTGCATCCG ATTGGTTTGC

12241 TCCGCGGTAC TCCGTGCGCG CCCTACCATT CACCCTGAGC AATTACAGAA GATCCTATGA

12301 GGCCTTTCTT TCTCAGTGCC GGGTGGACAT TCCCACCTGG GGAACCAAAC ATCCCTTGGG

12361 GATACTTTGG CACCATAAGG TGTCAACCCT GATTGATGAA ATGGTGTCGC GTCGAATGTA

12421 CCGCATCATG GAAAAATCAG GACAGGCTGC CTGGAAACAG GTTGTGAGCG AGGCTACGCT

12481 GTCTCGCATC AGTGGTTTGG ATGTGGTGGC TCATTTTCAG CATCTTGCCG CCATTGAAGC

-continued

12541 CGAGACCTGT AAATATTTGG CCTCTCGGAT GCCCATGCTA CACAACCTGC GCATGACAGG

12601 GTCAAATGTA ACCATAGTGT ATAATAGTAC TTTGAATCAG GTGTTAGCAA TCTTCCCGAC

12661 CTCTGAATCC CGGCCAAAGC TTCATGATTT TCAACAATGG TTAATAACTG TACATTCCTC

12721 CATATTTTCC TCCGTTGTGG CTTCCTGTAC TCTTTTTGTT GTGCTGTGGT TGCGAATTCC

12781 AATGCTACGT ACTGTTTTTG GTTTCCACTG GTTAGGGGCA ATTTTTCTTT CGAACTCACA

12841 GTGAATTACA CGGTGTGCCC ACCTTGCCTC ACCCGGCAAG CAGCCGCTGA GATCTACGAA

12901 CCCGGCAGGT CTCTTTGGTG CAGGATAGGG CATGATCGAT GTAGCGAGGA CGATCATGAC

12961 GAACTAGGGT TCTTGGTTCC GCCTGGCCTC TCCAGCGAAG GCCACTTGAC CAGTGTTTAC

13021 GCCTGGTTGG CGTTCCTGTC CTTCAGCTAT ACAGCCCAGT TCCATCCCGA GATATTTGGG

13081 ATAGGGAATG TGAGTAAAAT TTATGTTGAC ATCAAGCACC AATTCATCTG CGCCGAACAC

13141 GACGGGCAGA ACGCCACCCT GCCTCGCCAT GACAACATTT CAGCCGTGTT TCAGACCTAC

13201 TACCAACATC AGGTCGATGG CGGCAATTGG TTTCACCTGG AATGGCTGCG CCCCTTCTTT

13261 TCCTCTTGGT TGGTTTTAAA TGTTTCGTGG TTTCTCAGGC GTTCGCCTGC AAGCCATGTT

13321 TCAGTTCGAG TCTTTCAGAC ATCAAAACCA ACACCACCGC AGCACCAAAT TTTGTTGTCC

13381 TCCAGGACAT CAGCTGCCTT AGGCATGGCG ACCCGTCCTC TCCGGCGATT CGCAAAAGCT

13441 CTCAGTGCCG CACGGCGATA GGAACACCCG TGTATATCAC CATCACAGCC AATGTGACAG

13501 ATGAGAATTA TTTACATTCT TCTGATCTCC TCATGCTTTC TTCTTGCCTT TTCTATGCTT

13561 CTGAGATGAG TGAAAAGGGG TTCAAGGTGG TATTCGGCAA TGTGTCAGGC ATCGTGGCTG

13621 TGTGTGTCAA CTTTACCAGT TACGTCCAAC ATGTCAAGGA GTTTACCCAA CGCTCCTTGG

13681 TGGTCGAGCA TGTGCGACTG CTTCATTTCA TGACACCTGA AACCATGAGG TGGGCAACCG

13741 TTTTAGCCTG TCTTTTTGCC ATTCTGTTGG CAATTTGAAT GTTTAAGTAT GTTGGGGAAA

13801 TGCTTGACCG CGGGCTGTTG CTCGCCGTTG CTTTTTTTGT GGTGTATCGT GCCGTCTTGC

13861 TTTGTTGCGC CCGTCAACGT CGACGGGAAC GACAGCTCAA AGTTACAGCT GATTTACAAC

13921 TTGACGCTAT GTGAGCTGAA TGGCACAGAT TGGCTGGCTG GTAGATTTGA CTGGGCAGTG

13981 GAGTGTTTTG TCATTTTTCC CGTGTTGACT CACATTGTCT CCTATGGTGC CCTCACTACT

14041 AGCCATTTCC TTGACACAGT CGGTCTGGTC ACTGTGTCTG CCGCCGGGTT CCTTCATGAA

14101 CGGTATGTTT TGAGTAGCAT CTACGCGGTC TGTGCCCTGG CTGCGTTGAT TTGCTTCGTC

14161 ATTAGGCTTG CGAAGAACTG CATGTCCTGG CGCTACTCGT GTACCAGATA TACCAACTTC

14221 CTTTTGGACA CCAAGGGGAG ACTCTATCGT TGGCGATCGC CCGTCATCAT AGAGAAAAAG

14281 GGTAAAGTTG AGGTTGAAGG TCATTTGATC GACCTCAAAA GAGTTGTGCT TGATGGTTCC

14341 GTGGCAACCC CTATAACCAA AATTTCAGCG GAACAATGGG GTCGTCCTTA GATGACTTCT

14401 GCCATGATAG CACGGCTCCA CAAAAGGTGC TTTTGGCGTT TTCCATTACC TATACACCAG

14461 TGATGATATA TGCCCTAAAG GTAAGTCGCG GCCGACTGCT AGGGCTTTTG CACCTTTTGA

14521 TCTTTCTGAA CTGTGCTTTC ACCTTCGGGT ATATGACATT CACGCACTTT CAGAGTACAA

14581 ACAAGGTCGC GCTCACTATG GGAGCAGTAG TTGCACTCCT TTGGGGGGTG TACTCAGCCA

14641 TAGAAACCTG GAAATTCATC ACCTCCAGAT GCCGTTTGTG CTTGCTAGGC CGCAAGTACA

14701 TTCTGGCCCC TGCCCACCAC GTTGAGAGTG CCGCAGGCTT TCATCCGATT GCGGCAAATG

14761 ATAACCACGC ATTTGTCGTC CGGCGTCCCG GTTCCACTAC GGTCAACGGC ACATTGGTCC

14821 CCGGGTTGAA AAGCCTCGTG TTGGGTGGCA GAAAAGCTGT CAAACAGGGA GTGGTAAACC

14881 TTGTTAAATA TGCCAAGTAA CAACGGCAGG CAGCAGAAAA AAAGAAAGGG GGATGGCCAG

-continued

14941 CCAGTCAATC AGCTGTGTCA GATGCTGGGT AAAATTATTG CCCAGCAAAA TCAGTCCAGG

15001 GGCAAGGGAC CGGGAAAGAA AAATAACAAG AAAAACCCGG AGAAGCCCCA TTTTCCTCTA

15061 GCGACTGAAG ATGATGTCAG ACATCACTTT ACCCCGAGTG AGCGACAATT GTGTCTGTCG

15121 TCAATCCAGA CTGCCTTCAA TCAGGGCGCT GGAACTTGTA CCCTGTCAGA TTCAGGCAGG

15181 ATAAGTTACA CTGTGGAGTT TAGTTTGCCG ACGCATCACA CTGTGCGCCT GATCCGCGCT

15241 ACAGCATCAC CCTCAGCATG ATGAGCTGGC ATTCCTGGGT ATCCCAGTGT TTGAATTGGA

15301 AGAATGTGTG GTGAATGGCA CTGATTGACA TTGTGCTTCT AAGTCACCTA TTCAATTAGG

15361 GCGACCGTGT GGGAGTAGAA TTTAATTGGC GAGAACCACG CGGCCGAAAT TAAAAAAAAA

15421 AAAAAAAAAA AAAAAAAAAA AAAA

The cDNA consensus sequence of PRRS strain SD 02-10 at P83 has been assigned GenBank Accession number KU131561 (SEQ. ID. NO:5). The cDNA consensus sequence designated SEQ. ID. NO:5 is:

1 CGCCCGGGCA TGTGTTGGCT CCATGCCACG ACATTTGTAT TGTCAGGAGC TGTGACCACT

61 GGCACAGCCC AAAGCTTGCT GCACAGAAAC ACCCTTCTGT GACAGCCTCC TTCAGGGGAG

121 TTTAGGGGTC TGTCCCTAAC ACCTTGCTTC CGGAGTTGCA CTGCTTTACG GTCTCTCCAC

181 CCTTTAACCA TGTCTGGGAT ACTTGATCGG TGCACGTGCA CCCCCAATGC CAGGGTGTTT

241 ATGGCGGAGG GCCAAGTCTA CTGCACACGA TGTCTCAGTG CACGGTCTCT CCTTCCTCTG

301 AATCTCCAAG TTTCTGAACT AGGGGTGCTA GGCCTATTTT ACAGGCCCGA AGAGCCACTC

361 CGGTGGACGT TGCCACGTGC ATTCCCCACT GTTGAGTGCT CCCCCGCCGG GGCCTGCTGG

421 CTTTCTGCAA TTTTTCCAAT TGCACGAATG ACTAGTGGAA ATCTGAACTT CCAACAAAGA

481 ATGGTACGGG TCGCAGCTGA GCTTTACAGA GCCGGCCAGC TCACCCCTGC AGTCTTAAAG

541 GCTCTACAAG TTTATGAACG GGGCTGCCGC TGGTACCCCA TTGTAGGACC TGTCCCTGGA

601 GTGGCCGTTT ACGCCAACTC CTTACATGTG AGTGATAAAC CTTTCCCGGG AGCAACTCAC

661 GTGTTAACCA ACCTACCGCT CCCGCAAAGA CCAAAACCTG AAGACTTTTG CCCCTTTGAG

721 TGTGCCATGG CTACCGTCTA TGACATCGGT CGTGACGCCG TCATGTATGT AACCGAGGGA

781 AAAGTCTCCT GGGCCCCTCG TGGTGGGGAT GAAACAAGAT TTGAAACTGT CCCCGGTGGG

841 TTGAAGTTGA TTGCGGACCA ACTCTACTCC TCCTTCCCGC CCCATCACAC GGTGGACATA

901 TCTAAGTTCG CCCTCACAGC CCCTGGGCGC GGTGTATCCA TGCGGGTTGA ACGCCAGTGT

961 GGCTGCCTCC CCGCTGACAC TGTCCCTGAA GGCAACTGTT GGTGGAGCTT ATTCGATTCA

1021 CTCCCACTGG AAGTCCAGAA CAAAGAAATT CGCCATGCTA ACCAATTTGG CTACCAAACC

1081 AAGCATGGCG TCTCCGGCAA GTACCTTCAG CGGAGGCTGC AAGTTAATGG CCTCCGAGCA

1141 GTAACTGACT TGAATGGACC TATTGTCATA CAGTACTTCT CCGTTAGAGA GAGTTGGATC

1201 CGCCACTTGA AACTGGCGGA AGAACCCGGC CTCCCTGGGT TTGAGGACCT CCTCAGAATA

1261 AGGGTTGAAC CCAACACATC GCCATTGGCT AACGAGGATG AGAAAATCTT CCGATTTGGC

1321 AGCCATAAGT GGTACGGCGC TGGGAGGAGA GCAAGGAAAG CACGCCACAG TGCAATTGCT

1381 GCGGTCGCAG GCCGCGCTTC GTCTGCTCGT GAAATCCAGC AGGCCAAGAA GCATGAGGCT

1441 GCTGACGCCA ATAAGGTTGA GCACCTCAAA CGCTACTCCC CGCCCGCCGA AGGGAATTGC

1501 GGTTGGCACT GTATTTCTGC CATCGCCAAT CGAATGGTGA ATTCTAAATT TAAAACCACC

1561 CTTCCCGAAA GAGTGAGGCC TTCAGATGAC TGGGCCACTG ATGAGGATCT TGTGAATGTC

1621 ATCCAAATCC TCAGGCTCCC TGCGGCCTTG GACAGGAACG GTGCTTGTGC CAGCGCCAAG

1681 TACGTACTTA AGCTAGAAGG TGAGCATTGG ACTGTCACTG TGACCCCTGG GATGTCCCCT

-continued

1741 TCTTTGCTCC CTCTTGAATG TGTTCAGGGC TGTTGTGAGC ATAAGGGCGG TCTAGGTACC

1801 CCAGATGCAG TCGAGGTTTT CGGATTTGAC CCTGCCTGCC TCAACTGGTT GGCTGAGGTG

1861 ATGCACCTGC CTAGCAGTGC TATCCCAGCC GCTCTGGCCG AAATGTCCGG TGATTCCGGT

1921 CGTTCGGCTT CCCCGGTCAC CACCGTGTGG ACCGTTTCGC AGTTCTTTGC CCGCCACAAT

1981 GGAGGGAGTC ACCCTGACCA AGTGCGTTTA GGGAAAATTA TTAGCCTTTG TCAGGTGATT

2041 GAGGACTGCT GCTGTTCCCA GAACAAAACC AACCGGGTTA CCCCGGAGGA GGTCGCAGCA

2101 AAGATTGACT TGTACCTCCG TGGAGCGACA AGTCTTGAAG AATGCTTGGC CAGGCTTGAG

2161 AAAGCTCGCC CGCCACGCGT AATGGACACC TCCTTTGATT GGGATGTTGT GCTCCCTGGG

2221 GTTGAGGCGG CAACTCAGAC GACCGAATTG CCCCAGGTCA ACCAGTGTCG TGCTTTGGTC

2281 CCTGTTGTAA CTCAAAAGTC CTTGGACAAC AACTCGGTTC CCTTGACCGC CTTTTCACTG

2341 GCTAACTACT ACTACCGTGC GCAAGGTGAA GAAGTTCGTC ACCGTGAAAG ACTAACCGCC

2401 GTGCTCTCCA AATTGGAAGG GGTTGTCCGA GAGGAATATG GGCTCATGCC AACCGGGCCT

2461 GGTCCACGGC CCACATTGCC ACGCGGGCTC GACGAACTCA AAGATCAGAT GGAAGAGGAC

2521 TTGCTGAAAC TGGCTAACGC CCAGACGACT TCGGAGATGA TGGCCTGGGC AGTCGAGCAG

2581 GTCGACCTAA AAACTTGGGT CAAGAACTAC CCGCGGTGGA CACCACCACC CCCTCCGCCA

2641 AAAGTTCAGC CTCGAAAAAC GAAGTCTGCC AAGAGCTTGC TAGAGAGAAA GCCTGTCCCC

2701 GCCCCGCGCA GGAAGGTTGG GACCAATTGT GGCAGCCCGA TTTCATTGGG CGACAATATC

2761 CCTAACAGTT GGGAAGATTT GGCTGTTGGT GGCCCCTATG ATCCCCCGAC CCCACCTGAG

2821 CCGGCAACAC CTTCAGGTGA GCTGGTGGTT GTGTCCACAC CGCAATGCAT CTTCAGGCCG

2881 GCGACACCCT CGAGTGAGCC GGCTCTAATT CCCGCATCCC GCGGGGCTGT GTCTCGACCG

2941 GTGACACCCT TGAGTGAGCC GATCCCTGTG CCCGCACCGC GGCGTAAGTT TCAGCAGGTG

3001 AAAAGATTGA GTTCGGCAGC GGTAACCCCG CCGTACCAGG ACGAGCCCCT AAATTTGTCT

3061 GCTTCCTCTC AAACTGAATT TGAGGCCCCC TCCCTAGCAC CGCCGCAGAG CGAGGGTGTT

3121 TTGGGAGTGA AGGGGCAGGA AGCTGAGGAG GCCCTGAGTG AAATCTCGGA CATGTCGGGC

3181 GGCATTAAAC CTGCGTCCGT ATCATCAAGC AGCTCCTTGT CCAGCGTGAG AGTCACACGC

3241 CCAAAATACT CAGCTCAAGC CATCATAGAC TTGGGCGGGC CCTGCAGTGG GCATCTCCAA

3301 GAGGTAAAGG AAGCATGCCT CGGAATCATG CGCGAGGCAT GTGATGCGAC TAAGCTTGAT

3361 GACCCTGCTA CGCAGGAATG GCTTTCCCGC ATGTGGGACC GGGTGGACAT GCTGACTTGG

3421 CGCAACACGT CTGCCTACCA GGCGTTTCGT ACCTTAGATG GCAGGTTAAA GTTCCTCCCA

3481 AAAATGATAC TCGAGACACC GCCGCCCTAT CCGTGTGAGT TTGTGATGAT GCCTCACTCG

3541 CCTGCACCTT CCGTAGGTGC GGAGAGTGAC CTTACCATTG GCTCAGTCGC TACTGAAGAT

3601 GTTCCACGTA TCCTCGAGAA AATAGAAAAT GTCGGCGAGA TGACCAACCA GGGACCCTTG

3661 GCCTTCTCCG AGGATAAACC GGTGGATGAC CAGCTTGCCA AAGACCCCCG GATATCGTCG

3721 CAGAGTCCTG ACGAGAGCAC ATCAGCTCCG CCCACAGGCA CAGGAGGCGC CGGTTCATTT

3781 ACCGATTTGC CGCCTTCAGA CGGCGCGGAT GCGGACGGGG GGGGGCCGTT TCGGACGATA

3841 AAAAGAAAAG CTGAAGGGCT CTTTGACCGA CTGAGCCGAC AGGTTTTTAA CCTCGTCTCC

3901 CATCTCCCTG TTTTCTTCTC ACGCCTTTTC AACCCGGGCG GTAGTTATTC TCCGGGTGAT

3961 TGGGGTTTTG CAGCTTTTAC TCTATTGTGC CTCCTTTTAT GCTACAGTTA TCCAGCATTT

4021 GGTATTGCTC CCCTCTTGGG TGTGTTTTCT GGGTCTTCTC GGCGCGTCCG AATGGGGGTT

4081 TTTGGCTGCT GGTTGGCTTT TGCTGTTGGT CTGTTCAAGC CTGTGTCCGA CCCAGTCGGC

-continued

4141 GCTGCTTGTG AGTTTGATTC GCCAGAGTGT AGAAACATCC TTCATTCTTT TGAGCTTCTC

4201 AAACCTTGGG ACCCTGTTCG CGGCCTTGTT GTGGGCCCCG TCGGTCTCGG TCTTGCCATT

4261 CTTGGCAGGT TACTGGGCGG GGCACGCTGC ATCTGGCACT TTTTGCTTAG GCTTGGCATT

4321 GTTGCAGACT GTGTCTTGGC TGGAGCTTAT GTGCTTTCTC AAGGCAGGTG TAAAAAGTGC

4381 TGGGGATCTT GTATAAGAAC TGCTCCTAGT GAGGTCGCTT TTAATGTGTT TCCTTTTACA

4441 CGTGCGACCA GGTCGTCGCT TACTGACCTG TGCGATCGGT TTTGTGCGCC AAAAGGCATG

4501 GACCCCATTT TTCTCGCCAC TGGGTGGCGC GGGTGCTGGG CCGGCCGAAG CCCCATTGAG

4561 CAACCCTCTG AAAAACCCAT CGCGTTTGCC CAGTTGGATG AAAAGAAGAT TACGGCTAGG

4621 ACTGTCGTCG CCCAGCCTTA TGACCCTAAC CAAGCCGTAA AGTGCTTGCG GGTATTGCAG

4681 GCGGGTGGGG CAATGGTAGC TGAGGCAGTC CCAAAAGTTG TCAAGGTTTC CGCTGTCCCA

4741 TTCCGAGCCC CCTTCTTTCC CACCGGAGTG AAAGTTGACC CAGAATGCAG GGTTGTGGTT

4801 GACCCCGACA CTTTCACCGC AGCTCTCCGG TCTGGCTACT CCACCACAAA CCTCGTCCTT

4861 GGTACAGGGG ACTTTGCCCA GCTGAATGGA TTGAAAATCA GGCAGATTTC CAAGCCTTCA

4921 GGAGGAGGCC CACACCTCAC GGCTGCCCTG CATGTTGCTT GCTCGATGGC TTTGCACATG

4981 CTTGTTGGGA TTTATGTGAC TGCGGTGGGT TCTTGCGGCA CCGGCACCAA CGACCCGTGG

5041 TGCGCTAACC CGTTTGCCGT CCCTGGCTAC GGACCTGGCT CTCTTTGCAC GTCCAGGTTG

5101 TGCATTTCCC AACATGGCCT TACCCTGCCC TTGACAGCAC TCGTGGCGGG ATTCGGCATT

5161 CAAGAAATTG CCTTGGTCGT TTTGATTTTT GTTTCCATCG GAGGCATGGC TCACAGGTTA

5221 AGTTGCAAGG CTGACATGCT GTGTGTTTTG CTTGCAATTG CCAGCTATGT TTGGGTACCT

5281 CTTACCTGGT TGCTTTGTGT GTTTCCTTGC TGGTTGCGCT GTTTTTCTTT GCATCCCCTC

5341 ACCATCCTAT GGTTGGTTTT TTTCTTGATT TCTGTGAATA TGCCTTCAGG AATCTTGGCC

5401 ATGGTGCTGT TGGTTTCTCT TTGGCTTCTT GGTCGTTATA CTAATGTTGC TGGTCTTGTT

5461 ACCCCCTACG ACATTCATCA TTACACTAGT GGCCCCCGCG GTGTTGCCGC CTTGGCTACC

5521 GCACCAGATG GGACCTACTT GGCCGCTGTC CGCCGTGCTG CGTTAACCGG CCGTACCATG

5581 CTGTTTACCC CGTCCCAGCT TGGGTCTCTT CTTGAGGGTG CTTTCAGAAC TCGAAAACCC

5641 TCACTGAACA CCGTCAATGT GGTCGGGTCC TCCATGGGCT CTGGCGGGGT GTTCACCATT

5701 GACGGAAAAA TTAAGTGCGT AACTGCCGCA CATGTCCTTA CGGGCAATTC AGCTAGGATT

5761 TCCGGGGTCG GCTTCAATCA AATGCTTGAC TTTGACGTAA AGGGAGATTT CGCCATAGCT

5821 GATTGCCCGA ATTGGCAAGG GGTTGCCCCC AAGACCCAAT TCTGCAAGGA TGGATGGACT

5881 GGCCGTGCCT ATTGGCTGAC ATCCTCTGGC GTCGAACCCG GCGTCATTGG AAAAGGATTC

5941 GCCTTCTGCT TCACTGCGTG CGGCGATTCC GGGTCCCCAG TGATCACCGA GGCCGGTGAG

6001 CTTGTCGGCG TTCACACGGG ATCAAATAAA CAAGGAGGAG GCATCGTTAC GCGCCCCTCA

6061 GGCCAGTTTT GTAATGTGGC ACCCATCAAA CTAAGCGAAT TAAGTGAATT CTTTGCTGGG

6121 CCTAAGGTCC CGCTCGGTGA TGTAAAGGTT GGCAGCCACA TAATTAAAGA CATAGGCGAG

6181 GTGCCCTCAG ATCTTTGTGC CTTGCTTGCT GCCAAACCTG AACTGGAAGG GGGCCTCTCC

6241 ACCGTCCAAC TTCTTTGTGT GTTTTTCCTC CTGTGGAGGA TGATGGGACA TGCCTGGACG

6301 CCCTTGGTTG CTGTGGGTTT CTTTATCCTG AATGAGGTTC TCCCAGCCGT CCTGGTCCGG

6361 AGTGTTTTCT CCTTTGGAAT GTTTGTGCTA TCCTGGCTCA CGCCATGGTC TGCGCAAGTT

6421 CTGATGATCA GACTTCTAAC AGCAGCCCTT AACAGGAACA GATGGTCACT TGCCTTTTTC

6481 AGTCTTGGTG CAGTGACCGG TTTTGTCGCA GAATTTGCGG CTACTCAGGG GCATCCGTTG

6541 CAGGCTGTGA TGAATTTGAG CACCTATGCA TTCCTGCCTC GGATGATGGT TGTGACCTCA

-continued

6601 CCGGCCCCAG TGATCGCGTG TGGTGTCGTG CACCTACTTG CCATCATTTT GTACTTGTTT

6661 AAGTACCGCG GCCTGCACCA AATCCTTGTT GGCGACGGAG TGTTCTCTGC GGCTTTCTTC

6721 TTGCGATACT TTGCCGAGGG TAAGTTAAGG GAAGGGGTGT CGCAATCCTG TGGGATGGAT

6781 CATGAGTCTC TGACTGGTGC CCTCGCTATG AGACTCAGTG ACGAGGACTT GGATTTCCTT

6841 GCGAAATGGA CTGATTTTAA GTGCTTTGTT TCTGCGTCCA ACATGAGGAA TGCAGCGGGT

6901 CAATTTATTG AGGCTGCCTA TGCTAAAGCA CTTAGAATGG AGCTTGCCCA GTTGGTGCAG

6961 GTTGACAAAG TTCGAGGTAC TTTGGCCAAA CTCGAAGCTT TTGCTGATAC CGTGGCACCC

7021 CAGCTCTCGC CCGGTGACAT TGTTGTTGCT CTCGGCCATA CGCCTGTTGG CAGTATCTTC

7081 GACCTAAAGG TTGGTAGCAC CAAGCATACT CTCCAAGCCA TTGAGACCAG AGTCCTTGCT

7141 GGGTCCAAAA TGACCGTGGC GCGCGTCGTC AACCCGACCC CCACGCCACC ACCCGCACCC

7201 GTGCCCATCC CCCTCCCACC GAAAGTCCTG GAGAATGGCC CCAACGCTTG GGGGGATGAG

7261 GACCGTTTGA ATAAGAAGAA GAGGCGCAGG ATGGAAGCCC TCGGCATCTA CGTCATGGGC

7321 GGGAAAAAGT ACCAGAAATT CTGGGACAAG AATTCCGGTG ATGTGTTTTA TGAGGAGGTC

7381 CATAATAACA TAGATGAGTG GGAGTGTCTC AGAGTTGGCG ATCCTGCCGA CTTTGACCCT

7441 GAGAAGGGAA CTCTGTGTGG ACATGTCACC ATTGAAGACA AGGCTTACCG TGTTTACGCC

7501 TCCCCATCTG GTAAGAGGTT CTTGGTCCCC GTCAACCCAG AAAATGGAAG AGTCCAATGG

7561 GAAGCTGCAA AGCTTTCTGT GGAGCAGGCC CTTGGCATGA TGAACGTCGA CGGTGAGTTG

7621 ACTGCCAAAG AACTGGAGAA ACTAAAAAGA ATAATTGACA AACTCCAGAG CCTGACTAAG

7681 GAGCAGTGTT TAAACTGCTA GCCGCCAGCG GCTTGACCCG CTGTGGTCGC GGCGGCTTGG

7741 TTGTTACTGA AACAGCGGTA AAAATAGTCA AATTTCACAA CCGGACCTTC ACCCTGGGAC

7801 CTGTGAATTT AAAAGTGGCC AGTGAGGTTG AGCTAAAAGA CGCGATTGAG CACAATCAAC

7861 ACCCGGTTGC GAGACCGGTC GATGGTGGTG TTGTGCTTCT GCGTTCCGCG GTTCCTTCGC

7921 TTATAGACGT CTTGATCTCC GGTGCTGATG CATCTCCCAA GTTACTTGCC CACCACGGGC

7981 CGGGAAACAC TGGGATCGAT GGCACGCTCT GGGATTTTGA GTCCGAAGCC ACTAAAGAGG

8041 AAGTCGCACT TAGTGCGCAA ATAATACAGG CTTGTGACAT TAGGCGCGGC GACGCCCCTG

8101 AAATTGGTCT TCCTTACAAG CTGTACCCTG TTAGGGGTAA CCCTGAGCGA GTAAAAGGGG

8161 TTCTACAAAA TACAAGGTTT GGAGACATAC CTTACAAAAC CCCCAGTGAT ACTGGAAACC

8221 CAGTGCACGC GGCTGCCTGC CTTACGCCCA ATGCCACTCC GGTGACTGAT GGGCGCTCCG

8281 TTTTGGCCAC GACCATGCCC TCCGGGTTTG AGTTGTATGT ACCAACCATA CCAGCGTCTG

8341 TCCTTGATTA CCTTGATTCC AGACCTGACT GCCCTAAACA GCTGACAGAG CACGGCTGTG

8401 AAGATGCCGC ACTAAGAGAC CTCTCCAAAT ATGACTTGTC CACCCAAGGC TTTGTTTTAC

8461 CTGGGGTTCT TCGCCTTGTA CGGAAATACC TGTTTGCCCA TGTAGGTAAG TGCCCACCCG

8521 TTCATCGGCC TTCCACTTAC CCTGCTAAGA ATTCTATGGC TGGAATAAAT GGGAACAGGT

8581 TCCCAACCAA GGATATTCAG AGCGTCCCTG AGATCGACGT TCTGTGCGCA CAGGCTGTGC

8641 GGGAAAACTG GCAAACTGTT ACCCCTTGTA CTCTTAAGAA ACAGTATTGT GGGAAGAAGA

8701 AGACTAGGAC CATACTCGGC ACAAATAACT TCATCGCGCT AGCCCACCGA GCAGCGTTGA

8761 GTGGTGTTAC CCAGGGCTTC ATGAAGAAGG CGTTTAACTC GCCCATCGCC CTCGGAAAAA

8821 ACAAGTTTAA GGAGCTACAG ACTCCGGTCC TGGGCAGGTG TCTAGAAGCT GATCTTGCAT

8881 CCTGCGACCG ATCCACACCC GCAATTGTCC GCTGGTTTGC CGCCAACCTC CTTTATGAGC

8941 TTGCCTGCGC TGAAGAGCAT CTACCGTCGT ACGTGCTAAA CTGCTGCCAC GACTTACTGG

-continued

```
9001 TCACGCAGTC CGGCGCAGTG ACTAAGAGAG GTGGCCTGTC GTCTGGCGAC CCGATCACCT
9061 CTGTGTCTAA CACCATTTAC AGTTTGGTGA TCTACGCACA GCATATGGTG CTCAGTTACT
9121 TCAAAAGTGG TCACCCCCAT GGCCTCTTAT TCTTACAGGA CCAGCTAAAG TTTGAGGACA
9181 TGCTTAAGGT TCAACCCCTG ATCGTCTATT CGGACGACCT CGTGCTGTAT GCCGAGTCTC
9241 CCACTATGCC AAACTACCAC TGGTGGGTTG AGCATCTGAA TTTGATGCTG GGGTTTCAGA
9301 CGGACCCAAA GAAGACAGCC ATAACAGACT CGCCATCATT TTTGGGCTGT AGAATAATAA
9361 ATGGACGCCA GCTAGTCCCC AACCGTGACA GGATTCTCGC GGCCCTCGCC TACCACATGA
9421 AGGCGAGTAA TGTTTCTGAA TACTACGCCT CTGCGGCTGC AATACTCATG GACAGCTGTG
9481 CTTGTTTGGA GTATGATCCT GAATGGTTCG AAGAACTTGT AGTTGGAATA GCGCAATGCG
9541 CCCGCAAGGA TGGCTACAGC TTTCCCGGCC CGCCGTTCTA TATATCCATG TGGGAAAAAC
9601 TCAGATCCAA TTATGAGGGG AAGAAGTCGA GAGTGTGCGG GTACTGCGGG GCCCCGGCCC
9661 CGTATGCTAC CGCCTGTGGT CTCGACGTCT GCATTTACCA CACTCACTTC CACCAGCATT
9721 GTCCAGTCAT AATCTGGTGT GGCCATCCAG CCGGTTCTGG TTCTTGTAGT GAGTGCAGAT
9781 CCCCTGTGGG GAAAGGCACA AGCCCTTTAG ACGAGGTGCT GGAACAAGTC CCGTACAAGC
9841 CCCCACGGAC CGTTATCATG CATGTGGAGC AGGGTCTTAC CCCCCTTGAC CCAGGCAGAT
9901 ATCAGACTCG CCGCGGGTTA GTCTCCGTCA GGCGCGGGAT CAGGGGAAAT GAGGTTGAGC
9961 TACCAGACGG TGATTATGCC AGTACCGCCT TGCTCCCTAC CTGCAAAGAG ATCAACATGG
10021 TCGCTGTCGC TTCTAATGTA TTGCGCAGCA GGTTCATCAT TGGTCCACCC GGTGCGGGGA
10081 AAACATACTG GCTACTTCAA CAGGTCCAGG ATGGTGATGT TATTTACACA CCAACTCACC
10141 AGACCATGCT TGACATGATT AGAGCTTTGG GGACGTGCCG GTTCAACGTC CCGGCAGGCA
10201 CAACGCTGCA ATTCCCGGTC CCCTCCCGCA CCGGTCCGTG GGTTCGCATC CTAGCCGGCG
10261 GTTGGTGTCC TGGCAAGAAT TCCTTCCTGG ATGAAGCAGC GTATTGCAAT CACCTTGATG
10321 TCTTAAGGCT TCTTAGCAAA ACTACCCTCA CCTGTCTGGG AGACTTTAAA CAACTCCACC
10381 CAGTGGGTTT TGATTCTCAT TGCTATGTTT TTGACATCAT GCCTCAAACT CAACTGAAGA
10441 CCATCTGGAG GTTTGGACAA AATATCTGTG ATGCCATCCA ACCAGATTAC AGGGACAAAC
10501 TCATGTCCAT GGTCAACATG ACCCGTGTAA CCTACGTGGA AAAACCTGTC AGGTATGGGC
10561 AAGTCCTCAC CCCCTACCAC AGGGACCGAG AGGACGACGC CATCACCATT GACTCCAGTC
10621 AAGGCGCCAC ATTTGATGTG GTTACACTGC ATTTGCCCAC TAAAGATTCA CTCAACAGGC
10681 AAAGAGCCCT TGTTGCTATC ACCAGGGCAA GACATGCTAT CTTTGCGTAT GATCCACACA
10741 GGCAGCTGCA GAGCCTGTTT GATCTTCCTG CAAAAGGTAC ACCCGTCAAC CTTGCAGTGC
10801 ACCGCGATGG GCAGCTGATC GTGCTAGATA GAAATAACAA TGAATGCACG GTTGCTCAGG
10861 CTCTAGGTAA CGGGGATAAA TTTAGGGCCA CAGACAAGCG CGTTGTAGAT TCTCTCCGCG
10921 CCATTTGTGC TGATCTAGAA GGTACGAGCT CTCCGCTCCC CAAGGTCGCA CACAACTTGG
10981 GATTTTATTT CTCACCTGAT TTAACACAGT TTGCTAAACT CCCAGCAGAA CTTGCACCTC
11041 ACTGGCCCGT GGTGACAGCC CAGAACAATG AAAAGTGGCC AGATCGGCTG GTTACTAGCC
11101 TTCGCCCTAT CCATAAATAT AGCCGCGCGT GCATCGGTGC CGGCTATATG GTGGGCCCCT
11161 CGGTGTTTCT AGGCACTCCT GGGGTCGTGT CATACTATCT CACAAAATTT GTTAAGGGCG
11221 AGGCTCAAGT GCTTCCGGAG ACGGTTTTCA GCACCGGCCG AATTGAGGTA GACTGCCGGG
11281 AATATCTTGA TGACCAGGAG CGAGAAGTTG CTGCGTCCCT CCCACATGCC TTCATTGGCG
11341 ACGTCAAAGG CACTACCGTT GGAGGGTGCC ACCATGTCAC TTCCAGATAC CTCCCGCGCT
11401 TCCTTCCCAA GGAATCAGTT GCGGTAGTCG GGGTTTCAAG TCCCGGAAAA GCCGCGAAAG
```

-continued

11461 CATTGTGCAC ACTAACAGAT GTGTACCTCC CAGACCTTGA AGCCTATCTC CACCCGGAGA

11521 CCCCGTCCAA GTGCTGGAGA ATGATGTTGG ACTTCAAGGA AGTTCGACTA ATGGTCTGGA

11581 AAGACAAAAC AGCCTATTTC CAACTTGAAG GTCGCTATTT CACCTGGTAT CAGCTTGCCA

11641 GCTATGCCTC GTACATCCGT GTTCCTGTCA ACTCTACGGT GTACTTGGAC CCCTGCATGG

11701 GCCCCGCCCT TTGCAACAGG AGAGTCGTCG GGTCCACTCA TTGGGGGGCT GACCTTGCGG

11761 TCACCCCTTA TGATTACGGC GCTAAAATCA TCCTGTCTAG CGCGTACCAT GGTGAAATGC

11821 CCCCCGGATA CAAGATTCTG GCGTGCGCGG AATTCTCGGT GGACGACCCA GTCAAGTACA

11881 AACATACCTG GGGGTTTGAA TCGGATACAG CGTATCTGTA TGAGTTCACC GGAAACGGTG

11941 AGGACTGGGA GGATTACAAT GATGCGTTTC GTGCGCGCCA GGAAGGGAAA ATTTATAAGG

12001 CTACTGCCAC CAGCATGAAG TTTTATTTTC CCCCGGGCCC TGTCATTGAA CCAACTTTAG

12061 GCCTGAATTG AAATGAAATG GGGTCCATGC AAAGCCTTTT TAGCAAAATT GGCCAACTTT

12121 TTGTGGATGC TTTCACGGAG TTCTTGGTGT CTATTGTTGA TATCATTATA TTTTTGGCCA

12181 TCTTGTTTGG CTTCACCATC GCCGGTTGGC TGGTGGTCTT TTGCATCAGA TTGGTTTGCT

12241 CCGCGATACT CCGTGCGCGC CCTGCCATTC ACCCTGAGCA ATTACAGAAG ATCTTATGAG

12301 GCCTTTCTTT CCCAGTGCCA AGTGGACATT CCCACCTGGG GAACTAAACA CCCTTTGGGG

12361 ATGTTTTGGC ACCATAAGGT GTCAACCCTG ATTGATGAGA TGGTGTCGCG TCGAATGTAC

12421 CGCACCATGG AAAAAGCAGG ACAGGCTGCC TGGAAACAGG TGGTGAGCGA GGCTACGCTG

12481 TCTCGCATTA GTAGTTTGGA TGTGGTGGCT CATTTTCAGC ATCTTGCCGC CATTGAAGCC

12541 GAGACCTGTA AATATTTGGC CTCCCGGCTG CCCATGCTAC ATAACCTGCG CATGACAGGG

12601 TCAAATGTAA CCATAGTGTA TAATAGTACT TTAAATCAGG TGTTTGCTAT TTTCCCGACC

12661 CCTGGTTCCC GGCCAAAGCT TCATGATTTT CAGCAATGGC TAATCGCTGT ACACTCCTCC

12721 ATATTCTCCT CTGTTGCAGC TTCTTGTACT CTTTTTGTTG TGCTGTGGTT GCGGATGCCG

12781 ATGCTACGTA CTGTTTTTGG TTTCCGCTGG TTAGGGGCAA CTTTTCCTTC GAGCTCACGG

12841 TGAATTACAC GGTGTGCCCA CCTTGCCTCA CCCGGCAGGC GGCCGCACAG GCCTACGAAC

12901 CCGGTAGGTC TCTTTGGTGC AGGATAGGGT ACGATCGGTG TGGAGAGGAC GACCATGACG

12961 AGCTAGGGTT TATGGTACCG TCTGGCCTCT CCAGCGAAGG CCACTTGACC AGTGTTTACG

13021 CCTGGTTGGC GTTCTTGTCC TTCAGCTACA CAGCCCAGTT CCACCCCGAG ATATTCGGGA

13081 TAGGGAATGT GAGTCAAGTT TATGTTGACA CCAAACATCA ACTCATCTGC GCCAAACATG

13141 ACGGGCAGAA CACCACCTTG CCTCGTCATG ACAATATTTC AGCTGTGTTT CAGACCTATT

13201 ACCAACATCA AGTCGACGGC GGCAATTGGT TTCACCTAGA ATGGCTGCGT CCCTTCTTTT

13261 CCTCATGGTT GGTTTTAAAT GTCTCTTGGT TTCTCAGGCG TTCGCCTGCA AACCATGTTT

13321 CAGTTCGAGT CTTGCAGACA TTAAGACCAA CACCACCGCA GCGGCAGGCT TTGCTGTCCT

13381 CCAAGACATC AGTTGCCTTA GGCATCGCAA CTCGGCCCCT GAGGCGCTTC GCAAAATCCC

13441 TCAGTGCCGT ACGGCGATAG GGACACCTGT GTATATTACC ATCACAGCCA ATGTGACAGA

13501 TGAGAATTAT TTACATTCTT CTGATCTCCT CATGCTCTCT TCTTGCCTTT TCTACGCTTC

13561 TGAGATGAGT GAAAAGGGAT TTAAGGTGGT TTTTGGCAAT GTGTCAGGCA TCGTGGCTGT

13621 GTGTGTCAAT TTTACCAGCT ACGTCCAACA TGTCAGGGAG TTTACCCAAC GCTCCTTGAT

13681 GGTCGACCAT GTGCGGCTGC TCCATTTCAT GACACCTGAG ACCATGAGGT GGGCAACCGT

13741 TTTAGCCTGT CTTGTTGCCA TTCTGTTGGC AATTTGAATG TTTAAGTATG TTGGGGAAAT

13801 GCTTGACCGC GGGCTGTTGC TCGCGATTGC TTTCTTTGTG GTGTATCGTG CCGTTCTGTT

-continued

13861 CCACTGTGCT CGTCGACGCC AACGGCAACA GCAGCTCTCA TCTGCAATTG ATTTACAACT
13921 TGACGCTATG TGAGCTGAAT GGCACGGATT GGCTAGCTAA TAGATTTGAT TGGGCAGTGG
13981 AGAGCTTTGT CATCTTTCCT GTTTTGACTC ACATAGTCTC CTATGTTGCC CTCACCACCA
14041 GCCATTTCCT TGACACAATT GCTTTAGTCA CTGTATCTAC CGCCGGTTTT CTTCACGGGC
14101 GGTATGTCCT GAGTAGCATC TACGCGGTCT GTGCCCTGGC TGCGTTGACT TGCTTCGTCA
14161 TTAGGTTTGT AAAGAATTGC ATGTCTTGGC GCTACTCATG TACCAGATAT ACCAATTTTC
14221 TTCTGGACAC TAAGGGCAGA CTCTATCGTT GGCGGTCGCC TGTCATCATA GAGAAGAGGG
14281 GCAAAGTTGA GGTCGAAGGT CATCTGATCG ATCTCAAAAG AGTTGTGCTT GATGGTTCCG
14341 TGGCAACCCC TATAACCAGA GTTTCAGCGG AACAATGGGG TCGTCCTTAG ATGACTTTTG
14401 TCATGATAGT GCGGCTCCAC AAAAGGTGCT TTTGGCATTT TCTATTACCT ACACGCCAGT
14461 GATGATATAT GCCCTAAAGG TGAGTCGCGG CCGACTGCTA GGGCTGCTGC ACCTTTTGAT
14521 TTTCCTGAAC TGTGCTTTCA CCTTTGGGTA CATGACATTC ACGCACTTTC AGAGTACAAA
14581 TAAGGTCGCG CTCACTATGG GAGCAGTAGT TGCACTCCTT TGGGGGGTGT ACTCAGCCAT
14641 AGAAACCTGG AAATTCATCA CCTCCAGATG CCGTTTGTGC TTGCTAGGCC GCAAGTACAT
14701 TCTGGCCCCT GCCCACCACG TTGAAAGTGC CGCAGGCTTT CATCCGATTG CGGCAAATGA
14761 TAACCACGCA TTTGTCGTCC GGCGTCCCGG CTCCACTACG GTCAACGGCA CATTGGTGCC
14821 CGGGTTGAAA AGCCTCGTGT TGGGTGGCAG AAAAGCTGTT AAACAGGGAG TGGTAAACCT
14881 TGTCAAATAT GCCAAATAAC AACGGCAAGC AGCAGAAGAG AAAGAAGGGG GATGGCCAGC
14941 CAGTCAATCA GCTGTGCCAG ATGCTGGGTA AGATCATCGC CCAGCAAAAC CAGTCTAGAG
15001 GCAAGGGACC GGGGAAGAAA AATAAGAAGA AAAACCCGGA GAAGCCCCAT TTTCCTCTAG
15061 CTACTGAAGA TGATGTCAGA CATCACTTTA CCCCTAGTGA GCGGCAATTG TGTCTGTCGT
15121 CAATCCAGAC TGCCTTTAAT CAAGGCGCTG GGACTTGCAC CCTGTCAGAT TCAGGGAGGA
15181 TAAGTTACAC TGTGGAGTTT AGTTTGCCTA CGCATCATAC TGTGCGCTTG ATCCGCGTCA
15241 CAGCATCACC CTCAGCATGA TGGGCTGGCA TTCTGAGGCA TCCCAGTGTT TGAATTGGAA
15301 GAATGTGTGG TGAATGGCAC TGATTGACAT TGTGCCTCTA AGTCACCTAT TCAATTAGGG
15361 CGACCGTGTG GGGGTAATAT TTAATTGGCG AGAACCACAC GGCCGAAATT AAA

The cDNA consensus sequence of PRRS strain SD 03-15 at P83 has been assigned GenBank Accession number KU131560 (SEQ. ID. NO:6). The cDNA consensus sequence designated SEQ. ID. NO:6 is:

1 ATGATGTGTA GGGTATTCCC CCTACATACA CGACACTTCT GGTGTTTGTG TACCTTGGAG
61 GCGTGGGTAC AGCCCCGCCC CACCCCTTGG CCCCTGTTCT AGCCCAACAG GTATCCTTCT
121 CCCTCGGGGC GAGCGCGCCG CCTACTGCTC CCTTGCAGTA GGAAGGACCT CCCGAGTATT
181 TCCGGAGAGC ACCTGCTTTA CGGGATCTCC ACCCTTTAAC CATGTCTGGG ACGTTCTCCC
241 GGTGCATGTG CACCCCGGCT GCCCGGGTAT TTTGGAACGC CGGCCAAGTC TTTTGCACAC
301 GGTGTCTCAG TGCGCGGTCT CTTCTCTCTT CAGAACTTCA GGACACTGAC CTCGGTGCAA
361 TTGGATTGTT CCACAAGCCT AGGGACAAGC TTCACTGGAA AGTCCCCATC GGCATCCCTC
421 AGGTGGAATG TACTCCATCC GGGTGCTGTT GGCTCTCAGC TATATTCCCT ATAGCACGTA
481 TGACCTCTGG CAATCATAAC TTCCTCCAAC GACTTGTTAA GGTTGCTGAT GTTTTGTACC
541 GCGACGGTTG CTTGGCACCT CGACACCTTC GTGAACTCCA AGTTTACGAG CGCGGCTGCA
601 ACTGGTACCC GATCACGGGG CCCGTACCCG GGATGGGTTT GTTTGCGAAC TCCATGCACG
661 TATCCGACCA GCCGTTCCCT GGAGCCACCC ATGTGTTGAC TAACTCGCCT CTGCCTCAAC

-continued

721 GGGCGTGCCG GCAACCGTTC TGTCCATTTG AGGAAGCTCA TTCTAACGTG TATAGGTGGA

781 ATAAATTTGT GATTTTCACG GACTCCACTC TCAACGGCCA ATCTCGCATG ATGTGGACGC

841 CGGGATCCGA TGATTCAGCC GCCTTGGAGG CGCTACCGCC TGAATTAGAA CGTCAGGTCG

901 GAATCCTCAT TCGGAGTTTC CCTGCTCATC ACCCCGTTAA CCTGGCCGAC TGGGAGCTCA

961 CTGAGACCCC TGAGAATGGC TTCTCCTTCA GCACGTCTCA TTCTTGTGGT TATCTTGTCC

1021 AAAACCCCGA TGTGTTTGAT AGCAAGTGCT GGCTCACTTG CTTTTCGGGC CAGTCGGTCG

1081 AAGTGCGCCG CTGTGAAGAA CATTTAGCCA ACGCCCTTGG TTACCAAACC AAGTGGGGCG

1141 TGCACGGTAA GTACCTTCAG CGCAGGCTCC AAGTTCGCGG CATTCGTGCT GTAGTCGATC

1201 CTGATGGCCC CATTCACGTT GAAGCGCTGT CTTGCTCCCA GTCTTGGATC AGGCACCTGA

1261 CTCTGAATAA TGGTGTTACC CCAGGATTCG TTCGCCTGAC ATCCATTCGC ATTGTGCCGA

1321 ACACAGAGCC TACCACTTTC CGGATCTTTC GGTTTGGAGC GCATAAGTGG TATGGCGCTG

1381 CTGGCAAACG GGCTCGTGCC AAGCGTGCCG CTAAAAGTGG GAAAGATTCG GCTTCCACTC

1441 CCAAGGTTGC CCAGCCGGCC CTTACCTGTG GAGTCACCAC CTACTCTCCA CCAACAGACG

1501 GGTCTTGCGG TTGGCATGTC CTTGCCGCCA TAATGAACCG GATGATGAAC GGTGACTTCA

1561 CGTCCCCACT GCCTCAGTAC AATAGACCAG AAGACGATTG GGCTTCTGAT TATGATCTTG

1621 CTCAGGCGAT TCAATGTCTA CAACTGCCTG CAACCGTGGT TCGGAATCGT GCCTGTCCTA

1681 ACGCCAAGTA CCTTGTAAGA CTTAACGGGG TTCACTGGGA GGTAGAGGTG AGATCTGGAA

1741 TGGCTCCCCG CTCCCTTTCT CGTGAATGTG TAGTTGGCGT TTGCTCTGAA GGTTGTGTTG

1801 CTCCGCCTTA TCCAGCGGAC GGGCTTCCTA AACGCGCACT AGAGGCCTTG GCGTCTGCTT

1861 ACAGACTACC CTCCGATTGT GTTAGCTCTG GCATTGATGA CTTTCTTGCT AATCCACCCC

1921 CTCAGGAATT TTGGACTCTT GACAAAATGC TGACCTCCCC GTCACCAGAA CGGTCCGGCT

1981 TCTCTAGTTT GTATAAGTTA CTGTTAGAGG TTGTTCCGCA AAAGTGTGGT GCCACGGAAG

2041 GGGCTTTCAC CTATGCTGTT GAGAGGATGT TAAAGGATTG TCCGAGCTCT GAACAGGCCA

2101 TGGCCCTTCT GGCAAAAATT AAAGTTCCAT CCTCAAAGGC CCCGTCTGTG TCCCTGGACG

2161 GGTGTTTCCC TGCGGATATT CCGGCTGATT TCGAGCCAGC GTCTCGGGAA AGGCCCCGAA

2221 GTTCCAGCGT TGCTGTTGCC CTGTGTTCAC CGGATGCAGA AAGGTTCGAG GAAGTACCCC

2281 CAGAAGAAGT TCAAGAGAGA GGCTACAAGG CCGTCAACTC TGCACTCCTT GCCGAAAACC

2341 CCAATGATGA ACAGGCACAG GTGGTTGCCG GTGAACAACT GAAGCTCGGC GGTTGTAGTT

2401 TGGCAATCGG GAATGCTCAG TCCACTCCAG GCTCCATGGA AGAGAACATG CGCAATAGCC

2461 GGGAAGACGA ACCACTAGAT TTGTCCCTAC CAGCACTAGC TACCACGACG ACCCTTGTGA

2521 GAGAGCGAAT ACTCGACAAC CCAGGTCCTG ATGCCGGTAC CCTCCCTGCC ACCGTTCGAG

2581 AATTTGTCTC GACAGGGCCT ATGCTCCGTC ATGTTGAGCA TTGTGGCACG GAGTCTGGCG

2641 ACAGCAGTTC ACCTTTGGAT CTGTCTTATG CGCAAACTCC GGACCAGCCT TTAAATCTGT

2701 CCCTGGCCGC TTGGCCGGTG AAGACCACCG CGTCTGACCC TGGCTGGGTC CACGGTAGGT

2761 GCGAGCCTGT CTTTGTAAAG CCTCGAAAAG CTTTTTCTGA TGGCGATTCA GCCTTTCAGT

2821 TCGGGGGGCT TTCTGAGTCC AGCTCTGTCA TCGAGTTTGA CCGAACAAAA GATGCATCGG

2881 AGGTTGACGC TCCTGTCGGC TTGACGACTT CGAACGAGGC CCTCTCTGTG GTCGACCCTT

2941 TCGAATTTGC CGAACTCAAG CGCCCGCGTT TCTCCGCACA AGCCTTAATT GACCGAGGCG

3001 GCCCGCTTGC CGATGTCCAT GCAAAAATAA AGCACCGGGT GTATGAACAA TGCCTTCAAG

3061 CTTGTGAGCC TGGTAGCCGT GCAACCCCAG CCACCAAGAA GTGGCTCGAC AAAATGTGGG

-continued

```
3121 ACAGGGTGGA CATGAAAACT TGGCGCTGCA CCTCGCAGTT CCAAGCTGGT CGCATCCTTG

3181 CATCCCTCAA ATTCCTTCCT GACATGATTC AAGACGCACC GCCTCCTGTT CCCAGGAAGA

3241 ACCGAGCTAG TGACAACGCC GGTTTGAAGC AACTGGTGGC ACAGTGGGAT AGGAAATTGA

3301 GTGGAACCCC CCCCCCAAAA CCGGCTGGGT CAGTGCTTGA CCAGGCCGTC CCTCCACCCA

3361 CGGACGTCCA GCAAGAAGAT GTCACTCCTT CCGGCGGGCC ACTCCATGCG CCGGATTTCC

3421 CTAGTCGAGT TAGCACGAGC GGGGGTTGGA AAAGCCTTAT ACTTTCCGGG ACCCGTCTCG

3481 CAGGGTCTGT CAGTCAGCGC CTCATGACAC GGGTTTTTGA AGTTTTCTCC CATCTCCCAG

3541 CTTTTGCGCT CACACTTTTC TCGCCGCGGG GCTCTATGGC TCCAGGCGAT TGGTTGTTTG

3601 CAGGTATTGT TTTACTTGCT CTCTTGTTCT GTCGTTTTTA CCCGATACTC GGATGCCTTC

3661 CCTTATTGGG TGTCTTTTCT GGGTCTGTGC GGCGTGTTCG TCTGGGTGTT TTTGGTTCTT

3721 GGATGGCTTT TGCTGTATTT CTATTCTCGA CTCCATCCAA CCCAGTCGGT TCTTCTTGTG

3781 ACCACGATTC GCCGGAGTGT CATGCTGAGC TTTTGGTTCT TGAGCAGCGC CAACTTTGGG

3841 AACCTGTGCG CGGCCTTGTG GTCGGCCCCT CGGGCCTCCT ATGTGTCATT CTTGGCAAGT

3901 TACTCGGTGG GTCACGTTAT CTCTGGCATG TTCTCCTACG TTTATGCATG CTTACAGATT

3961 TGGCCCTTTC TCTTGTTTAT GTGGTGTCCC AGGGGCGTTG TCACAAGTGT TGGGGAAAGT

4021 GTATAAGGAC GGCTCCTGCT GAGGTAGCAC TTAATGTATT TCCTTTCTCG CGCGCCACCC

4081 GTAGCTCTCT TGTATCCTTG TGTGATCGGT TCCAAGCGCC TAAAGGAGTT GATCCTGTGC

4141 ACTTGGCAAC GGGTTGGCAC GGGTGTTGGT GTGGCGAGAG CCCCGTTCAT CAATCACACC

4201 AAAAGCCAAT AACCTATGCC AATTTGGATG AAAAGAAAAT ATCTGCCCAA ACGGTGGTTG

4261 CTGTCCCATA CGACCCCAGC CAGGCTATCA AATGCCTGAA AGTTCTGCAG GCGGGAGGGG

4321 CTATCGTAGA CCAGCCTACA CCTGAAGTTG TTCGCGTGTC CGAGGTCCCC TTCTCAGCCC

4381 CATTTTTCCC AAAAGTTCCT GTCAACCCGG ATTGCAGGAT TGTGGTGGAT TCGGACACTT

4441 TTGTGGCTGC GGTCCGCTGC GGTTACTCGA CAGCACAACT GGTCCTGGGC CGGGGCAATT

4501 TTGCCAAGCT AAATCAGACC CCCCTCAGGA GCTCTACCTC CACCAAAACG ACTGGGGGGG

4561 CCTCTTACAC CCTTGCTGTA GCTCAAGTGT CTGCGTGGAC TCTTGCCCAT TTCATCCTCG

4621 GCCTTTGGTT CACATCACCT CAAGTGTGTG GCCGAGGGAC CGCTGATCCA TGGTGTTCAA

4681 ATCCCTTTTC ATACCCTGCC TATGGCCCTG GAGTTGTATG CTCCTCTCGA CTTTGTGTGT

4741 CTGCCGATGG GGTCACCCTG CCATTGTTTT CAGCTGTGGC ACAACTCTCC GGCAGAGAGG

4801 TGGGGATTTT TATTTTGGTG CTTGTCTCCC TGATAGCTTT GGCCCATCGC TTGGCTCTTA

4861 AGGCAGACTT GTTAGTGGTC TTTTTGGCTT TTTGTGCTTA CGCCTGGCCC ATGAGTTCCT

4921 GGCTAATCTG CTTCTTTCCT ATACTCTTAA AGTGGATCAC CCTCCACCCT CTCACCATGC

4981 TTTGGGTGCA CTCATTCTTG GTGTTTTGCC TGCCAGCAGC CGGCGTCCTC TCACTAGGGA

5041 TAACTGGCCT TCTTTGGGCA ATCGGCCGCT TTACCCAGGT TGCCGGGATT ATTACACCTT

5101 ATGACATCCA CCAGTACACC TCCGGGCCGC GTGGTGCAGC TGCTGTGGCC ACAGCCCCAG

5161 AAGGCACTTA TATGGCCGCC GTCCGGAGAG CTGCTTTAAC TGGGCGATCT TTAATATTCA

5221 CCCCGTCAGC AGTTGGATCC CTCCTCGAAG GTGCTTTCAG GACTCATAAA CCCTGTCTTA

5281 ATACTGTGAA TGTTGTGGGC TCTTCCCTTG GTTCCGGAGG CGTTTTCACC ATTGATGGCA

5341 GAAGAACTGT TGTCACTGCT GCTCATGTGT TGAATGGCGA CACAGCTAGA GTTACCGGCG

5401 ACTCCTACAA CCGCATGCAC ACTTTCAAGA CCAATGGTGA TTATGCCTGG TCCCATGCTG

5461 ATGACTGGCA GGGCATTGCC CCCGTGGTCA AGGTAGTGAA GGGGTACCGC GGTCGTGCTT

5521 ATTGGCAAAC ATCAACTGGT GTCGAACCCG GCATCATTGG AGAAGGGTTT GCCTTCTGTT
```

-continued

5581 TCACTAATTG TGGTGATTCG GGGTCACCCG TCATCTCAGA ATCCGGTGAT CTCATCGGAA

5641 TTCACACCGG TTCAAACAAA CTCGGTTCTG GTCTTGTGAC GACCCCTGAA GGGGAGACCT

5701 GTACCATCAA AGAAACCAAG CTCTCCGACC TTTCCAGACA TTTTGCAGGC CCTAGTGTTC

5761 CTCTTGGTGA CATTAAATTA AGCCCGGCCA TCATCCCTGA TGTAACATCT ATTCCGAGTG

5821 ACTTGGCATC GCTCCTAGCC TCTGTCCCTG TGGTGGAAGG CGGCCTCTCG ACCGTTCAAC

5881 TTCTGTGTGT CTTTTTCCTT CTCTGGCGCA TGATGGGCCA TGCCTGGACA CCCATTGTTG

5941 CCGTGGGCTT CTTTCTGCTG AATGAAATCC TCCCAGCAGT TTTGGTCCGA GCCGTGTTTT

6001 CTTTTGCACT CTTTGTGCTT GCATGGGTCA CCCCCTGGTC CGCACAGGTG TTGATGATTA

6061 GACTCCTCAC GGCATCTCTC AACCGCAACA AGCTCTCTCT GGTGTTCTAC GCACTCGGGG

6121 GTATCGTCGG TTTGGCCGCT GAAATCGGGA CTTTCGCTGG CAGATTGCCT GAATTGTCTC

6181 AAGCCCTTTC GACCTACTGT TTCTTGCCTA GGGCCCTTGC CATGGCCAGT TGTGTCCCCA

6241 TCGTCATTAT TGGCGGACTT CATGCCCTCG GTGTAATTCT GTGGTTGTTC AAATACCGGT

6301 GCCTCCACAA CACGCTGGTT GGTGATGGGT GTTTTTCAAG TGCCTTCTTC CTGCGCTATT

6361 TTGCGGAGGG CAATCTGAGG AAAGGTGTTT CACAGTCCTG TGGCATGAAT AACGAGTCTC

6421 TGACGGCTGC TCTGGCTTGC AAGCTGTCGC AGGCTGATCT TGAATTTTTG TCCAGTTTAA

6481 CGAACTTCAA GTGCTTTGTG TCTGCTTCAA ATATGAAAAA TGCCGCCGGC CAGTACATTG

6541 AAGCAGCTTA TGCCAAGGCC TTGCGCCAAG AGTTGGCCTC TCTAGTTCAG GTTGATAAAA

6601 TGAAAGGAGT TTTGTCCAAG CTCGAGGCCT TTGCTGAAAC AGCCACCCCG TCCCTTGACA

6661 CAGGTGACGT GGTTGTTTTG CTTGGGCAGC ATCCTCACGG GTCTATCCTC GATATTAATG

6721 TGGGGACTGA AAGGAAAACT GTGTCCGTGC AAGAGACCCG GAACCTAGGC GGCTCCAAAT

6781 TCAGTGTTTG CACTGTCGTG TCCAACACAC CCGTGGACGC CTTAACCGGC ATCCCACTCC

6841 GGACACCAAC CCCTCTTTTT GAGAATGGTC CGCGTCATCG CGGTGAGGAA GACGATCTCA

6901 AAGTCGAGAG GATGAAGAAA CACTGTGTAT CCCTCGGCTT CCACAACATC AATGGCAAAG

6961 TCTACTGTAA GATCTGGGAT AAGTCTACCG GTGACACCTT TTACACCGAC GATTCCCGGT

7021 ATACCCACGA CCATGCTTTT CAGGACAGGT CAGCCGACTA CAGAGACAGG GACTACGAAG

7081 GTGTGCAAAC CGCCCCCCAA CAAGGCTTTG ATCCAAAGTC TGAAACCCCT GTTGGCACTG

7141 TAGTGATCGG CGGTATCACG TATAACAGGT ACCTGATTAA AGGTAAGGAG GTCCTGGTCC

7201 CCAAGCCTGA CAACTGCCTC GAAGCTGCCA AGCTGTCCCT TGAGCAGGCT CTCGCTGGGA

7261 TGGGCCAAAC TTGCGACCTT ACGGCTGCCG AGGTGGAAAA GCTGAAGCGC ATCATTAGTC

7321 AACTCCAAGG TTTGACCACT GAACAGGCTT TAAACTGTTA GCCGCCAGCG GCTTGACCCG

7381 CTGTGGCCGC GGCGGCTTAG TAGTGACTGA AACGGCGGTA AAAATTGTAA AATATCACAA

7441 CAGAACTTTC ACCTTAGGCC CTTTTGACCT GAAAGTCACT ACCGAGGCAG AGGTCAAGAA

7501 ATCAGCTGAG CAGGGCCACG CTGTTGTGGC AAATTTATGT TCTGGTGTCG TCTTGATGAG

7561 ACCTCACCCA CCGTCTCTTG TTGACGTTCT TTTGAAACCC GGACTTGACA CAAAACCCGG

7621 CATTCAGCCA GGGCATGGGG CCGGGAATAT GGGCGTGGAA GGTTCTATTT GGGATTTCGA

7681 AACCGCACCT ACAAAGGCAG AACTCGAGTT ATCCAAGCAA ATAATTCAAG CATGTGAAGT

7741 TAGGCGCGGG GACGCCCCGA ACCTCCAACT CCCTTACAAG CTCTATCCTG TTAGGGGGGA

7801 TCCTGAGCGG CATGAGGGCC GCCTTATCAA CACCAGGTTT GGAGATTTAT CTTACAAAAC

7861 TCCTCAAGAC ACCAAGTCCG CAATCCACGC GGCTTGTTGC CTGCACCCCA ACGGGGCCCC

7921 CGTGTCTGAT GGTAAATCAA CACTAGGTAC CACTCTTCAA CATGGTTTTG AGCTTTACGT

-continued

7981 CCCTACTGTG CCTTATAGTG TCATGGAGTA CCTCGATTCA CGCCCTGACA CCCCTTTTAT
8041 GTGCACCAAA CATGGCACTT CCAAGGCTGC TGCAGAGGAC CTTCAAAAAT ACGACCTGTC
8101 CACTCAAGGC TTCGTCCTGC CTGGGGTCCT ACGCCTAGTA CGTAGATACA TTTTTGGCCA
8161 TATTGGTAAG GCGCCGCCAT TGTTCCTCCC ATCAACCTAT CCCGCCAAGA ACTCTATGGC
8221 AGGGATCAAT GGCCAGAGAT TCCCAACAAA GGACGTTCAG AGCATACCTG AAATTGATGA
8281 AATGTGTGCC CGCGCCGTCA AAGAGAATTG GCAAACTGTG ACACCTTGTA CCCTCAAGAA
8341 ACAGTATTGT TCCAAGCCCA AAACCAGGAC CATCCTAGGC ACTAACAACT TTATTGCCTT
8401 GGCTCACAGA TCGGCGCTCA GTGGTGTTAC CCAGGCATTC ATGAAGAAGG CTTGGAAGTC
8461 CCCAATTGCC TTGGGAAAAA ACAAATTCAA GGAGCTGCAT TGCACCGTCG CCGGCAGGTG
8521 TCTTGAGGCT GACTTGGCCT CCTGTGACCG CAGCACCCCC GCCATTGTGA GATGGTTCGT
8581 CGCCAACCTC CTGTATGAAC TTGCGGGATG TGAAGAGTAC TTGCCTAGCT ATGTACTTAA
8641 TTGCTGCCAT GACCTTGTGG CAACACAGGA TGGTGCCTTC ACAAAACGCG GTGGCCTGTC
8701 GTCCGGGGAC CCCGTCACCA GTGTGTCTAA CACCGTATAT TCGCTGGTAA TCTATGCCCA
8761 GCACATGGTG TTGTCAGCCT TGAAAATGGG TCATGAAATC GGTCTTAAGT TCCTCGAGGA
8821 ACAGCTCAGA TTCGAGGACC TCCTCGAAAT TCAGCCTATG TTGGTATACT CTGATGACCT
8881 CGTTTTGTAC GCTGAAAGAC CCACTTTTCC TAATTATCAC TGGTGGGTCG AGCACCTTGA
8941 CCTAATGCTG GGTTTTAAAA CGGACCCAAA GAAGACCGTC ATAACTGATA AACCCAGCTT
9001 CCTCGGCTGC AGAATTGAGG CAGGGCGGCA GCTGGTCCCC AATCGCGACC GCATCCTGGC
9061 TGCTCTCGCA TATCACATGA AGGCGCAGAA TGCCTCAGAG TATTATGCGT CTGCTGCCGC
9121 AATCCTGATG GATTCATGCG CTTGCATTGA TCATGACCCC GAGTGGTATG AGGACCTCAT
9181 CTGCGGTATT GCCCGATGCG CCCGCCAAGA TGGTTATAGC TTCCCAGGTC CGGCGTTTTT
9241 CATGTCTATG TGGGAGAGGC TGAGAAGTCA CAATGAAGGG AAGAAATTCC GCCACTGCGG
9301 CATCTGTGAC GCCAAAGCCG ACTATGCATC CGCCTGTGGG CTCGATCTAT GTTTGTTCCA
9361 CTCGCACTTT CATCAACACT GTCCCGTCAC TCTGAGCTGC GGTCACCATG CCGGTTCAAG
9421 GGAATGTTCG CAGTGTCAGT CACCTGTTGG GGCTGGCAGA TCCCCTCTTG ATGCTGTGTT
9481 GAAACAAATT CCATACAAAC CTCCCCGCAC TGTCATCATG AAGGTGAGTA ACAAAACAAC
9541 GGCCCTCGAT CCGGGGAGGT ACCAGTCCCG TCGAGGCCTC GTTGCAGTCA AGAGAGGTAT
9601 CGCCGGCAAT GAAGTTGATC TTTCTGATGG AGACTACCAA GTGGTACCTC TTTTGCCGAC
9661 TTGCAAAGAC ATAAACATGG TGAAAGTGGC TTGCAATGTA CTACTCAGTA AGTTCATAGT
9721 GGGGCCACCA GGTTCCGGAA AGACCACCTG GCTACTAGAT CAAGTCCAAG ACGATGATGT
9781 CATTTACACA CCAACCCATC AGACTATGTT TGATATAGTT AGTGCTCTCA AAGTTTGCAG
9841 GTACTCTATT CCAGGAGCCT CAGGACTCCC TTTCCCACCA TCTGCCAGAT CCGGGCCGTG
9901 GGTTAGGCTT ATAGCCAGTG GGCACGTCCC TGGCCGCGTA TCTTACCTCG ATGAGGCCGG
9961 ATACTGTAAT CATCTGGACA TTCTCAGATT GCTCTCCAAA ACGCCCCTTG TGTGTTTGGG
10021 TGACCTTCAA CAGCTACACC CTGTCGGCTT TGATTCCTAC TGTTATGTGT TTGATCAGAT
10081 GCCCCAGAAG CAACTGACCG TTATTTACAG ATTTGGCCCT AACATCTGCG CGGCCATTCA
10141 GCCTTGTTAC AGAGAGAAGC TTGAATCCAA GGCTAGAAAC ACCAGGGTGG TTTTTGTCAA
10201 CCGGCCTGTG GCCTTTGGTC AGGTCCTGAC ACCATACCAT AAAGATCGCA TCGGCTCTGC
10261 GGTAACCATA GACTCATCCC AGGGAGCCAC CTTTGATATT GTGACACTGC ATCTACCGTC
10321 ACCAAAGTCC CTAACCAAAT CCCGAGCACT TGTGGCCATC ACTCGGGCAA GACACGGGTT
10381 GTTCATTTAT GACCCACATG ACCAGCTCCA GGAGTTTTTC AACTTAATCC CTGAGCTCAC

-continued

10441 AGATTGCAAC CTTGTGTTTA ACCGCGGGGA TGAGCTGGTA GTTCTGGATT CGGATAATGC

10501 AGTCACAACT GTAGCAAAGG CCCTAGAAAC AGGTCAATCT CGATTCCGAG TGTCAGACCC

10561 GAGGTGCAAG TCTCTCTTGG CCGCTTGTTC GGCCAGTCTG GAAGGGAGCT GTATGCCACT

10621 ACCGCAAGTA GCACATAATC TGGGGTTTTA CTTTTCCCCA GACAGTCCAG TATTTGCACC

10681 TCTGCCAAGA GAGTTGGCGT CACATTGGCC AGTGGTTACC CACCAGAATA ATCGGGCGTG

10741 GCCTGATCGA CTTGTCGCTA GTATGCGCCC AATCGATGCC CGCTACAGCA AGCCGATGGT

10801 CGGTGCAGGG TACGTAGTCG GGCCGTCCAC TTTTCTTGGT ACTCCCGGTG TGGTGTCATA

10861 CTACCTCACG CTATACATCA GGGGTGAGCC CCAGGCCCTG CCAGAAACAC TCGTTTCAAC

10921 GGGGCGTATA GCAACAGATT GTCGGGAGTA TCTCGATGCG GCTGAGGAGG AGGCAGCAAA

10981 AGAACTCCCC CACGCATTCA TTGGCGATGT CAAAGGTACC ACGGTGGGGG GTTGTCATCA

11041 CATCACGTCA AAATACTTAC CTAGGTCCCT GCCTAAAGAC TCTGTTGCCG TAGTTGGAGT

11101 GAGTTCACCC GGCAGGGCTG CTAAAGCCAT GTGCACCGTC ACCGATGTGT ATCTCCCTGA

11161 ACTCCGGCCG TATCTGCAAC CTGAGACGGC ATCAAAGTGC TGGAAACTTA AATTAGACTT

11221 CAGGGACGTC CGACTAATGG TCTGGAAAGG AGCTACCGCC TATTTCCAGT TGGAAGGGTT

11281 TACATGGTCG GCGCTGCCCG ACTATGCCAG GTTCATTCAG CTGCCCAAGG ATGCCGTTGT

11341 ATACATCGAT CCGTGTATAG GACCGGCAAC AGCCAACCGC AAGGTCGTGC GAACCACAGA

11401 CTGGCGGGCC GACCTGGCAG TGACACCGTA TGACTACGGT GCCCAGACTA TTTTAACAAC

11461 AGCCTGGTTC GAGGACCTCG GGCCACAGTG GAAGATTTTG GGGTTGCAGC CCTTTAGGCG

11521 AGCACTTGGT CTGGAAAACA CTGAGGATTG GGCAATTCTT GCACGCCGTA TGAATGACGG

11581 CAAAGACTAC ACTGACTATA ACTGGAATTG TGTTCGAGGA CGCCCACAAG CCATCTACGG

11641 GCGTGCTCGT GACCATACGT ATCATTTCGC CCCCGGCACG GAACTGCAGG TAGAGCTAGG

11701 TAAACCCCGG CTATCGCCTG AGCAGGTGCC GTGAATTTGG AGTGATGCAA TGGGGTCACT

11761 GTGGAGTAAA ATCAGCCAGC TGTTCGTGGA TGCCTTCACT GAGTTCTTGG TTAGTGTGGT

11821 TGATATTGTC ATCTTCCTTG CTATATTGTT TGGGTTCACC GTCGCAGGAT GGTTATTGGT

11881 CTTCCTTCTC AGAGTGGTTT GCTCCGCGTT TCTCCGTTCG CGCTCTGCCA TTCACTCTCC

11941 CGAACTATCG AAGATCCTAT GAAGGCTTGT TGCCCAACTG CAGACCGGAT GTCCCACAAT

12001 TTGCATTCAA GCACCCTTTG GGTATGTTGT GGCATATGCG AGTTTCCCAC CTGATTGATG

12061 AGATGGTCTC TCGCCGCATT TACCAGACCA TGGAACATTC AGGTCAAGCG GCCTGGAAGC

12121 AAGTAGTTGG TGAGGCCACT CTCACGAAGC TGTCAGGGCT CGATATAGTC ACTCACTTCC

12181 AACACCTGGC CGCAGTGGAG GCGGATTCTT GCCGCTTTCT CAGCTCACGA CTCGTGATGC

12241 TAAAAAATCT TGCCGTTGGC AATGTGAGCC TACAGTACAA CACCACGCTG GACCGCGTTG

12301 AGCTCATTTT TCCCACGTCA GGTACGAGGC CCAAGTTAAC CGACTTCAGA CAATGGCTCA

12361 TCAGTGTGCA CGCTTCCATT TTTTCCTCTG TGGCTTCATC TATCACCTTG TTTGTAGTGC

12421 TTTGGCTTCG AATTCCAGCT CTACGCTATG TTTTTGGTTT CCACTGGCCC ACGGCAACAC

12481 ATCATTCGAG CTGACCATCA ACTATACCAT ATGCAAGCCT TGTCTTACCA GTCAAGCAGC

12541 TCACCAAAGG CTTGAGCCCG GTCGCAATGT GTGGTGCAGA ATAGGGCATG AGACGTGTGA

12601 GGAGCGTGAC CATGATGAGT TGTTCATGCC CATCCCGTCC GGATACGATA ACATCAAACT

12661 TAAGGGTTAT TATGCCTGGC TGGCTTTTTT GTCCTTTTCC TACGCGGCCC AATTCCACCC

12721 GGAGTTGTTC GGGATTGGGA ATGTGTCGCG TGTCTTTGTG GACAAACATC ACCAGTTCAT

12781 TTGTGCCGAG CATGATGGAC AGAATTCGAC CGTATCTACT GGACACAACA TCTCTGCACT

-continued

12841 ATATGCGGCA TACTACCACC ACCAAATAGA CGGGGGTAAT TGGTTCCATT TGGAATGGCT

12901 GCGACCACTC TTTTCCTCCT GGTTGGTGCT CAATATATCA TGGTTTCTGA GGCGTTCGCC

12961 TGCAAGCCCT GTTTCTCGAC GCATCTATCA GATATTAAGA CCAACACGAC CGCGGCTGCC

13021 GGTTTCATGG TCCTTCAGGA CATCAATTGT TTCCAACCCC ACAGGGTCCC AGCAACGCAA

13081 AATGGAGCCC CCTTCAAAAA GTCGTCCCAA TGCCGTGAAG CTGTCGGCAC TCCCCAATAC

13141 ATCACAATAA CAGCTAATGT GACCGACGAA TCGTACTTGT ACAACGCGGA CTTGCTGATG

13201 CTTTCTGCGT GCCTTTTCTA CGCTTCAGAA ATGAGTGAGA AAGGCTTTAA AGTCATCTTC

13261 GGGAATGTCT CTGGCGTTGT TTCCGCTTGT GTCAATTTTA CAGATTATGT GGCCCATGTG

13321 ACCCAACACA CCCAGCAGCA TCACCTGGTA ATTGATCACA TTCGGCTGCT GCATTTCCTG

13381 ACACCATCTG CAATGAGGTG GGCTACAACC ATTGCTTGTT TGCTCGCCAT TCTCTTGGCG

13441 ATATGAGATG TTCTCACAAG TTGGGGCGTT CCTTGACTCC GCACTCTTGC TTCTGGTGGC

13501 TTTTTTTGCT GTGTACCGGC TTGTCTTGGT CCTTTGCCGA TGGCAACGGC AACAACTCGA

13561 CATACCAATA CATATATAAT TTGACGATAT GCGAGTTGAA TGGGACCGCG TGGCTGTCCG

13621 GCCATTTTGA TTGGGCAGTT GAGACTTTTG TGCTTTACCC GGTTGCCACT CACATCCTCT

13681 CACTGGGTTT TCTCACAACA AGTCATTTTT TTGACGCGCT CGGTCTCGGT GTTGTATCCA

13741 CTGCTGGATT TGTTGGCGGG CGGTATGTAC TCAGCAGCGT CTACGGCGCT TGTGCTTTCG

13801 CAGCGTTCGT GTGTTTTGCC ATCCGTATTG CGAAAAATTG CATGGCCTGC CGCTACGCCC

13861 GCACCCGGTT TACCAACTTC ATTGTGGACG ACCGGGGAGG AGTTCATCGA TGGAAGTCCC

13921 CAATAGTGGT GGAAAAATTG GGCAAAGCCG AAGTCGACGG CAGCCTTGTC ACCATCAAAC

13981 ATGTCGTCCT CGAAGGGGTT AAAGCTCAAC CTTTAACGAG GACTTCGGCC GAGCAATGGG

14041 AGGCCTAGAT GATTTTTGCA ACGATTCTAC CGCTGCACAA AAGCTCGTGC TGGCTTTCAG

14101 CATCACATAC ACACCTATAA TGATATATGC CCTTAAGGTG TCACGCGGCC GACTCCTGGG

14161 GCTGTTGCAC ATCCTAATAT TTCTGAACTG TTCCTTTACA TTCGGATACA TGACATATGT

14221 GCATTTTCAA TCCACCAACC GTGTCGCACT CACTCTGGGG GCTGTCGTCG CCCTTTTATG

14281 GGGTGCTTAC AGCCTCACAG AGTCATGGAA GTTTATCACT TCCAGATGCA GATTGTGTTG

14341 CCTTGGCCGG CGATACATTC TGGCCCCTGC CCATCACGTA GAAAGTGCTG CAGGTCTCCA

14401 TCCAATCTCA GCGTCTGGTA ACCGAGCATA CGCTGTGAGA AAGCCAGGAC TAACATCAGT

14461 GAACGGCACT CTAGTACCAG GACTTCGGAG CCTCGTGCTG GGCGGCAAAC GAGCTGTTAA

14521 ACGAGGAGTG GTTAACCTCG TCAAGTATGG CCGGTAGAAA CCAGAGCCAG AAGAAAAAGA

14581 AAAACACAGC TCCAATGGGG AATGGCCAGC CAGTCAATCA ACTGTGCCAG TTGCTGGGTG

14641 CAATGATAAA GTCCCAGCGC CAGCAACCTA GGGGAGGACA GGCCAAAAAG AAAAAGCCTG

14701 AGAAGCCACA TTTTCCCTTG GCTGCAGAAG ATGACATCCG GCACCACCTC ACCCAGACTG

14761 AACGCTCCCT CTGCTTGCAA TCGATCCAGA CGGCTTTCAA TCAAGGCGCG GGAACTGCGT

14821 TGCTTTCATC CAGCGGGAAG GTCAGTTTTC AAGTTGAGTT TATGCTGCCG GTTGCTCATA

14881 CAGTGCGCCT GATTCGCGTG ACTTCTACAT CCGCTAGTCA GGGTGCAAGT TAATTTGATG

14941 GTCAGGTGAA TGGTCGCGAT TGGCGTGTGG CCTTTGAGTC ACCTATTCAA TTAGGGCGAT

15001 CACATGGGGG TCATACTTAA TCAGGCAGGA ACCATGTGAC CGAAATTAAA AAAAAAAAAA

15061 AAAAAAAAAA AAAAAAA

The cDNA consensus sequence of PRRS strain SD 04-89 at P83 has been assigned GenBank Accession number KU131559 (SEQ. ID. NO:7). The cDNA consensus sequence designated SEQ. ID. NO:7 is:

```
1 TATGACGTAT AGGTGTTGGC TCTATGCCTT GGCATTTGTA TTGTCAGGAG CTGTGACCAT
61 TGGCACAGCC CAAAACTTGC TGCACAGAAA CACCCTTCTG TGATAGCCTC CTTCAGGGGA
121 GCTTAGGGTT TGTCCCTAGC ACCTTGCTTC CGGAGTTGCA CTGCTTTACG GTCTCTCCAC
181 CCCTTTAACC ATGTCTGGGA TACTTGATCG GTGCACGTGT ACCCCCAATG CCAGGGTGTT
241 TATGGCGGAG GGCCAAGTCT ACTGCACACG ATGCCTCAGT GCACGGTCTC TCCTTCCCCT
301 GAACCTCCAA GTTTCTGAGC TCGGGGTGCT AGGCCTATTC TACAGGCCCG AAGAGCCACT
361 CCGGTGGACG TTGCCACGTG CATTCCCCAC TGTTGAGTGC TCCCCCGCCG GGGCCTGCTG
421 GCTTTCTGCA ATCTTTCCAA TCGCACGAAT GACCAGTGGA AACCTGAACT TCCAACAAAG
481 AATGGTACGG GTCGCAGCTG AGCTTTACAG AGCCGGCCAG CTCACCCCTG CAGTCTTGAA
541 GGCTCTACAA GTTTATGAAC GGGGTTGCCG CTGGTACCCC ATTGTTGGAC CTGTCCCTGG
601 AGTGGCCGTT TTCGCCAATT CCCTACATGT GAGTGATAAA CCTTTCCCGG GAGCTACTCA
661 CGTGTTGACC AACCTGCCGC TCCCGCAGAG ACCCAAGCCT GAAGACTTTT GCCCCTTTGA
721 GTGTGCTATG GCTACTGTCT ATGACATTGG TCATGACGCC GTCATGTATG TGGCCGAAAG
781 GAAAATCTCC TGGGCCCCTC GTGGCGGGGA TGAAGTGAAA TTTGAAGCTG TCCCCGGGGA
841 GTTGAAGTTG ATTGCGAACC AGCTCCGCAC CTCCTTCCCG CCCCACCACA CAGTGGACAT
901 GTCTAAGTTC GCCTTCACAG CCCCTGGGTG TGGTGTTTCT ATGCGGGTCG AACGCCAACA
961 CGGCTGCCTT CCCGCTGACA CTGTCCCTGA AGGCAACTGC TGGTGGAGCT TGTTTGACTT
1021 GCTTCCACTG GAAGTTCAGA ACAAAGAAAT TCGCCATGCT AACCAATTTG GCTACCAGAC
1081 CAAGCATGGT GTCTCTGGCA AGTACCTACA GCGGAGGCTG CAAGTTAATG GTCTCCGAGC
1141 AGTAACTGAC CTAAACGGAC CTATCGTCGT ACAGTACTTC TCCGTTAAGG AGAGTTGGAT
1201 CCGCCATTTG AAACTGGCGG GAGAACCCAG CTACTCTGGG TTTGAGGACC TCCTCAGAAT
1261 AAGGGTTGAG CCTAACACGT CGCCATTGGC TGACAAGGAA GAAAAAATTT TCCGGTTTGG
1321 CAGTCACAAG TGGTACGGCG CTGGAAAGAG AGCAAGAAAA GCACGCTCTT GTGCGACTGC
1381 TACAGTCGCT GGCCGCGCCT TGTCCGTTCG TGAAACCCGG CAGGCCAAGG AGCACGAGGT
1441 TGCCGGCGCC AACAAGGCTG AGCACCTCAA ACACTACTCC CCGCCTGCCG AAGGGAATTG
1501 TGGTTGGCAC TGCATTTCCG CCATCGCCAA CCGGATGGTG AATTCCAAAT TTGAAACCAC
1561 CCTTCCCGAA AGAGTGAGAC CTTCAGATGA CTGGGCTACT GACGAGGATC TTGTGAATGC
1621 CATCCAAATC CTCAGACTCC CTGCGGCCTT AGACAGGAAC GGTGCTTGTA CTAGCGCCAA
1681 GTACGTACTT AAGCTGGAAG GTGAGCATTG GACTGTCACT GTGACCCCTG GGATGTCCCC
1741 TTCTTTGCTC CCTCTTGAAT GTGTTCAGGG CTGTTGTGGG CACAAGGGCG GTCTTGGTTC
1801 CCCAGATGCA GTCGAGGTCT CCGGGTTTGA CCCTGCCTGC CTTGACCGGC TGGCTGAGGT
1861 GATGCACCTG CCTAGCAGTG CTATCCCAGC CGCTCTGGCC GAAATGTCTG GCGATTCCGA
1921 TCGTTCGGCT TCTCTGGTCA CCACCGTGTG GACTGTTTCG CAGTTCTTTG CCCGTCACAG
1981 CGGAGGGAAT CACCCTGACC AAGTGCGCTT AGGGAAAATT ATCAGCCTTT GTCAGGTGAT
2041 TGAGGACTGC TGCTGTTCCC AGAACAAAAC CAACCGGGTC ACCCCGGAGG AGGTCGCAGC
2101 AAAGATTGAC CTGTACCTCC GTGGTGCAAC AAATCTTGAA GAATGCTTGG CCAGGCTTGA
2161 GAAAGCGCGC CCGCCACGCG TAATCGACAC CTCCTTTGAT TGGGGTGTTG TGCTCCCTGG
2221 GGTTGAGGCG GTAACCCAGA CGACCAAGCT GCCCCAGGTC AACCAGTGTC GTGCTCTGGT
2281 CCCTGTTGTG ACTCAAAAGT CCTTGGACAA CAACTCGGTC CCCCTGACCG CCTTTTCACT
```

-continued

2341 GGCTAACTAC TACTACCGTG CGCAAGGTGA CGAAGTTCGT CACCGTGAAA GACTAACCGC

2401 CGTGCTCTCC AAGTTGGAAA AGGTTGTTCG AGAAGAATAT GGGCTCATGC CAACCGAGCC

2461 TGGTTCACGG CCCACACTGC CACGCGGGCT CGACGAACTC AAAGACCAGA TGGAGGAGGA

2521 CTTGCTGAAA CTGGCTAACG CCCAGACGAC TTCGGACATG ATGGCCTGGG CGGTCGAGCA

2581 GGTTGACCTA AAAACTTGGG TCAAGAACTA CCCGCGGTGG ACACCACCAC CCCCTCCGCC

2641 AAAAGTTCAG CCTCGAAAAA CGAAGCCTGT CAAGAGCTTG CCGGAGAGAA AGCCTGTCCC

2701 CGCCCCGCGC AGGAAGGTTG GGTCCGATTG TGGCAGCCCG GTTTCATTAG GCGGCGATGT

2761 CCCTAACAGT TGGGAAGATT TGGCTGTTAG TAGCCCCTTT GATCTCCCGA CCCCACCTGA

2821 GCCGGCAACA CCTTCAAGTG AGCTGGTGAT TGTGTCCTCA CCGCAATGCA TCTTCAGGCC

2881 GGCGACACCC TTGAGTGAGC CGGCTCCAAT TCCCGCACCT CGCGGAACTG TGTCTCGACC

2941 GGTGACACCC TTGAGTGAGC CGATCCCTGT GCCCGCACCG CGGCGTAAGT TTCAGCAGGT

3001 GAAAAGATTG AGTTCGGCGG CGGCAATCCC ACCGTACCAG AACGAGCCCC TGGATTTGTC

3061 TGCTTCCTCA CAGACTGAAT ATGAGGCCTC TCCCCCAGCA CCGCCGCACC AGGGACCCTT

3121 GGCCTTCTCC GAGGATAAAC CGGTAGACGA CCAACTTGTC AACGACTCCC GGATATCGTC

3181 GCGGAGGCCT GACGAGAGCA CATCAGCTCC GTCCGCAGGC ACAGGTGGCG CCGGCTCTCT

3241 TACCGATTTG CCGCCTTCAG ATGGCGCGGA TGCGGACGGG GGGGGGCCGT TTCGGACGGT

3301 AAAAAGAAAA GCTGAAAGGC TCTTTGACCA ACTGAGCCGT CAGGTTTTTG ACCTCGTCTC

3361 CCATCTCCCT GTTTTCTTCT CACGCCTTTT CCACCCTGGC GGTGGTTATT CTCCGGGTGA

3421 TTGGGGTTTT GCAGCTTTTA CTCTATTGTG CCTCTTTTTA TGTTACAGTT ACCCAGCCTT

3481 TGGTATTGCT CCCCTCTTGG GTGTGTTTTC TGGGTCTTCT CGGCGCGTTC GAATGGGGGT

3541 TTTTGGCTGC TGGTTGGCTT TTGCTGTTGG TCTGTTCAAA CCTGTGTCCG ACCCAGTCGG

3601 CGCTGCTTGT GAGTTTGACT CGCCAGAGTG TAGAAACATC CTTCATTCTT TTGAGCTTCT

3661 CAAACCTTGG GACCCTGTTC GCAGCCTTGT TGTGGGCCCC GTCGGTCTCG GTCTTGCCAT

3721 TCTTGGCAGG TTACTGGGCG GGGCACGCTG CATCTGGCAC TTTTTGCTTA GGCTTGGCAT

3781 TGTTGCAGAC TGTATCTTGG CTGGAGCTTA CGTGCTTTCT CAAGGTAGGT GTAAAAAGTG

3841 CTGGGGATCT TGTATAAGAA CTGCTCCTAA TGAGGTCGCT TTTAACGTGT TTCCTTTCAC

3901 ACGTGCGACC AGGTCGTCAC TTATCGACCT GTGCGATCGG TTTTGTGCGC CAAAAGGAAT

3961 GGACCCCATT TTTCTCGCCA CTGGGTGGCG CGGGTGCTGG GCCGGCCGAA GCCCCATTGA

4021 GCAACCCTCT GAAAAACCCA TCGCGTTTGC CCAATTGGAT GAAAAGAAGA TTACGGCTAG

4081 GACTGTGGTC GCCCAGCCTT ATGACCCCAA CCAAGCCGTA AAGTGCTTGC GGGTATTGCA

4141 GGCGGGTGGG GCGATGGTGG CTGAGGCGGT CCCAAAAGTG GTCAAGGTTT CCGCTGTTCC

4201 ATTCCGAGCC CCCTTCTTTC CCACTGGAGT GAAAGTTGAC CCTGATTGCA GGGTCGTGGT

4261 TGACCCTGAC ACTTTCACTG CAGCTCTCCG GTCTGGCTAC TCCACCACAA ACCTCGTCCT

4321 TGGTGTAGGG GACTTTGCCC AGCTGAATGG ATTAAAAATC AGGCAAATTT CCAAGCCTTC

4381 AGGGGGAGGC CCACATCTCA TGGCTGCCCT GCATGTTGCC TGCTCGATGG CTCTGCACAT

4441 GCTTGTTGGG ATTTATGTGA CTGCGGTGGG TTCTTGCGGC ACCGGCACCA ACGACCCGTG

4501 GTGCGCTAAC CCGTTTGCCG TCCCTGGCTA CGGACCTGGC TCTCTCTGCA CGTCCAGATT

4561 GTGCATTTCC CAACACGGCC TTACCCTGCC CTTGACAGCA CTTGTGGCGG GATTCGGTAT

4621 TCAAGAAATT GCCTTGGTCG TTTTGATTTT TGTTTCCATC GGAGGCATGG CTCATAGGTT

4681 GAGCTGTAAG GCTGACATGC TGTTTGTTTT GCTTGCAATT GCCAGCTATG TTTGGGTACC

4741 TCTTACCTGG TTGCTTTGTG TGTTTCCTTG CTGGTTGCGC TGTTTTTCTT TGCACCCCCT

-continued

```
4801 CACCATCCTA TGGTTGGTGT TTTTCTTGAT TTCTGTGAAT ATGCCTTCAG GAATCTTGGC
4861 CATGGTGTTG TTGGTTTCTT TTTGGCTTCT TGGTCGTTAT ACTAATGTTG CTGGCCTTGT
4921 CACCCCCTAC GACATTCATC ATTACACCAG TGGCCCCCGC GGTGTTGCCG CCTTGGCTAC
4981 CGCACCAGAT GGGACCTACT TGGCCGCTGT CCGCCGCGCT GCGTTGACTG GCCGCACCAT
5041 GCTGTTTACC CCGTCCCAGC TTGGGTCTCT TCTTGAGGGT GCTTTCAGAA CTCGAAAGCC
5101 CTCACTGAAC ACCGTCAATG TGATCGGGTC CTCCATGGGC TCTGGCGGGG TGTTTACCAT
5161 CGACGGGAAA GTCAAGTGCG TAACTGCCGC ACATGTCCTT ACGGGCAATT CAGCTCGGGT
5221 TTCCGGGGTC GGCTTCAATC AAATGCTTGA CTTTGACGTA AAGGGAGATT TCGCTATAGC
5281 TGATTGCCCG AATTGGCAAG GGGCTGCCCC CAAGACCCAA TTCTGCACGG ATGGATGGAC
5341 TGGCCGTGCC TATTGGCTAA CATCCTCTGG CGTCGAACCC GGCGTCATTG GAAAAGGATT
5401 CGCCTTCTGC TTCACCGCAT GTGGCGATTC CGGGTCCCCA GTGATCACCG AGGCCGGTGA
5461 GCTTGTCGGC GTTCACACGG GATCGAATAA ACAAGGGGGG GGCATTGTTA CGCGCCCCTC
5521 AGGCCAGTTT TGTAATGTGG CACCCATCAA GCTAAGCGAA TTAAGTGAAT TCTTTGCTGG
5581 GCCTAAGGTC CCGCTCGGTG ATGTGAAGGT CGGCAGCCAC ATAATTAAAG ACATAAGCGA
5641 GGTGCCTTCA GATCTTTGTG CCTTGCTTGC TGCCAAACCT GAACTGGAAG GAGGCCTCTC
5701 CACCGTCCAA CTTCTTTGTG TGTTTTTCCT CCTGTGGAGA ATGATGGGAC ATGCCTGGAC
5761 GCCCTTGGTT GCTGTGAGTT TCTTTATTTT GAATGAGGTT CTCCCAGCCG TCCTGGTCCG
5821 GAGTGTTTTC TCCTTTGGAA TGTTTGTGCT ATCCTGGCTC ACGCCATGGT CTGCGCAAGT
5881 TCTGATGATC AGGCTTCTGA CAGCAGCTCT TAACAGGAAC AGATGGTCAC TTGCCTTTTT
5941 CAGCCTCGGT GCAGTGACCG GTTTTGTCGC AGATCTTGCG GCCACTCAGG GGCATCCGCT
6001 GCAGGCAGTG ATGAATTTGA GCACCTATGC ATTCCTGCCT CGGATGATGG TTGTGACCTC
6061 ACCAGTCCCA GTGATCACGT GTGGTGTCGT GCACCTACTT GCCATCATTT TGTACTTGTT
6121 TAAGTACCGT GGCCTGCACC ATATCCTTGT TGGCGATGGA GTGTTCTCTG CGGCTTTCTT
6181 CTTGAGATAC TTTGCCGAGG GAAAGTTGAG GGAAGGGGTG TCGCAATCCT GCGGAATGAA
6241 TCATGAGTCT CTGACTGGTG CCCTCGCTAT GAGACTCAAT GACGAGGACT TGGATTTCCT
6301 TATAAAATGG ACTGATTTTA AGTGCTTTGT TTCTGCGTCC AACATGAGGA ATGCAGCGGG
6361 TCAATTTATC GAGGCTGCCT ATGCTAAAGC ACTTAGAGTA GAACTGGCCC AGTTGGTGCA
6421 GGTTGATAAA GTTCGAGGTA CTTTGGCCAA ACTTGAAGCT TTTGCTGATA CCGTGGCACC
6481 TCAACTCTCG CCCGGTGACA TTGTTGTCGC TCTCGGCCAC ACGCCTGTTG GCAGTATCTT
6541 CGACCTAAAG GTTGGTAGCA CCAAGCATAC CCTCCAAGCC ATTGAGACCA GAGTCCTTGC
6601 TGGGTCCAAA ATGACCGTGG CGCGCGTCGT CGACCCGACC CCCACGCCCC CACCCGCACC
6661 CGTGCCCATC CCCCTCCCAC CGAAAGTTCT GGAGAATGGC CCCAACGCTT GGGGGGATGA
6721 GGACCGTTTG AATAAGAAGA AGAGGCGCAG GATGGAAGCC CTCGGCATCT ATGTTATGGG
6781 CGGGAAAAAG TACCAGAAAT TTTGGGACAA GAATTCCGGT GATGTGTTTT ATGAGGAGGT
6841 CCATAATAAC ACAGATGAGT GGGAGTGTCT CAGAGTTGGC GACCCTGCCG ACTTTGACCC
6901 TGAGAAGGGA ACTCTGTGTG GACATGTCAC CATTGAAAAC AAGGCTTACC ATGTTTACAC
6961 CTCCCCATCT GGTAAGAAGT TCTTGGTCCC CGTCAACCCA GAGAATGGAA GAGTTCAATG
7021 GGAAGCTGCA AAGCTTTCCG TGGAGCAGGC CCTAGGTATG ATGAATGTCG ACGGCGAACT
7081 GACTGCCAAA GAACTGGAGA AACTGAAAAG AATAATTGAC AAACTCCAGG GCCTGACTAA
7141 GGAGCAGTGT TTAAACTGCT AGCCGCCAGC GACTTGACCC GCTGTGGTCG CGGCGGCTTG
```

-continued

7201 GTTGTTACTG AAACAGCGGT AAAAATAGTC AAATTTCACA ACCGGACCTT CACCCTGGGA
7261 CCTGTGAATT TAAAAGTGGC CAGTGAGGTT GAGCTAAAAG ACGCGGTTGA GCACAACCAA
7321 CACCCGGTTG CGAGACCGAT CGATGGTGGA GTTGTGCTCC TGCGCTCCGC GGTTCCTTCG
7381 CTTATAGACG TCTTGATCTC CGGTGCTGAT GCATCTCCCA AGTTACTTGC CCATCACGGG
7441 CCGGGAAACA CTGGGATCGA TGGCACGCTC TGGGATTTTG AGTCCGAAGC CACTAAAGAG
7501 GAAGTCGCAC TCAGTGCGCA AATAATACAG GCTTGTGACA TTAGGCGCGG CGACGCTCCT
7561 GAAATTGGTC TCCCTTACAA GCTGTACCCT GTTAGGGGTA ACCCTGAGCG GGTGAAAGGA
7621 GTTTTGCAGA ATACAAGGTT TGGAGACATA CCTTACAAAA CCCCCAGTGA CACTGGAAGC
7681 CCAGTGCACG CGGCTGCTTG CCTTACGCCC AACGCCACTC CGGTGACTGA TGGGCGCTCC
7741 GTCTTGGCCA CGACCATGCC CCCCGGGTTT GAGTTATATG TACCGACCAT ACCAGCGTCT
7801 GTCCTTGATT ACCTTGACTC TAGGCCTGAC TGCCCTAAGC AGCTGACAGA GCACGGCTGC
7861 GAAGATGCCG CACTGAAAGA CCTCTCTAAA TATGACTTGT CCACCCAAGG CTTTGTTTTA
7921 CCTGGAGTTC TTCGCCTTGT GCGGAAATAC CTGTTTGCCC ATGTAGGTAA GTGCCCACCC
7981 GTTCATCGGC CTTCTACTTA CCCTGCTAAG AATTCTATGG CTGGAATAAA TGGGAACAGG
8041 TTCCCAACCA AGGACATTCA GAGCGTCCCT GAAATCGACG TTCTGTGCGC ACAGGCTGTG
8101 CGAGAAAACT GGCAAACTGT CACCCCTTGT ACTCTTAAGA AACAGTATTG CGGGAAGAAG
8161 AAGACTAGGA CCATACTCGG CACCAATAAC TTCATCGCAC TAGCCCACCG AGCAGTGTTG
8221 AGTGGTGTTA CCCAGGGCTT CATGAAAAAG GCGTTTAACT CGCCCATCGC CCTCGGAAAG
8281 AACAAGTTTA AGGAGCTACA GACTCCGGTC CTGGGCAGGT GCCTTGAAGC TGATCTCGCA
8341 TCCTGCGATC GATCCACGCC TGCAATTGTC CGCTGGTTTG CCGCCAACCT TCTTTATGAA
8401 CTTGCCTGTG CTGAAGAGTA TCTACCGTCG TACGTGCTGA ACTGCTGCCA CGACTTACTG
8461 GTCACGCAGT CCGGCGCAGT GACTAAGAGA GGTGGCCTGT CGTCTGGCGA CCCGATCACC
8521 TCTGTGTCTA ACACCATTTA TAGTTTGGTG ATCTATGCAC AGCATATGGT GCTTAGTTAC
8581 TTCAAAAGTG GTCACCCCCA TGGCCTTCTG TTCTTACAAG ACCAGCTAAA GTTTGAGGAC
8641 ATGCTCAAGG TTCAACCCCT GATCGTCTAT TCGGACGACC TCGTGCTGTA TGCCGAGTCT
8701 CCCACCATGC CAAACTATCA CTGGTGGGTT GAACATCTGA ATTTGATGCT GGGGTTTCAG
8761 ACGGACCCAA AGAAGACTGC AATAACAGAC TCGCCATCAT TTCTAGGCTG TAGAATAATA
8821 AATGGGCGCC AGCTGGTCCC CAACCGTGAC AGGATCCTCG CGGCCCTCGC CTATCACATG
8881 AAGGCGAGTA ATGTTTCTGA ATACTATGCC TCAGCGGCTG CAATACTCAT GGACAGCTGT
8941 GCTTGTTTGG AGTATGATCC TGAATGGTTT GAAGAACTTG TAGTTGGAAT AGCGCAGTGC
9001 GCCCGCAAGG ACGGCTATAG CTTTCCCGGC ACGCCGTTCT TCATGTCCAT GTGGGAAAAA
9061 CTCAGGTCCA ATTATGAGGG GAAGAAGTCG AGAGTGTGCG GGTACTGCGG GGCCCCGGCT
9121 CCGTACGCTA CTGCCTGTGG CCTCGACGTC TGCATTTACC ACACCCACTT CCACCAGCAT
9181 TGTCCAGTCA CAATCTGGTG TGGCCATCCA GCGGGTTCTG GTTCTTGTAG TGAGTGCAAA
9241 TCCCCTGTAG GGAAAGGCAC AAGCCCTTTA GACGAGGTGC TGGAACAAGT CCCGTATAAG
9301 CCCCCACGGA CCGTTATCAT GCATGTGGAG CAGGGTCTCA CCCCCCTTGA TCCAGGTAGA
9361 TACCAAACTC GCCGCGGACT AGTCTCTGTC AGGCGTGGAA TTAGGGGAAA TGAAGTTGAA
9421 CTACCAGACG GTGATTATGC TAGCACCGCC TTGCTCCCTA CCTGCAAAGA GATCAACATG
9481 GTCGCTGTCG CTTCCAATGT ATTGCGCAGC AGGTTCATCA TCGGCCCACC CGGTGCTGGG
9541 AAAACATACT GGCTCCTTCA ACAGGTCCAG GATGGTGATG TTATTTACAC ACCAACTCAC
9601 CAGACCATGC TTGACATGAT TAGGGCTTTG GGGACGTGCC GGTTCAACGT CCCGGCAGGT

-continued

9661 ACAACGCTGC AATTCCCCGT CCCCTCCCGC ACCGGTCCGT GGGTTCGCAT CCTAGCCGGC
9721 GGTTGGTGTC CTGGCAAGAA TTCCTTCCTA GATGAAGCAG CGTATTGCAA TCACCTTGAT
9781 GTTTTGAGGC TTCTTAGTAA AACTACCCTC ACCTGTCTAG GAGACTTCAA GCAACTCCAC
9841 CCAGTGGGTT TTGATTCTCA TTGCTATGTT TTTGACATCA TGCCTCAAAC TCAACTGAAG
9901 ACCATCTGGA GGTTTGGACA GAATATCTGT GATGCCATTC AGCCAGATTA CAGGGACAAA
9961 CTCATGTCCA TGGTCAACAC AACCCGTGTG ACCTACGTGG AAAAACCTGT TAGGTATGGG
10021 CAGGTCCTCA CCCCCTACCA TAGGGACCGA GAGGACGACG CCATCACTAT TGACTCCAGT
10081 CAAGGCGCCA CATTCGATGT GGTTACATTG CATTTGCCCA CTAAAGATTC ACTCAACAGG
10141 CAAAGAGCCC TTGTTGCCAT CACCAGGGCA AGACACGCTA TCTTTGCGTA TGACCCACAC
10201 AGGCAGCTGC AGGGCTTGTT TGATCTTCCT GCAAAAGGCA CACCCGTCAA CCTCGCAGTG
10261 CACCGCGACG GGCAGCTGAT CGTGCTGGAT AGAAATAACA AAGAATGCAC GGTTGCTCAG
10321 GCTCTAGGCA ACGGGGATAA ATTTAGGGCC ACAGACAAGT GTGTTGTAGA TTCTCTCCGC
10381 GCCATTTGTG CTGATCTAGA AGGGTCGAGC TCTCCGCTCC CCAAGGTCGC ACACAACTTG
10441 GGATTTTATT TCTCACCTGA TTTAACACAG TTTGCTAAAC TCCCAGTAGA ACTTGCACCT
10501 CACTGGCCCG TGGTGACAAC CCAGAACAAT GAAAAGTGGC CAGATCGGCT GGTTGCCAGC
10561 CTTCGCCCTA TCCATAAATA CAGCCGCGCG TGCATCGGTG CCGGCTATAT GGTGGGCCCT
10621 TCGGTGTTTC TAGGCACTCC TGGGGTCGTG TCATACTATC TCACAAAATT TGTTAAGGGC
10681 GAGGCTCAAT TGCTTCCGGA GACGGTTTTC AGCACCGGCC GAATTGAGGT AGACTGCCGG
10741 GAATATCTTG ATGATCGGGA GCGAGAAGTT GCTGCGTCCC TCCCACACGC TTTCATTGGC
10801 GACGTCAAAG GCACTACCGT TGGAGGATGT CATCATGTCA CCTCCAGATA CCTCCCGCGC
10861 GTCCTTCCCA AGGAATCAGT TGCGGTAGTC GGGGTTTCAA GCCCCGGAAA AGCCGCAAAA
10921 GCATTGTGCA CACTGACAGA TGTGTACCTC CCAGATCTTG AAGCCTATCT CCACCCGGAG
10981 ACCCAGTCCA AGTGCTGGAG AATGATGTTG GACTTCAAAG AAGTTCGACT AATGGTCTGG
11041 AAAGACAAAA CAGCCTATTT CCAACTTGAA GGTCGCTATT TCACCTGGTA TCAGCTTGCC
11101 AGCTATGCCT CGTACATCCG TGTTCCTGTC AACTCTACGG TGTACTTGGA CCCCTGCATG
11161 GGCCCCGCCC TTTGCAACAG GAGAGTCGTC GGGTCCACCC ACTGGGGGGC TGACCTCGCG
11221 GTCACCCCTT ATGATTACGG CGCTAAAATT ATCCTGTCTA GCGCGTACCA TGGTGAAATG
11281 CCCCCCGGAT ACAAAATTCT GGCGTGCGCG GAGTTCTCGT TGGATGACCC AGTTAAGTAC
11341 AAACATACCT GGGGGTTTGA ATCGGATACA GCGTATCTGT ATGAGTTCAC CGGAAACGGT
11401 GAGGACTGGG AGGATTACAA TGATGCGTTT CGTGCGCGCC AGGAAGGGAA AATTTATAAG
11461 GCCACTGCCA CCAGCTTGAA GTTTTATTTT CCCCCGGGCC CTGTCATTGA ACCAACTTTA
11521 GGCCTGAATT GAAATGAAAT GGGGTCCATG CAAAGCCTTT TTTACAAAGT TGGCCAACTT
11581 TTTGTGGATG CTTTCACGGA GTTCTTGGTG TCCATTGTTG ATATCATTAT ATTTTTGGCC
11641 ATTTTGTTTG GCTTCACCAT CGCCGGTTGG CTGGTGGTCT TTTGCATCAG ATTGGTTTGC
11701 TCCGCGATAC TCCGTGCGCG CCCTGCCATT CACTCTGAGC AATTACAGAA GATCTTATGA
11761 GGCCTTTCTT TCCCAGTGCC AAGTGGACAT TCCCACCTGG GGAACTAAAC ATCCTTTGGG
11821 GATACTTTGG CACCATAAGG TGTCAACCCT GATTGATGAA ATGGTGTCGC GTCGAATGTA
11881 CCGCATCATG GAAAAAGCAG GGCAGGCTGC CTGGAAACAG GTGGTGAGCG AGGCTACGCT
11941 GTCTCGCATT AGTAGTTTGG ATGTGGTGGC TCATTTTCAG CATCTAGCCG CCATTGAAGC
12001 CGAGACCTGT AAATATTTGG CCTCCCGGCT GCCCATGCTA CACAACCTGC GCATGACAGG

-continued

12061 TTCAAATGTA ACCATAGTGT ATAATAGCAC TTTGAATCAG GTGTTTGCTA TTTTTCCAAC

12121 CCCTGGTTCC CGGCCAAAGC GTCATGATTT TCAGCAATGG TTAATAGCTG TACATTCCTC

12181 CATATTTTCC TCTGTTGCAG CTTCTTGTAC TCTTTTTGTT GTGCTGTGGT TGCGGGTTCC

12241 AATACTACGT ACTGTTTTTG GTTTCCGCTG GTTAGGGGCA ATTTTTCTTT CGAACTCACA

12301 GTGAATTACA CGGTGTGTCC ACCTTGCCTC ACCCGGCAAG CAGCCGCAGA GATCTACGAA

12361 CCCGGTAGGT CTCTTTGGTG CAGGATAGGG TATGACCGAT GTGAGGAGGA TGATCATGAC

12421 GAGCTAGGGT TTATGGTACC GCCTGGCCTC TCCAGCGAAG GCCACTTGAC TAGTGTTTAC

12481 GCCTGGTTGG CGTTCTTGTC CTTCAGTTAC ACGGCCCAGT TCCATCCCGA GATATTCGGG

12541 ATAGGGAATG TAAGTCGAGT TTATGTTGAC ATCAAACATC AACTCATCTG CGCCGAACAT

12601 GACGGGCAGA ACACCACCTT GCCTCGTCAT GACAACATTT CAGCCGTGTT TCAGACCTAT

12661 TACCAACATC AAGTCGACGG CGGCAATTGG TTTCACCTAG AATGGCTTCG TCCCTTCTTT

12721 TCCTCGTGGT TGGTTTTAAA TGTCTCTTGG TTTCTCAGGC GTTCGCCTGC AAACCATGTT

12781 TCAGTTCGAG TCTTGCAGAC ATTAAGACCA ACACCACCGC AGCGGCAAGC TTTGCTGTCC

12841 TCCAAGACAT CAGTTGCCTT AGGCATCGCG ACTCGGCCTC TGAGGCGATT CGCAAAATCC

12901 CTCAGTGCCG TACGGCGATA GGGACACCTG TGTATGTTAC CATCACAGCC AATGTGACAG

12961 ATGAGAATTA TTTACATTCT TCTGATCTCC TCATGCTTTC TTCTTGCCTT TTCTATGCTT

13021 CTGAGATGAG TGAAAAGGGA TTTAAGGTGG TATTTGGCAA TGTGTCAGGC ATCGTGGCTG

13081 TGTGTGTCAA TTTTACCAGC TACGTCCAAC ATGTCAAGGA GTTTACCCAA CGCTCCCTGG

13141 TGGTCGACCA TGTGCGGTTG CTCCATTTCA TGACACCTGA GACCATGAGG TGGGCAACTG

13201 TTTTAGCCTG TCTTTTTGCC ATTCTGTTGG CAATTTGAAT GTTTAAGTAT GTTGGAGAAA

13261 TGCTTGACCG CGGGCTGTTG CTCGCAATTG CTTTCTTTGT GGTGTATCGT GCCGTTCTGT

13321 TTTGCTGTGC TCGTCAACGC CAGCAACGAC AGCAGCTCCC ATCTACAGCT GATTTACAAC

13381 TTGACGCTAT GTGAGCTGAA TGGCACAGAT TGGCTAGCTA AAAAATTTGA TTGGGCAGTG

13441 GAGAGTTTTG TTATCTTTCC CGTTTTGACT CACATTGTCT CCTATGGTGC CCTCACTGCC

13501 AGCCATTTCT TTGACACAGT CGCTTTAGTC ACTGTGTCTA CCGCCGGGTT TGTTCACGGG

13561 CGGTATGTCC TAAGTAGCAT CTACGCGGTC TGTGCCCTGG CTGCGTTGAC TTGCTTCGTC

13621 ATTAGGTTTG CAAAGAATTG CATGTCCTGG CGCTACGCGT GTACCAGATA TACCAACTTT

13681 CTTCTGGACA CTAAGGGCAG ACTCTATCGT TGGCGGTCGC CTGTCATCAT AGAGAAAAGG

13741 GGCAAAGTTG AGGTCGAAGG TCATCTGATC GACCTCAAAA GAGTTGTGCT TGATGGTTCC

13801 GTGGCAACCC CTATAACCAG AGTTTCAGCG GAACAATGGG GTCGTCCTTA GATGACTTCT

13861 GTCATGATAG CACGGCTCCA GGAAAGGTGC TTTTGGCGTT TTCTATTACC TACACGCCAG

13921 TGATGATATA TGCCCTAAAG GTGAGTCGCG GCCGACTGCT AGGGCTTCTG CACCTTTTGA

13981 TCTTCCTGAA TTGTGCTTTC ACCTTCGGGT ACATGACTTT CGCGCACTTT CAGAGTACAA

14041 ATAAGGTCGC GCTCACTATG GGAGCAGTAG TTGCACTCCT TTGGGGGGTG TACTCAGCCA

14101 TAGAAACCTG GAAATTCATC ACCTCCAGAT GCCGTTTGTG CTTGCTAGGC CGCAAGTACA

14161 TTCTGGCCCC TGCCCACCAC GTTGAAAGTG CCGCAGGCTT TCATCCGATT GCGGCAAATG

14221 ATAACCACGC ATTTGTCGTC CGGCGTCCCG GCTCCACTAC GGTCAACGGC ACATTGGTGC

14281 CCGGGTTAAA AAGCCTCGTG TTGGGTGGCA GAAAAGCTGT TAAACAGGGA GTGGTAAACC

14341 TTGTCAAATA TGCCAAATAA CAACGGCAAG CAGCAGAAGA GAAAGAAGGG GGATGGCCAG

14401 CCAGTCAATC AGCTGTGCCA GATGCTGGGT AAGATCATCG CTCAGCAAAA CCAGTCCAGA

14461 GGCAAGGGAC CGGGAAAGAA AAATAAGAAG AAAAACCCGG AGAAGCCCCA TTTTCCTCTA

-continued

```
14521 GCGACTGAAG ATGATGTCAG ACATCACTTT ACCCCTAGTG AGCGGCAATT GTGTCTGTCG
14581 TCAATCCAGA CCGCCTTTAA TCAAGGCGCT GGGACTTGCA CCCTGTCAGA TTCAGGGAGG
14641 ATAAGTTACA CTGTGGAGTT TAGTTTGCCT ACGCATCATA CTGTGCGCCT GATCCGCGTC
14701 ACAGCATCAC CCTCAGCATG ATGGGCTGGC ATTCTTGAGG CATCTCAGTG TTTGAATTGG
14761 AAGAATGTGT GGTGAATGGC ACTGATTGAC ATTGTGCCTC TAAGTCACCT ATTCAATTAG
14821 GGCGACCGTG TGGGGGTGAG ATTTAATTGG CGAGAACCAT GCGGCCGAAA TTAAAAAAAA
14881 AAAAA
```

The cDNA consensus sequence of PRRS strain MN 05-68 at P83 has been assigned GenBank Accession number KU131558 (SEQ. ID. NO:8). The cDNA consensus sequence designated SEQ. ID. NO:8 is:

```
   1 ATGACGTATA GGTGTTGGCT CTATGCCGTG ACATTTGTAT AGTCAGGAGC TGCGACCATT
  61 GGTACAGCCC AAAACTTGCT GCACGGGAAC GCCCTTCCGT GACAGCCTTC TTCAGGGGAG
 121 TTTAGGGATC TATCCCTAGC ACCTTGCTTC CGGAGTTGCA CTGCTTTACG GTCTCTCCAA
 181 CCCTTTAACC ATGTCTGGGA TACTTGATCG GTGCACGTGC ACCCCCAATG CCAGGGTGTT
 241 TATGGCGGAG GGCCAAGTCT ACTGCACACG ATGTCTCAGT GCACGGTCTC TCCTTCCTCT
 301 GAATCTCCAA GTCCCTGAGC TTGGGGTGCT GGGCCTATTT TACAGGCCCG AAGAGCCACT
 361 CCGGTGGACA TTGCCGCGTG CATTCCCCAC TGTCGAGTGC TCCCCCGCCG GGGCCTGCTG
 421 GCTTTCTGCG ATCTTCCCAA TTGCACGAAT GACCAGTGGA AACCTGAACT TTCAACAAAG
 481 AATGGTGCGG GTCGCAGCTG AGATTTACAG AGCCGGTCAG CTCACTCCCA CAGTCTTGAA
 541 GAATCTACAA GTTTATGAGC GGGGTTGCCG TTGGTACCCT ATTGTCGGGC CTGTCCCCGG
 601 AGTGGCCGTT TACGCCAACT CCCTACATGT GAGTGACAAA CCCTTTCCGG GAGCAACTCA
 661 TGTGTTAACT AATCTACCGC TCCCGCAGAG GCCCAAGCTT GAAGATTTTT GCCCCTTTGA
 721 GTGTGCTATG GCTGACGTCT ATGATATCGG TCATGACGCC GTCATGTACG TGGCCAAAGG
 781 GAAAGTCTCC TGGGCTCCTC GTGGTGGGGA CAAGACAAAA TTTGAAACTG TCCCTAGGGA
 841 GTTGAAGTTG ATCGCGAACC GACTCCATGT CTCCTTCCCG CCCCACCACG CAGTGGACAT
 901 GTCCCAGTTT GCGTTCATAA CCTTCGGGAG CGGTGTCTCT ATGCGGGTCG AGTGCCCACA
 961 TGGCTGTCTC CCCGCCAATA CCGTCCCTGA AGGCAACTGC TGGTGGCGCT TGTTTGACAT
1021 GCTTCCACCG GAGGTTCAGA ACGATGAAAT TCGCCGTGCC TGCCAATTCG GTTATCAAAC
1081 CAAGCATGGT GTCGCTGGCA AGTACCTACA ACGGAGGTTG CAAGCTAATG GCCTCCGAGC
1141 GGTGACTGAT ACAAGTGGGC CTATCGTTGT GCAGTTTTTC TCCGTTAAGG AGAGTTGGAT
1201 CCGCCACTTA AGGCTGGCGG ACGAACCTAG CCTTCCTGGT TTTGAGGACC TCCTCAGAAT
1261 AAGGGTTGAG CCCAACACGT CACCATTGGT TAGCAAGGAT GTGAAAATCT TCCGGTTCGG
1321 CAGTCACAAA TGGTACGGTG CTGGAAAGAG GGCAAAGAAA GCACGCTCTG GTGCGGCTGC
1381 CACGGTCATT CACCGCGCTT TGCCTGTTCG CGAAGCCCAG CAGACCAAGA CGCACAAGGT
1441 TGCTAGCGCT AACAGGGCTG AGTGTCTCAA GCGCTATTCT CCGCCTGCCG ATGGGAACTG
1501 TGGTTGGCAC TGCATTTCCG CCATCGCCAA CCGGATGGTG AATTCGAAAT TTGAGACCAC
1561 CCTTCCCGAA AGAGTGAGAC CTTCTGATGA TTGGGCTACC GACGAGGATC TTGTGAACGC
1621 CATTCAAATC CTCAAGCTCC CTGCGGCCTT GGACAGGAAC GGAGCTTGTG GTAGCGCCAA
1681 GTACGTGCTT AAGCTGGAAG GCGTGCATTG GACTGTCTCT GTGACCCCTG GGATGTCCCC
1741 CTCTTTGCTC CCCCTTGAAT GTGTTCAGGG CTGTTGTGAG CATAAGGACG GTTCTGGCCC
```

-continued

```
1801 CCCAGATGCG GTCGAGGTTT CCGGATTTGA CCCTGCCTGC CTTGACCGAC TGGCTGGGGT
1861 GATGCATTTA CCTAGCAGTG CTATCCCAGC CGCTCTGGCT GAAATGTCCG GCAACTCCAA
1921 TCGCCCGGCT TCCCCGGTCA ACACTGTGTG GACTGTTTCG CAATTCTATG CCCGTCACTT
1981 AGGAGGAGTT CATCCTGACC AGGTGTGCTT AGGGAAAATT ATTAGCCTCT GTCAAGTCAT
2041 TGAGGATTGC TGCTGCCATC AAAACAAAAC CAACCGGGCC ACCCCGGAAG AGGTCGCGGC
2101 AAAGATTGAT CAGTACCTCC GTGGTGCAAC AAGTCTTGAG GAATGCTTGA CTAGGCTTGA
2161 AAGGGTTTGC CCTCCGAGCG CTGCGGACAC CTCCTTTGAT TGGAATGTTG TGCTCCCTGG
2221 GGTTGAGGCT GCAACCCAGA CAACTAAACA GCTCCATGTC AACCGGTGCC GCGTTTTGGC
2281 TCCTGTCGTG ACTCAAGAGC CTTCGGACAA AGACTCGGTC CCTCTGACCG CCTTCTCGTT
2341 GTCCAATTAC TACTACCCGG CACAAGGTGA CGAGATTCAT CACCGTGAGA GGCTGAACTC
2401 CGTACTCTCT AAGTTGGAGG GGGTTGTTCG CGAGGAATAT GGGCTCACGC CAACTGAACC
2461 TGGTCCGCGA CCCGCACTAC CGAACGGGCT CGACGAGCTC AGAGACCAGA TGGAGATGGA
2521 TCTGCTGAGA CTAGTCAACG ATCAGGCAAC TTCAGAAATG ATGGCCCGGG CAGCTGAGCA
2581 GGTTGATCTA AAAGCTTGGG TCAAAAACTA CCCACGGTGG ACACCGCCGC CCACTCCACC
2641 AAGAGTTCAG CCTCGAAAAA CGAGGTCTGT CAAGAGCTTG CCAGGGGATA AGCCTGTCCC
2701 GGCTCCGCGT AGGAAGGTCA GATCTGATTG TGGCAGCCCG ATTTTGATGG GCGACAATGT
2761 TCCTAACGAT CGGGAAGATT TGACTGTTAA TGGGCCCCTT GACCTTTCGA CACCATCCGA
2821 GTCGATGACA CCTCTGAGTG AGCCTGCACT TATGCCCGCG TTGCAACATG TTTCTAGGTC
2881 GGCGACATCT TTGAGTGTGC CGACCCCAGT TCCTGTACCG CGCAGAGCTG TGTCCCGACC
2941 GGTGGCACCC TTGAGTGAGC CAACCTTTGA GTCTTCACCG CGACACAAAT TTCAAGAGGT
3001 GAAAGAAGTG AATCTGGCGG CAACAACGCC GACGCACCAA GACGAACCTC TAGATTTGTC
3061 TGCATCCTCA CAGACTGTAT GTGAGGCCTC TCCCCTAGCA CCGCCTCAGA ACATAGGTAT
3121 TCTGGGGGTG GAGGGGCAAG AAACTGAGGA AGTCCTGAGT GAAGTCTCGG ATATACCGTA
3181 TGACATTAAC CTTGCACCTG TGTCATCAAG CAGCTCCCTG TCAAGTGTAA AGATCACACG
3241 TCCGAAATAC TCAGCTCAAG CCATTATTGA CTCAGGCGGG CCCTGCAGTG GGCATCTTCG
3301 AAAGGGAAAA GAAGCATGCC TCAGCATCAT GCGCAGGGCT TGTGATGCGG CTAAGCTTAG
3361 TGACCCTGCC ACGCAAGAAT GGCTTTCTCG TATGTGGGAT AGGGTTGACA TGCTGACTTG
3421 GCGCAACACG TCTGCTTACC AGGCGTTGCG CATCTTAGAT GGCAGGTTTG GGTTCCTCCC
3481 GAAAATGATA CTCGAGACAC CACCGCCCTA TCCGTGTGGG TTTGTGATGC TGCCTCACAC
3541 GCCTGCACCT TCCGTGAGTG CAGAGAGCGA CATTACCATT GGTTCAGTTG CCTCTGAAGA
3601 TGTTCCACGC ATCCTCGGGA AAATAGAAAA CGCCGGCGAG ATGCCCAACC AGGGGCTCTT
3661 GGCGTCCCTT GAGGAAAAAC CGGTGCACGA CCAACCTGCC GAAGACTCCC GGATGCCGTT
3721 GCGGGGGTTT GACGAGAGCG TAACGGCTCC GTCCGCTGGT ACAGGTTGCG CTGACTCACC
3781 CACTGATTTG TCGCCTTCAG GTGGTGTGGA CGTGGACGGG GGGGGGCGT TACGGGCGGT
3841 AAGAAAGAAA GCTGAAAGGC TCTTCGATCA ATTGAGCCGC CAGGTTTTTA ACCTCGTCTC
3901 CCATCTCCCT GTTTTCTTCT CACACCTCTT CAAATCTGAC AGTGGTTATT CTCCGGGTGA
3961 TTGGGGTTTT GCAGCTTTTA CTCTATTTTG TCTCTTTTTA TGTTACAACT ACCCATTTTT
4021 TGGGTTTGCT CCCCTCTTGG GTGTGTTTTC TGGGTCTTCT CGGCGTGTGC GCATGGGGGT
4081 TTTTGGCTGC TGGTTGGCTT TTGCTGTTGG CCTGTTCAAA CCTGTGTCCG ACCCAGTCGG
4141 CACTGCTTGT GAATTTGACT CGCCAGAGTG TAGGAACGTC CTTCATTCTT TTGAGCTTCT
4201 CAAACCTTGG GACCCTGTTC GCAGCCTTGT TGTGGGCCCC GTCGGTCTCG GTCTTGCCAT
```

-continued

4261 TCTTGGCAGG TTACTGGGCG GGGCACGCTA CATCTGGCAT TTTTTGCTTA GGCTTGGCAT

4321 TGTTGCAGAT TGTGTCTTGG CTGGAGCTTA TGTGCTTTCT CAAGGTAGGT GTAAAAAGTG

4381 CTGGGGATCT TGTGTAAGAA CTGCTCCCAA TGAAATTGCC TTCAACGTGT TCCCTTTTAC

4441 GCGTGCGACC AGGTCGTCAC TCATCGACCT GTGCAACCGG TTTCGTGCGC CGAAAGGCAT

4501 GGACCCCATT TTTCTCGCTA CTGGGTGGCG CGGGTGCTGG ACCGGCCAAA GTCCCATTGA

4561 GCAACCCTCC GAAAAACCCA TCGCGTTCGC CCAGTTGGAT GAAAAGAGGA TCACGGCCAG

4621 AACTGTAGTT GCTCAGCCTT ATGATCCTAA CCAAGCCGTA AAGTGCCTGC GGGTGTTACA

4681 GGCGGGTGGG GCGATGGTGG CCGAGGCAGT CCCGAAAGTT GTCAAAGTTT CCGCTATCCC

4741 ATTCCGAGCC CCTTTTTTTC CCACCGGAGT GAAGGTTGAT CCTGAGTGCA GGATCGTAGT

4801 CGACCCCGAC ACTTTCACTA CTGCTCTTCG GTCTGGTTAC TCCACCACAA ACCTCGTCCT

4861 TGGTGTGGGG GACTTTGCCC AACTGAATGG ATTAAAAATC AGGCAAATTT CCAAGCCTTC

4921 GGGAGGAGGC CCACACCTCA TTGCTGCCCT GCATGTTGCT TGCTCGATGG CGTTGCACAT

4981 GCTTGCTGGG GTTTACGTAA CTGCAGTGGG GTCTTGCGGT ACCGGCACCA ACGATCCGTG

5041 GTGCACCAAC CCATTCGCCG TCCCTGGCTA CGGACCTGGC TCTCTCTGCA CGTCCAGGTT

5101 GTGCATCTCC CAACATGGCC TTACCTTGCC CTTGACAGCA CTTGTGGCAG GCTTCGGTCT

5161 TCAGGAAATT GCCTTGGTCG TTCTGATTTT TGTTTCCATC GGAGGCATGG CTCATAGGTT

5221 GAGTTGTAAG GCTGATATGC TGTGCGTCTT GCTCGCAATC GCCAGCTATG TTTGGGTACC

5281 CCTTACCTGG TTGCTCTGCG TGTTTCCTTG CTGGTTGCGC TGGTTCTCTT TGCACCCCCT

5341 CACCATCCTA TGGTTGGTGT TTTTCTTGAT TTCTGTAAAT ATGCCTTCAG GAACCTTAGC

5401 CGTGGTGTTA TTGGTCGCTC TTTGGCTTCT AGGCCGTTAC ACTAATGTTG TTGGTCTTGT

5461 CACCCCCTAC GATATCCATC ATTACACCAG CGGCCCTCGC GGTGTTGCCG CCTTGGCTAC

5521 CGCACCAGAT GGAACTTATT TGGCCGCTGT CCGCCGCGCT GCGTTGACTG GCCGTACCGT

5581 TCTGTTTACC CCGTCTCAGC TTGGGTCCCT TCTTGAGGGC GCTTTCAGGA CTCGAAAGCC

5641 CTCATTGAAC ACCGTTAATG TGGTCGGGTC CTCCATGGGC TCTGGCGGAG TGTTCACTAT

5701 CGATGGGAAA ATTAAGTGTG TGACTGCCGC ACATGTCCTT ACGGGCAACT CAGCCAGGGT

5761 TTCCGGGGTC GGCTTCAATC AGATGCTTGA CTTTGATGTA AAAGGAGATT TCGCCATAGC

5821 TGATTGCCCG AATTGGCAAG GGACTGCTCC TAAGACCCAA TTCTGCAAGG ACGGGTGGAC

5881 TGGCCGTGCC TATTGGCTAA CATCTTCTGG TGTCGAACCC GGTGTCATTG GAAATGGGTT

5941 CGCCTTCTGC TTCACCGCGT GCGGTGACTC CGGGTCTCCA GTGATCACCG AAGCCGGTGA

6001 GCTTGTCGGC GTTCACACAG GATCAAACAA ACAAGGAGGA GGCATTGTTA CGCGCCCCTC

6061 AGGCCAGTTT TGTAATGTGG CACCCATCAA GCTGAGCGAA TTAAGTGAGT TCTTTGCTGG

6121 ACCTAAGGTC CCGCTCGGTG ATGTGAAGGT TGGTAGCCAC ATAATTAAAG ACATATGCGA

6181 GGTACCTTCA GATCTTTGTG CCTTGCTTGC TGCCAAACCC GAATTGGAAG GAGGCCTCTC

6241 CACCGTCCAA CTTCTATGTG TATTTTTCCT CCTGTGGAGA ATGATGGGAC ATGCCTGGAC

6301 ACCCTTGGTT GCCGTGGGTT TTTTTATTTT GAATGAGATT CTTCCAGCTG TACTGGTCCG

6361 GAGTGTTTTC TCCTTCGGAA TGTTTGTGTT ATCTTGGCTC ACACCATGGT CTGCACAAGT

6421 TCTGATGATC AGGCTCCTCA CAGCAGCTCT TAATAGGAAC AGATTGTCAC TCGCCTTCTA

6481 CAGCCTTGGT GCGGCAACCG GTTTTGTCGC AGACCTAGCG GCGACCCAAG GGCATCCGTT

6541 GCACGCAGTA ATGAATTTGA GTACCTATGC CTTCCTGCCT CGGGTGATGG TTGTGACCTC

6601 ACCAGTCCCA GTAATCGCGT GTGGTGTTGT GCACCTCCTT GCCATAATTT TGTACTTGTT

-continued

6661 TAGGTACCGC TGCCTGCATG GTGTTCTTGT TGGCGATGGG GCGTTCTCTG CGGCTTTTTT

6721 TTTGCGATAC TTTGCTGAGG GGAAATTGAG GGAAGGGGTG TCGCAATCCT GCGGGATGAA

6781 TCATGAGTCG CTGACTGGTG CCCTCGCCAT GAGACTCAAT AACGAGGATT TGGATTTCCT

6841 CACTAAGTGG ACTGATTTTA AGTGCTTTGT TTCTGCTTCC AACATGAGGA ATGCAGCGGG

6901 CCAATTCATT GAGGCTGCCT ATGCCAAAGC ACTTAGAATA GAACTTGCCC AGCTGGTGCA

6961 GGTCGACAAG GTCCGAGGCA CTTTGGCCAA ACTTGAAGCT TTTGCCGACA CCGTGGCACC

7021 CCAACTCTCG CCCGGTGACA TTGTTGTCGC TCTTGGCCAT ACGCCTGTTG GCAGTGTCTT

7081 CGACCTGAAG GTTGGTAACA CCAAGCACAC TCTCCAAGCC ATTGAGACCA GGGTCCTTGC

7141 TGGGTCCAAA ATGACCGTGG CGCGCGTCGT CGACCCGACC CCCACGCCCC CACCCGCACC

7201 CGTACCCATC CCCCTCCCAC CGAAGGTTTT GGAGAACGGT CCAAACGCTT GGGGGGATGA

7261 AGATCGTTTG AATAAAAAGA AGAGGCGCAG GATGGAAGCT GTCGGCATCT TTGTTATGGG

7321 CGGAAAGAAA TACCAGAAAT TTTGGGACAA GAATTCCGGT GATGTGTTTT ATGAGGAGGT

7381 CCATGACAAT ACAGACGCGT GGGAGTGCCT CAGGGTTGAT AACTCTGCCG ACTTTGATCC

7441 CGAGAAGGGA ACTCTGTGTG GGCATACTAC CATTGAGAAT AAAACCTACA ATATCTACGC

7501 CTCCCCATCC GGCAAGAAGT TCCTGGTCCC TGCCAACTCA GAGGGCGGAA AAGTCCAGTG

7561 GGAAGCTGCA AAGCTCTCCG TGGAGCAGGC CCTTGGCATG ATGAATGTCG ACGGTGAACT

7621 GACAGCCAGA GAACTGGAGA AACTAAAAAA AATAATTGAC AAACTCCAGG ACCTGACCAA

7681 GGAGCAGTGT TTAAACTGCT AGCCGCCAGC GGCCTGACCC GCTGTGGTCG CGGCGGCTTA

7741 GTTGTTACTG AGACAGCGGT AAAAATAGTC AAATATCACA GCCGGACCTT CACCCTAGGA

7801 CCTGTAAATT TAAAAGTGGC TAGTGAGGTT GAGCTAAAAG ACGCGGTCGA GCATAACCAG

7861 CACCCGGTCG CAAGACCGGT TGATGGTGGT GTTGTGCTTC TGCGCTCCGC AGTTCCTTCG

7921 CTTATAGACG TCTTGATCTC CGGCGCTGAT GCATCTCCTA AGTTACTCGC TCGCCACGGG

7981 CCGGGAAATA CTGGGATCGA CGGCACGCTT TGGGATTTTG AGGCCGAGGC CACCAAAGAG

8041 GAGATCGCAC TCAGTGCGCA GATAATACAG GCTTGTGACA TTAGGCGCGG CGACGCACCC

8101 GAAATTGGTC TCCCTTATAA GCTGTACCCT GTTAGGGGCA ATCCCGAGCG GGTAAAAGGA

8161 GTTTTACAGA ATACAAGGTT CGGGGACATT CCTTATAAAA CCCCCAGTGA CACTGGAAGC

8221 CCAGTGCACG CGGCTGCCTG CCTCACGCCC AATGCCACTC CGGTGACTGA TGGGCGCTCC

8281 GTCTTGGCTA CAACCATGCC CTCCGGTTTT GAGTTGTACG TGCCGACCAT TCCAGCATCT

8341 GTCCTTGATT ACCTTGACTC CAGGCCTGAC TGCCCTAAAC AGTTGACAGA GCACGGCTGT

8401 GAGGATGCCG CATTAAGAGA CCTTTCCAAG TATGACTTGT CCACTCAAGG CTTTGTTTTG

8461 CCAGGAGTTC TTCGCCTTGT GCGTAAGTAC CTATTTGCTC ATGTGGGCAA GTGCCCGCCT

8521 ATTCATCGGC CTTCCACCTA CCCTGCCAAG AATTCTATGG CTGGAATAAA TGGGAACAGG

8581 TTTCCAACCA AGGACATCCA GGGCGTCCCT GAAATCGACG TCCTGTGCGC TCAGGCCGTG

8641 CGGGAAAACT GGCAGACTGT CACCCCTTGT ACCCTCAAGA AACAGTATTG TGGGAAGAAG

8701 AAGACTAGGA CAATACTCGG CACCAATAAT TTCATTGCAT TGGCCCACCG GGCAGCGTTG

8761 AGTGGCGTCA CCCAGGGCTT TATGAAAAAG GCGTTCAATT CGCCCATCGC CCTCGGAAAA

8821 AACAAATTTA AGGAGCTACA AACTCCGGTC TTAGGCAGGT GCCTAGAGGC TGACCTTGCA

8881 TCCTGCGATC GATCCACACC TGCGATTGTC CGCTGGTTTG CCGCCAATCT TCTTTATGAA

8941 CTTGCCTGTG CTGAGGAACA TCTACCATCG TACGTGCTGA ACTGCTGCCA CGACTTACTG

9001 GTCACGCAAT CCGGCGCGGT GACTAAGAGA GGTGGCCTGT CGTCTGGCGA CCCGATTACT

9061 TCTGTGTCAA ACACCATTTA TAGTTTGGTG ATATATGCAC AGCACATGGT GCTCAGTTAC

-continued

9121 TTTAAAAGTG GTCACCCTCA CGGCCTTCTG TTTCTGCAAG ACCAGCTAAA GTTTGAGGAC

9181 ATGCTCAAGG TTCAACCCCT GATCGTCTAT TCGGACGACC TCGTGTTGTA TGCCGAGTCT

9241 CCCACTATGC CAAACTACCA CTGGTGGGTT GAACATCTGA ATCTTATGTT GGGTTTTCAG

9301 ACGGACCCAA GAAAGACAGC CATAACAGAC TCACCATCTT TTCTAGGCTG TAGAATAATA

9361 AATGGGCGCC AGCTAGTCCC CCACCGTGAC AGGATTCTCG CGGCCCTTGC CTACCATATG

9421 AAGGCAAGCA ATGTTTCTGA ATACTACGCT TCGGCGGCCG CGATACTCAT GGACAGCTGT

9481 GCTTGTCTAG AGCATGATCC TGAATGGTTT GAAGAACTTG TGGTCGGAAT GGCGCAGTGT

9541 GCCCGCAAGG ACGGCTACAG CTTTCCCGGC CCGCCGTTCT TCTTGTCTAT GTGGGAAAAA

9601 CTCAGGTCTA ATTATGAGGG GAAGAAGTCG AGAGCGTGCG GATACTGCGG GGCCCCGGCT

9661 CCGTACGCTA CCGCCTGTGG CCTCGACGTC TGCATTTATC ACACCCATTT CCACCAGCAT

9721 TGTCCGGTCA TAATCTGGTG TGGTCATCCG GCGGGTTCTG GTTCTTGTAG TGAGTGCAAA

9781 CCCCCCCTTG GGAAAGGTAC AAGCCCTCTA GATGAGGTGT TGGAACAAGT CCCGTACAAG

9841 CCTCCGCGGA CCGTGATCAT GCACGTAGAG CAGGGTCTTA CTCCACTCGA CCCAGGTAGA

9901 TACCAAACCC GCCGCGGATT AGTCTCCGTT AGGCGTGGCA TTAGGGGAAA CGAAGTTGAA

9961 CTACCAGACG GTGATTATGC TAGTACCGCC TTGCTCCCCA CTTGTAAAGA GATCAACATG

10021 GTTGCTGTTG CTTCTAACGT GTTACGCAGC AGGTTCATCA TCGGTCCACC TGGTGCTGGT

10081 AAAACATACT GGCTCCTTCA ACAGGTCCAG GATGGTGATG TCATTTACAC GCCAACTCAT

10141 CAGACTATGC TTGACATGAT TAAGGCTTTG GGGACGTGCC GGTTCAACGT TCCAGCAGGC

10201 ACAACGCTGC AATTCCCTGC CCCCTCCCGC ACCGGCCCGT GGGTTCGCAT CCTGGCCGGC

10261 GGTTGGTGTC CTGGCAAGAA TTCCTTCCTG GATGAAGCAG CGTATTGCAA TCATCTTGAC

10321 GTCTTGAGGC TTCTTAGCAA AACTACCCTC ACCTGCCTGG GAGATTTCAA ACAACTCCAC

10381 CCGGTGGGTT TTGATTCCCA TTGCTATGTT TTTGACATTA TGCCTCAGAC TCAACTGAAG

10441 ACCATCTGGA GGTTTGGGCA GAACATCTGT GACGCCATTC AACCAGATTA TAGAGACAAA

10501 CTTGTGTCCA TGGTCAACAC AACCCGTGTA ACCTACGTGG AAAAACCTGT CAAGTATGGG

10561 CAAGTCCTCA CCCCCTACCA CAGGGACCGA GAGGACGGCG CCGTCACAAT TGACTCAAGT

10621 CAAGGCGCCA CATTTGATGT GGTTACACTG CATTTGCCCA CTAAAGATTC ACTCAACAGG

10681 CAAAGGGCCC TTGTTGCTAT CACCAGGGCA AGACATGCTA TCTTTGTGTA TGACCCACAC

10741 AGGCAATTGC AGAGCTTGTT TGATCTTCCT GCAAAAAGCA CACCCGTCAA TCTCGCAGTG

10801 CACCGTGACG AGCAGCTGAC CGTGTTAGAT AGAAATAACA AAGAGTGCAC GGTTGCTCAG

10861 GCTCTAGGCA ATGGGGATAA ATTTAGGGCC ACAGACAAGC GCGTTGTAGA TTCTCTCCGC

10921 GCCGTTTGTG CAGACCTGGA AGGGTCTAGC TCCCCGCTCC CCAAGGTTGC ACACAACTTG

10981 GGATTTTATT TCTCGCCTGA TTTGACACAG TTTGCTAAGC TTCCGGTAGA ACTTGCACCT

11041 CACTGGCCCG TGGTGACAAC CCAGAACAAT GAAAAGTGGC CAGACCGGTT GGTTGCTAGC

11101 CTTCGCCCTG TCCATGAGTA TAGCCGTGCG TGTGTCGGTG CCGGCTATAT GGTGGGCCCC

11161 TCAGTGTTCC TAGGCACTCC TGGGGTTGTG TCATACTATC TCACAAAATT TGTTAGAGGC

11221 GAGGCTCAAA TGCTTCCGGA GACAGTCTTC AGCACCGGCC GAATTGAGGT AGATTGCCGG

11281 GAGTACCTTG ATGATCGGGA GCGAGAAGTT GCTGAGTCCC TCCCACACGC CTTCATTGGC

11341 GACGTCAAAG GCACTACCGT TGGGGGATGT CACCATGTCA CCTCTAAATA CCTCCCGCGT

11401 TTCCTCCCCA AGGAATCGGT TGCGGTAGTT GGGGTTTCGA GCCCCGGGAA AGCCGCAAAA

11461 GCAGTTTGCA CATTGACAGA TGTGTACCTC CCAGACCTTG AAGCTTATCT CCACCCAGAG

-continued

11521 ACCCAGTCTA AGTGCTGGAA AATGATGTTG GACTTCAAGG AGGTTCGACT GATGGTCTGG

11581 AAAGATAAGA CGGCCTATTT TCAACTTGAA GGCCGCCATT TCACCTGGTA CCAGCTTGCA

11641 AGCTATGCCT CGTACATCCG AGTTCCTGTT AATTCTACGG TATATCTGGA CCCTTGCATG

11701 GGCCCTGCCC TTTGCAACAG GAGGGTTGTC GGGTCCACCC ATTGGGAAGC TGACCTCGCA

11761 GTCACCCCTT ATGATTATGG TGCCAAAATC ATTTTGTCTT GTGCATACCA TGGTGAAATG

11821 CCTCCCGGGT ACAAGATTCT GGCGTGCGCG GAGTTCTCGC TTGACGACCC AGTCAGGTAC

11881 AAACACACCT GGGGATTTGC ATCGGATATA GCGTATTTGT ACGAGTTCAC CGGAAACGGT

11941 GAGGACTGGG AGGATTACAA TGATGCGTTT CGTGCGCGCC AGAAAGGGAA AATTTACAAA

12001 GCCACTGCCG CCAGCATGAG GTTTTATTTT CCCCCGGGCC CTATCGTTGA ACCAACTTTG

12061 GGCCTAGACT GAAATGAAAT GGGGTCTATG CAAAGCCTCT TTGACAAAAT CGGCCAACTT

12121 TTTGTGGATG CCTTCACGGA ATTTTTGGTG TCCATTGTTG ATATCATCAT ATTTCTGGCC

12181 ATTTTGTTTG GCTTTACCAT CGCTGGCTGG CTGGTGGTCT TCTGCATCCG ACTGGTTTGC

12241 TCCGCGGTAC TCCGTGCGCG CCCTACCATT CACTCTGAGC AATTACAGAA GATCCTATGA

12301 GGCCTTTCTT TCTCAGTGCC AGGTGGACAT TCCCGCCTGG GGAACTAAAC ACCCCTTGGG

12361 GATGTTTTGG CACCATAAGG TGTCGACCCT GATTGATGAA ATGGTGTCGC GTCGAATGTA

12421 CCGCACCATG GAAAAAGCAG GACAGGCTGC CTGGAGACAG GTGGTAAGCG AGGCTACGTT

12481 GTCTCGCATT AGTGGTTTGG ATGTGGTGGC TCATTTTCAG CATCTTGCCG CCATTGAAGC

12541 TGAGACCTGC AAATACTTGG CCTCTCGGCT TCCCATGCTG CACAATCTGC GCATGACAGG

12601 GTCAAATGTA ACCATAGTGT ATAATAGCAC TTTGAATCAG GTGTTTGCTA TTTTTCCAAC

12661 CCCTGAATCC CGGCCGAAGC TTCATGATTT TCAGCAATGG CTAATAGCTG TGCATTCCTC

12721 CATATTTTCC TCCGTTGCAG CTTCTTGCAC TCTTTTTGTT GTGCTGTGGT TGCGGATTCC

12781 AACACTACGT ATTGTTTTTG GTTTCCACTG GTAAGGGGCA ATTTTTCCTT CGAGCTCACG

12841 GTGAATTACA CGGTGTGCCC GCTTTGCCTC ACCCGACAAG CAGCCTATGA GATCTATGAA

12901 TCACGCAGGT CTTTTTGGTG CAGGATAGGG CATGACCGAT GCAGTGAGGT CGACCACGAC

12961 GAGCTAGGGT TCATGGTTCC GTCTGGCCTC TCCAGCGAAG GCCACCTGAC CAGTGTTTAC

13021 GCCTGGTTGG CGTTCCTGTC CTTCAGCTAC ACGGCCCAGT TCCATCCCGA GATATTTGGG

13081 ATAGGGAATG TGAGTCGAGT TTATGTTGAC ATCAAGCACC AACTCATCTG CGCCGTTCAC

13141 GACGGGGAGA ACACCACCTT GCCTCGTCAT GACAACATTT CAGCCGTATT TCAGACCTAC

13201 TACCAGCATC AAGTCGACGG CGGCAATTGG TTTCACCTAG AATGGCTGCG TCCCTTCTTT

13261 TCCTCCTGGT TGGTTTTAAA TGTCTCGTGG TTTCTCAGGC GTTCGCCTGC AAGCCATGTT

13321 TCAGTTCAAG TCTTTCGGAC ATCAAAACCA ACACTACCGC AGCATCAGGC TTTGTTACCC

13381 TCCAGGACAT CAGCTGTCTT AGGCATGGCG ACTCGCCCTC TCAGACGATT CGCAAAAGCC

13441 CTCCGTGCCG CACGGCGCTA GGGACACCCG TGTACATCAC TGTTACAGCC AATGTCACGG

13501 ATGAGAATTA TTTACACTCC TCTGATCTCC TCATGCTTTC TTCTTGCCTT TTCTATGCTT

13561 CTGAGATGAG TGAAAAGGGA TTCAAGGTGA TATTTGGCAA TGTGTCAGGC ATCGTGGCCG

13621 TGTGTGTTAA TTTTACCAGC TACGTCCAAC ATGTCAAAGA GTTCACCCAA CGCTCTTTGG

13681 TGGTCGACCA TGTGCGGCTG CTCCATTTCA TGACACCTGA AACCATGAGG TGGGCAACCG

13741 TTTTAGCCTG TCTTGTTGCC ATCTTGCTGG CAATTTGAAT GTTTCAGTAT GTTGGGGAGA

13801 TGCTTGACCG CGGGCTGCTG CTTGCGATTG CTTTCTTTGT GGTGTATCGT GCCGTTCTGG

13861 TTTGCTGCAC TCGTCAGCGC CAACCAGAAC CACAGCTCTC ATCTTCAATT GATTTACAAC

13921 TTGACGCTAT GTGAGCTGAA TGGCACAGAA TGGCTGGGAG ACAAATTTAA TTGGGCAGTG

-continued

13981 GAGACCTTTG TCATCTTTCC CGTGTTAACT CACATTGTCT CATATGGTGC ACTCACCACT

14041 AGCCATTTCC TTGACACAGT CGGTCTGGTT ACTGTGTCTA CCGCCGGGTA TTATCACGGG

14101 CGGTATGTTT TGAGTAGTAT CTACGCGGTC TGCGCTCTGG CCGCGTTAAT TTGCTTCGTC

14161 ATTCGGCTTG CGAAGAACTG CATGTCCTGG CGCTACTCTT GTACCAGATA TACCAATTTC

14221 CTTCTGGACA CTAAGGGCAG ACTCTATCGC TGGCGGTCGC CCGTTATCAT AGAGAAAAGG

14281 GGTAAGGTTG AGGTCGGAAG TCACCTGATC GATCTCAAGA GAGTTGTGCT TGATGGTTCT

14341 GCGGCAACCC CTTTAACCAG AGTTTCAGCG GAACAATGGG GTCGTCTCTA GACGACTTTT

14401 GCTATGATAG CACGGCTCCA CAAAAGGTGT TTTTGGCGTT TTCCATTACC TACACGCCAG

14461 TAATGATTTA TGCCCTGAAG GTAAGTCGCG GCCGACTGTT AGGGCTTCTG CACCTTTTGA

14521 TCTTTCTGAA TTGTGCTTTT ACCTTCGGGT ACATGACATT TGTGCACTTT GATAGCACAA

14581 ATAAGGTCGC GCTCACTATG GGAGCAGTGG TTGCACTCCT TTGGGGGGTG TACTCGGCCA

14641 TAGAAACCTG GAAATTCATC ACCTCCAGAT GCCGTTTGTG CTTGCTAGGC CGCAAGTACA

14701 TTCTGGCCCC TGCCCACCAC GTCGAAAGTG CCGCGGGCTT TCATCCGATT GCGGCAAATG

14761 ATAACCACGC ATTTGTCGTC CGGCGTCCCG GCTCCACTAC GGTTAACGGC ACATTGGTGC

14821 CCGGGTTGAA AAGCCTCGTG TTGGGTGGCA GAAAAGCTGT AAAACAGGGA GTGGTAAACC

14881 TTGTCAAATA TGCCAAATAA CAACGGCAAG CAGCAAAAGA AAAAAAAGGG GAATGGCCAG

14941 CCAGTCAACC AGCTGTGCCA AATGTTGGGC AAAATCATCG CCCAGCAGAA CCAGTCCAGA

15001 GGTAAGGGAC CGGGAAAGAA AATTAAAAAG AAAAGCCCGG AGAAGCCCCA TTTTCCTCTA

15061 GCGACTGAGG ATGACGTCAG GCATCACTTT ACCCCTGGTG AGCGGCAATT GTGTCTGTCG

15121 TCAATCCAGA CTGCCTTTAA TCAAGGCGCT GGAACTTGCA CCCTGTCAGA TTCAGGGAGG

15181 ATAAGTTACG CTGTGGAGTT TAGTTTGCCG ACGCATCATA CTGTGCGCCT GATTCGCGTC

15241 ACAGCACCAC CTTCAGCGTG ATGGGCTGGC ATTCTTGAGA CATCCCGGCG TTAGAATTGG

15301 AAGAATGCGT GGTGAATGGC ACTGATTGAC ACTGTGCCTC TAAGTCACCT ATTCAGTTAG

15361 GGCGACCGTG TGGGGGTAGA GTTTAATTGG CGAGAACCAC ACGGCCGAAA TTAAAAAAAA

15421 AAAAAAAAAA AAAA

The cDNA consensus sequence of PRRS strain SD 11-21 at P83 has been assigned GenBank Accession number KU131557 (SEQ. ID. NO:9). The cDNA consensus sequence designated SEQ. ID. NO:9 is:

1 ATGACGTATA GGTGTTTGCT TTATGCCGCG GCATTTGTAT TGTCAGGAGC TGTGACCACT

61 GGCACAGCCC GAAACTTGCT GCACAGAAAC ACCCTTCTGT GACAGCCTCC TTCAGGGGAG

121 TTTAGGGGTT TCTCCCTAAC GCCCTGCTTC CGGAGTTGCA CTGCTTTACG GTCTCTCCAT

181 CCTTTTAACC ATGTCTGGGA TTCTTGATCG GTGCACGTGC ACCCCCAATG CCAGGGTGTT

241 TGTGGCAGAG GGCCAAGTCT ACTGCACACG ATGTCTCAGT GCACGGTCCC TCCTTCCCCT

301 AAATCTCCAA GTTTCTGAGC TTGGGGTACT TGGTTTATTC TACAGGCCCG AAGAGCCATT

361 ACGGTGGACG TTGCCACACG CATTCCCCAC TGTCGAGTGT GCTCCTGCTG GCGCTTGTTG

421 GCTTTCTGCA ATTTTTCCAA TTGCGCGAAT GACCAGTGGA AACCTGAATT TCCAGCAAAG

481 GCTGGTACGT GTCGCAGCCG AGCTTTACAG AGCCGGCCAG CTCACCCCTA CAAGCCTGAA

541 AACCTTACAG GTCTATGAAA GGGGTTGCCG TTGGTACCCC ATTGTTGGAC CTGTTCCTGG

601 AGTGGCCGTT TACGCCAACT CCCTACATGT GAGTGACAAA CCCTTCCCAG GAGCGACTCA

661 CGTGCTGACC AACTTACCAC TCCCGCAGAG ACCAAAATCT GAAGATTTCT GCCCCTTCGA

-continued

```
721  GTGCGCCACG GCCGCCGTCT ATGACATCGG CCATGACGCC GTCATGTATG TAACCGAGGA
781  AAAGGTTTCC TGGGCTCCTC GTGGCGGGGA TAAAGGGAAA TTTGAGACTG TTCCTGAGGG
841  GTTGAAGTTG ACTGCGGAAC GACTCTACAC CTCCTTCCCG CCTCACCATG CGGTGGACAT
901  GTCCCTTTTC ATCTTCACAG ACCTTGAGTG CGGCGCTTCC ATGCGGGTCG AACGCCAATA
961  TGGTTGCCTC TCTGCTGGCA CTGTCCCTGA AGGCAACTGC TGGTGGAGTC TGTTTGGCTC
1021 GCTTTCGTTA GAAGCTCAGT ATAAAGAAAT CCGCTACGCC GCCCAATTTG GCTATCAGAC
1081 CAAACATGGC GTTACTGGCA AGTACCTGCA GCGGAGGCTG CAAATTAATG GTCTCCGAGC
1141 AGTGGTTGAC CCGAATGGGC CTCTTGTCGT ACAGTATTTC TCCGTTAAGG AGAGCTGGAT
1201 GCGCCACGTG AGACTGGCGG AAGAGCCAGG CTATCCTGGG TTTGAGGATC TCCTCAGGAT
1261 AAGAGTCGAG CCCAACACGT TGCCTTTGTC CAACAAGGAC GAGAAAATCT TCCGTTTCGG
1321 CGGTTACAAG TGGTACGGTG CTGGGCGGAG GCAAGGAGA ACACGTGCAA GAGCAGTCAC
1381 CGCAGTTGCT AGTCATGCTC CGCCCGCTCG TGGGGCCCAG CAGGCCGAGA AGCACGAAGT
1441 TGCTAGTGCC AACAAGACTG AGCTCCTTAC GCACTACTCC CCACCTGCTG AAGGGAATTG
1501 CGGCTGGCAC TGCATCTCCG CCATCATGAA CCGGATGGTG CATTCCAAGT TTGAAACCGC
1561 CCTTTCCGAA AGAGTGAGAT CCCCGGAAGA CTGGGCGACT GATGAGGATC TTGTGAATAC
1621 TATTCAAATC CTCAGGCTCC CTGCGGCCTT AGACAGGAAC GGCGCCTGTA AAAACGCCAA
1681 GTACATCCTT AAGCTGGAAG GTGAGCACTG GACTGTTTCA GTGACCCCCG GAATGCCCCC
1741 CTCTTCACTT CCTCTTGAAT GCGTTCAGGG TTGTTGCGAG CATAAGGGCA ATTTTGACTC
1801 TCAAAACGCG GTCGGTTTCT TTGGGTTCGA CCCTGCCAGC CTTGACCGAC TCGCTGGGGT
1861 AATGCATCTG CCCAGCAGCG CCATCCCTGC CGCCCTGGCC GAGTTGTCTG GTGAACTTGA
1921 TTGTTCAACT CCCCCGGCCA CCACTGTGTG GACTACCTTG CAGTTTTATG CTCGTCTTGG
1981 TGGGGGGGAG CATCCTGATC AAGAGTGCTT GAGAAAAATC ATCAGCCTCT GTGAGGTGCT
2041 CGGGAGTTGC TGCTGTTCTC AGAGTAGGGT CAACCGGGTC ACCCCGGAAG AGGTCGCAGC
2101 AAAGATTGAC CTGTATCTTC GTGACGCAGC GAGTCTTGAA GAGTGCTTGG CTAGGCTTGA
2161 GAAAGCTCGC CCGCCAAGCA TGCTGGACAC CTCCTTTGAC TGGGATGTTG TACTCCCTGG
2221 TGTTGGGACG GCTGCTCGGG CAGCAGAACT ACCCCCCACC GATGAGTGTC GCGCTCTAGT
2281 CACTGCTGTG GCCCAAAGGC CTTCGCCGAA AGTTCAGCCT CGAAAGGCGG GGTCTGTTAA
2341 GAGTCTACCA GAGATCAGGC CTGTCCCTGC CCCACGCAGG AAGGTTAAGT CTAGTTGTGG
2401 TGATCTGGCC CCGTTGGGCG GCAATTTCCC TGATAGCTGG GAAGATTTGG CTGGTGGCTC
2461 CCTTAATCTC CAGATCTTAC CTGAGCCGGT GGCACAATCC TTTGAACCTG TGCCTGTCCC
2521 TGCACCGCGC AAGACTGCGC CTCGATTAGT GTCGTCATCA TTGGCGTCGA CCCCCGTACC
2581 TACACCACGA TGTGGGTTTC GGCAGTTTGA GGGAATGAAT TTGACAGCTG TGACCCTAGC
2641 ATGCCAGGAT GAGTCCCTCA ATTTGTCTGC ATCCTCGCAG ACTGAATATG AGGCTTCTCC
2701 TTTGGCATTG CAGCAGGGTG AGGATGTCCT TGCGGTGGGG GGACGAGAAG CCGAAGAAGT
2761 CCTGAGCGGA ATCTCGGGAA TGTCAGGTGG CATTAGATTA GCGCCCGCAT CATCAAGTAG
2821 CTCCTTGTCA AGCGTGGAGA TCACACGCCC GAAGTACTCA GCTCAAGCCA TCATTGACTC
2881 AGGTGGACCC TGTTGCGGGC ACCTTCAAGA GGTGAAAGAG AAATACCTTA ATGTCATGCG
2941 TGAGGCATGT GATGCGACTA AGCTCGATGA CCCTGCCACG CAAGAATGGC TCTCTCGCAT
3001 GTGGGAGAGG GTAGACATGC TAACCTGGCG CAACACGTCC ATCTTTCAAG CGCCTTTTAC
3061 CTTAGCTGAC AAGTTTAAGT CCCTCCCGAA GATGATACTC GAAACGCCGC CACCCTACCC
```

-continued

```
3121 TTGCGGGTTT GTGATGATGC CCCGCACGCC CGCACCTTCT GTGGGTGCGG AAAGCGACAT
3181 CACCGTTGGT TCAGTTGCTA CTGAAGATGT CCCGCGTATA CTCGGGGAGG TGGGAGATGT
3241 TGGCAAGATG ACCGGCCAGG AACCCTTAGA ATCCTTCGCA GATGAACTGG CAGATGACCA
3301 ACCTGCTAGG GAGTCCCGAA CACAAGCTCC TCCTGCAAGC ACAGGTAGCG CTGGTTTAGT
3361 TTTGGATTCT GGAGGGTCGC TGGGGCTCAC TGACCTGCCG CTCCCAAACA ATATAGACGC
3421 GGGCGGGAAA GGACCGTTTC ACGCGGTCAA GAAAAAAGCT GTAGGGTGCT TTGACCAACT
3481 GAGCCGCCGG GTTTTTGACA TCGTCTCCCA TCTCCCTGTT TTTTTTTCAC GCCTTTTCGC
3541 GCCCGGTGGT TTTTACTCTT CGGGTGACTG GAGTTTTGCA GCTTTTACTT TATTGTGTCT
3601 CTTTTTATGT TACAGTTATC CGGCCTTTGG TTTTGCTCCC CTCGTGGGTG TATTTTCTGG
3661 GTCTTCTCGG CGCGTGCGCA TGGGGGTTTT TGGCTGCTGG CTGGCTTTTG CTGTTGGTTT
3721 GTTCAAGCCT GCACCCGACC CAGTCGGTGC TGCTTGTGAG TTTGACTCGC CAGAGTGTAG
3781 AGACATCCTT CATTCTTTTG AGCTCCTGCA ACCTTGGGAC CCTGTTCGCA GCCTTGTGGT
3841 GGGCCCCGTC GGTCTCGGCC TTGCCATTTT TGGCAGGTTA CTGGGCGGGG CACGCTACGT
3901 CTGGCTGCTT TTGCTTAGGC TTGGCATCGT TTCAGACTGT ATCCTGGCTG GAGCCTATGT
3961 GCTTTCGCAA GGCAGGTGTA AAAAGTGTTG GGGATCTTGT ATAAGAACAG CCCCCAGTGA
4021 AGTTGCCTTC AATGTGTTTC CCTTTACACG CGCAACTAGA TCGTCACTTG TCAACCTGTG
4081 CGACCGGTTC TGTGCACCCA AGGGCATGGA CCCCATCTTC CTTGCCACAG GATGGCGCGG
4141 ATGCTGGTCC GGCCAGAGCC CCATTGAGCA ACCCTCTGAA AAACCCATAG CGTTCGCCCA
4201 GTTGGACGAA AAGAAAATCA CGGCTAGGAC TGTGGTTGCC CAGCCTTATG ACCCCAACCA
4261 AGCTGTGAAG TGCCTGCGAG TCCTCCAGGC GGGTGGAGCG ATGGTAGCCG AGGCAGTTCC
4321 AAAAGTAGTC AAAGTTTCTG CTGTCCCGTT TCGAGCCCCT TTTTTTCCTG CCGGAGTGAA
4381 AGTTGACCCT GAATGCAGGG TCGTGGTTGA CCCTGACACC TTTACAACCG CTCTCCGGAC
4441 CGGCTACTCC ACCACAAACC TCATTCTTGG TGTTGGGGAC TTTGCCCAGC TGAATGGGTT
4501 GAAGATCAGA CAAATTTCCA AGTCCCCAGG AGGGGGCCCT CACCTCATGG CGGCTTTACA
4561 TGTTGCTTGC TCGATGACTT TGCACATGCT TGTTGGGATT TATGTCACCA TGGTGGGTTC
4621 TTGTGGCTCT GGCACTAACG ATCCGTGGTG CACTAACCCG TTTGCCGTCC CTGTCTATGG
4681 GCCTGGCTCT CTCTGCACGT CCAGGTTGTG CATTTCCCAG CGTGGCCTGA CCCTGCCCTT
4741 AACAGCGCTT GTGGCAGGGT TTGGCGTTCA GGAAATCGCT TTGGTTGTTT TAATCTTTGT
4801 CTCCATCGGG GGTATGGCCC ACAGGTTGAG TTGCAAGGCT GACGTGCTGT GTATCCTGCT
4861 TGCTATTGTC AGCTATGTTT GGCCACCCCT TACCTGGTTG CTTTGTGTGT TTCCTTGCTG
4921 GTTGCGCTGG TTTTCTTTAC ATCCCCTTAC TATTCTATGG TTAGTGTTTT TCTTGATTTC
4981 TGTAAATACG CCCTCGGGAA TCTTGGCCTT GGTCCTGTTA ATCTCTCTTT GGCTCCTTGG
5041 TCGCTATACC AATGTTGCCG GCCTTGTCAC CCCTTATGAC ATTCACCATT ACACCAACGG
5101 CCCTCGCGGC GTTGCCGCCT TGGCCACTGC CCCGGATGGG ACCTACCTGG CTGCTGTCCG
5161 CCGTGCTGCG TTGACTGGCC GTACCATGCT GTTCACCCCG TCCCAACTTG GCTCGCTCCT
5221 TGAGGGCGCT TTTAGAACCC AAAAGCCTTC ACTGAACACT GTCAATGTAG TTGGGTCCTC
5281 CATGGGCTCC GGCGGGGTGT TCACCATTGA TGGGAAGATC AAATGTGTGA CCGCTGCTCA
5341 TGTCCTCACG GGTAACTCTG CCAGGGTTTC CGGGGTTGGC TTCAATCAAA TGTTGGACTT
5401 TGATGTTAAA GGGGATTTTG CCATAGCCGA TTGTCCGAAT TGGCAAGGAG TCGCCCCCAA
5461 GTCCCGGTTC TGCAAGGATG ATTGGACTGG CCGTGCTTAT TGGCTCACGT CCTCCGGCGT
5521 CGAACCCGGC GTCATTGGGC AAGGATTCGC CTTTTGTTTC ACCGCGTGCG GCGATTCCGG
```

-continued

5581 GTCCCCAGTG ATCACCGAGG CCGGGGAGCT TGTCGGTGTC CACACGGGAT CAAACAAACA
5641 AGGAGGAGGC ATTGTTACGC GCCCTTCAGG CCGGTTTTGT AATGTGACAC CCACCAAATT
5701 AAGTGAATTG AGTGAATTCT TCGCTGGACC TAGGGTCCCG CTTGGTGACG TGAAGGTTGG
5761 CAATCACATA ATCAAAGATA TAAATGAGGT GCCCTCAGAT CTCTGCGCCT TACTCGCTGC
5821 CAAACCCGAA TTGGAAGGAG GCCTCTCCAC CGTTCAACTT CTGTGCGTGT TTTTTCTCCT
5881 ATGGAGAATG ATGGGACATG CCTGGACACC CTTGGTTGCC GTTGGTTTTT TCATCTTGAA
5941 TGAAGTTCTC CCAGCAGTCC TGGTCCGGAG TGTCTTCTCC TTTGGAATGT TCGCACTGTC
6001 TTGGTTCACG CCGTGGTCTG CACAAATTCT AATGATCAGG CTCTTGACAG CAGCCCTAAA
6061 CAGAAACAGA TCGTCACTTG CCTTTTACAG CCTGGGCGCA CTAACCGGTT TTGTTGCAGA
6121 TCTTGCAACC AATCAGGGGT ATTTATTGCA CGCGGTCATG AATGTGAGCA CCTATGCATT
6181 CCTGCCTCGT GCAATGGCCG TGACCTCACC AGTCCCAATA GTTGCGTGTG GCGTTGTGCA
6241 CTTGCTTGCC ATCATTCTGT ACTTGTTCAA GTACCGTAGC CTGCATGCCG TCCTGGTCGG
6301 CGATGGTGCG TTTTCCGCGG CTTTCTTCTT GCGATACTTT GCGGAGGGAA AGTTGAGGGA
6361 AGGGGTGTCG CAGTCTTGCG GCATGAATCA TGAGTCACTA ACCGGTGCCC TCGCCATGAA
6421 ACTCAGCGAC GAAGACTTGG ACTTCCTCAC AAAATTGACT GATTTTAAGT GCTTTGTTTC
6481 TGCATCCAAC ATGAGGAATG CGGCGGGTCA ATTTATAGAG GCCGCCTACG CCAAAGCACT
6541 GAGGGTGGAA CTTGCCCAGT TGGTTCAAGT CGATAAAGTT CGAGGTGTCC TGGCCAAACT
6601 TGAAGCTTTC GCTGACACCG TGGCGCCTCA ACTTTCACCC GGTGACATTG TTGTCGCCCT
6661 TGGACACACA CCTGTCGGCA GCATTTTTGA CCTGAAGGTC GGCAATGTTA AGCACACTCT
6721 CCAGTCCATT GAGACCAGAA CCCTTGCCGG GTCTAAAATG ACTGTGGCGC GCGTCGTAGA
6781 CCCAACCCCC ACACCCCCGC CCGCACCTGT GCCCATTTCC CTCCCACCAA AGGTTTTGGA
6841 GAACGGTCCC AACGCCTGGG GGGATGAGAA CGGTTTGAAC AAAAAAAAGC GGCGCAAGAT
6901 GGAGGCCGTT GGCATTTACG TTATGGGCGG GAAAAAGTAT CAAAAATTTT GGGATAAGAA
6961 TTCTGGTGAT GTGTTCTATG AAGAAGTCCA CGACAACACA GACGCGTGGG AATGCCTCAG
7021 AGTTGACAAC CCTGCCGACT TGGATCCTGA GAGGGGAACC TTGTGTGGAC ACACCACCAT
7081 AGACAACAGG CCTTACCATG TTTATGCTTC TCCGTCTGGT AGGAAGTTTC TAGTCCCTGT
7141 CAACCCGGAG AGCGGAAAAG CTCAGTGGGA AGCTGCTAAG CTTTCTTTAG ATCAGGCCCT
7201 CAGTATGATG AATGTCGACG GCGAACTGAC CGCCAAAGAA GTGGAAAAAT TGAAGAGAAT
7261 AATTGACAAA CTCCAGGGCC TGACTAAGGA GCAGTGTTTA AACTGCTAGC CGCCAGCGGC
7321 TTGACCCGCT GTGGTCGCGG CGGCTTGGTT GTTACTGAGA CAGCGGTAAA GATAGTCAGG
7381 TTCCACAACC GGACCTTTAC CCTAGGGCCT GTGAATTTGA AAGTAGCTAG CGAAGTTGAG
7441 TTGAAGGACG CGGTCGAGCA CGGCCAACAC CCGGTCGCGA TACCAGCCGA TGGTGGCGTC
7501 GTGCTCCTGC GTTCCGCTGT TCCTTCGCTT ATAGACGTCC TGATCTCCGG TGCTGACGCA
7561 TCTCCCAGGT TGCTCGCCCG TCACGGACCG GGAAATACTG GGGTCAATGG CGCGCTTTGG
7621 GATTTTGAGT CTGAAGCTAC CAAAGAGGAA GTAGCACTTA GTGCGCAAAT AATACAGGCC
7681 TGTGACATTA GACGCGGCGA TGCACCTGAG ATTGGCCTTC CTTACAAGTT GTACCCTGTT
7741 AGGGGCAACC CTGAACGGGC AAGAGGGGTT CTAATGAACA CAAGATTTGG AGACATACCT
7801 TACAAGACCC CCAGCGACAC CGGGAGCCCG GTGCACGCGG CCGCCTGCCT TACGCCCAAC
7861 GCCACTCCAG TAACTGATGG GCGCTCCATC CTGGCCACGA CCATGCCCTC CGGGTTTGAA
7921 CTATATGTGC CGACCATTCC AGCGTCTGTC CTTGATTACC TTGACTCCAG ACCAGACTGT

-continued

7981 CCTAAACAGT TGACTGAGCA CGGGTGTGAA GATGCCGCGT TGAAGGACCT TTCTAAATAT

8041 GACCTGTCCA CCCAAGGCTT TGTGTTACCT GGAGTTCTAC GCCTCGTGCG AAAATATCTG

8101 TTTGCTCATG TAGGTAAGTG CCCGCCTGTC CACCGGCCCT CTACCTATCC TGCCAAGAAC

8161 TCCATGGCCG GAATAAATGG GAACAGGTTC CCAACCAAGG ATATTCAAAG CATCCCTGAG

8221 ATCGACGTTT TGTGTGCACA AGCTGTGCGA GAAAACTGGC AAACTGTTAC ACCCTGCACT

8281 CTTAAGAAGC AGTATTGCGG TAAAAAGAAG ACCAGGACCA TACTTGGCAC CAACAACTTC

8341 GTTGCGCTGG CCCACCGGGC GGCGCTGAGT GGTGTCACCC AGGGTTTCAT GAAGAAGGCG

8401 TTTAACTCAC CCATCGCCCT TGGGAAAAAT AAATTTAAGG AGCTACAGAC TCCAGTCTTG

8461 GGTAGGTGTC TTGAGGCTGA TCTCGCTTCC TGCGATCGAT CCACGCCTGC AATCGTTCGC

8521 TGGTTTGCCG CCAACCTTCT TTATGAACTT GCCTGTGCTG AGGAGCATTT ACCGTCGTAC

8581 GTGCTGAACT GTTGTCACGA CCTATTGGTC ACGCAGTCCG GCGCAGTGAC TAAGAGAGGT

8641 GGCCTGTCGT CCGGTGACCC AATCACCTCT GTGTCCAACA CCATTTATAG CTTGGTGATC

8701 TATGCACAGC ATATGGTGCT TAGTTACTTC AAAAGTGGTC ACCCCCATGG CCTTCTGTTT

8761 TTACAAGACC AGCTAAAGTT TGAAGACATG CTCAAAGTTC AACCCCTAAT CGTCTATTCG

8821 GACGACCTCG TGTTGTATGC CGAGTCTCCC ACCATGCCAA ACTATCACTG GTGGGTTGAA

8881 CACCTGAATT TGATGTTGGG ATTTCAGACG GACCCAAAGA AGACTGCAAT AACAGACTCA

8941 CCTTCATTCC TAGGTTGTAG AATAATAAAT GGCCGCCAGT TAGTACCCAA CCGTGACAGA

9001 ATTCTCGCGG CCCTTGCCTA TCACATGAAG GCGAGTAATG TTTCTGAGTA CTACGCCTCC

9061 GCAGCCGCAA TACTCATGGA CAGTTGTGCT TGTCTAGAGT ATGATCCTGA GTGGTTTGAA

9121 GAACTTGTGG TTGGAATGGC GCAGTGCGCC CGTAAGGACG GCTATAGTTT CCCCGGCCCG

9181 CCGTTCTTCT TGTCCATGTG GGAAAAGCTC AGGTCAAATT ATGAGGGGAA GAAGTTGAGA

9241 GTGTGTGGTT ATTGCGGAGC TTCAGCCCCG TATGCTACTG CCTGTGGCCT TGACGTTTGT

9301 GTTTACCACA CCCACTTTCA CCAGCATTGT CCAGTCATAA TATGGTGTGG CCACCCGGCG

9361 GGTTCTGGGT CCTGCGATGA GTGCAAATCC CCTACAGGGA AGGGTACAAG CCCTCTGGAT

9421 GAGGTCTTAA GACAAGTCCC TTATAAGCCT CCACGGACTA TTCTTATGCA TGTGGAGCAG

9481 GGCCTCACCC CCCTTGACCC AGGCAGATAC CAGACCCGCC GTGGGTTGGT TGCTGTCAGG

9541 CGCGGGATAA GGGGAAATGA AGTTGACCTG CCAGATGGTG ATTATGCCAG TACTGCCCTA

9601 CTCCCCACCT GCAAAGACAT AGACATGGTT GCTGTGGCCT CCAATGTGTT GCGCAGTAGG

9661 TTCATCATCG GCCCACCTGG CGCAGGGAAA ACACACTGGC TTCTTCAACA GGTTCAGGAT

9721 AGTGATGTCA TTTACACGCC AACCCATCAG ACCATGCTTG ACATGATCAA GGCTTTGGGG

9781 ACGTGCCGGT TCAATGTCCC GGCAGGCACA ACGCTGCAAT TCCCTGCCCC CTCCCGTACC

9841 GGCCCGTGGG TTCGCATCCT TGCCGGCGGT TGGTGTCCAG GTAAGAATTC CTTCCTGGAT

9901 GAAGCAGCGT ATTGCAATCA CCTTGACGTC TTGAGGCTTC TCAGCAAAAC TACCCTCACC

9961 TGTCTGGGGG ATTTCAAACA ACTCCACCCG GTGGGTTTTG ATTCTCATTG CTATGTTTTT

10021 GATATCATGC CTCAGACTCA ACTGAAGACC ATCTGGAGGT TTGGACAGAA TATCTGTGAC

10081 GCCATTCAGC CAGATTACAG GGACAAACTC GTGTCCATGG TCAACACAAC CCGTGTAACC

10141 TATGTGGAAA GACCTGTCAA GTATGGGCAA GTCCTCACCC CCTACCACAG AGACCGAGAG

10201 GATGGTGCTA TCACTATTGA CTCCAGTCAA GGCGCCACAT TTGATGTGGT CACATTGCAT

10261 TTGCCCACTA AAGATTCACT CAACAGGCAA AGAGCCCTTG TTGCTATCAC CAGGGCAAGG

10321 CATGCAATCT TTGTGTATGA CCCACACAGG CAACTGCAGA GCATGTTTCG TCTTCCTGCA

10381 AAAGGCACAC CTGTCAACCT TGCCGTGCAC CGTGACGAGC AGCTCATCGT ATTAGATAGA

-continued

10441 AATAACAAAG AGTGCACGGT TGTTCAGGCT TTAGGCAATG GGGACAAATT CAGGGCCAGT
10501 GACAAGCGCG TTGTAGATTC TCTTCGCGCC ATTTGTGCAG ATCTTGAAGG GTCGAGCTCC
10561 CCGCTCCCCA AGGTCGCACA CAACTTGGGA TTTTATTTCT CACCTGATTT GACACAGTTT
10621 GCTAAACTCC CGGCGGAACT TGCACCCCAC TGGCCCGTGG TGACAACTCA GAACAACGAA
10681 AATTGGCCAG ACCGGCTGGT TGCTAGCCTC CGCCCTATCC ACAAATATAG CCGCGCGTGC
10741 ATCGGAGCCG GCTATATGGT GGGCCCCTCA GTGTTTCTAG GCACTCCTGG GGTTGTGTCA
10801 TACTATCTCA CACAATTTGT CAAAGGGGAG GCTCAGGTGC TTCCGGAGAC GGTCTTCAGC
10861 ACCGGCCGAA TTGAGGTAGA TTGTCGAGAG TATCTTGATG ATCGGGAACG AGAAGTTGCT
10921 GAGTCCCTCC CACATGCCTT TATTGGCGAC GTCAAAGGCA CTACCGTTGG GGGATGTCAC
10981 CATGTCACTT CTAAATATCT CCCACGCTTC CTTCCCAAGG AATCAGTTGC GGTGGTTGGG
11041 GTTTCAAGCC CCGGGAAAGC CGCAAAAGCA GTTTGCACAT TAACAGATGT GTACCTCCCA
11101 GATCTTGAGG CTTACCTCCA TCCAGAGACC CAGTCTAAGT GCTGGAAAGT GATGTTGGAC
11161 TTCAAGGAAG TTCGACTGAT GGTCTGGAGA GATAAGACGG CCTACTTTCA ACTTGAAGGC
11221 CGCCATTTCA CCTGGTACCA GCTTGCAAGT TATGCCTCGT ACATCCGAGT TCCCGTTAAC
11281 TCTACGGTGT ACCTGGACCC CTGTATGGGC CCTGCCCTTT GCAACAGAAG AGTCGTTGGG
11341 TCTGCACATT GGGGAGCTGA CCTTGCAGTT ACCCCTTATG ATTATGGTGC CAAAATCATT
11401 CTGTCTAGTG CGCACCATGG TGAAATGCCT CCTGGGTACA GAATTCTAGC GTGCGCGGAG
11461 TTCTCGCTTG ATGACCCAGT GAGGTACAAA CACACTTGGG GGTTTGAATC GGATACAGCG
11521 TATCTGTACG AGTTCACCGG AAACGGTGAG GACTGGGAGG ATTACAATGA TGCGTTTCGT
11581 GCACGCCAGA AAGGGAAAAT TTATAAGGCC ACTGCCACCA GCATGAGATT TCATTTTCCC
11641 CCGGGTCCTG CCATTGAACC AACATTGGGC CTGAACTGAA ATGAAATGGG GGCTGTGCAG
11701 AGCCTTTTCG ACAAAATTTG CCAACTTTTT GTGGATGCTT TCACGGAATT TTTGGTGTCC
11761 ATTGTTGATA TCATCATATT TTTGGCCATT TTGTTTGGCT TCACCATCGC AGGCTGGCTG
11821 GTTGTCTTCT GTATCCGACT GGTTTGCTCC ACGGTACTCC GTGCGCGCTC TACCATTCAC
11881 CCTGAGCAAT TACAGAAGAT CCTATGAGGC CTTCCTTTCC CAGTGCCAAG TGGACATTCC
11941 CGCCTGGGGA ACTAAGCATC CCTTGGGGGT GCTTTGGCAC CACAAGGTGT CAACTCTGAT
12001 TGATGAAATG GTGTCGCGTC GAATGTACCG CATCATGGAA AAAGCAGGAC AGGCTGCCTG
12061 GAAACAGGTT GTGAGCGAAG CTACATTGTC TCGCATAAGT GGCTTGGATG TGGTGGCTCA
12121 TTTTCAGCAT CTTGCTGCCA TTGAAGCCGA GACTTGCAAA TATTTGGCCT CTCGGCTGCC
12181 CATGCTACAC AACCTAGTCA TGTCAGGGTC GAATGTAACC ATAGTGTATA ATAGCACTTT
12241 GGGTCAAGTG TTTGCCATTT TCCCAACCCC TGGTTCCCGG CCAAAACTTT CTGATTTTCA
12301 ACAATGGCTC ATAGCTGTGC ATTCTTCCAT ATTTTCTTCT GTTGCGGCTT CTTGTACTCT
12361 TTTTGTTGTG CTGTGGCTGC GAATTCCAAT ACTACGTACT GTTTTTGGTT TCCGCTGGTT
12421 AGGGGCAACT TTTCTTTCGA ACTCACAGTG AATTACACGG TGTGCCCACC CTGCCTCACC
12481 CGGCAAGCAG CCGCTGAGAT CTACGAACAC AGCGGGTCTC TTTGGTGCAG GATAGGGCAT
12541 GACCGATGTA GCCAGAGTGA TCATGACGAA CTAGGGTTCT TGGTTCCACC TGGCCTTTCC
12601 AGCGAGGGCC ACTTGACCAG TGTTTACGCC TGGCTGGCGT TCTTGTCTTT CAGCTACACA
12661 GCCCAGTTCC ACCCCGAGAT ATTTGGAATA GGGAATGTGA GTAGAGTTTA TGTTGACGTC
12721 ACTCACCAAC TCATCTGCGC CGAACACGAC GGGCAGAACA CCACCCTGCG TCGCCATGAC
12781 AATATCTCAG CCGTGTTTCA GACCTATTAC CAACATCAGG TCGATGGCGG CAATTGGTTT

-continued

12841 CACCTAGAAT GGCTGCGTCC CTTCTTTTCC TCTTGGCTGG TTTTGAATGT CTCGTGGTTT

12901 CTCAGGCGTT CGCCTGCAAA CCGTGTTTCA GTTCGAGTCT TTCAGACATC AAAACCAACA

12961 CCACCGCAGC TGCAGGCTTT GCTGTCCTCC AAGACATCAG CTGTCTTAGG CATGGCTACT

13021 CGTCCATTGA GGCGATTCGC AAAAGCCGTC AATGCCGCAC GGCGATAGGA ACGCCCGTGT

13081 ACATCACTGT CACGGCCAAT GTAACAGATG AGAATTACTT GCATTCCTCT GATCTCCTCA

13141 TGCTTTCCTC TTGCCTCTTC TATGCTTCTG AGATGAGTGA AAAGGGATTC AATGTGGTCT

13201 TCGGCAACGT GTCAGGCATT GTGGCTGTGT GTGTCAACTT TACCAGCTAT GTCCAACATG

13261 TTAAGGAGTT TACTCAGCGC TCTTTGGTGG TCGACCACGT GCGACTGCTT CATTTCATGA

13321 CACCTGCGAC CATGAGGTGG GCAACAGTTT TAGCCTGTCT TTTCGCCATC TTGTTGGCGA

13381 TTTGAATGTT TAAGTATGTT GGGGAAATGC TTGACCGCGG GCTACTGCTC GCAATTGCTT

13441 TTTTTCTGGT GTATCGTGCC GTTCTGTTTT GCTGCGCTCG TCAACGCCGC CAGCAACAGC

13501 AGCTCCCATT TACAGTTGAT TTATAACCTG ACGATATGCG AGCTGAATGG CACAGATTGG

13561 TTGAATCAAA AGTTTGATTG GGCAGTGGAG ACTTTTGTCA TTTTTCCTGT GTTGACCCAC

13621 ATTGTCTCCT ACGGTGCCCT TACCACCAGC CATTTCCTTG ACACGGCCGG CCTAATCACT

13681 GTGTCTACCG CCGGATATTA CCATGGGCGG TATGTGTTGA GTAGCATCTA CGCCGTCTTT

13741 GCCCTGGCTG CGTTGATTTG TTTTGTCATT AGGTTGACAA AAAACTGTAT GTCCTGGCGC

13801 TACTCATGTA CCAGATATAC CAACTTTCTT CTGGACACCA AAGGCAATCT CTATCGTTGG

13861 CGGTCACCCG TCGTTATAGA GAGAAGGGGT AAAGTTGAGG TTGGAGACCA CCTAATCGAC

13921 CTCAAAAGAG TTGTGCTTGA TGGTTCCGCG GCAACCCCTA TAACCAAGAT TTCAGCGGAA

13981 CAATGGGGTC GTCCCTAGAC GACTTCTGCA ATGACAGCAC AGCTGCACAA AAGGTGCTTT

14041 TGGCGTTTTC CATCACCTAT ACGCCAATAA TGATATATGC CCTGAAGGTA AGTCGCGGCC

14101 GACTGTTAGG GCTTTTGCAT CTTTTAATTT TCTTGAATTG TGCTTTCACC TTCGGGTACA

14161 TGACATTTGT TCATTTTCAG AGTACAAACA AGGTCGCGCT CACTATGGGA GCAGTTGTTG

14221 CACTCCTTTG GGGGGTGTAC TCAGCCATAG AAACCTGGAA ATTCATCACT TCCAGATGCC

14281 GTTTGTGCTT GCTAGGCCGC AGGTACATTC TGGCCCCTGC CCACCACGTT GAAAGTGCCG

14341 CGGGCTTTCA TCCGATTGCG GCAAGTGATA ACCACGCATT TGTCGTCCGG CGTCCCGGCT

14401 CCACTACTGT TAACGGCACA TTGGTGCCCG GGTTGAAAAG CCTCGTGTTG GGTGGCAGAA

14461 AAGCTGTTAA GCGGGGAGTG GTAAACCTCG TTAAATATGC CAAATAACAA CGGCAGGCAG

14521 CAAAAAAATA AGAAGGGGAG TGGCCAGCCA GTCAATCAGC TGTGCCAAAT GCTGGGCAAG

14581 ATCATCGCCC AGCAAAATCA GTCCAGAGGC AAGGGACCGG GTAAGAAAAA TAAGAAGAGA

14641 AACCCGGAGA AGCCCCATTT TCCTCTTGCG ACCGAAGATG ACGTCAGGCA TCACTTCACC

14701 CCCAGTGAAC GGCAATTGTG TCTGTCGTCG ATCCAGACTG CCTTCAACCA GGGCGCTGGA

14761 ACTTGCACCC TGTCAGATTC AGGGAGGATA AGTTACACTG TGGAGTTTAG TTTGCCGACG

14821 CACCACACTG TGCGCCTTAT TCGCGCCACA GCATCACCTC CATCGTGATG GGCTTACATT

14881 CTTGGAGCTC CTCAGTTTCA CAATTGGAAG AATGTGTGGT GAATGGCACT GATTGGCACT

14941 GTGCCTCTAA GTCACCTATT CAATTAGGGC GACCGTGTGG GGGTAGAGTT TAATTGGCGA

15001 GAACCATACG GCCGAAATTA AAAAAAAAAA AAAAAAAAAA AAAAAAA

A person skilled in the art would recognize the poly-adenosine tails of each of the genomic consensus sequences could vary in length from the above reported sequences.

EXAMPLE 2

The objective of this study is to evaluate the efficacy of experimental PRRSV vaccines in growing swine following heterologous challenge with a virulent PRRS virus. The efficacy of a test vaccine is based on the effectiveness of the vaccine to reduce lung lesions and viremia compared to a non-vaccinated control. The design of this study is given in Table 1.

TABLE 1

Study design.

| Treatment Group | PRRSV strain | FFU[1] titer/mL | Dose Volume | Route | Vaccination Day | Number of Animals |
|---|---|---|---|---|---|---|
| T01 | None[2] | N/A | 0.5 mL | IM[3] | Day 0 | 16 |
| T02 | SD 04-89 | $1.1 \times 10^7$ | 0.5 mL | IM | Day 0 | 10 |
| T03 | SD 03-15 | $3.8 \times 10^6$ | 0.5 mL | IM | Day 0 | 10 |
| T04 | SD 95-10 | $1.3 \times 10^7$ | 0.5 mL | IM | Day 0 | 10 |
| T05 | SD 11-21 | $4.0 \times 10^6$ | 0.5 mL | IM | Day 0 | 10 |
| T06 | SD 02-10 | $1.1 \times 10^7$ | 0.5 mL | IM | Day 0 | 10 |
| T07 | SD 95-47 | $2.4 \times 10^7$ | 0.5 mL | IM | Day 0 | 10 |
| T08 | ND 99-14 | $2.1 \times 10^7$ | 0.5 mL | IM | Day 0 | 10 |
| T09 | MN 05-68 | $1.6 \times 10^7$ | 0.5 mL | IM | Day 0 | 10 |

[1]Flourescent foci unit (FFU).

[2]Placebo control animals received phosphate-buffered saline (PBS).

[3]IM = Intramuscular.

The pre-challenge phase was from the day of arrival at the study site (Day −1) through day of challenge (Day 35). Blood samples for PRRSV serum antibody determination using fluorescent foci neutralization (FFN) testing were collected on Days 0, 14, 28 and 35. Blood samples for determination of PRRSV viremia were collected on Days 0 and 35. Nasal swabs to assess viral load were collected on Days 0 and 35. A body weight measurement (lbs) was taken on Day 0 and prior to the challenge on Day 35.

On Day 35, a 3 mL non-luer lock syringe was used to deliver a 2 mL dose intranasally, with approximately 1 mL per nostril. The post-challenge phase was from Day 35 to Day 49. All pigs were individually assessed for depression, body condition and respiratory distress on Days 35-49 and scored for each clinical sign. Blood samples for PRRSV serum antibody determination (FFN) were collected on Days 42 and 49. Blood samples for determination of PRRSV viremia were collected on Days 38, 42, 45, and 49. Nasal swabs to assess viral load were collected on Days 38, 42, 45, and 49. A body weight measurement was obtained at the time of necropsy on Day 49. On Day 49, animals were humanely euthanized as per the site standard operating procedure and lungs were scored by the Study Investigator who was blinded to treatment. Each of the seven pulmonary lobes was examined both visually and by palpation for gross characteristic lesions attributed to PRRSV. The amount of lesion/consolidation in each pulmonary lobe was scored as an actual between 0 and 100% of the lobe. The score for each lobe was entered into a weighted formula to calculate the percentage of lung with lesions.

Ninety-six weaned crossbred gilts and barrows approximately 3 weeks of age that were sero-negative to PRRSV and assessed to be in good health were utilized for this study. Upon arrival at the study site, selected study animal were randomly assigned to treatment groups (T01-T09) and study pen. Upon arrival all candidate animal that met the following inclusion criteria were included in the study and those that did not meet criteria were excluded: 1) seronegative for PRRSV by serum neutralization testing (FFN) on Day 0; and 2) animals clinically assessed to be in good health based on physical examination conducted on Day 0.

After arrival at the study site, the pigs were housed by treatment group in five BSL-2 environmentally-controlled containment rooms. Each containment room contained five pens capable of holding five pigs per pen. Within each of the vaccinate rooms, the two treatment groups were separated by a plastic sheeting barrier and groups did not share the same airspace. Biosecurity was strictly maintained between the two areas separating the vaccinate groups within the room. The pigs were fed production-appropriate, standard swine grower ration (NRC, 2012) ad libitum. The pigs had access to clean drinking water ad libitum.

General health observations were conducted once daily from time of arrival at the study site until the day prior to challenge (Day −1 through 34). All pigs were individually assessed for depression, body condition and respiratory distress on Days 35-49 and scored for each clinical sign as defined in the scoring system.

Animals that developed clinically significant concurrent disease prior to Day 35 were removed from the study. Any data collected from the pig prior to exclusion was not included in data analysis. Following challenge on Day 35, any pig found dead or sacrificed in extremis was necropsied to determine cause of death, if possible. Due to a death attributable to *S. suis* and a confirmed illness in the same pen (T08), EXCEDE® antibiotic (Zoetis Animal Health) was administered to individual study animals as needed and all animals on Day 30.

All candidate PRRSV strains were passed 83 times on MARC-145 cells. Titers for each of the eight (8) vaccines were determined, as shown in Table I. Sterility testing per USDA 9 C.F.R. requirements was successfully completed at Benchmark BioLabs, Lincoln, Nebr. Vaccines comprised the PRRSV in a pharmaceutically-acceptable excipient, i.e. physiological saline.

Immediately prior to use, three 1 mL stock vials of the PRRSV NADC-20 challenge strain were thawed at room temperature and 3 mLs of the stock was added to 297 mLs of Minimum Essential Medium Eagle with Earle's salts and L-glutamine (MEM) from Mediatech, Inc. in a sterile container. The inoculum (consisting of the viral stock and medium) was hand mixed and retained on wet ice during administration to animals. Prior to challenge, five (5) mLs of the challenge inoculum was aliquoted directly into a sterile container for submission to the diagnostic laboratory for titer determination. Titer results were $10^{2.75}$ $TCID_{50}$/mL.

Animal were the experimental unit. Differences between groups were assessed using two-sided tests at alpha=0.05.

Percentage of total lung with lesions was calculated according to the following formula:

$$\text{Percentage of total lung with lesions}=\{(0.10\times\text{left apical})+(0.10\times\text{left cardiac})+(0.25\times\text{left diaphragmatic})+(0.10\times\text{right apical})+(0.10\times\text{right cardiac})+(0.25\times\text{right diaphragmatic})+(0.10\times\text{intermediate})\}.$$

The influence of vaccination on the percentage of total lung lesions was evaluated by calculating the mitigated fraction and the associated 95% confidence interval (MF; CI; the FREQ procedure in SAS® software, SAS Institute, Cary N.C.) for each placebo/vaccinated pair. In addition, the percentage of total lung with lesions was transformed using the arcsine square root, prior to further analysis. The transformed data was analyzed by a mixed linear model that includes the fixed effect of treatment (the MIXED procedure in SAS® software) as the only factor. If the effect of treatment was statistically significant, pair-wise comparisons between the placebo and vaccinated groups were made using linear contrasts and an unadjusted alpha=0.05. The vaccine complied with the test if the vaccinated pigs, when compared with controls, showed a significant reduction in the lung lesion score.

Methods appropriate for repeated measures were used to evaluate the effect of vaccination on viremia values (the MIXED procedure in SAS® software, SAS Institute, Cary N.C.) under the assumption of a normal distribution. Data was transformed prior to analysis to stabilize the residuals. The statistical model included treatment, time, and treatment by time interaction as fixed effects. If the treatment by time interaction was significant, the effects of the vaccine within that time treatment were evaluated. Within time, comparisons were made between vaccinated and non-vaccinated animals. If the interaction was not significant, the main effect of treatment was assessed. Comparisons were made between vaccinated and non-vaccinated animals. Least squares means, standard errors, 95% confidence intervals of the mean, and ranges were presented as appropriate.

Methods appropriate for repeated measures of continuous or binomial data were used to evaluate the effect of vaccination on serum antibody and nasal swab values (the MIXED or GLIMMIX procedure in SAS® software, SAS Institute, Cary N.C.) under the assumption of a normal/binomial distribution. Data was transformed prior to analysis to stabilize the residuals. The statistical model included treatment, time, and treatment by time interaction as fixed effects. If the treatment by time interaction was significant, the effects of within time treatment were evaluated. Within time, comparisons were made between vaccinated and non-vaccinated animals. If the interaction was not significant, the main effect of treatment was assessed. Comparisons were made between vaccinated and non-vaccinated animals. Least squares means, standard errors, 95% confidence intervals of the mean, and ranges were presented as appropriate.

Body weight (Days 35 and 49), depression score, respiratory score and body condition scores (Days 35-49) were statistically analyzed using an ANCOVA appropriate for repeated measures (the MIXED procedure). Day 0 values were included as a covariate, if appropriate. Treatment group, time and the group by time interaction were included in the model as fixed effects. If the interaction term was significant, within time group effects were evaluated by comparing each vaccination group to the control using an unadjusted alpha=0.05. If the interaction was not significant, the main effect of group was evaluated, and if significant, group effects were evaluated by comparing each vaccination group to the control using an unadjusted alpha=0.05. Mortality was not assessed since there was only one death during the study.

The mean percent lung involvement in the control group was 37.9% (Table 2) which was in agreement with the expected pathology for this PRRSV challenge model (range 30 to 50%, L. Kesl of Veterinary Resources, Inc., personal communication) using Type-2 strain NADC-20. It was concluded that the PRRS viral challenge was adequate to assess the vaccine strain candidates.

Mean lung lesion scores are presented in Table 2. With the exception of the vaccine containing PRRSV EU-like (i.e. Type 1 PRRSV) strain SD 03-15, all experimental vaccines reduced ($P<0.05$) lung lesions compared to the control group. Notably, strains SD 95-10, SD 11-21 and ND 99-14 induced a high degree of protection resulting in very low lung involvement (2.7%, 1.0% and 1.6%, respectively). Strains SD 95-47 and MN 05-68 also performed well, while strains SD 04-89 and SD 02-10 were acceptable. The mitigated fraction of each vaccine versus the control group is shown in Table 3. These results indicated that pigs vaccinated with attenuated PRRSV strains SD 95-10 (T04), SD 11-21 (T05) and ND 99-14 (T08) had at least a 90% probability of having less severe lung lesions than pigs in the control group.

TABLE 2

Mean Lung Lesion Scores.

| Treatment Group | Vaccine | Estimate[1] | Standard Error | Mean[2] |
|---|---|---|---|---|
| T01 | None (PBS only) | 0.6633 | 0.05594 | 37.91% |
| T02 | Strain SD 04-89 | 0.3861* | 0.07075 | 14.14% |
| T03 | Strain SD 03-15 | 0.4885 | 0.07075 | 22.02% |
| T04 | Strain SD 95-10 | 0.1662* | 0.07075 | 2.74% |
| T05 | Strain SD 11-21 | 0.0988* | 0.07075 | 0.97% |
| T06 | Strain SD 02-10 | 0.3642* | 0.07075 | 12.69% |
| T07 | Strain SD 95-47 | 0.2073* | 0.07075 | 4.24% |
| T08 | Strain ND 99-14 | 0.1252* | 0.07458 | 1.56% |
| T09 | Strain MN 05-68 | 0.2316* | 0.07075 | 5.27% |

[1]Untransformed means.
[2]Back transformed means.
*Versus T01, significantly different at $P < 0.05$.

TABLE 3

Lung Lesion Scores.

| Treatment Group Comparison | Mitigated Fraction[1] | 95% confidence interval |
|---|---|---|
| Control (T01) versus SD 04-89 (T02) | 0.5875 | 0.2266, 0.9484 |
| Control (T01) versus SD 03-15 (T03) | 0.3125 | −0.1838, 0.8088 |
| Control (T01) versus SD 95-10 (T04) | 0.9000 | 0.7077, 1.0000 |
| Control (T01) versus SD 11-21 (T05) | 0.9688 | 0.9017, 1.0000 |
| Control (T01) versus SD 02-10 (T06) | 0.7000 | 0.3092, 1.0000 |
| Control (T01) versus SD 95-47 (T07) | 0.8000 | 0.5290, 1.0000 |
| Control (T01) versus ND 99-14 (T08) | 0.9028 | 0.7152, 1.0000 |
| Control (T01) versus MN 05-68 (T09) | 0.7875 | 0.4986, 1.0000 |

[1]Mitigated fraction means the relative increase in the probability that the lung lesions of vaccinates (T02-T09) will be less severe than the lung lesions of non-vaccinates (T01).

Geometric means of PRRSV enumerated by qtRT-PCR from nasal secretions are presented in Table 4, as an indication of viral shedding. With the exception of pigs vaccinated with strain SD 02-10, vaccine virus was detected in the nasal swabs of all vaccinated groups at Day 35. Pigs vaccinated with strains SD 03-15, SD 95-10 and SD 95-47 had statistically greater ($P<0.05$) genomic copies/mL than the pigs of the control group with mean values of 277, 337 and 7 genomic copies/mL, respectively. Upon challenge on Day 35, all groups shed some virus at Day 38, 42, 45 and 49 (3, 7, 10 and 14 days post challenge (DPC), respectively). Pigs vaccinated with strains SD 95-10, SD 95-47 and ND 99-14 had a lower ($P<0.05$) level of shedding than controls at all time-points post challenge. By 10 and 14 DPC, all vaccine strains induced a reduction ($P<0.05$) in shedding compared to the controls, with the exception of strains SD 04-89 and SD 03-15.

TABLE 4

Geometric Means of PRRSV Genomic Copies/mL in Nasal Swab.

| Treatment Group | Vaccine | Day 0 | Day 35 | Day 38 | Day 42 | Day 45 | Day 49 |
|---|---|---|---|---|---|---|---|
| T01 | None (PBS only) | 0 | 0 | 285500 | 66956 | 8805 | 1375 |
| T02 | Strain SD 04-89 | 0 | 1 | 776071 | 26115 | 3157 | 1360 |
| T03 | Strain SD 03-15 | 0 | 277* | 3200* | 3200* | 3871 | 2201 |
| T04 | Strain SD 95-10 | 0 | 337* | 158* | 368* | 28* | 89* |
| T05 | Strain SD 11-21 | 0 | 1 | 529399 | 5521* | 75* | 16* |
| T06 | Strain SD 02-10 | 0 | 0 | 215539 | 14541 | 158* | 3* |
| T07 | Strain SD 95-47 | 0 | 7* | 4193* | 3544* | 38* | 26* |
| T08 | Strain ND 99-14 | 0 | 3 | 343* | 710* | 159* | 30* |
| T09 | Strain MN 05-68 | 0 | 5 | 105* | 38680 | 459* | 12* |

*Within day versus T01, significantly different at P < 0.05.

Geometric means of PRRSV enumerated by qtRT-PCR (genomic copies/mL) from serum are presented in Table 5. All vaccinated groups had some measurable viremia attributable to the vaccination on Day 35, although the levels in the groups vaccinated with SD 04-89 and SD 11-21 were not statistically different from the control (P>0.05, which were negative. Upon challenge on Day 35, all groups were viremic at 3, 7, 10 and 14 DPC. Pigs vaccinated with strains SD 95-10 and ND 99-14 had lower (P<0.05) levels of viremia than controls at all time-points post challenge. By 10 and 14 DPC, all vaccine strains induced a reduction (P<0.05) in viremia compared to the controls, with the exception of strains SD 04-89 and SD 03-15.

TABLE 5

Geometric Means of PRRSV Genomic Copies/mL in Serum.

| Treatment Group | Vaccine Strain | Day 0 | Day 35 | Day 38 | Day 42 | Day 45 | Day 49 |
|---|---|---|---|---|---|---|---|
| T01 | None | 0 | 0 | 2903710 | 17470074 | 5039915 | 429509 |
| T02 | SD 04-89 | 0 | 51 | 1616541 | 25183510 | 2328418 | 95654 |
| T03 | SD 03-15 | 0 | 3840* | 206281* | 591903* | 813498* | 217313 |
| T04 | SD 95-10 | 0 | 20528 | 5122* | 7787* | 5176* | 377* |
| T05 | SD 11-21 | 0 | 5 | 2782331 | 1590087* | 45034* | 2835* |
| T06 | SD 02-10 | 2 | 2617* | 611028 | 3408898 | 647775* | 30347* |
| T07 | SD 95-47 | 0 | 5711* | 504891 | 1407041* | 44550* | 9692* |
| T08 | ND 99-14 | 0 | 357* | 21432* | 95434* | 3358* | 1177* |
| T09 | MN 05-68 | 0 | 1578* | 47685* | 2888361 | 183890* | 10337* |

*Within day versus T01, significantly different at P < 0.05.

Seroconversion was determined by measuring geometric mean fluorescent foci neutralization (FFN) titers, as shown in Table 6. Control animals remained seronegative through Day 35 (day of challenge), began to seroconvert by Day 42 (7 DPC) and had seroconverted by Day 49 (14 DPC). All vaccinate groups had seroconverted by Day 14 after vaccination, with the exception of SD 03-15. Geometric mean titers in all vaccinate groups exceeded (P<0.05) the one of the controls on Days 28, 35 and 42 and were similar to or less than the one of the controls on Day 49. Peak FFN titer response in the vaccinate groups occurred on Days 35 and 42. Strains SD 95-10, SD 11-21, SD 95-47 and ND 99-14 appeared to elicit the most robust serological response.

TABLE 6

Geometric Means of Fluorescent Foci Neutralization (FFN) Titers.

| Treatment Group | Vaccine Strain | Day 0 | Day 35 | Day 38 | Day 42 | Day 45 | Day 49 |
|---|---|---|---|---|---|---|---|
| T01 | None | 0 | 0.00 | 0.00 | 0.11 | 1.26 | 122.59 |
| T02 | SD 04-89 | 0 | 1.20* | 4.75* | 12.13* | 78.38* | 74.94 |
| T03 | SD 03-15 | 0 | 0.67 | 3.83* | 15.87* | 21.43* | 17.11* |
| T04 | SD 95-10 | 0 | 27.90* | 3.42* | 119.51* | 104.10* | 52.54* |
| T05 | SD 11-21 | 0 | 26.04* | 48.56* | 137.26* | 147.18* | 84.57 |
| T06 | SD 02-10 | 0 | 10.16* | 30.10* | 52.59* | 97.29* | 69.91 |
| T07 | SD 95-47 | 0 | 11.66* | 34.62* | 111.85* | 121.79* | 35.73* |
| T08 | ND 99-14 | 0 | 15.89* | 5.92* | 125.04* | 107.19* | 73.05 |
| T09 | MN 05-68 | 0 | 19.86* | 16.14* | 97.92* | 97.40* | 43.27* |

*Within day versus T01, significantly different at P < 0.05.

Least square mean body weights are included in Table 7. The Day 0 body weight was used as a covariate in the analysis. On day of challenge (Day 35), the four groups vaccinated with strains SD 03-15, SD 95-1 0, ND 99-14 and MN 05-68, respectively had lower mean body weights (P<0.05) than the ones of the control. All other groups had mean body weights similar (P>0.05) to the one of the control group. On day of necropsy (Day 49), at 14 DPC, the three groups vaccinated with strains SD 11-2 1, SD 95-47 and ND 99-14 had mean body weights that exceeded (P<0.05) the one of the control. Body weights of all other groups were similar (P>0.05) to the one of the control.

TABLE 7

Least Square Mean Body Weights (lbs).

| Treatment Group | Vaccine Strain | Day 35 LS Mean ± SEM | Day 49 LS Mean ± SEM |
|---|---|---|---|
| T01 | None | 51.2967 ± 1.2386 | 57.7779 ± 1.8550 |
| T02 | SD 04-89 | 49.5986 ± 1.5763 | 58.6786 ± 2.3529 |
| T03 | SD 03-15 | 46.6000* ± 1.5601 | 63.3200 ± 2.3420 |
| T04 | SD 95-10 | 42.2323* ± 1.5604 | 60.1423 ± 2.3422 |
| T05 | SD 11-21 | 51.4161 ± 1.5695 | 65.7061* ± 2.3483 |
| T06 | SD 02-10 | 50.6237 ± 1.5651 | 62.2837 ± 2.3454 |
| T07 | SD 95-47 | 51.0636 ± 1.5614 | 66.3136* ± 2.3429 |
| T08 | ND 99-14 | 45.2815* ± 1.6536 | 63.9593* ± 2.4748 |
| T09 | MN 05-68 | 44.4676* ± 1.5620 | 60.4576 ± 2.3433 |

*Within day versus T01, significantly different at P < 0.05.

Means of the summed clinical scores (respiratory+depression+body condition) were collected for each animal and averaged for each group. Clinical signs were not apparent in any group for up to 7 days after challenge. On Days 42 and 43, clinical signs were evident in some of the vaccine groups but their mean score did not differ (P<0.05) from the one of controls. From Day 44 to 49, all vaccine groups had a lower (P<0.05) summed score than controls, except for groups vaccinated with strains SD 04-89 and SD 02-10 on Day 44.

In conclusion, eight attenuated PRRSV vaccine strains have been successfully evaluated in a viral challenge model. With the exception of the EU-like strain SD 03-15, all strains elicit some protection against challenge with the virulent NADC-20 Type-2 PRRSV. Four strains, SD 11-21, SD 95-10, SD 95-47, and ND 99-14, confer the greatest protection as demonstrated by higher reduction of lung lesions and viremia.

EXAMPLE 3

The objective of this study is to evaluate the cross-protective efficacy of four experimental PRRSV vaccines in growing swine following a challenge with two distinct virulent PRRSV Type-2 strains. Efficacy is evaluated by the extent of lung lesions and viremia. The study was conducted in BSL-2 facilities at Veterinary Resources, Inc. (VRI), Cambridge, Iowa. The study design is presented in Table 8.

TABLE 8

Study design.

| Treatment Group | PRRSV strain | FFU[1] titer/mL | PRRSV Challenge | Vaccination Day/ Challenge | Number of Animals |
|---|---|---|---|---|---|
| T01 | None[2] | N/A | MN-184 | Day 0/35 | 10 |
| T02 | SD 95-10 | $1.3 \times 10^7$ | MN-184 | Day 0/35 | 10 |
| T03 | SD 11-21 | $4.0 \times 10^6$ | MN-184 | Day 0/35 | 10 |
| T04 | ND 99-14 | $2.1 \times 10^7$ | MN-184 | Day 0/35 | 10 |
| T05 | MN 05-68 | $1.6 \times 10^7$ | MN-184 | Day 0/35 | 10 |
| T06 | None[2] | N/A | KS-11 | Day 0/35 | 10 |
| T07 | SD 95-10 | $1.3 \times 10^7$ | KS-11 | Day 0/35 | 10 |
| T08 | SD 11-21 | $4.0 \times 10^6$ | KS-11 | Day 0/35 | 10 |
| T09 | ND 99-14 | $2.1 \times 10^7$ | KS-11 | Day 0/35 | 10 |
| T10 | MN 05-68 | $1.6 \times 10^7$ | KS-11 | Day 0/35 | 10 |

[1]Flourescent foci unit (FFU).

[2]Placebo control animals received phosphate-buffered saline (PBS).

Study personnel who conducted health observations or collected samples were blinded to the treatment identity as well as to assignment of pigs to the treatment groups. One hundred (100) crossbred gilts and barrows approximately 3 weeks of age that were seronegative to PRSSV by virus neutralizing testing (FFN) and assessed to be in good health were utilized for this study. Pigs were sourced from Wilson Prairie View Farms, Burlington, Wis. On Day −1, pigs were allotted to treatment and pen and housed by treatment group within pens in three BSL-2 containment rooms. Within each room the four vaccinate groups were separated by an empty pen or alley way and a solid pen partition to prevent any direct contact and waste contamination into other pens. Pigs were fed standard commercial medicated (CTC/DENAGARD® antibiotic) starter diets (NRC, 2012) ad libitum. Pigs had access to clean drinking water ad libitum.

General health observations were conducted once daily from time of arrival at the study site until the day prior to challenge (Day −3 through 34). All pigs were individually assessed for depression, body condition and respiratory distress on Days 35-49 and scored for each clinical sign.

Prior to weaning and shipment to VRI, each pig was treated with a single dose of VITAL E-500 (Vitamin E), a single dose of EXCEDE® antibiotic (ceftiofur cystalline, Zoetis Animal Health), and was vaccinated with INGELVAC CIRCOFLEX® vaccine (Boehringer Ingelheim Vetmedica). In addition, all pigs were administered a single dose of EXCEDE® antibiotic on either Day 13 or Day 14.

Any pig which exhibited signs of clinical illness or injury was removed from the study. Pertinent samples were submitted to the Iowa State University Veterinary Diagnostics Laboratory (VDL) for diagnostic evaluation. The date, reason, and disposition of the animal removed from the study post-challenge were recorded. Data collected on pigs removed from the study were excluded from the statistical analyses.

All candidate PRRSV strains were passed 83 times on MARC-145 cells. Titers for each of the four (4) vaccines were determined. Sterility testing per USDA 9 CFR requirements was successfully completed at Benchmark BioLabs, Lincoln, Nebr. Vaccines were prepared as in Example 2.

Each of the 100 pigs enrolled in the study were vaccinated on Day 0. Pigs were injected with their assigned treatment as a 0.5 mL intramuscular dose in the right side of the neck. Within one hour following the injections, the Study Investigator examined each pig for any adverse event.

The post-vaccination phase was from Day 1 through Day 35. Blood samples for PRRSV serum antibody determination using fluorescent foci neutralization (FFN) testing were collected on Days −1, 14, 28, and 35. For the FFN assay, twofold dilutions of serum (1:4 to 1:512) were mixed each with an equal volume of culture medium containing 100 focus forming units (FFU) of the test PRRSV strain (MN-184). The mixture was incubated at 37° C. for 1 h and then added to confluent cultures of MARC-145 cells in 96-well tissue culture plates. After about 1 day the plates were fixed in 80% (v/v) acetone in water and infected cells (foci) detected by incubation with fluorescein isothiocyanate conjugated (FITC) anti-N-protein monoclonal antibody SDOW17. The serum neutralization FFN titer was expressed as the reciprocal of the highest dilution that reduced focus formation by about 90% as compared to a serum control. Blood samples for determination of PRRSV viremia were collected on Days −1, 14 and 35. Nasal swabs to assess viral shedding were collected on Days −1, 14 and 35. A body weight measurement (lb) was taken on Day −1 and prior to the challenge on Day 35 using a scale calibrated with certified weights.

The MN-184 PRRSV challenge strain (obtained from Iowa State University VDL) was isolated in 2001 from a swine herd experiencing severe reproductive disease and sow mortality in southern Minnesota. The KS-11 PRRSV challenge strain (obtained from Kansas State University VDL) was isolated in 2011 from a swine herd experiencing severe reproductive disease in northeast Kansas. On Day 35, the challenge material was prepared by thawing the frozen aliquots of MN-184 and KS-11 immediately prior to challenge. Challenge material was in a ready-to-use form requiring no dilution. A sample of each inoculum (MN-184 and KS-11) was submitted to the ISUVDL for titer determination. Day 0 titers for MN-184 and KS-11 strain were determined to be $4.2\times10^5$ and $6.7\times10^3$ $TCID_{50}$/ml, respectively. A 3 mL non-luer lock syringe was used to deliver a 2 mL dose intranasally, with approximately 1 mL per nostril.

The post-challenge phase was from Day 35 to Day 49. All pigs were individually assessed for depression, body condition and respiratory distress on Days 35 to 49 and scored for each clinical sign. Rectal temperature (° F.) was also recorded during this same time period using a calibrated thermometer. Blood samples for PRRSV neutralizing antibody determination (FFN) were collected on Days 42 and 49. Blood samples for determination of PRRSV viremia were collected on Days 38, 42, 45, and 49. Nasal swabs to assess viral shedding were collected on Days 38, 42, 45, and 49. A body weight measurement (lb) was obtained at the time of necropsy on Day 49 using a scale calibrated with certified weights. On Day 49, animals were humanely euthanized, and lungs were excised and scored by the Study Investigator who was blinded to treatment. Each of the seven pulmonary lobes was examined both visually and by palpation for gross characteristic lesions attributed to PRRSV. The amount of lesion/consolidation in each pulmonary lobe was scored as an actual value between 0 and 100% of the lobe. The score for each lobe was entered into a weighted formula to calculate the percentage of lung with lesions.

Percentage of total lung with lesions was calculated according to the formula and procedure given in Example 2.

Rectal temperature, depression score, respiratory score and body condition scores (Days 35 to 49) were statistically analyzed using methods appropriate for repeated measures (the MIXED procedure). Clinical scores were summed within a day for each animal. The summed scores were statistically analyzed as described above for the individual scores.

Average daily weight gain (ADWG) was determined for the following periods: Day −1 to 35; Day −1 to 49; and Day 35 to Day 49. Average daily weight gain (ADWG) for each period was analyzed using ANOVA (the MIXED procedure). Treatment was included in the model as a fixed effect and block was included as a random effect. If the main effect of treatment was significant, treatment effects were evaluated by comparing each vaccination group to the control using an unadjusted alpha=0.05.

One pig (T09) died on Day 28 from a suspected *S. suis* infection. Two pigs, one from T03 and another from T09, were removed from the study due to bronchopneumonia associated with *Bordetella bronchiseptica*. None of the adverse events were attributed to the vaccines.

The mean percent of lung lesions in the control group challenged with MN-184 was 52.4% which was in agreement with the expected pathology for this PRRSV challenge strain. The mean percent of lung lesions in the control group challenged with KS-11 was 22.5%. This PRRSV strain had not been previously used as challenge material thus the expected degree of lung pathology was unknown. The level achieved in this study was considered adequate to evaluate the vaccine candidates.

For prevention of disease associated with PRRSV, the post-challenge lung lesions and viremia were the primary outcome variables. The vaccine was considered effective if the mean lung lesion score and viremia levels of the vaccinated group was significantly less ($P<0.05$) than that of the control group.

The mean lung lesion scores (back-transformed means) are shown in Table 9. All vaccinated pigs had significantly less ($P<0.05$) lung lesions compared to the non-vaccinated control pigs when challenged with MN-184. Pigs challenged with the KS-11 strain and vaccinated with the SD 95-10, SD 11-21, and ND 99-14 strains had significantly less ($P<0.05$) lung lesions when compared to the non-vaccinated control pigs. Pigs vaccinated with the MN 05-68 strain and challenged with the KS-11 strain had similar ($P>0.05$) lung lesions to the non-vaccinated control pigs.

The effect of vaccination on lung lesion score was evaluated by calculating the mitigated fraction and the associated 95% confidence interval from the un-transformed data. As shown in Table 10, the mitigated fraction ranged from −0.06 to 0.98. The 95% confidence interval included 0 for pigs vaccinated with the MN 05-68 strain and challenged with the KS-11 strain, indicating no effect of vaccination on lung lesion scores. All other vaccines, regardless of challenge strain, indicated an effect of vaccination on reducing lung lesion scores.

TABLE 9

Mean Lung Score - Percent of Lung Involvement.

| Treatment Group | Vaccine strain | Challenge Strain | Estimate[1] | Standard Error | Mean[2] |
|---|---|---|---|---|---|
| T01 | Control | MN-184 | 0.8090 | 0.1026 | 52.4% |
| T02 | SD 95-10 | MN-184 | 0.2551* | 0.1026 | 6.4% |
| T03 | SD 11-21 | MN-184 | 0.2478* | 0.1043 | 6.0% |
| T04 | ND 99-14 | MN-184 | 0.1575* | 0.1026 | 2.5% |
| T05 | MN 05-68 | MN-184 | 0.3039* | 0.1026 | 8.9% |
| T06 | Control | KS-11 | 0.4937 | 0.08280 | 22.5% |
| T07 | SD 95-10 | KS-11 | 0.1142* | 0.08280 | 1.3% |
| T08 | SD 11-21 | KS-11 | 0.1651* | 0.08280 | 2.7% |
| T09 | ND 99-14 | KS-11 | 0.0873* | 0.09257 | 0.8% |
| T10 | MN 05-68 | KS-11 | 0.4936 | 0.08280 | 22.5% |

[1]Untransformed mean.

[2]Back-transformed mean.

*Within a challenge strain versus the control, significantly different at $P < 0.05$.

TABLE 10

| Lung Lesion Scores | | |
|---|---|---|
| Treatment Group Comparison | Mitigated Fraction[1] | 95% confidence interval |
| Control (T01) versus SD95-10 (T02) | 0.90 | 0.74, 1.00 |
| Control (T01) versus SD 11-21 (T03) | 0.91 | 0.76, 1.00 |
| Control (T01) versus ND 99-14 (T04) | 0.98 | 0.93, 1.00 |
| Control (T01) versus MN 05-68 (T05) | 0.88 | 0.69, 1.00 |
| Control (T06) versus SD95-10 (T07) | 0.77 | 0.49, 1.00 |
| Control (T06) versus SD 11-21 (T08) | 0.58 | 0.16, 1.00 |
| Control (T06) versus ND 99-14 (T09) | 0.78 | 0.48, 1.00 |
| Control (T06) versus MN 05-68 (T10) | −0.06 | −0.58, 0.46 |

[1]Mitigated fraction means the relative increase in the probability that the lung lesions of vaccinates (T02-T05, T07-T10) will be less severe than the lung lesions of non-vaccinates (T01, T06).

Results of the analysis for nasal shedding data are summarized in Table 11. The treatment by time interaction for the vaccinated groups was highly significant (P<0.0001) compared to challenge controls. Vaccine virus shedding was detected in all vaccine groups on Day 14. By Day 35, only pigs vaccinated with the MN 05-68 strain in the MN-184 challenge room were shedding vaccine virus at levels greater (P<0.05) than the control pigs.

Upon challenge with the MN-184 strain, pigs vaccinated with the ND 99-14 strain had reduced (P<0.05) shedding compared to control pigs at each post-challenge time point (Days 38, 42, 45, and 49). Pigs vaccinated with the SD 95-10 and MN 05-68 strains showed significantly reduced (P<0.05) shedding on Days 42, 45, and 49 compared to control pigs. Pigs vaccinated with the SD 11-21 strain had higher shedding compared to the control pigs on Day 38, but lower (P<0.05) shedding on Days 42, 45, and 49.

Upon challenge with the KS-11 strain, pigs vaccinated with the SD 95-10 and ND 99-14 strains had reduced (P<0.05) nasal shedding on Days 38, 42, and 45 when compared to control pigs. Pigs vaccinated with the SD 11-21 strain demonstrated significantly less nasal shedding on Days 38, 42, and 49 when compared to control pigs. Pigs vaccinated with the MN 05-68 strain had reduced (P<0.05) shedding on Day 38 when compared to control pigs but the two treatment groups were not different (P>0.05) on Days 42, 45, and 49.

TABLE 11

| Geometric Means of PRRSV Genomic Copies/mL in Nasal Swabs. | | | | | | | |
|---|---|---|---|---|---|---|---|
| Vaccine strain | Day −1 | Day 14 | Day 35 | Day 38 | Day 42 | Day 45 | Day 49 |
| Challenge strain MN-184 | | | | | | | |
| T01: Control | 0.34 | 0.34 | 0.34 | 1336.82 | 44675.37 | 19723.17 | 1092.89 |
| T02: SD 95-10 | 0.34 | 14042.29* | 4.62 | 162.56 | 72.39* | 19.18* | 1.05* |
| T03: SD 11-21 | 0.34 | 322.05* | 0.34 | 87613.34* | 778.30* | 79.82* | 5.04* |
| T04: ND 99-14 | 0.34 | 6417.89* | 6.51 | 21.66* | 45.01* | 484.22* | 21.34* |
| T05: MN 05-68 | 0.34 | 1924.61* | 11.20* | 165.58 | 1846.89* | 1098.49* | 44.52* |
| Challenge strain KS-11 | | | | | | | |
| T06: Control | 0.08 | 0.08 | 0.08 | 1940.27 | 8247.61 | 1451.58 | 28.76 |
| T07: SD 95-10 | 0.08 | 2874.26* | 1.12 | 3.38* | 103.92* | 6.75* | 9.87 |
| T08: SD 11-21 | 0.08 | 67.94* | 1.20 | 39.59* | 734.61* | 389.33 | 0.78* |
| T09: ND 99-14 | 0.06 | 468.14* | 1.94 | 23.25* | 309.32* | 22.99* | 21.70 |
| T10: MN 05-68 | 0.08 | 55.84* | 4.15 | 1.95* | 2345.55 | 840.51 | 41.01 |

*Within a challenge strain versus the control, significantly different at P < 0.05.

The results of the analysis for viremia are summarized in Table 12. The treatment by time interaction was highly significant (P<0.0001) for the vaccinated groups compared to challenge controls. As expected, all vaccinated groups had higher (P<0.05) viremia levels compared to their respective control group at Days 14 and 35 post-vaccination due to the presence of the vaccine virus.

TABLE 12

| Geometric Means of PRRSV Genomic Copies/mL in Serum. | | | | | | | |
|---|---|---|---|---|---|---|---|
| Vaccine strain | Day −1 | Day 14 | Day 35 | Day 38 | Day 42 | Day 45 | Day 49 |
| Challenge strain MN-184 | | | | | | | |
| T01: Control | 1 | 1 | 1 | 1268568 | 12755842 | 8025222 | 4958926 |
| T02: SD 95-10 | 1 | 117788357* | 9817* | 26175* | 10984* | 29315* | 225* |
| T03: SD 11-21 | 1 | 58407* | 105* | 421636* | 295462* | 140786* | 2225* |
| T04: ND 99-14 | 1 | 24935423* | 5065* | 3810* | 3988* | 117277* | 49706* |
| T05: MN 05-68 | 1 | 5581677* | 24552* | 7305* | 763523* | 497076* | 58676* |
| Challenge strain KS-11 | | | | | | | |
| T06: Control | 0 | 0 | 1 | 128142 | 626622 | 865358 | 705737 |
| T07: SD 95-10 | 0 | 11960258* | 745* | 1756* | 9635* | 618* | 17* |
| T08: SD 11-21 | 0 | 104036* | 394* | 714* | 45674 | 120113 | 3492* |
| T09: ND 99-14 | 0 | 4049078* | 742* | 193* | 527* | 480* | 288* |
| T10: MN 05-68 | 0 | 2252609* | 353* | 91* | 1686* | 256349 | 40242* |

*Within a challenge strain versus the control, significantly different at P < 0.05.

Upon challenge with the MN-184 strain, all vaccinated groups had lower (P<0.05) viremia levels when compared to the control group at each time point post-challenge (Days 38, 42, 45, and 49). Upon challenge with the KS-11 strain, pigs vaccinated with the SD 95-10 and ND 99-14 strains had lower (P<0.05) viremia levels at each time point post-challenge (Days 38, 42, 45, and 49). Pigs vaccinated with the MN 05-68 strain had lower (P<0.05) viremia levels when compared to the control pigs on Days 38, 42, and 49 and pigs vaccinated with the SD 11-21 strain had reduced (P<0.05) viremia levels on Day 38, and 49 when compared to the control pigs.

The results of the analysis for serology are summarized in Table 13. The treatment by time interaction was highly significant (P<0.0001) for the vaccinated groups compared to the challenge controls. All pigs were seronegative on Day −1 prior to vaccination. Virus neutralizing antibodies were detected in pigs vaccinated with the SD 95-10 and ND 99-14 strains, regardless of the challenge strain, starting on Day 28 and remained present throughout the duration of the study. Virus neutralizing antibodies were higher (P<0.05) in pigs vaccinated with the SD 95-10 and ND 99-14 strains compared to the control pigs at Days 28, 35, 42, and 49.

TABLE 13

Geometric Means of Fluorescent Foci Neutralization (FFN) Titers.

| Treatment Group | Vaccine strain | Day −1 | Day 14 | Day 28 | Day 35 | Day 42 | Day 49 |
|---|---|---|---|---|---|---|---|
| Challenge strain MN-184 | | | | | | | |
| T01 | Control | 0 | 0 | 0 | 0 | 0 | 0 |
| T02 | SD 95-10 | 0 | 0 | 4* | 3* | 2* | 10* |
| T03 | SD 11-21 | 0 | 0 | 0 | 0 | 2* | 4* |
| T04 | ND 99-14 | 0 | 0 | 6* | 12* | 12* | 13* |
| T05 | MN 05-68 | 0 | 0 | 0 | 0 | 0 | 1* |
| Challenge strain KS-11 | | | | | | | |
| T06 | Control | 0 | 0 | 0 | 0 | 0 | 0 |
| T07 | SD 95-10 | 0 | 0 | 2* | 3* | 4* | 12* |
| T08 | SD 11-21 | 0 | 0 | 0 | 0 | 0 | 2* |
| T09 | ND 99-14 | 0 | 0 | 24* | 14* | 19* | 22* |
| T10 | MN 05-68 | 0 | 0 | 0 | 0 | 0 | 1* |

*Within a challenge strain versus the control, significantly different at P < 0.05.

Upon challenge with the MN-184 strain, virus neutralizing antibodies did not appear in pigs vaccinated with the SD 11-21 strain until Day 42 and remained thru Day 49. Virus neutralizing antibodies were higher (P<0.05) than control pigs at both time points. Pigs vaccinated with the MN 05-68 strain did not have detectable virus neutralizing antibody levels until Day 49, however, levels were greater (P<0.05) than the ones of the pigs in the control group.

Upon challenge with the KS-11 strain, pigs vaccinated with the SD 11-21 and MN 05-68 strain did not have detectable virus neutralizing antibody levels until Day 49, but levels for both vaccine strains were greater (P<0.05) compared to control pigs.

No virus neutralizing antibodies were detected in either of the control groups throughout the duration of the study. This is not unexpected, as virus neutralizing antibodies are often not detected until 28-35 days post-exposure.

The analysis for rectal temperature and summed clinical scores (respiratory+depression+body condition) was performed as described above. A highly significant (P<0.0005) treatment by time interaction was observed for both challenge groups.

Upon challenge with the MN-184 strain, pigs vaccinated with the SD 95-10, ND 99-14 and MN 05-68 strains had consistently lower (P<0.05) body temperatures and clinical scores when compared to control pigs starting around six days post challenge (Day 41). Pigs vaccinated with the SD 11-21 strain had consistently lower (P<0.05) body temperatures and fewer (P<0.05) clinical signs starting around eight days post-challenge (Day 43) compared to control pigs. Significant reductions (P<0.05) in body temperatures were noted as early as two days post-challenge in pigs vaccinated with the SD 95-10, ND 99-14 and MN 05-68 strains.

Upon challenge with the KS-11 strain, pigs vaccinated with either of the four vaccine strains had a significant reduction (P<0.05) in clinical scores starting nine days post-challenge (Day 44) when compared to control pigs and continued to have fewer (P<0.05) clinical signs thru the completion of the study. Body temperatures were reduced (P<0.05) in the SD 95-10, SD 11-21, and ND 99-14 groups beginning around six days post-challenge. Pigs vaccinated with the MN 05-68 strain only had lower (P<0.05) body temperatures when compared to control pigs on Days 37 and 46.

The analysis of the body weight gain data is shown in Table 14 given as least square means of body weight gain by period. There was a vaccine effect for body weight gain during the post-challenge period of Day 35-49. This resulted in a vaccine effect for the overall treatment period from Day −1 to Day 49. There were no body weight gain differences (P>0.05) between groups during the pre-challenge period (Days −1 to 35). During the post-challenge period (Day 35-49), all vaccinated groups, regardless of the vaccine strain, had improved (P<0.05) ADWG when compared to control pigs for both the MN-184 and KS-11 challenges. Vaccination with the SD 95-10, ND 99-14, and MN 05-68 strains improved (P<0.05) overall ADWG (Day −1 to 49) compared to control pigs in the MN-184 challenge room. Overall ADWG was not different (P>0.05) compared to control pigs in pigs vaccinated with SD 11-21 and challenged with MN-184. Vaccination with all strains improved (P<0.05) overall ADWG (Days −1 to 49) compared to control pigs in the KS-11 challenge room.

TABLE 14

Least Square Mean Body Weight Gain (lb).

| Treatment Group | Vaccine strain | Days −1 to 35 | Days −1 to 49 | Days 35 to 49 |
|---|---|---|---|---|
| Challenge strain MN-184 | | | | |
| T01 | Control | 1.1734 | 1.0024 | 0.5637 |
| T02 | SD 95-10 | 1.0445 | 1.1741* | 1.4865* |
| T03 | SD 11-21 | 1.1092 | 1.1166 | 1.1235* |
| T04 | ND 99-14 | 1.1485 | 1.2016* | 1.3229* |
| T05 | MN 05-68 | 1.1008 | 1.1608* | 1.2994* |
| Challenge strain KS-11 | | | | |
| T06 | Control | 1.2081 | 1.0754 | 0.7707 |
| T07 | SD 95-10 | 1.2153 | 1.3028* | 1.5486* |
| T08 | SD 11-21 | 1.1967 | 1.2150* | 1.2879* |
| T09 | ND 99-14 | 1.2452 | 1.2569* | 1.3080* |
| T10 | MN 05-68 | 1.2233 | 1.2383* | 1.3029* |

*Within a challenge strain versus the control, significantly different at P < 0.05.

In conclusion, all vaccinated groups were viremic and were shedding vaccine virus at 14 and 35 days post-vaccination.

Upon challenge with the MN-184 strain, all vaccines reduce (P<0.05) lung lesions, viremia, nasal shedding, clinical signs and rectal temperature during the post-challenge period. In addition, all vaccines improve ($P<0.05$) ADWG during the post-challenge period.

Upon challenge with the KS-11 strain, pigs vaccinated with the SD 95-10, SD 11-21, and ND 99-14 strains have reduced ($P<0.05$) lung lesions, viremia, nasal shedding, clinical signs and rectal temperature during the post-challenge period. In addition, all vaccine strains significantly improve ($P<0.05$) ADWG during the post-challenge period.

Three of the four vaccine strains are effective in reducing lung lesions and viremia following challenges with both strains of PRRSV. The SD 95-10, SD 11-21, and ND 99-14 strains are effective against both challenge strains. The MN 05-68 strain was only effective in reducing lung lesions upon MN-184 challenge and did not reduce lung lesions in pigs challenged with the KS-11 strain.

EXAMPLE 4

The objective of this study is to prepare the master seed virus (MSV) of Porcine Reproductive and Respiratory Syndrome Virus (PRRSV) strain ND 99-14. This seed will be used for PRRSV vaccine development.

PRRSV ND 99-14 strain has been modified by passing in the MARC-145 cells 83 times (P83) including two rounds of plaque purification and one round of sucrose gradient purification, prior to the initial characterization and sequencing as described in Example 1. The ND 99-14 strain has been further attenuated by passing 12 times (P95) in MARC-145 cells in the growth medium OPTI-MEM® I (Life Technologies) supplemented with 5% fetal bovine serum (FBS; Sigma Aldrich) and 50 μg gentamicin/mL (Life Technologies), and an additional 5 passages have been performed in the same growth medium supplemented with 2% FBS without gentamicin. The $100^{th}$ passage (P100) of PRRSV ND 99-14 has been used as the Pre-Master Seed Virus (Pre-MSV).

The following procedure is used to determine the titer of PRRSV MSV ND 99-14. MARC-145 cells are seeded into 96-well plates at a density of $0.75\text{-}1.5\times10^4$ cells in 100 μL of growth medium (OPTI-MEM® I media supplemented with 5% FBS and 50 μg/mL gentamycin). Cells are incubated in 37±2° C. and 5±1% $CO_2$ incubator for 48-72 hours until cells are over 95% confluent. On the day of titration, all media is removed from the 96-well plate and replaced with 100 μL of fresh growth media.

Ten-fold serial dilutions of the MSV are prepared with diluent (OPTI-MEM® I media, 50 μg/mL gentamycin) and transferred to corresponding wells on the plates prepared as above along with a negative control consisting of diluent alone. Titration plates are incubated in 37±2° C. with 5±1% $CO_2$ incubator for 4 days. At the end of the incubation period, each plate is observed for the presence of virus-induced cytopathic effect (CPE) in each sample well using an inverted microscope. The 50% tissue culture infectious dose ($TCID_{50}$) is calculated using the Reed-Muench method and titer is recorded as $\log_{10} TCID_{50}$/mL. The mean titer of the PRRSV MSV ND 99-14 is 3.50 $\log_{10} TCID_{50}$/mL. There have been no distinguishable differences in the titers over the course of MSV preparation.

The PRRS ND 99-14 MLV strain has been denoted as a "master seed virus (MSV)," and has been deposited under conditions that assure that access to the cultures will be available during the pendency of this patent application to one determined by the Commissioner of Patents and Trademarks to be entitled thereto under 37 C.F.R. § 1.14 and 35 U.S.C. § 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the deposited culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it. A deposit of PRRSV MSV ND 99-14 was entered into the permanent collection of the Patent Depository of the American Type Culture Laboratory, located at 10801 University Blvd., Manassas, Va., 20110-2209, USA, on Dec. 2, 2015 under the terms of the Budapest Treaty, whereupon it was assigned accession number ATCC PTA-122675 by the repository.

EXAMPLE 5

The objective of this study is to use next generation sequencing to establish genetic identity, obtain a consensus sequence, and assess genomic variants (subpopulations) that exist within PRRSV Strain ND 99-14 passage 84 and passage 100 preparations, both described in Example 4.

Sequence characterization using the massive parallel sequencing (MP-Sep) system is a standard procedure comprised of several steps which include: nucleic acid extraction from the virus preparations, cDNA library synthesis and quantitation, clonal amplification and enrichment of DNA library by PCR and sequencing of the library by the Roche/454 next generation sequencing platform. Sequencing by synthesis is used to simultaneously determine the nucleotide order of the fragments in the cDNA library. Genome identification and characterization were performed using bioinformatics analyses of the resulting fragments by mapping each data set to the reference sequence. The reference sequence used in this analysis by BioReliance consisted of the full length sequence PRRSV ND 99-14 passage 83 (P83) disclosed in Example 1 (SEQ ID NO:4).

Sequencing of the PRRSV ND 99-14 genome resulted in the complete genome coverage for both P84 and P100 samples. The complete consensus genomes for P84 and P100 can be found in SEQ ID NO: 10 and SEQ ID NO: 11, respectively. The cDNA consensus sequences have also been deposited with GenBank. The cDNA consensus sequence of PRRS strain ND 99-14 at P84 has been assigned GenBank Accession number KU131567 (SEQ. ID. NO:10). The cDNA consensus sequence designated SEQ. ID. NO:10 is:

1 ATGACGTATA GTTGTTGGCT CTATGTCGTG ACATTTGTAT AGTCAGGAGC TGCGACCATT
61 GGTACAGCCC AAAACTTGCT GCGCGGGAAC GCCCTTCCGT GACAGCCTTC TTCAGGGGAG
121 TTTAGGGGTC TATCCCTAGC ACCTTGCTTC CGGAGTTGCA CTGCTTTACG GTCTCTCCAC
181 CCCTTTAACC ATGTCTGGGA TACTTGATCG GTGCACGTGT ACCCCCAATG CCAGGGTGTT
241 TGTGGCGGAG GGCCAAGTCT ACTGCACACG ATGTCTCAGT GCACGGTCTC TCCTTCCTTT
301 GAATCTCCAA GTTTCTGAGC TTGGGGTGCT GGGCTTATTT TATAGGCCCG AAGAGCCGCT
361 CCGGTGGACG TTGCCACGTG CATTCCCCAC TGTCGAGTGC TCCCCCGCCG GGGCCTGCTG
421 GCTTTCTGCG ATTTTTCCAA TTGCACGAAT GACCAGTGGA AACCTGAACT TTCAACAAAG
481 AATAGTGCGG GTCGCAGCTG AGCTCTACAG AGCCGGTCAG CTCACCCCCG TAGTCTTGAA
541 GAATCTACAG GTTTATGAAC GGGGTTGCCG TTGGTACCCC ATCGTTGGAC CTGTTCCTGG
601 AGTGGCTGTT TATGCCAATT CCTTACACGT GAGTGACAAA CCTTTCCCGG GAGCAACTCA
661 TGTGTTAACC AACCTACCGC TCCCGCAGAG GCCCAAGCCT GAAGACTTTT GCCCCTTTGA
721 GTGTGCTATG GCTGACGTCT ATGACATTGG TCATGACGCT GTCATGTATG TGGCCGGAGG
781 GAGAGTCTCC TGGGCCCCTC GTGGCGGGGA CAAAGGAAAA TTTGAAATAG TTCCCAAGGA
841 GTTGAAGTTG ATTGCGAATC GACTCCACAT TTCCTTCCCG CCCCACCACG CAGTGGACAT
901 GTCCAAGTTT GCCTTTATAA GCCCTGGGAG TGGTGTTTCC ATGCGGGTCG AGTACCAACA
961 TGGCTGTCTC CCCGCTGATA CTGTCCCTGA AGGAAACTGT TGGTGGCGCT TGTTTGACTT
1021 GCTTCCACCG GAAGTTCAGA ACAAAGAGAT TCGCCATGCT AACCAACTCG GCTATCAGAC
1081 CAAGCATGGT GTCGCTGGCA AGTACCTACA GCGGAGGCTG CAAGTTAATG GACTCCGAGC
1141 AGTAACTGAC GCGAATGGAC CTATCGTCAT ACAGTATTTT TGTGATAGGG AAAGCTGGAT
1201 CCGCCACTTA AGACTGGTAG AAGAACCTAG CCTCCCTGGG TTTGAGGACC TCCTCAGAAT
1261 AAGAGTTGAG CCCAATACGT TGCCATTGGT TGGCGAGGAT GAGAAAATCT TCCGATTTGG
1321 CAATCACAAA TGGTACGGTG CTGGAAAGAG GGCAAGGAAA GCACGCTTTG GTGCGGCTGC
1381 CACGGTCGCT CACCGCGCTT TGCCCGCTCA CGAAACCCAG CAGGCCAAGA AGCACGAAGT
1441 TACCAGCGCC AACAGGGCTG AGCATCTCGA GCACTATTCC CCGCCTACCG ACGGGAACTG
1501 TGGTTGGCAC TGCGTTTCCG CCATTGTCAA CCGGATTGTG AATTCCAAAT TTGAAACCAC
1561 CCTTCCCGAG AGAGTGAGAC CTTTAGATGA CTGGGCTACT GACGAGGATC TTGTGAATAC
1621 TATCCAAATC CTCAGGCTCC CTGCGGCCTT GGACAGGAAC GGTGCTTGTG TCGGCGCCAA
1681 GTACGTGCTC AAGCTGGAAG GTGTGCACTG GACAGTCTCT GTGGCCCCTG GGATGACCCC
1741 TTCTCTGCTC CCCCTTGAAT GTGTTCAGGG CTGTTGTGAG CATAAGAGCG GTCTTGGTCC
1801 CCCAGATGTG GCTGAAGTTT CCGGATTTGA CCCTGCCTGC CTTAACCGAC TGGCTGAGGT
1861 AATGCACTTG CCTAGTTGTG TCATCCCAGC TGCTCTGGCT GAAATGTCCG ACGACCCCAA
1921 TCGCCCGGCT TCCCCAGTCA CCACTGTGTG GACTATTTCG CAATTCTTTG CCCATTATAG
1981 AGGAGGAGAG CACCCTGATC AGGTGTGCTT AGGGAAAATC ATCAGCCTTT GTCAGGTGAT
2041 TGAGGAATGC TGTTGTTCCC AGAACAAAAC CAACCGGGCC ACCCCGGAAG AGGTCGCGGC
2101 AAAAATTGAC CAGTACCTCC GTGATGCAGC AAGCCTTGGA GAATGCTTAG CCAAGCTTGA
2161 GAGGGCTCGC CCGCCGAGCG CGATGGACAC CTCCTTTGAT TGGAATGTTG TGCTTCCTGG
2221 GGTTGAGGCG GCGAACCAGA CGACCAAACA GCTCCATGTC AACCAGCACC GTGCTTCGGT
2281 TCCTGCCATG ACTCAGGAGC CTTTGGACAA AGACTCGGTC CCTTTGACCG CCTTCTCGCT
2341 GTCTAATTGC TACTACCCTG CACAAGGTGA CGAGGTTCGT CACCGTGAGA GGCTGATCTC
2401 CGTGCTCTCT AAGTTGGAGG AGGTTGTTCG TGAGGAATAT GGGCTCACGC CAACTGGATC

-continued

2461 TGGCCCGCGA CCCGCACTGC CGAACGGGCT CGACGAGCTC AAAGACCAGA TGGAAGAGGA
2521 TCTGTTGAAA CTGGTCAACG CCCAGGCAAC TTCAGAAATG ATGGCCCGGG CAGCTGAGCA
2581 GGTTGATCTA AAAGTTTGGG TCAAAAATTA CCCACGGTGG ACACCGCCAC CCCCTCCACC
2641 AAGAGTTCAG CCTCGAAAAA CAAAGTCTGC TAAGAGCCTG CCAGAGAACA AGCCTGTCCC
2701 TGCTCCGCGC AGGAAAGTCA GATCTGATTG TGGCAGCCCG ACTTTGAGGG GCAACAATGT
2761 TCCTAACGGT TGGGAAGACT TGGCCGTTGG TGGTCCTCTT GATCTTTCGA CACCATCCGA
2821 GCCGATGACA CCTCTGAGTG AGCCTGCACT TATGCCCGTG TTGCAACATA TTTCTGGACC
2881 AGTGACGCCT TTGAGCGTGC CGGCCCCTAT TCCTGCACCG CGTAAAGCTG TGTCCCGACC
2941 GATGGCGCCC TCGAGTGAGC CAATTTTTGT GTCTGCACCG CGGCAAAAAT TTCAGCAGGT
3001 GGAAGAAGCA AATCTGGCGG CAACAACGCT GACATACCAG GACGAACCTA TAGATCTGTC
3061 AGCATCCTCA CAGACTGAAT ATGAGGCTCC TTCCCTAGCA CCACTGCAGA ACATAGGTAC
3121 TCTGGAGGTG GGGGGGCAAG AAGCTGAGGA AATTCTGAGT GAAACCTCGG ATATACCGAA
3181 TGACATCAAC CCTGTGCCTG TATCATCAAG CAGCTCCTTG TCAAGCGTTA AGATCACACG
3241 CCCAAGACAC TCAGCTCAAG CCATCATCGA CTCGGGCGGG CCCTGCAGTG GGCATCTCCA
3301 AAGGGAGAAA GAAGCGTGCC TCCGCATCAT GCGTGAGGCT TGTGATGCGA CTAAGCTTAG
3361 TGACCCTGCC ACGCAGGAAT GGCTTTCTCG CATGTGGGAT AGGGTGGACA TGCTGACTTG
3421 GCGCAACACG TCTGCTTTCC AGGCGTTTCG CATCTTAGAC GGCAGGCTTG AGTTTCTTCC
3481 AAAGATGATA CTCGAGACGC CGCCGCCCTA CCCGTGTGGG TTTGTGATGC TGCCTCACAC
3541 CCCTGCACCT TCCGTGAGTG CAGAGAGCGA CCTTACCATC GGTTCAGTCG CCACTGAAGA
3601 TATTCCACGC ATCCTCGGGA AAATAGAAAA CACCAGTGAG ATGATCAACC AGGGACCCTT
3661 GGCATCCTCT GAGGAAAAAC CGGCATACAA CCAACCCGCT AAGGACTCCC TGATATCGTC
3721 GCGGGGGTTT GACGAGAGCA CAGCAGCTCC GTCCGCAGGT ACGGGTGGCG CCGGCTTGTT
3781 TACTGATTTG CCACCTTCAG ACGGTGTAGA TGCGGACGGG GGGGGGCCGC TGCAGACGGT
3841 GAAAAAGAAC GCTGAAAGGC TCCTCGACCG ATTGAGCCGT CAGGTTTTTA ACCTCGTCTC
3901 CCATCTCCCT GTTTTCCTCT CACACCTCTT CAAATCTGAC AGTGGTTATT CTCCGGGTGA
3961 TTGGGGTTTT GCAGCTTTTA CTCTATTTTG CCTCTTTTTA TGTTACAGCT ACCCATTCTT
4021 TGGTTTCGCT CCCCTTTTGG GTGTGTTTTC TGGGTCTTCT CGGCGCGTGC GCATGGGGGT
4081 TTTTGGCTGC TGGTTGGCTT TTGCTGTTGG TTTGTTCAAG CCTGTGTCCG ACCCAGTCGG
4141 CACTGCTTGT GAGTTTGATT CGCCAGAGTG TAGGAATGTC CTTCATTCTT TTGAGCTTCT
4201 CAAACCTTGG GACCCTGTTC GCAGCCTTGT TGTGGGCCCC GTCGGTCTCG GTCTTGCCAT
4261 TCTTGGCAGG TTACTGGGCG GGGCACGCTA CATCTGGCAT TTTCTGCTTA GGCTTGGCAT
4321 TGTTACAGAC TGTATCCTGG CTGGAGCTTA TGTGCTTTCT CAAGGTAGGT GTAAAAAGTG
4381 CTGGGGATCT TGCATAAGAA CAGCTCCTAA TGAGATTGCC TTTAACGTGT TCCCTTTTAC
4441 ACGTGCGACT AGGTCGTCAC TCATCGACCT GTGCAATCGG TTTTGTGCGC CAAAGGGCAT
4501 GGACCCTATT CTCCTCGCCA CTGGGTGGCG TGGGTGCTGG ACCGGCCGAA GCCCCATTGA
4561 ACAACCCTCT GAAAAACCCA TCGCGTTTGC CCAGTTGGAC GAAAAGAGGA TTACGGCCAG
4621 GACCGTGGTC GCCCAGCCTT ATGACCCCAA CCAAGCCGTA AAGTGCTTGC GGGTGTTACA
4681 GGCGGGCGGG GCGATGGTGG CTGAGGCAGT CCCAAAAGTG GTCAAAGTTT CCGCTATTCC
4741 ATTCCGAGCC CCCTTTTTTC CCACCGGAGT GAAAGTTGAC CCTGAGTGTA GGATCGTGGT
4801 TGACCCCGAC ACTTTTACTA CAGCCCTCCG GTCCGGCTAT TCCACCACAA ACCTCGTTCT

-continued

4861 TGGTGTGGGG GACTTTGCCC AGCTGAATGG ATTAAAAATC AGGCAAATTT CCAAGCCTTC

4921 GGGAGGAGGC CCGCACCTCA TTGCTGCCCT ACATGTTGCC TGCTCGATGG CGTTGCACAT

4981 GCTTGCTGGG GTTTATGTAA CTGCAGTGGG GTCTTGCGGT ACCGGCACCA ACGATCCGTG

5041 GTGCACCAAC CCGTTTGCCG TCCCTGGCTA CGGGCCTGGT ACTCTTTGCA CGTCCAGATT

5101 GTGCATCTCC CAACATGGCC TTACCCTGCC CTTGACAGCA CTTGTGGCAG GATTCGGTCT

5161 TCAGGAAATT GCCTTGGTTG TTTTGATTTT CGTTTCCATC GGAGGCATGG CTCACAGGTT

5221 GAGTTGCAAG GCTGACATGC TGTGCGTTTT ACTTGCAATC GCCAGCTATG TTTGGGTGCC

5281 CCTTACCTGG TTTCTTTGTG TGTTTCCTTG CTGGTTGCGC TGGTTCTCTT TGCATCCCCT

5341 CACCATCCTA TGGTTGGTGT TTTTCTTGAT TTCTGTAAAT GTGCCTTCGG GAATCTTGGC

5401 TGTGGTGTTG TTAGTTTCTC TTTGGCTCTT AGGTCGTTAC ACTAATGTTG CTGGTCTTGT

5461 CACCCCATAT GACATTCATC ATCACACCAG TGGCCCCCGA GGTGTTGCCG CCTTGGCTAC

5521 TGCACCGGAT GGGACCTACT TGGCCGCCGT TCGCCGTGCT GCGTTGACCG GTCGTACCAT

5581 GCTGTTTACC CCGTCTCAGC TTGGGTCCCT TCTTGAGGGT GCTTTCAGAA CTCAAAAGCC

5641 CTCACTGAAC ACCGTCAATG TGGTCGGATC CTCTATGGGC TCCGGCGGGG TGTTCACCAT

5701 CGACGGGAAA ATTAAGTGCG TAACAGCCGC ACATGTCCTT ACGGGTAATT CAGCTAGGGT

5761 TTCCGGGGTC GGCTTCAACC AAATGCTTGA TTTTGATGTG AAAGGGGACT TCGCCATAGC

5821 TGATTGCCCG AATTGGCAAG GAGCTGCCCC CAAGACCCAA TTCTGCGAGG ATGGATGGAC

5881 TGGCCGTGCC TATTGGCTGA CATCCTCTGG AGTCGAACCC GGTGTCATTG GGAATGGATT

5941 CGCCTTCTGC TTCACCGCGT GCGGCGATTC TGGATCCCCG GTGATTACCG AAGCCGGTGA

6001 GCTTGTCGGC GTTCACACAG GATCAAACAA ACAAGGAGGA GGCATAGTCA CACGCCCCTC

6061 AGGCCAGTTT TGTAATGTGG CGCCCATCAA GCTGAGCGAA TTGAGTGAAT TCTTCGCTGG

6121 ACCTAAGGTC CCGCTCGGTG ATGTGAAGAT TGGCAGCCAC ATAATTAAAG ACGTATGCGA

6181 GGTACCTTCA GATCTTTGCG CCTTGCTCGC TGCCAAACCC GAACTGGAAG GAGGCCTCTC

6241 CACCGTCCAA CTTCTGTGTG TGTTTTTCCT CCTGTGGAGA ATGATGGGAC ATGCCTGGAC

6301 GCCCTTGGTT GCTGTGGGGT TTTTTATCTT GAATGAGGTT CTCCCAGCTG TCCTGGTCCG

6361 GAGTGTCTTC TCCTTTGGTA TGTTTGTGCT ATCTTGGCTT ACACCATGGT CTGCGCAAGT

6421 CCTGATGATC AGGCTTCTAA CAGCAGCTCT TAACAGGAAC AGGGGGTCAC TCGCCTTCTA

6481 CAGCCTCGGT GCAGTGACCG GATTTATCGC AGATCTTGCA GCAACTCAGG GGCATCCGCT

6541 GCAGGCAGTG ATGAACTTAA GCACCTATGC CTTCCTGCCT CGGATGATGG TTGTGACCTC

6601 ACCAGTCCCA GTGCTTGCTT GTGGTGTTGT GCACCTCCTT GCCATAATTT TGTACCTGTT

6661 TAAGCACCGT TGCCTGCATT ATGTCCTTGT TGGCGATGGA GTGTTCTCTA AAGCCTTCTT

6721 CTTGCGATAC TTTGCCGAAG GGAAGTTGAG GGAAGGGGTG TCGCAGTCCT GCGGGATGAA

6781 TCACGAGTCA CTGACTGGTG CCCTCGCTAT GAGACTCAAT GACGAAGACT TGGACTTCCT

6841 TACGAAATGG ACTGATTTTA AGTGCTTTGT TTCTGCGTCC AACATGAGGA ATGCAGCGGG

6901 CCAATTCATC GAGGCTGCCT ATGCAAAAGC ACTTAGAATT GAGCTTGCCC AGTTAGTACA

6961 GGTTGATAAG GTTCGAGGTA CTTTGGCCAA ACTTGAAGCC TTTGCTGATA CCGTGGCACC

7021 CCAGCTCTCG CCCGGTGACA TTGTTGTTGC TCTTGGCCAC ACGCCTGTTG GCAGTATCTT

7081 CGACCTAAAG GTTGGCAGTA CCAAGCATAC CCTCCAGGCC ATTGAGACCA GAGTCCTTGC

7141 CGGGTCCAAA ATGACCGTGG CGCGTGTCGT TGATCCAACC CCCACGCCCC CACCCGCACC

7201 CGTGCCCATC CCCCTCCCAC CGAAAGTCCT GGAGAACGGC CCCAACGCCT GGGGGGATGA

7261 GGACCGGTTG AATAAGAGGA AGAGACGCAG GATGGAAGCC GTCGGCATCT TTGTTATGGG

-continued

7321 TGGGAAGAAG TACCAAAAAT TTTGGGACAA GAATTCCGGT GATGTGTTTT ACGAGGAGGT
7381 CCATGATAAC ACAGATGCGT GGGAGTGCCT CAGAGTTGGT GACCCTGCCG ACTTTGACCC
7441 TGAGAAGGGA ACTCTGTGTG GGCATACTAC CATTGAAGAC AAGGCTTATA ATGTCTACAC
7501 CTCCCCATCT GGCAGGAAGT TCCTGGTCCC CGTCAACCCA GAGAGCGGAA GAGCCCAATG
7561 GGAAGCTGCA AAGCTTTCCG TAGAGCAGGC CCTTAGCATG ATGAATGTCG ACGGTGAGCT
7621 GACAGCCAAA GAACTGGAGA AACTGAAAAG AATAATTGAC AAACTCCAGG GCCTAACTAA
7681 GGAGCAGTGT TTAAACTGCT AGCCGCCAGC GGCTTGACCC GCTGTGGTCG CGGCGGCTTG
7741 GTTGTTACTG AGACAGCGGT GAAAATAGTT AAATTTCACA ACCGGACCTT CACCCTAGGA
7801 CCTGTGAATT TAAAAGTGGC CAGTGAGGTT GAGCTAAAAG ACGCAGTCGA GCATAACCAA
7861 CACCCGGTTG CAAGACCGGT TGATGGTGGT GTTGTGCTCC TGCGCTCCGC AGTTCCTTCG
7921 CTTATAGACG TCTTGATCTC TGGCGCTGAT GCATCTCCTA AGTTACTCGC CCACCACGGG
7981 CCGGGAAACA CTGGGATCGA TGGTTCGCTT TGGGATTTTG AGGCCGAGGC CACCAAAGAG
8041 GAAATTGCAC TCAGTGCGCA AATAATACAG GCTTGTGACA TTAGGCGCGG CGACGCACCC
8101 GAAATTGGTC TTCCTTATAA GCTGCACCCT GTTAGGGGCA ACCCTGAGCG GGTAAAAGGG
8161 GTTTTACAGA ATACAAGGTT TGGAGACATA CCTTATAAAA CCCCCAGTGA CACTGGGAGC
8221 CCAGTGCACG CGGCTGCCTG CCTCACGCCC AATGCCACTC CGGTGACTGA CGGTCGTTCC
8281 GTCTTGGCTA CGACCATGCC CTCCGGTTTT GAGTTGTATG TACCGACCAT TCCAGCGTCT
8341 GTCCTTGATT ATCTTGATTC CAGGCCTGAT TGCCCCAAAC AGTTGACAGA GCACGGCTGT
8401 GAGGATGCCG CATTAAGAGA CCTCTCCAAG TATGACTTGT CCACCCAAGG CTTTGTCTTG
8461 CCTGGAGTTC TTCGCCTTGT GCGTAAGTAC CTGTTTGCTC ATGTGGGTAA GTGCCCGCCT
8521 ATTCATCGGC CTTCCACTTA CCCTGCCAAG AATTCCATGG CTGGAATAAA TGGGAACAGG
8581 TTTCCAACCA AGGACATTCA GAGCGTCCCT GAAATCGACG TTTTGTGCGC ACAGGCCGTG
8641 CGAGAAAACT GGCAAACTGT TACTCCTTGT ACCCTCAAGA AGCAGTATTG CGGGAAGAAG
8701 AAGACTAGGA CAATACTCGG CACTAATAAC TTCATTGCGC TGGCCCACCG GGCAGCATTG
8761 AGTGGTGTCA CCCAGGGCTT CATGAAAAAA GCGTTTAACT CGCCCATCGC ACTCGGGAAA
8821 AACAAATTCA AGGAGCTGCA GACTCCGGTC TTGGGCAGAT GTCTTGAAGC TGACCTTGCA
8881 TCCTGTGACC GATCCACACC CGCAATTGTC CGCTGGTTTG CCGCCAATCT TCTTTATGAA
8941 CTTGCCTGTG CTGAGGAGCA TATACCATCG TACGTGTTGA ACTGCTGCCA CGACTTACTG
9001 GTCACGCAGT CCGGCGCGGT GACTAAGAGA GGTGGCCTAT CGTCTGGCGA CCCGATTACT
9061 TCTGTATCAA ACACCATTTA CAGCTTGGTG ATATATGCAC AGCACATGGT ACTCAGTTAT
9121 TTTAAAAGTG GTCACCCCCA TGGCCTTCTG TTTCTACAAG ACCAGCTAAA GTTTGAGGAC
9181 ATGCTCAAGG TTCAGCCCCT GATCGTCTAT TCGGACGACC TCGTGCTGTA CGCCGAGTCT
9241 CCCACCATGC CAAACTACCA CTGGTGGGTT GAACATCTGA ACCTGATGCT GGGTTTTCAG
9301 ACGGACCCAA AGAAGACAGC TATAACAGAC TCGCCATCAT TTTTGGGTTG TAGGATAATA
9361 AATGGACGCC AGTTAGTCCC CAACCGTGAC AGGATCCTCG CGGCCCTCGC CTACCATATG
9421 AAGGCAAACA ATGTTTCTGA ATACTACGCC TCGGCGGCTG CAATACTCAT GGACAGTTGT
9481 GCTTGTTTGG AGTACGATCC TGAGTGGTTT GAAGAGCTCG TGGTTGGGAT GGCGCAGTGC
9541 GCCCGCAAGG ACGGCTACAG TTTTCCTGGC CCGCCGTTCT TCTTGTCCAT GTGGGAAAAA
9601 CTCAGGTCCA ATCATGAGGG GAAGAAGTCT AGAATGTGCG GGTACTGTGG GGCCCCAGCT
9661 CCGTATGCCA CTGCCTGTGG CCTTGATGTT TGTATTTATC ACACCCACTT CCACCAGCAT

-continued

9721 TGTCCAGTCA TAATCTGGTG TGGCCATCCG GCGGGTTCTG GCTCTTGTAG TGAGTGCAAA

9781 CCCCCCCTAG GGAAAGGCAC AAGCCCTCTA GATGTGGTGT TAGAACAAGT CCCGTACAAG

9841 CCTCCACGAA CTGTAATCAT GCATGTGGAG CAGGGTCTCA CCCCTCTTGA CCCAGGCAGA

9901 TACCAGACTC GCCGCGGATT AGTCTCCGTT AGGCGTGGCA TCAGGGGAAA CGAAATCGAC

9961 CTACCAGACG GTGATTATGC TAGTACCGCC TTGCTCCCCA CTTGTAAAGA TATCAACATG

10021 GTCGCTGTCG CTTCCAATGT GTTGCGCAGC AGGTTCATCA TCGGTCCACC CGGTGCTGGT

10081 AAAACATACT GGCTCCTTCA ACAGGTCCAG GATGGTGATG TCATTTACAC GCCAACTCAT

10141 CAGACCATGC TTGACATGAT CAAGGCTTTG GGGACGTGCC GGTTCAACGC CCCAGCAGGC

10201 ACAACGCTGC AATTCCCTGC TCCCTCCCGT ACCGGCCCGT GGGTTCGCAT CCTGGCCGGC

10261 GGTTGGTGTC CTGGCAAGAA TTCCTTCCTG GATGAAGCAG CGTATTGTAA TCACCTTGAT

10321 GTCTTGAGGC TTCTTAGCAA AACTACCCTC ACCTGTCTGG GAGATTTCAA ACAACTCCAC

10381 CCAGTGGGTT TTGATTCTCA TTGCTATGTT TTTGACATCA TGCCTCAGAC TCAACTGAAG

10441 ACCATCTGGA GGTTTGGACA GAATATCTGT GATGCCATTC AGCCAGATTA CAGGGACAAA

10501 CTTGTGTCCA TGGTCAACAC AACCCGTGTA ACCTACGTGG AAAGACCTGT CAAGCATGGG

10561 CAGGTCCTCA CCCCTTACCA CAGGGACCGA GAGGACGGCG CCATCACAAT TGACTCCAGT

10621 CAAGGCGCCA CATTTGATGT GGTTACATTG CATTTGCCCA CTAAAGATTC ACTCAACAGG

10681 CAAAGAGCCC TTGTTGCTAT CACCAGGGCG AGACATGCTA TCTTTGTGTA TGACCCACAT

10741 AGGCAACTGC AGAGCATGTT TGATCTTCCT GCAAAAGGCA CACCCGTCAA CCTTGCCGTG

10801 CACCGTGACG AGCAGCTGAT CGTACTAGAT AGAAATAACA AAGAGTGCAC GGTTGCTCAG

10861 GCTCTAGGCA ATGGGGACAA ATTCAGGGCC ACAGACAAGC GCGTTGTAGA TTCTCTCCGC

10921 GCCATTTGTG CAGATCTTGA AGGGTCGAGC TCCCCGCTCC CCAAGGTCGC ACATAACTTG

10981 GGATTTTATT TCTCACCTGA TTTGACACAG TTTGCTAAAC TCCCGGCAGA ACTTGCACCC

11041 CACTGGCCCG TGGTGACAAC CCAGAACAAT GAAAAGTGGC CAGACAGGCT GGTTGCCAGC

11101 CTCCGCCCTA TCCATAAATA TAGCCGCGCA TGCATTGGAG CCGGCTATAT GGTGGGCCCT

11161 TCGGTGTTTC TAGGCACCCC TGGGGTTGTG TCATACTATC TCACAAAATT TGTTAAGGGG

11221 GAGGCTCAGG TGCTTCCGGA GACAGTCTTC AGCACCGGCC GAATTGAGGT AGATTGCCGG

11281 GAGTATCTTG ATGATCGGGA ACGAGAAGTT GCTGAGTCCC TCCCACATGC CTTCATTGGC

11341 GACGTCAAAG GCACTACCGT TGGGGGATGT CACCATGTCA CCTCTAAATA CCTTCCGCGC

11401 TTCCTTCCTA AGGAATCAGT TGCGGTGGTT GGGGTTTCGA GCCCCGGGAA AGCCGCAAAA

11461 GCAGTCTGCA CATTAACAGA TGTGTATCTC CCAGACCTTG AAGTTTACCT CCACCCAGAG

11521 ACCCAATCCA AGTGCTGGAA AATAATGTTG GACTTCAAGG AAGTCCGACT GATGGTCTGG

11581 AAAGACAAAA CGGCCTATTT TCAACTTGAA GGCCGCCATT TCACCTGGTA TCAGCTTGCA

11641 AGCTATGCCT CGTACATCCG AGTTCCTGTT AACTCTACGG TGTATTTGGA CCCCTGCATG

11701 GGCCCTGCCC TTTGCAACAG AAGAGTTGTC GGGTCCACTC ATTGGGGGGC TGACCTCGCA

11761 GTCACCCCTT ATGATTATGG TGCCAAAATC ATTCTGTCTA GTGCATACCA TGGTGAAATG

11821 CCTCCTGGGT ACAAAATCCT GGCGTGCGCG GAGTTCTCGC TTGACGACCC AGTGAGGTAC

11881 AAACACACCT GGGGGTTTGA ATCGGACACA GCGTATCTGT ACGAGTTCAC CGGAAACGGT

11941 GAGGACTGGG AGGATTACAA TGACGCATTT CGTGCGCGCC AGAAAGGGAA AATTTATAAG

12001 GCCACTGCCA CCAGCATGAG GTTTCATTTT CCCCCGGGCC CCATCATTGA ACCAACTTTA

12061 GGCCTGAACT GAAATGAGAT GGGGGCTATG CAAAGCCTTT TCTACAAAAT TGGCCAACTT

12121 TTTGTGGATG CTTTCACGGA ATTTTTGGTG TCCATTGTTG ATATCATCAT ATTTTTGGCC

-continued

12181 ATTTTGTTTG GCTTCACCAT CGCCGGTTGG CTGGTGGTCT TCTGCATCCG ATTGGTTTGC

12241 TCCGCGGTAC TCCGTGCGCG CCCTACCATT CACCCTGAGC AATTACAGAA GATCCTATGA

12301 GGCCTTTCTT TCTCAGTGCC GGGTGGACAT TCCCACCTGG GGAACCAAAC ATCCCTTGGG

12361 GATACTTTGG CACCATAAGG TGTCAACCCT GATTGATGAA ATGGTGTCGC GTCGAATGTA

12421 CCGCATCATG GAAAAATCAG GACAGGCTGC CTGGAAACAG GTTGTGAGCG AGGCTACGCT

12481 GTCTCGCATC AGTGGTTTGG ATGTGGTGGC TCATTTTCAG CATCTTGCCG CCATTGAAGC

12541 CGAGACCTGT AAATATTTGG CCTCTCGGAT GCCCATGCTA CACAACCTGC GCATGACAGG

12601 GTCAAATGTA ACCATAGTGT ATAATAGTAC TTTGAATCAG GTGTTAGCAA TCTTCCCGAC

12661 CTCTGAATCC CGGCCAAAGC TTCATGATTT TCAACAATGG TTAATAACTG TACATTCCTC

12721 CATATTTTCC TCCGTTGTGG CTTCCTGTAC TCTTTTTGTT GTGCTGTGGT TGCGAATTCC

12781 AATGCTACGT ACTGTTTTTG GTTTCCACTG GTTAGGGGCA ATTTTTCTTT CGAACTCACA

12841 GTGAATTACA CGGTGTGCCC ACCTTGCCTC ACCCGGCAAG CAGCCGCTGA GATCTACGAA

12901 CCCGGCAGGT CTCTTTGGTG CAGGATAGGG CATGATCGAT GTAGCGAGGA CGATCATGAC

12961 GAACTAGGGT TCTTGGTTCC GCCTGGCCTC TCCAGCGAAG GCCACTTGAC CAGTGTTTAC

13021 GCCTGGTTGG CGTTCCTGTC CTTCAGCTAT ACAGCCCAGT TCCATCCCGA GATATTTGGG

13081 ATAGGGAATG TGAGTAAAAT TTATGTTGAC ATCAAGCACC AATTCATCTG CGCCGAACAC

13141 GACGGGCAGA ACGCCACCCT GCCTCGCCAT GACAACATTT CAGCCGTGTT TCAGACCTAC

13201 TACCAACATC AGGTCGATGG CGGCAATTGG TTTCACCTGG AATGGCTGCG CCCCTTCTTT

13261 TCCTCTTGGT TGGTTTTAAA TGTTTCGTGG TTTCTCAGGC GTTCGCCTGC AAGCCATGTT

13321 TCAGTTCGAG TCTTTCAGAC ATCAAAACCA ACACCACCGC AGCACCAAAT TTTGTTGTCC

13381 TCCAGGACAT CAGCTGCCTT AGGCATGGCG ACCCGTCCTC TCCGGCGATT CGCAAAAGCT

13441 CTCAGTGCCG CACGGCGATA GGAACACCCG TGTATATCAC CATCACAGCC AATGTGACAG

13501 ATGAGAATTA TTTACATTCT TCTGATCTCC TCATGCTTTC TTCTTGCCTT TTCTATGCTT

13561 CTGAGATGAG TGAAAAGGGG TTCAAGGTGG TATTCGGCAA TGTGTCAGGC ATCGTGGCTG

13621 TGTGTGTCAA CTTTACCAGT TACGTCCAAC ATGTCAAGGA GTTTACCCAA CGCTCCTTGG

13681 TGGTCGAGCA TGTGCGACTG CTTCATTTCA TGACACCTGA AACCATGAGG TGGGCAACCG

13741 TTTTAGCCTG TCTTTTTGCC ATTCTGTTGG CAATTTGAAT GTTTAAGTAT GTTGGGGAAA

13801 TGCTTGACCG CGGGCTGTTG CTCGCCGTTG CTTTTTTTGT GGTGTATCGT GCCGTCTTGC

13861 TTTGTTGCGC CCGTCAACGT CGACGGGAAC GACAGCTCAA AGTTACAGCT GATTTACAAC

13921 TTGACGCTAT GTGAGCTGAA TGGCACAGAT TGGCTGGCTG GTAGATTTGA CTGGGCAGTG

13981 GAGTGTTTTG TCATTTTTCC CGTGTTGACT CACATTGTCT CCTATGGTGC CCTCACTACT

14041 AGCCATTTCC TTGACACAGT CGGTCTGGTC ACTGTGTCTG CCGCCGGGTT CCTTCATGAA

14101 CGGTATGTTT TGAGTAGCAT CTACGCGGTC TGTGCCCTGG CTGCGTTGAT TTGCTTCGTC

14161 ATTAGGCTTG CGAAGAACTG CATGTCCTGG CGCTACTCGT GTACCAGATA TACCAACTTC

14221 CTTTTGGACA CCAAGGGGAG ACTCTATCGT TGGCGATCGC CCGTCATCAT AGAGAAAAAG

14281 GGTAAAGTTG AGGTTGAAGG TCATTTGATC GACCTCAAAA GAGTTGTGCT TGATGGTTCC

14341 GTGGCAACCC CTATAACCAA AATTTCAGCG GAACAATGGG GTCGTCCTTA GATGACTTCT

14401 GCCATGATAG CACGGCTCCA CAAAAGGTGC TTTTGGCGTT TTCCATTACC TATACACCAG

14461 TGATGATATA TGCCCTAAAG GTAAGTCGCG GCCGACTGCT AGGGCTTTTG CACCTTTTGA

14521 TCTTTCTGAA CTGTGCTTTC ACCTTCGGGT ATATGACATT CACGCACTTT CAGAGTACAA

-continued

14581 ACAAGGTCGC GCTCACTATG GGAGCAGTAG TTGCACTCCT TTGGGGGGTG TACTCAGCCA

14641 TAGAAACCTG GAAATTCATC ACCTCCAGAT GCCGTTTGTG CTTGCTAGGC CGCAAGTACA

14701 TTCTGGCCCC TGCCCACCAC GTTGAGAGTG CCGCAGGCTT TCATCCGATT GCGGCAAATG

14761 ATAACCACGC ATTTGTCGTC CGGCGTCCCG GTTCCACTAC GGTCAACGGC ACATTGGTCC

14821 CCGGGTTGAA AAGCCTCGTG TTGGGTGGCA GAAAAGCTGT CAAACAGGGA GTGGTAAACC

14881 TTGTTAAATA TGCCAAGTAA CAACGGCAGG CAGCAGAAAA AAAGAAAGGG GGATGGCCAG

14941 CCAGTCAATC AGCTGTGTCA GATGCTGGGT AAAATTATTG CCCAGCAAAA TCAGTCCAGG

15001 GGCAAGGGAC CGGGAAAGAA AAATAACAAG AAAAACCCGG AGAAGCCCCA TTTTCCTCTA

15061 GCGACTGAAG ATGATGTCAG ACATCACTTT ACCCCGAGTG AGCGACAATT GTGTCTGTCG

15121 TCAATCCAGA CTGCCTTCAA TCAGGGCGCT GGAACTTGTA CCCTGTCAGA TTCAGGCAGG

15181 ATAAGTTACA CTGTGGAGTT TAGTTTGCCG ACGCATCACA CTGTGCGCCT GATCCGCGCT

15241 ACAGCATCAC CCTCAGCATG ATGAGCTGGC ATTCCTGGGT ATCCCAGTGT TTGAATTGGA

15301 AGAATGTGTG GTGAATGGCA CTGATTGACA TTGTGCTTCT AAGTCACCTA TTCAATTAGG

15361 GCGACCGTGT GGGAGTAGAA TTTAATTGGC GAGAACCACG CGGCCGAAAT TAAAAAAAAA

15421 AAAAAAAAAA AAAAAAAAAA AAAA

The cDNA consensus sequence of PRRS strain ND 99-14 at P100 has been assigned GenBank Accession number KU131569 (SEQ. ID. NO:11). The cDNA consensus sequence designated SEQ. ID. NO:11 is:

1 ATGACGTATA GTTGTTGGCT CTATGTCGTG ACATTTGTAT AGTCAGGAGC TGCGACCATT

61 GGTACAGCCC AAAACTTGCT GCGCGGGAAC GCCCTTCCGT GACAGCCTTC TTCAGGGGAG

121 TTTAGGGGTC TATCCCTAGC ACCTTGCTTC CGGAGTTGCA CTGCTTTACG GTCTCTCCAC

181 CCCTTTAACC ATGTCTGGGA TACTTGATCG GTGCACGTGT ACCCCCAATG CCAGGGTGTT

241 TGTGGCGGAG GGCCAAGTCT ACTGCACACG ATGTCTCAGT GCACGGTCTC TCCTTCCTTT

301 GAATCTCCAA GTTTCTGAGC TTGGGGTGCT GGGCTTATTT TATAGGCCCG AAGAGCCGCT

361 CCGGTGGACG TTGCCACGTG CATTCCCCAC TGTCGAGTGC TCCCCCGCCG GGGCCTGCTG

421 GCTTTCTGCG ATTTTTCCAA TTGCACGAAT GACCAGTGGA AACCTGAACT TTCAACAAAG

481 AATAGTGCGG GTCGCAGCTG AGCTCTACAG AGCCGGTCAG CTCACCCCCG TAGTCTTGAA

541 GAATCTACAG GTTTATGAAC GGGGTTGCCG TTGGTACCCC ATCGTTGGAC CTGTTCCTGG

601 AGTGGCTGTT TATGCCAATT CCTTACACGT GAGTGACAAA CCTTTCCCGG GAGCAACTCA

661 TGTGTTAACC AACCTACCGC TCCCGCAGAG GCCCAAGCCT GAAGACTTTT GCCCCTTTGA

721 GTGTGCTATG GCTGACGTCT ATGACATTGG TCATGACGCT GTCATGTATG TGGCCGGAGG

781 GAGAGTCTCC TGGGCCCCTC GTGGCGGGGA CAAAGGAAAA TTTGAAATAG TTCCCAAGGA

841 GTTGAAGTTG ATTGCGAATC GACTCCACAT TTCCTTCCCG CCCCACCACG CAGTGGACAT

901 GTCCAAGTTT GCCTTTATAA GCCCTGGGAG TGGTGTTTCC ATGCGGGTCG AGTACCAACA

961 TGGCTGTCTC CCCGCTGATA CTGTCCCTGA AGGAAACTGT TGGTGGCGCT TGTTTGACTT

1021 GCTTCCACCG GAAGTTCAGA ACAAAGAGAT TCGCCATGCT AACCAACTCG GCTATCAGAC

1081 CAAGCATGGT GTCGCTGGCA AGTACCTACA GCGGAGGCTG CAAGTTAATG GACTCCGAGC

1141 AGTAACTGAC GCGAATGGAC CTATCGTCAT ACAGTATTTT TGTGATAGGG AAAGCTGGAT

1201 CCGCCACTTA AGACTGGTAG AAGAACCTAG CCTCCCTGGG TTTGAGGACC TCCTCAGAAT

1261 AAGAGTTGAG CCCAATACGT TGCCATTGGT TGGCGAGGAT GAGAAAATCT TCCGATTTGG

1321 CAATCACAAA TGGTACGGTG CTGGAAAGAG GGCAAGGAAA GCACGCTTTG GTGCGGCTGC

-continued

```
1381 CACGGTCGCT CACCGCGCTT TGCCCGCTCA CGAAACCCAG CAGGCCAAGA AGCACGAAGT
1441 TACCAGCGCC AACAGGGCTG AGCATCTCGA GCACTATTCC CCGCCTACCG ACGGGAACTG
1501 TGGTTGGCAC TGCGTTTCCG CCATTGTCAA CCGGATTGTG AATTCCAAAT TTGAAACCAC
1561 CCTTCCCGAG AGAGTGAGAC CTTTAGATGA CTGGGCTACT GACGAGGATC TTGTGAATAC
1621 TATCCAAATC CTCAGGCTCC CTGCGGCCTT GGACAGGAAC GGTGCTTGTG TCGGCGCCAA
1681 GTACGTGCTC AAGCTGGAAG GTGTGCACTG GACAGTCTCT GTGGCCCCTG GGATGACCCC
1741 TTCTCTGCTC CCCCTTGAAT GTGTTCAGGG CTGTTGTGAG CATAAGAGCG GTCTTGGTCC
1801 CCCAGATGTG GCTGAAGTTT CCGGATTTGA CCCTGCCTGC CTTAACCGAC TGGCTGAGGT
1861 AATGCACTTG CCTAGTTGTG TCATCCCAGC TGCTCTGGCT GAAATGTCCG ACGACCCCAA
1921 TCGCCCGGCT TCCCCAGTCA CCACTGTGTG GACTATTTCG CAATTCTTTG CCCATTATAG
1981 AGGAGGAGAG CACCCTGATC AGGTGTGCTT AGGGAAAATC ATCAGCCTTT GTCAGGTGAT
2041 TGAGGAATGC TGTTGTTCCC AGAACAAAAC CAACCGGGCC ACCCCGGAAG AGGTCGCGGC
2101 AAAAATTGAC CAGTACCTCC GTGATGCAGC AAGCCTTGGA GAATGCTTAG CCAAGCTTGA
2161 GAGGGCTCGC CCGCCGAGCG CGATGGACAC CTCCTTTGAT TGGAATGTTG TGCTTCCTGG
2221 GGTTGAGGCG GCGAACCAGA CGACCAAACA GCTCCATGTC AACCAGCACC GTGCTTCGGT
2281 TCCTGCCATG ACTCAGGAGC CTTTGGACAA AGACTCGGTC CCTTTGACCG CCTTCTCGCT
2341 GTCTAATTGC TACTACCCTG CACAAGGTGA CGAGGTTCGT CACCGTGAGA GGCTGATCTC
2401 CGTGCTCTCT AAGTTGGAGG AGGTTGTTCG TGAGGAATAT GGGCTCACGC CAACTGGATC
2461 TGGCCCGCGA CCCGCACTGC CGAACGGGCT CGACGAGCTC AAAGACCAGA TGGAAGAGGA
2521 TCTGTTGAAA CTGGTCAACG CCCAGGCAAC TTCAGAAATG ATGGCCCGGG CAGCTGAGCA
2581 GGTTGATCTA AAAGTTTGGG TCAAAAATTA CCCACGGTGG ACACCGCCAC CCCCTCCACC
2641 AAGAGTTCAG CCTCGAAAAA CAAAGTCTGC TAAGAGCCTG CCAGAGAACA AGCCTGTCCC
2701 TGCTCCGCGC AGGAAAGTCA GATCTGATTG TGGCAGCCCG ACTTTGAGGG GCAACAATGT
2761 TCCTAACGGT TGGGAAGACT TGGCCGTTGG TGGTCCTCTT GATCTTTCGA CACCATCCGA
2821 GCCGATGACA CCTCTGAGTG AGCCTGCACT TATGCCCGTG TTGCAACATA TTTCTGGACC
2881 AGTGACGCCT TTGAGCGTGC CGGCCCCTAT TCCTGCACCG CGTAAAGCTG TGTCCCGACC
2941 GATGGCGCCC TCGAGTGAGC CAATTTTTGT GTCTGCACCG CGGCAAAAAT TTCAGCAGGT
3001 GGAAGAAGCA AATCTGGCGG CAACAACGCT GACATACCAG GACGAACCTA TAGATCTGTC
3061 AGCATCCTCA CAGACTGAAT ATGAGGCTCC TTCCCTAGCA CCACTGCAGA ACATAGGTAC
3121 TCTGGAGGTG GGGGGGCAAG AAGCTGAGGA AATTCTGAGT GAAACCTCGG ATATACCGAA
3181 TGACATCAAC CCTGTGCCTG TATCATCAAG CAGCTCCTTG TCAAGCGTTA AGATCACACG
3241 CCCAAGACAC TCAGCTCAAG CCATCATCGA CTCGGGCGGG CCCTGCAGTG GGCATCTCCA
3301 AAGGGAGAAA GAAGCGTGCC TCCGCATCAT GCGTGAGGCT TGTGATGCGA CTAAGCTTAG
3361 TGACCCTGCC ACGCAGGAAT GGCTTTCTCG CATGTGGGAT AGGGTGGACA TGCTGACTTG
3421 GCGCAACACG TCTGCTTTCC AGGCGTTTCG CATCTTAGAC GGCAGGCTTG AGTTTCTTCC
3481 AAAGATGATA CTCGAGACGC CGCCGCCCTA CCCGTGTGGG TTTGTGATGC TGCCTCACAC
3541 CCCTGCACCT TCCGTGAGTG CAGAGAGCGA CCTTACCATC GGTTCAGTCG CCACTGAAGA
3601 TATTCCACGC ATCCTCGGGA AAATAGAAAA CACCAGTGAG ATGATCAACC AGGGACCCTT
3661 GGCATCCTCT GAGGAAAAAC CGGCATACAA CCAACCCGCT AAGGACTCCC TGATATCGTC
3721 GCGGGGGTTT GACGAGAGCA CAGCAGCTCC GTCCGCAGGT ACGGGTGGCG CCGGCTTGTT
```

-continued

3781 TACTGATTTG CCACCTTCAG ACGGTGTAGA TGCGGACGGG GGGGGGCCGC TGCAGACGGT

3841 GAAAAAGAAC GCTGAAAGGC TCCTCGACCG ATTGAGCCGT CAGGTTTTTA ACCTCGTCTC

3901 CCATCTCCCT GTTTTCCTCT CACACCTCTT CAAATCTGAC AGTGGTTATT CTCCGGGTGA

3961 TTGGGGTTTT GCAGCTTTTA CTCTATTTTG CCTCTTTTTA TGTTACAGCT ACCCATTCTT

4021 TGGTTTCGCT CCCCTTTTGG GTGTGTTTTC TGGGTCTTCT CGGCGCGTGC GCATGGGGGT

4081 TTTTGGCTGC TGGTTGGCTT TTGCTGTTGG TTTGTTCAAG CCTGTGTCCG ACCCAGTCGG

4141 CACTGCTTGT GAGTTTGATT CGCCAGAGTG TAGGAATGTC CTTCATTCTT TTGAGCTTCT

4201 CAAACCTTGG GACCCTGTTC GCAGCCTTGT TGTGGGCCCC GTCGGTCTCG GTCTTGCCAT

4261 TCTTGGCAGG TTACTGGGCG GGGCACGCTA CATCTGGCAT TTTCTGCTTA GGCTTGGCAT

4321 TGTTACAGAC TGTATCCTGG CTGGAGCTTA TGTGCTTTCT CAAGGTAGGT GTAAAAAGTG

4381 CTGGGGATCT TGCATAAGAA CAGCTCCTAA TGAGATTGCC TTTAACGTGT TCCCTTTTAC

4441 ACGTGCGACT AGGTCGTCAC TCATCGACCT GTGCAATCGG TTTTGTGCGC CAAAGGGCAT

4501 GGACCCTATT CTCCTCGCCA CTGGGTGGCG TGGGTGCTGG ACCGGCCGAA GCCCCATTGA

4561 ACAACCCTCT GAAAAACCCA TCGCGTTTGC CCAGTTGGAC GAAAAGAGGA TTACGGCCAG

4621 GACCGTGGTC GCCCAGCCTT ATGACCCCAA CCAAGCCGTA AAGTGCTTGC GGGTGTTACA

4681 GGCGGGCGGG GCGATGGTGG CTGAGGCAGT CCCAAAAGTG GTCAAAGTTT CCGCTATTCC

4741 ATTCCGAGCC CCCTTTTTTC CCACCGGAGT GAAAGTTGAC CCTGAGTGTA GGATCGTGGT

4801 TGACCCCGAC ACTTTTACTA CAGCCCTCCG GTCCGGCTAT TCCACCACAA ACCTCGTTCT

4861 TGGTGTGGGG GACTTTGCCC AGCTGAATGG ATTAAAAATC AGGCAAATTT CCAAGCCTTC

4921 GGGAGGAGGC CCGCACCTCA TTGCTGCCCT ACATGTTGCC TGCTCGATGG CGTTGCACAT

4981 GCTTGCTGGG GTTTATGTAA CTGCAGTGGG GTCTTGCGGT ACCGGCACCA ACGATCCGTG

5041 GTGCACCAAC CCGTTTGCCG TCCCTGGCTA CGGGCCTGGT ACTCTTTGCA CGTCCAGATT

5101 GTGCATCTCC CAACATGGCC TTACCCTGCC CTTGACAGCA CTTGTGGCAG GATTCGGTCT

5161 TCAGGAAATT GCCTTGGTTG TTTTGATTTT CGTTTCCATC GGAGGCATGG CTCACAGGTT

5221 GAGTTGCAAG GCTGACATGC TGTGCGTTTT ACTTGCAATC GCCAGCTATG TTTGGGTGCC

5281 CCTTACCTGG TTTCTTTGTG TGTTTCCTTG CTGGTTGCGC TGGTTCTCTT TGCATCCCCT

5341 CACCATCCTA TGGTTGGTGT TTTTCTTGAT TTCTGTAAAT GTGCCTTCGG GAATCTTGGC

5401 TGTGGTGTTG TTAGTTTCTC TTTGGCTCTT AGGTCGTTAC ACTAATGTTG CTGGTCTTGT

5461 CACCCCATAT GACATTCATC ATCACACCAG TGGCCCCCGA GGTGTTGCCG CCTTGGCTAC

5521 TGCACCGGAT GGGACCTACT TGGCCGCCGT TCGCCGTGCT GCGTTGACCG GTCGTACCAT

5581 GCTGTTTACC CCGTCTCAGC TTGGGTCCCT TCTTGAGGGT GCTTTCAGAA CTCAAAAGCC

5641 CTCACTGAAC ACCGTCAATG TGGTCGGATC CTCTATGGGC TCCGGCGGGG TGTTCACCAT

5701 CGACGGGAAA ATTAAGTGCG TAACAGCCGC ACATGTCCTT ACGGGTAATT CAGCTAGGGT

5761 TTCCGGGGTC GGCTTCAACC AAATGCTTGA TTTTGATGTG AAAGGGGACT TCGCCATAGC

5821 TGATTGCCCG AATTGGCAAG GAGCTGCCCC CAAGACCCAA TTCTGCGAGG ATGGATGGAC

5881 TGGCCGTGCC TATTGGCTGA CATCCTCTGG AGTCGAACCC GGTGTCATTG GGAATGGATT

5941 CGCCTTCTGC TTCACCGCGT GCGGCGATTC TGGATCCCCG GTGATTACCG AAGCCGGTGA

6001 GCTTGTCGGC GTTCACACAG GATCAAACAA ACAAGGAGGA GGCATAGTCA CACGCCCCTC

6061 AGGCCAGTTT TGTAATGTGG CGCCCATCAA GCTGAGCGAA TTGAGTGAAT TCTTCGCTGG

6121 ACCTAAGGTC CCGCTCGGTG ATGTGAAGAT TGGCAGCCAC ATAATTAAAG ACGTATGCGA

6181 GGTACCTTCA GATCTTTGCG CCTTGCTCGC TGCCAAACCC GAACTGGAAG GAGGCCTCTC

-continued

```
6241 CACCGTCCAA CTTCTGTGTG TGTTTTTCCT CCTGTGGAGA ATGATGGGAC ATGCCTGGAC
6301 GCCCTTGGTT GCTGTGGGGT TTTTTATCTT GAATGAGGTT CTCCCAGCTG TCCTGGTCCG
6361 GAGTGTCTTC TCCTTTGGTA TGTTTGTGCT ATCTTGGCTT ACACCATGGT CTGCGCAAGT
6421 CCTGATGATC AGGCTTCTAA CAGCAGCTCT TAACAGGAAC AGGGGGTCAC TCGCCTTCTA
6481 CAGCCTCGGT GCAGTGACCG GATTTATCGC AGATCTTGCA GCAACTCAGG GGCATCCGCT
6541 GCAGGCAGTG ATGAACTTAA GCACCTATGC CTTCCTGCCT CGGATGATGG TTGTGACCTC
6601 ACCAGTCCCA GTGCTTGCTT GTGGTGTTGT GCACCTCCTT GCCATAATTT TGTACCTGTT
6661 TAAGCACCGT TGCCTGCATT ATGTCCTTGT TGGCGATGGA GTGTTCTCTA AAGCCTTCTT
6721 CTTGCGATAC TTTGCCGAAG GGAAGTTGAG GGAAGGGGTG TCGCAGTCCT GCGGGATGAA
6781 TCACGAGTCA CTGACTGGTG CCCTCGCTAT GAGACTCAAT GACGAAGACT TGGACTTCCT
6841 TACGAAATGG ACTGATTTTA AGTGCTTTGT TTCTGCGTCC AACATGAGGA ATGCAGCGGG
6901 CCAATTCATC GAGGCTGCCT ATGCAAAAGC ACTTAGAATT GAGCTTGCCC AGTTAGTACA
6961 GGTTGATAAG GTTCGAGGTA CTTTGGCCAA ACTTGAAGCC TTTGCTGATA CCGTGGCACC
7021 CCAGCTCTCG CCCGGTGACA TTGTTGTTGC TCTTGGCCAC ACGCCTGTTG GCAGTATCTT
7081 CGACCTAAAG GTTGGCAGTA CCAAGCATAC CCTCCAGGCC ATTGAGACCA GAGTCCTTGC
7141 CGGGTCCAAA ATGACCGTGG CGCGTGTCGT TGATCCAACC CCCACGCCCC CACCCGCACC
7201 CGTGCCCATC CCCCTCCCAC CGAAAGTCCT GGAGAACGGC CCCAACGCCT GGGGGGATGA
7261 GGACCGGTTG AATAAGAGGA AGAGACGCAG GATGGAAGCC GTCGGCATCT TTGTTATGGG
7321 TGGGAAGAAG TACCAAAAAT TTTGGGACAA GAATTCCGGT GATGTGTTTT ACGAGGAGGT
7381 CCATGATAAC ACAGATGCGT GGGAGTGCCT CAGAGTTGGT GACCCTGCCG ACTTTGACCC
7441 TGAGAAGGGA ACTCTGTGTG GGCATACTAC CATTGAAGAC AAGGCTTATA ATGTCTACAC
7501 CTCCCCATCT GGCAGGAAGT TCCTGGTCCC CGTCAACCCA GAGAGCGGAA GAGCCCAATG
7561 GGAAGCTGCA AAGCTTTCCG TAGAGCAGGC CCTTAGCATG ATGAATGTCG ACGGTGAGCT
7621 GACAGCCAAA GAACTGGAGA AACTGAAAAG AATAATTGAC AAACTCCAGG GCCTAACTAA
7681 GGAGCAGTGT TTAAACTGCT AGCCGCCAGC GGCTTGACCC GCTGTGGTCG CGGCGGCTTG
7741 GTTGTTACTG AGACAGCGGT GAAAATAGTT AAATTTCACA ACCGGACCTT CACCCTAGGA
7801 CCTGTGAATT TAAAAGTGGC CAGTGAGGTT GAGCTAAAAG ACGCAGTCGA GCATAACCAA
7861 CACCCGGTTG CAAGACCGGT TGATGGTGGT GTTGTGCTCC TGCGCTCCGC AGTTCCTTCG
7921 CTTATAGACG TCTTGATCTC TGGCGCTGAT GCATCTCCTA AGTTACTCGC CCACCACGGG
7981 CCGGGAAACA CTGGGATCGA TGGTTCGCTT TGGGATTTTG AGGCCGAGGC CACCAAAGAG
8041 GAAATTGCAC TCAGTGCGCA AATAATACAG GCTTGTGACA TTAGGCGCGG CGACGCACCC
8101 GAAATTGGTC TTCCTTATAA GCTGCACCCT GTTAGGGGCA ACCCTGAGCG GGTAAAAGGG
8161 GTTTTACAGA ATACAAGGTT TGGAGACATA CCTTATAAAA CCCCCAGTGA CACTGGGAGC
8221 CCAGTGCACG CGGCTGCCTG CCTCACGCCC AATGCCACTC CGGTGACTGA CGGTCGTTCC
8281 GTCTTGGCTA CGACCATGCC CTCCGGTTTT GAGTTGTATG TACCGACCAT TCCAGCGTCT
8341 GTCCTTGATT ATCTTGATTC CAGGCCTGAT TGCCCCAAAC AGTTGACAGA GCACGGCTGT
8401 GAGGATGCCG CATTAAGAGA CCTCTCCAAG TATGACTTGT CCACCCAAGG CTTTGTCTTG
8461 CCTGGAGTTC TTCGCCTTGT GCGTAAGTAC CTGTTTGCTC ATGTGGGTAA GTGCCCGCCT
8521 ATTCATCGGC CTTCCACTTA CCCTGCCAAG AATTCCATGG CTGGAATAAA TGGGAACAGG
8581 TTTCCAACCA AGGACATTCA GAGCGTCCCT GAAATCGACG TTTTGTGCGC ACAGGCCGTG
```

-continued

8641 CGAGAAAACT GGCAAACTGT TACTCCTTGT ACCCTCAAGA AGCAGTATTG CGGGAAGAAG

8701 AAGACTAGGA CAATACTCGG CACTAATAAC TTCATTGCGC TGGCCCACCG GGCAGCATTG

8761 AGTGGTGTCA CCCAGGGCTT CATGAAAAAA GCGTTTAACT CGCCCATCGC ACTCGGGAAA

8821 AACAAATTCA AGGAGCTGCA GACTCCGGTC TTGGGCAGAT GTCTTGAAGC TGACCTTGCA

8881 TCCTGTGACC GATCCACACC CGCAATTGTC CGCTGGTTTG CCGCCAATCT TCTTTATGAA

8941 CTTGCCTGTG CTGAGGAGCA TATACCATCG TACGTGTTGA ACTGCTGCCA CGACTTACTG

9001 GTCACGCAGT CCGGCGCGGT GACTAAGAGA GGTGGCCTAT CGTCTGGCGA CCCGATTACT

9061 TCTGTATCAA ACACCATTTA CAGCTTGGTG ATATATGCAC AGCACATGGT ACTCAGTTAT

9121 TTTAAAAGTG GTCACCCCCA TGGCCTTCTG TTTCTACAAG ACCAGCTAAA GTTTGAGGAC

9181 ATGCTCAAGG TTCAGCCCCT GATCGTCTAT TCGGACGACC TCGTGCTGTA CGCCGAGTCT

9241 CCCACCATGC CAAACTACCA CTGGTGGGTT GAACATCTGA ACCTGATGCT GGGTTTTCAG

9301 ACGGACCCAA AGAAGACAGC TATAACAGAC TCGCCATCAT TTTTGGGTTG TAGGATAATA

9361 AATGGACGCC AGTTAGTCCC CAACCGTGAC AGGATCCTCG CGGCCCTCGC CTACCATATG

9421 AAGGCAAACA ATGTTTCTGA ATACTACGCC TCGGCGGCTG CAATACTCAT GGACAGTTGT

9481 GCTTGTTTGG AGTACGATCC TGAGTGGTTT GAAGAGCTCG TGGTTGGGAT GGCGCAGTGC

9541 GCCCGCAAGG ACGGCTACAG TTTTCCTGGC CCGCCGTTCT TCTTGTCCAT GTGGGAAAAA

9601 CTCAGGTCCA ATCATGAGGG GAAGAAGTCT AGAATGTGCG GGTACTGTGG GGCCCCAGCT

9661 CCGTATGCCA CTGCCTGTGG CCTTGATGTT TGTATTTATC ACACCCACTT CCACCAGCAT

9721 TGTCCAGTCA TAATCTGGTG TGGCCATCCG GCGGGTTCTG GCTCTTGTAG TGAGTGCAAA

9781 CCCCCCCTAG GGAAAGGCAC AAGCCCTCTA GATGTGGTGT TAGAACAAGT CCCGTACAAG

9841 CCTCCACGAA CTGTAATCAT GCATGTGGAG CAGGGTCTCA CCCCTCTTGA CCCAGGCAGA

9901 TACCAGACTC GCCGCGGATT AGTCTCCGTT AGGCGTGGCA TCAGGGGAAA CGAAATCGAC

9961 CTACCAGACG GTGATTATGC TAGTACCGCC TTGCTCCCCA CTTGTAAAGA TATCAACATG

10021 GTCGCTGTCG CTTCCAATGT GTTGCGCAGC AGGTTCATCA TCGGTCCACC CGGTGCTGGT

10081 AAAACATACT GGCTCCTTCA ACAGGTCCAG GATGGTGATG TCATTTACAC GCCAACTCAT

10141 CAGACCATGC TTGACATGAT CAAGGCTTTG GGGACGTGCC GGTTCAACGC CCCAGCAGGC

10201 ACAACGCTGC AATTCCCTGC TCCCTCCCGT ACCGGCCCGT GGGTTCGCAT CCTGGCCGGC

10261 GGTTGGTGTC CTGGCAAGAA TTCCTTCCTG GATGAAGCAG CGTATTGTAA TCACCTTGAT

10321 GTCTTGAGGC TTCTTAGCAA AACTACCCTC ACCTGTCTGG GAGATTTCAA ACAACTCCAC

10381 CCAGTGGGTT TTGATTCTCA TTGCTATGTT TTTGACATCA TGCCTCAGAC TCAACTGAAG

10441 ACCATCTGGA GGTTTGGACA GAATATCTGT GATGCCATTC AGCCAGATTA CAGGGACAAA

10501 CTTGTGTCCA TGGTCAACAC AACCCGTGTA ACCTACGTGG AAAGACCTGT CAAGCATGGG

10561 CAGGTCCTCA CCCCTTACCA CAGGGACCGA GAGGACGGCG CCATCACAAT TGACTCCAGT

10621 CAAGGCGCCA CATTTGATGT GGTTACATTG CATTTGCCCA CTAAAGATTC ACTCAACAGG

10681 CAAAGAGCCC TTGTTGCTAT CACCAGGGCG AGACATGCTA TCTTTGTGTA TGACCCACAT

10741 AGGCAACTGC AGAGCATGTT TGATCTTCCT GCAAAAGGCA CACCCGTCAA CCTTGCCGTG

10801 CACCGTGACG AGCAGCTGAT CGTACTAGAT AGAAATAACA AAGAGTGCAC GGTTGCTCAG

10861 GCTCTAGGCA ATGGGGACAA ATTCAGGGCC ACAGACAAGC GCGTTGTAGA TTCTCTCCGC

10921 GCCATTTGTG CAGATCTTGA AGGGTCGAGC TCCCCGCTCC CCAAGGTCGC ACATAACTTG

10981 GGATTTTATT TCTCACCTGA TTTGACACAG TTTGCTAAAC TCCCGGCAGA ACTTGCACCC

11041 CACTGGCCCG TGGTGACAAC CCAGAACAAT GAAAAGTGGC CAGACAGGCT GGTTGCCAGC

-continued

11101 CTCCGCCCTA TCCATAAATA TAGCCGCGCA TGCATTGGAG CCGGCTATAT GGTGGGCCCT

11161 TCGGTGTTTC TAGGCACCCC TGGGGTTGTG TCATACTATC TCACAAAATT TGTTAAGGGG

11221 GAGGCTCAGG TGCTTCCGGA GACAGTCTTC AGCACCGGCC GAATTGAGGT AGATTGCCGG

11281 GAGTATCTTG ATGATCGGGA ACGAGAAGTT GCTGAGTCCC TCCCACATGC CTTCATTGGC

11341 GACGTCAAAG GCACTACCGT TGGGGGATGT CACCATGTCA CCTCTAAATA CCTTCCGCGC

11401 TTCCTTCCTA AGGAATCAGT TGCGGTGGTT GGGGTTTCGA GCCCCGGGAA AGCCGCAAAA

11461 GCAGTCTGCA CATTAACAGA TGTGTATCTC CCAGACCTTG AAGTTTACCT CCACCCAGAG

11521 ACCCAATCCA AGTGCTGGAA AATAATGTTG GACTTCAAGG AAGTCCGACT GATGGTCTGG

11581 AAAGACAAAA CGGCCTATTT TCAACTTGAA GGCCGCCATT TCACCTGGTA TCAGCTTGCA

11641 AGCTATGCCT CGTACATCCG AGTTCCTGTT AACTCTACGG TGTATTTGGA CCCCTGCATG

11701 GGCCCTGCCC TTTGCAACAG AAGAGTTGTC GGGTCCACTC ATTGGGGGGC TGACCTCGCA

11761 GTCACCCCTT ATGATTATGG TGCCAAAATC ATTCTGTCTA GTGCATACCA TGGTGAAATG

11821 CCTCCTGGGT ACAAAATCCT GGCGTGCGCG GAGTTCTCGC TTGACGACCC AGTGAGGTAC

11881 AAACACACCT GGGGGTTTGA ATCGGACACA GCGTATCTGT ACGAGTTCAC CGGAAACGGT

11941 GAGGACTGGG AGGATTACAA TGACGCATTT CGTGCGCGCC AGAAAGGGAA AATTTATAAG

12001 GCCACTGCCA CCAGCATGAG GTTTCATTTT CCCCCGGGCC CCATCATTGA ACCAACTTTA

12061 GGCCTGAACT GAAATGAGAT GGGGGCTATG CAAAGCCTTT TCTACAAAAT TGGCCAACTT

12121 TTTGTGGATG CTTTCACGGA ATTTTTGGTG TCCATTGTTG ATATCATCAT ATTTTTGGCC

12181 ATTTTGTTTG GCTTCACCAT CGCCGGTTGG CTGGTGGTCT TCTGCATCCG ATTGGTTTGC

12241 TCCGCGGTAC TCCGTGCGCG CCCTACCATT CACCCTGAGC AATTACAGAA GATCCTATGA

12301 GGCCTTTCTT TCTCAGTGCC GGGTGGACAT TCCCACCTGG GGAACCAAAC ATCCCTTGGG

12361 GATACTTTGG CACCATAAGG TGTCAACCCT GATTGATGAA ATGGTGTCGC GTCGAATGTA

12421 CCGCATCATG GAAAAATCAG GACAGGCTGC CTGGAAACAG GTTGTGAGCG AGGCTACGCT

12481 GTCTCGCATC AGTGGTTTGG ATGTGGTGGC TCATTTTCAG CATCTTGCCG CCATTGAAGC

12541 CGAGACCTGT AAATATTTGG CCTCTCGGAT GCCCATGCTA CACAACCTGC GCATGACAGG

12601 GTCAAATGTA ACCATAGTGT ATAATAGTAC TTTGAATCAG GTGTTAGCAA TCTTCCCGAC

12661 CTCTGAATCC CGGCCAAAGC TTCATGATTT TCAACAATGG TTAATAACTG TACATTCCTC

12721 CATATTTTCC TCCGTTGTGG CTTCCTGTAC TCTTTTTGTT GTGCTGTGGT TGCGAATTCC

12781 AATGCTACGT ACTGTTTTTG GTTTCCACTG GTTAGGGGCA ATTTTTCTTT CGAACTCACA

12841 GTGAATTACA CGGTGTGCCC ACCTTGCCTC ACCCGGCAAG CAGCCGCTGA GATCTACGAA

12901 CCCGGCAGGT CTCTTTGGTG CAGGATAGGG CATGATCGAT GTAGCGAGGA CGATCATGAC

12961 GAACTAGGGT TCTTGGTTCC GCCTGGCCTC TCCAGCGAAG GCCACTTGAC CAGTGTTTAC

13021 GCCTGGTTGG CGTTCCTGTC CTTCAGCTAT ACAGCCCAGT TCCATCCCGA GATATTTGGG

13081 ATAGGGAATG TGAGTAAAAT TTATGTTGAC ATCAAGCACC AATTCATCTG CGCCGAACAC

13141 GACGGGCAGA ACGCCACCCT GCCTCGCCAT GACAACATTT CAGCCGTGTT TCAGACCTAC

13201 TACCAACATC AGGTCGATGG CGGCAATTGG TTTCACCTGG AATGGCTGCG CCCCTTCTTT

13261 TCCTCTTGGT TGGTTTTAAA TGTTTCGTGG TTTCTCAGGC GTTCGCCTGC AAGCCATGTT

13321 TCAGTTCGAG TCTTTCAGAC ATCAAAACCA ACACCACCGC AGCACCAAAT TTTGTTGTCC

13381 TCCAGGACAT CAGCTGCCTT AGGCATGGCG ACCCGTCCTC TCCGGCGATT CGCAAAAGCT

13441 CTCAGTGCCG CACGGCGATA GGAACACCCG TGTATATCAC CATCACAGCC AATGTGACAG

-continued

```
13501 ATGAGAATTA TTTACATTCT TCTGATCTCC TCATGCTTTC TTCTTGCCTT TTCTATGCTT

13561 CTGAGATGAG TGAAAAGGGG TTCAAGGTGG TATTCGGCAA TGTGTCAGGC ATCGTGGCTG

13621 TGTGTGTCAA CTTTACCAGT TACGTCCAAC ATGTCAAGGA GTTTACCCAA CGCTCCTTGG

13681 TGGTCGAGCA TGTGCGACTG CTTCATTTCA TGACACCTGA AACCATGAGG TGGGCAACCG

13741 TTTTAGCCTG TCTTTTTGCC ATTCTGTTGG CAATTTGAAT GTTTAAGTAT GTTGGGGAAA

13801 TGCTTGACCG CGGGCTGTTG CTCGCCGTTG CTTTTTTTGT GGTGTATCGT GCCGTCTTGC

13861 TTTGTTGCGC CCGTCAACGT CGACGGGAAC GACAGCTCAA AGTTACAGCT GATTTACAAC

13921 TTGACGCTAT GTGAGCTGAA TGGCACAGAT TGGCTGGCTG GTAGATTTGA CTGGGCAGTG

13981 GAGTGTTTTG TCATTTTTCC CGTGTTGACT CACATTGTCT CCTATGGTGC CCTCACTACT

14041 AGCCATTTCC TTGACACAGT CGGTCTGGTC ACTGTGTCTG CCGCCGGGTT CCTTCATGAA

14101 CGGTATGTTT TGAGTAGCAT CTACGCGGTC TGTGCCCTGG CTGCGTTGAT TTGCTTCGTC

14161 ATTAGGCTTG CGAAGAACTG CATGTCCTGG CGCTACTCGT GTACCAGATA TACCAACTTC

14221 CTTTTGGACA CCAAGGGGAG ACTCTATCGT TGGCGATCGC CCGTCATCAT AGAGAAAAAG

14281 GGTAAAGTTG AGGTTGAAGG TCATTTGATC GACCTCAAAA GAGTTGTGCT TGATGGTTCC

14341 GTGGCAACCC CTATAACCAA AATTTCAGCG GAACAATGGG GTCGTCCTTA GATGACTTCT

14401 GCCATGATAG CACGGCTCCA CAAAAGGTGC TTTTGGCGTT TTCCATTACC TATACACCAG

14461 TGATGATATA TGCCCTAAAG GTAAGTCGCG GCCGACTGCT AGGGCTTTTG CACCTTTTGA

14521 TCTTTCTGAA CTGTGCTTTC ACCTTCGGGT ATATGACATT CACGCACTTT CAGAGTACAA

14581 ACAAGGTCGC GCTCACTATG GGAGCAGTAG TTGCACTCCT TTGGGGGGTG TACTCAGCCA

14641 TAGAAACCTG GAAATTCATC ACCTCCAGAT GCCGTTTGTG CTTGCTAGGC CGCAAGTACA

14701 TTCTGGCCCC TGCCCACCAC GTTGAGAGTG CCGCAGGCTT TCATCCGATT GCGGCAAATG

14761 ATAACCACGC ATTTGTCGTC CGGCGTCCCG GTTCCACTAC GGTCAACGGC ACATTGGTCC

14821 CCGGGTTGAA AAGCCTCGTG TTGGGTGGCA GAAAAGCTGT CAAACAGGGA GTGGTAAACC

14881 TTGTTAAATA TGCCAAGTAA CAACGGCAGG CAGCAGAAAA AAAGAAAGGG GGATGGCCAG

14941 CCAGTCAATC AGCTGTGTCA GATGCTGGGT AAAATTATTG CCCAGCAAAA TCAGTCCAGG

15001 GGCAAGGGAC CGGGAAAGAA AAATAACAAG AAAAACCCGG AGAAGCCCCA TTTTCCTCTA

15061 GCGACTGAAG ATGATGTCAG ACATCACTTT ACCCCGAGTG AGCGACAATT GTGTCTGTCG

15121 TCAATCCAGA CTGCCTTCAA TCAGGGCGCT GGAACTTGTA CCCTGTCAGA TTCAGGCAGG

15181 ATAAGTTACA CTGTGGAGTT TAGTTTGCCG ACGCATCACA CTGTGCGCCT GATCCGCGCT

15241 ACAGCATCAC CCTCAGCATG ATGAGCTGGC ATTCCTGGGT ATCCCAGTGT TTGAATTGGA

15301 AGAATGTGTG GTGAATGGCA CTGATTGACA TTGTGCTTCT AAGTCACCTA TTCAATTAGG

15361 GCGACCGTGT GGGAGTAGAA TTTAATTGGC GAGAACCACG CGGCCGAAAT TAAAAAAAAA

15421 AAAAAAAAAA AAAAAAAAAA AAAA
```

A person skilled in the art would recognize the poly-adenosine tails of each of the genomic consensus sequences could vary in length from the above reported sequences.

Variant identification was also performed to determine the number and frequency of nucleotide changes in the virus population for both passages. Table 15 shows the 7 nucleotide changes found in P84 and P100 compared to the reference sequence. Overall the variant positions were consistent between the passages with the exception of 2 nucleotide changes in P84 which were not present in P100. Furthermore, the frequencies of each variant were similar between the passages and were detected at relatively low frequencies suggesting that similar sub-populations are found in both P84 and P100 of ND 99-14.

TABLE 15

PRRSV ND 99-14 Sequence Variants.

| | Reference | Variant | Frequency (% of Population) | |
|---|---|---|---|---|
| Position | Base | Base | P84 | P100 |
| 1,120 | G | T | 19.73% | 17.27% |
| 2,276 | C | T | 77.41% | 73.92% |

TABLE 15-continued

| PRRSV ND 99-14 Sequence Variants. | | | | |
|---|---|---|---|---|
| | Reference | Variant | Frequency (% of Population) | |
| Position | Base | Base | P84 | P100 |
| 2,680 | G | A | 26.39% | 19.42% |
| 6,001 | G | A | 19.57% | 7.26% |
| 8,745 | C | T | 31.18% | 29.78% |
| 13,699 | T | C | 15.68% | ND |
| 14,005 | T | C | 5.12% | ND |

ND = not detected.

EXAMPLE 6

The objective of this study is to prepare the master seed virus (MSV) of Porcine Reproductive and Respiratory Syndrome Virus (PRRSV) strain SD 11-21. This seed will be used for PRRSV vaccine development.

PRRSV SD 11-21 strain has been modified by passing in the MARC-145 cells 83 times (P83) including two rounds of plaque purification and one round of sucrose gradient purification, prior to the initial characterization and sequencing as described in Example 1. The SD 11-21 strain has been further attenuated by passing 12 times (P95) in MARC-145 cells in the growth medium Opti-MEM® I (Life Technologies) supplemented with 5% fetal bovine serum (FBS; Sigma Aldrich) and 50 µg gentamicin/mL (Life Technologies), and an additional 5 passages have been performed in the same growth medium supplemented with 2% FBS without gentamicin. The $100^{th}$ passage (P100) of PRRSV SD 11-21 has been used to prepare the Pre-Master Seed Virus (Pre-MSV).

The following procedure is used to determine the titer of PRRSV MSV SD 11-21. MARC-145 cells are seeded into 96-well plates at a density of $0.75\text{-}1.5\times10^4$ cells in 100 µL of growth medium (OPTI-MEM® I media supplemented with 5% FBS and 50 µg/mL gentamycin). Cells are incubated in 37±2° C. and 5±1% $CO_2$ incubator for 48-72 hours until cells are over 95% confluent. On the day of titration, all media is removed from the 96-well plate and was replaced with 100 µL of fresh growth media.

Ten-fold serial dilutions of the MSV are prepared with diluent (OPTI-MEM® I media, 50 µg/mL gentamycin) and transferred to corresponding wells on the plates prepared as above along with a negative control consisting of diluent alone. Titration plates are incubated in 37±2° C. with 5±1% $CO_2$ incubator for 4 days. At the end of the incubation period, each plate is observed for the presence of virus-induced cytopathic effect (CPE) in each sample well using an inverted microscope. The 50% tissue culture infectious dose ($TCID_{50}$) was calculated using the Reed-Muench method and titer is recorded as $\log_{10}$ $TCID_{50}$/mL. The mean titer of the PRRSV MSV SD 11-21 is 3.25 $\log_{10}$ $TCID_{50}$/mL. There were no distinguishable differences in the titers over the course of MSV preparation.

The PRRS SD 11-21 MLV strain has been denoted as a "master seed virus (MSV)," and has been deposited under conditions that assure that access to the cultures will be available during the pendency of this patent application to one determined by the Commissioner of Patents and Trademarks to be entitled thereto under 37 C.F.R. § 1.14 and 35 U.S.C. § 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the deposited culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it. A deposit of PRRSV MSV SD 11-21 was entered into the permanent collection of the Patent Depository of the American Type Culture Laboratory, located at 10801 University Blvd., Manassas, Va., 20110-2209, USA, on Dec. 2, 2015 under the terms of the Budapest Treaty, whereupon it was assigned accession number ATCC PTA-122674 by the repository.

EXAMPLE 7

The objective of this study is to use next generation sequencing to establish genetic identity, obtain a consensus sequence, and assess genomic variants (subpopulations) that exist within PRRSV Strain SD 11-21 passage 84 and passage 100 preparations, both described in Example 6.

Sequence characterization using the massive parallel sequencing (MP-Sep) system is a standard procedure comprised of several steps which include: nucleic acid extraction from the virus preparations, cDNA library synthesis and quantitation, clonal amplification and enrichment of DNA library by PCR and sequencing of the library by the Roche/454 next generation sequencing platform. Sequencing by synthesis is used to simultaneously determine the nucleotide order of the fragments in the cDNA library. Genome identification and characterization were performed using bioinformatics analyses of the resulting fragments by mapping each data set to the reference sequence. The reference sequence used in this analysis by BioReliance consisted of the full length sequence PRRSV SD 11-21 passage 83 (P83) disclosed in Example 1 (SEQ ID NO:9).

Sequencing of the PRRSV SD 11-21 genome resulted in the complete genome coverage for both P84 and P100 samples. The complete consensus genomes for P84 and P100 can be found in SEQ ID NO: 12 and SEQ ID NO: 13, respectively. The cDNA consensus sequences have also been deposited with GenBank. The cDNA consensus sequence of PRRS strain SD 11-21 at P84 was assigned GenBank Accession number KU131566 (SEQ. ID. NO:12). The cDNA consensus sequence designated SEQ. ID. NO:12 is:

```
 1  ATGACGTATA GGTGTTTGCT TTATGCCGCG GCATTTGTAT TGTCAGGAGC TGTGACCACT

61  GGCACAGCCC GAAACTTGCT GCACAGAAAC ACCCTTCTGT GACAGCCTCC TTCAGGGGAG
```

-continued

```
121 TTTAGGGGTT TCTCCCTAAC GCCCTGCTTC CGGAGTTGCA CTGCTTTACG GTCTCTCCAT
181 CCTTTTAACC ATGTCTGGGA TTCTTGATCG GTGCACGTGC ACCCCCAATG CCAGGGTGTT
241 TGTGGCAGAG GGCCAAGTCT ACTGCACACG ATGTCTCAGT GCACGGTCCC TCCTTCCCCT
301 AAATCTCCAA GTTTCTGAGC TTGGGGTACT TGGTTTATTC TACAGGCCCG AAGAGCCATT
361 ACGGTGGACG TTGCCACACG CATTCCCCAC TGTCGAGTGT GCTCCTGCTG GCGCTTGTTG
421 GCTTTCTGCA ATTTTTCCAA TTGCGCGAAT GACCAGTGGA AACCTGAATT TCCAGCAAAG
481 GCTGGTACGT GTCGCAGCCG AGCTTTACAG AGCCGGCCAG CTCACCCCTA CAAGCCTGAA
541 AACCTTACAG GTCTATGAAA GGGGTTGCCG TTGGTACCCC ATTGTTGGAC CTGTTCCTGG
601 AGTGGCCGTT TACGCCAACT CCCTACATGT GAGTGACAAA CCCTTCCCAG GAGCGACTCA
661 CGTGCTGACC AACTTACCAC TCCCGCAGAG ACCAAAATCT GAAGATTTCT GCCCCTTCGA
721 GTGCGCCACG GCCGCCGTCT ATGACATCGG CCATGACGCC GTCATGTATG TAACCGAGGA
781 AAAGGTTTCC TGGGCTCCTC GTGGCGGGGA TAAAGGGAAA TTTGAGACTG TTCCTGAGGG
841 GTTGAAGTTG ACTGCGGAAC GACTCTACAC CTCCTTCCCG CCTCACCATG CGGTGGACAT
901 GTCCCTTTTC ATCTTCACAG ACCTTGAGTG CGGCGCTTCC ATGCGGGTCG AACGCCAATA
961 TGGTTGCCTC TCTGCTGGCA CTGTCCCTGA AGGCAACTGC TGGTGGAGTC TGTTTGGCTC
1021 GCTTTCGTTA GAAGCTCAGT ATAAAGAAAT CCGCTACGCC GCCCAATTTG GCTATCAGAC
1081 CAAACATGGC GTTACTGGCA AGTACCTGCA GCGGAGGCTG CAAATTAATG GTCTCCGAGC
1141 AGTGGTTGAC CCGAATGGGC CTCTTGTCGT ACAGTATTTC TCCGTTAAGG AGAGCTGGAT
1201 GCGCCACGTG AGACTGGCGG AAGAGCCAGG CTATCCTGGG TTTGAGGATC TCCTCAGGAT
1261 AAGAGTCGAG CCCAACACGT TGCCTTTGTC CAACAAGGAC GAGAAAATCT TCCGTTTCGG
1321 CGGTTACAAG TGGTACGGTG CTGGGCGGAG GGCAAGGAGA ACACGTGCAA GAGCAGTCAC
1381 CGCAGTTGCT AGTCATGCTC CGCCCGCTCG TGGGGCCCAG CAGGCCGAGA AGCACGAAGT
1441 TGCTAGTGCC AACAAGACTG AGCTCCTTAC GCACTACTCC CCACCTGCTG AAGGGAATTG
1501 CGGCTGGCAC TGCATCTCCG CCATCATGAA CCGGATGGTG CATTCCAAGT TTGAAACCGC
1561 CCTTTCCGAA AGAGTGAGAT CCCCGGAAGA CTGGGCGACT GATGAGGATC TTGTGAATAC
1621 TATTCAAATC CTCAGGCTCC CTGCGGCCTT AGACAGGAAC GGCGCCTGTA AAAACGCCAA
1681 GTACATCCTT AAGCTGGAAG GTGAGCACTG GACTGTTTCA GTGACCCCCG GAATGCCCCC
1741 CTCTTCACTT CCTCTTGAAT GCGTTCAGGG TTGTTGCGAG CATAAGGGCA ATTTTGACTC
1801 TCAAAACGCG GTCGGTTTCT TTGGGTTCGA CCCTGCCAGC CTTGACCGAC TCGCTGGGGT
1861 AATGCATCTG CCCAGCAGCG CCATCCCTGC CGCCCTGGCC GAGTTGTCTG GTGAACTTGA
1921 TTGTTCAACT CCCCCGGCCA CCACTGTGTG GACTACCTTG CAGTTTTATG CTCGTCTTGG
1981 TGGGGGGGAG CATCCTGATC AAGAGTGCTT GAGAAAAATC ATCAGCCTCT GTGAGGTGCT
2041 CGGGAGTTGC TGCTGTTCTC AGAGTAGGGT CAACCGGGTC ACCCCGGAAG AGGTCGCAGC
2101 AAAGATTGAC CTGTATCTTC GTGACGCAGC GAGTCTTGAA GAGTGCTTGG CTAGGCTTGA
2161 GAAAGCTCGC CCGCCAAGCA TGCTGGACAC CTCCTTTGAC TGGGATGTTG TACTCCCTGG
2221 TGTTGGGACG GCTGCTCGGG CAGCAGAACT ACCCCCCACC GATGAGTGTC GCGCTCTAGT
2281 CACTGCTGTG GCCCAAAGGC CTTCGCCGAA AGTTCAGCCT CGAAAGGCGG GGTCTGTTAA
2341 GAGTCTACCA GAGATCAGGC CTGTCCCTGC CCCACGCAGG AAGGTTAAGT CTAGTTGTGG
2401 TGATCTGGCC CCGTTGGGCG GCAATTTCCC TGATAGCTGG GAAGATTTGG CTGGTGGCTC
2461 CCTTAATCTC CAGATCTTAC CTGAGCCGGT GGCACAATCC TTTGAACCTG TGCCTGTCCC
2521 TGCACCGCGC AAGACTGCGC CTCGATTAGT GTCGTCATCA TTGGCGTCGA CCCCCGTACC
```

-continued

2581 TACACCACGA TGTGGGTTTC GGCAGTTTGA GGGAATGAAT TTGACAGCTG TGACCCTAGC

2641 ATGCCAGGAT GAGTCCCTCA ATTTGTCTGC ATCCTCGCAG ACTGAATATG AGGCTTCTCC

2701 TTTGGCATTG CAGCAGGGTG AGGATGTCCT TGCGGTGGGG GGACGAGAAG CCGAAGAAGT

2761 CCTGAGCGGA ATCTCGGGAA TGTCAGGTGG CATTAGATTA GCGCCCGCAT CATCAAGTAG

2821 CTCCTTGTCA AGCGTGGAGA TCACACGCCC GAAGTACTCA GCTCAAGCCA TCATTGACTC

2881 AGGTGGACCC TGTTGCGGGC ACCTTCAAGA GGTGAAAGAG AAATACCTTA ATGTCATGCG

2941 TGAGGCATGT GATGCGACTA AGCTCGATGA CCCTGCCACG CAAGAATGGC TCTCTCGCAT

3001 GTGGGAGAGG GTAGACATGC TAACCTGGCG CAACACGTCC ATCTTTCAAG CGCCTTTTAC

3061 CTTAGCTGAC AAGTTTAAGT CCCTCCCGAA GATGATACTC GAAACGCCGC CACCCTACCC

3121 TTGCGGGTTT GTGATGATGC CCCGCACGCC CGCACCTTCT GTGGGTGCGG AAAGCGACAT

3181 CACCGTTGGT TCAGTTGCTA CTGAAGATGT CCCGCGTATA CTCGGGGAGG TGGGAGATGT

3241 TGGCAAGATG ACCGGCCAGG AACCCTTAGA ATCCTTCGCA GATGAACTGG CAGATGACCA

3301 ACCTGCTAGG GAGTCCCGAA CACAAGCTCC TCCTGCAAGC ACAGGTAGCG CTGGTTTAGT

3361 TTTGGATTCT GGAGGGTCGC TGGGGCTCAC TGACCTGCCG CTCCCAAACA ATATAGACGC

3421 GGGCGGGAAA GGACCGTTTC ACGCGGTCAA GAAAAAAGCT GTAGGGTGCT TTGACCAACT

3481 GAGCCGCCGG GTTTTTGACA TCGTCTCCCA TCTCCCTGTT TTTTTTTCAC GCCTTTTCGC

3541 GCCCGGTGGT TTTTACTCTT CGGGTGACTG GAGTTTTGCA GCTTTTACTT TATTGTGTCT

3601 CTTTTTATGT TACAGTTATC CGGCCTTTGG TTTTGCTCCC CTCGTGGGTG TATTTTCTGG

3661 GTCTTCTCGG CGCGTGCGCA TGGGGGTTTT TGGCTGCTGG CTGGCTTTTG CTGTTGGTTT

3721 GTTCAAGCCT GCACCCGACC CAGTCGGTGC TGCTTGTGAG TTTGACTCGC CAGAGTGTAG

3781 AGACATCCTT CATTCTTTTG AGCTCCTGCA ACCTTGGGAC CCTGTTCGCA GCCTTGTGGT

3841 GGGCCCCGTC GGTCTCGGCC TTGCCATTTT TGGCAGGTTA CTGGGCGGGG CACGCTACGT

3901 CTGGCTGCTT TTGCTTAGGC TTGGCATCGT TTCAGACTGT ATCCTGGCTG GAGCCTATGT

3961 GCTTTCGCAA GGCAGGTGTA AAAAGTGTTG GGGATCTTGT ATAAGAACAG CCCCCAGTGA

4021 AGTTGCCTTC AATGTGTTTC CCTTTACACG CGCAACTAGA TCGTCACTTG TCAACCTGTG

4081 CGACCGGTTC TGTGCACCCA AGGGCATGGA CCCCATCTTC CTTGCCACAG GATGGCGCGG

4141 ATGCTGGTCC GGCCAGAGCC CCATTGAGCA ACCCTCTGAA AAACCCATAG CGTTCGCCCA

4201 GTTGGACGAA AAGAAAATCA CGGCTAGGAC TGTGGTTGCC CAGCCTTATG ACCCCAACCA

4261 AGCTGTGAAG TGCCTGCGAG TCCTCCAGGC GGGTGGAGCG ATGGTAGCCG AGGCAGTTCC

4321 AAAAGTAGTC AAAGTTTCTG CTGTCCCGTT TCGAGCCCCT TTTTTTCCTG CCGGAGTGAA

4381 AGTTGACCCT GAATGCAGGG TCGTGGTTGA CCCTGACACC TTTACAACCG CTCTCCGGAC

4441 CGGCTACTCC ACCACAAACC TCATTCTTGG TGTTGGGGAC TTTGCCCAGC TGAATGGGTT

4501 GAAGATCAGA CAAATTTCCA AGTCCCCAGG AGGGGGCCCT CACCTCATGG CGGCTTTACA

4561 TGTTGCTTGC TCGATGACTT TGCACATGCT TGTTGGGATT TATGTCACCA TGGTGGGTTC

4621 TTGTGGCTCT GGCACTAACG ATCCGTGGTG CACTAACCCG TTTGCCGTCC CTGTCTATGG

4681 GCCTGGCTCT CTCTGCACGT CCAGGTTGTG CATTTCCCAG CGTGGCCTGA CCCTGCCCTT

4741 AACAGCGCTT GTGGCAGGGT TTGGCGTTCA GGAAATCGCT TTGGTTGTTT TAATCTTTGT

4801 CTCCATCGGG GGTATGGCCC ACAGGTTGAG TTGCAAGGCT GACGTGCTGT GTATCCTGCT

4861 TGCTATTGTC AGCTATGTTT GGCCACCCCT TACCTGGTTG CTTTGTGTGT TTCCTTGCTG

4921 GTTGCGCTGG TTTTCTTTAC ATCCCCTTAC TATTCTATGG TTAGTGTTTT TCTTGATTTC

-continued

4981 TGTAAATACG CCCTCGGGAA TCTTGGCCTT GGTCCTGTTA ATCTCTCTTT GGCTCCTTGG

5041 TCGCTATACC AATGTTGCCG GCCTTGTCAC CCCTTATGAC ATTCACCATT ACACCAACGG

5101 CCCTCGCGGC GTTGCCGCCT TGGCCACTGC CCCGGATGGG ACCTACCTGG CTGCTGTCCG

5161 CCGTGCTGCG TTGACTGGCC GTACCATGCT GTTCACCCCG TCCCAACTTG GCTCGCTCCT

5221 TGAGGGCGCT TTTAGAACCC AAAAGCCTTC ACTGAACACT GTCAATGTAG TTGGGTCCTC

5281 CATGGGCTCC GGCGGGGTGT TCACCATTGA TGGGAAGATC AAATGTGTGA CCGCTGCTCA

5341 TGTCCTCACG GGTAACTCTG CCAGGGTTTC CGGGGTTGGC TTCAATCAAA TGTTGGACTT

5401 TGATGTTAAA GGGGATTTTG CCATAGCCGA TTGTCCGAAT TGGCAAGGAG TCGCCCCCAA

5461 GTCCCGGTTC TGCAAGGATG ATTGGACTGG CCGTGCTTAT TGGCTCACGT CCTCCGGCGT

5521 CGAACCCGGC GTCATTGGGC AAGGATTCGC CTTTTGTTTC ACCGCGTGCG GCGATTCCGG

5581 GTCCCCAGTG ATCACCGAGG CCGGGGAGCT TGTCGGTGTC CACACGGGAT CAAACAAACA

5641 AGGAGGAGGC ATTGTTACGC GCCCTTCAGG CCGGTTTTGT AATGTGACAC CCACCAAATT

5701 AAGTGAATTG AGTGAATTCT TCGCTGGACC TAGGGTCCCG CTTGGTGACG TGAAGGTTGG

5761 CAATCACATA ATCAAAGATA TAAATGAGGT GCCCTCAGAT CTCTGCGCCT TACTCGCTGC

5821 CAAACCCGAA TTGGAAGGAG GCCTCTCCAC CGTTCAACTT CTGTGCGTGT TTTTTCTCCT

5881 ATGGAGAATG ATGGGACATG CCTGGACACC CTTGGTTGCC GTTGGTTTTT TCATCTTGAA

5941 TGAAGTTCTC CCAGCAGTCC TGGTCCGGAG TGTCTTCTCC TTTGGAATGT TCGCACTGTC

6001 TTGGTTCACG CCGTGGTCTG CACAAATTCT AATGATCAGG CTCTTGACAG CAGCCCTAAA

6061 CAGAAACAGA TCGTCACTTG CCTTTTACAG CCTGGGCGCA CTAACCGGTT TTGTTGCAGA

6121 TCTTGCAACC AATCAGGGGT ATTTATTGCA CGCGGTCATG AATGTGAGCA CCTATGCATT

6181 CCTGCCTCGT GCAATGGCCG TGACCTCACC AGTCCCAATA GTTGCGTGTG GCGTTGTGCA

6241 CTTGCTTGCC ATCATTCTGT ACTTGTTCAA GTACCGTAGC CTGCATGCCG TCCTGGTCGG

6301 CGATGGTGCG TTTTCCGCGG CTTTCTTCTT GCGATACTTT GCGGAGGGAA AGTTGAGGGA

6361 AGGGGTGTCG CAGTCTTGCG GCATGAATCA TGAGTCACTA ACCGGTGCCC TCGCCATGAA

6421 ACTCAGCGAC GAAGACTTGG ACTTCCTCAC AAAATTGACT GATTTTAAGT GCTTTGTTTC

6481 TGCATCCAAC ATGAGGAATG CGGCGGGTCA ATTTATAGAG GCCGCCTACG CCAAAGCACT

6541 GAGGGTGGAA CTTGCCCAGT TGGTTCAAGT CGATAAAGTT CGAGGTGTCC TGGCCAAACT

6601 TGAAGCTTTC GCTGACACCG TGGCGCCTCA ACTTTCACCC GGTGACATTG TTGTCGCCCT

6661 TGGACACACA CCTGTCGGCA GCATTTTTGA CCTGAAGGTC GGCAATGTTA AGCACACTCT

6721 CCAGTCCATT GAGACCAGAA CCCTTGCCGG GTCTAAAATG ACTGTGGCGC GCGTCGTAGA

6781 CCCAACCCCC ACACCCCCGC CCGCACCTGT GCCCATTTCC CTCCCACCAA AGGTTTTGGA

6841 GAACGGTCCC AACGCCTGGG GGGATGAGAA CGGTTTGAAC AAAAAAAAGC GGCGCAAGAT

6901 GGAGGCCGTT GGCATTTACG TTATGGGCGG GAAAAAGTAT CAAAAATTTT GGGATAAGAA

6961 TTCTGGTGAT GTGTTCTATG AAGAAGTCCA CGACAACACA GACGCGTGGG AATGCCTCAG

7021 AGTTGACAAC CCTGCCGACT TGGATCCTGA GAGGGGAACC TTGTGTGGAC ACACCACCAT

7081 AGACAACAGG CCTTACCATG TTTATGCTTC TCCGTCTGGT AGGAAGTTTC TAGTCCCTGT

7141 CAACCCGGAG AGCGGAAAAG CTCAGTGGGA AGCTGCTAAG CTTTCTTTAG ATCAGGCCCT

7201 CAGTATGATG AATGTCGACG GCGAACTGAC CGCCAAAGAA GTGGAAAAAT TGAAGAGAAT

7261 AATTGACAAA CTCCAGGGCC TGACTAAGGA GCAGTGTTTA AACTGCTAGC CGCCAGCGGC

7321 TTGACCCGCT GTGGTCGCGG CGGCTTGGTT GTTACTGAGA CAGCGGTAAA GATAGTCAGG

7381 TTCCACAACC GGACCTTTAC CCTAGGGCCT GTGAATTTGA AAGTAGCTAG CGAAGTTGAG

-continued

```
7441 TTGAAGGACG CGGTCGAGCA CGGCCAACAC CCGGTCGCGA TACCAGCCGA TGGTGGCGTC
7501 GTGCTCCTGC GTTCCGCTGT TCCTTCGCTT ATAGACGTCC TGATCTCCGG TGCTGACGCA
7561 TCCCCCAGGT TGCTCGCCCG TCACGGACCG GGAAATACTG GGGTCAATGG CGCGCTTTGG
7621 GATTTTGAGT CTGAAGCTAC CAAAGAGGAA GTAGCACTTA GTGCGCAAAT AATACAGGCC
7681 TGTGACATTA GACGCGGCGA TGCACCTGAG ATTGGCCTTC CTTACAAGTT GTACCCTGTT
7741 AGGGGCAACC CTGAACGGGC AAGAGGGGTT CTAATGAACA CAAGATTTGG AGACATACCT
7801 TACAAGACCC CCAGCGACAC CGGGAGCCCG GTGCACGCGG CCGCCTGCCT TACGCCCAAC
7861 GCCACTCCAG TAACTGATGG GCGCTCCATC CTGGCCACGA CCATGCCCTC CGGGTTTGAA
7921 CTATATGTGC CGACCATTCC AGCGTCTGTC CTTGATTACC TTGACTCCAG ACCAGACTGT
7981 CCTAAACAGT TGACTGAGCA CGGGTGTGAA GATGCCGCGT TGAAGGACCT TTCTAAATAT
8041 GACCTGTCCA CCCAAGGCTT TGTGTTACCT GGAGTTCTAC GCCTCGTGCG AAAATATCTG
8101 TTTGCTCATG TAGGTAAGTG CCCGCCTGTC CACCGGCCCT CTACCTATCC TGCCAAGAAC
8161 TCCATGGCCG GAATAAATGG GAACAGGTTC CCAACCAAGG ATATTCAAAG CATCCCTGAG
8221 ATCGACGTTT TGTGTGCACA AGCTGTGCGA GAAAACTGGC AAACTGTTAC ACCCTGCACT
8281 CTTAAGAAGC AGTATTGCGG TAAAAAGAAG ACCAGGACCA TACTTGGCAC CAACAACTTC
8341 GTTGCGCTGG CCCACCGGGC GGCGCTGAGT GGTGTCACCC AGGGTTTCAT GAAGAAGGCG
8401 TTTAACTCAC CCATCGCCCT TGGGAAAAAT AAATTTAAGG AGCTACAGAC TCCAGTCTTG
8461 GGTAGGTGTC TTGAGGCTGA TCTCGCTTCC TGCGATCGAT CCACGCCTGC AATCGTTCGC
8521 TGGTTTGCCG CCAACCTTCT TTATGAACTT GCCTGTGCTG AGGAGCATTT ACCGTCGTAC
8581 GTGCTGAACT GTTGTCACGA CCTATTGGTC ACGCAGTCCG GCGCAGTGAC TAAGAGAGGT
8641 GGCCTGTCGT CCGGTGACCC AATCACCTCT GTGTCCAACA CCATTTATAG CTTGGTGATC
8701 TATGCACAGC ATATGGTGCT TAGTTACTTC AAAAGTGGTC ACCCCCATGG CCTTCTGTTT
8761 TTACAAGACC AGCTAAAGTT TGAAGACATG CTCAAAGTTC AACCCCTAAT CGTCTATTCG
8821 GACGACCTCG TGTTGTATGC CGAGTCTCCC ACCATGCCAA ACTATCACTG GTGGGTTGAA
8881 CACCTGAATT TGATGTTGGG ATTTCAGACG GACCCAAAGA AGACTGCAAT AACAGACTCA
8941 CCTTCATTCC TAGGTTGTAG AATAATAAAT GGCCGCCAGT TAGTACCCAA CCGTGACAGA
9001 ATTCTCGCGG CCCTTGCCTA TCACATGAAG GCGAGTAATG TTTCTGAGTA CTACGCCTCC
9061 GCAGCCGCAA TACTCATGGA CAGTTGTGCT TGTCTAGAGT ATGATCCTGA GTGGTTTGAA
9121 GAACTTGTGG TTGGAATGGC GCAGTGCGCC CGTAAGGACG GCTATAGTTT CCCCGGCCCG
9181 CCGTTCTTCT TGTCCATGTG GGAAAAGCTC AGGTCAAATT ATGAGGGGAA GAAGTTGAGA
9241 GTGTGTGGTT ATTGCGGAGC TTCAGCCCCG TATGCTACTG CCTGTGGCCT TGACGTTTGT
9301 GTTTACCACA CCCACTTTCA CCAGCATTGT CCAGTCATAA TATGGTGTGG CCACCCGGCG
9361 GGTTCTGGGT CCTGCGATGA GTGCAAATCC CCTACAGGGA AGGGTACAAG CCCTCTGGAT
9421 GAGGTCTTAA GACAAGTCCC TTATAAGCCT CCACGGACTA TTCTTATGCA TGTGGAGCAG
9481 GGCCTCACCC CCCTTGACCC AGGCAGATAC CAGACCCGCC GTGGGTTGGT TGCTGTCAGG
9541 CGCGGGATAA GGGGAAATGA AGTTGACCTG CCAGATGGTG ATTATGCCAG TACTGCCCTA
9601 CTCCCCACCT GCAAAGACAT AGACATGGTT GCTGTGGCCT CCAATGTGTT GCGCAGTAGG
9661 TTCATCATCG GCCCACCTGG CGCAGGGAAA ACACACTGGC TTCTTCAACA GGTTCAGGAT
9721 AGTGATGTCA TTTACACGCC AACCCATCAG ACCATGCTTG ACATGATCAA GGCTTTGGGG
9781 ACGTGCCGGT TCAATGTCCC GGCAGGCACA ACGCTGCAAT TCCCTGCCCC CTCCCGTACC
```

-continued

9841 GGCCCGTGGG TTCGCATCCT TGCCGGCGGT TGGTGTCCAG GTAAGAATTC CTTCCTGGAT

9901 GAAGCAGCGT ATTGCAATCA CCTTGACGTC TTGAGGCTTC TCAGCAAAAC TACCCTCACC

9961 TGTCTGGGGG ATTTCAAACA ACTCCACCCG GTGGGTTTTG ATTCTCATTG CTATGTTTTT

10021 GATATCATGC CTCAGACTCA ACTGAAGACC ATCTGGAGGT TTGGACAGAA TATCTGTGAC

10081 GCCATTCAGC CAGATTACAG GGACAAACTC GTGTCCATGG TCAACACAAC CCGTGTAACC

10141 TATGTGGAAA GACCTGTCAA GTATGGGCAA GTCCTCACCC CCTACCACAG AGACCGAGAG

10201 GATGGTGCTA TCACTATTGA CTCCAGTCAA GGCGCCACAT TTGATGTGGT CACATTGCAT

10261 TTGCCCACTA AAGATTCACT CAACAGGCAA AGAGCCCTTG TTGCTATCAC CAGGGCAAGG

10321 CATGCAATCT TTGTGTATGA CCCACACAGG CAACTGCAGA GCATGTTTCG TCTTCCTGCA

10381 AAAGGCACAC CTGTCAACCT TGCCGTGCAC CGTGACGAGC AGCTCATCGT ATTAGATAGA

10441 AATAACAAAG AGTGCACGGT TGTTCAGGCT TTAGGCAATG GGGACAAATT CAGGGCCAGT

10501 GACAAGCGCG TTGTAGATTC TCTTCGCGCC ATTTGTGCAG ATCTTGAAGG GTCGAGCTCC

10561 CCGCTCCCCA AGGTCGCACA CAACTTGGGA TTTTATTTCT CACCTGATTT GACACAGTTT

10621 GCTAAACTCC CGGCGGAACT TGCACCCCAC TGGCCCGTGG TGACAACTCA GAACAACGAA

10681 AATTGGCCAG ACCGGCTGGT TGCTAGCCTC CGCCCTATCC ACAAATATAG CCGCGCGTGC

10741 ATCGGAGCCG GCTATATGGT GGGCCCCTCA GTGTTTCTAG GCACTCCTGG GGTTGTGTCA

10801 TACTATCTCA CACAATTTGT CAAAGGGGAG GCTCAGGTGC TTCCGGAGAC GGTCTTCAGC

10861 ACCGGCCGAA TTGAGGTAGA TTGTCGAGAG TATCTTGATG ATCGGGAACG AGAAGTTGCT

10921 GAGTCCCTCC CACATGCCTT TATTGGCGAC GTCAAAGGCA CTACCGTTGG GGGATGTCAC

10981 CATGTCACTT CTAAATATCT CCCACGCTTC CTTCCCAAGG AATCAGTTGC GGTGGTTGGG

11041 GTTTCAAGCC CCGGGAAAGC CGCAAAAGCA GTTTGCACAT TAACAGATGT GTACCTCCCA

11101 GATCTTGAGG CTTACCTCCA TCCAGAGACC CAGTCTAAGT GCTGGAAAGT GATGTTGGAC

11161 TTCAAGGAAG TTCGACTGAT GGTCTGGAGA GATAAGACGG CCTACTTTCA ACTTGAAGGC

11221 CGCCATTTCA CCTGGTACCA GCTTGCAAGT TATGCCTCGT ACATCCGAGT TCCCGTTAAC

11281 TCTACGGTGT ACCTGGACCC CTGTATGGGC CCTGCCCTTT GCAACAGAAG AGTCGTTGGG

11341 TCTGCACATT GGGGAGCTGA CCTTGCAGTT ACCCCTTATG ATTATGGTGC CAAAATCATT

11401 CTGTCTAGTG CGCACCATGG TGAAATGCCT CCTGGGTACA GAATTCTAGC GTGCGCGGAG

11461 TTCTCGCTTG ATGACCCAGT GAGGTACAAA CACACTTGGG GGTTTGAATC GGATACAGCG

11521 TATCTGTACG AGTTCACCGG AAACGGTGAG GACTGGGAGG ATTACAATGA TGCGTTTCGT

11581 GCACGCCAGA AAGGGAAAAT TTATAAGGCC ACTGCCACCA GCATGAGATT TCATTTTCCC

11641 CCGGGTCCTG CCATTGAACC AACATTGGGC CTGAACTGAA ATGAAATGGG GGCTGTGCAG

11701 AGCCTTTTCG ACAAAATTTG CCAACTTTTT GTGGATGCTT TCACGGAATT TTTGGTGTCC

11761 ATTGTTGATA TCATCATATT TTTGGCCATT TTGTTTGGCT TCACCATCGC AGGCTGGCTG

11821 GTTGTCTTCT GTATCCGACT GGTTTGCTCC ACGGTACTCC GTGCGCGCTC TACCATTCAC

11881 CCTGAGCAAT TACAGAAGAT CCTATGAGGC CTTCCTTTCC CAGTGCCAAG TGGACATTCC

11941 CGCCTGGGGA ACTAAGCATC CCTTGGGGGT GCTTTGGCAC CACAAGGTGT CAACTCTGAT

12001 TGATGAAATG GTGTCGCGTC GAATGTACCG CATCATGGAA AAAGCAGGAC AGGCTGCCTG

12061 GAAACAGGTT GTGAGCGAAG CTACATTGTC TCGCATAAGT GGCTTGGATG TGGTGGCTCA

12121 TTTTCAGCAT CTTGCTGCCA TTGAAGCCGA GACTTGCAAA TATTTGGCCT CTCGGCTGCC

12181 CATGCTACAC AACCTAGTCA TGTCAGGGTC GAATGTAACC ATAGTGTATA ATAGCACTTT

12241 GGGTCAAGTG TTTGCCATTT TCCCAACCCC TGGTTCCCGG CCAAAACTTT CTGATTTTCA

-continued

12301 ACAATGGCTC ATAGCTGTGC ATTCTTCCAT ATTTTCTTCT GTTGCGGCTT CTTGTACTCT

12361 TTTTGTTGTG CTGTGGCTGC GAATTCCAAT ACTACGTACT GTTTTTGGTT TCCGCTGGTT

12421 AGGGGCAACT TTTCTTTCGA ACTCACAGTG AATTACACGG TGTGCCCACC CTGCCTCACC

12481 CGGCAAGCAG CCGCTGAGAT CTACGAACAC AGCGGGTCTC TTTGGTGCAG GATAGGGCAT

12541 GACCGATGTA GCCAGAGTGA TCATGACGAA CTAGGGTTCT TGGTTCCACC TGGCCTTTCC

12601 AGCGAGGGCC ACTTGACCAG TGTTTACGCC TGGCTGGCGT TCTTGTCTTT CAGCTACACA

12661 GCCCAGTTCC ACCCCGAGAT ATTTGGAATA GGGAATGTGA GTAGAGTTTA TGTTGACGTC

12721 ACTCACCAAC TCATCTGCGC CGAACACGAC GGGCAGAACA CCACCCTGCG TCGCCATGAC

12781 AATATCTCAG CCGTGTTTCA GACCTATTAC CAACATCAGG TCGATGGCGG CAATTGGTTT

12841 CACCTAGAAT GGCTGCGTCC CTTCTTTTCC TCTTGGCTGG TTTTGAATGT CTCGTGGTTT

12901 CTCAGGCGTT CGCCTGCAAA CCGTGTTTCA GTTCGAGTCT TTCAGACATC AAAACCAACA

12961 CCACCGCAGC TGCAGGCTTT GCTGTCCTCC AAGACATCAG CTGTCTTAGG CATGGCTACT

13021 CGTCCATTGA GGCGATTCGC AAAAGCCGTC AATGCCGCAC GGCGATAGGA ACGCCCGTGT

13081 ACATCACTGT CACGGCCAAT GTAACAGATG AGAATTACTT GCATTCCTCT GATCTCCTCA

13141 TGCTTTCCTC TTGCCTCTTC TATGCTTCTG AGATGAGTGA AAAGGGATTC AATGTGGTCT

13201 TCGGCAACGT GTCAGGCATT GTGGCTGTGT GTGTCAACTT TACCAGCTAT GTCCAACATG

13261 TTAAGGAGTT TACTCAGCGC TCTTTGGTGG TCGACCACGT GCGACTGCTT CATTTCATGA

13321 CACCTGCGAC CATGAGGTGG GCAACAGTTT TAGCCTGTCT TTTCGCCATC TTGTTGGCGA

13381 TTTGAATGTT TAAGTATGTT GGGGAAATGC TTGACCGCGG GCTACTGCTC GCAATTGCTT

13441 TTTTTCTGGT GTATCGTGCC GTTCTGTTTT GCTGCGCTCG TCAACGCCGC CAGCAACAGC

13501 AGCTCCCATT TACAGTTGAT TTATAACCTG ACGATATGCG AGCTGAATGG CACAGATTGG

13561 TTGAATCAAA AGTTTGATTG GGCAGTGGAG ACTTTTGTCA TTTTTCCTGT GTTGACCCAC

13621 ATTGTCTCCT ACGGTGCCCT TACCACCAGC CATTTCCTTG ACACGGCCGG CCTAATCACT

13681 GTGTCTACCG CCGGATATTA CCATGGGCGG TATGTGTTGA GTAGCATCTA CGCCGTCTTT

13741 GCCCTGGCTG CGTTGATTTG TTTTGTCATT AGGTTGACAA AAAACTGTAT GTCCTGGCGC

13801 TACTCATGTA CCAGATATAC CAACTTTCTT CTGGACACCA AAGGCAATCT CTATCGTTGG

13861 CGGTCACCCG TCGTTATAGA GAGAAGGGGT AAAGTTGAGG TTGGAGACCA CCTAATCGAC

13921 CTCAAAAGAG TTGTGCTTGA TGGTTCCGCG GCAACCCCTA TAACCAAGAT TTCAGCGGAA

13981 CAATGGGGTC GTCCCTAGAC GACTTCTGCA ATGACAGCAC AGCTGCACAA AAGGTGCTTT

14041 TGGCGTTTTC CATCACCTAT ACGCCAATAA TGATATATGC CCTGAAGGTA AGTCGCGGCC

14101 GACTGTTAGG GCTTTTGCAT CTTTTAATTT TCTTGAATTG TGCTTTCACC TTCGGGTACA

14161 TGACATTTGT TCATTTTCAG AGTACAAACA AGGTCGCGCT CACTATGGGA GCAGTTGTTG

14221 CACTCCTTTG GGGGGTGTAC TCAGCCATAG AAACCTGGAA ATTCATCACT TCCAGATGCC

14281 GTTTGTGCTT GCTAGGCCGC AGGTACATTC TGGCCCCTGC CCACCACGTT GAAAGTGCCG

14341 CGGGCTTTCA TCCGATTGCG GCAAGTGATA ACCACGCATT TGTCGTCCGG CGTCCCGGCT

14401 CCACTACTGT TAACGGCACA TTGGTGCCCG GGTTGAAAAG CCTCGTGTTG GGTGGCAGAA

14461 AAGCTGTTAA GCGGGGAGTG GTAAACCTCG TTAAATATGC CAAATAACAA CGGCAGGCAG

14521 CAAAAAAATA AGAAGGGGAG TGGCCAGCCA GTCAATCAGC TGTGCCAAAT GCTGGGCAAG

14581 ATCATCGCCC AGCAAAATCA GTCCAGAGGC AAGGGACCGG GTAAGAAAAA TAAGAAGAGA

14641 AACCCGGAGA AGCCCCATTT TCCTCTTGCG ACCGAAGATG ACGTCAGGCA TCACTTCACC

-continued

14701 CCCAGTGAAC GGCAATTGTG TCTGTCGTCG ATCCAGACTG CCTTCAACCA GGGCGCTGGA

14761 ACTTGCACCC TGTCAGATTC AGGGAGGATA AGTTACACTG TGGAGTTTAG TTTGCCGACG

14821 CACCACACTG TGCGCCTTAT TCGCGCCACA GCATCACCTC CATCGTGATG GGCTTACATT

14881 CTTGGAGCTC CTCAGTTTCA CAATTGGAAG AATGTGTGGT GAATGGCACT GATTGGCACT

14941 GTGCCTCTAA GTCACCTATT CAATTAGGGC GACCGTGTGG GGGTTTAGTT TAATTGGCGA

15001 GAACCACGCG GCCGAAATTA AAAAAAAAAA AAAAAAAAAA AAAAAAA

The cDNA consensus sequence of PRRS strain SD 11-21 at P100 was assigned GenBank Accession number KU131568 (SEQ. ID. NO:13). The cDNA consensus sequence designated SEQ. ID. NO:13 is:

1 ATGACGTATA GGTGTTTGCT TTATGCCGCG GCATTTGTAT TGTCAGGAGC TGTGACCACT

61 GGCACAGCCC GAAACTTGCT GCACAGAAAC ACCCTTCTGT GACAGCCTCC TTCAGGGGAG

121 TTTAGGGGTT TCTCCCTAAC GCCCTGCTTC CGGAGTTGCA CTGCTTTACG GTCTCTCCAT

181 CCTTTTAACC ATGTCTGGGA TTCTTGATCG GTGCACGTGC ACCCCCAATG CCAGGGTGTT

241 TGTGGCAGAG GGCCAAGTCT ACTGCACACG ATGTCTCAGT GCACGGTCCC TCCTTCCCCT

301 AAATCTCCAA GTTTCTGAGC TTGGGGTACT TGGTTTATTC TACAGGCCCG AAGAGCCATT

361 ACGGTGGACG TTGCCACACG CATTCCCCAC TGTCGAGTGT GCTCCTGCTG GCGCTTGTTG

421 GCTTTCTGCA ATTTTTCCAA TTGCGCGAAT GACCAGTGGA AACCTGAATT TCCAGCAAAG

481 GCTGGTACGT GTCGCAGCCG AGCTTTACAG AGCCGGCCAG CTCACCCCTA CAAGCCTGAA

541 AACCTTACAG GTCTATGAAA GGGGTTGCCG TTGGTACCCC ATTGTTGGAC CTGTTCCTGG

601 AGTGGCCGTT TACGCCAACT CCCTACATGT GAGTGACAAA CCCTTCCCAG GAGCGACTCA

661 CGTGCTGACC AACTTACCAC TCCCGCAGAG ACCAAAATCT GAAGATTTCT GCCCCTTCGA

721 GTGCGCCACG GCCGCCGTCT ATGACATCGG CCATGACGCC GTCATGTATG TAACCGAGGA

781 AAAGGTTTCC TGGGCTCCTC GTGGCGGGGA TAAAGGGAAA TTTGAGACTG TTCCTGAGGG

841 GTTGAAGTTG ACTGCGGAAC GACTCTACAC CTCCTTCCCG CCTCACCATG CGGTGGACAT

901 GTCCCTTTTC ATCTTCACAG ACCTTGAGTG CGGCGCTTCC ATGCGGGTCG AACGCCAATA

961 TGGTTGCCTC TCTGCTGGCA CTGTCCCTGA AGGCAACTGC TGGTGGAGTC TGTTTGGCTC

1021 GCTTTCGTTA GAAGCTCAGT ATAAAGAAAT CCGCTACGCC GCCCAATTTG GCTATCAGAC

1081 CAAACATGGC GTTACTGGCA AGTACCTGCA GCGGAGGCTG CAAATTAATG GTCTCCGAGC

1141 AGTGGTTGAC CCGAATGGGC CTCTTGTCGT ACAGTATTTC TCCGTTAAGG AGAGCTGGAT

1201 GCGCCACGTG AGACTGGCGG AAGAGCCAGG CTATCCTGGG TTTGAGGATC TCCTCAGGAT

1261 AAGAGTCGAG CCCAACACGT TGCCTTTGTC CAACAAGGAC GAGAAAATCT TCCGTTTCGG

1321 CGGTTACAAG TGGTACGGTG CTGGGCGGAG GGCAAGGAGA ACACGTGCAA GAGCAGTCAC

1381 CGCAGTTGCT AGTCATGCTC CGCCCGCTCG TGGGGCCCAG CAGGCCGAGA AGCACGAAGT

1441 TGCTAGTGCC AACAAGACTG AGCTCCTTAC GCACTACTCC CCACCTGCTG AAGGGAATTG

1501 CGGCTGGCAC TGCATCTCCG CCATCATGAA CCGGATGGTG CATTCCAAGT TTGAAACCGC

1561 CCTTTCCGAA AGAGTGAGAT CCCCGGAAGA CTGGGCGACT GATGAGGATC TTGTGAATAC

1621 TATTCAAATC CTCAGGCTCC CTGCGGCCTT AGACAGGAAC GGCGCCTGTA AAAACGCCAA

1681 GTACATCCTT AAGCTGGAAG GTGAGCACTG GACTGTTTCA GTGACCCCCG GAATGCCCCC

1741 CTCTTCACTT CCTCTTGAAT GCGTTCAGGG TTGTTGCGAG CATAAGGGCA ATTTTGACTC

1801 TCAAAACGCG GTCGGTTTCT TTGGGTTCGA CCCTGCCAGC CTTGACCGAC TCGCTGGGGT

1861 AATGCATCTG CCCAGCAGCG CCATCCCTGC CGCCCTGGCC GAGTTGTCTG GTGAACTTGA

-continued

1921 TTGTTCAACT CCCCCGGCCA CCACTGTGTG GACTACCTTG CAGTTTTATG CTCGTCTTGG

1981 TGGGGGGGAG CATCCTGATC AAGAGTGCTT GAGAAAAATC ATCAGCCTCT GTGAGGTGCT

2041 CGGGAGTTGC TGCTGTTCTC AGAGTAGGGT CAACCGGGTC ACCCCGGAAG AGGTCGCAGC

2101 AAAGATTGAC CTGTATCTTC GTGACGCAGC GAGTCTTGAA GAGTGCTTGG CTAGGCTTGA

2161 GAAAGCTCGC CCGCCAAGCA TGCTGGACAC CTCCTTTGAC TGGGATGTTG TACTCCCTGG

2221 TGTTGGGACG GCTGCTCGGG CAGCAGAACT ACCCCCCACC GATGAGTGTC GCGCTCTAGT

2281 CACTGCTGTG GCCCAAAGGC CTTCGCCGAA AGTTCAGCCT CGAAAGGCGG GGTCTGTTAA

2341 GAGTCTACCA GAGATCAGGC CTGTCCCTGC CCCACGCAGG AAGGTTAAGT CTAGTTGTGG

2401 TGATCTGGCC CCGTTGGGCG GCAATTTCCC TGATAGCTGG GAAGATTTGG CTGGTGGCTC

2461 CCTTAATCTC CAGATCTTAC CTGAGCCGGT GGCACAATCC TTTGAACCTG TGCCTGTCCC

2521 TGCACCGCGC AAGACTGCGC CTCGATTAGT GTCGTCATCA TTGGCGTCGA CCCCCGTACC

2581 TACACCACGA TGTGGGTTTC GGCAGTTTGA GGGAATGAAT TTGACAGCTG TGACCCTAGC

2641 ATGCCAGGAT GAGTCCCTCA ATTTGTCTGC ATCCTCGCAG ACTGAATATG AGGCTTCTCC

2701 TTTGGCATTG CAGCAGGGTG AGGATGTCCT TGCGGTGGGG GGACGAGAAG CCGAAGAAGT

2761 CCTGAGCGGA ATCTCGGGAA TGTCAGGTGG CATTAGATTA GCGCCCGCAT CATCAAGTAG

2821 CTCCTTGTCA AGCGTGGAGA TCACACGCCC GAAGTACTCA GCTCAAGCCA TCATTGACTC

2881 AGGTGGACCC TGTTGCGGGC ACCTTCAAGA GGTGAAAGAG AAATACCTTA ATGTCATGCG

2941 TGAGGCATGT GATGCGACTA AGCTCGATGA CCCTGCCACG CAAGAATGGC TCTCTCGCAT

3001 GTGGGAGAGG GTAGACATGC TAACCTGGCG CAACACGTCC ATCTTTCAAG CGCCTTTTAC

3061 CTTAGCTGAC AAGTTTAAGT CCCTCCCGAA GATGATACTC GAAACGCCGC CACCCTACCC

3121 TTGCGGGTTT GTGATGATGC CCCGCACGCC CGCACCTTCT GTGGGTGCGG AAAGCGACAT

3181 CACCGTTGGT TCAGTTGCTA CTGAAGATGT CCCGCGTATA CTCGGGGAGG TGGGAGATGT

3241 TGGCAAGATG ACCGGCCAGG AACCCTTAGA ATCCTTCGCA GATGAACTGG CAGATGACCA

3301 ACCTGCTAGG GAGTCCCGAA CACAAGCTCC TCCTGCAAGC ACAGGTAGCG CTGGTTTAGT

3361 TTTGGATTCT GGAGGGTCGC TGGGGCTCAC TGACCTGCCG CTCCCAAACA ATATAGACGC

3421 GGGCGGGAAA GGACCGTTTC ACGCGGTCAA GAAAAAAGCT GTAGGGTGCT TTGACCAACT

3481 GAGCCGCCGG GTTTTTGACA TCGTCTCCCA TCTCCCTGTT TTTTTTTCAC GCCTTTTCGC

3541 GCCCGGTGGT TTTTACTCTT CGGGTGACTG GAGTTTTGCA GCTTTTACTT TATTGTGTCT

3601 CTTTTTATGT TACAGTTATC CGGCCTTTGG TTTTGCTCCC CTCGTGGGTG TATTTTCTGG

3661 GTCTTCTCGG CGCGTGCGCA TGGGGGTTTT TGGCTGCTGG CTGGCTTTTG CTGTTGGTTT

3721 GTTCAAGCCT GCACCCGACC CAGTCGGTGC TGCTTGTGAG TTTGACTCGC CAGAGTGTAG

3781 AGACATCCTT CATTCTTTTG AGCTCCTGCA ACCTTGGGAC CCTGTTCGCA GCCTTGTGGT

3841 GGGCCCCGTC GGTCTCGGCC TTGCCATTTT TGGCAGGTTA CTGGGCGGGG CACGCTACGT

3901 CTGGCTGCTT TTGCTTAGGC TTGGCATCGT TTCAGACTGT ATCCTGGCTG GAGCCTATGT

3961 GCTTTCGCAA GGCAGGTGTA AAAAGTGTTG GGGATCTTGT ATAAGAACAG CCCCCAGTGA

4021 AGTTGCCTTC AATGTGTTTC CCTTTACACG CGCAACTAGA TCGTCACTTG TCAACCTGTG

4081 CGACCGGTTC TGTGCACCCA AGGGCATGGA CCCCATCTTC CTTGCCACAG GATGGCGCGG

4141 ATGCTGGTCC GGCCAGAGCC CCATTGAGCA ACCCTCTGAA AAACCCATAG CGTTCGCCCA

4201 GTTGGACGAA AAGAAAATCA CGGCTAGGAC TGTGGTTGCC CAGCCTTATG ACCCCAACCA

4261 AGCTGTGAAG TGCCTGCGAG TCCTCCAGGC GGGTGGAGCG ATGGTAGCCG AGGCAGTTCC

-continued

4321 AAAAGTAGTC AAAGTTTCTG CTGTCCCGTT TCGAGCCCCT TTTTTTCCTG CCGGAGTGAA

4381 AGTTGACCCT GAATGCAGGG TCGTGGTTGA CCCTGACACC TTTACAACCG CTCTCCGGAC

4441 CGGCTACTCC ACCACAAACC TCATTCTTGG TGTTGGGGAC TTTGCCCAGC TGAATGGGTT

4501 GAAGATCAGA CAAATTTCCA AGTCCCCAGG AGGGGGCCCT CACCTCATGG CGGCTTTACA

4561 TGTTGCTTGC TCGATGACTT TGCACATGCT TGTTGGGATT TATGTCACCA TGGTGGGTTC

4621 TTGTGGCTCT GGCACTAACG ATCCGTGGTG CACTAACCCG TTTGCCGTCC CTGTCTATGG

4681 GCCTGGCTCT CTCTGCACGT CCAGGTTGTG CATTTCCCAG CGTGGCCTGA CCCTGCCCTT

4741 AACAGCGCTT GTGGCAGGGT TTGGCGTTCA GGAAATCGCT TTGGTTGTTT TAATCTTTGT

4801 CTCCATCGGG GGTATGGCCC ACAGGTTGAG TTGCAAGGCT GACGTGCTGT GTATCCTGCT

4861 TGCTATTGTC AGCTATGTTT GGCCACCCCT TACCTGGTTG CTTTGTGTGT TTCCTTGCTG

4921 GTTGCGCTGG TTTTCTTTAC ATCCCCTTAC TATTCTATGG TTAGTGTTTT TCTTGATTTC

4981 TGTAAATACG CCCTCGGGAA TCTTGGCCTT GGTCCTGTTA ATCTCTCTTT GGCTCCTTGG

5041 TCGCTATACC AATGTTGCCG GCCTTGTCAC CCCTTATGAC ATTCACCATT ACACCAACGG

5101 CCCTCGCGGC GTTGCCGCCT TGGCCACTGC CCCGGATGGG ACCTACCTGG CTGCTGTCCG

5161 CCGTGCTGCG TTGACTGGCC GTACCATGCT GTTCACCCCG TCCCAACTTG GCTCGCTCCT

5221 TGAGGGCGCT TTTAGAACCC AAAAGCCTTC ACTGAACACT GTCAATGTAG TTGGGTCCTC

5281 CATGGGCTCC GGCGGGGTGT TCACCATTGA TGGGAAGATC AAATGTGTGA CCGCTGCTCA

5341 TGTCCTCACG GGTAACTCTG CCAGGGTTTC CGGGGTTGGC TTCAATCAAA TGTTGGACTT

5401 TGATGTTAAA GGGGATTTTG CCATAGCCGA TTGTCCGAAT TGGCAAGGAG TCGCCCCCAA

5461 GTCCCGGTTC TGCAAGGATG ATTGGACTGG CCGTGCTTAT TGGCTCACGT CCTCCGGCGT

5521 CGAACCCGGC GTCATTGGGC AAGGATTCGC CTTTTGTTTC ACCGCGTGCG GCGATTCCGG

5581 GTCCCCAGTG ATCACCGAGG CCGGGGAGCT TGTCGGTGTC CACACGGGAT CAAACAAACA

5641 AGGAGGAGGC ATTGTTACGC GCCCTTCAGG CCGGTTTTGT AATGTGACAC CCACCAAATT

5701 AAGTGAATTG AGTGAATTCT TCGCTGGACC TAGGGTCCCG CTTGGTGACG TGAAGGTTGG

5761 CAATCACATA ATCAAAGATA TAAATGAGGT GCCCTCAGAT CTCTGCGCCT TACTCGCTGC

5821 CAAACCCGAA TTGGAAGGAG GCCTCTCCAC CGTTCAACTT CTGTGCGTGT TTTTTCTCCT

5881 ATGGAGAATG ATGGGACATG CCTGGACACC CTTGGTTGCC GTTGGTTTTT TCATCTTGAA

5941 TGAAGTTCTC CCAGCAGTCC TGGTCCGGAG TGTCTTCTCC TTTGGAATGT TCGCACTGTC

6001 TTGGTTCACG CCGTGGTCTG CACAAATTCT AATGATCAGG CTCTTGACAG CAGCCCTAAA

6061 CAGAAACAGA TCGTCACTTG CCTTTTACAG CCTGGGCGCA CTAACCGGTT TTGTTGCAGA

6121 TCTTGCAACC AATCAGGGGT ATTTATTGCA CGCGGTCATG AATGTGAGCA CCTATGCATT

6181 CCTGCCTCGT GCAATGGCCG TGACCTCACC AGTCCCAATA GTTGCGTGTG GCGTTGTGCA

6241 CTTGCTTGCC ATCATTCTGT ACTTGTTCAA GTACCGTAGC CTGCATGCCG TCCTGGTCGG

6301 CGATGGTGCG TTTTCCGCGG CTTTCTTCTT GCGATACTTT GCGGAGGGAA AGTTGAGGGA

6361 AGGGGTGTCG CAGTCTTGCG GCATGAATCA TGAGTCACTA ACCGGTGCCC TCGCCATGAA

6421 ACTCAGCGAC GAAGACTTGG ACTTCCTCAC AAAATTGACT GATTTTAAGT GCTTTGTTTC

6481 TGCATCCAAC ATGAGGAATG CGGCGGGTCA ATTTATAGAG GCCGCCTACG CCAAAGCACT

6541 GAGGGTGGAA CTTGCCCAGT TGGTTCAAGT CGATAAAGTT CGAGGTGTCC TGGCCAAACT

6601 TGAAGCTTTC GCTGACACCG TGGCGCCTCA ACTTTCACCC GGTGACATTG TTGTCGCCCT

6661 TGGACACACA CCTGTCGGCA GCATTTTTGA CCTGAAGGTC GGCAATGTTA AGCACACTCT

6721 CCAGTCCATT GAGACCAGAA CCCTTGCCGG GTCTAAAATG ACTGTGGCGC GCGTCGTAGA

-continued

6781 CCCAACCCCC ACACCCCCGC CCGCACCTGT GCCCATTTCC CTCCCACCAA AGGTTTTGGA
6841 GAACGGTCCC AACGCCTGGG GGGATGAGAA CGGTTTGAAC AAAAAAAAGC GGCGCAAGAT
6901 GGAGGCCGTT GGCATTTACG TTATGGGCGG GAAAAAGTAT CAAAAATTTT GGGATAAGAA
6961 TTCTGGTGAT GTGTTCTATG AAGAAGTCCA CGACAACACA GACGCGTGGG AATGCCTCAG
7021 AGTTGACAAC CCTGCCGACT TGGATCCTGA GAGGGGAACC TTGTGTGGAC ACACCACCAT
7081 AGACAACAGG CCTTACCATG TTTATGCTTC TCCGTCTGGT AGGAAGTTTC TAGTCCCTGT
7141 CAACCCGGAG AGCGGAAAAG CTCAGTGGGA AGCTGCTAAG CTTTCTTTAG ATCAGGCCCT
7201 CAGTATGATG AATGTCGACG GCGAACTGAC CGCCAAAGAA GTGGAAAAAT TGAAGAGAAT
7261 AATTGACAAA CTCCAGGGCC TGACTAAGGA GCAGTGTTTA AACTGCTAGC CGCCAGCGGC
7321 TTGACCCGCT GTGGTCGCGG CGGCTTGGTT GTTACTGAGA CAGCGGTAAA GATAGTCAGG
7381 TTCCACAACC GGACCTTTAC CCTAGGGCCT GTGAATTTGA AAGTAGCTAG CGAAGTTGAG
7441 TTGAAGGACG CGGTCGAGCA CGGCCAACAC CCGGTCGCGA TACCAGCCGA TGGTGGCGTC
7501 GTGCTCCTGC GTTCCGCTGT TCCTTCGCTT ATAGACGTCC TGATCTCCGG TGCTGACGCA
7561 TCCCCCAGGT TGCTCGCCCG TCACGGACCG GGAAATACTG GGGTCAATGG CGCGCTTTGG
7621 GATTTTGAGT CTGAAGCTAC CAAAGAGGAA GTAGCACTTA GTGCGCAAAT AATACAGGCC
7681 TGTGACATTA GACGCGGCGA TGCACCTGAG ATTGGCCTTC CTTACAAGTT GTACCCTGTT
7741 AGGGGCAACC CTGAACGGGC AAGAGGGGTT CTAATGAACA CAAGATTTGG AGACATACCT
7801 TACAAGACCC CCAGCGACAC CGGGAGCCCG GTGCACGCGG CCGCCTGCCT TACGCCCAAC
7861 GCCACTCCAG TAACTGATGG GCGCTCCATC CTGGCCACGA CCATGCCCTC CGGGTTTGAA
7921 CTATATGTGC CGACCATTCC AGCGTCTGTC CTTGATTACC TTGACTCCAG ACCAGACTGT
7981 CCTAAACAGT TGACTGAGCA CGGGTGTGAA GATGCCGCGT TGAAGGACCT TTCTAAATAT
8041 GACCTGTCCA CCCAAGGCTT TGTGTTACCT GGAGTTCTAC GCCTCGTGCG AAAATATCTG
8101 TTTGCTCATG TAGGTAAGTG CCCGCCTGTC CACCGGCCCT CTACCTATCC TGCCAAGAAC
8161 TCCATGGCCG GAATAAATGG GAACAGGTTC CCAACCAAGG ATATTCAAAG CATCCCTGAG
8221 ATCGACGTTT TGTGTGCACA AGCTGTGCGA GAAAACTGGC AAACTGTTAC ACCCTGCACT
8281 CTTAAGAAGC AGTATTGCGG TAAAAAGAAG ACCAGGACCA TACTTGGCAC CAACAACTTC
8341 GTTGCGCTGG CCCACCGGGC GGCGCTGAGT GGTGTCACCC AGGGTTTCAT GAAGAAGGCG
8401 TTTAACTCAC CCATCGCCCT TGGGAAAAAT AAATTTAAGG AGCTACAGAC TCCAGTCTTG
8461 GGTAGGTGTC TTGAGGCTGA TCTCGCTTCC TGCGATCGAT CCACGCCTGC AATCGTTCGC
8521 TGGTTTGCCG CCAACCTTCT TTATGAACTT GCCTGTGCTG AGGAGCATTT ACCGTCGTAC
8581 GTGCTGAACT GTTGTCACGA CCTATTGGTC ACGCAGTCCG GCGCAGTGAC TAAGAGAGGT
8641 GGCCTGTCGT CCGGTGACCC AATCACCTCT GTGTCCAACA CCATTTATAG CTTGGTGATC
8701 TATGCACAGC ATATGGTGCT TAGTTACTTC AAAAGTGGTC ACCCCCATGG CCTTCTGTTT
8761 TTACAAGACC AGCTAAAGTT TGAAGACATG CTCAAAGTTC AACCCCTAAT CGTCTATTCG
8821 GACGACCTCG TGTTGTATGC CGAGTCTCCC ACCATGCCAA ACTATCACTG GTGGGTTGAA
8881 CACCTGAATT TGATGTTGGG ATTTCAGACG GACCCAAAGA AGACTGCAAT AACAGACTCA
8941 CCTTCATTCC TAGGTTGTAG AATAATAAAT GGCCGCCAGT TAGTACCCAA CCGTGACAGA
9001 ATTCTCGCGG CCCTTGCCTA TCACATGAAG GCGAGTAATG TTTCTGAGTA CTACGCCTCC
9061 GCAGCCGCAA TACTCATGGA CAGTTGTGCT TGTCTAGAGT ATGATCCTGA GTGGTTTGAA
9121 GAACTTGTGG TTGGAATGGC GCAGTGCGCC CGTAAGGACG GCTATAGTTT CCCCGGCCCG

-continued

9181 CCGTTCTTCT TGTCCATGTG GGAAAAGCTC AGGTCAAATT ATGAGGGGAA GAAGTTGAGA

9241 GTGTGTGGTT ATTGCGGAGC TTCAGCCCCG TATGCTACTG CCTGTGGCCT TGACGTTTGT

9301 GTTTACCACA CCCACTTTCA CCAGCATTGT CCAGTCATAA TATGGTGTGG CCACCCGGCG

9361 GGTTCTGGGT CCTGCGATGA GTGCAAATCC CCTACAGGGA AGGGTACAAG CCCTCTGGAT

9421 GAGGTCTTAA GACAAGTCCC TTATAAGCCT CCACGGACTA TTCTTATGCA TGTGGAGCAG

9481 GGCCTCACCC CCCTTGACCC AGGCAGATAC CAGACCCGCC GTGGGTTGGT TGCTGTCAGG

9541 CGCGGGATAA GGGGAAATGA AGTTGACCTG CCAGATGGTG ATTATGCCAG TACTGCCCTA

9601 CTCCCCACCT GCAAAGACAT AGACATGGTT GCTGTGGCCT CCAATGTGTT GCGCAGTAGG

9661 TTCATCATCG GCCCACCTGG CGCAGGGAAA ACACACTGGC TTCTTCAACA GGTTCAGGAT

9721 AGTGATGTCA TTTACACGCC AACCCATCAG ACCATGCTTG ACATGATCAA GGCTTTGGGG

9781 ACGTGCCGGT TCAATGTCCC GGCAGGCACA ACGCTGCAAT TCCCTGCCCC CTCCCGTACC

9841 GGCCCGTGGG TTCGCATCCT TGCCGGCGGT TGGTGTCCAG GTAAGAATTC CTTCCTGGAT

9901 GAAGCAGCGT ATTGCAATCA CCTTGACGTC TTGAGGCTTC TCAGCAAAAC TACCCTCACC

9961 TGTCTGGGGG ATTTCAAACA ACTCCACCCG GTGGGTTTTG ATTCTCATTG CTATGTTTTT

10021 GATATCATGC CTCAGACTCA ACTGAAGACC ATCTGGAGGT TTGGACAGAA TATCTGTGAC

10081 GCCATTCAGC CAGATTACAG GGACAAACTC GTGTCCATGG TCAACACAAC CCGTGTAACC

10141 TATGTGGAAA GACCTGTCAA GTATGGGCAA GTCCTCACCC CCTACCACAG AGACCGAGAG

10201 GATGGTGCTA TCACTATTGA CTCCAGTCAA GGCGCCACAT TTGATGTGGT CACATTGCAT

10261 TTGCCCACTA AAGATTCACT CAACAGGCAA AGAGCCCTTG TTGCTATCAC CAGGGCAAGG

10321 CATGCAATCT TTGTGTATGA CCCACACAGG CAACTGCAGA GCATGTTTCG TCTTCCTGCA

10381 AAAGGCACAC CTGTCAACCT TGCCGTGCAC CGTGACGAGC AGCTCATCGT ATTAGATAGA

10441 AATAACAAAG AGTGCACGGT TGTTCAGGCT TTAGGCAATG GGGACAAATT CAGGGCCAGT

10501 GACAAGCGCG TTGTAGATTC TCTTCGCGCC ATTTGTGCAG ATCTTGAAGG GTCGAGCTCC

10561 CCGCTCCCCA AGGTCGCACA CAACTTGGGA TTTTATTTCT CACCTGATTT GACACAGTTT

10621 GCTAAACTCC CGGCGGAACT TGCACCCCAC TGGCCCGTGG TGACAACTCA GAACAACGAA

10681 AATTGGCCAG ACCGGCTGGT TGCTAGCCTC CGCCCTATCC ACAAATATAG CCGCGCGTGC

10741 ATCGGAGCCG GCTATATGGT GGGCCCCTCA GTGTTTCTAG GCACTCCTGG GGTTGTGTCA

10801 TACTATCTCA CACAATTTGT CAAAGGGGAG GCTCAGGTGC TTCCGGAGAC GGTCTTCAGC

10861 ACCGGCCGAA TTGAGGTAGA TTGTCGAGAG TATCTTGATG ATCGGGAACG AGAAGTTGCT

10921 GAGTCCCTCC CACATGCCTT TATTGGCGAC GTCAAAGGCA CTACCGTTGG GGGATGTCAC

10981 CATGTCACTT CTAAATATCT CCCACGCTTC CTTCCCAAGG AATCAGTTGC GGTGGTTGGG

11041 GTTTCAAGCC CCGGGAAAGC CGCAAAAGCA GTTTGCACAT TAACAGATGT GTACCTCCCA

11101 GATCTTGAGG CTTACCTCCA TCCAGAGACC CAGTCTAAGT GCTGGAAAGT GATGTTGGAC

11161 TTCAAGGAAG TTCGACTGAT GGTCTGGAGA GATAAGACGG CCTACTTTCA ACTTGAAGGC

11221 CGCCATTTCA CCTGGTACCA GCTTGCAAGT TATGCCTCGT ACATCCGAGT TCCCGTTAAC

11281 TCTACGGTGT ACCTGGACCC CTGTATGGGC CCTGCCCTTT GCAACAGAAG AGTCGTTGGG

11341 TCTGCACATT GGGGAGCTGA CCTTGCAGTT ACCCCTTATG ATTATGGTGC CAAAATCATT

11401 CTGTCTAGTG CGCACCATGG TGAAATGCCT CCTGGGTACA GAATTCTAGC GTGCGCGGAG

11461 TTCTCGCTTG ATGACCCAGT GAGGTACAAA CACACTTGGG GGTTTGAATC GGATACAGCG

11521 TATCTGTACG AGTTCACCGG AAACGGTGAG GACTGGGAGG ATTACAATGA TGCGTTTCGT

11581 GCACGCCAGA AAGGGAAAAT TTATAAGGCC ACTGCCACCA GCATGAGATT TCATTTTCCC

-continued

11641 CCGGGTCCTG CCATTGAACC AACATTGGGC CTGAACTGAA ATGAAATGGG GGCTGTGCAG

11701 AGCCTTTTCG ACAAAATTTG CCAACTTTTT GTGGATGCTT TCACGGAATT TTTGGTGTCC

11761 ATTGTTGATA TCATCATATT TTTGGCCATT TTGTTTGGCT TCACCATCGC AGGCTGGCTG

11821 GTTGTCTTCT GTATCCGACT GGTTTGCTCC ACGGTACTCC GTGCGCGCTC TACCATTCAC

11881 CCTGAGCAAT TACAGAAGAT CCTATGAGGC CTTCCTTTCC CAGTGCCAAG TGGACATTCC

11941 CGCCTGGGGA ACTAAGCATC CCTTGGGGGT GCTTTGGCAC CACAAGGTGT CAACTCTGAT

12001 TGATGAAATG GTGTCGCGTC GAATGTACCG CATCATGGAA AAAGCAGGAC AGGCTGCCTG

12061 GAAACAGGTT GTGAGCGAAG CTACATTGTC TCGCATAAGT GGCTTGGATG TGGTGGCTCA

12121 TTTTCAGCAT CTTGCTGCCA TTGAAGCCGA GACTTGCAAA TATTTGGCCT CTCGGCTGCC

12181 CATGCTACAC AACCTAGTCA TGTCAGGGTC GAATGTAACC ATAGTGTATA ATAGCACTTT

12241 GGGTCAAGTG TTTGCCATTT TCCCAACCCC TGGTTCCCGG CCAAAACTTT CTGATTTTCA

12301 ACAATGGCTC ATAGCTGTGC ATTCTTCCAT ATTTTCTTCT GTTGCGGCTT CTTGTACTCT

12361 TTTTGTTGTG CTGTGGCTGC GAATTCCAAT ACTACGTACT GTTTTTGGTT TCCGCTGGTT

12421 AGGGGCAACT TTTCTTTCGA ACTCACAGTG AATTACACGG TGTGCCCACC CTGCCTCACC

12481 CGGCAAGCAG CCGCTGAGAT CTACGAACAC AGCGGGTCTC TTTGGTGCAG GATAGGGCAT

12541 GACCGATGTA GCCAGAGTGA TCATGACGAA CTAGGGTTCT TGGTTCCACC TGGCCTTTCC

12601 AGCGAGGGCC ACTTGACCAG TGTTTACGCC TGGCTGGCGT TCTTGTCTTT CAGCTACACA

12661 GCCCAGTTCC ACCCCGAGAT ATTTGGAATA GGGAATGTGA GTAGAGTTTA TGTTGACGTC

12721 ACTCACCAAC TCATCTGCGC CGAACACGAC GGGCAGAACA CCACCCTGCG TCGCCATGAC

12781 AATATCTCAG CCGTGTTTCA GACCTATTAC CAACATCAGG TCGATGGCGG CAATTGGTTT

12841 CACCTAGAAT GGCTGCGTCC CTTCTTTTCC TCTTGGCTGG TTTTGAATGT CTCGTGGTTT

12901 CTCAGGCGTT CGCCTGCAAA CCGTGTTTCA GTTCGAGTCT TTCAGACATC AAAACCAACA

12961 CCACCGCAGC TGCAGGCTTT GCTGTCCTCC AAGACATCAG CTGTCTTAGG CATGGCTACT

13021 CGTCCATTGA GGCGATTCGC AAAAGCCGTC AATGCCGCAC GGCGATAGGA ACGCCCGTGT

13081 ACATCACTGT CACGGCCAAT GTAACAGATG AGAATTACTT GCATTCCTCT GATCTCCTCA

13141 TGCTTTCCTC TTGCCTCTTC TATGCTTCTG AGATGAGTGA AAAGGGATTC AATGTGGTCT

13201 TCGGCAACGT GTCAGGCATT GTGGCTGTGT GTGTCAACTT TACCAGCTAT GTCCAACATG

13261 TTAAGGAGTT TACTCAGCGC TCTTTGGTGG TCGACCACGT GCGACTGCTT CATTTCATGA

13321 CACCTGCGAC CATGAGGTGG GCAACAGTTT TAGCCTGTCT TTTCGCCATC TTGTTGGCGA

13381 TTTGAATGTT TAAGTATGTT GGGGAAATGC TTGACCGCGG GCTACTGCTC GCAATTGCTT

13441 TTTTTCTGGT GTATCGTGCC GTTCTGTTTT GCTGCGCTCG TCAACGCCGC CAGCAACAGC

13501 AGCTCCCATT TACAGTTGAT TTATAACCTG ACGATATGCG AGCTGAATGG CACAGATTGG

13561 TTGAATCAAA AGTTTGATTG GGCAGTGGAG ACTTTTGTCA TTTTTCCTGT GTTGACCCAC

13621 ATTGTCTCCT ACGGTGCCCT TACCACCAGC CATTTCCTTG ACACGGCCGG CCTAATCACT

13681 GTGTCTACCG CCGGATATTA CCATGGGCGG TATGTGTTGA GTAGCATCTA CGCCGTCTTT

13741 GCCCTGGCTG CGTTGATTTG TTTTGTCATT AGGTTGACAA AAAACTGTAT GTCCTGGCGC

13801 TACTCATGTA CCAGATATAC CAACTTTCTT CTGGACACCA AAGGCAATCT CTATCGTTGG

13861 CGGTCACCCG TCGTTATAGA GAGAAGGGGT AAAGTTGAGG TTGGAGACCA CCTAATCGAC

13921 CTCAAAAGAG TTGTGCTTGA TGGTTCCGCG GCAACCCCTA TAACCAAGAT TTCAGCGGAA

13981 CAATGGGGTC GTCCCTAGAC GACTTCTGCA ATGACAGCAC AGCTGCACAA AAGGTGCTTT

-continued

```
14041 TGGCGTTTTC CATCACCTAT ACGCCAATAA TGATATATGC CCTGAAGGTA AGTCGCGGCC

14101 GACTGTTAGG GCTTTTGCAT CTTTTAATTT TCTTGAATTG TGCTTTCACC TTCGGGTACA

14161 TGACATTTGT TCATTTTCAG AGTACAAACA AGGTCGCGCT CACTATGGGA GCAGTTGTTG

14221 CACTCCTTTG GGGGGTGTAC TCAGCCATAG AAACCTGGAA ATTCATCACT TCCAGATGCC

14281 GTTTGTGCTT GCTAGGCCGC AGGTACATTC TGGCCCCTGC CCACCACGTT GAAAGTGCCG

14341 CGGGCTTTCA TCCGATTGCG GCAAGTGATA ACCACGCATT TGTCGTCCGG CGTCCCGGCT

14401 CCACTACTGT TAACGGCACA TTGGTGCCCG GGTTGAAAAG CCTCGTGTTG GGTGGCAGAA

14461 AAGCTGTTAA GCGGGGAGTG GTAAACCTCG TTAAATATGC CAAATAACAA CGGCAGGCAG

14521 CAAAAAAATA AGAAGGGGAG TGGCCAGCCA GTCAATCAGC TGTGCCAAAT GCTGGGCAAG

14581 ATCATCGCCC AGCAAAATCA GTCCAGAGGC AAGGGACCGG GTAAGAAAAA TAAGAAGAGA

14641 AACCCGGAGA AGCCCCATTT TCCTCTTGCG ACCGAAGATG ACGTCAGGCA TCACTTCACC

14701 CCCAGTGAAC GGCAATTGTG TCTGTCGTCG ATCCAGACTG CCTTCAACCA GGGCGCTGGA

14761 ACTTGCACCC TGTCAGATTC AGGGAGGATA AGTTACACTG TGGAGTTTAG TTTGCCGACG

14821 CACCACACTG TGCGCCTTAT TCGCGCCACA GCATCACCTC CATCGTGATG GGCTTACATT

14881 CTTGGAGCTC CTCAGTTTCA CAATTGGAAG AATGTGTGGT GAATGGCACT GATTGGCACT

14941 GTGCCTCTAA GTCACCTATT CAATTAGGGC GACCGTGTGG GGGTTTAGTT TAATTGGCGA

15001 GAACCACGCG GCCGAAATTA AAAAAAAAAA AAAAAAAAAA AAAAAAA
```

A person skilled in the art would recognize the poly-adenosine tails of each of the genomic consensus sequences could vary in length from the above reported sequences.

Variant identification has been performed to determine the number and frequency of nucleotide changes in the virus population for both passages. Table 16 shows the 11 nucleotide changes found in P84 and P 100 compared to the reference sequence. Six of the 11 variant positions are consistent between the passages with the exception of 5 nucleotide changes in P100 which were not present in P84. These changes suggest that a little less roughly half of the subpopulation variants arose during the passage of the virus from 84 to 100.

TABLE 16

PRRSV SD 11-21 Sequence Variants.

| Position | Reference Base | Variant Base | Frequency (% of Population) P84 | P100 |
|---|---|---|---|---|
| 811 | T | C | 11.85% | 11.90% |
| 1,469 | A | G | 8.45% | 5.29% |
| 3,235 | A | T | 5.21% | 5.71% |
| 7,563 | T | C | 97.46% | 96.73% |
| 7,760 | C | T | ND | 13.07% |
| 12,314 | G | A | ND | 22.39% |
| 12,911 | C | T | ND | 22.39% |
| 12,914 | C | T | ND | 8.53% |
| 14,039 | T | A | ND | 5.00% |
| 14,985 | AG | TT | 100.00% | 99.03% |
| 15,007 | TA | CG | 97.73% | 96.38% |

ND = not detected.

EXAMPLE 8

The objective of this study is to evaluate the dose response and onset-of-immunity (OOI) of an experimental modified live PRRSV vaccine in a vaccination-challenge study. Vaccines are evaluated on their ability to reduce lung lesions, viral load in the lungs and blood, and clinical signs. The study was conducted in BSL-2 facilities at Veterinary Resources, Inc., Cambridge, Iowa, using similar procedures and conditions as described in Examples 2 and 3. Laboratory assays were conducted at the Iowa State University Veterinary Diagnostic Laboratory, Ames, Iowa, as described in Examples 2 and 3. Eighty (80) clinically healthy, 14 or 15 day old weaned pigs that were seronegative to PRRSV were enrolled in the study. Pigs were randomly assigned to one of four treatment groups (n=20/group). Treatment groups included a placebo-matched control group and three PRRSV vaccine dose groups (2.7, 4.1 or 5.1 $\log_{10}$ $TCID_{50}$/mL).

Pigs received their respective vaccine or placebo intramuscularly (1.0 mL) in the right side of the neck on Day 0. Vaccines are formulated to include the SD 11-21 PRRSV strain, a stabilizer and a preservative (gentamicin). OPTI-MEM® I Reduced Serum Medium is used as the blending diluent. Vaccines are prepared using master seed virus (MSV) at the highest passage level intended for production (MSV+5) grown on master cell stock (MCS) at the highest passage level (MCS+20). The median tissue culture infective dose ($TCID_{50}$) for each vaccine was determined by infecting MARC-145 cells. No local or systemic adverse reactions were observed following vaccination. Compared to the placebo control group, a transient increase in rectal temperature was observed by Day 2 post-vaccination in all vaccine groups, but remained within the normal physiological range and was not observed thereafter.

At Day 28 post vaccination, all pigs were challenged with 4 mL (1 mL/nostril and 2 mL IM) of PRRSV strain NADC-20 (passage 3) at $3.98\times10^4$ $TCID_{50}$/mL. The mean percent of lung lesion involvement in the placebo group was 54%. The level achieved in this study was considered adequate to evaluate the vaccine candidates.

Results of the statistical analysis of the lung lesion scores are summarized in Tables 17 and 18. The main effect of treatment was statistically significant (P<0.0001). Vaccinated pigs in all dose groups had significantly lower (P<0.05) lung lesion scores than control pigs (Table 17). Linear and quadratic contrasts were not statistically significant. The mitigated fractions are provided in Table 18. The mitigated fraction for groups T02 (2.7 logs), T03 (4.1 logs) and T04 (5.1 logs) compared to group T01 (placebo) was significant. Vaccination with T02, T03 and T04 increased the probability by 0.9200, 0.9450 and 0.9789, respectively, that a vaccinated animal would have less lung lesions than a non-vaccinated control animal.

TABLE 17

Mean Lung Lesion Score[1]

| Treatment Group | Estimate[2] | Standard Error | Mean[3] |
|---|---|---|---|
| T01: Placebo | 0.8288 | 0.04258 | 54.33 |
| T02: 2.7 $\log_{10}$ $TCID_{50}$/mL | 0.1804 | 0.04183 | 3.22* |
| T03: 4.1 $\log_{10}$ $TCID_{50}$/mL | 0.1650 | 0.04243 | 2.70* |
| T04: 5.1 $\log_{10}$ $TCID_{50}$/mL | 0.1662 | 0.04308 | 2.74* |

[1]Arcsine Transformed Percent Lung Involvement.
[2]Untransformed means.
[3]Back transformed means.
*T01 versus T02, T03 or T04 significantly different at P < 0.05.

TABLE 18

Mitigated Fraction - Lung Lesion Scores

| Group Comparison | Mitigated Fraction | 95% Confidence Interval |
|---|---|---|
| Placebo versus 2.7 $\log_{10}$ $TCID_{50}$/mL | 0.9200 | 0.7834, 1.0000 |
| Placebo versus 4.1 $\log_{10}$ $TCID_{50}$/mL | 0.9450 | 0.8461, 1.0000 |
| Placebo versus 5.1 $\log_{10}$ $TCID_{50}$/mL | 0.9789 | 0.9347, 1.0000 |

On Day 42, BAL fluid was obtained aseptically from excised lungs. An aliquot of the BAL fluid was submitted to ISUVDL for qRT-PCR analysis of the presence of PRRSV nucleic acids. Results are summarized in Table 19. Vaccinated pigs in all three dose groups had significantly lower (P<0.05) viral loads in the lungs when compared to control pigs. The main effect of treatment was significant (P<0.0001).

No pigs were positive for viremia on Day −1. At time of challenge (Day 28), all pigs in the placebo control group were negative, whereas 95%, 75% and 89% of pigs in groups T02, T03 and T04 were positive due to the presence of the vaccine virus. All pigs in all groups were positive post-challenge on Day 42, but values in the vaccinated groups (T02, T03 and T04) were significantly lower (P<0.05) than values in the placebo control group (T01).

All study animals were weighed individually in pounds on day of challenge (Day 28) and day of necropsy (Day 42) and their weight recorded. Average daily weight gain (ADWG) was determined for the following periods: day prior to vaccination to day of challenge (Day −1 to Day 28); day prior to vaccination to day of necropsy (Day −1 to Day 42); and day of challenge to day of necropsy (Day 28 to Day 42). The main effect of treatment was not significant (P=0.2304) prior to challenge (Day −1 to 28). During the challenge period (Day 28 to 42) and for the entire 42 day study period, the main effect of treatment was significant (P<0.0001). For each of these two periods, pigs in the vaccinated groups gained more weight (P<0.05) than those pigs in the placebo control group.

All animals were evaluated for depression, body condition, and respiratory distress on a daily basis for 14 days post-challenge (Days 28-42) and scored for each clinical sign. Depression score, respiratory score and body condition scores were summarized by time. Clinical scores were also summed within a day for each animal. On Day 8, values in T02 and T04 were significantly lower (P<0.05) than values in the placebo control group (T01). On Day 9, values in T02 were significantly lower (P<0.05) than values in T01. On Days 10-14, values in all vaccinated groups (T02, T03, and T04) were significantly lower (P<0.05) than values in T01. There was no effect of dose on clinical signs.

In conclusion, all dose levels of vaccine are effective in reducing (P<0.05) lung lesions, viral load in the lungs, viremia, and clinical signs. No local or systemic adverse reaction to the vaccine at any dose level has been observed.

TABLE 19

Geometric Means of PRRSV Genomic Copies/mL in BAL Fluid

| Treatment Group | Estimate[1] | Standard Error | Geometric Mean[2] | 95% confidence interval[2] Lower Bound | Upper Bound |
|---|---|---|---|---|---|
| T01: Placebo | 8.9071 | 0.2545 | 807351537 | 250619135 | 2600824971 |
| T02: 2.7 logs | 6.1271 | 0.2545 | 1340130* | 416005 | 4317131 |
| T03: 4.1 logs | 6.2598 | 0.2545 | 1818858* | 564612 | 5859320 |
| T04: 5.1 logs | 6.3339 | 0.2611 | 2157074* | 649559 | 7163277 |

*T01 versus T02, T03 or T04 significantly different at P < 0.05.
[1]Untransformed means.
[2]Back transformed means.

Blood samples for determination of PRRSV antibody levels and PRRSV viremia were collected from all study animals on Days −1, 28 (prior to challenge) and 42. Serology and viremia were determined by ELISA and qRT-PCR methodology, respectively. As determined by ELISA antibody titer, all pigs were seronegative on Day −1. ELISA values in all vaccinated groups were significantly higher (P<0.05) than values in the placebo group on both Days 28 and 42.

A derived benefit of vaccine efficacy is a significant improvement (P<0.05) in average daily weight gain compared to control animals. Thus, a 28-day onset of immunity (001) is achievable in pigs vaccinated as early as 14-15 days of age.

As a summary, Table 20 lists the various PRRS virus vaccine strains and references to their consensus genomic cDNA sequences.

TABLE 20

| PRRS virus vaccine strains. | | | | | |
|---|---|---|---|---|---|
| Strain | Passage | ATCC Accession Number | GenBank Accession Number | SEQ ID Number | cDNA length (number of bases) |
| SD 95-10 | P83 | none | KU131565 | SEQ. ID NO: 1 | 15386 |
| SD 95-47 | P83 | none | KU131564 | SEQ. ID NO: 2 | 15444 |
| SD 98-163 | P83 | none | KU131563 | SEQ. ID. NO: 3 | 15013 |
| ND 99-14 | P83 | none | KU131562 | SEQ. ID. NO: 4 | 15444 |
| | P84 | none | KU131567 | SEQ. ID. NO: 10 | 15444 |
| | P100 | PTA-122675 | KU131569 | SEQ. ID. NO: 11 | 15444 |
| SD 02-10 | P83 | none | KU131561 | SEQ. ID. NO: 5 | 15423 |
| SD 03-15 | P83 | none | KU131560 | SEQ. ID. NO: 6 | 15078 |
| SD 04-89 | P83 | none | KU131559 | SEQ. ID. NO: 7 | 14885 |
| MN 05-68 | P83 | none | KU131558 | SEQ. ID. NO: 8 | 15434 |
| SD 11-21 | P83 | none | KU131557 | SEQ. ID. NO: 9 | 15047 |
| | P84 | none | KU131566 | SEQ. ID. NO: 12 | 15047 |
| | P100 | PTA-122674 | KU131568 | SEQ. ID. NO: 13 | 15047 |

EXAMPLE 9

The objective of this study was to demonstrate the lack of reversion-to-virulence of Master Seed Virus (MSV) SD 11-21 X+1 of Porcine Reproductive and Respiratory Syndrome Virus (PRRSV) vaccine, modified live virus in pigs.

A total of eighty (80) clinically healthy, 14-15 day old weaned pigs, seronegative to PRRSV and negative for PRRSV by RT-qPCR were enrolled over four separate backpassages. Each backpassage contained twenty pigs, with 10 pigs in the control group and 10 pigs in the Investigational Veterinary Product (IVP) group. Pigs were randomly allocated to treatment group on either D−2 or D−1. In backpassage 1 (BP), the IVP consisted of SD 11-21 MSV X+1. In BP 2-4, the IVP consisted of PRRSV isolated from broncho-alveolar lavage (BAL) fluid from pigs in the previous backpassage. The control product was phosphate buffered saline (PBS). An animal was considered clinically affected by PRRSV if it exhibited pyrexia and clinical signs typical of PRRSV infection; it died or was removed due to PRRSV based on the diagnostic report; or it had gross lung lesions attributable to PRRSV.

Titer of the PRRSV SD 11-21 MSV was 3.3 $\log_{10}$ $TCID_{50}$ (796-70-23Sep14). The MSV X+1 was generated in order to achieve a titer level of a typical vaccine dose, including overage. In order to generate the X+1, confluent MARC-145 cells were infected with PRRSV Master Seed Virus (MSV) SD 11-21 (796-70-23Sep14) and PRRSV SD 11-21 X+1 was harvested when over 95% of cytopathic effect (CPE) was observed.

On Day 0, pigs in the IVP group were administered 1.0 ml of the IVP intranasally (IN; 0.5 ml/nare). Pigs were observed daily for clinical signs (depression, respiratory, and body condition) and pyrexia for 14 day in BP 1-3 and for 21 days in BP 4. Pigs were euthanized on D14 in BP 1-3 and on D21 in BP 4. Lungs were excised, and evaluated for the presence of gross lung lesions. Broncho-alveolar lavage (BAL) fluid was collected and analyzed for PRRSV by RT-qPCR and virus isolation was conducted. (Table 21). RT-qPCR was conducted using the EZ-PRRSV MPX 4.0 RT-PCR kit (Tetracore). BAL fluids positive for PRRSV by RT-qPCR were concentrated with a sucrose cushion and pooled. The pooled material was tested for PRRSV by RT-qPCR and the titer was determined by cytopathic effect (CPE) prior to administration to the next group of animals. The inability to isolate the virus in animals following a backpassage deemed the MSV stable and free from reversion to virulence. PRRSV present in the pooled BAL fluid from the last backpassage that tested positive by RT-qPCR was compared both phenotypically and genotypically to the PRRSV in the original MSV X+1. Phenotypic comparison was conducted by IFA testing, using a PRRSV specific antibody, and the genotypic comparison was conducted by comparing genomic sequencing of the ORF5 gene.

Virus titer for the MSV X+1 was 8.2 $\log_{10}$ $TCID_{50}$/ml. The median tissue culture infective dose ($TCID_{50}$) for each virus was determined by infecting MARC-145 cells with 10-fold serial dilutions of the virus and incubating the infected cells for 4 days. At the end of the incubation period each infection was examined for the presence or absence of virus induced cytopathic effect (CPE) and scored as positive or negative. The data collected was then used to calculate the titer of the virus using the Reed-Muench method for $TCID_{50}$ calculation and reported as $\log_{10}$ $TCID_{50}$/ml. Potency of the MSV X+1 exceeded the expected targeted release dose of the product. Virus titers of the material administered in BP 2 and 3 were 2.1 and 2.6 $\log_{10}$ $TCID_{50}$/ml, respectively. Material administered in BP 4 was negative for CPE. No pig administered the IVP in any of the four backpassages was positive for the case definition of a pig clinically affected with PRRSV. Additionally, virus from pooled BAL fluid from the last positive backpassage was shown to be phenotypically similar to the MSV X+1 and a genotypic match to the MSV X+1 when comparing the ORF5 gene.

This study demonstrates the lack of reversion-to-virulence and confirms the genetic stability of a Master Seed Virus SD 11-21 X+1 of Porcine Reproductive and Respiratory Syndrome Virus Vaccine, Modified Live Virus administered to 14-15 day old pigs.

TABLE 21

| BAL fluid virus isolation results by backpassage | | | | |
|---|---|---|---|---|
| | Individual BAL fluid Samples | | Pooled Positive BAL fluid Samples | |
| Backpassage | Number of Positive RT-qPCR samples | Number of Positive Virus Isolation samples | RT-qPCR (+/−) | Titer of Pooled Material ($\log_{10}$ $TCID_{50}$) |
| 1 | 5/10 | 3/10 | Positive | 2.1 |
| 2 | 3/10 | 2/10 | Positive | 2.6 |
| 3 | 3/10 | 0/10 | Negative | Negative |
| 4 | 0/10 | 0/10 | NA | NA |

NA—Not applicable; all individual BAL fluids were by both PCR and immunofluorescence so no pool was generated.

EXAMPLE 10

The objective of this study was to assess the shedding and transmission of a porcine reproductive and respiratory syndrome virus (PRRSV) SD 11-21 Master Seed Virus (MSV) from vaccinated to sentinel animals. Twenty (20) clinically healthy, 14 day old, weaned pigs, seronegative to PRRSV and negative for PRRSV by RT-qPCR were enrolled. On D−1, pigs were physically examined, and randomly allocated to either the sentinel/control group or the PRRSV SD 11-21 MSV X+1 treatment group. The PRRSV SD 11-21 MSV X+1 was generated as in Example 9. Pigs were housed in pens with 4 pigs/pen, with each pen containing two pigs/treatment group.

On D0, pigs in the MSV X+1 treatment group were vaccinated with 1.0 ml intramuscularly (IM) in the right side of the neck while sentinel pigs were left untreated. Nasal swabs and serum samples were collected on D−1, D3, D5, D7, D10, D14, D17, and D21 and were tested for PRRSV by RT-qPCR. On D21, pigs were humanely euthanized and lungs were excised. Broncho-alveolar lavage (BAL) fluid was aseptically collected and tested for PRRSV by RT-qPCR. In addition, tissue samples were collected from the lung, spleen, tonsil, thymus, and the right and left tracheobronchial lymph nodes and were tested for PRRSV by RT-qPCR. If a tissue sample tested positive for PRRSV by RT-qPCR, the sample was identity tested by genomic sequencing using the ORF5 region and compared to the ORF5 region of the MSV X+1. Body weights were collected on D−1 and D21.

Nine out of ten vaccinated pigs (90%) had at least one nasal swab positive for PRRSV during the 21 day study period. Some pigs (4/9) were still shedding vaccine at the end of the 21 day study period. All vaccinated pigs were viremic from D3-D21. Additionally, all BAL fluids and tissue samples from the vaccinated pigs were positive for PRRSV by RT-qPCR on D21. The nucleotide sequences of the RNA isolated from tissue samples showed 99.67-100% similarities to the MSV X+1, indicating the only virus present in the pigs originated from the vaccine virus. One out of ten sentinel pigs (10%) was considered positive for vaccine virus. A single nasal swab was positive during the 21 day sampling period. No serum sample, BAL fluid sample, or tissue sampled, tested positive for PRRSV by RT-qPCR in any of the sentinel pigs.

The MSV X+1 is shed from vaccinated animals for at least 21 days following administration. Transmission of the MSV X+1 from vaccinated to sentinel animals is limited, as no vaccine virus was detected in any of the sentinel animals outside of a single positive nasal swab.

EXAMPLE 11

The objective of this study was to evaluate the efficacy of an experimental modified-live PRRSV vaccine containing a type-2 PRRSV strain (SD 11-21) at 4.45 $\log_{10}$ $TCID_{50}$/mL when administered to PRRSV seronegative 14-day old piglets that were subsequently challenged with a contemporary virulent type-2 PRRSV strain (NC-174). The NC-174 PRRS virus was isolated from serum samples of 9 week old pigs experiencing respiratory symptoms on a swine farm in Harrells, N.C. Detailed symptomatic observations from the farm were anorexia, lethargy, hyperpnea, dyspnea, 15% morbidity and 5% mortality. The vaccine was evaluated on its ability to reduce lung lesions, viral load in the lungs and blood, and clinical signs. Forty (40) clinically healthy, 14 day old weaned pigs that were seronegative to PRRSV were enrolled in the study. Pigs were ranked by decreasing body weight and randomly assigned to one of two treatment groups (n=20/group). Treatment groups included the experimental vaccine and a placebo-matched control group. Pigs were housed by treatment group to prevent exposure due to shedding of the vaccine virus up to time of challenge. At challenge, pigs were commingled such that there were two pigs from each treatment group in a pen.

Pigs received the vaccine or placebo intramuscularly (1.0 mL) in the right side of the neck on Day 0. Blood samples were collected on Days −1, 28, 35 and 42 and the serum tested for PRRSV antibody levels by ELISA and for viral load by quantitative PCR (qRT-PCR). At Day 28, all pigs were challenged with 4 mL (1 mL/nostril and 2 mL IM) of PRRSV strain NC-174 (lineage 1, passage 3) at $1.3\times10^6$ $TCID_{50}$/mL. Clinical scores representing respiratory distress, depression and body condition were recorded daily from Day 28 to 42. Pigs were weighed on Day −1, 28 and 42 to evaluate weight gain. Pigs were euthanized on Day 42, lungs were excised, and the extent of lung lesions was determined. Broncho-alveolar lavage (BAL) fluids were collected on Day 42 and tested for PRRSV by qRT-PCR.

No local or systemic adverse reactions were observed following vaccination. The experimental vaccine was effective in reducing ($P<0.05$) percent lung lesions (45.9% in controls vs 4.0% in vaccinates), viral load in the lungs (decreased 95%), viremia (at 14 days post challenge), and clinical signs. Mitigated fraction evaluation of the lung lesion data indicated that vaccination increased the probability by 0.9368 that a vaccinated animal would have less lung lesions than a non-vaccinated control animal.

A derived benefit of vaccine efficacy was a significant improvement ($P<0.05$) in average daily weight gain compared to control animals (0.43 vs 0.25 kg/day) during the 14-day challenge period.

In conclusion, administration of an experimental PRRSV vaccine containing strain SD 11-21 as a single 1.0 mL dose to naïve 14-day old pigs was safe and effective against challenge with the contemporary PRRSV field strain NC-174.

EXAMPLE 12

The objective of this study was to confirm a minimum of 26 weeks (182 day) duration of immunity of an experimental modified-live PRRSV vaccine containing a type-2 PRRSV strain (SD 11-21) at 4.45 $\log_{10}$ $TCID_{50}$/mL when administered to PRRSV seronegative 14-day old piglets that were subsequently challenged with a virulent type-2 PRRSV strain (NADC-20). The vaccine was evaluated on its ability to reduce lung lesions, viral load in the lungs and blood, and clinical signs. Sixty-four (64) clinically healthy, 14-day old weaned pigs that were seronegative to PRRSV were enrolled in the study. Pigs were blocked by litter and randomly assigned to one of two treatment groups (n=32/group). Treatment groups included the experimental vaccine (T02) and a placebo-matched control group (T01). Pigs were housed by treatment group to prevent exposure due to shedding of the vaccine virus up to time of challenge. At challenge, pigs were commingled such that there were two pigs from each treatment group in a pen.

Pigs received the vaccine or placebo intramuscularly (1.0 mL) in the right side of the neck on Day 0. Blood samples were collected on Days −1, 28, 112, 168, 181, 189 and 196 and the serum tested for PRRSV antibody levels by ELISA and for viral load by quantitative PCR (qRT-PCR). At Day 182, all pigs were challenged with 10 mL (4 mL/nostril and 2 mL IM) of PRRSV strain NADC-20 at $10^{6.7}$ $TCID_{50}$/mL. Clinical scores representing respiratory distress, depression and body condition were recorded daily from Day 182 to 196. Pigs were euthanized on Day 196 (14 days post-challenge), lungs were excised, and the extent of lung lesions was determined. Broncho-alveolar lavage (BAL) fluids were collected and tested for PRRSV by qRT-PCR.

The experimental vaccine was effective in reducing ($P<0.05$) percent lung lesions (12.3% in controls vs 1.1% in vaccinates). Mitigated fraction evaluation of the lung lesion data indicated that vaccination increased the probability by 0.6566 that a vaccinated animal would have less lung lesions than a non-vaccinated control animal.

Results from this study confirmed that the administration of an experimental PRRSV vaccine containing strain SD 11-21 as a single 1.0 mL dose to naïve 14-day old pigs was effective against a virulent PRRSV challenge given 26 weeks later.

```
SEQUENCE LISTING
<160> NUMBER OF SEQ ID NOS: 13

<210> SEQ ID NO 1
<211> LENGTH: 15386
<212> TYPE: DNA
<213> Artificial Sequence

<400> 1
atgacgtata ggtgttggct ctatgccatg acatttgtat agtcaggagc tgcgaccatt      60

ggtacagccc aaaacttgct gcacggaaac gcccttccgt gacagccctc ttcaggggag     120

tttaggggtc tatccctagc accttgcttc cggagttgca ctgctttacg gtctctccaa     180

ccctttaacc atgtctggga tacttgatcg gtgcacgtgt acccccaatg ccagggtgtt     240

catggcggag ggccaagtct actgcacacg atgtctcagt gcacggtctc tccttcctct     300

gaatctccaa gttcccgagc ttggagtgct gggcctattt tacaggcccg aagagccgct     360

ccggtggacg ttgccacgtg cattccccac tgtcgagtgc tcccccgccg gggcttgctg     420

gctttctgcg atcttcccaa ttgcacgaat gaccagtgga aacctgaact ttcaacaaag     480

aatggtgcgg gtcgctgccg agatttacag agccggccag ctcacccctg cagtcttgaa     540

ggctctacaa gtttatgaac ggggttgccg ctggtacccc attgtcggac ctgtccctgg     600

agtggccgtt ttcgccaact ccctacatgt gagtgacaaa ccttttccgg gagcaactca     660

tgtgttaacc aatctaccgc tcccgcagag gcccaagcct gaagactttt gccctttga     720

gtgtgctatg gctgacatct atgacatcgg tcatgacgcc gtcatgtatg tggccggaga     780

gaaagtctcc tgggcccctc gtggcgggga tgaagtgaaa tttgaaaatg ttcccaagga     840

gttgaagttg attgcgaacc gactccacat ctccttcccg ccccaccacg tagtggacat     900

gtccaagttt accttcatag cccccgggag tggtgtctcc atgcgggttg agtgccaaca     960

cggctgcctc cccgctgata ctgttcctga aggaaactgc tggtggcgct tgttcgactc    1020

gctcccgccg gaagtccagc acaaagaaat tcgctatgct aaccaatttg gttatcaaac    1080

caagcatggt gtctctggca agtacctaca gcggaggctg caagttaacg gtctccgagc    1140

agtgaccgac gtacatggac ctatcgtcat acagtacttc tctgttaagg agagttggat    1200

ccgccacttc aggctggcgg aagaacctag cctccctggg ttcgaagacc tcctcagaat    1260

tagggttgag cccaatacat caccactggc tggcgaggat gggaagatct tccggtttgg    1320

cagtcacaag tggtacggtg ctggaaggag agcaaggaaa gcacgttctg gtgcgaccac    1380

catggtcgct catcgcgctt tgtccgctcg tgaaacccag caggcaaaga aggacgaggg    1440

tgccgacgct aacaaggctg agcatctcaa gcactactct ccgcccgccg aagggaactg    1500

tggttggcac tgtatttccg ccatcgccaa ccggatgata aattccaaat ttgaaactac    1560

ccttcccgaa agagtaaggc ctctggatga ctgggctact gacgaggatc ttgtgaatac    1620

catccaaatc ctcaggctcc ccgcggcctt ggataggaac ggtgcttgta gtagcgccaa    1680

gtacgtgctt aagctggaag gtgtgcattg gactgtctct gtgacccctg ggatgtcccc    1740

ttccttgctc cccctgaat gtgttcaggg ctgttgcgag cataagggcg gttttggctc    1800
```

-continued

```
cccagatgcg gtcgaagttt ccggatttga ccctgcctgc cttgaccgac tggctgaggt   1860
aatgcacttg cctagcagtg ccatcccagc cgctctggcc gaaatgtccg gcgactccaa   1920
tcgtccggct tccccggtca acactgtgtg gactgtttcg caattctatg cccgtcatac   1980
aggaggaaat catcctgacc aggtgtgctt agagcagatc attaatctct gtcaggttat   2040
tgaggtttgt tgctgccatc aaaacaaaac caaccgggcc accccggaag aggtcgcggc   2100
aaagattgat cagtacctcc gtggtgcaac aaatcttgaa gaatgcttga ccaggcttga   2160
gagggtttgc ccgccgagcg ctgcggacac ctcctttgat tggaatgttg tgctccctgg   2220
ggttgaggct gcaactcaga caaccaaaca gccccacgtc aaccagtgct gcgctctggt   2280
tcctgtcgtg actcaagagc ctttggacaa agactcggtc cctctgaccg ccttctcgct   2340
gtccaattgc tactaccctg cacaaggtga agaggttcgt caccgtgaga gactaaactc   2400
cgtactctcg aagttggagg gggctgttcg tgaggaatat gggctcacgc caactgaacc   2460
tggcctgcaa cccgcactac cgaacgggct cgacgaactt aaagaccgga tggaggagga   2520
tctgctgaaa ctagtcaacg ctcaggcaac ttcagaaatg atggcctggg cagccgagca   2580
gattgattta aaagcttggg tcaaaaacta cccacggtgg acaccgccac cccctccacc   2640
aagagctcag cctcggaaaa cgaagtctgt taagagcttg ccagggaaca agcctatccc   2700
tgctccacgc aggaaggtca gatctgattt gactgttaat ggcccccttg atctttcgac   2760
accatccgag ccgatgacac ccctgagtga gcctgcactt atgcccgcgt tgcaacatat   2820
ttctaggcca gtgacatctt tgagtgagcc ggtcccagtt cctgcaccgc gtagagctgt   2880
gtcccgaccg gtgacgccct tgagtgggcc aacttttgag tttgcgccgc gacacaaatt   2940
tcagcaggtg ggagaagtga atctggcggc aacaacgctg acgcaccagg acgaacctct   3000
agatttgtct gcatcctcac agactgaata tgaggcttct cccctagtac caccgcagaa   3060
catgggtatc ctgggggtgg gggggcaaga ggctgaagaa gttctgagtg aaatctcgga   3120
tatactgagt gacattaacc ctgcacctgt gtcattaagc agctccctgt caagtgttaa   3180
gatcacacgc ccaaaatact cagctcaagc catcattgac tcgggcgggc cctgcagtgg   3240
gcatctccga agggaaaaag aagcatgcct cagcgtcatg cgtgaggctt gtgatgcggc   3300
taaacttagc gaccctgcca cgcaggaatg gctttctcgc atgtgggata gggttgacat   3360
gctgacctgg cgcaataagt ctgcttacca ggcgtttcgc atcttggatg gcaggtttga   3420
gtttctccca aagatgatac tcgagacacc gccgccctat ccgtgtgggt ttgtgatgct   3480
gcctcacacg cctgcacctt ccgtgagtgc agagagtgac cttaccattg gttcagtcgc   3540
cactgaagat gttccacgca tcctcgggaa aatagaaaac gccggcgagg tgcccaacca   3600
ggggctctcg gcatcctccg ggaagaaccc gatgtatgac caacctgcca aagactcccg   3660
gatgtcgtcg cgggggtttg acgagagcat aacggctccg tccgtaggta caggtggcgc   3720
tgacttactc actgatttgc caccttcagg tggtgtggat gtggacgggg gggggccgtt   3780
acggacggta agaaagaaaa ttgaaaggct cttcgaccaa tttagccgtc aggtttttaa   3840
cctcgtctcc catctccctg ttttcttctc acacctcttc aaacctgaca gtggttattc   3900
tccgggtgat tggggtttg cagctttcac tctactttgc ctctttttgt gttatagcta   3960
cccattcttt ggcttcgctc ccctcttggg tgtattttct gggtcttctc ggagggtgcg   4020
catgggggtt tttggctgct ggttggcttt tgctgttggc ctgttcaagc ctgtgtccga   4080
cccagtcggc actgcttgtg aatttgactc gccagagtgt aggaacgtcc ttcattcttt   4140
tgagcttctc aaaccttggg accctgttcg cagccttgtt gtgggccccg caggtctcgg   4200
tcttgccatt cttggcaggt tactgggcgg ggcacgctac atctggcatt ttttgcttag   4260
```

-continued

```
gcttggcatt gttgcagatt gtgtcttggc tggagcttat gtgctttctc aaggtaggtg   4320
taaaaagtgc tggggatctt gtataagaac tgctcctaat gaaatcgcct tcaacgtgtt   4380
ccctttcacg cgtgcgacca ggtcgtcact catcgacctg tgcgaccggt ttcgtgcgcc   4440
aaaaggcatg gaccctgttt tcctcgctac tgggtggcgc gggtgctgga ccggtcaaag   4500
tcccattgag caaccctctg aaaaacccat cgcgttcgcc cagttggatg aaaagaggat   4560
cacggctaga actgtggtcg ctcagcctta tgatcctaac caagccgtaa agtgcttgcg   4620
ggtgctacag gcgggtgggg cgatggtggc cgaggcagtc ccaaaagtgg tcaaggtttc   4680
cgctattcca ttccgagccc cctttttttcc caccggagtg aaggttgatc ctgagtgcag   4740
gatcgtggtc gaccccgaca cttttactac agctctccgg tctggttact ccaccacaaa   4800
cctcgtcctt ggtgtggggg actttgccca attgaatgga ttgaaaatca ggcaaatttc   4860
caagccttcg ggaggaggcc cacacctcat tgctgccctg catgttgcgt gctctatggc   4920
gttgcacatg cttgctgggg tttatgtaac tgcagtgggg tcttgcggta ccggcaccaa   4980
cgatccgtgg tgcactaacc cattcgccgt ccctggctac ggacctggct ctctctgcac   5040
gtccagattg tgcatctccc aacatggcct caccctgccc ttgacagcac ttgtggcagg   5100
attcggtctt caggaaattg ccttagtcgt tttgattttc gtttccatcg gaggcatggc   5160
tcataggttg agttgtaagg ctgacatgct gtgcatctta cttgcaatcg ccagctatgt   5220
ttgggtaccc cttacctggt tgctctgtgt gtttccttgc tggttgcgct ggttcacttt   5280
gcaccctctc accatcctat ggttggtgtt tttcctgatt tctgtaaata tgccttcggg   5340
aatcttggcc atggtgttat tggttgctct ttggctttta ggccgttata ctaatgttgt   5400
tggtcttgtt acccccctatg atattcacca ttacaccagt ggcccccgcg gtgtagccgc   5460
cttggccacc gcaccagatg ggacttactt ggccgctgtc cgccgcgctg cgttgactgg   5520
ccgcaccgtg ctgtttaccc cgtctcagct tgggtccctt cttgagggcg ctttcaggac   5580
tcgaaagccc tcattgaaca ccgtcaatgt ggtcgggtcc tccatgggct ctggcggagt   5640
gttcactatc gacgggaaaa tcaagtgcgt gactgccgca catgtcctta cgggtaattc   5700
agccagggtt tccggggtcg gcttcaatca aatgcttgac tttaatgtaa agggggactt   5760
cgccatagct gattgcccga attggcaagg ggctgctccc aagacccaat tctgcgagga   5820
tggatggact ggtcgtgcct attggctgac atcctctggt gtcgaacccg gtatcattgg   5880
gaatggattt gccttctgct tcaccgcgtg cggcgattct ggatccccag tgattaccga   5940
agccggtgag cttgtcggcg ttcacacagg atcgaacaaa caaggaggag gcattgtcac   6000
gcgcccctcg ggccagtttt gtaatgtggc gcccatcaag ctgagcgaat tgagtgaatt   6060
cttcgctgga cctaaggtcc cgctcggtga tgtgaaggtt ggcagccaca taattaaaga   6120
catatgcgag gtaccttcag acctttgcgc cttgcttgct gccaaacccg aactggaagg   6180
aggcctctct accgtccaac ttctgtgtgt gtttttcctc ctgtggagaa tgatggggca   6240
tgcctggacg cccttggttg ctgtggggtt ttttatcttg aatgaggtcc tcccagctgt   6300
cctggtccgg agtgttttct cctttggaat gtttgtgcta tcttggctca cgccatggtc   6360
tgcgcaagtt ctgatgatca ggcttctaac agcagctctt aacaggaaca gattttcact   6420
cgccttttac agccttggtg cagcgaccgg ttttgtcgca gatctggcga caactcaagg   6480
gcatccgttg caggcagtaa tgaatttaag tacctatgcc ttcctgcctc ggatgatggt   6540
tgtgacatca ccagtcccag tgattgcgtg tggtgttgtg cacctccttg ccataatttt   6600
gtacttgttc aagtaccgtt gcctgcacaa tgtccttgtt ggcgacggag cgttctctgc   6660
```

-continued

```
ggcttttttc ttgcgatact ttgccgaggg aaagttgaga gaaggggtgt cgcagtcctg   6720
cgggatgaat cacgagtcac tgactggagc cctcgctatg agactcaatg acgaggactt   6780
ggacttcctt acgaaatgga ctgattttaa gtgctttgtt tctgcttcca atatgaggaa   6840
tgcagcgggc caattcatcg aggcagccta tgctaaagca cttagaatag aacttgccca   6900
gttggtgcag gtcgacaagg ttcgaggtgt tttggccaaa cttgaagctt ttgctgatac   6960
tgtggcaccc caactctcgc ccggtgacat tgtcgttgct cttggccata cgcctgttgg   7020
tagtatcttc gacctaaagg ttggtagcac caagcatact ctccaagcca ttgagaccag   7080
agtccttgcc gggtccaaga tgaccgtggc gcgcgtcgtt gacccaaccc ccacgccccc   7140
acccgcaccc gtgcctatcc ccctcccgcc aaaaattctg gagaatggtc ccaacgcctg   7200
gggggatgag gaccgtttga ataagaagaa gaggcgcagg atggaagccg ttggcatctt   7260
tgttatgggc gggaagaagt accagaaatt ttgggacaag agctccggtg atgtgtttta   7320
cgaggaagtc catgataaca cagatgcatg ggagtgcttc agagttgaca accctgccga   7380
ctttgaccct gagaagggaa ctctgtgtgg gcataccacc attgaaaata aggcttacaa   7440
tgtctacgtc tccccatctg gcaggaagtt tctagtccct gtcaacccag agagtggaaa   7500
agcccaatgg gaagctgcaa ggctttccgt ggagcaggcc cttggcatga tgaatgtcaa   7560
cggtgaactg acagccaaag aactggagaa actgaaaaga ataattgaca aactccagga   7620
cctgactaag gagcagtgtt taaactgcta gccgccagcg gcttgacccg ctgtggtcgc   7680
ggcggcttag ttgttactga gacagcggta aaaatagtca aatttcacaa ccggaccttc   7740
accctaggac ccgtaaactt aaaagtggcc agtgaggttg agctaaaaga cgcggtcgag   7800
cataaccaac acccggttgc aagaccggtt gatggcggtg ttgtgctcct gcgctccgca   7860
gttccttcgc ttatagacgt cttgatctcc ggcgctgatg catctcctaa gttactcgcc   7920
cgccacgggc cgggaaacac tggcatcgat ggcacgcttt gggactttga ggccgaggcc   7980
actagagagg aaattgcact cagtgcgcaa ataatacagg cttgtgacat taggcgcggc   8040
gacgcgcccg aaattggtct tccttataag ctgtaccctg ttaggggcaa ccctgagcgg   8100
gtaaaaggag ttttacagaa cacaaggttt ggagacatac cttacaaaac ccccagtgac   8160
actggaagcc cagtacacgc ggctgcctgc ctcacgccca atgccactcc ggtgactgat   8220
gggcgctccg tcttggctac gactatgccc tccggttttg agttgtatgt accgaccatt   8280
ccagcgtctg tccttgatta tcttgattct aggcctgact gccctaaaca gttgacagag   8340
cacggttgtg aggatgccgc attgagagac ctctccaagt atgacttgtc cacccaaggt   8400
tttgttttgc ctggagttct tcgccttgtg cggaagtacc tgtttgccca tgtgggtaag   8460
tgcccgtccg ttcatcggcc ttccacttac cctgccaaga attctatggc tggaataaat   8520
gggaacaggt ttccaaccaa ggacattcag agcgtccctg aaatcgacgt tctgtgcgca   8580
caggccgtgc gagagaactg gcaaactgtc accccttgta ccctcaagaa acagtattgt   8640
gggaagaaga agactaggac aatactcggc accaataact tcattgcgtt ggcccaccga   8700
gcagcgttga gtggtgtcac ccagggcttc atgaaaaagg cgtttaactc gcccatcgcc   8760
ctcgggaaaa acaaatttaa ggagctgcag actccggtct taggcaggtg ccttgaagct   8820
gatcttgcat cctgcgatcg atccacacca gcaattgttc gctggtttgc cgccaatctt   8880
ctttatgaac ttgcctgtgc tgaggagcat ctgccatcgt acgtgctgaa ctgctgccac   8940
gacttactgg tcacgcagtc cggcgcggtg actaagagag gtggcctgtc gtctggcgac   9000
ccgattactt ctgtgtcaaa caccatttac agcttggtga tatatgcaca gcacatggtg   9060
ctcagttact ttaaaagtgg tcaccctcat ggccttctgt ttctgcaaga ccagctgaag   9120
```

-continued

```
tttgaggaca tgctcaaggt tcaacccctg atcgtctatt cggacgacct cgtgctgtat    9180
gccgagtctc ccaccatgcc aaactaccac tggtgggtgg aacatctgaa tcttatgctg    9240
ggttttcaga cggacccaag gaagacagcc ataacagatt cgccatcatt tctaggctgt    9300
aggataataa atggacgcca actagtcccc aaccgtgaca ggatcctcgc ggccctcgct    9360
taccatatga aggcaagcaa tgtttctgaa tactacgcct cggcggctgc aatactcatg    9420
gacagctgtg cttgtttaga gtatgatcct gaatggtttg aagagctcgt ggttgggatg    9480
gcgcagtgcg cccgcaagga cggctatagt ttccctggcc cgccgttctt cttgtccatg    9540
tgggaaaaac tcaggtccaa tcatgaaggg aagaagtcca gaatgtgcgg gtactgcggg    9600
gccccggctc cgtacgccac tgcctgtggc ctcgacgtct gtgtttatca cacccacttt    9660
caccagcatt gtccagtcat aatctggtgt ggccatccgg ctggttctgg ttcttgcagt    9720
gagtgcaaac ccccttagg gaaaggcaca agccctctag atgaggtgtt agaacaagtc     9780
ccgtacaagc ctccacggac tgtaatcatg catgtggagc agggtctcac ccctcttgac    9840
ccaggtagat accagactcg ccgcggatta gtctccgtta ggcgtggcat caggggaaat    9900
gaagttgacc taccagacgg tgattatgct agtaccgccc tgctccccac ttgtaaagag    9960
atcaacatgg tcgctgtcgc ctctaacgtg ttgcgcagca ggttcatcat cggtccgcct   10020
ggtgctggga aaacatactg gctccttcaa caggtccaag atggtgatgt catttacacg   10080
ccgactcacc agaccatgct cgacatgatt agggctttgg ggacgtgccg gttcaacgtc   10140
ccggcaggta caacgctgca attccccgcc ccctcccgta ccggcccgtg ggttcgcatc   10200
ctagccggcg gttggtgtcc tggtaagaat tccttcctgg atgaagcagc gtattgcaat   10260
caccttgatg tcttgaggct tcttagcaaa actaccctta cctgcctagg agacttcaaa   10320
caactccacc cggtgggttt tgactctcat tgctatgttt ttgacatcat gcctcagacc   10380
caactgaaga ccatctggag gtttggacag aacatctgtg atgccatcca accagattac   10440
agggacaaac ttgtatccat ggtcaacaca acccgtgtaa cctacgtgga aagacctgtc   10500
aattatgggc aagtcctcac cccttaccac agggaccgag aggacggcgc catcacaatt   10560
gactccagtc aaggcgccac atttgatgtg gttacactgc atctgcccac taaagactca   10620
ctcaacaggc aaagagccct tgttgctatc accagggcaa gacatgctat ctttgtgtat   10680
gacccacaca ggcaactgca gagcatgttt gatcttcctg cgaaaggcac acccgtcaac   10740
ctcgctgtgc accgtgacga gcagctgatc gtactagata gaaataacaa agaatgcacg   10800
gttgctcagg ctctaggcaa tggggataaa ttcagggcca cagacaagcg cgttgtagat   10860
tctctctgcg ccatttgtgc agatctggaa gggtcgagct ctccgctccc caaggtcgca   10920
cacaacttgg ggttttattt ctcacctgat ttgacacagt ttgctaaact cccggtagaa   10980
cttgcacccc actggcccgt ggtgacaacc cagaacaatg aaaagtggcc agaccggctg   11040
gttgccagtc ttcgccctgt ccataagtat agccgtgcgt gcatcggtgc cggctacatg   11100
gtgggcccct cagtgtttct aggcacccct ggggttgtgt catactatct cacaaaattt   11160
gtcaagggcg aggctcaaat gcttccggag acagttttca gcaccggccg aattgaggta   11220
gattgccggg agtatcttga tgaccgggaa cgagaaattg ctgagtccct cccccatgcc   11280
ttcattggcg acgtcaaagg cactaccgtt ggaggatgtc accatgtcac ctccaaatac   11340
cttccgcgct tccttcccaa ggaatcagtc gcggtagtcg ggtttcaag ccccgggaaa    11400
gccgcaaaag cagtttgcac attaacagat gtgtacctcc cagaccttga ggcttacctc   11460
cacccagaga cccagtccag gtgctggaaa atgatgttgg acttcaagga agttcgactg   11520
```

-continued

```
atggtctgga aagacaagac ggcctatttt caacttgaag gccgccattt cacctggtat   11580
cagcttgcga gctatgcctc gtacatccga gttcctgtta actctacggt gtatttggac   11640
ccatgcatgg gccctgccct ttgcaataga agggttgtcg ggtccaccca ttggggagct   11700
gacctcgcag tcactcctta tgattatggt gccaagatca ttttgtctag tgcataccat   11760
ggtgaaatgc ctcctgggta caaaatccta gcgtgtgcgg agttctcgct tgatgatcca   11820
gtgaggtaca agcacacctg gggatttgaa tcggatacag cgtatctgta cgagttcacc   11880
ggaaacggtg aggactggga ggattacaat gatgcgtttc gtgcgcgcca gaaagggaaa   11940
atttataagg ccactgccac cagcatgagg tttcattttc cccgggcccc tgtcattgaa   12000
ccaactttgg gcctgaactg aaatgaaatg gggctatgc aaagcctttt ctacaaaatt   12060
ggccaacttt ttgtggatgc tttcacggag tttttggtgt ccattgttga tatcatcata   12120
tttctggcca ttttgtttgg cttcaccatc gccggctggc tggtggtctt ctgcatccga   12180
ttggtttgct ccgcggtact ccgtgcgcgc cctaccgttc accctgagca attacagaag   12240
atcttatgag gcctttcttt ctcagtgcca ggtggacatt cccacctggg gaaccaaaca   12300
tcccttgggg atgctttggc accataaggt gtcaaccctg attgatgaaa tggtgtcgcg   12360
tcgaatgtac cgcatcatgg aaaaagcagg acaggctgcc tggaaacagg tggtgagcga   12420
ggccacgctg tctcgtatta gtggtttgga tgtggtggct cattttcagc atcttgctgc   12480
cattgaagcc gagaactgta aatatttggc ctctcggctg cccatgctac acaacctgcg   12540
catgacaggg tcaaatgtaa ccttagtgta taatagcact ttgaatcagg tgttcgctat   12600
ctttccaacc cctggttccc ggccaaagct tcatgatttt cagcaatggc taatagctgt   12660
acattcctct atattttcct ccgttgcggc ttcttgtact ctttttgttg tgctgtggtt   12720
gcgaatccca attctacgta ctgtttttgg tttccactgg ttaggggcaa tttctctttc   12780
gaactcacag tgaattacac ggtgtgccca ccttgcctca cccgacaagc agccgctgag   12840
atctatgaac ccggcaggtc tctttggtgc aggataggga atgaccgatg tagtgagagc   12900
gatcatgacg aactagggtt catggttccg tctggcctct ccagcgaagg ccacttgacc   12960
agtgtttacg cttggttggc gtttctgtcc ttcagctaca cggcccagtt ccatcccgag   13020
atatttggga tagggaatgt gagtaaagtt tatgttgaca tcaagcacca attaatctgc   13080
gccgttcatg acgggcagaa caccaccttg cctcgccatg acaatatttc agccgtattt   13140
cagacctatt atcaacatca ggtcgacggc ggcaactggt ttcacctaga atggctgcgt   13200
cccttctttt cctcttggtt ggttttaaat gtttcgtggt ttctcaggcg ttcgcctgca   13260
agccatgttt cagttcgagt ctttcggaca tcaagaccaa cactaccgca gcatcaggct   13320
ttgtcgtcct ccaggacatc agctgcctta ggcatggcga ctcgtcctct cagacgattc   13380
gcaaaagctc tcagtgccgc acggcgatag ggacgcccgt gtacatcacc atgacagcca   13440
atgtcacaga tgagaattat ttgcattctt ctgatctcct catgctttct tcttgccttt   13500
tctatgcttc tgagatgagt gaaaagggat tcaaggtggt gtttggcaat gtgtcaggca   13560
tcgtggctgt gtgtgtcaac tttaccagct acgtccaaca cgtcaaggag ttcacccaac   13620
gctccttggt agtcgatcat gtgcggctgc ttcacttcat gacacctgag accatgaggt   13680
gggcaaccgt tttagcctgt ctttttgcca tcttgctggc aatttgaatg ttcaagtatg   13740
ttggggaaat gcttgaccgc gggctgttgc tcgcgattgc ctttttttgtg gtgtatcgtg   13800
ccgttctgtt ttgctgtgat cgtcgacgcc aacagcaaca gcagctctca tttccagttg   13860
atttataact tgacgttatg cgagctgaat ggcacagatt ggctggttga taaatttgat   13920
tgggcagtgg agacttttgt cattttttccc gtgttgactc acattgtttc ttatggtgca   13980
```

-continued

```
ctcaccacca gccatttcct tgacacagtt ggtctggtta ctgtatccgc cgccgggttt  14040

tgtcacgggc ggtatgtctt gagtagcatc tacgcggtct gtgccctggc tgcgttggtt  14100

tgctttgtca tcagatttgc gaagaactgc atgtcctggc gctactcatg tactagatac  14160

accaacttcc ttctagacac taagggcaga ctctatcgtt ggcggtcgcc tgtcatcata  14220

gagaaaaggg gcaaggttga ggtcgaaggc catctgatcg acctcaaaaa agttgtgctt  14280

gatggttccg cggcaacccc tttaaccaga atttcagcgg aacaatggtg tcgtccctag  14340

acgacttttg caatgatagc acagctccac ggaaggtgct cttggcgttt tctatcacct  14400

acacgccagt gatgatatat gctctaaagg taagtcgcgg ccgactgttg gggcttctgc  14460

accttttgat tttctgaac tgtgccttta ccttcgggta catgacattc acgcactttc  14520

agagcacaaa tagggtcgcg ctcactatgg gagcagtagt cgcactcctt tggggggtgt  14580

actcagccat agaaacctgg aaattcatca cctccagatg ccgtttgtgc ttgctaggcc  14640

gcaagtacat tttggcccct gcccaccacg tcgaaagtgc cgcgggcttt catccgattg  14700

cggcaaatga taaccacgca tttgtcgtcc ggcgtcccgg ctccactacg gtcaacggca  14760

cattggtgcc cgggttgaaa agcctcgtgt tgggtggcag aaaagctgtt aaacagggag  14820

tggtaaacct tgtcaaatat gccaaataac aacggcaagc agcaaaagaa aaagaagggg  14880

aatggccagc cagtcaatca gctgtgccag atgctgggta agatcatcgc ccagcaaaac  14940

cagtccagag gtaagggacc ggggaagaaa aataagaaga aaaacccgga gaagccccat  15000

tttcctctag cgaccgaaga tgacgtcagg catcacttta cccctagtga gcggcaattg  15060

tgtctgtcgt cgatccagac tgcctttaac cagggcgctg gaacttgcac cctgtcagac  15120

tcagggagga taagttacac tgtggagttt agtttgccga cgcatcatac tgtgcgcctg  15180

attcgcgcca cagcatcaac ctcagcatga tgggctggca ttcttgaagc accacagtgt  15240

taggattgga agaatgtgtg gtgaatggca ctgattgaca ctgtgcctct aagtcaccta  15300

ttcaattagg gcgaccgtgt gggggtaaag tttaattggc gagaaccatg cggccgcaat  15360

taaaaaaaaa aaaaaaaaaa aaaaaa                                       15386

<210> SEQ ID NO 2
<211> LENGTH: 15444
<212> TYPE: DNA
<213> Artificial Sequence

<400> 2
tatgtacgta taggtgttgg ctctatgcct ttggcatttg tattgtcagg agctgtgacc     60

attggcacag cccaaaactt gctacacaga aacacccttc tgtgatagcc tccttcaggg    120

gagcttaggg tttgtcccta gcaccttgct tccggagttg cactgcttta cggtctctcc    180

accccttttaa ccatgtctgg gatacttgat cggtgcacgt gtacccccaa tgccagggtg    240

tttatggcgg agggccaagt ctactgcaca cgatgcctca gtgcacggtc tctccttccc    300

ctgaacctcc aagtttctga gctcggggtg ctaggcctat tctacaggcc cgaagagcca    360

ctccggtgga cgttgccacg tgcattcccc actgttgagt gctcccccgc cggggcctgc    420

tggctttctg caatctttcc aatcgcacga atgaccagtg gaaacctgaa cttccaacaa    480

agaatggtac gggtcgcagc tgagctttac agagccggcc agctcacccc tgcagtcttg    540

aaggctctac aagtttatga acggggttgc cgctggtacc ccattgttgg acctgtccct    600

ggagtggccg ttttcgccaa ttccctacat gtgagtgata aacctttccc gggagcaact    660

cacgtgttga ccaacctgcc gctcccgcag agacccaagc ctgaagactt ttgccccttt    720

gagtgtgcta tggctactgt ctatgacatt ggtcatgacg ccgtcatgta tgtggccgaa    780
```

-continued

```
aggaaaatct cctgggcccc tcgtggcgag gatgaagtga aatttgaagc tgtccccggg    840
gagttgaagt tgattgcgaa ccggctccgc acctccttcc cgccccacca cacagtggac    900
atgtctaagt tcgccttcac agcccctggg tgtggtgttt ctatgcgggt cgaatgccaa    960
cacggctgcc ttcccgctga cactgtccct gaaggcaact gctggtggag cttgtttgac   1020
ttgcttccac tggaagttca gaacaaagaa attcgccatg ctaaccaatt tggctaccag   1080
accaagcatg gtgtctctgg caaataccta cagcgtaggc tgcaagttaa tggtctccga   1140
gcagtaactg acctaaacgg acctatcgtc gtacagtact tctccgttaa ggagagttgg   1200
atccgccatt tgaaactggc gggagaaccc agctactctg ggtttgagga cctcctcaga   1260
ataagggttg agcctaacac gtcgccattg gctgacaagg aagaaaaaat tttccggttt   1320
ggcagtcaca agtggtacgg cgctggaaag agagcaagaa aagcgcgctc ttgtgcgact   1380
gctacagtcg ctggccgcgc tttgtccgtt tgtgaaaccc ggcaggccaa ggagcacgag   1440
gttgccggcg ccaacaaggc tgagcacctc aaacactact ccccgcctgc cgaagggaat   1500
tgtggttggc actgcatttc cgccatcgcc aaccggatgg tgaattccaa atttgaaacc   1560
acccttcccg aaagagtgag accttcagat gactgggcta ctgacgagga tcttgtgaat   1620
gccatccaaa tcctcagact ccctgcggcc ttagacagga acggtgcttg tactagcgcc   1680
aagtacgtac ttaagctgga aggtgagcat tggactgtca ctgtgacccc tgggatgtcc   1740
ccttctttgc tccctcttga atgtgttcag ggctgttgtg ggcacaaggg cggtcttggt   1800
accccagatg cagtcgaggt ctccggattt gaccctgcct gccttgaccg gctggctgag   1860
gtgatgcacc tgcctagcag tgctatccca gccgctctgg ccgaaatgtc tggcgattcc   1920
gatcgttcgg cttctccggt caccaccgtg tggactgttt cgcagttctt tgcccgtcac   1980
agcggaggga atcaccctga ccaagtgcgc ttagggaaaa ttatcagtct ttgtcaggtg   2040
attgaggact gctgctgttc ccagaacaaa accaaccggg tcaccccgga ggaggtcgca   2100
gcaaagattg acctgtacct ccgtggtgca acaaatcttg aagaatgctt ggccaggctt   2160
gagaaagcgc gcccgccgcg cgtaatcgac accttctttg attgggatgt tgtgctccct   2220
ggggttgagg cggcaaccca gacgatcaag ctgccccagg tcaaccagtg tcgtgctctg   2280
gtccctgttg tgactcaaaa gtccttggac aacaactcgg tcccctgac cgccttttca    2340
ctggctaact actactaccg tgcgcaaggt gacgaagttc gtcaccgtga aagactaacc   2400
gccgtgctct ccaagttgga aaaggttgtt cgagaagaat atgggctcat gccaaccgag   2460
cctggtccac ggcccacact gccacgcggg ctcgacgaac tcaaagacca gatggaggag   2520
gacttgctga aactggctaa cgcccagacg acttcggaca tgatggcctg ggcagtcgag   2580
caggttgact taaaaacttg ggtcaagaac tacccgcggt ggacaccacc acccccctccg   2640
ccaaaagttc agcctcgaaa aacgaagcct gtcaagagct tgccggagag aaagcctgtc   2700
cccgccccgc gcaggaaggt tgggtccgat tgtggcagcc cggtttcatt aggcggcgat   2760
gtccctaaca gttgggaaga tttggctgtt agtagcccct ttgatctccc gacctcacct   2820
gagccggcaa caccttcaag tgagctggtg attgtgtcct caccgcaatg catcttcagg   2880
ccggcgacac ccttgagtga gccggctcca attcccgcac ctcgcggaac tgtgtctcga   2940
ccggtgacac ccttgagtga gccgatccct gtgcccgcac cgcggcgtaa gtttcagcag   3000
gtgaaaagat tgagttcggc ggcggcaatc ccaccgtacc agaacgagcc cctggatttg   3060
tctgcttcct cacagactga atatgaggcc tctcccccag caccgccgca gagcgggggc   3120
gttctgggag tagaggggca tgaagctgag gaaaccccga gtgaaatctc ggacatgtcg   3180
ggtaacatta aacctgcgtc cgtgtcatca agcagctcct tgtccagcgt gagaatcaca   3240
```

-continued

```
cgcccaaaat actcagctca agccatcatc gactcgggcg ggccctgcag tgggcatctc   3300
caagaggtaa aggaaacatg ccttagtgtc atgcgcgagg catgtgatgc gactaagctt   3360
gatgaccctg ctacgcagga atggctttct cgcatgtggg atcgggtgga catgctgact   3420
tggcgcaata cgtctgctta ccaggcgatt tgcaccttag atggcaggtt aaagttcctc   3480
ccaaaaatga tactcgagac accgccgccc tatccgtgtg agtttgtgat gatgcctcac   3540
acgcctgcac cttccgtagg tgcggagagc gaccttacca ttggctcagt tgctactgaa   3600
gatgttccac gcatcctcga gaaaatagaa aatgtcggcg agatggccaa ccagggaccc   3660
ttggccttct ccgaggataa accggtagat gaccaacttg tcaacgaccc ccggataccg   3720
tcgcggaggc ctgacgagag cacatcagct ccgtccgcag gcacaggtgg cgccggctct   3780
tttaccgatt tgccgccttc agatggcgcg gatgcggacg gggggggccc gtttcggacg   3840
gtaaaaagaa aagctgaaag gctctttgac caactgagcc gtcaggtttt tgacctcgtc   3900
tcccatctcc ctgttttctt ctcacgcctt ttctaccctg gcggtggtta ttctccgggt   3960
gattggggtt ttgcagcttt tactctattg tgcctctttt tatgttacag ttacccagcc   4020
tttggtattg ctcccctctt gggtgtgttt tctgggtctt ctcggcgcgt tcgaatgggg   4080
gtttttggct gctggttggc ttttgctgtt ggtctgttca agcctgtgtc cgacccagtc   4140
ggcgctgctt gtgagtttga ctcgccagag tgtagaaaca tccttcattc ttttgagctt   4200
ctcaaacctt gggaccctgt tcgcagcctt gttgtgggcc ccgtcggtct cggtcttgcc   4260
attcttggca ggctactggg cggggcacgc tgtatctggc actttttgct taggcttggc   4320
attgttgcag actgtatctt ggctggagct tacgtgcttt ctcaaggtag gtgtaaaaag   4380
tgctggggat cttgtataag aactgctcct aatgaggtcg cttttaacgt gtttcctttc   4440
acacgtgcga ccaggtcgtc acttatcgac ctgtgcgatc ggttttgtgc accaaaagga   4500
atggacccca tttttctcgc cactgggtgg cgcgggtgct gggccggccg aagccccatt   4560
gagcaaccct ctgaaaaacc catcgcgttt gcccaattgg atgaaaagaa gattacggct   4620
aggactgtgg tcgcccagcc ttatgacccc aaccaagccg taaagtgctt gcgggtgttg   4680
caggcgggtg gggcgatggt ggctgaggcg gtcccaaaag tggtcaaggt ttccgctgtt   4740
ccattccgag ccccccttctt tcccactgga gtgaaagttg atcctgattg cagggtcgtg   4800
gttgaccctg atactttcac tgcagctctc cggtctggct actccaccac aaacctcgtc   4860
cttggtgtag gggactttgc ccagctgaat ggattaaaaa tcaggcaaat ttccaagcct   4920
tcagggggag gcccacatct catggctgcc ctgcatgttg cctgctcgat ggctctgcac   4980
atgcttgctg ggatctatgt gactgcggtg ggttcttgcg gcaccggcac caacgacccg   5040
tggtgcgcta acccgtttgc cgtccctggc tacggacctg gctctctctg cacgtccaga   5100
ttgtgcattt cccaacacgg ccttaccctg cccttgacag cacttgtggc gggattcggt   5160
attcaagaaa ttgccttagt cgttttgatt tttgtttcca tcggaggcat ggctcatagg   5220
ttgagctgta aggctgacat gctgtttgtt ttgcttgcaa tcgccagcta tgtttgggta   5280
cctcttacct ggttgctttg tgtgtttcct tgctggttgc gctgtttttc tttgcacccc   5340
ctcaccgtcc tatggttggt gtttttcttg atttctgtga atatgccttc aggaatcttg   5400
gccatggtgt tgttggtttc tctttggctt cttggtcgtt atactaatgt tgctggcctt   5460
gtcacccccct acgacattca ccattacacc agcggccccc gcggtgttgc cgccttggct   5520
accgctccag atgggaccta cttggccgct gtccgccgcg ctgcgttgac tggccgcacc   5580
atgctgttta ccccgtccca gcttgggtct cttcttgagg gtgctttcag aactcgaaag   5640
```

-continued

```
ccctcactga acaccgtcaa tgtgatcggg tcctccatgg gctctggcgg ggtgtttacc   5700
atcgacggga aagtcaagtg cgtaactgcc gcacatgtcc ttacgggcaa ttcagctcgg   5760
gtttccgggg tcggcttcaa tcaaatgctt gactttgacg taaagggaga ttttgctata   5820
gctgattgcc cgaattggca aggggctgcc cccaagaccc aattctgcac ggatggatgg   5880
actggccgtg cctattggct aacatcctct ggcgtcgaac ccggcgtcat tggaaaagga   5940
ttcgccttct gcttcaccgc atgtggcgat tccgggtccc cagtgatcac cgaggccggt   6000
gagcttgtcg gcgttcacac gggatcgaat aaacaagggg ggggcattgt tacgcgcccc   6060
tcaggccagt tttgtaatgt ggcacccatc aagctaagcg aattaagtga attctttgct   6120
gggcctaagg tcccgctcgg tgatgtgaag gtcggcagcc acataattat agacataagc   6180
gaggtgcctt cagatctttg tgccttgctt gctgccaaac ctgaactgga aggaggcctc   6240
tccaccgtcc aacttctttg tgtgtttttt ctcctgtgga gaatgatggg acatgcctgg   6300
acgcccttgg ttgctgtgag tttctttatt ctgaatgagg ttctccctgc cgtcctggtc   6360
cggagtgttt tctcctttgg aatgtttgtg ctatcctggc tcacgccatg gtctgcgcaa   6420
gttctgatga tcaggcttct gacagcagct cttaacagga acagatggtc acttgccttt   6480
ttcagcctcg gtgcagtgac cggttttgtc gcagatcttg cggccactca ggggcatccg   6540
ttgcaggcag tgatgaattt gagcacctat gcattcctgc ctcggatgat ggttgtgacc   6600
tcaccagtcc cagtgatcac gtgtggtgtc gtgcacctac ttgccatcat tttgtacttg   6660
tttaagtacc gtggcctgca ccatatcctt gttggcgatg gagtgttctc tgcggctttc   6720
ttcttgagat actttgccga gggaaagttg agggaagggg tgtcgcaatc ctgcggaatg   6780
aatcatgagt ctctgactgg tgccctcgct atgagactca atgacgagga cttggatttc   6840
cttatgaaat ggactgattt taagtgcttt gtttctgcgt ccaacatgag gaatgcagcg   6900
ggtcaattta tcgaggctgc ctatgctaaa gcacttagag tagaactggc ccagttggtg   6960
caggttgata aagttcgagg tactttggcc aaacttgaag cttttgctga taccgtggca   7020
cctcaactct cgcccggtga cattgttgtc gctctcggcc acacgcctgt tggcagtatc   7080
ttcgacctaa aggttggtag caccaagcat accctccaag ccattgagac cagagtcctt   7140
gctgggtcca aaatgaccgt ggcgcgcgtc gtcgacccga cccccacgcc cccgcccgca   7200
cccgtgccca tcccccctcc accgaaagtt ctggagaatg gccccaacgc ttggggggat   7260
gaggaccgtt tgaataagaa gaagaggcgc aggatggaag ccctcggcat ctatgttatg   7320
ggcgggaaaa agtaccagaa attttgggac aagaattccg gtgatgtgtt ttatgaggag   7380
gtccataata acacagatga ttgggagtgt ctcagagttg gcgaccctgc cgactttgac   7440
cctgagaagg gaactctgtg tggacatgtc accattgaaa acaaggctta ccatgtttac   7500
acctccccat ctggtaagaa gttcttggtc cccgtcaacc cagagaatgg aagagttcaa   7560
tgggaagctg caaagctttc cgtggagcag gccctaggta tgatgaatgt cgacggcgaa   7620
ctgactgcca aagaactgga gaaactgaaa agaataattg acaaactcca gggcctgact   7680
aaggagcagt gtttaaactg ctagccgcta gcgacttgac ccgctgtggt cgcggcggct   7740
tggttgttac tgaaacagcg gtaaaaatag tcaaatttca caaccggacc ttcaccctgg   7800
gacctgtgaa tttaaaagtg gccagtgagg ttgagctaaa agacgcggtt gagcacaacc   7860
aacacccggt tgcgagaccg atcgatggtg gagttgtgct cctgcgttcc gcggttcctt   7920
cgcttataga cgtcttgatc tccggtgctg atgcatctcc caagttactt gcccatcacg   7980
ggccgggaaa cactgggatc gatggcacgc tctgggattt tgagtccgaa gccactaaag   8040
aggaagtcgc actcagtgcg caaataatac aggcttgtga cattaggcgc ggcgacgctc   8100
```

-continued

```
ctgaaattgg tctcccttac aagctgtacc ctgttagggg taaccctgag cgggtgaaag   8160
gagttctgca gaatacaagg tttggagaca taccttacaa aacccccagt gacactggaa   8220
gcccagtgca cgcggctgcc tgccttacgc ccaacgccac tccggtgact gatgggcgct   8280
ccgtcttggc cacgaccatg ccccccgggt ttgagttata tgtaccgacc atacctgcgt   8340
ctgtccttga ttaccttgac tctaggcctg actgccctaa acagctgaca gagcacggct   8400
gcgaagatgc cgcactgaaa gacctctcca aatatgactt gtccacccaa ggctttgttt   8460
tacctggagt tcttcgcctt gtgcggaaat acctgtttgc ccatgtaggt aagtgcccac   8520
ccgttcatcg gccttctact taccctgcta agaattctat ggctggaata aatgggaata   8580
ggttcccaac caaggacatt cagagcgtcc ctgaaatcga cgttctgtgc gcacaggctg   8640
tgcgagaaaa ctggcaaact gtcacccctt gcactcttaa gaaacagtat tgcgggaaga   8700
agaagactag gaccatactc ggcaccaata acttcatcgc actagcccac cgagcagtgt   8760
tgagtggtgt tacccagggc ttcatgaaaa aggcgtttaa ctcgcccatc gccctcggaa   8820
agaacaagtt taaggagcta cagactccgg tcctgggcag gtgccttgaa gctgatctcg   8880
catcctgcga tcgatccacg cctgcaattg tccgctggtt tgccgccaac cttctttatg   8940
aacttgcctg tgctgaagag catctaccgt cgtacgtgct gaactgctgc cacgacttac   9000
tggtcacgca gtccggcgca gtgactaaga gaggtggcct gtcgtctggc gacccgatca   9060
cctctgtgtc taacaccatt tatagtttgg tgatctatgc acagcatatg gtgcttagtt   9120
acttcaaaag tggtcacccc catggccttc tgttcttaca agaccagcta aagtttgagg   9180
acatgctcaa ggttcaaccc ctgatcgtct attcggacga cctcgtgctg tatgccgagt   9240
ctcccaccat gccaaactat cactggtggg ttgaacatct gaatttgatg ctggggtttc   9300
agacggaccc aaagaagaca gcaataacag actcgccatc atttctaggc tgtagaataa   9360
taaatgggcg ccagctagtc cccaaccgtg acaggatcct cgcggccctc gcctatcaca   9420
tgaaggcgag taatgtttct gaatactatg cctcagcggc tgcaatactc atggacagct   9480
gtgcttgttt ggagtatgat cctgaatggt ttgaagaact tgtagttgga atagcgcagt   9540
gcgcccgcaa ggacggctac agctttcccg gcacgccgtt cttcatgtcc atgtgggaaa   9600
aactcaggtc caattatgag ggggaagaagt cgagagtgtg cgggtactgc ggggccccgg   9660
ccccgtacgc tactgcctgt ggcctcgacg tctgcattta ccacacccac ttccaccagc   9720
attgtccagt cacaatctgg tgtggccatc cagcgggttc tggttcttgt agtgagtgca   9780
aatcccctgt agggaaaggc acaagccctt tagacgaggt gctggaacaa gtcccgtata   9840
agcccccacg gaccgttatc atgcatgtgg agcagggtct caccccccctt gatccaggta   9900
gataccaaac tcgccgcgga ctggtctctg tcaggcgtgg aattagggga aatgaagttg   9960
aactaccaga cggtgattat gctagcaccg ccttgctccc tacctgcaaa gagatcaaca  10020
tggtcgctgt cgcttccaat gtattgcgca gcaggttcat catcggccca cccggtgctg  10080
ggaaaacata ctggctcctt caacaggtcc aggatggtga tgttatttac acaccaactc  10140
accagaccat gcttgacatg attagggctt tggggacgtg ccggttcaac gtcccggcag  10200
gcacaacgct gcaattcccc gtcccctccc gcaccggtcc gtgggttcgc atcctagccg  10260
gcggttggtg tcctggcaag aattccttcc tagatgaagc agcgtattgc aaccaccttg  10320
atgttttgag gcttctcagt aaaactaccc tcacctgtct aggagacttc aagcaactcc  10380
acccagtggg ttttgattct cattgctatg tttttgacat catgcctcaa actcaactga  10440
agaccatctg gaggtttgga cagaatatct gtgatgccat tcagccagat tacagggaca  10500
```

-continued

```
aactcatgtc catggtcaac acaacccgtg tgacctacgt ggaaaaacct gtcaggtatg   10560
ggcaggtcct cacccccctac cacagggacc gagaggacga cgccatcact attgactcca   10620
gtcaaggcgc cacattcgat gtggttacgt tgcatttgcc cactaaagat tcactcaaca   10680
ggcaaagagc ccttgttgcc atcaccaggg caagacacgc tatctttgcg tatgacccac   10740
acaggcagct gcagggctta tttgatcttc ctgcaaaagg cacacccgtc aacctcgcag   10800
tgcaccgcga cgggcagctg atcgtgctgg atagaaataa caaagaatgc acggttgctc   10860
aggctctagg caacggggat aaatttaggg ccacagataa gcgtgttgta gattctctcc   10920
gcgccatttg tgctgatcta gaagggtcga gctctccgct ccccaaggtc gcacacaact   10980
tgggatttta tttctcacct gatttaacac agtttgctaa actcccagta gaacttgcac   11040
ctcactggcc cgtggtgaca acccagaaca atgaaaagtg gccagatcgg ctggttgcca   11100
gccttcgccc tatccataaa tacagccgcg cgtgcatcgg tgccggctat atggtgggcc   11160
cttcggtgtt tctaggcact cctggggtcg tgtcatacta tctcacaaaa tttgttaagg   11220
gcgaggctca attgcttcca gagacggttt tcagcaccgg ccgaattgag gtagactgcc   11280
gggaatatct tgatgatcgg gagcgagaag ttgctgcgtc cctcccacac gctttcattg   11340
gcgacgtcaa aggcactacc gttggaggat gtcatcatgt cacctccaga tacctcccgc   11400
gcgtccttcc caaggaatca gttgcggtag tcggggtttc aagccccgga aaagccgcga   11460
aagcattgtg cacactgaca gatgtgtacc tcccagatct tgaagcctat ctccacccgg   11520
agacccagtc caagtgctgg aaaatgatgt tggacttcaa agaagttcga ctaatggtct   11580
ggaaagacaa aacagcctat ttccaacttg aaggtcgcta tttcacctgg tatcagcttg   11640
ccagctatgc ctcgtacatc cgtgttcctg tcaactctac ggtgtacttg gacccctgca   11700
tgggccccgc cctttgcaac aggagagtcg tcgggtccac ccattggggg gctgacctcg   11760
cggtcacccc ttatgattac ggcgctaaaa ttatcctgtc tagcgcgtac catggtgaaa   11820
tgccccccgg atacaaaatt ctggcgtgcg cggagttctc gttggatgac ccagttaagt   11880
acaaacatac ctgggggttt gaatcggata cagcgtatct gtatgagttc accggaaacg   11940
gtgaggactg ggaggattac aatgatgcgt ttcgtgcgcg ccaggaaggg aaaatttaca   12000
aggccactgc caccagcttg aagtttcatt ttcccccggg ccctgtcatt gaaccaactt   12060
taggcctgaa ttgaaatgaa atggggtcca tgcaaagcct ttttcacaaa attggccaac   12120
tttttgtgga tgctttcacg gagttcttgg tgtccattgt tgatatcatc atatttttgg   12180
ccattttgtt tggcttcacc atcgccggtt ggctggtggt cttttgcatc agattggttt   12240
gctccgcgat actccgtacg cgctctgcca ttcactctga gcaattacag aagatcttat   12300
gaggcctttc tttcccagtg ccaagtggac attcccacct ggggaactaa acatcctttg   12360
gggattctct ggcaccataa ggtgtcaacc ctgattgatg aaatggtgtc gcgtcgaatg   12420
taccgcatca tggaaaaatc agggcaggct gcctggaaac aggtggtgag cgaggctacg   12480
ctgtctcgca ttagtagttt ggatgtggtg gctcattttc agcatctagc cgccattgaa   12540
gccgagacct gtaaatattt ggcctcccgg ctgcccatgc tacacaacct gcgcatgaca   12600
ggttcaaatg taaccatagt gtataatagc actttgaatc aggtgtttgc tatttttcca   12660
acctctggtt cccggccaaa gcttcatgat tttcagcaat ggttaatagc tgtacattcc   12720
tccatatttt cctctgttgc agcttcttgt actctttttg ttgtgctgtg gttgcgtgtt   12780
ccaatactac gtactgtttt tggtttccgc tggttagggg caatttttct ttcgaactca   12840
cagtgaatta cacggtgtgt ccaccttgcc tcacccggca agcagccgca gagatctacg   12900
aacccggtag gtctctttgg tgcaggatag ggtatgaccg atgtgaggag gatgatcatg   12960
```

-continued

```
acgagctagg gtttatggta ccgcctggcc tctccagcga aggccacttg actagtgttt  13020
acgcctggtt ggcgttcttg tccttcagct acacggccca gttccatccc gagatattcg  13080
ggatagggaa tgtgagtcga gtttatgttg acatcaaaca tcaactcatc tgcgccgaac  13140
atgacgggca gaacaccacc ttgcctcgtc atgacaacat ttcagccgtg tttcagacct  13200
attaccaaca tcaagtcgat ggcggcaatt ggtttcacct agaatggctt cgtcccttct  13260
tttcctcgtg gctggtttta aatgtctctt ggtttctcag gcgttcgcct gcaaaccatg  13320
tttcagttcg agtctcgcag atattgagac caacaccacc gcagcggcaa gctttgctgt  13380
cctccaagac atcagttgcc ttaggcatcg cgactcggcc tctgaggcga ttcgcaaaat  13440
ccctcagtgc cgtacggcga tagggacacc cgtgtatatt actatcacag ccaatgtgac  13500
agatgagaat tatttacatt cttctgatct cctcatgctt tcttcttgcc ttttctatgc  13560
ttctgagatg agtgaaaagg gatttaaggt ggtatttggc aatgtgtcag gcatcgtggc  13620
tgtgtgtgtc aattttacca gctacgtcca acatgtcaag gagttcaccc aacgctccct  13680
ggtggtcgac catgtgcggt tgctccattt catgacacct gagaccatga ggtgggcaac  13740
tgttttagcc tgtcttgttg ccattctgtt ggcaatttga atgtttaagt atgttggaga  13800
aatgcttgac cgcgggctgt tgctcgcaat tgctttcttt gtggtgtatc gtgccgttct  13860
gttttgctgt gctcgccaac gccagcagcg acagcagctc ccatctacag ctgatttaca  13920
acttgacgct atgtgagctg aatggcacag attggctagc tgacaaattt gattgggcag  13980
cggagagttt tgtcatcttt cccgttttga ctcacattgt ctcctatggt gccctcacta  14040
ctagccattt ccttgacacg gtcgctttag ccactgtgtc taccgccggg tttgttcacg  14100
ggcggtatgt cctaagtagc atctacgcgg tctgtgccct ggctgcgttg acttgcttcg  14160
tcattaggtt tgcaaagaat tgcatgtcct ggcgctacgc gtgtaccaga tataccaact  14220
ttcttctgga cactaagggc agactctatc gttggcggtc gcctgtcatc atagagaaaa  14280
ggggcaaagt tgaggtcgaa ggtcatctga tcgacctcaa aagagttgtg cttgatggtt  14340
ccgtggcaac ccctataacc agagtttcag cggaacaatg ggtcgtcct tagatgactt  14400
ctgtcatgat agcacggctc cagaaaaggt gcttttggcg ttttctatta cctacacgcc  14460
agtgatgata tatgccctaa aggtgagtcg cggccgactg ctagggcttc tgcacctttt  14520
gatcttcctg aattgtgctt tcaccttcgg gtacatgact ttcgcgcact ttcagagtac  14580
aaataaggtc gcgctcacta tgggagcagt agttgcactc ctttgggggg tgtactcagc  14640
catagaaacc tggaaattca tcacctccag atgccgtttg tgcttgctag gccgcaagta  14700
cattctggcc cctgcccacc acgttgaaag tgccgcaggc tttcatccga ttgcggcaaa  14760
tgataaccac gcatttgtcg tccggcgtcc cggctccact acggtcaacg gcacattggt  14820
gcccgggtta aaaagcctcg tgttgggtgg cagaaaagct gttaaacagg gagtggtaaa  14880
ccttgtcaaa tatgccaaat aacaacggca agcagcagaa gagaaagaag gggggatggcc  14940
agccagtcaa tcagctgtgc cagatgctgg gtaagatcat cgctcagcaa aaccagtcca  15000
gaggcaaggg accgggaaag aaaaataaga agaaaaaccc ggagaagccc cattttcctc  15060
tagcgactga agatgatgtc agacatcact ttacccctag tgagcggcaa ttgtgtctgt  15120
cgtcaatcca gaccgccttt aatcaaggcg ctgggacttg caccctgtca gattcaggga  15180
ggataagtta cactgtggag tttagtttgc ctacgcatca tactgtgcgc ctgatccgcg  15240
tcacagcatc accctcagca tgatgggctg gcattcttga gacatctcag tgtttgaatt  15300
ggaagaatgt gtggtgaatg gcactgattg acattgtgcc tctaagtcac ctattcaatt  15360
```

-continued agggcgaccg tgtgggggtg agatttaatt ggcgagaacc atgcggccga aattaaaaaa 15420
aaaaaaaaaa aaaaaaaaaa aaaa 15444

<210> SEQ ID NO 3
<211> LENGTH: 15013
<212> TYPE: DNA
<213> Artificial Sequence

<400> 3
atgacgtata ggtgttggct ctatgccacg gcatttgtat tgtcaggagc tgtgaccatt 60
ggcacagccc aaaacttgct gcacggaaaa cgcccttccg tgacagcctt cttcagggga 120
gcttaggggt ctgtccctaa caccttgctt ctggagttgc actgctttac ggtctctcca 180
accctttaac catgtctggg atacttgatc ggtgcacgtg cacccccaat gccagggtgt 240
ttatggcgga gggccaagtc tactgcacac gatgtctcag tgcacggtct ctccttcctc 300
tgaatctcca agtttctgag cttggagtgc tgggcctatt ttataggccc gaagagccac 360
tccggtggac gttgccacgt gcatacccca ctgtcgagtg ctcccccgcc ggggcctgct 420
ggctttctgc gatctttcca attgcacgaa tgaccagtgg gaacctgaac tttcaacaaa 480
gaatggtgcg ggtcgcagct gagatttaca gagtcggtca gctcaccccc acagtcttga 540
agaatctaca agtttatgaa cggggttgcc gctggtaccc cattgtcgga cctgtccctg 600
gagtggccgt tttcgccaat tccctacatg tgagtgacaa accttttccg ggagcaactc 660
atgtgttaac taatctaccg ctcccgcaga ggcccaagcc tgaagacttt tgtccttttg 720
agtgtgctat ggctgacatc tatgacattg gtcatgacgc cgtcatgtat gtggccggag 780
ggaaagtctc ctgggcccct cgtggcgggg atgaagggaa atttgaaact gtccccgagg 840
agttgaagtt aattgcgaac cgacttcaca tctccttccc gccccaccac gtagtggaca 900
tatctaagtt tgcctttata gcccccggga gtggtgtctc catgcgggtt gagtgccaac 960
atggctgcct ccccgctgat actgttcctg gagggaactg ctggtggcgc ttgttcgact 1020
cgctcccacc ggaagttcag aataaagaaa ttcgctatgc taaccaattt ggttatcaaa 1080
ccaagcatgg tgtctctggc aagtacctac agcggaggct gcaagttaat ggtctccgag 1140
cagtgactga tacaagtggg cctatcgtcg tacagtattt ctctgttaag gagagttgga 1200
tccgccactt aaggctggcg gaagaaccta gcctccctgg gtttgaggac ctcctcagaa 1260
taagggttga gcccaatacg tcaccattgg ttggcaagga tgtgaaaatc ttccggtttg 1320
gcaatcacaa atggtacggc gctggaaaga gagcaaggaa atcacgctct ggtgcgactg 1380
ccacggtcgc tcaccgcgct ttacccgttc gtgaaaccct gcaggctaag aggcgcgagg 1440
ttgccagcgc caacagggct gagcatatca agcactatta tccgccagcc gacggaaact 1500
gtggttggca ctgcatttcc gctattgtca accggatggt gaattctaaa tttgaaactg 1560
ctcttcccga gagagcgaga ccttctgatg actgggctac tgacgaggac cttgtgaata 1620
ccatccaaat cctcagactc cctgcggcct tggacaggga cggtgcttgt gttagcgcca 1680
agtacgtgct taaactagaa ggcgagcatt ggactgtctc tgtgacccct gggatgtccc 1740
cttctttgct ccccccttgaa tgtgttcagg gctgttgtga acataagaac ggccttggtc 1800
ccccagatgc ggtcgaaagt tttggatttg accctgcctg ccttgaccga ctggctgagg 1860
taatgcactt gcctagtagt gtcatcccag ctgctctggc cgaaatgtcc ggtgacccca 1920
attgtccggc atccccggtc accactgtgt ggactgtttc acaattcttt gcccgccaca 1980
gaggaggaga gcaccctgat caggtgcgct taggaaagat catcagcctt tgtcaagttg 2040
ttgaggaatg ctgttgccat cagaataaaa ccaaccgggc caccccggaa gaggtcgcgg 2100
caaagattaa tcagtacctc catggtgcaa caagtcttga agactgcttg actaggcttg 2160

-continued

```
agagggcttg cccgccgagt gctgcggaca ccttctttga ttggaacgtt gtgctccctg   2220
gggttgaggc tgcaactccg ccacccccctc caccaagagt tcagcctcga aaaacaaagt   2280
ctgtcaagag cttgccggga aacaatcctg tccccgctcc acgcaggaag gttagatctg   2340
actgtggcag cccgattttg acgggcgaca atgatctttc gacgccatcc gagccgatga   2400
catctctgaa tgagcctgcg cttatgcctg cgttgcaatg tatctctagg ccagtgacat   2460
ctttgagtgt gccggcccca gttcctgcac cgcgtagagc tgtgtcccga ccggtgacgc   2520
ccttgagtga gccagttttt ttgtctgcac cgcgacacaa atttcagcag gtgaaagaag   2580
cgaatctggt ggcaacaacg ctgatgtgcc aggacgaacc tctagatttg tctgcatcct   2640
cacagactga atatgaagct tccccccccag caccactgca gaacatgggt attctggagg   2700
tgggggggaca agaagctgtg gaagttctga gtgaaatctc ggatacactg aatgacacca   2760
accctgcacc tgtgtcatca agcagctccc tgtcaagtgt taagatcaca cgcccaaaat   2820
actcagctca agccatcatt gattcgggcg ggccctgcag tgggcacctc cgaaggggaa   2880
aagaagcatg cctcagcctc atgcgtgagg cttgtgatgc ggctaagctt agtgaccctg   2940
ccacgcaaga atggcttttct cgcatgtggg atagggttga catgctgacc tggcgcaaca   3000
cgtctgccta ccaggcgttt cgcatcttag atggtaggtt tgagtttctc ccaaagatga   3060
tactcgagac accgccgccc tacccgtgtg ggtttgtgat gctgcctcac acgcctgcac   3120
cttccgtgag tgcagagagc gaccttacca ttggttcagt cgccactgaa gatgttccac   3180
gcattctcgg gaaaatagaa aacgccggcg agacgcccaa ccaggggctc ttggcaccct   3240
tcggggaaga accggtgtgc gaccaacctg tcaaagactc ccggatgttg tcgcgggggt   3300
ttgacgagag cacgacggct ccgtccgcag gtacaggtgg cgctgactta cccactgatt   3360
tgccaccttc agatggtgtg gatgcggacg gggtggggct gttacggacg gtaagaaaga   3420
aagctgaaag gctcttcgac caattgagcc gtcaggtttt taacctcgtc tcccatctcc   3480
ctgttttctt ctcacacctc ttcaaatctg acagtggtta ttctccgggt gattggggtt   3540
ttgcagcttt tactttattt tgcctctttt tatgttacag ctacccattc ttcggtttcg   3600
ctcccctctt gggtgtgttt tctgggtctt ctcggcgcgt gcgcatgggg gtttttggct   3660
gctggttggc ttttgctgtt ggcctgttca agcctgtgtc cgacccagtc ggcactgctt   3720
gtgagtttga ctcgccagag tgtaggaacg tccttcattc ttttgagctt ctcaaacctt   3780
gggaccctgt ccgcagcctt gttgtgggcc ccgtcggtct cggtcttgcc attcttggca   3840
ggttactggg cggggcacgc tacatctggc atttttttcct taggcttggc attgttgcag   3900
attgcttctt ggctggagct tatgtgcttt ctcaaggtag gtgtaaaaaa tgctggggat   3960
cttgtgtaag aactgctcct aatgaaatcg ccttcaacgt gttccctttt acgcgtgcga   4020
ccaggtcgtc actcatcgac ctgtgcgatc ggttttgtgc gccaaaaggc atggacccca   4080
ttttcctcgc tactgggtgg cgtgggtgct ggaccggccg gagtcccatt gagcaaccct   4140
ctgaaaaacc tatcgcgttc gcccagttgg atgagaagag gattacggct agaactgtgg   4200
tcgttcagcc ttatgatcct aaccaagccg taaagtgctt gcgggtgtta caggcgggtg   4260
gggcgatggt ggccgaggca gtcccaaaag tggtcaaggt ttccgccatt ccattccgag   4320
ctcccttttt tcccaccgga gtgaaggttg atcctgagtg caggatcgtg gtcgaccccg   4380
acacttttac tacagctctc cggtctggtt actccaccac aaacctcgtc cttggtgtgg   4440
gggactttgc ccaactgaat ggattaaaaa tcaggcaaat ttccaagtct tcgggggggag   4500
gcccacacct cattgctgcc ctgcatgttg cttgctcgat ggcgttgcac atgcttgctg   4560
```

-continued

```
gggtttatgt aactgcagtg gggtcttgcg gtaccggcac caatgatccg tggtgcacta   4620
acccattcgc cgtccctggc tacggacctg gctctctctg cacgtccaga ttgtgcatct   4680
cccaacatgg ccttaccctg cccttgacag cacttgtggc aggattcggt cttcaggaaa   4740
ttgccttagt cgttttgatt tttgtttcca tcggaggcat ggctcatagg ttgagttgca   4800
aggctgatat gctgtgcgtc ttacttgcaa tcgcaagcta tgtttgggta ccccttacct   4860
ggttgctctg tgtgtttcct tgctggttgc gctggttctc tttgcaccct ctcaccatcc   4920
tatggttggt gtttttctta atttccgtaa atatgccttc gggaatcttg gccgtggtgt   4980
tattggttgc tctttggctt ctaggccgtt atactaatgt tgttggtctt gttacccccct   5040
atgatattca tcatcacacc agtggccccc gcggtgttgc cgccttggct accgcaccgg   5100
atgggactta tttggccgct gtccgccgcg ctgcgttgac tggccgcacc gtgttgttta   5160
ccccgtccca gcttgggtcc ctccttgagg gcgctttcag aactcgaaag ccctcactga   5220
acaccgtcaa tgtggtcggg tcctctatgg gctctggcgg agtgttcact atcgatggga   5280
aaattaagtg cgtgactgcc gcacatgtcc ttacgggtaa ttcagctagg gtttccgggg   5340
ttggcttcaa tcaaatgctt gactttgatg taaaagggga cttcgccata gctgattgcc   5400
cgaattggca aggggctgct cctaagaccc aattctgcga ggatgggtgg actggccgtg   5460
cctattggct gacatcctct ggtgtcgaac ccggcgtcat tgggaatgga ttcgccttct   5520
gcttcaccgc gtgcggcgat tctgggtccc cagtgatcac cgaagccggt gagcttgtcg   5580
gcgttcacac aggatcaaat aaacaaggag gaggcattgt tacgcgcccc tcaggccagt   5640
tttgtaatgt ggcacccatc aagctgagcg aattaagtga gttctttgct ggacctaagg   5700
tcccgctcgg tgatgtgaag gttggcagcc acataattaa agatatatgc gaggtacctt   5760
cagacctttg cgccttgctt gccgccaaac ccgaattgga aggaggcctc tccaccgtcc   5820
aacttttatg tgtgtttttc ctcctgtgga gaatgatggg acatgcctgg acacccttgg   5880
ttgctgtggg ttttttatc ttgaatgaag tcctcccagc tgtcctggtc cggagtgttt   5940
tctcctttgg aatgtttgtg ctatcttggc tcacaccatg gtctgcgcaa gttctgatga   6000
tcaggcttct aacagcagct ctcaacagga acagattgtc actcgccttt tacagccttg   6060
gtgcggcgac cggctttgtc gcagatctgg cggcaactca agggcatccg ttgcaagcag   6120
taatgaattt aagtacctat gccttcctgc ctcggatgat ggttgtgacc tcaccagtcc   6180
cagttattgc gtgtggtgtc gtgcacctcc ttgccataat tttgtacttg tttaagtacc   6240
gctgcctgca caatgttctt gttggcgatg gagcgttctc tgcggctttc tttttgcgat   6300
actttgccga ggggaaattg agggaagggg tgtcgcaatc ctgcgggatg aatcatgagt   6360
cgctgactgg tgccctcgct atgagactca atgacgagga cttggatttc cttacgaaat   6420
ggactgattt taagtgcttt gtttctgcgt ccaacatgag gaatgcggcg ggccagttca   6480
tcgaggctgc ctatgcaaaa gcacttagaa ttgaacttgc ccagttggtg caggttgata   6540
aggttcgagg tactatggcc aaacttgaag cttttgctga taccgtggca ccccaactct   6600
cgcccggtga cattgttgtt gctcttggcc atacacctgt tggcggtatc ttcgacctaa   6660
aggttggtag caccaagcac accctccaat ccattgagac cagagtcctt gccgggtcca   6720
aaatgaccgt ggcgcgtgtc gttgacccaa cccccacacc cccacccgca cccgtgccca   6780
tcccccctccc accgaaagtt ctggagaatg gtcctaacgc ctgggggggat gaggatcgtt   6840
tgaacaagaa gaagaggcgc aggatggaag ccgtcggcat ctttgttatg ggtggaaaga   6900
aataccagaa attttgggac aagaattccg gtgatgtgtt ttatgaggag gtccatgata   6960
acacagacgc gtgggagtgc ctcagagttg acaaccctgc cgactttgac cctgagaagg   7020
```

-continued

```
gaactctgtg tgggcatact accattgaag gtaaggctta caatgtctac gcctccccat   7080
ctggcaagaa gtttctggtc cccgtcaacc cagagagtgg aagagcccaa tgggaagctg   7140
caaagctttc cgtggagcag gcccttggca tgatgaatgt cgacggtgag ctgacagcca   7200
aagaactgga gaaactgaaa agaataattg acaaactcca gggtctgact aaggagcagt   7260
gtttaaactg ttagccgcca gcggcttgac ccgctgtggt cgcggcggct tggttgttac   7320
tgagacagcg gtaaaaatag tcaaatttca caaccggacc ttcaccctag gacctgtgaa   7380
cttaaaagtg gccagtgagg ttgagctaaa agacgcggtc gagcacaacc aacacccggt   7440
tgcaagaccg gttgatggtg gcgttgtact cctgcgcccc gcagttcctt cgcttgtaga   7500
tgtcttgatc tctggcgctg atgcatcccc taagttactc gcccgccatg ggccgggaaa   7560
cactgggatc gatggcacgc tttgggattt tgagaccgaa gccaccaaag aggaaattac   7620
acttagtgcg caaataatac aggcttgtga cattaggcgc ggcgacgcac ctgaaattgg   7680
tctcccttat aagctgcacc ctgttagggg caaccctgag cggataaaag gagttttaca   7740
gaatacaagg tttggggaca taccttacaa aacccccagt gacactggca gcccagtgca   7800
tgcggctgcc tgcctcacgc ccaatgccac tccggtgacc gatgggcgct ccgtcttggc   7860
tacgactatg ccctccggtt ttgagttgta tataccgacc attccatcgt ctgtccttga   7920
ttatcttgat tctaggcctg actgccccaa acagttaaca gagcacggct gtgaggatgc   7980
cgcattgaga gacctctcca agtatgactt gtccacccaa ggctttgttt tgcctggagt   8040
tcttcgccta gtgcgtaagt acctgtttgc tcatgtgggt aagtgcccgc ccgttcatcg   8100
gccttccact tatcctgcca agaactctat ggctggaata aatgggaaca ggtttccaac   8160
caaggacatt cagagcatcc ctgaaatcga cgttctgtgc gcacaggctg tgcgagaaaa   8220
ctggcaaact gttacccctt gcaccctcaa gaaacaatat tgtgggaaga agaagactag   8280
gacaatactc ggcaccaata acttcgttgc gttggcccac cgggcagcgt tgagtggtgt   8340
cacccagggc tttatgaaaa aggcgtttaa ctcgcccatt gccctcggga aaaacaaatt   8400
taaagagcta cagactccgg tcttaggcag gtgccttgaa gctgatcttg catcctgcga   8460
tcggtccaca cctgcaattg tccgctggtt tgccgccaat cttctttatg aacttgcctg   8520
tactgaagaa catctaccgt cgtacgtgct gaactgctgc cacgacctac tggtcacgca   8580
gtccggcgcg gtgactaaga gaggtggcct gtcgtctggc gacccgatta cctctgtgtc   8640
aaacaccatt tacagcttag tgatatatgc acagcacatg gtgctcagtt actttaaaag   8700
tggtcaccct cacggccttc tgtttctgca agaccagcta aagtttgagg acatgctcaa   8760
ggttcaaccc ctgatcgtct attcggacga cctcgtgctg tatgccgagt ctcccaccat   8820
gccaaactac cactggtggg ttgaacatct gaatcttatg ttgggttttc aaacggaccc   8880
aaggaagaca gccataacag actcaccatc ttttctaggc tgtagaataa taaatgggcg   8940
ccagctagtc ccccaccgtg acaggattct cgcggccctt gcctaccata tgaaagcaag   9000
caatgtttct gaatattacg cctcggcggc tgcaatactc atggacagct gtgcttgttt   9060
agagtatgat cctgaatggt ttgaagagct cgtggttggg atggcgcagt gcgcccgcaa   9120
ggacggctac agttttcctg gcccgccgtt cttcttgtcc atgtgggaaa aactcaggtc   9180
caaccacgag ggaaagaagt ccagaatgtg cgggtactgc ggggccccgg ctccgtacgc   9240
cactgcctgt ggcctcgatg tctgtgttta ccacacccac ttccaccagc attgtccagt   9300
cataatctgg tgtggccatc cggcgggttc tggttcttgt agtgagtgca aaccccccct   9360
agggaaaggc acaagccctc tggatgaggt gttggaacaa gtcccgtaca agcctccgcg   9420
```

-continued

```
gactgtaatc atgcatgtgg agcagggtct cacccctctt gacccaggta gataccaaac    9480
tcgccgcgga ttagtctccg ttaggcgtgg catcagggga aatgaagttg acctaccaga    9540
cggtgattat gccagtaccg ccctgctccc tacttgtaaa gagatcaaca tggtcgctgt    9600
cgcctctaat gtgttgcgca gcaggttcat catcggtccg cccggtgctg ggaaaacata    9660
ctggctcctt caacaggtcc aggatggtga tgtcatttac acaccaactc accagaccat    9720
gcttgacatg attagggctt tgggggcgtg ccggttcaac gtcccagcag gcacaacgct    9780
gcaattccct gccccctccc ataccggccc gtgggttcgc atcctagccg gcggttggtg    9840
tcctggtaag aattccttcc tggatgaagc agcgtattgt aatcaccttg atgtcttgag    9900
gctccttagc aaaactaccc tcacctgtct aggagatttc aaacaactcc acccagtggg    9960
ttttgattct cattgctatg tttttgacat tatgcctcag actcaactga agaccatctg   10020
gagatttgga cagaatatct gcgatgccat tcagccagat tacagggaca aacttgtatc   10080
catggtcaac acaacccgtg taacctactt ggaaaaacct gtcaagtatg ggcaagtcct   10140
cacccettac cacagggacc gagaggacgg cgccatcaca attgactcta gtcaaggcgc   10200
cacatttgat gtggttacac tgtatttgcc cactaaagat tcactcaaca ggcaaagagc   10260
ccttgttgct atcaccaggg caagacatgc tatctttgtg tatgacccac acaggcaact   10320
gcagagcatg tttgatcttc ccgcgaaagg cacacccgtc aacctcgctg tgcaccgtga   10380
cgagcagctg atcgtactag atagaaacaa caaagaatgc tcggttgctc aggctctagg   10440
caatggggat aaattcaggg ccacagacaa gcgcgttgta gattctctcc gcgccatttg   10500
tgcagatctt gaagggtcga gctccccgct tcccaaggtc gcacacaact tgggatttta   10560
tttctcgcct gatttgacac agtttgccaa actcccggta gaacttgcac cccactggcc   10620
cgtggtgaca acacagaaca atgaaaagtg gccagaccgg ttggttgcta gccttcgccc   10680
tgtccataag tatagccgcg cgtgcatcgg tgccggctac atggtgggcc cctcagtgtt   10740
tctaggcacc cctggggttg tgtcatacta tctcacaaaa tttgtcaggg gcgaggctca   10800
aatgcttccg gagacagtct tcagcaccgg ccgaattgag gtagattgcc gggagtacct   10860
tgatgaccgg gagcgagaaa ttgctgagtc cctcccccat gctttcattg gtgacgtcaa   10920
aggtactacc gttggaggat gtcaccatgt cacctccaaa taccttccgc gcttccttcc   10980
caaggaatca gtcgcggtag tcggggtttc aagccccggg aaagccgcaa aagcagtttg   11040
cacattaaca gatgtgtatc tcccagacct tgaagcttac ctccacccag agacccagtc   11100
caagtgctgg aaaatgatgt tggacttcaa ggaagttcga ctgatggtct ggaaaggcaa   11160
gacggcctat tttcaacttg aaggccgcca tttcacctgg tatcagcttg caagctacgc   11220
ctcgtacatc cgagtacctg ttaattctac ggtgtatttg gacccctgca tgggccctgc   11280
cctttgcaac agaagagttg tcgggtccac ccattgggga gccgacctcg cagtcacccc   11340
ttatgattac ggtgccaaag tcattctgtc tagtgcatac catggtgaaa tgcctcctgg   11400
gtacaaaatc ctggcgtgcg cggagttctc gcttgacgat ccagttaggt acaaacgcac   11460
ctgggggttt gaatcggata cagcgtatct gtatgagttc accggaaacg gtgaggactg   11520
ggaagactac aatgatgcgt ttcgtgcgcg ccagaaaggg aaaatttata aggccactgc   11580
caccagcatg aggtttcatt ttcccccggg ccctgttatt gaaccaactt taggcctgaa   11640
ttgagatgaa atggggtcta tgcaaagcct ctttaacaaa attggccaac tttttgtgga   11700
tgctttcacg gaatttttgg tgtccattgt tgatatcatc atatttttgg ccattttgtt   11760
tggcttcacc atcgcaggtt ggctggtggt cttctgcatc agattggttt gctccgcggt   11820
actccgtgcg cgccctgcca ttcaccctga gcaattacag aagatcctat gaggcctttc   11880
```

-continued

```
tttctcagtg ccgggtggac attcccacct ggggaactaa acatcctttg gggatattgt   11940
ggcaccataa ggtgtcaacc ctgattgatg aaatggtgtc gcgtcgaatg taccgcacca   12000
tggaaaaagc aggacaggct gcctggaaac aggtggtgag cgaggccacg ttgtctcgca   12060
ttagtggttt ggatgtggtg gctcattttc agcatcttgc cgccattgaa gccgagacct   12120
gtaaatattt ggtttctcgg ctgcccatgc tacacaacct gcgcatgaca gggtcaaatg   12180
taaccatagt gtataatagc actttaaatc aggtgtttgc catttttcca acccctggtt   12240
cccggccaag gcctcatgat tttcagcaat ggctaatagc tgtgcattcc tccatatttt   12300
cctctgttgc ggcttcttgt actctttttg ttgtgctgtg gttgcggatc ccaatgctac   12360
gtactgtttt tggtttccac tggtcagggg caatttttct ttcgaactca cggtgaatta   12420
cacggtgtgc ccaccttgcc tcacccggca agcagccgct gagatctacg aatccggcag   12480
gtctctttgg tgcaggatag ggcatgaccg atgtagtgag gacgatcacg acgaactagg   12540
gttcatggtt ccgcctggcc tctccagcga aggccactta accagtgttt atgcctggtt   12600
ggcgttcctg tctttcagct acacggccca attccatccc gagatatttg ggatagggaa   12660
tgtgagtaaa gtttatgttg acgtcaagca ccaattcatc tgcgccgttc atgacggaca   12720
aaacaccacc ttgccccgcc atgacaacat ttcagccgta tttcagacct actatcaaca   12780
tcaggtcgac ggcggcaatt ggttccacct agaatggctg cgtcccttct tttcctcttg   12840
gttagtttta aatgtttcgt ggtttctcag gcgttcgcct gcaagccatg tttcagttca   12900
agtctttcag acatcaaaac caacaccact gcagcatcag gcttcgttgt cctccaggac   12960
atcagctgcc ttaggtatgg cgactcgtcc tctccgacga ttcgcaaaag ctctcaatgc   13020
cgcacggcga tagggacacc cgtgtatatt accatcacag ccaatgtgtc agacgagaat   13080
tacttacatt cttcagatct cctcatgctt tcttcttgcc ttttctatgc ctctgagatg   13140
agtgaaaagg ggttcaaggt gatatttggc aatgtttcag gcattgtggc tgtgtgtgtc   13200
aactttacca gctacgtcca acatgttagg gagttcaccc aacgctctct ggcggtcgat   13260
catgtgcggc tgcttcattt catgacacct gagaccatga ggtgggcaac cgttttagcc   13320
tgtcttgttg ccatcctttt ggcaatttga atgtttaagt atgttgggga aatgcttgac   13380
cgcgggctat tgctcgcgat tgcctttttt gtggtgtatc gtgccgttct gttttgctgt   13440
gatcgtcaac gccagcagca acagcagctc tcattttcag tcgatttata acttgacgct   13500
atgtgagctg aatggcacag attggctggc tggtaaattt gattgggcag tggagacttt   13560
tgttatcttt cccgtgttga ctcacattgt ttcctatggt gcacttacca ccagccattt   13620
ccttgacaca gttggtctgg ttattgtgtc caccgccggg ttttatcatg ggcggtatgt   13680
cttgagtagc gtctacgcag tctgtgccct ggctgcgttg attcgctttg tcattagatt   13740
tgcgaagaac tgcatgtcct ggcgctactc atgtaccaga tataccaact tccttctaga   13800
taccaagggc aaactctatc gttggcggtc gcctgttatc atagagaaag gggtaaggt    13860
tgaggtcgaa ggtcacctga tcgacctcaa aagagttgtg cttgatggtt ccgtggcaac   13920
tcctttaacc agagtttcag ctgaacaatg gggtcgtccc tagacgactt ttgcaatgat   13980
agcacggctc cgcaaaaggt gcttctggcg ttttccatta cctacacgcc agtgatgata   14040
tatgctctga aggtaagtcg cggccgcctg ctagggcttc tgcacctttt aatctttctg   14100
aattgtgctt tcaccttcgg gtacatgaca ttcgcgaact ttcagagcac aaacagggtt   14160
gcgctcacta tgggagcagt agttgcactt ctttgggggg tgtactcagc catagaaacc   14220
tggaaattca tcacctccag atgccgtttg tgcttgctag gccgcaggta cattctggcc   14280
```

-continued

```
cctgcccacc acgtcgaaag tgtcgcaggc tttcatccga ttgcggcaag tgataaccac  14340
gcatttgtcg tccggcgtcc cggctccact acggttaacg gcacattggt gcccgggttg  14400
aaaagcctcg tgttgggtgg cagaaaagct gttaaacagg gagtggtaaa ccttgtcaaa  14460
tatgccaaat aacaatggca ggcagcaaaa aagaaataag ggggacggcc agccagtcaa  14520
tcagctgtgt cagatgctgg gtaagatcat cgcccagcaa aatcagtcca gaggcagggg  14580
accggggaag aaaaataaaa agaaaaaccc ggagaagccc cattttcctc tagcgaccga  14640
agatgacgtc aggcatcact tcacccctag tgagcggcaa ttgtgtctgt cgtcgatcca  14700
gactgccttt aaccagggcg ctggaacttg taccctgtca gattcaggga ggataagtta  14760
cactgtggag tttagtttgc cgacgcatca cactgtgcgc ctgattcgcg ccacagcatc  14820
accctcagcg tgatgggctg gcattcttga agcacctcag tgttagaatt ggaagaatgt  14880
gtggtggatg gcactgattg acactgtgcc tctaagtcac ctattcaatt agggcgaccg  14940
tgtgggggta aagtttaatt ggcgagaacc atgcggccga aattaaaaaa aaaaaaaaaa  15000
aaaaaaaaaa aaa                                                     15013
```

<210> SEQ ID NO 4
<211> LENGTH: 15444
<212> TYPE: DNA
<213> Artificial Sequence

<400> 4

```
atgacgtata gttgttggct ctatgtcgtg acatttgtat agtcaggagc tgcgaccatt     60
ggtacagccc aaaacttgct gcgcgggaac gcccttccgt gacagccttc ttcaggggag    120
tttaggggtc tatccctagc accttgcttc cggagttgca ctgctttacg gtctctccac    180
ccctttaacc atgtctggga tacttgatcg gtgcacgtgt acccccaatg ccagggtgtt    240
tgtggcggag ggccaagtct actgcacacg atgtctcagt gcacggtctc tccttccttt    300
gaatctccaa gtttctgagc ttggggtgct gggcttattt tataggcccg aagagccgct    360
ccggtggacg ttgccacgtg cattccccac tgtcgagtgc tcccccgccg gggcctgctg    420
gctttctgcg atttttccaa ttgcacgaat gaccagtgga aacctgaact ttcaacaaag    480
aatagtgcgg gtcgcagctg agctctacag agccggtcag ctcacccccg tagtcttgaa    540
gaatctacag gtttatgaac ggggttgccg ttggtacccc atcgttggac ctgttcctgg    600
agtggctgtt tatgccaatt ccttacacgt gagtgacaaa cctttcccgg gagcaactca    660
tgtgttaacc aacctaccgc tcccgcagag gcccaagcct gaagactttt gccccctttga   720
gtgtgctatg gctgacgtct atgacattgg tcatgacgct gtcatgtatg tggccggagg    780
gagagtctcc tgggcccctc gtggcgggga caaaggaaaa tttgaaatag ttcccaagga    840
gttgaagttg attgcgaatc gactccacat ttccttcccg ccccaccacg cagtggacat    900
gtccaagttt gcctttataa gccctgggag tggtgtttcc atgcgggtcg agtaccaaca    960
tggctgtctc cccgctgata ctgtccctga aggaaactgt tggtggcgct tgtttgactt   1020
gcttccaccg gaagttcaga acaaagagat tcgccatgct aaccaactcg gctatcagac   1080
caagcatggt gtcgctggca agtacctaca gcggaggctg caagttaatg gactccgagc   1140
agtaactgac gcgaatggac ctatcgtcat acagtatttt tgtgataggg aaagctggat   1200
ccgccactta agactggtag aagaacctag cctccctggg tttgaggacc tcctcagaat   1260
aagagttgag cccaatacgt tgccattggt tggcgaggat gagaaaatct tccgatttgg   1320
caatcacaaa tggtacggtg ctggaaagag ggcaaggaaa gcacgctttg gtgcggctgc   1380
cacggtcgct caccgcgctt tgcccgctca cgaaacccag caggccaaga agcacgaagt   1440
taccagcgcc aacagggctg agcatctcga gcactattcc ccgcctaccg acgggaactg   1500
```

-continued

```
tggttggcac tgcgtttccg ccattgtcaa ccggattgtg aattccaaat ttgaaaccac   1560
ccttcccgag agagtgagac ctttagatga ctgggctact gacgaggatc ttgtgaatac   1620
tatccaaatc ctcaggctcc ctgcggcctt ggacaggaac ggtgcttgtg tcggcgccaa   1680
gtacgtgctc aagctggaag gtgtgcactg gacagtctct gtggcccctg ggatgacccc   1740
ttctctgctc cccttgaat gtgttcaggg ctgttgtgag cataagagcg gtcttggtcc    1800
cccagatgtg gctgaagttt ccggatttga ccctgcctgc cttaaccgac tggctgaggt   1860
aatgcacttg cctagttgtg tcatcccagc tgctctggct gaaatgtccg acgaccccaa   1920
tcgcccggct tccccagtca ccactgtgtg gactatttcg caattctttg cccattatag   1980
aggaggagag caccctgatc aggtgtgctt agggaaaatc atcagccttt gtcaggtgat   2040
tgaggaatgc tgttgttccc agaacaaaac caaccgggcc accccggaag aggtcgcggc   2100
aaaaattgac cagtacctcc gtgatgcagc aagccttgga gaatgcttag ccaagcttga   2160
gagggctcgc ccgccgagcg cgatggacac ctcctttgat tggaatgttg tgcttcctgg   2220
ggttgaggcg gcgaaccaga cgaccaaaca gctccatgtc aaccagcacc gtgctccggt   2280
tcctgccatg actcaggagc ctttggacaa agactcggtc cctttgaccg ccttctcgct   2340
gtctaattgc tactaccctg cacaaggtga cgaggttcgt caccgtgaga ggctgatctc   2400
cgtgctctct aagttggagg aggttgttcg tgaggaatat gggctcacgc caactggatc   2460
tggcccgcga cccgcactgc cgaacgggct cgacgagctc aaagaccaga tggaagagga   2520
tctgttgaaa ctggtcaacg cccaggcaac ttcagaaatg atggcccggg cagctgagca   2580
ggttgatcta aaagtttggg tcaaaaatta cccacggtgg acaccgccac cccctccacc   2640
aagagttcag cctcgaaaaa caaagtctgc taagagcctg ccagagaaca agcctgtccc   2700
tgctccgcgc aggaaagtca gatctgattg tggcagcccg actttgaggg gcaacaatgt   2760
tcctaacggt tgggaagact tggccgttgg tggtcctctt gatctttcga caccatccga   2820
gccgatgaca cctctgagtg agcctgcact tatgcccgtg ttgcaacata tttctggacc   2880
agtgacgcct ttgagcgtgc cggcccctat tcctgcaccg cgtaaagctg tgtcccgacc   2940
gatggcgccc tcgagtgagc caatttttgt gtctgcaccg cggcaaaaat ttcagcaggt   3000
ggaagaagca aatctggcgg caacaacgct gacataccag gacgaaccta tagatctgtc   3060
agcatcctca cagactgaat atgaggctcc ttccctagca ccactgcaga acataggtac   3120
tctggaggtg ggggggcaag aagctgagga aattctgagt gaaacctcgg atataccgaa   3180
tgacatcaac cctgtgcctg tatcatcaag cagctccttg tcaagcgtta agatcacacg   3240
cccaagacac tcagctcaag ccatcatcga ctcgggcggg ccctgcagtg ggcatctcca   3300
aagggagaaa gaagcgtgcc tccgcatcat gcgtgaggct tgtgatgcga ctaagcttag   3360
tgaccctgcc acgcaggaat ggctttctcg catgtgggat agggtggaca tgctgacttg   3420
gcgcaacacg tctgctttcc aggcgtttcg catcttagac ggcaggcttg agtttcttcc   3480
aaagatgata ctcgagacgc cgccgcccta cccgtgtggg tttgtgatgc tgcctcacac   3540
ccctgcacct tccgtgagtg cagagagcga ccttaccatc ggttcagtcg ccactgaaga   3600
tattccacgc atcctcggga aaatagaaaa caccagtgag atgatcaacc agggaccctt   3660
ggcatcctct gaggaaaaac cggcatacaa ccaacccgct aaggactccc tgatatcgtc   3720
gcgggggttt gacgagagca cagcagctcc gtccgcaggt acgggtggcg ccggcttgtt   3780
tactgatttg ccaccttcag acggtgtaga tgcggacggg ggggggccgc tgcagacggt   3840
gaaaaagaac gctgaaaggc tcctcgaccg attgagccgt caggttttta acctcgtctc   3900
```

-continued ccatctccct gttttcctct cacacctctt caaatctgac agtggttatt ctccgggtga 3960
ttggggtttt gcagctttta ctctattttg cctcttttta tgttacagct acccattctt 4020
tggtttcgct cccctttgg gtgtgtttc tgggtcttct cggcgcgtgc gcatgggggt 4080
ttttggctgc tggttggctt ttgctgttgg tttgttcaag cctgtgtccg acccagtcgg 4140
cactgcttgt gagtttgatt cgccagagtg taggaatgtc cttcattctt ttgagcttct 4200
caaaccttgg gaccctgttc gcagccttgt tgtgggcccc gtcggtctcg gtcttgccat 4260
tcttggcagg ttactgggcg gggcacgcta catctggcat tttctgctta ggcttggcat 4320
tgttacagac tgtatcctgg ctggagctta tgtgctttct caaggtaggt gtaaaaagtg 4380
ctggggatct tgcataagaa cagctcctaa tgagattgcc tttaacgtgt tccctttac 4440 acgtgcgact aggtcgtcac tcatcgacct gtgcaatcgg ttttgtgcgc caaagggcat 4500
ggaccctatt ctcctcgcca ctgggtggcg tgggtgctgg accggccgaa gccccattga 4560
acaaccctct gaaaaaccca tcgcgtttgc ccagttggac gaaaagagga ttacggccag 4620
gaccgtggtc gcccagcctt atgaccccaa ccaagccgta aagtgcttgc gggtgttaca 4680
ggcgggcggg gcgatggtgg ctgaggcagt cccaaaagtg gtcaaagttt ccgctattcc 4740
attccgagcc cccttttttc ccaccggagt gaaagttgac cctgagtgta ggatcgtggt 4800
tgaccccgac acttttacta cagccctccg gtccggctat tccaccacaa acctcgttct 4860
tggtgtgggg gactttgccc agctgaatgg attaaaaatc aggcaaattt ccaagccttc 4920
gggaggaggc ccgcacctca ttgctgccct acatgttgcc tgctcgatgg cgttgcacat 4980
gcttgctggg gtttatgtaa ctgcagtggg gtcttgcggt accggcacca acgatccgtg 5040
gtgcaccaac ccgtttgccg tccctggcta cgggcctggt actctttgca cgtccagatt 5100
gtgcatctcc caacatggcc ttaccctgcc cttgacagca cttgtggcag gattcggtct 5160
tcaggaaatt gccttggttg ttttgatttt cgtttccatc ggaggcatgg ctcacaggtt 5220
gagttgcaag gctgacatgc tgtgcgtttt acttgcaatc gccagctatg tttgggtgcc 5280
ccttacctgg tttctttgtg tgtttccttg ctggttgcgc tggttctctt tgcatcccct 5340
caccatccta tggttggtgt ttttcttgat ttctgtaaat gtgccttcgg gaatcttggc 5400
tgtggtgttg ttagtttctc tttggctctt aggtcgttac actaatgttg ctggtcttgt 5460
caccccatat gacattcatc atcacaccag tggcccccga ggtgttgccg ccttggctac 5520
tgcaccggat gggacctact tggccgccgt tcgccgtgct gcgttgaccg gtcgtaccat 5580
gctgtttacc ccgtctcagc ttgggtccct tcttgagggt gctttcagaa ctcaaaagcc 5640
ctcactgaac accgtcaatg tggtcggatc ctctatgggc tccggcgggg tgttcaccat 5700
cgacgggaaa attaagtgcg taacagccgc acatgtcctt acgggtaatt cagctagggt 5760
ttccggggtc ggcttcaacc aaatgcttga ttttgatgtg aaaggggact tcgccatagc 5820
tgattgcccg aattggcaag gagctgcccc caagacccaa ttctgcgagg atggatggac 5880
tggccgtgcc tattggctga catcctctgg agtcgaaccc ggtgtcattg ggaatggatt 5940
cgccttctgc ttcaccgcgt gcggcgattc tggatccccg gtgattaccg aagccggtga 6000
gcttgtcggc gttcacacag gatcaaacaa acaaggagga ggcatagtca cacgcccctc 6060
aggccagttt tgtaatgtgg cgcccatcaa gctgagcgaa ttgagtgaat tcttcgctgg 6120
acctaaggtc ccgctcggtg atgtgaagat tggcagccac ataattaaag acgtatgcga 6180
ggtaccttca gatctttgcg ccttgctcgc tgccaaaccc gaactggaag gaggcctctc 6240
caccgtccaa cttctgtgtg tgtttttcct cctgtggaga atgatgggac atgcctggac 6300
gcccttggtt gctgtggggt tttttatctt gaatgaggtt ctcccagctg tcctggtccg 6360

-continued

```
gagtgtcttc tcctttggta tgtttgtgct atcttggctt acaccatggt ctgcgcaagt   6420
cctgatgatc aggcttctaa cagcagctct taacaggaac agggggtcac tcgccttcta   6480
cagcctcggt gcagtgaccg gatttatcgc agatcttgca gcaactcagg ggcatccgct   6540
gcaggcagtg atgaacttaa gcacctatgc cttcctgcct cggatgatgg ttgtgacctc   6600
accagtccca gtgcttgctt gtggtgttgt gcacctcctt gccataattt tgtacctgtt   6660
taagcaccgt tgcctgcatt atgtccttgt tggcgatgga gtgttctcta aagccttctt   6720
cttgcgatac tttgccgaag ggaagttgag ggaaggggtg tcgcagtcct gcgggatgaa   6780
tcacgagtca ctgactggtg ccctcgctat gagactcaat gacgaagact tggacttcct   6840
tacgaaatgg actgatttta agtgctttgt ttctgcgtcc aacatgagga atgcagcggg   6900
ccaattcatc gaggctgcct atgcaaaagc acttagaatt gagcttgccc agttagtaca   6960
ggttgataag gttcgaggta ctttggccaa acttgaagcc tttgctgata ccgtggcacc   7020
ccagctctcg cccggtgaca ttgttgttgc tcttggccac acgcctgttg gcagtatctt   7080
cgacctaaag gttggcagta ccaagcatac cctccaggcc attgagacca gagtccttgc   7140
cgggtccaaa atgaccgtgg cgcgtgtcgt tgatccaacc cccacgcccc cacccgcacc   7200
cgtgcccatc cccctcccac cgaaagtcct ggagaacggc cccaacgcct gggggatga    7260
ggaccggttg aataagagga agagacgcag gatggaagcc gtcggcatct ttgttatggg   7320
tgggaagaag taccaaaaat tttgggacaa gaattccggt gatgtgtttt acgaggaggt   7380
ccatgataac acagatgcgt gggagtgcct cagagttggt gaccctgccg actttgaccc   7440
tgagaaggga actctgtgtg ggcatactac cattgaagac aaggcttata atgtctacac   7500
ctccccatct ggcaggaagt tcctggtccc cgtcaaccca gagagcggaa gagcccaatg   7560
ggaagctgca aagctttccg tagagcaggc ccttagcatg atgaatgtcg acggtgagct   7620
gacagccaaa gaactggaga aactgaaaag aataattgac aaactccagg gcctaactaa   7680
ggagcagtgt ttaaactgct agccgccagc ggcttgaccc gctgtggtcg cggcggcttg   7740
gttgttactg agacagcggt gaaaatagtt aaatttcaca accggacctt caccctagga   7800
cctgtgaatt taaaagtggc cagtgaggtt gagctaaaag acgcagtcga gcataaccaa   7860
cacccggttg caagaccggt tgatggtggt gttgtgctcc tgcgctccgc agttccttcg   7920
cttatagacg tcttgatctc tggcgctgat gcatctccta agttactcgc ccaccacggg   7980
ccgggaaaca ctgggatcga tggttcgctt tgggattttg aggccgaggc caccaaagag   8040
gaaattgcac tcagtgcgca aataatacag gcttgtgaca ttaggcgcgg cgacgcaccc   8100
gaaattggtc ttccttataa gctgcaccct gttaggggca accctgagcg ggtaaaaggg   8160
gttttacaga atacaaggtt tggagacata ccttataaaa cccccagtga cactgggagc   8220
ccagtgcacg cggctgcctg cctcacgccc aatgccactc cggtgactga cggtcgttcc   8280
gtcttggcta cgaccatgcc ctccggtttt gagttgtatg taccgaccat tccagcgtct   8340
gtccttgatt atcttgattc caggcctgat tgccccaaac agttgacaga gcacggctgt   8400
gaggatgccg cattaagaga cctctccaag tatgacttgt ccacccaagg ctttgtcttg   8460
cctggagttc ttcgccttgt gcgtaagtac ctgtttgctc atgtgggtaa gtgcccgcct   8520
attcatcggc cttccactta ccctgccaag aattccatgg ctggaataaa tgggaacagg   8580
tttccaacca aggacattca gagcgtccct gaaatcgacg ttttgtgcgc acaggccgtg   8640
cgagaaaact ggcaaactgt tactccttgt accctcaaga agcagtattg cgggaagaag   8700
aagactagga caatactcgg cactaataac ttcattgcgc tggcccaccg ggcagcattg   8760
```

-continued

```
agtggtgtca cccagggctt catgaaaaaa gcgtttaact cgcccatcgc actcgggaaa    8820
aacaaattca aggagctgca gactccggtc ttgggcagat gtcttgaagc tgaccttgca    8880
tcctgtgacc gatccacacc cgcaattgtc cgctggtttg ccgccaatct tctttatgaa    8940
cttgcctgtg ctgaggagca tataccatcg tacgtgttga actgctgcca cgacttactg    9000
gtcacgcagt ccggcgcggt gactaagaga ggtggcctat cgtctggcga cccgattact    9060
tctgtatcaa acaccattta cagcttggtg atatatgcac agcacatggt actcagttat    9120
tttaaaagtg gtcaccccca tggccttctg tttctacaag accagctaaa gtttgaggac    9180
atgctcaagg ttcagcccct gatcgtctat tcggacgacc tcgtgctgta cgccgagtct    9240
cccaccatgc caaactacca ctggtgggtt gaacatctga acctgatgct gggttttcag    9300
acggacccaa agaagacagc tataacagac tcgccatcat tttgggttg taggataata    9360
aatggacgcc agttagtccc caaccgtgac aggatcctcg cggccctcgc ctaccatatg    9420
aaggcaaaca atgtttctga atactacgcc tcggcggctg caatactcat ggacagttgt    9480
gcttgtttgg agtacgatcc tgagtggttt gaagagctcg tggttgggat ggcgcagtgc    9540
gcccgcaagg acggctacag ttttcctggc ccgccgttct tcttgtccat gtgggaaaaa    9600
ctcaggtcca atcatgaggg gaagaagtct agaatgtgcg ggtactgtgg ggccccagct    9660
ccgtatgcca ctgcctgtgg ccttgatgtt tgtatttatc acacccactt ccaccagcat    9720
tgtccagtca taatctggtg tggccatccg gcgggttctg gctcttgtag tgagtgcaaa    9780
ccccccctag ggaaaggcac aagccctcta gatgtggtgt tagaacaagt cccgtacaag    9840
cctccacgaa ctgtaatcat gcatgtggag cagggtctca cccctcttga cccaggcaga    9900
taccagactc gccgcggatt agtctccgtt aggcgtggca tcaggggaaa cgaaatcgac    9960
ctaccagacg gtgattatgc tagtaccgcc ttgctcccca cttgtaaaga tatcaacatg   10020
gtcgctgtcg cttccaatgt gttgcgcagc aggttcatca tcggtccacc cggtgctggt   10080
aaaacatact ggctccttca acaggtccag gatggtgatg tcatttacac gccaactcat   10140
cagaccatgc ttgacatgat caaggctttg ggacgtgcc ggttcaacgc cccagcaggc    10200
acaacgctgc aattccctgc tccctcccgt accggcccgt gggttcgcat cctggccggc   10260
ggttggtgtc ctggcaagaa ttccttcctg gatgaagcag cgtattgtaa tcaccttgat   10320
gtcttgaggc ttcttagcaa aactaccctc acctgtctgg gagatttcaa acaactccac   10380
ccagtgggtt ttgattctca ttgctatgtt tttgacatca tgcctcagac tcaactgaag   10440
accatctgga ggtttggaca gaatatctgt gatgccattc agccagatta cagggacaaa   10500
cttgtgtcca tggtcaacac aacccgtgta acctacgtgg aaagacctgt caagcatggg   10560
caggtcctca ccccttacca cagggaccga gaggacggcg ccatcacaat tgactccagt   10620
caaggcgcca catttgatgt ggttacattg catttgccca ctaaagattc actcaacagg   10680
caaagagccc ttgttgctat caccagggcg agacatgcta tctttgtgta tgacccacat   10740
aggcaactgc agagcatgtt tgatcttcct gcaaaaggca cacccgtcaa ccttgccgtg   10800
caccgtgacg agcagctgat cgtactagat agaaataaca aagagtgcac ggttgctcag   10860
gctctaggca atggggacaa attcagggcc acagacaagc gcgttgtaga ttctctccgc   10920
gccatttgtg cagatcttga agggtcgagc tccccgctcc ccaaggtcgc acataacttg   10980
ggattttatt tctcacctga tttgacacag tttgctaaac tcccggcaga acttgcaccc   11040
cactggcccg tggtgacaac ccagaacaat gaaaagtggc cagacaggct ggttgccagc   11100
ctccgcccta tccataaata tagccgcgca tgcattggag ccggctatat ggtgggccct   11160
tcggtgtttc taggcacccc tggggttgtg tcatactatc tcacaaaatt tgttaagggg   11220
```

-continued gaggctcagg tgcttccgga gacagtcttc agcaccggcc gaattgaggt agattgccgg 11280
gagtatcttg atgatcggga acgagaagtt gctgagtccc tcccacatgc cttcattggc 11340
gacgtcaaag gcactaccgt tgggggatgt caccatgtca cctctaaata ccttccgcgc 11400
ttccttccta aggaatcagt tgcggtggtt ggggtttcga gccccgggaa agccgcaaaa 11460
gcagtctgca cattaacaga tgtgtatctc ccagaccttg aagtttacct ccacccagag 11520
acccaatcca agtgctggaa aataatgttg gacttcaagg aagtccgact gatggtctgg 11580
aaagacaaaa cggcctattt tcaacttgaa ggccgccatt tcacctggta tcagcttgca 11640
agctatgcct cgtacatccg agttcctgtt aactctacgg tgtatttgga cccctgcatg 11700
ggccctgccc tttgcaacag aagagttgtc gggtccactc attgggggc tgacctcgca 11760
gtcacccctt atgattatgg tgccaaaatc attctgtcta gtgcatacca tggtgaaatg 11820
cctcctgggt acaaaatcct ggcgtgcgcg gagttctcgc ttgacgaccc agtgaggtac 11880
aaacacacct gggggtttga atcggacaca gcgtatctgt acgagttcac cggaaacggt 11940
gaggactggg aggattacaa tgacgcattt cgtgcgcgcc agaaagggaa aatttataag 12000
gccactgcca ccagcatgag gtttcatttt cccccgggcc ccatcattga accaacttta 12060
ggcctgaact gaaatgagat gggggctatg caaagccttt tctacaaaat tggccaactt 12120
tttgtggatg ctttcacgga atttttggtg tccattgttg atatcatcat atttttggcc 12180
attttgtttg gcttcaccat cgccggttgg ctggtggtct tctgcatccg attggtttgc 12240
tccgcggtac tccgtgcgcg ccctaccatt caccctgagc aattacagaa gatcctatga 12300
ggcctttctt tctcagtgcc gggtggacat tcccacctgg ggaaccaaac atcccttggg 12360
gatactttgg caccataagg tgtcaaccct gattgatgaa atggtgtcgc gtcgaatgta 12420
ccgcatcatg gaaaaatcag gacaggctgc ctggaaacag gttgtgagcg aggctacgct 12480
gtctcgcatc agtggtttgg atgtggtggc tcattttcag catcttgccg ccattgaagc 12540
cgagacctgt aaatatttgg cctctcggat gcccatgcta cacaacctgc gcatgacagg 12600
gtcaaatgta accatagtgt ataatagtac tttgaatcag gtgttagcaa tcttcccgac 12660
ctctgaatcc cggccaaagc ttcatgattt tcaacaatgg ttaataactg tacattcctc 12720
catattttcc tccgttgtgg cttcctgtac tctttttgtt gtgctgtggt tgcgaattcc 12780
aatgctacgt actgtttttg gtttccactg gttaggggca atttttcttt cgaactcaca 12840
gtgaattaca cggtgtgccc accttgcctc acccggcaag cagccgctga gatctacgaa 12900
cccggcaggt ctctttggtg caggataggg catgatcgat gtagcgagga cgatcatgac 12960
gaactagggt tcttggttcc gcctggcctc tccagcgaag gccacttgac cagtgtttac 13020
gcctggttgg cgttcctgtc cttcagctat acagcccagt tccatcccga gatatttggg 13080
atagggaatg tgagtaaaat ttatgttgac atcaagcacc aattcatctg cgccgaacac 13140
gacgggcaga acgccaccct gcctcgccat gacaacattt cagccgtgtt tcagacctac 13200
taccaacatc aggtcgatgg cggcaattgg tttcacctgg aatggctgcg ccccttcttt 13260
tcctcttggt tggttttaaa tgtttcgtgg tttctcaggc gttcgcctgc aagccatgtt 13320
tcagttcgag tctttcagac atcaaaacca acaccaccgc agcaccaaat tttgttgtcc 13380
tccaggacat cagctgcctt aggcatggcg acccgtcctc tccggcgatt cgcaaaagct 13440
ctcagtgccg cacggcgata ggaacacccg tgtatatcac catcacagcc aatgtgacag 13500
atgagaatta tttacattct tctgatctcc tcatgctttc ttcttgcctt ttctatgctt 13560
ctgagatgag tgaaaagggg ttcaaggtgg tattcggcaa tgtgtcaggc atcgtggctg 13620

-continued

```
tgtgtgtcaa ctttaccagt tacgtccaac atgtcaagga gtttacccaa cgctccttgg  13680

tggtcgagca tgtgcgactg cttcatttca tgacacctga aaccatgagg tgggcaaccg  13740

ttttagcctg tctttttgcc attctgttgg caatttgaat gtttaagtat gttggggaaa  13800

tgcttgaccg cgggctgttg ctcgccgttg cttttttttgt ggtgtatcgt gccgtcttgc  13860

tttgttgcgc ccgtcaacgt cgacgggaac gacagctcaa agttacagct gatttacaac  13920

ttgacgctat gtgagctgaa tggcacagat tggctggctg gtagatttga ctgggcagtg  13980

gagtgttttg tcatttttcc cgtgttgact cacattgtct cctatggtgc cctcactact  14040

agccatttcc ttgacacagt cggtctggtc actgtgtctg ccgccgggtt ccttcatgaa  14100

cggtatgttt tgagtagcat ctacgcggtc tgtgccctgg ctgcgttgat ttgcttcgtc  14160

attaggcttg cgaagaactg catgtcctgg cgctactcgt gtaccagata taccaacttc  14220

cttttggaca ccaaggggag actctatcgt tggcgatcgc ccgtcatcat agagaaaaag  14280

ggtaaagttg aggttgaagg tcatttgatc gacctcaaaa gagttgtgct tgatggttcc  14340

gtggcaaccc ctataaccaa aatttcagcg gaacaatggg gtcgtcctta gatgacttct  14400

gccatgatag cacggctcca caaaaggtgc ttttggcgtt ttccattacc tatacaccag  14460

tgatgatata tgccctaaag gtaagtcgcg gccgactgct agggcttttg cacctttttga  14520

tctttctgaa ctgtgctttc accttcgggt atatgacatt cacgcacttt cagagtacaa  14580

acaaggtcgc gctcactatg ggagcagtag ttgcactcct ttggggggtg tactcagcca  14640

tagaaacctg gaaattcatc acctccagat gccgtttgtg cttgctaggc cgcaagtaca  14700

ttctggcccc tgcccaccac gttgagagtg ccgcaggctt tcatccgatt gcggcaaatg  14760

ataaccacgc atttgtcgtc cggcgtcccg gttccactac ggtcaacggc acattggtcc  14820

ccgggttgaa aagcctcgtg ttgggtggca gaaaagctgt caaacaggga gtggtaaacc  14880

ttgttaaata tgccaagtaa caacggcagg cagcagaaaa aaagaaaggg ggatggccag  14940

ccagtcaatc agctgtgtca gatgctgggt aaaattattg cccagcaaaa tcagtccagg  15000

ggcaagggac cgggaaagaa aaataacaag aaaaacccgg agaagcccca ttttcctcta  15060

gcgactgaag atgatgtcag acatcacttt accccgagtg agcgacaatt gtgtctgtcg  15120

tcaatccaga ctgccttcaa tcagggcgct ggaacttgta ccctgtcaga ttcaggcagg  15180

ataagttaca ctgtggagtt tagtttgccg acgcatcaca ctgtgcgcct gatccgcgct  15240

acagcatcac cctcagcatg atgagctggc attcctgggt atcccagtgt ttgaattgga  15300

agaatgtgtg gtgaatggca ctgattgaca ttgtgcttct aagtcaccta ttcaattagg  15360

gcgaccgtgt gggagtagaa tttaattggc gagaaccacg cggccgaaat taaaaaaaaa  15420

aaaaaaaaaa aaaaaaaaaa aaaa                                         15444
```

<210> SEQ ID NO 5
<211> LENGTH: 15413
<212> TYPE: DNA
<213> Artificial Sequence

<400> 5

```
cgcccgggca tgtgttggct ccatgccacg acatttgtat tgtcaggagc tgtgaccact     60

ggcacagccc aaagcttgct gcacagaaac acccttctgt gacagcctcc ttcaggggag    120

tttaggggtc tgtccctaac accttgcttc cggagttgca ctgctttacg gtctctccac    180

cctttaacca tgtctgggat acttgatcgg tgcacgtgca cccccaatgc cagggtgttt    240

atggcggagg gccaagtcta ctgcacacga tgtctcagtg cacggtctct ccttcctctg    300

aatctccaag tttctgaact aggggtgcta ggcctatttt acaggcccga agagccactc    360

cggtggacgt tgccacgtgc attccccact gttgagtgct cccccgccgg ggcctgctgg    420
```

-continued ctttctgcaa tttttccaat tgcacgaatg actagtggaa atctgaactt ccaacaaaga 480
atggtacggg tcgcagctga gctttacaga gccggccagc tcacccctgc agtcttaaag 540
gctctacaag tttatgaacg gggctgccgc tggtacccca ttgtaggacc tgtccctgga 600
gtggccgttt acgccaactc cttacatgtg agtgataaac ctttcccggg agcaactcac 660
gtgttaacca acctaccgct cccgcaaaga ccaaaacctg aagacttttg ccccttttgag 720
tgtgccatgg ctaccgtcta tgacatcggt cgtgacgccg tcatgtatgt aaccgaggga 780
aaagtctcct gggcccctcg tggtggggat gaaacaagat ttgaaactgt ccccggtggg 840
ttgaagttga ttgcggacca actctactcc tccttcccgc cccatcacac ggtggacata 900
tctaagttcg ccctcacagc ccctgggcgc ggtgtatcca tgcgggttga acgccagtgt 960
ggctgcctcc ccgctgacac tgtccctgaa ggcaactgtt ggtggagctt attcgattca 1020
ctcccactgg aagtccagaa caaagaaatt cgccatgcta accaatttgg ctaccaaacc 1080
aagcatggcg tctccggcaa gtaccttcag cggaggctgc aagttaatgg cctccgagca 1140
gtaactgact tgaatggacc tattgtcata cagtacttct ccgttagaga gagttggatc 1200
cgccacttga aactggcgga agaacccggc ctccctgggt ttgaggacct cctcagaata 1260
agggttgaac ccaacacatc gccattggct aacgaggatg agaaaatctt ccgatttggc 1320
agccataagt ggtacggcgc tgggaggaga gcaaggaaag cacgccacag tgcaattgct 1380
gcggtcgcag gccgcgcttc gtctgctcgt gaaatccagc aggccaagaa gcatgaggct 1440
gctgacgcca ataaggttga gcacctcaaa cgctactccc cgcccgccga agggaattgc 1500
ggttggcact gtatttctgc catcgccaat cgaatggtga attctaaatt taaaaccacc 1560
cttcccgaaa gagtgaggcc ttcagatgac tgggccactg atgaggatct tgtgaatgtc 1620
atccaaatcc tcaggctccc tgcggccttg gacaggaacg gtgcttgtgc cagcgccaag 1680
tacgtactta agctagaagg tgagcattgg actgtcactg tgacccctgg gatgtcccct 1740
tctttgctcc ctcttgaatg tgttcagggc tgttgtgagc ataagggcgg tctaggtacc 1800
ccagatgcag tcgaggtttt cggatttgac cctgcctgcc tcaactggtt ggctgaggtg 1860
atgcacctgc ctagcagtgc tatcccagcc gctctggccg aaatgtccgg tgattccggt 1920
cgttcggctt ccccggtcac caccgtgtgg accgtttcgc agttctttgc ccgccacaat 1980
ggagggagtc accctgacca agtgcgttta gggaaaatta ttagcctttg tcaggtgatt 2040
gaggactgct gctgttccca gaacaaaacc aaccgggtta ccccggagga ggtcgcagca 2100
aagattgact tgtacctccg tggagcgaca agtcttgaag aatgcttggc caggcttgag 2160
aaagctcgcc cgccacgcgt aatggacacc tcctttgatt gggatgttgt gctccctggg 2220
gttgaggcgg caactcagac gaccgaattg ccccaggtca accagtgtcg tgctttggtc 2280
cctgttgtaa ctcaaaagtc cttggacaac aactcggttc ccttgaccgc cttttcactg 2340
gctaactact actaccgtgc gcaaggtgaa gaagttcgtc accgtgaaag actaaccgcc 2400
gtgctctcca aattggaagg ggttgtccga gaggaatatg ggctcatgcc aaccgggcct 2460
ggtccacggc ccacattgcc acgcgggctc gacgaactca aagatcagat ggaagaggac 2520
ttgctgaaac tggctaacgc ccagacgact tcggagatga tggcctgggc agtcgagcag 2580
gtcgacctaa aaacttgggt caagaactac ccgcggtgga caccaccacc ccctccgcca 2640
aaagttcagc ctcgaaaaac gaagtctgcc aagagcttgc tagagagaaa gcctgtcccc 2700
gccccgcgca ggaaggttgg gaccaattgt ggcagcccga tttcattggg cgacaatatc 2760
cctaacagtt gggaagattt ggctgttggt ggcccctatg atcccccgac cccacctgag 2820

-continued

```
ccggcaacac cttcaggtga gctggtggtt gtgtccacac cgcaatgcat cttcaggccg   2880
gcgacaccct cgagtgagcc ggctctaatt cccgcatccc gcggggctgt gtctcgaccg   2940
gtgacaccct tgagtgagcc gatccctgtg cccgcaccgc ggcgtaagtt tcagcaggtg   3000
aaaagattga gttcggcagc ggtaaccccg ccgtaccagg acgagcccct aaatttgtct   3060
gcttcctctc aaactgaatt tgaggccccc tccctagcac cgccgcagag cgagggtgtt   3120
ttgggagtga aggggcagga agctgaggag gccctgagtg aaatctcgga catgtcgggc   3180
ggcattaaac ctgcgtccgt atcatcaagc agctccttgt ccagcgtgag agtcacacgc   3240
ccaaaatact cagctcaagc catcatagac ttgggcgggc cctgcagtgg gcatctccaa   3300
gaggtaaagg aagcatgcct cggaatcatg cgcgaggcat gtgatgcgac taagcttgat   3360
gaccctgcta cgcaggaatg gctttcccgc atgtgggacc gggtggacat gctgacttgg   3420
cgcaacacgt ctgcctacca ggcgtttcgt accttagatg gcaggttaaa gttcctccca   3480
aaaatgatac tcgagacacc gccgccctat ccgtgtgagt ttgtgatgat gcctcactcg   3540
cctgcacctt ccgtaggtgc ggagagtgac cttaccattg gctcagtcgc tactgaagat   3600
gttccacgta tcctcgagaa aatagaaaat gtcggcgaga tgaccaacca gggacccttg   3660
gccttctccg aggataaacc ggtggatgac cagcttgcca aagacccccg gatatcgtcg   3720
cagagtcctg acgagagcac atcagctccg cccacaggca caggaggcgc cggttcattt   3780
accgatttgc cgccttcaga cggcgcggat gcggacgggg gggggccgtt tcggacgata   3840
aaaagaaaag ctgaagggct ctttgaccga ctgagccgac aggtttttaa cctcgtctcc   3900
catctccctg ttttcttctc acgccttttc aacccgggcg gtagttattc tccgggtgat   3960
tggggttttg cagcttttac tctattgtgc ctccttttat gctacagtta tccagcattt   4020
ggtattgctc ccctcttggg tgtgttttct gggtcttctc ggcgcgtccg aatgggggtt   4080
tttggctgct ggttggcttt tgctgttggt ctgttcaagc ctgtgtccga cccagtcggc   4140
gctgcttgtg agtttgattc gccagagtgt agaaacatcc ttcattcttt tgagcttctc   4200
aaaccttggg accctgttcg cggccttgtt gtgggccccg tcggtctcgg tcttgccatt   4260
cttggcaggt tactgggcgg ggcacgctgc atctggcact tttgcttag gcttggcatt    4320
gttgcagact gtgtcttggc tggagcttat gtgctttctc aaggcaggtg taaaaagtgc   4380
tggggatctt gtataagaac tgctcctagt gaggtcgctt ttaatgtgtt tccttttaca   4440
cgtgcgacca ggtcgtcgct tactgacctg tgcgatcggt tttgtgcgcc aaaaggcatg   4500
gaccccattt ttctcgccac tgggtggcgc gggtgctggg ccggccgaag ccccattgag   4560
caaccctctg aaaaacccat cgcgtttgcc cagttggatg aaaagaagat tacggctagg   4620
actgtcgtcg cccagcctta tgaccctaac caagccgtaa agtgcttgcg ggtattgcag   4680
gcgggtgggg caatggtagc tgaggcagtc ccaaaagttg tcaaggtttc cgctgtccca   4740
ttccgagccc ccttctttcc caccggagtg aaagttgacc cagaatgcag ggttgtggtt   4800
gaccccgaca ctttcaccgc agctctccgg tctggctact ccaccacaaa cctcgtcctt   4860
ggtacagggg actttgccca gctgaatgga ttgaaaatca ggcagatttc caagccttca   4920
ggaggaggcc cacacctcac ggctgccctg catgttgctt gctcgatggc tttgcacatg   4980
cttgttggga tttatgtgac tgcggtgggt tcttgcggca ccggcaccaa cgacccgtgg   5040
tgcgctaacc cgtttgccgt ccctggctac ggacctggct ctctttgcac gtccaggttg   5100
tgcatttccc aacatggcct taccctgccc ttgacagcac tcgtggcggg attcggcatt   5160
caagaaattg ccttggtcgt tttgattttt gtttccatcg gaggcatggc tcacaggtta   5220
agttgcaagg ctgacatgct gtgtgttttg cttgcaattg ccagctatgt ttgggtacct   5280
```

-continued

```
cttacctggt tgctttgtgt gtttccttgc tggttgcgct gtttttcttt gcatcccctc   5340
accatcctat ggttggtttt tttcttgatt tctgtgaata tgccttcagg aatcttggcc   5400
atggtgctgt tggtttctct ttggcttctt ggtcgttata ctaatgttgc tggtcttgtt   5460
acccccctacg acattcatca ttacactagt ggcccccgcg gtgttgccgc cttggctacc   5520
gcaccagatg ggacctactt ggccgctgtc cgccgtgctg cgttaaccgg ccgtaccatg   5580
ctgtttaccc cgtcccagct tgggtctctt cttgagggtg ctttcagaac tcgaaaaccc   5640
tcactgaaca ccgtcaatgt ggtcgggtcc tccatgggct ctggcggggt gttcaccatt   5700
gacggaaaaa ttaagtgcgt aactgccgca catgtcctta cgggcaattc agctaggatt   5760
tccggggtcg gcttcaatca aatgcttgac tttgacgtaa agggagattt cgccatagct   5820
gattgcccga attggcaagg ggttgccccc aagacccaat tctgcaagga tggatggact   5880
ggccgtgcct attggctgac atcctctggc gtcgaacccg gcgtcattgg aaaaggattc   5940
gccttctgct tcactgcgtg cggcgattcc gggtccccag tgatcaccga ggccggtgag   6000
cttgtcggcg ttcacacggg atcaaataaa caaggaggag gcatcgttac gcgcccctca   6060
ggccagtttt gtaatgtggc acccatcaaa ctaagcgaat taagtgaatt ctttgctggg   6120
cctaaggtcc cgctcggtga tgtaaaggtt ggcagccaca taattaaaga cataggcgag   6180
gtgccctcag atctttgtgc cttgcttgct gccaaacctg aactggaagg gggcctctcc   6240
accgtccaac ttctttgtgt gtttttcctc ctgtggagga tgatgggaca tgcctggacg   6300
cccttggttg ctgtgggttt ctttatcctg aatgaggttc tcccagccgt cctggtccgg   6360
agtgttttct cctttggaat gtttgtgcta tcctggctca cgccatggtc tgcgcaagtt   6420
ctgatgatca gacttctaac agcagccctt aacaggaaca gatggtcact tgccttttc   6480
agtcttggtg cagtgaccgg ttttgtcgca gaatttgcgg ctactcaggg gcatccgttg   6540
caggctgtga tgaatttgag cacctatgca ttcctgcctc ggatgatggt tgtgacctca   6600
ccggccccag tgatcgcgtg tggtgtcgtg cacctacttg ccatcatttt gtacttgttt   6660
aagtaccgcg gcctgcacca aatccttgtt ggcgacggag tgttctctgc ggctttcttc   6720
ttgcgatact ttgccgaggg taagttaagg gaaggggtgt cgcaatcctg tgggatggat   6780
catgagtctc tgactggtgc cctcgctatg agactcagtg acgaggactt ggatttcctt   6840
gcgaaatgga ctgattttaa gtgctttgtt tctgcgtcca acatgaggaa tgcagcgggt   6900
caatttattg aggctgccta tgctaaagca cttagaatgg agcttgccca gttggtgcag   6960
gttgacaaag ttcgaggtac tttggccaaa ctcgaagctt ttgctgatac cgtggcaccc   7020
cagctctcgc ccggtgacat tgttgttgct ctcggccata cgcctgttgg cagtatcttc   7080
gacctaaagg ttggtagcac caagcatact ctccaagcca ttgagaccag agtccttgct   7140
gggtccaaaa tgaccgtggc gcgcgtcgtc aacccgaccc ccacgccacc acccgcaccc   7200
gtgcccatcc ccctcccacc gaaagtcctg gagaatggcc ccaacgcttg gggggatgag   7260
gaccgtttga ataagaagaa gaggcgcagg atggaagccc tcggcatcta cgtcatgggc   7320
gggaaaaagt accagaaatt ctgggacaag aattccggtg atgtgtttta tgaggaggtc   7380
cataataaca tagatgagtg ggagtgtctc agagttggcg atcctgccga ctttgaccct   7440
gagaagggaa ctctgtgtgg acatgtcacc attgaagaca aggcttaccg tgtttacgcc   7500
tccccatctg gtaagaggtt cttggtcccc gtcaacccag aaaatggaag agtccaatgg   7560
gaagctgcaa agctttctgt ggagcaggcc cttggcatga tgaacgtcga cggtgagttg   7620
actgccaaag aactggagaa actaaaaaga ataattgaca aactccagag cctgactaag   7680
```

-continued

```
gagcagtgtt taaactgcta gccgccagcg gcttgacccg ctgtggtcgc ggcggcttgg    7740
ttgttactga aacagcggta aaaatagtca aatttcacaa ccggaccttc accctgggac    7800
ctgtgaattt aaaagtggcc agtgaggttg agctaaaaga cgcgattgag cacaatcaac    7860
acccggttgc gagaccggtc gatggtggtg ttgtgcttct gcgttccgcg gttccttcgc    7920
ttatagacgt cttgatctcc ggtgctgatg catctcccaa gttacttgcc caccacgggc    7980
cgggaaacac tgggatcgat ggcacgctct gggattttga gtccgaagcc actaaagagg    8040
aagtcgcact tagtgcgcaa ataatacagg cttgtgacat taggcgcggc gacgcccctg    8100
aaattggtct tccttacaag ctgtaccctg ttaggggtaa ccctgagcga gtaaaagggg    8160
ttctacaaaa tacaaggttt ggagacatac cttacaaaac ccccagtgat actggaaacc    8220
cagtgcacgc ggctgcctgc cttacgccca atgccactcc ggtgactgat gggcgctccg    8280
ttttggccac gaccatgccc tccgggtttg agttgtatgt accaaccata ccagcgtctg    8340
tccttgatta ccttgattcc agacctgact gccctaaaca gctgacagag cacggctgtg    8400
aagatgccgc actaagagac ctctccaaat atgacttgtc cacccaaggc tttgttttac    8460
ctggggttct tcgccttgta cggaaatacc tgtttgccca tgtaggtaag tgcccacccg    8520
ttcatcggcc ttccacttac cctgctaaga attctatggc tggaataaat gggaacaggt    8580
tcccaaccaa ggatattcag agcgtccctg agatcgacgt tctgtgcgca caggctgtgc    8640
gggaaaactg gcaaactgtt accccttgta ctcttaagaa acagtattgt gggaagaaga    8700
agactaggac catactcggc acaaataact tcatcgcgct agcccaccga gcagcgttga    8760
gtggtgttac ccagggcttc atgaagaagg cgtttaactc gcccatcgcc ctcggaaaaa    8820
acaagtttaa ggagctacag actccggtcc tgggcaggtg tctagaagct gatcttgcat    8880
cctgcgaccg atccacaccc gcaattgtcc gctggtttgc cgccaacctc ctttatgagc    8940
ttgcctgcgc tgaagagcat ctaccgtcgt acgtgctaaa ctgctgccac gacttactgg    9000
tcacgcagtc cggcgcagtg actaagagag gtggcctgtc gtctggcgac ccgatcacct    9060
ctgtgtctaa caccatttac agtttggtga tctacgcaca gcatatggtg ctcagttact    9120
tcaaaagtgg tcacccccat ggcctcttat tcttacagga ccagctaaag tttgaggaca    9180
tgcttaaggt tcaacccctg atcgtctatt cggacgacct cgtgctgtat gccgagtctc    9240
ccactatgcc aaactaccac tggtgggttg agcatctgaa tttgatgctg ggggtttcaga    9300
cggacccaaa gaagacagcc ataacagact cgccatcatt tttgggctgt agaataataa    9360
atggacgcca gctagtcccc aaccgtgaca ggattctcgc ggccctcgcc taccacatga    9420
aggcgagtaa tgtttctgaa tactacgcct ctgcggctgc aatactcatg gacagctgtg    9480
cttgtttgga gtatgatcct gaatggttcg aagaacttgt agttggaata gcgcaatgcg    9540
cccgcaagga tggctacagc tttcccggcc cgccgttcta tatatccatg tgggaaaaac    9600
tcagatccaa ttatgagggg aagaagtcga gagtgtgcgg gtactgcggg gccccggccc    9660
cgtatgctac cgcctgtggt ctcgacgtct gcatttacca cactcacttc caccagcatt    9720
gtccagtcat aatctggtgt ggccatccag ccggttctgg ttcttgtagt gagtgcagat    9780
cccctgtggg gaaaggcaca agccctttag acgaggtgct ggaacaagtc ccgtacaagc    9840
ccccacggac cgttatcatg catgtggagc agggtcttac ccccccttgac ccaggcagat    9900
atcagactcg ccgcgggtta gtctccgtca ggcgcgggat caggggaaat gaggttgagc    9960
taccagacgg tgattatgcc agtaccgcct tgctccctac ctgcaaagag atcaacatgg   10020
tcgctgtcgc ttctaatgta ttgcgcagca ggttcatcat tggtccaccc ggtgcgggga   10080
aaacatactg gctacttcaa caggtccagg atggtgatgt tatttacaca ccaactcacc   10140
```

-continued

```
agaccatgct tgacatgatt agagctttgg ggacgtgccg gttcaacgtc ccggcaggca   10200
caacgctgca attcccggtc ccctcccgca ccggtccgtg ggttcgcatc ctagccggcg   10260
gttggtgtcc tggcaagaat tccttcctgg atgaagcagc gtattgcaat caccttgatg   10320
tcttaaggct tcttagcaaa actaccctca cctgtctggg agactttaaa caactccacc   10380
cagtgggttt tgattctcat tgctatgttt ttgacatcat gcctcaaact caactgaaga   10440
ccatctggag gtttggacaa aatatctgtg atgccatcca accagattac agggacaaac   10500
tcatgtccat ggtcaacatg acccgtgtaa cctacgtgga aaaacctgtc aggtatgggc   10560
aagtcctcac cccctaccac agggaccgag aggacgacgc catcaccatt gactccagtc   10620
aaggcgccac atttgatgtg gttacactgc atttgcccac taaagattca ctcaacaggc   10680
aaagagccct tgttgctatc accagggcaa gacatgctat ctttgcgtat gatccacaca   10740
ggcagctgca gagcctgttt gatcttcctg caaaaggtac acccgtcaac cttgcagtgc   10800
accgcgatgg gcagctgatc gtgctagata gaaataacaa tgaatgcacg gttgctcagg   10860
ctctaggtaa cggggataaa tttagggcca cagacaagcg cgttgtagat tctctccgcg   10920
ccatttgtgc tgatctagaa ggtacgagct ctccgctccc caaggtcgca cacaacttgg   10980
gattttattt ctcacctgat ttaacacagt ttgctaaact cccagcagaa cttgcacctc   11040
actggcccgt ggtgacagcc cagaacaatg aaaagtggcc agatcggctg gttactagcc   11100
ttcgccctat ccataaatat agccgcgcgt gcatcggtgc cggctatatg gtgggcccct   11160
cggtgtttct aggcactcct ggggtcgtgt catactatct cacaaaattt gttaagggcg   11220
aggctcaagt gcttccggag acggttttca gcaccggccg aattgaggta gactgccggg   11280
aatatcttga tgaccaggag cgagaagttg ctgcgtccct cccacatgcc ttcattggcg   11340
acgtcaaagg cactaccgtt ggagggtgcc accatgtcac ttccagatac ctcccgcgct   11400
tccttcccaa ggaatcagtt gcggtagtcg gggtttcaag tcccggaaaa gccgcgaaag   11460
cattgtgcac actaacagat gtgtacctcc cagaccttga agcctatctc cacccggaga   11520
ccccgtccaa gtgctggaga atgatgttgg acttcaagga agttcgacta atggtctgga   11580
aagacaaaac agcctatttc caacttgaag gtcgctattt cacctggtat cagcttgcca   11640
gctatgcctc gtacatccgt gttcctgtca actctacggt gtacttggac ccctgcatgg   11700
gccccgccct ttgcaacagg agagtcgtcg ggtccactca ttggggggct gaccttgcgg   11760
tcacccctta tgattacggc gctaaaatca tcctgtctag cgcgtaccat ggtgaaatgc   11820
cccccggata caagattctg gcgtgcgcgg aattctcggt ggacgaccca gtcaagtaca   11880
aacatacctg gggtttgaa tcggatacag cgtatctgta tgagttcacc ggaaacggtg   11940
aggactggga ggattacaat gatgcgtttc gtgcgcgcca ggaagggaaa atttataagg   12000
ctactgccac cagcatgaag ttttattttc ccccgggccc tgtcattgaa ccaactttag   12060
gcctgaattg aaatgaaatg gggtccatgc aaagcctttt tagcaaaatt ggccaacttt   12120
ttgtggatgc tttcacggag ttcttggtgt ctattgttga tatcattata tttttggcca   12180
tcttgtttgg cttcaccatc gccggttggc tggtggtctt ttgcatcaga ttggtttgct   12240
ccgcgatact ccgtgcgcgc cctgccattc accctgagca attacagaag atcttatgag   12300
gcctttcttt cccagtgcca agtggacatt cccacctggg gaactaaaca ccctttgggg   12360
atgttttggc accataaggt gtcaaccctg attgatgaga tggtgtcgcg tcgaatgtac   12420
cgcaccatgg aaaaagcagg acaggctgcc tggaaacagg tggtgagcga ggctacgctg   12480
tctcgcatta gtagtttgga tgtggtggct cattttcagc atcttgccgc cattgaagcc   12540
```

-continued

```
gagacctgta aatatttggc ctcccggctg cccatgctac ataacctgcg catgacaggg   12600
tcaaatgtaa ccatagtgta taatagtact ttaaatcagg tgtttgctat tttcccgacc   12660
cctggttccc ggccaaagct tcatgatttt cagcaatggc taatcgctgt acactcctcc   12720
atattctcct ctgttgcagc ttcttgtact ctttttgttg tgctgtggtt gcggatgccg   12780
atgctacgta ctgtttttgg tttccgctgg ttaggggcaa cttttccttc gagctcacgg   12840
tgaattacac ggtgtgccca ccttgcctca cccggcaggc ggccgcacag gcctacgaac   12900
ccggtaggtc tctttggtgc aggatagggt acgatcggtg tggagaggac gaccatgacg   12960
agctagggtt tatggtaccg tctggcctct ccagcgaagg ccacttgacc agtgtttacg   13020
cctggttggc gttcttgtcc ttcagctaca cagcccagtt ccaccccgag atattcggga   13080
tagggaatgt gagtcaagtt tatgttgaca ccaaacatca actcatctgc gccaaacatg   13140
acgggcagaa caccaccttg cctcgtcatg acaatatttc agctgtgttt cagacctatt   13200
accaacatca agtcgacggc ggcaattggt ttcacctaga atggctgcgt cccttctttt   13260
cctcatggtt ggttttaaat gtctcttggt ttctcaggcg ttcgcctgca aaccatgttt   13320
cagttcgagt cttgcagaca ttaagaccaa caccaccgca gcggcaggct ttgctgtcct   13380
ccaagacatc agttgcctta ggcatcgcaa ctcggcccct gaggcgcttc gcaaaatccc   13440
tcagtgccgt acggcgatag ggacacctgt gtatattacc atcacagcca atgtgacaga   13500
tgagaattat ttacattctt ctgatctcct catgctctct tcttgccttt tctacgcttc   13560
tgagatgagt gaaaagggat ttaaggtggt ttttggcaat gtgtcaggca tcgtggctgt   13620
gtgtgtcaat tttaccagct acgtccaaca tgtcagggag tttacccaac gctccttgat   13680
ggtcgaccat gtgcggctgc tccatttcat gacacctgag accatgaggt gggcaaccgt   13740
tttagcctgt cttgttgcca ttctgttggc aatttgaatg tttaagtatg ttggggaaat   13800
gcttgaccgc gggctgttgc tcgcgattgc tttctttgtg gtgtatcgtg ccgttctgtt   13860
ccactgtgct cgtcgacgcc aacggcaaca gcagctctca tctgcaattg atttacaact   13920
tgacgctatg tgagctgaat ggcacggatt ggctagctaa tagatttgat tgggcagtgg   13980
agagctttgt catctttcct gttttgactc acatagtctc ctatgttgcc ctcaccacca   14040
gccatttcct tgacacaatt gctttagtca ctgtatctac cgccggtttt cttcacgggc   14100
ggtatgtcct gagtagcatc tacgcggtct gtgccctggc tgcgttgact tgcttcgtca   14160
ttaggtttgt aaagaattgc atgtcttggc gctactcatg taccagatat accaattttc   14220
ttctggacac taagggcaga ctctatcgtt ggcggtcgcc tgtcatcata gagaagaggg   14280
gcaaagttga ggtcgaaggt catctgatcg atctcaaaag agttgtgctt gatggttccg   14340
tggcaacccc tataaccaga gtttcagcgg aacaatgggg tcgtccttag atgacttttg   14400
tcatgatagt gcggctccac aaaaggtgct tttggcattt tctattacct acacgccagt   14460
gatgatatat gccctaaagg tgagtcgcgg ccgactgcta gggctgctgc accttttgat   14520
tttcctgaac tgtgctttca cctttgggta catgacattc acgcactttc agagtacaaa   14580
taaggtcgcg ctcactatgg gagcagtagt tgcactcctt tggggggtgt actcagccat   14640
agaaacctgg aaattcatca cctccagatg ccgtttgtgc ttgctaggcc gcaagtacat   14700
tctggcccct gcccaccacg ttgaaagtgc cgcaggcttt catccgattg cggcaaatga   14760
taaccacgca tttgtcgtcc ggcgtcccgg ctccactacg gtcaacggca cattggtgcc   14820
cgggttgaaa agcctcgtgt tgggtggcag aaaagctgtt aaacagggag tggtaaacct   14880
tgtcaaatat gccaaataac aacggcaagc agcagaagag aaagaagggg gatggccagc   14940
cagtcaatca gctgtgccag atgctgggta agatcatcgc ccagcaaaac cagtctagag   15000
```

-continued gcaagggacc ggggaagaaa aataagaaga aaaacccgga gaagccccat tttcctctag 15060
ctactgaaga tgatgtcaga catcacttta cccctagtga gcggcaattg tgtctgtcgt 15120
caatccagac tgcctttaat caaggcgctg ggacttgcac cctgtcagat tcagggagga 15180
taagttacac tgtggagttt agtttgccta cgcatcatac tgtgcgcttg atccgcgtca 15240
cagcatcacc ctcagcatga tgggctggca ttctgaggca tcccagtgtt tgaattggaa 15300
gaatgtgtgg tgaatggcac tgattgacat tgtgcctcta agtcacctat tcaattaggg 15360
cgaccgtgtg ggggtaatat ttaattggcg agaaccacac ggccgaaatt aaa 15413

<210> SEQ ID NO 6
<211> LENGTH: 15078
<212> TYPE: DNA
<213> Artificial Sequence

<400> 6
atgatgtgta gggtattccc cctacataca cgacacttct ggtgtttgtg taccttggag 60
gcgtgggtac agccccgccc caccccttgg cccctgttct agcccaacag gtatccttct 120
ccctcggggc gagcgcgccg cctactgctc ccttgcagta ggaaggacct cccgagtatt 180
tccggagagc acctgcttta cggatctcc acccttttaac catgtctggg acgttctccc 240
ggtgcatgtg caccccggct gcccgggtat tttggaacgc cggccaagtc ttttgcacac 300
ggtgtctcag tgcgcggtct cttctctctt cagaacttca ggacactgac ctcggtgcaa 360
ttggattgtt ccacaagcct agggacaagc ttcactggaa agtccccatc ggcatccctc 420
aggtggaatg tactccatcc gggtgctgtt ggctctcagc tatattccct atagcacgta 480
tgacctctgg caatcataac ttcctccaac gacttgttaa ggttgctgat gttttgtacc 540
gcgacggttg cttggcacct cgacaccttc gtgaactcca agtttacgag cgcggctgca 600
actggtaccc gatcacgggg cccgtacccg ggatgggttt gtttgcgaac tccatgcacg 660
tatccgacca gccgttccct ggagccaccc atgtgttgac taactcgcct ctgcctcaac 720
gggcgtgccg gcaaccgttc tgtccatttg aggaagctca ttctaacgtg tataggtgga 780
ataaatttgt gattttcacg gactccactc tcaacggcca atctcgcatg atgtggacgc 840
cgggatccga tgattcagcc gccttggagg cgctaccgcc tgaattagaa cgtcaggtcg 900
gaatcctcat tcggagtttc cctgctcatc accccgttaa cctggccgac tgggagctca 960
ctgagacccc tgagaatggc ttctccttca gcacgtctca ttcttgtggt tatcttgtcc 1020
aaaaccccga tgtgtttgat agcaagtgct ggctcacttg cttttcgggc cagtcggtcg 1080
aagtgcgccg ctgtgaagaa catttagcca acgcccttgg ttaccaaacc aagtggggcg 1140
tgcacggtaa gtaccttcag cgcaggctcc aagttcgcgg cattcgtgct gtagtcgatc 1200
ctgatggccc cattcacgtt gaagcgctgt cttgctccca gtcttggatc aggcacctga 1260
ctctgaataa tggtgttacc ccaggattcg ttcgcctgac atccattcgc attgtgccga 1320
acacagagcc taccactttc cggatctttc ggtttggagc gcataagtgg tatggcgctg 1380
ctggcaaacg ggctcgtgcc aagcgtgccg ctaaaagtgg gaaagattcg gcttccactc 1440
ccaaggttgc ccagccggcc cttacctgtg gagtcaccac ctactctcca ccaacagacg 1500
ggtcttgcgg ttggcatgtc cttgccgcca taatgaaccg gatgatgaac ggtgacttca 1560
cgtccccact gcctcagtac aatagaccag aagacgattg ggcttctgat tatgatcttg 1620
ctcaggcgat tcaatgtcta caactgcctg caaccgtggt tcggaatcgt gcctgtccta 1680
acgccaagta ccttgtaaga cttaacgggg ttcactggga ggtagaggtg agatctggaa 1740
tggctccccg ctccctttct cgtgaatgtg tagttggcgt ttgctctgaa ggttgtgttg 1800

-continued ctccgcctta tccagcggac gggcttccta aacgcgcact agaggccttg gcgtctgctt 1860
acagactacc ctccgattgt gttagctctg gcattgatga ctttcttgct aatccacccc 1920
ctcaggaatt ttggactctt gacaaaatgc tgacctcccc gtcaccagaa cggtccggct 1980
tctctagttt gtataagtta ctgttagagg ttgttccgca aaagtgtggt gccacggaag 2040
gggctttcac ctatgctgtt gagaggatgt taaaggattg tccgagctct gaacaggcca 2100
tggcccttct ggcaaaaatt aaagttccat cctcaaaggc cccgtctgtg tccctggacg 2160
ggtgtttccc tgcggatatt ccggctgatt tcgagccagc gtctcgggaa aggcccccgaa 2220 gttccagcgt tgctgttgcc ctgtgttcac cggatgcaga aggttcgag gaagtacccc 2280 cagaagaagt tcaagagaga ggctacaagg ccgtcaactc tgcactcctt gccgaaaacc 2340
ccaatgatga acaggcacag gtggttgccg gtgaacaact gaagctcggc ggttgtagtt 2400
tggcaatcgg gaatgctcag tccactccag gctccatgga agagaacatg cgcaatagcc 2460
gggaagacga accactagat ttgtccctac cagcactagc taccacgacg acccttgtga 2520
gagagcgaat actcgacaac ccaggtcctg atgccggtac cctccctgcc accgttcgag 2580
aatttgtctc gacagggcct atgctccgtc atgttgagca ttgtggcacg gagtctggcg 2640
acagcagttc acctttggat ctgtcttatg cgcaaactcc ggaccagcct ttaaatctgt 2700
ccctggccgc ttggccggtg aagaccaccg cgtctgaccc tggctgggtc cacggtaggt 2760
gcgagcctgt ctttgtaaag cctcgaaaag ctttttctga tggcgattca gcctttcagt 2820
tcggggggct ttctgagtcc agctctgtca tcgagtttga ccgaacaaaa gatgcatcgg 2880
aggttgacgc tcctgtcggc ttgacgactt cgaacgaggc cctctctgtg gtcgaccctt 2940
tcgaatttgc cgaactcaag cgcccgcgtt tctccgcaca agccttaatt gaccgaggcg 3000
gcccgcttgc cgatgtccat gcaaaaataa agcaccgggt gtatgaacaa tgccttcaag 3060
cttgtgagcc tggtagccgt gcaaccccag ccaccaagaa gtggctcgac aaaatgtggg 3120
acagggtgga catgaaaact tggcgctgca cctcgcagtt ccaagctggt cgcatccttg 3180
catccctcaa attccttcct gacatgattc aagacgcacc gcctcctgtt cccaggaaga 3240
accgagctag tgacaacgcc ggtttgaagc aactggtggc acagtgggat aggaaattga 3300
gtggaacccc cccccaaaa ccggctgggt cagtgcttga ccaggccgtc cctccaccca 3360
cggacgtcca gcaagaagat gtcactcctt ccggcgggcc actccatgcg ccggatttcc 3420
ctagtcgagt tagcacgagc gggggttgga aaagccttat actttccggg acccgtctcg 3480
cagggtctgt cagtcagcgc ctcatgacac gggtttttga agttttctcc catctcccag 3540
cttttgcgct cacacttttc tcgccgcggg gctctatggc tccaggcgat tggttgtttg 3600
caggtattgt tttacttgct ctcttgttct gtcgttttta cccgatactc ggatgccttc 3660
ccttattggg tgtcttttct gggtctgtgc ggcgtgttcg tctgggtgtt tttggttctt 3720
ggatggcttt tgctgtattt ctattctcga ctccatccaa cccagtcggt tcttcttgtg 3780
accacgattc gccggagtgt catgctgagc ttttggttct tgagcagcgc caactttggg 3840
aacctgtgcg cggccttgtg gtcggcccct cgggcctcct atgtgtcatt cttggcaagt 3900
tactcggtgg gtcacgttat ctctggcatg ttctcctacg tttatgcatg cttacagatt 3960
tggccctttc tcttgtttat gtggtgtccc aggggcgttg tcacaagtgt tggggaaagt 4020
gtataaggac ggctcctgct gaggtagcac ttaatgtatt tcctttctcg cgcgccaccc 4080
gtagctctct tgtatccttg tgtgatcggt tccaagcgcc taaaggagtt gatcctgtgc 4140
acttggcaac gggttggcac gggtgttggt gtggcgagag ccccgttcat caatcacacc 4200
aaaagccaat aacctatgcc aatttggatg aaaagaaaat atctgcccaa acggtggttg 4260

-continued

```
ctgtcccata cgaccccagc caggctatca aatgcctgaa agttctgcag gcgggagggg   4320
ctatcgtaga ccagcctaca cctgaagttg ttcgcgtgtc cgaggtcccc ttctcagccc   4380
catttttccc aaaagttcct gtcaacccgg attgcaggat tgtggtggat tcggacactt   4440
ttgtggctgc ggtccgctgc ggttactcga cagcacaact ggtcctgggc cggggcaatt   4500
ttgccaagct aaatcagacc cccctcagga gctctacctc caccaaaacg actgggggga   4560
cctcttacac ccttgctgta gctcaagtgt ctgcgtggac tcttgcccat ttcatcctcg   4620
gcctttggtt cacatcacct caagtgtgtg gccgagggac cgctgatcca tggtgttcaa   4680
atccctttc ataccctgcc tatggccctg gagttgtatg ctcctctcga ctttgtgtgt   4740
ctgccgatgg ggtcaccctg ccattgtttt cagctgtggc acaactctcc ggcagagagg   4800
tggggatttt tattttggtg cttgtctccc tgatagcttt ggcccatcgc ttggctctta   4860
aggcagactt gttagtggtc tttttggctt tttgtgctta cgcctggccc atgagttcct   4920
ggctaatctg cttctttcct atactcttaa agtggatcac cctccaccct ctcaccatgc   4980
tttgggtgca ctcattcttg gtgttttgcc tgccagcagc cggcgtcctc tcactaggga   5040
taactggcct tctttgggca atcggccgct ttacccaggt tgccgggatt attacacctt   5100
atgacatcca ccagtacacc tccgggccgc gtggtgcagc tgctgtggcc acagccccag   5160
aaggcactta tatggccgcc gtccggagag ctgctttaac tgggcgatct ttaatattca   5220
ccccgtcagc agttggatcc ctcctcgaag gtgctttcag gactcataaa ccctgtctta   5280
atactgtgaa tgttgtgggc tcttcccttg gttccggagg cgttttcacc attgatggca   5340
gaagaactgt tgtcactgct gctcatgtgt tgaatggcga cacagctaga gttaccggcg   5400
actcctacaa ccgcatgcac actttcaaga ccaatggtga ttatgcctgg tcccatgctg   5460
atgactggca gggcattgcc cccgtggtca aggtagtgaa ggggtaccgc ggtcgtgctt   5520
attggcaaac atcaactggt gtcgaacccg gcatcattgg agaagggttt gccttctgtt   5580
tcactaattg tggtgattcg gggtcacccg tcatctcaga atccggtgat ctcatcggaa   5640
ttcacaccgg ttcaaacaaa ctcggttctg gtcttgtgac gacccctgaa ggggagacct   5700
gtaccatcaa agaaaccaag ctctccgacc tttccagaca ttttgcaggc cctagtgttc   5760
ctcttggtga cattaaatta agcccggcca tcatccctga tgtaacatct attccgagtg   5820
acttggcatc gctcctagcc tctgtccctg tggtggaagg cggcctctcg accgttcaac   5880
ttctgtgtgt ctttttcctt ctctggcgca tgatgggcca tgcctggaca cccattgttg   5940
ccgtgggctt ctttctgctg aatgaaatcc tcccagcagt tttggtccga gccgtgtttt   6000
cttttgcact ctttgtgctt gcatgggtca ccccctggtc cgcacaggtg ttgatgatta   6060
gactcctcac ggcatctctc aaccgcaaca agctctctct ggtgttctac gcactcgggg   6120
gtatcgtcgg tttggccgct gaaatcggga ctttcgctgg cagattgcct gaattgtctc   6180
aagccctttc gacctactgt ttcttgccta gggcccttgc catggccagt tgtgtcccca   6240
tcgtcattat tggcggactt catgccctcg gtgtaattct gtggttgttc aaataccggt   6300
gcctccacaa cacgctggtt ggtgatgggt gtttttcaag tgccttcttc ctgcgctatt   6360
ttgcggaggg caatctgagg aaaggtgttt cacagtcctg tggcatgaat aacgagtctc   6420
tgacggctgc tctggcttgc aagctgtcgc aggctgatct tgaatttttg tccagtttaa   6480
cgaacttcaa gtgctttgtg tctgcttcaa atatgaaaaa tgccgccggc cagtacattg   6540
aagcagctta tgccaaggcc ttgcgccaag agttggcctc tctagttcag gttgataaaa   6600
tgaaaggagt tttgtccaag ctcgaggcct ttgctgaaac agccaccccg tcccttgaca   6660
```

-continued

```
caggtgacgt ggttgttttg cttgggcagc atcctcacgg gtctatcctc gatattaatg   6720

tggggactga aaggaaaact gtgtccgtgc aagagacccg gaacctaggc ggctccaaat   6780

tcagtgtttg cactgtcgtg tccaacacac ccgtggacgc cttaaccggc atcccactcc   6840

ggacaccaac ccctcttttt gagaatggtc cgcgtcatcg cggtgaggaa gacgatctca   6900

aagtcgagag gatgaagaaa cactgtgtat ccctcggctt ccacaacatc aatggcaaag   6960

tctactgtaa gatctgggat aagtctaccg gtgacacctt ttacaccgac gattcccggt   7020

atacccacga ccatgctttt caggacaggt cagccgacta cagagacagg gactacgaag   7080

gtgtgcaaac cgccccccaa caaggctttg atccaaagtc tgaaacccct gttggcactg   7140

tagtgatcgg cggtatcacg tataacaggt acctgattaa aggtaaggag gtcctggtcc   7200

ccaagcctga caactgcctc gaagctgcca agctgtccct tgagcaggct ctcgctggga   7260

tgggccaaac ttgcgacctt acggctgccg aggtggaaaa gctgaagcgc atcattagtc   7320

aactccaagg tttgaccact gaacaggctt taaactgtta gccgccagcg gcttgacccg   7380

ctgtggccgc ggcggcttag tagtgactga aacggcggta aaaattgtaa aatatcacaa   7440

cagaactttc accttaggcc cttttgacct gaaagtcact accgaggcag aggtcaagaa   7500

atcagctgag cagggccacg ctgttgtggc aaatttatgt tctggtgtcg tcttgatgag   7560

acctcaccca ccgtctcttg ttgacgttct tttgaaaccc ggacttgaca caaaacccgg   7620

cattcagcca gggcatgggg ccgggaatat gggcgtggaa ggttctattt gggatttcga   7680

aaccgcacct acaaaggcag aactcgagtt atccaagcaa ataattcaag catgtgaagt   7740

taggcgcggg gacgccccga acctccaact cccttacaag ctctatcctg ttagggggga   7800

tcctgagcgg catgagggcc gccttatcaa caccaggttt ggagatttat cttacaaaac   7860

tcctcaagac accaagtccg caatccacgc ggcttgttgc ctgcacccca acggggcccc   7920

cgtgtctgat ggtaaatcaa cactaggtac cactcttcaa catggttttg agctttacgt   7980

ccctactgtg ccttatagtg tcatggagta cctcgattca cgccctgaca cccctttttat   8040

gtgcaccaaa catggcactt ccaaggctgc tgcagaggac cttcaaaaat acgacctgtc   8100

cactcaaggc ttcgtcctgc ctggggtcct acgcctagta cgtagataca tttttggcca   8160

tattggtaag gcgccgccat tgttcctccc atcaacctat cccgccaaga actctatggc   8220

agggatcaat ggccagagat tcccaacaaa ggacgttcag agcatacctg aaattgatga   8280

aatgtgtgcc cgcgccgtca aagagaattg gcaaactgtg acaccttgta ccctcaagaa   8340

acagtattgt tccaagccca aaaccaggac catcctaggc actaacaact ttattgcctt   8400

ggctcacaga tcggcgctca gtggtgttac ccaggcattc atgaagaagg cttggaagtc   8460

cccaattgcc ttgggaaaaa acaaattcaa ggagctgcat tgcaccgtcg ccggcaggtg   8520

tcttgaggct gacttggcct cctgtgaccg cagcaccccc gccattgtga gatggttcgt   8580

cgccaacctc ctgtatgaac ttgcgggatg tgaagagtac ttgcctagct atgtacttaa   8640

ttgctgccat gaccttgtgg caacacagga tggtgccttc acaaaacgcg gtggcctgtc   8700

gtccggggac cccgtcacca gtgtgtctaa caccgtatat tcgctggtaa tctatgccca   8760

gcacatggtg ttgtcagcct tgaaaatggg tcatgaaatc ggtcttaagt tcctcgagga   8820

acagctcaga ttcgaggacc tcctcgaaat tcagcctatg ttggtatact ctgatgacct   8880

cgttttgtac gctgaaagac ccacttttcc taattatcac tggtgggtcg agcaccttga   8940

cctaatgctg ggttttaaaa cggacccaaa gaagaccgtc ataactgata aacccagctt   9000

cctcggctgc agaattgagg cagggcggca gctggtcccc aatcgcgacc gcatcctggc   9060

tgctctcgca tatcacatga aggcgcagaa tgcctcagag tattatgcgt ctgctgccgc   9120
```

-continued aatcctgatg gattcatgcg cttgcattga tcatgacccc gagtggtatg aggacctcat 9180
ctgcggtatt gcccgatgcg cccgccaaga tggttatagc ttcccaggtc cggcgttttt 9240
catgtctatg tgggagaggc tgagaagtca caatgaaggg aagaaattcc gccactgcgg 9300
catctgtgac gccaaagccg actatgcatc cgcctgtggg ctcgatctat gtttgttcca 9360
ctcgcacttt catcaacact gtcccgtcac tctgagctgc ggtcaccatg ccggttcaag 9420
ggaatgttcg cagtgtcagt cacctgttgg ggctggcaga tcccctcttg atgctgtgtt 9480
gaaacaaatt ccatacaaac ctccccgcac tgtcatcatg aaggtgagta acaaaacaac 9540
ggccctcgat ccggggaggt accagtcccg tcgaggcctc gttgcagtca agagaggtat 9600
cgccggcaat gaagttgatc tttctgatgg agactaccaa gtggtacctc ttttgccgac 9660
ttgcaaagac ataaacatgg tgaaagtggc ttgcaatgta ctactcagta agttcatagt 9720
ggggccacca ggttccggaa agaccacctg gctactagat caagtccaag acgatgatgt 9780
catttacaca ccaacccatc agactatgtt tgatatagtt agtgctctca aagtttgcag 9840
gtactctatt ccaggagcct caggactccc tttcccacca tctgccagat ccgggccgtg 9900
ggttaggctt atagccagtg ggcacgtccc tggccgcgta tcttacctcg atgaggccgg 9960
atactgtaat catctggaca ttctcagatt gctctccaaa acgccccttg tgtgtttggg 10020
tgaccttcaa cagctacacc ctgtcggctt tgattcctac tgttatgtgt ttgatcagat 10080
gccccagaag caactgaccg ttatttacag atttggccct aacatctgcg cggccattca 10140
gccttgttac agagagaagc ttgaatccaa ggctagaaac accagggtgg tttttgtcaa 10200
ccggcctgtg gcctttggtc aggtcctgac accataccat aaagatcgca tcggctctgc 10260
ggtaaccata gactcatccc agggagccac ctttgatatt gtgacactgc atctaccgtc 10320
accaaagtcc ctaaccaaat cccgagcact tgtggccatc actcgggcaa gacacgggtt 10380
gttcatttat gacccacatg accagctcca ggagtttttc aacttaatcc ctgagctcac 10440
agattgcaac cttgtgttta accgcgggga tgagctggta gttctggatt cggataatgc 10500
agtcacaact gtagcaaagg ccctagaaac aggtcaatct cgattccgag tgtcagaccc 10560
gaggtgcaag tctctcttgg ccgcttgttc ggccagtctg gaagggagct gtatgccact 10620
accgcaagta gcacataatc tggggtttta cttttcccca gacagtccag tatttgcacc 10680
tctgccaaga gagttggcgt cacattggcc agtggttacc caccagaata atcgggcgtg 10740
gcctgatcga cttgtcgcta gtatgcgccc aatcgatgcc cgctacagca agccgatggt 10800
cggtgcaggg tacgtagtcg ggccgtccac ttttcttggt actcccggtg tggtgtcata 10860
ctacctcacg ctatacatca ggggtgagcc ccaggccctg ccagaaacac tcgtttcaac 10920
ggggcgtata gcaacagatt gtcgggagta tctcgatgcg gctgaggagg aggcagcaaa 10980
agaactcccc cacgcattca ttggcgatgt caaaggtacc acggtggggg gttgtcatca 11040
catcacgtca aaatacttac ctaggtccct gcctaaagac tctgttgccg tagttggagt 11100
gagttcaccc ggcagggctg ctaaagccat gtgcaccgtc accgatgtgt atctccctga 11160
actccggccg tatctgcaac ctgagacggc atcaaagtgc tggaaactta aattagactt 11220
cagggacgtc cgactaatgg tctggaaagg agctaccgcc tatttccagt tggaagggtt 11280
tacatggtcg gcgctgcccg actatgccag gttcattcag ctgcccaagg atgccgttgt 11340
atacatcgat ccgtgtatag gaccggcaac agccaaccgc aaggtcgtgc gaaccacaga 11400
ctggcgggcc gacctggcag tgacaccgta tgactacggt gcccagacta ttttaacaac 11460
agcctggttc gaggacctcg ggccacagtg gaagattttg gggttgcagc cctttaggcg 11520

-continued

```
agcacttggt ctggaaaaca ctgaggattg ggcaattctt gcacgccgta tgaatgacgg   11580
caaagactac actgactata actggaattg tgttcgagga cgcccacaag ccatctacgg   11640
gcgtgctcgt gaccatacgt atcatttcgc cccggcacg gaactgcagg tagagctagg   11700
taaaccccgg ctatcgcctg agcaggtgcc gtgaatttgg agtgatgcaa tggggtcact   11760
gtggagtaaa atcagccagc tgttcgtgga tgccttcact gagttcttgg ttagtgtggt   11820
tgatattgtc atcttccttg ctatattgtt tgggttcacc gtcgcaggat ggttattggt   11880
cttccttctc agagtggttt gctccgcgtt tctccgttcg cgctctgcca ttcactctcc   11940
cgaactatcg aagatcctat gaaggcttgt tgcccaactg cagaccggat gtcccacaat   12000
ttgcattcaa gcaccctttg ggtatgttgt ggcatatgcg agtttcccac ctgattgatg   12060
agatggtctc tcgccgcatt taccagacca tggaacattc aggtcaagcg gcctggaagc   12120
aagtagttgg tgaggccact ctcacgaagc tgtcagggct cgatatagtc actcacttcc   12180
aacacctggc cgcagtggag gcggattctt gccgctttct cagctcacga ctcgtgatgc   12240
taaaaaatct tgccgttggc aatgtgagcc tacagtacaa caccacgctg gaccgcgttg   12300
agctcatttt tcccacgtca ggtacgaggc ccaagttaac cgacttcaga caatggctca   12360
tcagtgtgca cgcttccatt ttttcctctg tggcttcatc tatcaccttg tttgtagtgc   12420
tttggcttcg aattccagct ctacgctatg tttttggttt ccactggccc acggcaacac   12480
atcattcgag ctgaccatca actataccat atgcaagcct tgtcttacca gtcaagcagc   12540
tcaccaaagg cttgagcccg gtcgcaatgt gtggtgcaga atagggcatg agacgtgtga   12600
ggagcgtgac catgatgagt tgttcatgcc catcccgtcc ggatacgata acatcaaact   12660
taagggttat tatgcctggc tggctttttt gtccttttcc tacgcggccc aattccaccc   12720
ggagttgttc gggattggga atgtgtcgcg tgtctttgtg gacaaacatc accagttcat   12780
ttgtgccgag catgatggac agaattcgac cgtatctact ggacacaaca tctctgcact   12840
atatgcggca tactaccacc accaaataga cgggggtaat tggttccatt tggaatggct   12900
gcgaccactc ttttcctcct ggttggtgct caatatatca tggtttctga ggcgttcgcc   12960
tgcaagccct gtttctcgac gcatctatca gatattaaga ccaacacgac cgcggctgcc   13020
ggtttcatgg tccttcagga catcaattgt ttccaacccc acagggtccc agcaacgcaa   13080
aatggagccc ccttcaaaaa gtcgtcccaa tgccgtgaag ctgtcggcac tccccaatac   13140
atcacaataa cagctaatgt gaccgacgaa tcgtacttgt acaacgcgga cttgctgatg   13200
ctttctgcgt gccttttcta cgcttcagaa atgagtgaga aaggctttaa agtcatcttc   13260
gggaatgtct ctggcgttgt ttccgcttgt gtcaatttta cagattatgt ggcccatgtg   13320
acccaacaca cccagcagca tcacctggta attgatcaca ttcggctgct gcatttcctg   13380
acaccatctg caatgaggtg ggctacaacc attgcttgtt tgctcgccat tctcttggcg   13440
atatgagatg ttctcacaag ttggggcgtt ccttgactcc gcactcttgc ttctggtggc   13500
ttttttgct gtgtaccggc ttgtcttggt cctttgccga tggcaacggc aacaactcga   13560
cataccaata catatataat ttgacgatat gcgagttgaa tgggaccgcg tggctgtccg   13620
gccattttga ttgggcagtt gagacttttg tgctttaccc ggttgccact cacatcctct   13680
cactgggttt tctcacaaca agtcattttt ttgacgcgct cggtctcggt gttgtatcca   13740
ctgctggatt tgttggcggg cggtatgtac tcagcagcgt ctacggcgct tgtgctttcg   13800
cagcgttcgt gtgttttgcc atccgtattg cgaaaaattg catggcctgc cgctacgccc   13860
gcacccggtt taccaacttc attgtggacg accggggagg agttcatcga tggaagtccc   13920
caatagtggt ggaaaaattg ggcaaagccg aagtcgacgg cagccttgtc accatcaaac   13980
```

-continued

```
atgtcgtcct cgaaggggtt aaagctcaac ctttaacgag gacttcggcc gagcaatggg   14040
aggcctagat gatttttgca acgattctac cgctgcacaa aagctcgtgc tggctttcag   14100
catcacatac acacctataa tgatatatgc ccttaaggtg tcacgcggcc gactcctggg   14160
gctgttgcac atcctaatat ttctgaactg ttcctttaca ttcggataca tgacatatgt   14220
gcattttcaa tccaccaacc gtgtcgcact cactctgggg gctgtcgtcg cccttttatg   14280
gggtgcttac agcctcacag agtcatggaa gtttatcact tccagatgca gattgtgttg   14340
ccttggccgg cgatacattc tggcccctgc ccatcacgta gaaagtgctg caggtctcca   14400
tccaatctca gcgtctggta accgagcata cgctgtgaga aagccaggac taacatcagt   14460
gaacggcact ctagtaccag gacttcggag cctcgtgctg ggcggcaaac gagctgttaa   14520
acgaggagtg gttaacctcg tcaagtatgg ccggtagaaa ccagagccag aagaaaaaga   14580
aaaacacagc tccaatgggg aatggccagc cagtcaatca actgtgccag ttgctgggtg   14640
caatgataaa gtcccagcgc cagcaaccta ggggaggaca ggccaaaaag aaaaagcctg   14700
agaagccaca ttttcccttg gctgcagaag atgacatccg gcaccacctc acccagactg   14760
aacgctccct ctgcttgcaa tcgatccaga cggctttcaa tcaaggcgcg ggaactgcgt   14820
tgctttcatc cagcgggaag gtcagttttc aagttgagtt tatgctgccg gttgctcata   14880
cagtgcgcct gattcgcgtg acttctacat ccgctagtca gggtgcaagt taatttgatg   14940
gtcaggtgaa tggtcgcgat tggcgtgtgg cctttgagtc acctattcaa ttagggcgat   15000
cacatggggg tcatacttaa tcaggcagga accatgtgac cgaaattaaa aaaaaaaaaa   15060
aaaaaaaaaa aaaaaaaa                                                 15078
```

<210> SEQ ID NO 7
<211> LENGTH: 14885
<212> TYPE: DNA
<213> Artificial Sequence

<400> 7

```
tatgacgtat aggtgttggc tctatgcctt ggcatttgta ttgtcaggag ctgtgaccat      60
tggcacagcc caaaacttgc tgcacagaaa cacccttctg tgatagcctc cttcagggga     120
gcttagggtt tgtccctagc accttgcttc cggagttgca ctgctttacg gtctctccac     180
ccctttaacc atgtctggga tacttgatcg gtgcacgtgt acccccaatg ccagggtgtt     240
tatggcggag ggccaagtct actgcacacg atgcctcagt gcacggtctc tccttcccct     300
gaacctccaa gtttctgagc tcggggtgct aggcctattc tacaggcccg aagagccact     360
ccggtggacg ttgccacgtg cattccccac tgttgagtgc tcccccgccg gggcctgctg     420
gctttctgca atctttccaa tcgcacgaat gaccagtgga aacctgaact tccaacaaag     480
aatggtacgg gtcgcagctg agctttacag agccggccag ctcacccctg cagtcttgaa     540
ggctctacaa gtttatgaac ggggttgccg ctggtacccc attgttggac ctgtccctgg     600
agtggccgtt ttcgccaatt ccctacatgt gagtgataaa cctttcccgg gagctactca     660
cgtgttgacc aacctgccgc tcccgcagag acccaagcct gaagactttt gccccttga     720
gtgtgctatg gctactgtct atgacattgg tcatgacgcc gtcatgtatg tggccgaaag     780
gaaaatctcc tgggcccctc gtggcgggga tgaagtgaaa tttgaagctg tccccgggga     840
gttgaagttg attgcgaacc agctccgcac ctccttcccg ccccaccaca cagtggacat     900
gtctaagttc gccttcacag cccctgggtg tggtgtttct atgcgggtcg aacgccaaca     960
cggctgcctt cccgctgaca ctgtccctga aggcaactgc tggtggagct tgtttgactt    1020
gcttccactg gaagttcaga acaaagaaat tcgccatgct aaccaatttg gctaccagac    1080
```

-continued caagcatggt gtctctggca agtacctaca gcggaggctg caagttaatg gtctccgagc 1140
agtaactgac ctaaacggac ctatcgtcgt acagtacttc tccgttaagg agagttggat 1200
ccgccatttg aaactggcgg gagaacccag ctactctggg tttgaggacc tcctcagaat 1260
aagggttgag cctaacacgt cgccattggc tgacaaggaa gaaaaaattt tccggtttgg 1320
cagtcacaag tggtacggcg ctggaaagag agcaagaaaa gcacgctctt gtgcgactgc 1380
tacagtcgct ggccgcgcct tgtccgttcg tgaaacccgg caggccaagg agcacgaggt 1440
tgccggcgcc aacaaggctg agcacctcaa acactactcc ccgcctgccg aagggaattg 1500
tggttggcac tgcatttccg ccatcgccaa ccggatggtg aattccaaat ttgaaaccac 1560
ccttcccgaa agagtgagac cttcagatga ctgggctact gacgaggatc ttgtgaatgc 1620
catccaaatc ctcagactcc ctgcggcctt agacaggaac ggtgcttgta ctagcgccaa 1680
gtacgtactt aagctggaag gtgagcattg gactgtcact gtgacccctg ggatgtcccc 1740
ttctttgctc cctcttgaat gtgttcaggg ctgttgtggg cacaagggcg gtcttggttc 1800
cccagatgca gtcgaggtct ccgggtttga ccctgcctgc cttgaccggc tggctgaggt 1860
gatgcacctg cctagcagtg ctatcccagc cgctctggcc gaaatgtctg gcgattccga 1920
tcgttcggct tctctggtca ccaccgtgtg gactgtttcg cagttctttg cccgtcacag 1980
cggagggaat caccctgacc aagtgcgctt agggaaaatt atcagccttt gtcaggtgat 2040
tgaggactgc tgctgttccc agaacaaaac caaccgggtc accccggagg aggtcgcagc 2100
aaagattgac ctgtacctcc gtggtgcaac aaatcttgaa gaatgcttgg ccaggcttga 2160
gaaagcgcgc ccgccacgcg taatcgacac ctcctttgat tggggtgttg tgctccctgg 2220
ggttgaggcg gtaacccaga cgaccaagct gccccaggtc aaccagtgtc gtgctctggt 2280
ccctgttgtg actcaaaagt ccttggacaa caactcggtc cccctgaccg ccttttcact 2340
ggctaactac tactaccgtg cgcaaggtga cgaagttcgt caccgtgaaa gactaaccgc 2400
cgtgctctcc aagttggaaa aggttgttcg agaagaatat gggctcatgc caaccgagcc 2460
tggttcacgg cccacactgc cacgcgggct cgacgaactc aaagaccaga tggaggagga 2520
cttgctgaaa ctggctaacg cccagacgac ttcggacatg atggcctggg cggtcgagca 2580
ggttgaccta aaaacttggg tcaagaacta cccgcggtgg acaccaccac cccctccgcc 2640
aaaagttcag cctcgaaaaa cgaagcctgt caagagcttg ccggagagaa agcctgtccc 2700
cgccccgcgc aggaaggttg ggtccgattg tggcagcccg gtttcattag gcggcgatgt 2760
ccctaacagt tgggaagatt tggctgttag tagccccttt gatctcccga ccccacctga 2820
gccggcaaca ccttcaagtg agctggtgat tgtgtcctca ccgcaatgca tcttcaggcc 2880
ggcgacaccc ttgagtgagc cggctccaat tcccgcacct cgcggaactg tgtctcgacc 2940
ggtgacaccc ttgagtgagc cgatccctgt gcccgcaccg cggcgtaagt ttcagcaggt 3000
gaaaagattg agttcggcgg cggcaatccc accgtaccag aacgagcccc tggatttgtc 3060
tgcttcctca cagactgaat atgaggcctc tcccccagca ccgccgcacc agggaccctt 3120
ggccttctcc gaggataaac cggtagacga ccaacttgtc aacgactccc ggatatcgtc 3180
gcggaggcct gacgagagca catcagctcc gtccgcaggc acaggtggcg ccggctctct 3240
taccgatttg ccgccttcag atggcgcgga tgcggacggg ggggggccgt ttcggacggt 3300
aaaaagaaaa gctgaaaggc tctttgacca actgagccgt caggtttttg acctcgtctc 3360
ccatctccct gttttcttct cacgcctttt ccaccctggc ggtggttatt ctccgggtga 3420
ttggggtttt gcagctttta ctctattgtg cctcttttta tgttacagtt acccagcctt 3480
tggtattgct cccctcttgg gtgtgttttc tgggtcttct cggcgcgttc gaatgggggt 3540

-continued

```
ttttggctgc tggttggctt ttgctgttgg tctgttcaaa cctgtgtccg acccagtcgg   3600
cgctgcttgt gagtttgact cgccagagtg tagaaacatc cttcattctt ttgagcttct   3660
caaaccttgg gaccctgttc gcagccttgt tgtgggcccc gtcggtctcg gtcttgccat   3720
tcttggcagg ttactgggcg gggcacgctg catctggcac tttttgctta ggcttggcat   3780
tgttgcagac tgtatcttgg ctggagctta cgtgctttct caaggtaggt gtaaaaagtg   3840
ctggggatct tgtataagaa ctgctcctaa tgaggtcgct tttaacgtgt ttcctttcac   3900
acgtgcgacc aggtcgtcac ttatcgacct gtgcgatcgg ttttgtgcgc caaaaggaat   3960
ggaccccatt tttctcgcca ctgggtggcg cgggtgctgg gccggccgaa gccccattga   4020
gcaaccctct gaaaaaccca tcgcgtttgc ccaattggat gaaaagaaga ttacggctag   4080
gactgtggtc gcccagcctt atgaccccaa ccaagccgta aagtgcttgc gggtattgca   4140
ggcgggtggg gcgatggtgg ctgaggcggt cccaaaagtg gtcaaggttt ccgctgttcc   4200
attccgagcc cccttctttc ccactggagt gaaagttgac cctgattgca gggtcgtggt   4260
tgaccctgac actttcactg cagctctccg gtctggctac tccaccacaa acctcgtcct   4320
tggtgtaggg gactttgccc agctgaatgg attaaaaatc aggcaaattt ccaagccttc   4380
agggggaggc ccacatctca tggctgccct gcatgttgcc tgctcgatgg ctctgcacat   4440
gcttgttggg atttatgtga ctgcggtggg ttcttgcggc accggcacca acgacccgtg   4500
gtgcgctaac ccgtttgccg tccctggcta cggacctggc tctctctgca cgtccagatt   4560
gtgcatttcc caacacggcc ttaccctgcc cttgacagca cttgtggcgg gattcggtat   4620
tcaagaaatt gccttggtcg ttttgatttt tgtttccatc ggaggcatgg ctcataggtt   4680
gagctgtaag gctgacatgc tgtttgtttt gcttgcaatt gccagctatg tttgggtacc   4740
tcttacctgg ttgctttgtg tgtttccttg ctggttgcgc tgtttttctt tgcacccct   4800
caccatccta tggttggtgt ttttcttgat ttctgtgaat atgccttcag gaatcttggc   4860
catggtgttg ttggtttctt tttggcttct tggtcgttat actaatgttg ctggccttgt   4920
cacccctac gacattcatc attacaccag tggcccccgc ggtgttgccg ccttggctac   4980
cgcaccagat gggacctact tggccgctgt ccgccgcgct gcgttgactg gccgcaccat   5040
gctgtttacc ccgtcccagc ttgggtctct tcttgagggt gctttcagaa ctcgaaagcc   5100
ctcactgaac accgtcaatg tgatcgggtc ctccatgggc tctggcgggg tgtttaccat   5160
cgacgggaaa gtcaagtgcg taactgccgc acatgtcctt acgggcaatt cagctcgggt   5220
ttccggggtc ggcttcaatc aaatgcttga ctttgacgta aagggagatt tcgctatagc   5280
tgattgcccg aattggcaag gggctgcccc caagacccaa ttctgcacgg atggatggac   5340
tggccgtgcc tattggctaa catcctctgg cgtcgaaccc ggcgtcattg gaaaaggatt   5400
cgccttctgc ttcaccgcat gtggcgattc cgggtcccca gtgatcaccg aggccggtga   5460
gcttgtcggc gttcacacgg gatcgaataa acaagggggg ggcattgtta cgcgcccctc   5520
aggccagttt tgtaatgtgg cacccatcaa gctaagcgaa ttaagtgaat tctttgctgg   5580
gcctaaggtc ccgctcggtg atgtgaaggt cggcagccac ataattaaag acataagcga   5640
ggtgccttca gatctttgtg ccttgcttgc tgccaaacct gaactggaag gaggcctctc   5700
caccgtccaa cttctttgtg tgtttttct cctgtggaga atgatgggac atgcctggac   5760
gcccttggtt gctgtgagtt tctttatttt gaatgaggtt ctcccagccg tcctggtccg   5820
gagtgttttc tcctttggaa tgtttgtgct atcctggctc acgccatggt ctgcgcaagt   5880
tctgatgatc aggcttctga cagcagctct taacaggaac agatggtcac ttgcctttt   5940
```

-continued

```
cagcctcggt gcagtgaccg gttttgtcgc agatcttgcg gccactcagg ggcatccgct   6000
gcaggcagtg atgaatttga gcacctatgc attcctgcct cggatgatgg ttgtgacctc   6060
accagtccca gtgatcacgt gtggtgtcgt gcacctactt gccatcattt tgtacttgtt   6120
taagtaccgt ggcctgcacc atatccttgt tggcgatgga gtgttctctg cggctttctt   6180
cttgagatac tttgccgagg gaaagttgag ggaaggggtg tcgcaatcct gcggaatgaa   6240
tcatgagtct ctgactggtg ccctcgctat gagactcaat gacgaggact tggatttcct   6300
tataaaatgg actgatttta agtgctttgt ttctgcgtcc aacatgagga atgcagcggg   6360
tcaatttatc gaggctgcct atgctaaagc acttagagta gaactggccc agttggtgca   6420
ggttgataaa gttcgaggta ctttggccaa acttgaagct tttgctgata ccgtggcacc   6480
tcaactctcg cccggtgaca ttgttgtcgc tctcggccac acgcctgttg gcagtatctt   6540
cgacctaaag gttggtagca ccaagcatac cctccaagcc attgagacca gagtccttgc   6600
tgggtccaaa atgaccgtgg cgcgcgtcgt cgacccgacc cccacgcccc cacccgcacc   6660
cgtgcccatc cccctcccac cgaaagttct ggagaatggc cccaacgctt ggggggatga   6720
ggaccgtttg aataagaaga agaggcgcag gatggaagcc ctcggcatct atgttatggg   6780
cgggaaaaag taccagaaat tttgggacaa gaattccggt gatgtgtttt atgaggaggt   6840
ccataataac acagatgagt gggagtgtct cagagttggc gaccctgccg actttgaccc   6900
tgagaaggga actctgtgtg gacatgtcac cattgaaaac aaggcttacc atgtttacac   6960
ctccccatct ggtaagaagt tcttggtccc cgtcaaccca gagaatggaa gagttcaatg   7020
ggaagctgca aagctttccg tggagcaggc cctaggtatg atgaatgtcg acggcgaact   7080
gactgccaaa gaactggaga aactgaaaag aataattgac aaactccagg gcctgactaa   7140
ggagcagtgt ttaaactgct agccgccagc gacttgaccc gctgtggtcg cggcggcttg   7200
gttgttactg aaacagcggt aaaaatagtc aaatttcaca accggacctt caccctggga   7260
cctgtgaatt taaaagtggc cagtgaggtt gagctaaaag acgcggttga gcacaaccaa   7320
cacccggttg cgagaccgat cgatggtgga gttgtgctcc tgcgctccgc ggttccttcg   7380
cttatagacg tcttgatctc cggtgctgat gcatctccca agttacttgc ccatcacggg   7440
ccgggaaaca ctgggatcga tggcacgctc tgggattttg agtccgaagc cactaaagag   7500
gaagtcgcac tcagtgcgca aataatacag gcttgtgaca ttaggcgcgg cgacgctcct   7560
gaaattggtc tcccttacaa gctgtaccct gttaggggta accctgagcg ggtgaaagga   7620
gttttgcaga atacaaggtt tggagacata ccttacaaaa cccccagtga cactggaagc   7680
ccagtgcacg cggctgcttg ccttacgccc aacgccactc cggtgactga tgggcgctcc   7740
gtcttggcca cgaccatgcc ccccgggttt gagttatatg taccgaccat accagcgtct   7800
gtccttgatt accttgactc taggcctgac tgccctaagc agctgacaga gcacggctgc   7860
gaagatgccg cactgaaaga cctctctaaa tatgacttgt ccacccaagg ctttgtttta   7920
cctggagttc ttcgccttgt gcggaaatac ctgtttgccc atgtaggtaa gtgcccaccc   7980
gttcatcggc cttctactta ccctgctaag aattctatgg ctggaataaa tgggaacagg   8040
ttcccaacca aggacattca gagcgtccct gaaatcgacg ttctgtgcgc acaggctgtg   8100
cgagaaaact ggcaaactgt caccccttgt actcttaaga aacagtattg cgggaagaag   8160
aagactagga ccatactcgg caccaataac ttcatcgcac tagcccaccg agcagtgttg   8220
agtggtgtta cccagggctt catgaaaaag gcgtttaact cgcccatcgc cctcggaaag   8280
aacaagttta aggagctaca gactccggtc ctgggcaggt gccttgaagc tgatctcgca   8340
tcctgcgatc gatccacgcc tgcaattgtc cgctggtttg ccgccaacct tctttatgaa   8400
```

-continued

```
cttgcctgtg ctgaagagta tctaccgtcg tacgtgctga actgctgcca cgacttactg   8460
gtcacgcagt ccggcgcagt gactaagaga ggtggcctgt cgtctggcga cccgatcacc   8520
tctgtgtcta acaccattta tagtttggtg atctatgcac agcatatggt gcttagttac   8580
ttcaaaagtg gtcaccccca tggccttctg ttcttacaag accagctaaa gtttgaggac   8640
atgctcaagg ttcaacccct gatcgtctat tcggacgacc tcgtgctgta tgccgagtct   8700
cccaccatgc caaactatca ctggtgggtt gaacatctga atttgatgct ggggtttcag   8760
acggacccaa agaagactgc aataacagac tcgccatcat ttctaggctg tagaataata   8820
aatgggcgcc agctggtccc caaccgtgac aggatcctcg cggccctcgc ctatcacatg   8880
aaggcgagta atgtttctga atactatgcc tcagcggctg caatactcat ggacagctgt   8940
gcttgtttgg agtatgatcc tgaatggttt gaagaacttg tagttggaat agcgcagtgc   9000
gcccgcaagg acggctatag ctttcccggc acgccgttct tcatgtccat gtgggaaaaa   9060
ctcaggtcca attatgaggg gaagaagtcg agagtgtgcg ggtactgcgg ggccccggct   9120
ccgtacgcta ctgcctgtgg cctcgacgtc tgcatttacc acacccactt ccaccagcat   9180
tgtccagtca caatctggtg tggccatcca gcgggttctg gttcttgtag tgagtgcaaa   9240
tcccctgtag ggaaaggcac aagccccttta gacgaggtgc tggaacaagt cccgtataag   9300
cccccacgga ccgttatcat gcatgtggag cagggtctca ccccccttga tccaggtaga   9360
taccaaactc gccgcggact agtctctgtc aggcgtggaa ttaggggaaa tgaagttgaa   9420
ctaccagacg gtgattatgc tagcaccgcc ttgctcccta cctgcaaaga gatcaacatg   9480
gtcgctgtcg cttccaatgt attgcgcagc aggttcatca tcggcccacc cggtgctggg   9540
aaaacatact ggctccttca acaggtccag gatggtgatg ttatttacac accaactcac   9600
cagaccatgc ttgacatgat tagggctttg gggacgtgcc ggttcaacgt cccggcaggt   9660
acaacgctgc aattccccgt cccctcccgc accggtccgt gggttcgcat cctagccggc   9720
ggttggtgtc ctggcaagaa ttccttccta gatgaagcag cgtattgcaa tcaccttgat   9780
gttttgaggc ttcttagtaa aactaccctc acctgtctag gagacttcaa gcaactccac   9840
ccagtgggtt ttgattctca ttgctatgtt tttgacatca tgcctcaaac tcaactgaag   9900
accatctgga ggtttggaca gaatatctgt gatgccattc agccagatta cagggacaaa   9960
ctcatgtcca tggtcaacac aacccgtgtg acctacgtgg aaaaacctgt taggtatggg  10020
caggtcctca cccccctacca tagggaccga gaggacgacg ccatcactat tgactccagt  10080
caaggcgcca cattcgatgt ggttacattg catttgccca ctaaagattc actcaacagg  10140
caaagagccc ttgttgccat caccagggca agacacgcta tctttgcgta tgacccacac  10200
aggcagctgc agggcttgtt tgatcttcct gcaaaaggca cacccgtcaa cctcgcagtg  10260
caccgcgacg ggcagctgat cgtgctggat agaaataaca aagaatgcac ggttgctcag  10320
gctctaggca acggggataa atttagggcc acagacaagt gtgttgtaga ttctctccgc  10380
gccatttgtg ctgatctaga agggtcgagc tctccgctcc ccaaggtcgc acacaacttg  10440
ggattttatt tctcacctga tttaacacag tttgctaaac tcccagtaga acttgcacct  10500
cactggcccg tggtgacaac ccagaacaat gaaaagtggc cagatcggct ggttgccagc  10560
cttcgcccta tccataaata cagccgcgcg tgcatcggtg ccggctatat ggtgggccct  10620
tcggtgtttc taggcactcc tggggtcgtg tcatactatc tcacaaaatt tgttaagggc  10680
gaggctcaat tgcttccgga gacggttttc agcaccggcc gaattgaggt agactgccgg  10740
gaatatcttg atgatcggga gcgagaagtt gctgcgtccc tcccacacgc tttcattggc  10800
```

-continued

```
gacgtcaaag gcactaccgt tggaggatgt catcatgtca cctccagata cctcccgcgc   10860
gtccttccca aggaatcagt tgcggtagtc ggggtttcaa gccccggaaa agccgcaaaa   10920
gcattgtgca cactgacaga tgtgtacctc ccagatcttg aagcctatct ccacccggag   10980
acccagtcca agtgctggag aatgatgttg gacttcaaag aagttcgact aatggtctgg   11040
aaagacaaaa cagcctattt ccaacttgaa ggtcgctatt tcacctggta tcagcttgcc   11100
agctatgcct cgtacatccg tgttcctgtc aactctacgg tgtacttgga cccctgcatg   11160
ggccccgccc tttgcaacag gagagtcgtc gggtccaccc actggggggc tgacctcgcg   11220
gtcacccctt atgattacgg cgctaaaatt atcctgtcta gcgcgtacca tggtgaaatg   11280
ccccccggat acaaaattct ggcgtgcgcg gagttctcgt tggatgaccc agttaagtac   11340
aaacatacct gggggtttga atcggataca gcgtatctgt atgagttcac cggaaacggt   11400
gaggactggg aggattacaa tgatgcgttt cgtgcgcgcc aggaagggaa aatttataag   11460
gccactgcca ccagcttgaa gttttatttt cccccgggcc ctgtcattga accaacttta   11520
ggcctgaatt gaaatgaaat ggggtccatg caaagccttt tttacaaagt tggccaactt   11580
tttgtggatg ctttcacgga gttcttggtg tccattgttg atatcattat atttttggcc   11640
attttgtttg gcttcaccat cgccggttgg ctggtggtct tttgcatcag attggtttgc   11700
tccgcgatac tccgtgcgcg ccctgccatt cactctgagc aattacagaa gatcttatga   11760
ggcctttctt tcccagtgcc aagtggacat tcccacctgg ggaactaaac atcctttggg   11820
gatactttgg caccataagg tgtcaaccct gattgatgaa atggtgtcgc gtcgaatgta   11880
ccgcatcatg gaaaaagcag ggcaggctgc ctggaaacag gtggtgagcg aggctacgct   11940
gtctcgcatt agtagtttgg atgtggtggc tcattttcag catctagccg ccattgaagc   12000
cgagacctgt aaatatttgg cctcccggct gcccatgcta cacaacctgc gcatgacagg   12060
ttcaaatgta accatagtgt ataatagcac tttgaatcag gtgtttgcta tttttccaac   12120
ccctggttcc cggccaaagc gtcatgattt tcagcaatgg ttaatagctg tacattcctc   12180
catattttcc tctgttgcag cttcttgtac tctttttgtt gtgctgtggt tgcgggttcc   12240
aatactacgt actgtttttg gtttccgctg gttaggggca atttttcttt cgaactcaca   12300
gtgaattaca cggtgtgtcc accttgcctc acccggcaag cagccgcaga gatctacgaa   12360
cccggtaggt ctctttggtg caggataggg tatgaccgat gtgaggagga tgatcatgac   12420
gagctagggt ttatggtacc gcctggcctc tccagcgaag gccacttgac tagtgtttac   12480
gcctggttgg cgttcttgtc cttcagttac acggcccagt tccatcccga gatattcggg   12540
atagggaatg taagtcgagt ttatgttgac atcaaacatc aactcatctg cgccgaacat   12600
gacgggcaga acaccacctt gcctcgtcat gacaacattt cagccgtgtt tcagacctat   12660
taccaacatc aagtcgacgg cggcaattgg tttcacctag aatggcttcg tcccttcttt   12720
tcctcgtggt tggttttaaa tgtctcttgg tttctcaggc gttcgcctgc aaaccatgtt   12780
tcagttcgag tcttgcagac attaagacca acaccaccgc agcggcaagc tttgctgtcc   12840
tccaagacat cagttgcctt aggcatcgcg actcggcctc tgaggcgatt cgcaaaatcc   12900
ctcagtgccg tacggcgata gggacacctg tgtatgttac catcacagcc aatgtgacag   12960
atgagaatta tttacattct tctgatctcc tcatgctttc ttcttgcctt ttctatgctt   13020
ctgagatgag tgaaaaggga tttaaggtgg tatttggcaa tgtgtcaggc atcgtggctg   13080
tgtgtgtcaa ttttaccagc tacgtccaac atgtcaagga gtttacccaa cgctccctgg   13140
tggtcgacca tgtgcggttg ctccatttca tgacacctga gaccatgagg tgggcaactg   13200
ttttagcctg tctttttgcc attctgttgg caatttgaat gtttaagtat gttggagaaa   13260
```

-continued

```
tgcttgaccg cgggctgttg ctcgcaattg ctttctttgt ggtgtatcgt gccgttctgt  13320
tttgctgtgc tcgtcaacgc cagcaacgac agcagctccc atctacagct gatttacaac  13380
ttgacgctat gtgagctgaa tggcacagat tggctagcta aaaaatttga ttgggcagtg  13440
gagagttttg ttatctttcc cgttttgact cacattgtct cctatggtgc cctcactgcc  13500
agccatttct ttgacacagt cgctttagtc actgtgtcta ccgccgggtt tgttcacggg  13560
cggtatgtcc taagtagcat ctacgcggtc tgtgccctgg ctgcgttgac ttgcttcgtc  13620
attaggtttg caaagaattg catgtcctgg cgctacgcgt gtaccagata taccaacttt  13680
cttctggaca ctaagggcag actctatcgt tggcggtcgc ctgtcatcat agagaaaagg  13740
ggcaaagttg aggtcgaagg tcatctgatc gacctcaaaa gagttgtgct tgatggttcc  13800
gtggcaaccc ctataaccag agtttcagcg gaacaatggg gtcgtcctta gatgacttct  13860
gtcatgatag cacggctcca ggaaaggtgc ttttggcgtt ttctattacc tacacgccag  13920
tgatgatata tgccctaaag gtgagtcgcg gccgactgct agggcttctg caccttttga  13980
tcttcctgaa ttgtgctttc accttcgggt acatgacttt cgcgcacttt cagagtacaa  14040
ataaggtcgc gctcactatg ggagcagtag ttgcactcct ttggggggtg tactcagcca  14100
tagaaacctg gaaattcatc acctccagat gccgtttgtg cttgctaggc cgcaagtaca  14160
ttctggcccc tgcccaccac gttgaaagtg ccgcaggctt tcatccgatt gcggcaaatg  14220
ataaccacgc atttgtcgtc cggcgtcccg gctccactac ggtcaacggc acattggtgc  14280
ccgggttaaa aagcctcgtg ttgggtggca gaaaagctgt taaacaggga gtggtaaacc  14340
ttgtcaaata tgccaaataa caacggcaag cagcagaaga gaaagaaggg ggatggccag  14400
ccagtcaatc agctgtgcca gatgctgggt aagatcatcg ctcagcaaaa ccagtccaga  14460
ggcaagggac cgggaaagaa aaataagaag aaaaacccgg agaagcccca ttttcctcta  14520
gcgactgaag atgatgtcag acatcacttt accccctagtg agcggcaatt gtgtctgtcg  14580
tcaatccaga ccgcctttaa tcaaggcgct gggacttgca ccctgtcaga ttcagggagg  14640
ataagttaca ctgtggagtt tagtttgcct acgcatcata ctgtgcgcct gatccgcgtc  14700
acagcatcac cctcagcatg atgggctggc attcttgagg catctcagtg tttgaattgg  14760
aagaatgtgt ggtgaatggc actgattgac attgtgcctc taagtcacct attcaattag  14820
ggcgaccgtg tgggggtgag atttaattgg cgagaaccat gcggccgaaa ttaaaaaaaa  14880
aaaaa                                                              14885
```

<210> SEQ ID NO 8
<211> LENGTH: 15434
<212> TYPE: DNA
<213> Artificial Sequence

<400> 8

```
atgacgtata ggtgttggct ctatgccgtg acatttgtat agtcaggagc tgcgaccatt     60
ggtacagccc aaaacttgct gcacgggaac gcccttccgt gacagccttc ttcaggggag    120
tttagggatc tatccctagc accttgcttc cggagttgca ctgctttacg gtctctccaa    180
ccctttaacc atgtctggga tacttgatcg gtgcacgtgc acccccaatg ccagggtgtt    240
tatggcggag ggccaagtct actgcacacg atgtctcagt gcacggtctc tccttcctct    300
gaatctccaa gtccctgagc ttggggtgct gggcctattt tacaggcccg aagagccact    360
ccggtggaca ttgccgcgtg cattccccac tgtcgagtgc tccccccgccg gggcctgctg    420
gctttctgcg atcttcccaa ttgcacgaat gaccagtgga aacctgaact ttcaacaaag    480
aatggtgcgg gtcgcagctg agatttacag agccggtcag ctcactccca cagtcttgaa    540
```

-continued

```
gaatctacaa gtttatgagc ggggttgccg ttggtaccct attgtcgggc ctgtccccgg    600
agtggccgtt tacgccaact ccctacatgt gagtgacaaa ccctttccgg gagcaactca    660
tgtgttaact aatctaccgc tcccgcagag gcccaagctt gaagattttt gcccctttga    720
gtgtgctatg gctgacgtct atgatatcgg tcatgacgcc gtcatgtacg tggccaaagg    780
gaaagtctcc tgggctcctc gtggtgggga caagacaaaa tttgaaactg tccctaggga    840
gttgaagttg atcgcgaacc gactccatgt ctccttcccg ccccaccacg cagtggacat    900
gtcccagttt gcgttcataa ccttcgggag cggtgtctct atgcgggtcg agtgcccaca    960
tggctgtctc cccgccaata ccgtccctga aggcaactgc tggtggcgct tgtttgacat   1020
gcttccaccg gaggttcaga acgatgaaat tcgccgtgcc tgccaattcg gttatcaaac   1080
caagcatggt gtcgctggca agtacctaca acggaggttg caagctaatg gcctccgagc   1140
ggtgactgat acaagtgggc ctatcgttgt gcagtttttc tccgttaagg agagttggat   1200
ccgccactta aggctggcgg acgaacctag ccttcctggt tttgaggacc tcctcagaat   1260
aagggttgag cccaacacgt caccattggt tagcaaggat gtgaaaatct tccggttcgg   1320
cagtcacaaa tggtacggtg ctggaaagag ggcaaagaaa gcacgctctg gtgcggctgc   1380
cacggtcatt caccgcgctt tgcctgttcg cgaagcccag cagaccaaga cgcacaaggt   1440
tgctagcgct aacagggctg agtgtctcaa gcgctattct ccgcctgccg atgggaactg   1500
tggttggcac tgcatttccg ccatcgccaa ccggatggtg aattcgaaat ttgagaccac   1560
ccttcccgaa agagtgagac cttctgatga ttgggctacc gacgaggatc ttgtgaacgc   1620
cattcaaatc ctcaagctcc ctgcggcctt ggacaggaac ggagcttgtg gtagcgccaa   1680
gtacgtgctt aagctggaag gcgtgcattg gactgtctct gtgacccctg ggatgtcccc   1740
ctctttgctc cccccttgaat gtgttcaggg ctgttgtgag cataaggacg gttctggccc   1800
cccagatgcg gtcgaggttt ccggatttga ccctgcctgc cttgaccgac tggctggggt   1860
gatgcattta cctagcagtg ctatcccagc cgctctggct gaaatgtccg gcaactccaa   1920
tcgcccggct tccccggtca acactgtgtg gactgtttcg caattctatg cccgtcactt   1980
aggaggagtt catcctgacc aggtgtgctt agggaaaatt attagcctct gtcaagtcat   2040
tgaggattgc tgctgccatc aaaacaaaac caaccgggcc accccggaag aggtcgcggc   2100
aaagattgat cagtacctcc gtggtgcaac aagtcttgag gaatgcttga ctaggcttga   2160
aagggtttgc cctccgagcg ctgcggacac ctcctttgat tggaatgttg tgctccctgg   2220
ggttgaggct gcaacccaga caactaaaca gctccatgtc aaccggtgcc gcgttttggc   2280
tcctgtcgtg actcaagagc cttcggacaa agactcggtc cctctgaccg ccttctcgtt   2340
gtccaattac tactacccgg cacaaggtga cgagattcat caccgtgaga ggctgaactc   2400
cgtactctct aagttggagg gggttgttcg cgaggaatat gggctcacgc caactgaacc   2460
tggtccgcga cccgcactac cgaacgggct cgacgagctc agagaccaga tggagatgga   2520
tctgctgaga ctagtcaacg atcaggcaac ttcagaaatg atggcccggg cagctgagca   2580
ggttgatcta aaagcttggg tcaaaaacta cccacggtgg acaccgccgc ccactccacc   2640
aagagttcag cctcgaaaaa cgaggtctgt caagagcttg ccaggggata agcctgtccc   2700
ggctccgcgt aggaaggtca gatctgattg tggcagcccg attttgatgg gcgacaatgt   2760
tcctaacgat cgggaagatt tgactgttaa tgggcccctt gacctttcga caccatccga   2820
gtcgatgaca cctctgagtg agcctgcact tatgcccgcg ttgcaacatg tttctaggtc   2880
ggcgacatct ttgagtgtgc cgaccccagt tcctgtaccg cgcagagctg tgtcccgacc   2940
ggtggcaccc ttgagtgagc caacctttga gtcttcaccg cgacacaaat ttcaagaggt   3000
```

-continued

```
gaaagaagtg aatctggcgg caacaacgcc gacgcaccaa gacgaacctc tagatttgtc   3060
tgcatcctca cagactgtat gtgaggcctc tcccctagca ccgcctcaga acataggtat   3120
tctgggggtg gaggggcaag aaactgagga agtcctgagt gaagtctcgg atataccgta   3180
tgacattaac cttgcacctg tgtcatcaag cagctccctg tcaagtgtaa agatcacacg   3240
tccgaaatac tcagctcaag ccattattga ctcaggcggg ccctgcagtg ggcatcttcg   3300
aaagggaaaa gaagcatgcc tcagcatcat gcgcagggct tgtgatgcgg ctaagcttag   3360
tgaccctgcc acgcaagaat ggctttctcg tatgtgggat agggttgaca tgctgacttg   3420
gcgcaacacg tctgcttacc aggcgttgcg catcttagat ggcaggtttg ggttcctccc   3480
gaaaatgata ctcgagacac caccgcccta tccgtgtggg tttgtgatgc tgcctcacac   3540
gcctgcacct tccgtgagtg cagagagcga cattaccatt ggttcagttg cctctgaaga   3600
tgttccacgc atcctcggga aaatagaaaa cgccggcgag atgcccaacc aggggctctt   3660
ggcgtccctt gaggaaaaac cggtgcacga ccaacctgcc gaagactccc ggatgccgtt   3720
gcgggggttt gacgagagcg taacggctcc gtccgctggt acaggttgcg ctgactcacc   3780
cactgatttg tcgccttcag gtggtgtgga cgtggacggg gggggggcgt tacgggcggt   3840
aagaaagaaa gctgaaaggc tcttcgatca attgagccgc caggttttta acctcgtctc   3900
ccatctccct gttttcttct cacacctctt caaatctgac agtggttatt ctccgggtga   3960
ttggggtttt gcagctttta ctctattttg tctcttttta tgttacaact acccattttt   4020
tgggtttgct cccctcttgg gtgtgttttc tgggtcttct cggcgtgtgc gcatgggggt   4080
ttttggctgc tggttggctt ttgctgttgg cctgttcaaa cctgtgtccg acccagtcgg   4140
cactgcttgt gaatttgact cgccagagtg taggaacgtc cttcattctt ttgagcttct   4200
caaaccttgg gaccctgttc gcagccttgt tgtgggcccc gtcggtctcg gtcttgccat   4260
tcttggcagg ttactgggcg gggcacgcta catctggcat tttttgctta ggcttggcat   4320
tgttgcagat tgtgtcttgg ctggagctta tgtgctttct caaggtaggt gtaaaaagtg   4380
ctggggatct tgtgtaagaa ctgctcccaa tgaaattgcc ttcaacgtgt tccctttttac   4440
gcgtgcgacc aggtcgtcac tcatcgacct gtgcaaccgg tttcgtgcgc cgaaaggcat   4500
ggaccccatt tttctcgcta ctgggtggcg cgggtgctgg accggccaaa gtcccattga   4560
gcaaccctcc gaaaaaccca tcgcgttcgc ccagttggat gaaaagagga tcacggccag   4620
aactgtagtt gctcagcctt atgatcctaa ccaagccgta aagtgcctgc gggtgttaca   4680
ggcgggtggg gcgatggtgg ccgaggcagt cccgaaagtt gtcaaagttt ccgctatccc   4740
attccgagcc cctttttttc ccaccggagt gaaggttgat cctgagtgca ggatcgtagt   4800
cgaccccgac actttcacta ctgctcttcg gtctggttac tccaccacaa acctcgtcct   4860
tggtgtgggg gactttgccc aactgaatgg attaaaaatc aggcaaattt ccaagccttc   4920
gggaggaggc ccacacctca ttgctgccct gcatgttgct tgctcgatgg cgttgcacat   4980
gcttgctggg gtttacgtaa ctgcagtggg gtcttgcggt accggcacca acgatccgtg   5040
gtgcaccaac ccattcgccg tccctggcta cggacctggc tctctctgca cgtccaggtt   5100
gtgcatctcc caacatggcc ttaccttgcc cttgacagca cttgtggcag gcttcggtct   5160
tcaggaaatt gccttggtcg ttctgatttt tgtttccatc ggaggcatgg ctcataggtt   5220
gagttgtaag gctgatatgc tgtgcgtctt gctcgcaatc gccagctatg tttgggtacc   5280
ccttacctgg ttgctctgcg tgtttccttg ctggttgcgc tggttctctt tgcacccccct   5340
caccatccta tggttggtgt ttttcttgat ttctgtaaat atgccttcag gaaccttagc   5400
```

-continued

```
cgtggtgtta ttggtcgctc tttggcttct aggccgttac actaatgttg ttggtcttgt   5460
caccccctac gatatccatc attacaccag cggccctcgc ggtgttgccg ccttggctac   5520
cgcaccagat ggaacttatt tggccgctgt ccgccgcgct gcgttgactg gccgtaccgt   5580
tctgtttacc ccgtctcagc ttgggtccct tcttgagggc gctttcagga ctcgaaagcc   5640
ctcattgaac accgttaatg tggtcgggtc ctccatgggc tctggcggag tgttcactat   5700
cgatgggaaa attaagtgtg tgactgccgc acatgtcctt acgggcaact cagccagggt   5760
ttccggggtc ggcttcaatc agatgcttga ctttgatgta aaaggagatt tcgccatagc   5820
tgattgcccg aattggcaag ggactgctcc taagacccaa ttctgcaagg acgggtggac   5880
tggccgtgcc tattggctaa catcttctgg tgtcgaaccc ggtgtcattg gaaatgggtt   5940
cgccttctgc ttcaccgcgt gcggtgactc cgggtctcca gtgatcaccg aagccggtga   6000
gcttgtcggc gttcacacag gatcaaacaa acaaggagga ggcattgtta cgcgcccctc   6060
aggccagttt tgtaatgtgg cacccatcaa gctgagcgaa ttaagtgagt tctttgctgg   6120
acctaaggtc ccgctcggtg atgtgaaggt tggtagccac ataattaaag acatatgcga   6180
ggtaccttca gatctttgtg ccttgcttgc tgccaaaccc gaattggaag gaggcctctc   6240
caccgtccaa cttctatgtg tatttttcct cctgtggaga atgatgggac atgcctggac   6300
acccttggtt gccgtgggtt tttttatttt gaatgagatt cttccagctg tactggtccg   6360
gagtgttttc tccttcggaa tgtttgtgtt atcttggctc acaccatggt ctgcacaagt   6420
tctgatgatc aggctcctca cagcagctct taataggaac agattgtcac tcgccttcta   6480
cagccttggt gcggcaaccg gttttgtcgc agacctagcg gcgacccaag ggcatccgtt   6540
gcacgcagta atgaatttga gtacctatgc cttcctgcct cgggtgatgg ttgtgacctc   6600
accagtccca gtaatcgcgt gtggtgttgt gcacctcctt gccataattt tgtacttgtt   6660
taggtaccgc tgcctgcatg gtgttcttgt tggcgatggg gcgttctctg cggctttttt   6720
tttgcgatac tttgctgagg ggaaattgag ggaaggggtg tcgcaatcct gcgggatgaa   6780
tcatgagtcg ctgactggtg ccctcgccat gagactcaat aacgaggatt tggatttcct   6840
cactaagtgg actgatttta agtgctttgt ttctgcttcc aacatgagga atgcagcggg   6900
ccaattcatt gaggctgcct atgccaaagc acttagaata gaacttgccc agctggtgca   6960
ggtcgacaag gtccgaggca ctttggccaa acttgaagct tttgccgaca ccgtggcacc   7020
ccaactctcg cccggtgaca ttgttgtcgc tcttggccat acgcctgttg gcagtgtctt   7080
cgacctgaag gttggtaaca ccaagcacac tctccaagcc attgagacca gggtccttgc   7140
tgggtccaaa atgaccgtgg cgcgcgtcgt cgacccgacc cccacgcccc cacccgcacc   7200
cgtacccatc cccctcccac cgaaggtttt ggagaacggt ccaaacgctt ggggggatga   7260
agatcgtttg aataaaaaga agaggcgcag gatggaagct gtcggcatct ttgttatggg   7320
cggaaagaaa taccagaaat tttgggacaa gaattccggt gatgtgtttt atgaggaggt   7380
ccatgacaat acagacgcgt gggagtgcct cagggttgat aactctgccg actttgatcc   7440
cgagaaggga actctgtgtg ggcatactac cattgagaat aaaacctaca atatctacgc   7500
ctccccatcc ggcaagaagt tcctggtccc tgccaactca gagggcggaa aagtccagtg   7560
ggaagctgca aagctctccg tggagcaggc ccttggcatg atgaatgtcg acggtgaact   7620
gacagccaga gaactggaga aactaaaaaa aataattgac aaactccagg acctgaccaa   7680
ggagcagtgt ttaaactgct agccgccagc ggcctgaccc gctgtggtcg cggcggctta   7740
gttgttactg agacagcggt aaaaatagtc aaatatcaca gccggacctt caccctagga   7800
cctgtaaatt taaaagtggc tagtgaggtt gagctaaaag acgcggtcga gcataaccag   7860
```

-continued

```
cacccggtcg caagaccggt tgatggtggt gttgtgcttc tgcgctccgc agttccttcg    7920
cttatagacg tcttgatctc cggcgctgat gcatctccta agttactcgc tcgccacggg    7980
ccgggaaata ctgggatcga cggcacgctt tgggattttg aggccgaggc caccaaagag    8040
gagatcgcac tcagtgcgca gataatacag gcttgtgaca ttaggcgcgg cgacgcaccc    8100
gaaattggtc tcccttataa gctgtaccct gttaggggca atcccgagcg ggtaaaagga    8160
gttttacaga atacaaggtt cggggacatt ccttataaaa cccccagtga cactggaagc    8220
ccagtgcacg cggctgcctg cctcacgccc aatgccactc cggtgactga tgggcgctcc    8280
gtcttggcta caaccatgcc ctccggtttt gagttgtacg tgccgaccat tccagcatct    8340
gtccttgatt accttgactc caggcctgac tgccctaaac agttgacaga gcacggctgt    8400
gaggatgccg cattaagaga cctttccaag tatgacttgt ccactcaagg ctttgttttg    8460
ccaggagttc ttcgccttgt gcgtaagtac ctatttgctc atgtgggcaa gtgcccgcct    8520
attcatcggc cttccaccta ccctgccaag aattctatgg ctggaataaa tgggaacagg    8580
tttccaacca aggacatcca gggcgtccct gaaatcgacg tcctgtgcgc tcaggccgtg    8640
cgggaaaact ggcagactgt caccccttgt accctcaaga aacagtattg tgggaagaag    8700
aagactagga caatactcgg caccaataat ttcattgcat tggcccaccg ggcagcgttg    8760
agtggcgtca cccagggctt tatgaaaaag gcgttcaatt cgcccatcgc cctcggaaaa    8820
aacaaattta aggagctaca aactccggtc ttaggcaggt gcctagaggc tgaccttgca    8880
tcctgcgatc gatccacacc tgcgattgtc cgctggtttg ccgccaatct tctttatgaa    8940
cttgcctgtg ctgaggaaca tctaccatcg tacgtgctga actgctgcca cgacttactg    9000
gtcacgcaat ccggcgcggt gactaagaga ggtggcctgt cgtctggcga cccgattact    9060
tctgtgtcaa acaccattta tagtttggtg atatatgcac agcacatggt gctcagttac    9120
tttaaaagtg gtcaccctca cggccttctg tttctgcaag accagctaaa gtttgaggac    9180
atgctcaagg ttcaacccct gatcgtctat tcggacgacc tcgtgttgta tgccgagtct    9240
cccactatgc caaactacca ctggtgggtt gaacatctga atcttatgtt gggttttcag    9300
acggacccaa gaaagacagc cataacagac tcaccatctt ttctaggctg tagaataata    9360
aatgggcgcc agctagtccc ccaccgtgac aggattctcg cggcccttgc ctaccatatg    9420
aaggcaagca atgtttctga atactacgct tcggcggccg cgatactcat ggacagctgt    9480
gcttgtctag agcatgatcc tgaatggttt gaagaacttg tggtcggaat ggcgcagtgt    9540
gcccgcaagg acggctacag ctttcccggc ccgccgttct tcttgtctat gtgggaaaaa    9600
ctcaggtcta attatgaggg gaagaagtcg agagcgtgcg gatactgcgg ggccccggct    9660
ccgtacgcta ccgcctgtgg cctcgacgtc tgcatttatc acacccattt ccaccagcat    9720
tgtccggtca taatctggtg tggtcatccg gcgggttctg gttcttgtag tgagtgcaaa    9780
cccccccttg ggaaaggtac aagccctcta gatgaggtgt tggaacaagt cccgtacaag    9840
cctccgcgga ccgtgatcat gcacgtagag cagggtctta ctccactcga cccaggtaga    9900
taccaaaccc gccgcggatt agtctccgtt aggcgtggca ttaggggaaa cgaagttgaa    9960
ctaccagacg gtgattatgc tagtaccgcc ttgctcccca cttgtaaaga gatcaacatg   10020
gttgctgttg cttctaacgt gttacgcagc aggttcatca tcggtccacc tggtgctggt   10080
aaaacatact ggctccttca acaggtccag gatggtgatg tcatttacac gccaactcat   10140
cagactatgc ttgacatgat taaggctttg gggacgtgcc ggttcaacgt tccagcaggc   10200
acaacgctgc aattccctgc cccctcccgc accggcccgt gggttcgcat cctggccggc   10260
```

-continued

```
ggttggtgtc ctggcaagaa ttccttcctg gatgaagcag cgtattgcaa tcatcttgac   10320
gtcttgaggc ttcttagcaa aactaccctc acctgcctgg gagatttcaa acaactccac   10380
ccggtgggtt ttgattccca ttgctatgtt tttgacatta tgcctcagac tcaactgaag   10440
accatctgga ggtttgggca gaacatctgt gacgccattc aaccagatta tagagacaaa   10500
cttgtgtcca tggtcaacac aacccgtgta acctacgtgg aaaaacctgt caagtatggg   10560
caagtcctca ccccctacca cagggaccga gaggacggcg ccgtcacaat tgactcaagt   10620
caaggcgcca catttgatgt ggttacactg catttgccca ctaaagattc actcaacagg   10680
caaagggccc ttgttgctat caccagggca agacatgcta tctttgtgta tgacccacac   10740
aggcaattgc agagcttgtt tgatcttcct gcaaaaagca cacccgtcaa tctcgcagtg   10800
caccgtgacg agcagctgac cgtgttagat agaaataaca aagagtgcac ggttgctcag   10860
gctctaggca atggggataa atttagggcc acagacaagc gcgttgtaga ttctctccgc   10920
gccgtttgtg cagacctgga agggtctagc tccccgctcc ccaaggttgc acacaacttg   10980
ggattttatt tctcgcctga tttgacacag tttgctaagc ttccggtaga acttgcacct   11040
cactggcccg tggtgacaac ccagaacaat gaaaagtggc cagaccggtt ggttgctagc   11100
cttcgccctg tccatgagta tagccgtgcg tgtgtcggtg ccggctatat ggtgggcccc   11160
tcagtgttcc taggcactcc tggggttgtg tcatactatc tcacaaaatt tgttagaggc   11220
gaggctcaaa tgcttccgga gacagtcttc agcaccggcc gaattgaggt agattgccgg   11280
gagtaccttg atgatcggga gcgagaagtt gctgagtccc tcccacacgc cttcattggc   11340
gacgtcaaag gcactaccgt tggggggatgt caccatgtca cctctaaata cctcccgcgt   11400
ttcctcccca aggaatcggt tgcggtagtt ggggtttcga gccccgggaa agccgcaaaa   11460
gcagtttgca cattgacaga tgtgtacctc ccagaccttg aagcttatct ccacccagag   11520
acccagtcta agtgctggaa aatgatgttg gacttcaagg aggttcgact gatggtctgg   11580
aaagataaga cggcctattt tcaacttgaa ggccgccatt tcacctggta ccagcttgca   11640
agctatgcct cgtacatccg agttcctgtt aattctacgg tatatctgga cccttgcatg   11700
ggccctgccc tttgcaacag gagggttgtc gggtccaccc attgggaagc tgacctcgca   11760
gtcacccctt atgattatgg tgccaaaatc attttgtctt gtgcatacca tggtgaaatg   11820
cctcccgggt acaagattct ggcgtgcgcg gagttctcgc ttgacgaccc agtcaggtac   11880
aaacacacct ggggatttgc atcggatata gcgtatttgt acgagttcac cggaaacggt   11940
gaggactggg aggattacaa tgatgcgttt cgtgcgcgcc agaaagggaa aatttacaaa   12000
gccactgccg ccagcatgag gttttatttt cccccgggcc ctatcgttga accaactttg   12060
ggcctagact gaaatgaaat ggggtctatg caaagcctct ttgacaaaat cggccaactt   12120
tttgtggatg ccttcacgga atttttggtg tccattgttg atatcatcat atttctggcc   12180
attttgtttg gctttaccat cgctggctgg ctggtggtct tctgcatccg actggtttgc   12240
tccgcggtac tccgtgcgcg ccctaccatt cactctgagc aattacagaa gatcctatga   12300
ggcctttctt tctcagtgcc aggtggacat tcccgcctgg ggaactaaac accccttggg   12360
gatgttttgg caccataagg tgtcgaccct gattgatgaa atggtgtcgc gtcgaatgta   12420
ccgcaccatg gaaaaagcag gacaggctgc ctggagacag gtggtaagcg aggctacgtt   12480
gtctcgcatt agtggtttgg atgtggtggc tcattttcag catcttgccg ccattgaagc   12540
tgagacctgc aaatacttgg cctctcggct tcccatgctg cacaatctgc gcatgacagg   12600
gtcaaatgta accatagtgt ataatagcac tttgaatcag gtgtttgcta tttttccaac   12660
ccctgaatcc cggccgaagc ttcatgattt tcagcaatgg ctaatagctg tgcattcctc   12720
```

-continued

```
catattttcc tccgttgcag cttcttgcac tctttttgtt gtgctgtggt tgcggattcc   12780
aacactacgt attgtttttg gtttccactg gtaaggggca atttttcctt cgagctcacg   12840
gtgaattaca cggtgtgccc gctttgcctc acccgacaag cagcctatga gatctatgaa   12900
tcacgcaggt ctttttggtg caggataggg catgaccgat gcagtgaggt cgaccacgac   12960
gagctagggt tcatggttcc gtctggcctc tccagcgaag gccacctgac cagtgtttac   13020
gcctggttgg cgttcctgtc cttcagctac acggcccagt tccatcccga gatatttggg   13080
atagggaatg tgagtcgagt ttatgttgac atcaagcacc aactcatctg cgccgttcac   13140
gacggggaga acaccacctt gcctcgtcat gacaacattt cagccgtatt tcagacctac   13200
taccagcatc aagtcgacgg cggcaattgg tttcacctag aatggctgcg tcccttcttt   13260
tcctcctggt tggttttaaa tgtctcgtgg tttctcaggc gttcgcctgc aagccatgtt   13320
tcagttcaag tctttcggac atcaaaacca acactaccgc agcatcaggc tttgttaccc   13380
tccaggacat cagctgtctt aggcatggcg actcgccctc tcagacgatt cgcaaaagcc   13440
ctccgtgccg cacggcgcta gggacacccg tgtacatcac tgttacagcc aatgtcacgg   13500
atgagaatta tttacactcc tctgatctcc tcatgctttc ttcttgcctt ttctatgctt   13560
ctgagatgag tgaaaaggga ttcaaggtga tatttggcaa tgtgtcaggc atcgtggccg   13620
tgtgtgttaa ttttaccagc tacgtccaac atgtcaaaga gttcacccaa cgctctttgg   13680
tggtcgacca tgtgcggctg ctccatttca tgacacctga aaccatgagg tgggcaaccg   13740
ttttagcctg tcttgttgcc atcttgctgg caatttgaat gtttcagtat gttggggaga   13800
tgcttgaccg cgggctgctg cttgcgattg ctttctttgt ggtgtatcgt gccgttctgg   13860
tttgctgcac tcgtcagcgc caaccagaac cacagctctc atcttcaatt gatttacaac   13920
ttgacgctat gtgagctgaa tggcacagaa tggctgggag acaaatttaa ttgggcagtg   13980
gagacctttg tcatctttcc cgtgttaact cacattgtct catatggtgc actcaccact   14040
agccatttcc ttgacacagt cggtctggtt actgtgtcta ccgccgggta ttatcacggg   14100
cggtatgttt tgagtagtat ctacgcggtc tgcgctctgg ccgcgttaat ttgcttcgtc   14160
attcggcttg cgaagaactg catgtcctgg cgctactctt gtaccagata taccaatttc   14220
cttctggaca ctaagggcag actctatcgc tggcggtcgc ccgttatcat agagaaaagg   14280
ggtaaggttg aggtcggaag tcacctgatc gatctcaaga gagttgtgct tgatggttct   14340
gcggcaaccc ctttaaccag agtttcagcg gaacaatggg gtcgtctcta gacgactttt   14400
gctatgatag cacggctcca caaaaggtgt ttttggcgtt ttccattacc tacacgccag   14460
taatgattta tgccctgaag gtaagtcgcg gccgactgtt agggcttctg caccttttga   14520
tctttctgaa ttgtgctttt accttcgggt acatgacatt tgtgcacttt gatagcacaa   14580
ataaggtcgc gctcactatg ggagcagtgg ttgcactcct ttggggggtg tactcggcca   14640
tagaaacctg gaaattcatc acctccagat gccgtttgtg cttgctaggc cgcaagtaca   14700
ttctggcccc tgcccaccac gtcgaaagtg ccgcgggctt tcatccgatt gcggcaaatg   14760
ataaccacgc atttgtcgtc cggcgtcccg gctccactac ggttaacggc acattggtgc   14820
ccgggttgaa aagcctcgtg ttgggtggca gaaaagctgt aaaacaggga gtggtaaacc   14880
ttgtcaaata tgccaaataa caacggcaag cagcaaaaga aaaaaaaggg gaatggccag   14940
ccagtcaacc agctgtgcca aatgttgggc aaaatcatcg cccagcagaa ccagtccaga   15000
ggtaagggac cgggaaagaa aattaaaaag aaaagcccgg agaagcccca ttttcctcta   15060
gcgactgagg atgacgtcag gcatcacttt acccctggtg agcggcaatt gtgtctgtcg   15120
```

-continued

```
tcaatccaga ctgcctttaa tcaaggcgct ggaacttgca ccctgtcaga ttcagggagg  15180

ataagttacg ctgtggagtt tagtttgccg acgcatcata ctgtgcgcct gattcgcgtc  15240

acagcaccac cttcagcgtg atgggctggc attcttgaga catcccggcg ttagaattgg  15300

aagaatgcgt ggtgaatggc actgattgac actgtgcctc taagtcacct attcagttag  15360

ggcgaccgtg tgggggtaga gtttaattgg cgagaaccac acggccgaaa ttaaaaaaaa  15420

aaaaaaaaaa aaaa                                                    15434
```

<210> SEQ ID NO 9
<211> LENGTH: 15047
<212> TYPE: DNA
<213> Artificial Sequence

<400> 9

```
atgacgtata ggtgtttgct ttatgccgcg gcatttgtat tgtcaggagc tgtgaccact     60

ggcacagccc gaaacttgct gcacagaaac acccttctgt gacagcctcc ttcaggggag    120

tttaggggtt tctccctaac gccctgcttc cggagttgca ctgctttacg gtctctccat    180

ccttttaacc atgtctggga ttcttgatcg gtgcacgtgc acccccaatg ccagggtgtt    240

tgtggcagag ggccaagtct actgcacacg atgtctcagt gcacggtccc tccttcccct    300

aaatctccaa gtttctgagc ttggggtact tggtttattc tacaggcccg aagagccatt    360

acggtggacg ttgccacacg cattccccac tgtcgagtgt gctcctgctg gcgcttgttg    420

gctttctgca atttttccaa ttgcgcgaat gaccagtgga aacctgaatt tccagcaaag    480

gctggtacgt gtcgcagccg agctttacag agccggccag ctcaccccta caagcctgaa    540

aaccttacag gtctatgaaa ggggttgccg ttggtacccc attgttggac ctgttcctgg    600

agtggccgtt tacgccaact ccctacatgt gagtgacaaa cccttcccag gagcgactca    660

cgtgctgacc aacttaccac tcccgcagag accaaaatct gaagatttct gccccttcga    720

gtgcgccacg gccgccgtct atgacatcgg ccatgacgcc gtcatgtatg taaccgagga    780

aaaggtttcc tgggctcctc gtggcgggga taaagggaaa tttgagactg ttcctgaggg    840

gttgaagttg actgcggaac gactctacac ctccttcccg cctcaccatg cggtggacat    900

gtccctttc atcttcacag accttgagtg cggcgcttcc atgcgggtcg aacgccaata    960

tggttgcctc tctgctggca ctgtccctga aggcaactgc tggtggagtc tgtttggctc   1020

gctttcgtta gaagctcagt ataaagaaat ccgctacgcc gcccaatttg gctatcagac   1080

caaacatggc gttactggca agtacctgca gcggaggctg caaattaatg gtctccgagc   1140

agtggttgac ccgaatgggc ctcttgtcgt acagtatttc tccgttaagg agagctggat   1200

gcgccacgtg agactggcgg aagagccagg ctatcctggg tttgaggatc tcctcaggat   1260

aagagtcgag cccaacacgt tgcctttgtc caacaaggac gagaaaatct tccgtttcgg   1320

cggttacaag tggtacggtg ctgggcggag ggcaaggaga acacgtgcaa gagcagtcac   1380

cgcagttgct agtcatgctc cgcccgctcg tggggcccag caggccgaga agcacgaagt   1440

tgctagtgcc aacaagactg agctccttac gcactactcc ccacctgctg aagggaattg   1500

cggctggcac tgcatctccg ccatcatgaa ccggatggtg cattccaagt ttgaaaccgc   1560

cctttccgaa agagtgagat ccccggaaga ctgggcgact gatgaggatc ttgtgaatac   1620

tattcaaatc ctcaggctcc ctgcggcctt agacaggaac ggcgcctgta aaaacgccaa   1680

gtacatcctt aagctggaag gtgagcactg gactgtttca gtgacccccg gaatgccccc   1740

ctcttcactt cctcttgaat gcgttcaggg ttgttgcgag cataagggca attttgactc   1800

tcaaaacgcg gtcggtttct ttgggttcga ccctgccagc cttgaccgac tcgctggggt   1860

aatgcatctg cccagcagcg ccatccctgc cgccctggcc gagttgtctg gtgaacttga   1920
```

-continued

```
ttgttcaact cccccggcca ccactgtgtg gactaccttg cagttttatg ctcgtcttgg   1980
tggggggggag catcctgatc aagagtgctt gagaaaaatc atcagcctct gtgaggtgct   2040
cgggagttgc tgctgttctc agagtagggt caaccgggtc accccggaag aggtcgcagc   2100
aaagattgac ctgtatcttc gtgacgcagc gagtcttgaa gagtgcttgg ctaggcttga   2160
gaaagctcgc ccgccaagca tgctggacac ctcctttgac tgggatgttg tactccctgg   2220
tgttgggacg gctgctcggg cagcagaact accccccacc gatgagtgtc gcgctctagt   2280
cactgctgtg gcccaaaggc cttcgccgaa agttcagcct cgaaaggcgg ggtctgttaa   2340
gagtctacca gagatcaggc ctgtccctgc cccacgcagg aaggttaagt ctagttgtgg   2400
tgatctggcc ccgttgggcg gcaatttccc tgatagctgg gaagatttgg ctggtggctc   2460
ccttaatctc cagatcttac ctgagccggt ggcacaatcc tttgaacctg tgcctgtccc   2520
tgcaccgcgc aagactgcgc ctcgattagt gtcgtcatca ttggcgtcga cccccgtacc   2580
tacaccacga tgtgggtttc ggcagtttga gggaatgaat ttgacagctg tgaccctagc   2640
atgccaggat gagtccctca atttgtctgc atcctcgcag actgaatatg aggcttctcc   2700
tttggcattg cagcagggtg aggatgtcct tgcggtgggg ggacgagaag ccgaagaagt   2760
cctgagcgga atctcgggaa tgtcaggtgg cattagatta gcgcccgcat catcaagtag   2820
ctccttgtca agcgtggaga tcacacgccc gaagtactca gctcaagcca tcattgactc   2880
aggtggaccc tgttgcgggc accttcaaga ggtgaaagag aaatacctta atgtcatgcg   2940
tgaggcatgt gatgcgacta agctcgatga ccctgccacg caagaatggc tctctcgcat   3000
gtgggagagg gtagacatgc taacctggcg caacacgtcc atctttcaag cgccttttac   3060
cttagctgac aagtttaagt ccctcccgaa gatgatactc gaaacgccgc caccctaccc   3120
ttgcgggttt gtgatgatgc ccgcacgccc cgcaccttct gtgggtgcgg aaagcgacat   3180
caccgttggt tcagttgcta ctgaagatgt cccgcgtata ctcggggagg tgggagatgt   3240
tggcaagatg accggccagg aacccttaga atccttcgca gatgaactgg cagatgacca   3300
acctgctagg gagtcccgaa cacaagctcc tcctgcaagc acaggtagcg ctggtttagt   3360
tttggattct ggagggtcgc tggggctcac tgacctgccg ctcccaaaca atatagacgc   3420
gggcgggaaa ggaccgtttc acgcggtcaa gaaaaaagct gtagggtgct ttgaccaact   3480
gagccgccgg gtttttgaca tcgtctccca tctccctgtt ttttttcac gccttttcgc   3540
gcccggtggt ttttactctt cgggtgactg gagttttgca gcttttactt tattgtgtct   3600
ctttttatgt tacagttatc cggcctttgg ttttgctccc ctcgtgggtg tattttctgg   3660
gtcttctcgg cgcgtgcgca tgggggtttt tggctgctgg ctggcttttg ctgttggttt   3720
gttcaagcct gcacccgacc cagtcggtgc tgcttgtgag tttgactcgc cagagtgtag   3780
agacatcctt cattcttttg agctcctgca accttgggac cctgttcgca gccttgtggt   3840
gggccccgtc ggtctcggcc ttgccatttt tggcaggtta ctgggcgggg cacgctacgt   3900
ctggctgctt ttgcttaggc ttggcatcgt ttcagactgt atcctggctg gagcctatgt   3960
gctttcgcaa ggcaggtgta aaaagtgttg gggatcttgt ataagaacag cccccagtga   4020
agttgccttc aatgtgtttc cctttacacg cgcaactaga tcgtcacttg tcaacctgtg   4080
cgaccggttc tgtgcaccca agggcatgga ccccatcttc cttgccacag gatggcgcgg   4140
atgctggtcc ggccagagcc ccattgagca accctctgaa aaacccatag cgttcgccca   4200
gttggacgaa aagaaaatca cggctaggac tgtggttgcc cagccttatg accccaacca   4260
agctgtgaag tgcctgcgag tcctccaggc gggtggagcg atggtagccg aggcagttcc   4320
```

-continued

```
aaaagtagtc aaagtttctg ctgtcccgtt tcgagcccct ttttttcctg ccggagtgaa   4380
agttgaccct gaatgcaggg tcgtggttga ccctgacacc tttacaaccg ctctccggac   4440
cggctactcc accacaaacc tcattcttgg tgttggggac tttgcccagc tgaatgggtt   4500
gaagatcaga caaatttcca agtccccagg agggggccct cacctcatgg cggctttaca   4560
tgttgcttgc tcgatgactt tgcacatgct tgttgggatt tatgtcacca tggtgggttc   4620
ttgtggctct ggcactaacg atccgtggtg cactaacccg tttgccgtcc ctgtctatgg   4680
gcctggctct ctctgcacgt ccaggttgtg catttcccag cgtggcctga ccctgcccct   4740
aacagcgctt gtggcagggt ttggcgttca ggaaatcgct ttggttgttt taatctttgt   4800
ctccatcggg ggtatggccc acaggttgag ttgcaaggct gacgtgctgt gtatcctgct   4860
tgctattgtc agctatgttt ggccacccct tacctggttg ctttgtgtgt ttccttgctg   4920
gttgcgctgg ttttctttac atccccttac tattctatgg ttagtgtttt tcttgatttc   4980
tgtaaatacg ccctcgggaa tcttggcctt ggtcctgtta atctctcttt ggctccttgg   5040
tcgctatacc aatgttgccg gccttgtcac cccttatgac attcaccatt acaccaacgg   5100
ccctcgcggc gttgccgcct tggccactgc cccggatggg acctacctgg ctgctgtccg   5160
ccgtgctgcg ttgactggcc gtaccatgct gttcaccccg tcccaacttg gctcgctcct   5220
tgagggcgct tttagaaccc aaaagccttc actgaacact gtcaatgtag ttgggtcctc   5280
catgggctcc ggcggggtgt tcaccattga tgggaagatc aaatgtgtga ccgctgctca   5340
tgtcctcacg ggtaactctg ccagggtttc cggggttggc ttcaatcaaa tgttggactt   5400
tgatgttaaa ggggattttg ccatagccga ttgtccgaat tggcaaggag tcgcccccaa   5460
gtcccggttc tgcaaggatg attggactgg ccgtgcttat tggctcacgt cctccggcgt   5520
cgaacccggc gtcattgggc aaggattcgc cttttgtttc accgcgtgcg gcgattccgg   5580
gtccccagtg atcaccgagg ccggggagct tgtcggtgtc cacacgggat caaacaaaca   5640
aggaggaggc attgttacgc gcccttcagg ccggttttgt aatgtgacac ccaccaaatt   5700
aagtgaattg agtgaattct tcgctggacc tagggtcccg cttggtgacg tgaaggttgg   5760
caatcacata atcaaagata taaatgaggt gccctcagat ctctgcgcct tactcgctgc   5820
caaacccgaa ttggaaggag gcctctccac cgttcaactt ctgtgcgtgt tttttctcct   5880
atggagaatg atgggacatg cctggacacc cttggttgcc gttggttttt tcatcttgaa   5940
tgaagttctc ccagcagtcc tggtccggag tgtcttctcc tttggaatgt tcgcactgtc   6000
ttggttcacg ccgtggtctg cacaaattct aatgatcagg ctcttgacag cagccctaaa   6060
cagaaacaga tcgtcacttg ccttttacag cctgggcgca ctaaccggtt ttgttgcaga   6120
tcttgcaacc aatcaggggt atttattgca cgcggtcatg aatgtgagca cctatgcatt   6180
cctgcctcgt gcaatggccg tgacctcacc agtcccaata gttgcgtgtg gcgttgtgca   6240
cttgcttgcc atcattctgt acttgttcaa gtaccgtagc ctgcatgccg tcctggtcgg   6300
cgatggtgcg ttttccgcgg ctttcttctt gcgatacttt gcggagggaa agttgaggga   6360
aggggtgtcg cagtcttgcg gcatgaatca tgagtcacta accggtgccc tcgccatgaa   6420
actcagcgac gaagacttgg acttcctcac aaaattgact gattttaagt gctttgtttc   6480
tgcatccaac atgaggaatg cggcgggtca atttatagag gccgcctacg ccaaagcact   6540
gagggtggaa cttgcccagt tggttcaagt cgataaagtt cgaggtgtcc tggccaaact   6600
tgaagctttc gctgacaccg tggcgcctca actttcaccc ggtgacattg ttgtcgccct   6660
tggacacaca cctgtcggca gcatttttga cctgaaggtc ggcaatgtta agcacactct   6720
ccagtccatt gagaccagaa cccttgccgg gtctaaaatg actgtggcgc gcgtcgtaga   6780
```

-continued cccaacccccc acaccccccgc ccgcacctgt gcccatttcc ctcccaccaa aggttttgga 6840
gaacggtccc aacgcctggg gggatgagaa cggtttgaac aaaaaaaagc ggcgcaagat 6900
ggaggccgtt ggcatttacg ttatgggcgg gaaaaagtat caaaaatttt gggataagaa 6960
ttctggtgat gtgttctatg aagaagtcca cgacaacaca gacgcgtggg aatgcctcag 7020
agttgacaac cctgccgact tggatcctga gaggggaacc ttgtgtggac acaccaccat 7080
agacaacagg ccttaccatg tttatgcttc tccgtctggt aggaagtttc tagtccctgt 7140
caacccggag agcggaaaag ctcagtggga agctgctaag ctttctttag atcaggccct 7200
cagtatgatg aatgtcgacg gcgaactgac cgccaaagaa gtggaaaaat tgaagagaat 7260
aattgacaaa ctccagggcc tgactaagga gcagtgttta aactgctagc cgccagcggc 7320
ttgacccgct gtggtcgcgg cggcttggtt gttactgaga cagcggtaaa gatagtcagg 7380
ttccacaacc ggacctttac cctagggcct gtgaatttga aagtagctag cgaagttgag 7440
ttgaaggacg cggtcgagca cggccaacac ccggtcgcga taccagccga tggtggcgtc 7500
gtgctcctgc gttccgctgt tccttcgctt atagacgtcc tgatctccgg tgctgacgca 7560
tctcccaggt tgctcgcccg tcacggaccg ggaaatactg gggtcaatgg cgcgctttgg 7620
gattttgagt ctgaagctac caaagaggaa gtagcactta gtgcgcaaat aatacaggcc 7680
tgtgacatta gacgcggcga tgcacctgag attggccttc cttacaagtt gtaccctgtt 7740
aggggcaacc ctgaacgggc aagaggggtt ctaatgaaca caagatttgg agacatacct 7800
tacaagaccc ccagcgacac cgggagcccg gtgcacgcgg ccgcctgcct tacgcccaac 7860
gccactccag taactgatgg gcgctccatc ctggccacga ccatgccctc cgggtttgaa 7920
ctatatgtgc cgaccattcc agcgtctgtc cttgattacc ttgactccag accagactgt 7980
cctaaacagt tgactgagca cgggtgtgaa gatgccgcgt tgaaggacct ttctaaatat 8040
gacctgtcca cccaaggctt tgtgttacct ggagttctac gcctcgtgcg aaaatatctg 8100
tttgctcatg taggtaagtg cccgcctgtc caccggccct ctacctatcc tgccaagaac 8160
tccatggccg gaataaatgg gaacaggttc ccaaccaagg atattcaaag catccctgag 8220
atcgacgttt tgtgtgcaca agctgtgcga gaaaactggc aaactgttac accctgcact 8280
cttaagaagc agtattgcgg taaaaagaag accaggacca tacttggcac caacaacttc 8340
gttgcgctgg cccaccgggc ggcgctgagt ggtgtcaccc agggtttcat gaagaaggcg 8400
tttaactcac ccatcgccct tggaaaaaat aaatttaagg agctacagac tccagtcttg 8460
ggtaggtgtc ttgaggctga tctcgcttcc tgcgatcgat ccacgcctgc aatcgttcgc 8520
tggtttgccg ccaaccttct ttatgaactt gcctgtgctg aggagcattt accgtcgtac 8580
gtgctgaact gttgtcacga cctattggtc acgcagtccg gcgcagtgac taagagaggt 8640
ggcctgtcgt ccggtgaccc aatcacctct gtgtccaaca ccatttatag cttggtgatc 8700
tatgcacagc atatggtgct tagttacttc aaaagtggtc acccccatgg ccttctgttt 8760
ttacaagacc agctaaagtt tgaagacatg ctcaaagttc aacccctaat cgtctattcg 8820
gacgacctcg tgttgtatgc cgagtctccc accatgccaa actatcactg gtgggttgaa 8880
cacctgaatt tgatgttggg atttcagacg gacccaaaga agactgcaat aacagactca 8940
ccttcattcc taggttgtag aataataaat ggccgccagt tagtacccaa ccgtgacaga 9000
attctcgcgg cccttgccta tcacatgaag gcgagtaatg tttctgagta ctacgcctcc 9060
gcagccgcaa tactcatgga cagttgtgct tgtctagagt atgatcctga gtggtttgaa 9120
gaacttgtgg ttggaatggc gcagtgcgcc cgtaaggacg gctatagttt ccccggcccg 9180

-continued

```
ccgttcttct tgtccatgtg ggaaaagctc aggtcaaatt atgaggggaa gaagttgaga    9240
gtgtgtggtt attgcggagc ttcagccccg tatgctactg cctgtggcct tgacgtttgt    9300
gtttaccaca cccactttca ccagcattgt ccagtcataa tatggtgtgg ccacccggcg    9360
ggttctgggt cctgcgatga gtgcaaatcc cctacaggga agggtacaag ccctctggat    9420
gaggtcttaa gacaagtccc ttataagcct ccacggacta ttcttatgca tgtggagcag    9480
ggcctcaccc cccttgaccc aggcagatac cagacccgcc gtgggttggt tgctgtcagg    9540
cgcgggataa ggggaaatga agttgacctg ccagatggtg attatgccag tactgcccta    9600
ctccccacct gcaaagacat agacatggtt gctgtggcct ccaatgtgtt gcgcagtagg    9660
ttcatcatcg gcccacctgg cgcagggaaa acacactggc ttcttcaaca ggttcaggat    9720
agtgatgtca tttacacgcc aacccatcag accatgcttg acatgatcaa ggctttgggg    9780
acgtgccggt tcaatgtccc ggcaggcaca acgctgcaat tccctgcccc ctcccgtacc    9840
ggcccgtggg ttcgcatcct tgccggcggt tggtgtccag gtaagaattc cttcctggat    9900
gaagcagcgt attgcaatca ccttgacgtc ttgaggcttc tcagcaaaac taccctcacc    9960
tgtctggggg atttcaaaca actccacccg gtgggttttg attctcattg ctatgttttt   10020
gatatcatgc ctcagactca actgaagacc atctggaggt ttggacagaa tatctgtgac   10080
gccattcagc cagattacag ggacaaactc gtgtccatgg tcaacacaac ccgtgtaacc   10140
tatgtggaaa gacctgtcaa gtatgggcaa gtcctcaccc cctaccacag agaccgagag   10200
gatggtgcta tcactattga ctccagtcaa ggcgccacat ttgatgtggt cacattgcat   10260
ttgcccacta aagattcact caacaggcaa agagcccttg ttgctatcac cagggcaagg   10320
catgcaatct ttgtgtatga cccacacagg caactgcaga gcatgtttcg tcttcctgca   10380
aaaggcacac ctgtcaacct tgccgtgcac cgtgacgagc agctcatcgt attagataga   10440
aataacaaag agtgcacggt tgttcaggct ttaggcaatg gggacaaatt cagggccagt   10500
gacaagcgcg ttgtagattc tcttcgcgcc atttgtgcag atcttgaagg gtcgagctcc   10560
ccgctcccca aggtcgcaca caacttggga ttttatttct cacctgattt gacacagttt   10620
gctaaactcc cggcggaact tgcaccccac tggcccgtgg tgacaactca gaacaacgaa   10680
aattggccag accggctggt tgctagcctc cgccctatcc acaaatatag ccgcgcgtgc   10740
atcggagccg gctatatggt gggcccctca gtgtttctag gcactcctgg ggttgtgtca   10800
tactatctca cacaatttgt caaaggggag gctcaggtgc ttccggagac ggtcttcagc   10860
accggccgaa ttgaggtaga ttgtcgagag tatcttgatg atcgggaacg agaagttgct   10920
gagtccctcc cacatgcctt tattggcgac gtcaaaggca ctaccgttgg gggatgtcac   10980
catgtcactt ctaaatatct cccacgcttc cttcccaagg aatcagttgc ggtggttggg   11040
gtttcaagcc ccgggaaagc cgcaaaagca gtttgcacat taacagatgt gtacctccca   11100
gatcttgagg cttacctcca tccagagacc cagtctaagt gctggaaagt gatgttggac   11160
ttcaaggaag ttcgactgat ggtctggaga gataagacgg cctactttca acttgaaggc   11220
cgccatttca cctggtacca gcttgcaagt tatgcctcgt acatccgagt tcccgttaac   11280
tctacggtgt acctggaccc ctgtatgggc cctgcccttt gcaacagaag agtcgttggg   11340
tctgcacatt ggggagctga ccttgcagtt accccttatg attatggtgc caaaatcatt   11400
ctgtctagtg cgcaccatgg tgaaatgcct cctgggtaca gaattctagc gtgcgcggag   11460
ttctcgcttg atgacccagt gaggtacaaa cacacttggg ggtttgaatc ggatacagcg   11520
tatctgtacg agttcaccgg aaacggtgag gactgggagg attacaatga tgcgtttcgt   11580
gcacgccaga aagggaaaat ttataaggcc actgccacca gcatgagatt tcattttccc   11640
```

-continued

```
ccgggtcctg ccattgaacc aacattgggc ctgaactgaa atgaaatggg ggctgtgcag   11700
agccttttcg acaaaatttg ccaacttttt gtggatgctt tcacggaatt tttggtgtcc   11760
attgttgata tcatcatatt tttggccatt ttgtttggct tcaccatcgc aggctggctg   11820
gttgtcttct gtatccgact ggtttgctcc acggtactcc gtgcgcgctc taccattcac   11880
cctgagcaat tacagaagat cctatgaggc cttcctttcc cagtgccaag tggacattcc   11940
cgcctgggga actaagcatc ccttgggggt gctttggcac cacaaggtgt caactctgat   12000
tgatgaaatg gtgtcgcgtc gaatgtaccg catcatggaa aaagcaggac aggctgcctg   12060
gaaacaggtt gtgagcgaag ctacattgtc tcgcataagt ggcttggatg tggtggctca   12120
ttttcagcat cttgctgcca ttgaagccga gacttgcaaa tatttggcct ctcggctgcc   12180
catgctacac aacctagtca tgtcagggtc gaatgtaacc atagtgtata atagcacttt   12240
gggtcaagtg tttgccattt tcccaacccc tggttcccgg ccaaaacttt ctgattttca   12300
acaatggctc atagctgtgc attcttccat attttcttct gttgcggctt cttgtactct   12360
ttttgttgtg ctgtggctgc gaattccaat actacgtact gtttttggtt tccgctggtt   12420
aggggcaact tttctttcga actcacagtg aattacacgg tgtgcccacc ctgcctcacc   12480
cggcaagcag ccgctgagat ctacgaacac agcgggtctc tttggtgcag gatagggcat   12540
gaccgatgta gccagagtga tcatgacgaa ctagggttct tggttccacc tggcctttcc   12600
agcgagggcc acttgaccag tgtttacgcc tggctggcgt tcttgtcttt cagctacaca   12660
gcccagttcc accccgagat atttggaata gggaatgtga gtagagttta tgttgacgtc   12720
actcaccaac tcatctgcgc cgaacacgac gggcagaaca ccaccctgcg tcgccatgac   12780
aatatctcag ccgtgtttca gacctattac caacatcagg tcgatggcgg caattggttt   12840
cacctagaat ggctgcgtcc cttcttttcc tcttggctgg ttttgaatgt ctcgtggttt   12900
ctcaggcgtt cgcctgcaaa ccgtgtttca gttcgagtct ttcagacatc aaaaccaaca   12960
ccaccgcagc tgcaggcttt gctgtcctcc aagacatcag ctgtcttagg catggctact   13020
cgtccattga ggcgattcgc aaaagccgtc aatgccgcac ggcgatagga acgcccgtgt   13080
acatcactgt cacggccaat gtaacagatg agaattactt gcattcctct gatctcctca   13140
tgctttcctc ttgcctcttc tatgcttctg agatgagtga aaagggattc aatgtggtct   13200
tcggcaacgt gtcaggcatt gtggctgtgt gtgtcaactt taccagctat gtccaacatg   13260
ttaaggagtt tactcagcgc tctttggtgg tcgaccacgt gcgactgctt catttcatga   13320
cacctgcgac catgaggtgg gcaacagttt tagcctgtct tttcgccatc ttgttggcga   13380
tttgaatgtt taagtatgtt ggggaaatgc ttgaccgcgg gctactgctc gcaattgctt   13440
tttttctggt gtatcgtgcc gttctgtttt gctgcgctcg tcaacgccgc cagcaacagc   13500
agctcccatt tacagttgat ttataacctg acgatatgcg agctgaatgg cacagattgg   13560
ttgaatcaaa agtttgattg ggcagtggag acttttgtca tttttcctgt gttgacccac   13620
attgtctcct acggtgccct taccaccagc catttccttg acacggccgg cctaatcact   13680
gtgtctaccg ccggatatta ccatgggcgg tatgtgttga gtagcatcta cgccgtcttt   13740
gccctggctg cgttgatttg ttttgtcatt aggttgacaa aaaactgtat gtcctggcgc   13800
tactcatgta ccagatatac caactttctt ctggacacca aaggcaatct ctatcgttgg   13860
cggtcacccg tcgttataga gagaaggggt aaagttgagg ttggagacca cctaatcgac   13920
ctcaaaagag ttgtgcttga tggttccgcg gcaaccccta taaccaagat ttcagcggaa   13980
caatggggtc gtccctagac gacttctgca atgacagcac agctgcacaa aaggtgcttt   14040
```

-continued

```
tggcgttttc catcacctat acgccaataa tgatatatgc cctgaaggta agtcgcggcc   14100
gactgttagg gcttttgcat cttttaattt tcttgaattg tgctttcacc ttcgggtaca   14160
tgacatttgt tcattttcag agtacaaaca aggtcgcgct cactatggga gcagttgttg   14220
cactcctttg gggggtgtac tcagccatag aaacctggaa attcatcact tccagatgcc   14280
gtttgtgctt gctaggccgc aggtacattc tggcccctgc ccaccacgtt gaaagtgccg   14340
cgggctttca tccgattgcg gcaagtgata accacgcatt tgtcgtccgg cgtcccggct   14400
ccactactgt taacggcaca ttggtgcccg ggttgaaaag cctcgtgttg ggtggcagaa   14460
aagctgttaa gcggggagtg gtaaacctcg ttaaatatgc caaataacaa cggcaggcag   14520
caaaaaaata agaaggggag tggccagcca gtcaatcagc tgtgccaaat gctgggcaag   14580
atcatcgccc agcaaaatca gtccagaggc aagggaccgg gtaagaaaaa taagaagaga   14640
aacccggaga agccccattt tcctcttgcg accgaagatg acgtcaggca tcacttcacc   14700
cccagtgaac ggcaattgtg tctgtcgtcg atccagactg ccttcaacca gggcgctgga   14760
acttgcaccc tgtcagattc agggaggata agttacactg tggagtttag tttgccgacg   14820
caccacactg tgcgccttat tcgcgccaca gcatcacctc catcgtgatg ggcttacatt   14880
cttggagctc ctcagtttca caattggaag aatgtgtggt gaatggcact gattggcact   14940
gtgcctctaa gtcacctatt caattagggc gaccgtgtgg gggtagagtt taattggcga   15000
gaaccatacg gccgaaatta aaaaaaaaaa aaaaaaaaaa aaaaaaa                 15047
```

<210> SEQ ID NO 10
<211> LENGTH: 15444
<212> TYPE: DNA
<213> Artificial Sequence

<400> 10

```
atgacgtata gttgttggct ctatgtcgtg acatttgtat agtcaggagc tgcgaccatt      60
ggtacagccc aaaacttgct gcgcgggaac gcccttccgt gacagccttc ttcaggggag     120
tttaggggtc tatccctagc accttgcttc cggagttgca ctgctttacg gtctctccac     180
ccctttaacc atgtctggga tacttgatcg gtgcacgtgt acccccaatg ccagggtgtt     240
tgtggcggag ggccaagtct actgcacacg atgtctcagt gcacggtctc tccttccttt     300
gaatctccaa gtttctgagc ttggggtgct gggcttattt tataggcccg aagagccgct     360
ccggtggacg ttgccacgtg cattccccac tgtcgagtgc tcccccgccg ggcctgctg      420
gctttctgcg atttttccaa ttgcacgaat gaccagtgga aacctgaact ttcaacaaag     480
aatagtgcgg gtcgcagctg agctctacag agccggtcag ctcacccccg tagtcttgaa     540
gaatctacag gtttatgaac ggggttgccg ttggtacccc atcgttggac ctgttcctgg     600
agtggctgtt tatgccaatt ccttacacgt gagtgacaaa cctttcccgg gagcaactca     660
tgtgttaacc aacctaccgc tcccgcagag gcccaagcct gaagactttt gcccctttga     720
gtgtgctatg gctgacgtct atgacattgg tcatgacgct gtcatgtatg tggccggagg     780
gagagtctcc tgggcccctc gtggcgggga caaaggaaaa tttgaaatag ttcccaagga     840
gttgaagttg attgcgaatc gactccacat ttccttcccg ccccaccacg cagtggacat     900
gtccaagttt gcctttataa gccctgggag tggtgtttcc atgcgggtcg agtaccaaca     960
tggctgtctc cccgctgata ctgtccctga aggaaactgt tggtggcgct tgtttgactt    1020
gcttccaccg gaagttcaga acaaagagat tcgccatgct aaccaactcg gctatcagac    1080
caagcatggt gtcgctggca agtacctaca gcggaggctg caagttaatg gactccgagc    1140
agtaactgac gcgaatggac ctatcgtcat acagtatttt tgtgataggg aaagctggat    1200
ccgccactta agactggtag aagaacctag cctccctggg tttgaggacc tcctcagaat    1260
```

-continued

```
aagagttgag cccaatacgt tgccattggt tggcgaggat gagaaaatct tccgatttgg   1320
caatcacaaa tggtacggtg ctggaaagag ggcaaggaaa gcacgctttg gtgcggctgc   1380
cacggtcgct caccgcgctt tgcccgctca cgaaacccag caggccaaga agcacgaagt   1440
taccagcgcc aacagggctg agcatctcga gcactattcc ccgcctaccg acgggaactg   1500
tggttggcac tgcgtttccg ccattgtcaa ccggattgtg aattccaaat ttgaaaccac   1560
ccttcccgag agagtgagac ctttagatga ctgggctact gacgaggatc ttgtgaatac   1620
tatccaaatc ctcaggctcc ctgcggcctt ggacaggaac ggtgcttgtg tcggcgccaa   1680
gtacgtgctc aagctggaag gtgtgcactg gacagtctct gtggcccctg ggatgacccc   1740
ttctctgctc cccccttgaat gtgttcaggg ctgttgtgag cataagagcg gtcttggtcc   1800
cccagatgtg gctgaagttt ccggatttga ccctgcctgc cttaaccgac tggctgaggt   1860
aatgcacttg cctagttgtg tcatcccagc tgctctggct gaaatgtccg acgaccccaa   1920
tcgcccggct tccccagtca ccactgtgtg gactatttcg caattctttg cccattatag   1980
aggaggagag caccctgatc aggtgtgctt agggaaaatc atcagccttt gtcaggtgat   2040
tgaggaatgc tgttgttccc agaacaaaac caaccgggcc accccggaag aggtcgcggc   2100
aaaaattgac cagtacctcc gtgatgcagc aagccttgga gaatgcttag ccaagcttga   2160
gagggctcgc ccgccgagcg cgatggacac ctcctttgat tggaatgttg tgcttcctgg   2220
ggttgaggcg gcgaaccaga cgaccaaaca gctccatgtc aaccagcacc gtgcttcggt   2280
tcctgccatg actcaggagc ctttggacaa agactcggtc cctttgaccg ccttctcgct   2340
gtctaattgc tactaccctg cacaaggtga cgaggttcgt caccgtgaga ggctgatctc   2400
cgtgctctct aagttggagg aggttgttcg tgaggaatat gggctcacgc caactggatc   2460
tggcccgcga cccgcactgc cgaacgggct cgacgagctc aaagaccaga tggaagagga   2520
tctgttgaaa ctggtcaacg cccaggcaac ttcagaaatg atggcccggg cagctgagca   2580
ggttgatcta aaagtttggg tcaaaaatta cccacggtgg acaccgccac cccctccacc   2640
aagagttcag cctcgaaaaa caaagtctgc taagagcctg ccagagaaca agcctgtccc   2700
tgctccgcgc aggaaagtca gatctgattg tggcagcccg actttgaggg gcaacaatgt   2760
tcctaacggt tgggaagact tggccgttgg tggtcctctt gatctttcga caccatccga   2820
gccgatgaca cctctgagtg agcctgcact tatgcccgtg ttgcaacata tttctggacc   2880
agtgacgcct ttgagcgtgc cggcccctat tcctgcaccg cgtaaagctg tgtcccgacc   2940
gatggcgccc tcgagtgagc caatttttgt gtctgcaccg cggcaaaaat ttcagcaggt   3000
ggaagaagca aatctggcgg caacaacgct gacataccag gacgaaccta tagatctgtc   3060
agcatcctca cagactgaat atgaggctcc ttccctagca ccactgcaga acataggtac   3120
tctggaggtg ggggggcaag aagctgagga aattctgagt gaaacctcgg atataccgaa   3180
tgacatcaac cctgtgcctg tatcatcaag cagctccttg tcaagcgtta agatcacacg   3240
cccaagacac tcagctcaag ccatcatcga ctcgggcggg ccctgcagtg ggcatctcca   3300
aagggagaaa gaagcgtgcc tccgcatcat gcgtgaggct tgtgatgcga ctaagcttag   3360
tgaccctgcc acgcaggaat ggctttctcg catgtgggat agggtggaca tgctgacttg   3420
gcgcaacacg tctgctttcc aggcgtttcg catcttagac ggcaggcttg agtttcttcc   3480
aaagatgata ctcgagacgc cgccgcccta cccgtgtggg tttgtgatgc tgcctcacac   3540
ccctgcacct tccgtgagtg cagagagcga ccttaccatc ggttcagtcg ccactgaaga   3600
tattccacgc atcctcggga aaatagaaaa caccagtgag atgatcaacc agggaccctt   3660
```

-continued

```
ggcatcctct gaggaaaaac cggcatacaa ccaacccgct aaggactccc tgatatcgtc   3720
gcgggggttt gacgagagca cagcagctcc gtccgcaggt acgggtggcg ccggcttgtt   3780
tactgatttg ccaccttcag acggtgtaga tgcggacggg ggggggccgc tgcagacggt   3840
gaaaaagaac gctgaaaggc tcctcgaccg attgagccgt caggttttta acctcgtctc   3900
ccatctccct gttttcctct cacacctctt caaatctgac agtggttatt ctccgggtga   3960
ttggggtttt gcagctttta ctctattttg cctcttttta tgttacagct acccattctt   4020
tggtttcgct ccccttttgg gtgtgttttc tgggtcttct cggcgcgtgc gcatgggggt   4080
ttttggctgc tggttggctt ttgctgttgg tttgttcaag cctgtgtccg acccagtcgg   4140
cactgcttgt gagtttgatt cgccagagtg taggaatgtc cttcattctt ttgagcttct   4200
caaaccttgg gaccctgttc gcagccttgt tgtgggcccc gtcggtctcg gtcttgccat   4260
tcttggcagg ttactgggcg gggcacgcta catctggcat ttctgcttta ggcttggcat   4320
tgttacagac tgtatcctgg ctggagctta tgtgctttct caaggtaggt gtaaaaagtg   4380
ctggggatct tgcataagaa cagctcctaa tgagattgcc tttaacgtgt tccctttttac   4440
acgtgcgact aggtcgtcac tcatcgacct gtgcaatcgg ttttgtgcgc caaagggcat   4500
ggacccctatt ctcctcgcca ctgggtggcg tgggtgctgg accggccgaa gccccattga   4560
acaaccctct gaaaaaccca tcgcgtttgc ccagttggac gaaaagagga ttacggccag   4620
gaccgtggtc gcccagcctt atgaccccaa ccaagccgta aagtgcttgc gggtgttaca   4680
ggcgggcggg gcgatggtgg ctgaggcagt cccaaaagtg gtcaaagttt ccgctattcc   4740
attccgagcc cccttttttc ccaccggagt gaaagttgac cctgagtgta ggatcgtggt   4800
tgaccccgac acttttacta cagccctccg gtccggctat tccaccacaa acctcgttct   4860
tggtgtgggg gactttgccc agctgaatgg attaaaaatc aggcaaattt ccaagccttc   4920
gggaggaggc ccgcacctca ttgctgccct acatgttgcc tgctcgatgg cgttgcacat   4980
gcttgctggg gtttatgtaa ctgcagtggg gtcttgcggt accggcacca acgatccgtg   5040
gtgcaccaac ccgtttgccg tccctggcta cgggcctggt actctttgca cgtccagatt   5100
gtgcatctcc caacatggcc ttaccctgcc cttgacagca cttgtggcag gattcggtct   5160
tcaggaaatt gccttggttg ttttgatttt cgtttccatc ggaggcatgg ctcacaggtt   5220
gagttgcaag gctgacatgc tgtgcgtttt acttgcaatc gccagctatg tttgggtgcc   5280
ccttacctgg tttctttgtg tgtttccttg ctggttgcgc tggttctctt tgcatcccct   5340
caccatccta tggttggtgt ttttcttgat ttctgtaaat gtgccttcgg gaatcttggc   5400
tgtggtgttg ttagtttctc tttggctctt aggtcgttac actaatgttg ctggtcttgt   5460
caccccatat gacattcatc atcacaccag tggcccccga ggtgttgccg ccttggctac   5520
tgcaccggat gggacctact tggccgccgt tcgccgtgct gcgttgaccg gtcgtaccat   5580
gctgtttacc ccgtctcagc ttgggtccct tcttgagggt gctttcagaa ctcaaaagcc   5640
ctcactgaac accgtcaatg tggtcggatc ctctatgggc tccggcgggg tgttcaccat   5700
cgacgggaaa attaagtgcg taacagccgc acatgtcctt acgggtaatt cagctagggt   5760
ttccggggtc ggcttcaacc aaatgcttga ttttgatgtg aaaggggact tcgccatagc   5820
tgattgcccg aattggcaag gagctgcccc caagacccaa ttctgcgagg atggatggac   5880
tggccgtgcc tattggctga catcctctgg agtcgaaccc ggtgtcattg ggaatggatt   5940
cgccttctgc ttcaccgcgt gcggcgattc tggatccccg gtgattaccg aagccggtga   6000
gcttgtcggc gttcacacag gatcaaacaa acaaggagga ggcatagtca cacgccccctc   6060
aggccagttt tgtaatgtgg cgcccatcaa gctgagcgaa ttgagtgaat tcttcgctgg   6120
```

-continued

```
acctaaggtc ccgctcggtg atgtgaagat tggcagccac ataattaaag acgtatgcga   6180
ggtaccttca gatctttgcg ccttgctcgc tgccaaaccc gaactggaag gaggcctctc   6240
caccgtccaa cttctgtgtg tgtttttcct cctgtggaga atgatgggac atgcctggac   6300
gcccttggtt gctgtggggt tttttatctt gaatgaggtt ctcccagctg tcctggtccg   6360
gagtgtcttc tcctttggta tgtttgtgct atcttggctt acaccatggt ctgcgcaagt   6420
cctgatgatc aggcttctaa cagcagctct taacaggaac agggggtcac tcgccttcta   6480
cagcctcggt gcagtgaccg gatttatcgc agatcttgca gcaactcagg ggcatccgct   6540
gcaggcagtg atgaacttaa gcacctatgc cttcctgcct cggatgatgg ttgtgacctc   6600
accagtccca gtgcttgctt gtggtgttgt gcacctcctt gccataattt tgtacctgtt   6660
taagcaccgt tgcctgcatt atgtccttgt tggcgatgga gtgttctcta aagccttctt   6720
cttgcgatac tttgccgaag ggaagttgag ggaaggggtg tcgcagtcct gcgggatgaa   6780
tcacgagtca ctgactggtg ccctcgctat gagactcaat gacgaagact tggacttcct   6840
tacgaaatgg actgatttta agtgctttgt ttctgcgtcc aacatgagga atgcagcggg   6900
ccaattcatc gaggctgcct atgcaaaagc acttagaatt gagcttgccc agttagtaca   6960
ggttgataag gttcgaggta ctttggccaa acttgaagcc tttgctgata ccgtggcacc   7020
ccagctctcg cccggtgaca ttgttgttgc tcttggccac acgcctgttg gcagtatctt   7080
cgacctaaag gttggcagta ccaagcatac cctccaggcc attgagacca gagtccttgc   7140
cgggtccaaa atgaccgtgg cgcgtgtcgt tgatccaacc cccacgcccc cacccgcacc   7200
cgtgcccatc cccctcccac cgaaagtcct ggagaacggc cccaacgcct ggggggatga   7260
ggaccggttg aataagagga agagacgcag gatggaagcc gtcggcatct ttgttatggg   7320
tgggaagaag taccaaaaat tttgggacaa gaattccggt gatgtgtttt acgaggaggt   7380
ccatgataac acagatgcgt gggagtgcct cagagttggt gaccctgccg actttgaccc   7440
tgagaaggga actctgtgtg ggcatactac cattgaagac aaggcttata atgtctacac   7500
ctccccatct ggcaggaagt tcctggtccc cgtcaaccca gagagcggaa gagcccaatg   7560
ggaagctgca aagctttccg tagagcaggc ccttagcatg atgaatgtcg acggtgagct   7620
gacagccaaa gaactggaga aactgaaaag aataattgac aaactccagg gcctaactaa   7680
ggagcagtgt ttaaactgct agccgccagc ggcttgaccc gctgtggtcg cggcggcttg   7740
gttgttactg agacagcggt gaaaatagtt aaatttcaca accggacctt caccctagga   7800
cctgtgaatt taaaagtggc cagtgaggtt gagctaaaag acgcagtcga gcataaccaa   7860
cacccggttg caagaccggt tgatggtggt gttgtgctcc tgcgctccgc agttccttcg   7920
cttatagacg tcttgatctc tggcgctgat gcatctccta agttactcgc ccaccacggg   7980
ccgggaaaca ctgggatcga tggttcgctt tgggattttg aggccgaggc caccaaagag   8040
gaaattgcac tcagtgcgca aataatacag gcttgtgaca ttaggcgcgg cgacgcaccc   8100
gaaattggtc ttccttataa gctgcaccct gttaggggca accctgagcg ggtaaaaggg   8160
gttttacaga atacaaggtt tggagacata ccttataaaa cccccagtga cactgggagc   8220
ccagtgcacg cggctgcctg cctcacgccc aatgccactc cggtgactga cggtcgttcc   8280
gtcttggcta cgaccatgcc ctccggtttt gagttgtatg taccgaccat tccagcgtct   8340
gtccttgatt atcttgattc caggcctgat tgccccaaac agttgacaga gcacggctgt   8400
gaggatgccg cattaagaga cctctccaag tatgacttgt ccacccaagg ctttgtcttg   8460
cctggagttc ttcgccttgt gcgtaagtac ctgtttgctc atgtgggtaa gtgcccgcct   8520
```

-continued

```
attcatcggc cttccactta ccctgccaag aattccatgg ctggaataaa tgggaacagg   8580
tttccaacca aggacattca gagcgtccct gaaatcgacg ttttgtgcgc acaggccgtg   8640
cgagaaaact ggcaaactgt tactccttgt accctcaaga agcagtattg cgggaagaag   8700
aagactagga caatactcgg cactaataac ttcattgcgc tggcccaccg ggcagcattg   8760
agtggtgtca cccagggctt catgaaaaaa gcgtttaact cgcccatcgc actcgggaaa   8820
aacaaattca aggagctgca gactccggtc ttgggcagat gtcttgaagc tgaccttgca   8880
tcctgtgacc gatccacacc cgcaattgtc cgctggtttg ccgccaatct tctttatgaa   8940
cttgcctgtg ctgaggagca tataccatcg tacgtgttga actgctgcca cgacttactg   9000
gtcacgcagt ccggcgcggt gactaagaga ggtggcctat cgtctggcga cccgattact   9060
tctgtatcaa acaccattta cagcttggtg atatatgcac agcacatggt actcagttat   9120
tttaaaagtg gtcacccccca tggccttctg tttctacaag accagctaaa gtttgaggac   9180
atgctcaagg ttcagcccct gatcgtctat tcggacgacc tcgtgctgta cgccgagtct   9240
cccaccatgc caaactacca ctggtgggtt gaacatctga acctgatgct gggttttcag   9300
acggacccaa agaagacagc tataacagac tcgccatcat ttttgggttg taggataata   9360
aatggacgcc agttagtccc caaccgtgac aggatcctcg cggccctcgc ctaccatatg   9420
aaggcaaaca atgtttctga atactacgcc tcggcggctg caatactcat ggacagttgt   9480
gcttgtttgg agtacgatcc tgagtggttt gaagagctcg tggttgggat ggcgcagtgc   9540
gcccgcaagg acggctacag ttttcctggc ccgccgttct tcttgtccat gtgggaaaaa   9600
ctcaggtcca atcatgaggg gaagaagtct agaatgtgcg ggtactgtgg ggccccagct   9660
ccgtatgcca ctgcctgtgg ccttgatgtt tgtatttatc acacccactt ccaccagcat   9720
tgtccagtca taatctggtg tggccatccg gcgggttctg gctcttgtag tgagtgcaaa   9780
ccccccctag ggaaaggcac aagccctcta gatgtggtgt tagaacaagt cccgtacaag   9840
cctccacgaa ctgtaatcat gcatgtggag cagggtctca cccctcttga cccaggcaga   9900
taccagactc gccgcggatt agtctccgtt aggcgtggca tcaggggaaa cgaaatcgac   9960
ctaccagacg gtgattatgc tagtaccgcc ttgctcccca cttgtaaaga tatcaacatg  10020
gtcgctgtcg cttccaatgt gttgcgcagc aggttcatca tcggtccacc cggtgctggt  10080
aaaacatact ggctccttca acaggtccag gatggtgatg tcatttacac gccaactcat  10140
cagaccatgc ttgacatgat caaggctttg ggacgtgcc ggttcaacgc cccagcaggc   10200
acaacgctgc aattccctgc tccctcccgt accggcccgt gggttcgcat cctggccggc  10260
ggttggtgtc ctggcaagaa ttccttcctg gatgaagcag cgtattgtaa tcaccttgat  10320
gtcttgaggc ttcttagcaa aactaccctc acctgtctgg gagatttcaa acaactccac  10380
ccagtgggtt ttgattctca ttgctatgtt tttgacatca tgcctcagac tcaactgaag  10440
accatctgga ggtttggaca gaatatctgt gatgccattc agccagatta cagggacaaa  10500
cttgtgtcca tggtcaacac aacccgtgta acctacgtgg aaagacctgt caagcatggg  10560
caggtcctca ccccttacca cagggaccga gaggacggcg ccatcacaat tgactccagt  10620
caaggcgcca catttgatgt ggttacattg catttgccca ctaaagattc actcaacagg  10680
caaagagccc ttgttgctat caccagggcg agacatgcta tctttgtgta tgacccacat  10740
aggcaactgc agagcatgtt tgatcttcct gcaaaaggca cacccgtcaa ccttgccgtg  10800
caccgtgacg agcagctgat cgtactagat agaaataaca aagagtgcac ggttgctcag  10860
gctctaggca atggggacaa attcagggcc acagacaagc gcgttgtaga ttctctccgc  10920
gccatttgtg cagatcttga agggtcgagc tccccgctcc ccaaggtcgc acataacttg  10980
```

-continued

```
ggattttatt tctcacctga tttgacacag tttgctaaac tcccggcaga acttgcaccc   11040
cactggcccg tggtgacaac ccagaacaat gaaaagtggc cagacaggct ggttgccagc   11100
ctccgcccta tccataaata tagccgcgca tgcattggag ccggctatat ggtgggccct   11160
tcggtgtttc taggcacccc tggggttgtg tcatactatc tcacaaaatt tgttaagggg   11220
gaggctcagg tgcttccgga gacagtcttc agcaccggcc gaattgaggt agattgccgg   11280
gagtatcttg atgatcggga acgagaagtt gctgagtccc tcccacatgc cttcattggc   11340
gacgtcaaag gcactaccgt tgggggatgt caccatgtca cctctaaata ccttccgcgc   11400
ttccttccta aggaatcagt tgcggtggtt ggggtttcga gccccgggaa agccgcaaaa   11460
gcagtctgca cattaacaga tgtgtatctc ccagaccttg aagtttacct ccacccagag   11520
acccaatcca agtgctggaa aataatgttg gacttcaagg aagtccgact gatggtctgg   11580
aaagacaaaa cggcctattt tcaacttgaa ggccgccatt tcacctggta tcagcttgca   11640
agctatgcct cgtacatccg agttcctgtt aactctacgg tgtatttgga cccctgcatg   11700
ggccctgccc tttgcaacag aagagttgtc gggtccactc attgggggc tgacctcgca   11760
gtcacccctt atgattatgg tgccaaaatc attctgtcta gtgcatacca tggtgaaatg   11820
cctcctgggt acaaaatcct ggcgtgcgcg gagttctcgc ttgacgaccc agtgaggtac   11880
aaacacacct gggggtttga atcggacaca gcgtatctgt acgagttcac cggaaacggt   11940
gaggactggg aggattacaa tgacgcattt cgtgcgcgcc agaaagggaa aatttataag   12000
gccactgcca ccagcatgag gtttcatttt cccccgggcc ccatcattga accaacttta   12060
ggcctgaact gaaatgagat gggggctatg caaagccttt tctacaaaat tggccaactt   12120
tttgtggatg ctttcacgga atttttggtg tccattgttg atatcatcat atttttggcc   12180
attttgtttg gcttcaccat cgccggttgg ctggtggtct tctgcatccg attggtttgc   12240
tccgcggtac tccgtgcgcg ccctaccatt caccctgagc aattacagaa gatcctatga   12300
ggcctttctt tctcagtgcc gggtggacat tcccacctgg ggaaccaaac atcccttggg   12360
gatactttgg caccataagg tgtcaaccct gattgatgaa atggtgtcgc gtcgaatgta   12420
ccgcatcatg gaaaaatcag gacaggctgc ctggaaacag gttgtgagcg aggctacgct   12480
gtctcgcatc agtggtttgg atgtggtggc tcattttcag catcttgccg ccattgaagc   12540
cgagacctgt aaatatttgg cctctcggat gcccatgcta cacaacctgc gcatgacagg   12600
gtcaaatgta accatagtgt ataatagtac tttgaatcag gtgttagcaa tcttcccgac   12660
ctctgaatcc cggccaaagc ttcatgattt tcaacaatgg ttaataactg tacattcctc   12720
catattttcc tccgttgtgg cttcctgtac tctttttgtt gtgctgtggt tgcgaattcc   12780
aatgctacgt actgtttttg gtttccactg gttaggggca atttttcttt cgaactcaca   12840
gtgaattaca cggtgtgccc accttgcctc acccggcaag cagccgctga gatctacgaa   12900
cccggcaggt ctctttggtg caggataggg catgatcgat gtagcgagga cgatcatgac   12960
gaactagggt tcttggttcc gcctggcctc tccagcgaag gccacttgac cagtgtttac   13020
gcctggttgg cgttcctgtc cttcagctat acagcccagt tccatcccga gatatttggg   13080
atagggaatg tgagtaaaat ttatgttgac atcaagcacc aattcatctg cgccgaacac   13140
gacgggcaga acgccaccct gcctcgccat gacaacattt cagccgtgtt tcagacctac   13200
taccaacatc aggtcgatgg cggcaattgg tttcacctgg aatggctgcg cccccttcttt   13260
tcctcttggt tggttttaaa tgtttcgtgg tttctcaggc gttcgcctgc aagccatgtt   13320
tcagttcgag tctttcagac atcaaaacca acaccaccgc agcaccaaat tttgttgtcc   13380
```

-continued

```
tccaggacat cagctgcctt aggcatggcg acccgtcctc tccggcgatt cgcaaaagct   13440

ctcagtgccg cacggcgata ggaacacccg tgtatatcac catcacagcc aatgtgacag   13500

atgagaatta tttacattct tctgatctcc tcatgctttc ttcttgcctt ttctatgctt   13560

ctgagatgag tgaaaagggg ttcaaggtgg tattcggcaa tgtgtcaggc atcgtggctg   13620

tgtgtgtcaa ctttaccagt tacgtccaac atgtcaagga gtttacccaa cgctccttgg   13680

tggtcgagca tgtgcgactg cttcatttca tgacacctga aaccatgagg tgggcaaccg   13740

ttttagcctg tctttttgcc attctgttgg caatttgaat gtttaagtat gttggggaaa   13800

tgcttgaccg cgggctgttg ctcgccgttg cttttttttgt ggtgtatcgt gccgtcttgc   13860

tttgttgcgc ccgtcaacgt cgacgggaac gacagctcaa agttacagct gatttacaac   13920

ttgacgctat gtgagctgaa tggcacagat tggctggctg gtagatttga ctgggcagtg   13980

gagtgttttg tcatttttcc cgtgttgact cacattgtct cctatggtgc cctcactact   14040

agccatttcc ttgacacagt cggtctggtc actgtgtctg ccgccgggtt ccttcatgaa   14100

cggtatgttt tgagtagcat ctacgcggtc tgtgccctgg ctgcgttgat ttgcttcgtc   14160

attaggcttg cgaagaactg catgtcctgg cgctactcgt gtaccagata taccaacttc   14220

cttttggaca ccaaggggag actctatcgt tggcgatcgc ccgtcatcat agagaaaaag   14280

ggtaaagttg aggttgaagg tcatttgatc gacctcaaaa gagttgtgct tgatggttcc   14340

gtggcaaccc ctataaccaa aatttcagcg gaacaatggg gtcgtcctta gatgacttct   14400

gccatgatag cacggctcca caaaaggtgc ttttggcgtt ttccattacc tatacaccag   14460

tgatgatata tgccctaaag gtaagtcgcg gccgactgct agggcttttg caccttttga   14520

tctttctgaa ctgtgctttc accttcgggt atatgacatt cacgcacttt cagagtacaa   14580

acaaggtcgc gctcactatg ggagcagtag ttgcactcct ttggggggtg tactcagcca   14640

tagaaacctg gaaattcatc acctccagat gccgtttgtg cttgctaggc cgcaagtaca   14700

ttctggcccc tgcccaccac gttgagagtg ccgcaggctt tcatccgatt gcggcaaatg   14760

ataaccacgc atttgtcgtc cggcgtcccg gttccactac ggtcaacggc acattggtcc   14820

ccgggttgaa aagcctcgtg ttgggtggca gaaaagctgt caaacaggga gtggtaaacc   14880

ttgttaaata tgccaagtaa caacggcagg cagcagaaaa aaagaaaggg ggatggccag   14940

ccagtcaatc agctgtgtca gatgctgggt aaaattattg cccagcaaaa tcagtccagg   15000

ggcaagggac cgggaaagaa aaataacaag aaaaacccgg agaagcccca ttttcctcta   15060

gcgactgaag atgatgtcag acatcacttt accccgagtg agcgacaatt gtgtctgtcg   15120

tcaatccaga ctgccttcaa tcagggcgct ggaacttgta ccctgtcaga ttcaggcagg   15180

ataagttaca ctgtggagtt tagtttgccg acgcatcaca ctgtgcgcct gatccgcgct   15240

acagcatcac cctcagcatg atgagctggc attcctgggt atcccagtgt ttgaattgga   15300

agaatgtgtg gtgaatggca ctgattgaca ttgtgcttct aagtcaccta ttcaattagg   15360

gcgaccgtgt gggagtagaa tttaattggc gagaaccacg cggccgaaat taaaaaaaaa   15420

aaaaaaaaaa aaaaaaaaaa aaaa                                           15444
```

<210> SEQ ID NO 11
<211> LENGTH: 15444
<212> TYPE: DNA
<213> Artificial Sequence

<400> 11

```
atgacgtata gttgttggct ctatgtcgtg acatttgtat agtcaggagc tgcgaccatt      60

ggtacagccc aaaacttgct gcgcgggaac gcccttccgt gacagccttc ttcaggggag     120

tttaggggtc tatccctagc accttgcttc cggagttgca ctgctttacg gtctctccac     180
```

-continued

```
ccctttaacc atgtctggga tacttgatcg gtgcacgtgt acccccaatg ccagggtgtt    240
tgtggcggag ggccaagtct actgcacacg atgtctcagt gcacggtctc tccttccttt    300
gaatctccaa gtttctgagc ttggggtgct gggcttattt tataggcccg aagagccgct    360
ccggtggacg ttgccacgtg cattccccac tgtcgagtgc tcccccgccg gggcctgctg    420
gctttctgcg atttttccaa ttgcacgaat gaccagtgga aacctgaact ttcaacaaag    480
aatagtgcgg gtcgcagctg agctctacag agccggtcag ctcacccccg tagtcttgaa    540
gaatctacag gtttatgaac ggggttgccg ttggtacccc atcgttggac ctgttcctgg    600
agtggctgtt tatgccaatt ccttacacgt gagtgacaaa cctttcccgg gagcaactca    660
tgtgttaacc aacctaccgc tcccgcagag gcccaagcct gaagactttt gcccctttga    720
gtgtgctatg gctgacgtct atgacattgg tcatgacgct gtcatgtatg tggccggagg    780
gagagtctcc tgggcccctc gtggcgggga caaaggaaaa tttgaaatag ttcccaagga    840
gttgaagttg attgcgaatc gactccacat ttccttcccg ccccaccacg cagtggacat    900
gtccaagttt gcctttataa gccctgggag tggtgtttcc atgcgggtcg agtaccaaca    960
tggctgtctc cccgctgata ctgtccctga aggaaactgt tggtggcgct tgtttgactt   1020
gcttccaccg gaagttcaga acaaagagat tcgccatgct aaccaactcg gctatcagac   1080
caagcatggt gtcgctggca agtacctaca gcggaggctg caagttaatg gactccgagc   1140
agtaactgac gcgaatggac ctatcgtcat acagtatttt tgtgataggg aaagctggat   1200
ccgccactta agactggtag aagaacctag cctccctggg tttgaggacc tcctcagaat   1260
aagagttgag cccaatacgt tgccattggt tggcgaggat gagaaaatct tccgatttgg   1320
caatcacaaa tggtacggtg ctggaaagag ggcaaggaaa gcacgctttg gtgcggctgc   1380
cacggtcgct caccgcgctt tgcccgctca cgaaacccag caggccaaga agcacgaagt   1440
taccagcgcc aacagggctg agcatctcga gcactattcc ccgcctaccg acgggaactg   1500
tggttggcac tgcgtttccg ccattgtcaa ccggattgtg aattccaaat ttgaaaccac   1560
ccttcccgag agagtgagac ctttagatga ctgggctact gacgaggatc ttgtgaatac   1620
tatccaaatc ctcaggctcc ctgcggcctt ggacaggaac ggtgcttgtg tcggcgccaa   1680
gtacgtgctc aagctggaag gtgtgcactg gacagtctct gtggcccctg ggatgacccc   1740
ttctctgctc cccttgaat gtgttcaggg ctgttgtgag cataagagcg gtcttggtcc   1800
cccagatgtg gctgaagttt ccggatttga ccctgcctgc cttaaccgac tggctgaggt   1860
aatgcacttg cctagttgtg tcatcccagc tgctctggct gaaatgtccg acgaccccaa   1920
tcgcccggct tccccagtca ccactgtgtg gactatttcg caattctttg cccattatag   1980
aggaggagag caccctgatc aggtgtgctt agggaaaatc atcagccttt gtcaggtgat   2040
tgaggaatgc tgttgttccc agaacaaaac caaccgggcc accccggaag aggtcgcggc   2100
aaaaattgac cagtacctcc gtgatgcagc aagccttgga gaatgcttag ccaagcttga   2160
gagggctcgc ccgccgagcg cgatggacac ctcctttgat tggaatgttg tgcttcctgg   2220
ggttgaggcg gcgaaccaga cgaccaaaca gctccatgtc aaccagcacc gtgcttcggt   2280
tcctgccatg actcaggagc ctttggacaa agactcggtc cctttgaccg ccttctcgct   2340
gtctaattgc tactaccctg cacaaggtga cgaggttcgt caccgtgaga ggctgatctc   2400
cgtgctctct aagttggagg aggttgttcg tgaggaatat gggctcacgc caactggatc   2460
tggcccgcga cccgcactgc cgaacgggct cgacgagctc aaagaccaga tggaagagga   2520
tctgttgaaa ctggtcaacg cccaggcaac ttcagaaatg atggcccggg cagctgagca   2580
```

-continued

```
ggttgatcta aaagtttggg tcaaaaatta cccacggtgg acaccgccac cccctccacc   2640
aagagttcag cctcgaaaaa caaagtctgc taagagcctg ccagagaaca agcctgtccc   2700
tgctccgcgc aggaaagtca gatctgattg tggcagcccg actttgaggg gcaacaatgt   2760
tcctaacggt tgggaagact tggccgttgg tggtcctctt gatctttcga caccatccga   2820
gccgatgaca cctctgagtg agcctgcact tatgcccgtg ttgcaacata tttctggacc   2880
agtgacgcct ttgagcgtgc cggcccctat tcctgcaccg cgtaaagctg tgtcccgacc   2940
gatggcgccc tcgagtgagc caatttttgt gtctgcaccg cggcaaaaat ttcagcaggt   3000
ggaagaagca aatctggcgg caacaacgct gacataccag gacgaaccta tagatctgtc   3060
agcatcctca cagactgaat atgaggctcc ttccctagca ccactgcaga acataggtac   3120
tctggaggtg ggggggcaag aagctgagga aattctgagt gaaacctcgg atataccgaa   3180
tgacatcaac cctgtgcctg tatcatcaag cagctccttg tcaagcgtta agatcacacg   3240
cccaagacac tcagctcaag ccatcatcga ctcgggcggg ccctgcagtg ggcatctcca   3300
aagggagaaa gaagcgtgcc tccgcatcat gcgtgaggct tgtgatgcga ctaagcttag   3360
tgaccctgcc acgcaggaat ggctttctcg catgtgggat agggtggaca tgctgacttg   3420
gcgcaacacg tctgctttcc aggcgtttcg catcttagac ggcaggcttg agtttcttcc   3480
aaagatgata ctcgagacgc cgccgcccta cccgtgtggg tttgtgatgc tgcctcacac   3540
ccctgcacct tccgtgagtg cagagagcga ccttaccatc ggttcagtcg ccactgaaga   3600
tattccacgc atcctcggga aaatagaaaa caccagtgag atgatcaacc agggaccctt   3660
ggcatcctct gaggaaaaac cggcatacaa ccaacccgct aaggactccc tgatatcgtc   3720
gcgggggttt gacgagagca cagcagctcc gtccgcaggt acgggtggcg ccggcttgtt   3780
tactgatttg ccaccttcag acggtgtaga tgcggacggg ggggggccgc tgcagacggt   3840
gaaaaagaac gctgaaaggc tcctcgaccg attgagccgt caggttttta acctcgtctc   3900
ccatctccct gttttcctct cacacctctt caaatctgac agtggttatt ctccgggtga   3960
ttggggtttt gcagctttta ctctattttg cctcttttta tgttacagct acccattctt   4020
tggtttcgct ccccttttgg gtgtgttttc tgggtcttct cggcgcgtgc gcatgggggt   4080
ttttggctgc tggttggctt ttgctgttgg tttgttcaag cctgtgtccg acccagtcgg   4140
cactgcttgt gagtttgatt cgccagagtg taggaatgtc cttcattctt ttgagcttct   4200
caaaccttgg gaccctgttc gcagccttgt tgtgggcccc gtcggtctcg gtcttgccat   4260
tcttggcagg ttactgggcg gggcacgcta catctggcat tttctgctta ggcttggcat   4320
tgttacagac tgtatcctgg ctggagctta tgtgctttct caaggtaggt gtaaaaagtg   4380
ctggggatct tgcataagaa cagctcctaa tgagattgcc tttaacgtgt tcccttttac   4440
acgtgcgact aggtcgtcac tcatcgacct gtgcaatcgg ttttgtgcgc caaagggcat   4500
ggaccctatt ctcctcgcca ctgggtggcg tgggtgctgg accggccgaa gccccattga   4560
acaaccctct gaaaaaccca tcgcgtttgc ccagttggac gaaaagagga ttacggccag   4620
gaccgtggtc gcccagcctt atgaccccaa ccaagccgta aagtgcttgc gggtgttaca   4680
ggcgggcggg gcgatggtgg ctgaggcagt cccaaaagtg gtcaaagttt ccgctattcc   4740
attccgagcc cccttttttc ccaccggagt gaaagttgac cctgagtgta ggatcgtggt   4800
tgaccccgac acttttacta cagccctccg gtccggctat tccaccacaa acctcgttct   4860
tggtgtgggg gactttgccc agctgaatgg attaaaaatc aggcaaattt ccaagccttc   4920
gggaggaggc ccgcacctca ttgctgccct acatgttgcc tgctcgatgg cgttgcacat   4980
gcttgctggg gtttatgtaa ctgcagtggg gtcttgcggt accggcacca acgatccgtg   5040
```

-continued

```
gtgcaccaac ccgtttgccg tccctggcta cgggcctggt actctttgca cgtccagatt   5100
gtgcatctcc caacatggcc ttaccctgcc cttgacagca cttgtggcag gattcggtct   5160
tcaggaaatt gccttggttg ttttgatttt cgtttccatc ggaggcatgg ctcacaggtt   5220
gagttgcaag gctgacatgc tgtgcgtttt acttgcaatc gccagctatg tttgggtgcc   5280
ccttacctgg tttctttgtg tgtttccttg ctggttgcgc tggttctctt tgcatcccct   5340
caccatccta tggttggtgt ttttcttgat ttctgtaaat gtgccttcgg gaatcttggc   5400
tgtggtgttg ttagtttctc tttggctctt aggtcgttac actaatgttg ctggtcttgt   5460
caccccatat gacattcatc atcacaccag tggcccccga ggtgttgccg ccttggctac   5520
tgcaccggat gggacctact tggccgccgt tcgccgtgct gcgttgaccg gtcgtaccat   5580
gctgtttacc ccgtctcagc ttgggtccct tcttgagggt gctttcagaa ctcaaaagcc   5640
ctcactgaac accgtcaatg tggtcggatc ctctatgggc tccggcgggg tgttcaccat   5700
cgacgggaaa attaagtgcg taacagccgc acatgtcctt acgggtaatt cagctagggt   5760
ttccggggtc ggcttcaacc aaatgcttga ttttgatgtg aaaggggact tcgccatagc   5820
tgattgcccg aattggcaag gagctgcccc caagacccaa ttctgcgagg atggatggac   5880
tggccgtgcc tattggctga catcctctgg agtcgaaccc ggtgtcattg ggaatggatt   5940
cgccttctgc ttcaccgcgt gcggcgattc tggatccccg gtgattaccg aagccggtga   6000
gcttgtcggc gttcacacag gatcaaacaa acaaggagga ggcatagtca cacgcccctc   6060
aggccagttt tgtaatgtgg cgcccatcaa gctgagcgaa ttgagtgaat tcttcgctgg   6120
acctaaggtc ccgctcggtg atgtgaagat tggcagccac ataattaaag acgtatgcga   6180
ggtaccttca gatctttgcg ccttgctcgc tgccaaaccc gaactggaag gaggcctctc   6240
caccgtccaa cttctgtgtg tgtttttcct cctgtggaga atgatgggac atgcctggac   6300
gcccttggtt gctgtggggt tttttatctt gaatgaggtt ctcccagctg tcctggtccg   6360
gagtgtcttc tcctttggta tgtttgtgct atcttggctt acaccatggt ctgcgcaagt   6420
cctgatgatc aggcttctaa cagcagctct taacaggaac agggggtcac tcgccttcta   6480
cagcctcggt gcagtgaccg gatttatcgc agatcttgca gcaactcagg ggcatccgct   6540
gcaggcagtg atgaacttaa gcacctatgc cttcctgcct cggatgatgg ttgtgacctc   6600
accagtccca gtgcttgctt gtggtgttgt gcacctcctt gccataattt tgtacctgtt   6660
taagcaccgt tgcctgcatt atgtccttgt tggcgatgga gtgttctcta aagccttctt   6720
cttgcgatac tttgccgaag ggaagttgag ggaaggggtg tcgcagtcct gcgggatgaa   6780
tcacgagtca ctgactggtg ccctcgctat gagactcaat gacgaagact tggacttcct   6840
tacgaaatgg actgatttta agtgctttgt ttctgcgtcc aacatgagga atgcagcggg   6900
ccaattcatc gaggctgcct atgcaaaagc acttagaatt gagcttgccc agttagtaca   6960
ggttgataag gttcgaggta ctttggccaa acttgaagcc tttgctgata ccgtggcacc   7020
ccagctctcg cccggtgaca ttgttgttgc tcttggccac acgcctgttg gcagtatctt   7080
cgacctaaag gttggcagta ccaagcatac cctccaggcc attgagacca gagtccttgc   7140
cgggtccaaa atgaccgtgg cgcgtgtcgt tgatccaacc cccacgcccc cacccgcacc   7200
cgtgcccatc cccctcccac cgaaagtcct ggagaacggc ccccaacgcct gggggatga    7260
ggaccggttg aataagagga agagacgcag gatggaagcc gtcggcatct ttgttatggg   7320
tgggaagaag taccaaaaat tttgggacaa gaattccggt gatgtgtttt acgaggaggt   7380
ccatgataac acagatgcgt gggagtgcct cagagttggt gaccctgccg actttgaccc   7440
```

-continued

```
tgagaaggga actctgtgtg ggcatactac cattgaagac aaggcttata atgtctacac   7500
ctccccatct ggcaggaagt tcctggtccc cgtcaaccca gagagcggaa gagcccaatg   7560
ggaagctgca aagctttccg tagagcaggc ccttagcatg atgaatgtcg acggtgagct   7620
gacagccaaa gaactggaga aactgaaaag aataattgac aaactccagg gcctaactaa   7680
ggagcagtgt ttaaactgct agccgccagc ggcttgaccc gctgtggtcg cggcggcttg   7740
gttgttactg agacagcggt gaaaatagtt aaatttcaca accggacctt caccctagga   7800
cctgtgaatt taaaagtggc cagtgaggtt gagctaaaag acgcagtcga gcataaccaa   7860
cacccggttg caagaccggt tgatggtggt gttgtgctcc tgcgctccgc agttccttcg   7920
cttatagacg tcttgatctc tggcgctgat gcatctccta agttactcgc ccaccacggg   7980
ccgggaaaca ctgggatcga tggttcgctt tgggattttg aggccgaggc caccaaagag   8040
gaaattgcac tcagtgcgca aataatacag gcttgtgaca ttaggcgcgg cgacgcaccc   8100
gaaattggtc ttccttataa gctgcaccct gttaggggca accctgagcg ggtaaaaggg   8160
gttttacaga atacaaggtt tggagacata ccttataaaa cccccagtga cactgggagc   8220
ccagtgcacg cggctgcctg cctcacgccc aatgccactc cggtgactga cggtcgttcc   8280
gtcttggcta cgaccatgcc ctccggtttt gagttgtatg taccgaccat tccagcgtct   8340
gtccttgatt atcttgattc caggcctgat tgccccaaac agttgacaga gcacggctgt   8400
gaggatgccg cattaagaga cctctccaag tatgacttgt ccacccaagg ctttgtcttg   8460
cctggagttc ttcgccttgt gcgtaagtac ctgtttgctc atgtgggtaa gtgcccgcct   8520
attcatcggc cttccactta ccctgccaag aattccatgg ctggaataaa tgggaacagg   8580
tttccaacca aggacattca gagcgtccct gaaatcgacg ttttgtgcgc acaggccgtg   8640
cgagaaaact ggcaaactgt tactccttgt accctcaaga agcagtattg cgggaagaag   8700
aagactagga caatactcgg cactaataac ttcattgcgc tggcccaccg ggcagcattg   8760
agtggtgtca cccagggctt catgaaaaaa gcgtttaact cgcccatcgc actcgggaaa   8820
aacaaattca aggagctgca gactccggtc ttgggcagat gtcttgaagc tgaccttgca   8880
tcctgtgacc gatccacacc cgcaattgtc cgctggtttg ccgccaatct tctttatgaa   8940
cttgcctgtg ctgaggagca tataccatcg tacgtgttga actgctgcca cgacttactg   9000
gtcacgcagt ccggcgcggt gactaagaga ggtggcctat cgtctggcga cccgattact   9060
tctgtatcaa acaccattta cagcttggtg atatatgcac agcacatggt actcagttat   9120
tttaaaagtg gtcaccccca tggccttctg tttctacaag accagctaaa gtttgaggac   9180
atgctcaagg ttcagcccct gatcgtctat tcggacgacc tcgtgctgta cgccgagtct   9240
cccaccatgc caaactacca ctggtgggtt gaacatctga acctgatgct gggttttcag   9300
acggacccaa agaagacagc tataacagac tcgccatcat tttgggttg taggataata   9360
aatggacgcc agttagtccc caaccgtgac aggatcctcg cggccctcgc ctaccatatg   9420
aaggcaaaca atgtttctga atactacgcc tcggcggctg caatactcat ggacagttgt   9480
gcttgtttgg agtacgatcc tgagtggttt gaagagctcg tggttgggat ggcgcagtgc   9540
gcccgcaagg acggctacag ttttcctggc ccgccgttct tcttgtccat gtgggaaaaa   9600
ctcaggtcca atcatgaggg gaagaagtct agaatgtgcg ggtactgtgg ggccccagct   9660
ccgtatgcca ctgcctgtgg ccttgatgtt tgtatttatc acacccactt ccaccagcat   9720
tgtccagtca taatctggtg tggccatccg gcgggttctg gctcttgtag tgagtgcaaa   9780
ccccccctag ggaaaggcac aagccctcta gatgtggtgt tagaacaagt cccgtacaag   9840
cctccacgaa ctgtaatcat gcatgtggag cagggtctca cccctcttga cccaggcaga   9900
```

-continued

```
taccagactc gccgcggatt agtctccgtt aggcgtggca tcaggggaaa cgaaatcgac    9960
ctaccagacg gtgattatgc tagtaccgcc ttgctcccca cttgtaaaga tatcaacatg   10020
gtcgctgtcg cttccaatgt gttgcgcagc aggttcatca tcggtccacc cggtgctggt   10080
aaaacatact ggctccttca acaggtccag gatggtgatg tcatttacac gccaactcat   10140
cagaccatgc ttgacatgat caaggctttg ggacgtgcc  ggttcaacgc cccagcaggc   10200
acaacgctgc aattccctgc tccctcccgt accggcccgt gggttcgcat cctggccggc   10260
ggttggtgtc ctggcaagaa ttccttcctg gatgaagcag cgtattgtaa tcaccttgat   10320
gtcttgaggc ttcttagcaa aactaccctc acctgtctgg gagatttcaa acaactccac   10380
ccagtgggtt ttgattctca ttgctatgtt tttgacatca tgcctcagac tcaactgaag   10440
accatctgga ggtttggaca gaatatctgt gatgccattc agccagatta cagggacaaa   10500
cttgtgtcca tggtcaacac aacccgtgta acctacgtgg aaagacctgt caagcatggg   10560
caggtcctca ccccttacca cagggaccga gaggacggcg ccatcacaat tgactccagt   10620
caaggcgcca catttgatgt ggttacattg catttgccca ctaaagattc actcaacagg   10680
caaagagccc ttgttgctat caccagggcg agacatgcta tctttgtgta tgacccacat   10740
aggcaactgc agagcatgtt tgatcttcct gcaaaaggca cacccgtcaa ccttgccgtg   10800
caccgtgacg agcagctgat cgtactagat agaaataaca aagagtgcac ggttgctcag   10860
gctctaggca atggggacaa attcagggcc acagacaagc gcgttgtaga ttctctccgc   10920
gccatttgtg cagatcttga agggtcgagc tccccgctcc ccaaggtcgc acataacttg   10980
ggattttatt tctcacctga tttgacacag tttgctaaac tcccggcaga acttgcaccc   11040
cactggcccg tggtgacaac ccagaacaat gaaaagtggc cagacaggct ggttgccagc   11100
ctccgcccta tccataaata tagccgcgca tgcattggag ccggctatat ggtgggccct   11160
tcggtgtttc taggcacccc tggggttgtg tcatactatc tcacaaaatt tgttaagggg   11220
gaggctcagg tgcttccgga gacagtcttc agcaccggcc gaattgaggt agattgccgg   11280
gagtatcttg atgatcggga acgagaagtt gctgagtccc tcccacatgc cttcattggc   11340
gacgtcaaag gcactaccgt tgggggatgt caccatgtca cctctaaata ccttccgcgc   11400
ttccttccta aggaatcagt tgcggtggtt ggggtttcga gccccgggaa agccgcaaaa   11460
gcagtctgca cattaacaga tgtgtatctc ccagaccttg aagtttacct ccacccagag   11520
acccaatcca agtgctggaa aataatgttg gacttcaagg aagtccgact gatggtctgg   11580
aaagacaaaa cggcctattt tcaacttgaa ggccgccatt tcacctggta tcagcttgca   11640
agctatgcct cgtacatccg agttcctgtt aactctacgg tgtatttgga cccctgcatg   11700
ggccctgccc tttgcaacag aagagttgtc gggtccactc attgggggc  tgacctcgca   11760
gtcacccctt atgattatgg tgccaaaatc attctgtcta gtgcatacca tggtgaaatg   11820
cctcctgggt acaaaatcct ggcgtgcgcg gagttctcgc ttgacgaccc agtgaggtac   11880
aaacacacct gggggtttga atcggacaca gcgtatctgt acgagttcac cggaaacggt   11940
gaggactggg aggattacaa tgacgcattt cgtgcgcgcc agaaagggaa aatttataag   12000
gccactgcca ccagcatgag gtttcatttt cccccgggcc ccatcattga accaacttta   12060
ggcctgaact gaaatgagat gggggctatg caaagccttt tctacaaaat tggccaactt   12120
tttgtggatg ctttcacgga atttttggtg tccattgttg atatcatcat atttttggcc   12180
attttgtttg gcttcaccat cgccggttgg ctggtggtct tctgcatccg attggtttgc   12240
tccgcggtac tccgtgcgcg ccctaccatt caccctgagc aattacagaa gatcctatga   12300
```

-continued

```
ggcctttctt tctcagtgcc gggtggacat tcccacctgg ggaaccaaac atcccttggg   12360
gatactttgg caccataagg tgtcaaccct gattgatgaa atggtgtcgc gtcgaatgta   12420
ccgcatcatg gaaaaatcag gacaggctgc ctggaaacag gttgtgagcg aggctacgct   12480
gtctcgcatc agtggtttgg atgtggtggc tcattttcag catcttgccg ccattgaagc   12540
cgagacctgt aaatatttgg cctctcggat gcccatgcta cacaacctgc gcatgacagg   12600
gtcaaatgta accatagtgt ataatagtac tttgaatcag gtgttagcaa tcttcccgac   12660
ctctgaatcc cggccaaagc ttcatgattt tcaacaatgg ttaataactg tacattcctc   12720
catattttcc tccgttgtgg cttcctgtac tctttttgtt gtgctgtggt tgcgaattcc   12780
aatgctacgt actgtttttg gtttccactg gttaggggca atttttcttt cgaactcaca   12840
gtgaattaca cggtgtgccc accttgcctc acccggcaag cagccgctga gatctacgaa   12900
cccggcaggt ctctttggtg caggataggg catgatcgat gtagcgagga cgatcatgac   12960
gaactagggt tcttggttcc gcctggcctc tccagcgaag gccacttgac cagtgtttac   13020
gcctggttgg cgttcctgtc cttcagctat acagcccagt tccatcccga gatatttggg   13080
atagggaatg tgagtaaaat ttatgttgac atcaagcacc aattcatctg cgccgaacac   13140
gacgggcaga acgccaccct gcctcgccat gacaacattt cagccgtgtt tcagacctac   13200
taccaacatc aggtcgatgg cggcaattgg tttcacctgg aatggctgcg ccccttcttt   13260
tcctcttggt tggttttaaa tgtttcgtgg tttctcaggc gttcgcctgc aagccatgtt   13320
tcagttcgag tctttcagac atcaaaacca acaccaccgc agcaccaaat tttgttgtcc   13380
tccaggacat cagctgcctt aggcatggcg acccgtcctc tccggcgatt cgcaaaagct   13440
ctcagtgccg cacggcgata ggaacacccg tgtatatcac catcacagcc aatgtgacag   13500
atgagaatta tttacattct tctgatctcc tcatgctttc ttcttgcctt ttctatgctt   13560
ctgagatgag tgaaaagggg ttcaaggtgg tattcggcaa tgtgtcaggc atcgtggctg   13620
tgtgtgtcaa ctttaccagt tacgtccaac atgtcaagga gtttacccaa cgctccttgg   13680
tggtcgagca tgtgcgactg cttcatttca tgacacctga aaccatgagg tgggcaaccg   13740
ttttagcctg tctttttgcc attctgttgg caatttgaat gtttaagtat gttggggaaa   13800
tgcttgaccg cgggctgttg ctcgccgttg ctttttttgt ggtgtatcgt gccgtcttgc   13860
tttgttgcgc ccgtcaacgt cgacgggaac gacagctcaa agttacagct gatttacaac   13920
ttgacgctat gtgagctgaa tggcacagat tggctggctg gtagatttga ctgggcagtg   13980
gagtgttttg tcatttttcc cgtgttgact cacattgtct cctatggtgc cctcactact   14040
agccatttcc ttgacacagt cggtctggtc actgtgtctg ccgccgggtt ccttcatgaa   14100
cggtatgttt tgagtagcat ctacgcggtc tgtgccctgg ctgcgttgat ttgcttcgtc   14160
attaggcttg cgaagaactg catgtcctgg cgctactcgt gtaccagata taccaacttc   14220
cttttggaca ccaaggggag actctatcgt tggcgatcgc ccgtcatcat agagaaaaag   14280
ggtaaagttg aggttgaagg tcatttgatc gacctcaaaa gagttgtgct tgatggttcc   14340
gtggcaaccc ctataaccaa aatttcagcg gaacaatggg gtcgtcctta gatgacttct   14400
gccatgatag cacggctcca caaaaggtgc ttttggcgtt ttccattacc tatacaccag   14460
tgatgatata tgccctaaag gtaagtcgcg gccgactgct agggcttttg caccttttga   14520
tctttctgaa ctgtgctttc accttcgggt atatgacatt cacgcacttt cagagtacaa   14580
acaaggtcgc gctcactatg ggagcagtag ttgcactcct ttgggggggtg tactcagcca   14640
tagaaacctg gaaattcatc acctccagat gccgtttgtg cttgctaggc cgcaagtaca   14700
ttctggcccc tgcccaccac gttgagagtg ccgcaggctt tcatccgatt gcggcaaatg   14760
```

-continued ataaccacgc atttgtcgtc cggcgtcccg gttccactac ggtcaacggc acattggtcc 14820
ccgggttgaa aagcctcgtg ttgggtggca gaaaagctgt caaacaggga gtggtaaacc 14880
ttgttaaata tgccaagtaa caacggcagg cagcagaaaa aaagaaaggg ggatggccag 14940
ccagtcaatc agctgtgtca gatgctgggt aaaattattg cccagcaaaa tcagtccagg 15000
ggcaagggac cgggaaagaa aaataacaag aaaaaacccgg agaagcccca ttttcctcta 15060
gcgactgaag atgatgtcag acatcacttt accccgagtg agcgacaatt gtgtctgtcg 15120
tcaatccaga ctgccttcaa tcagggcgct ggaacttgta ccctgtcaga ttcaggcagg 15180
ataagttaca ctgtggagtt tagtttgccg acgcatcaca ctgtgcgcct gatccgcgct 15240
acagcatcac cctcagcatg atgagctggc attcctgggt atcccagtgt ttgaattgga 15300
agaatgtgtg gtgaatggca ctgattgaca ttgtgcttct aagtcaccta ttcaattagg 15360
gcgaccgtgt gggagtagaa tttaattggc gagaaccacg cggccgaaat taaaaaaaaa 15420
aaaaaaaaaa aaaaaaaaaa aaaa 15444

<210> SEQ ID NO 12
<211> LENGTH: 15047
<212> TYPE: DNA
<213> Artificial Sequence
<400> 12
atgacgtata ggtgtttgct ttatgccgcg gcatttgtat tgtcaggagc tgtgaccact 60
ggcacagccc gaaacttgct gcacagaaac acccttctgt gacagcctcc ttcaggggag 120
tttaggggtt tctccctaac gccctgcttc cggagttgca ctgctttacg gtctctccat 180
ccttttaacc atgtctggga ttcttgatcg gtgcacgtgc acccccaatg ccagggtgtt 240
tgtggcagag ggccaagtct actgcacacg atgtctcagt gcacggtccc tccttcccct 300
aaatctccaa gtttctgagc ttggggtact tggtttattc tacaggcccg aagagccatt 360
acggtggacg ttgccacacg cattccccac tgtcgagtgt gctcctgctg gcgcttgttg 420
gctttctgca atttttccaa ttgcgcgaat gaccagtgga aacctgaatt tccagcaaag 480
gctggtacgt gtcgcagccg agctttacag agccggccag ctcaccccta caagcctgaa 540
aaccttacag gtctatgaaa ggggttgccg ttggtacccc attgttggac ctgttcctgg 600
agtggccgtt tacgccaact ccctacatgt gagtgacaaa cccttcccag gagcgactca 660
cgtgctgacc aacttaccac tcccgcagag accaaaatct gaagatttct gccccttcga 720
gtgcgccacg gccgccgtct atgacatcgg ccatgacgcc gtcatgtatg taaccgagga 780
aaaggtttcc tgggctcctc gtggcgggga taaagggaaa tttgagactg ttcctgaggg 840
gttgaagttg actgcggaac gactctacac ctccttcccg cctcaccatg cggtggacat 900 gtccctttc atcttcacag accttgagtg cggcgcttcc atgcgggtcg aacgccaata 960
tggttgcctc tctgctggca ctgtccctga aggcaactgc tggtggagtc tgtttggctc 1020
gctttcgtta gaagctcagt ataaagaaat ccgctacgcc gcccaatttg gctatcagac 1080
caaacatggc gttactggca agtacctgca gcggaggctg caaattaatg gtctccgagc 1140
agtggttgac ccgaatgggc ctcttgtcgt acagtatttc tccgttaagg agagctggat 1200
gcgccacgtg agactggcgg aagagccagg ctatcctggg tttgaggatc tcctcaggat 1260
aagagtcgag cccaacacgt tgcctttgtc caacaaggac gagaaaatct tccgtttcgg 1320
cggttacaag tggtacggtg ctgggcggag ggcaaggaga acacgtgcaa gagcagtcac 1380
cgcagttgct agtcatgctc cgcccgctcg tggggcccag caggccgaga agcacgaagt 1440
tgctagtgcc aacaagactg agctccttac gcactactcc ccacctgctg aagggaattg 1500

-continued

```
cggctggcac tgcatctccg ccatcatgaa ccggatggtg cattccaagt ttgaaaccgc   1560
cctttccgaa agagtgagat ccccggaaga ctgggcgact gatgaggatc ttgtgaatac   1620
tattcaaatc ctcaggctcc ctgcggcctt agacaggaac ggcgcctgta aaaacgccaa   1680
gtacatcctt aagctggaag gtgagcactg gactgtttca gtgacccccg gaatgccccc   1740
ctcttcactt cctcttgaat gcgttcaggg ttgttgcgag cataagggca attttgactc   1800
tcaaaacgcg gtcggtttct ttgggttcga ccctgccagc cttgaccgac tcgctggggt   1860
aatgcatctg cccagcagcg ccatccctgc cgccctggcc gagttgtctg gtgaacttga   1920
ttgttcaact cccccggcca ccactgtgtg gactaccttg cagttttatg ctcgtcttgg   1980
tggggggggag catcctgatc aagagtgctt gagaaaaatc atcagcctct gtgaggtgct   2040
cgggagttgc tgctgttctc agagtagggt caaccgggtc accccggaag aggtcgcagc   2100
aaagattgac ctgtatcttc gtgacgcagc gagtcttgaa gagtgcttgg ctaggcttga   2160
gaaagctcgc ccgccaagca tgctggacac ctcctttgac tgggatgttg tactccctgg   2220
tgttgggacg gctgctcggg cagcagaact acccccccacc gatgagtgtc gcgctctagt   2280
cactgctgtg gcccaaaggc cttcgccgaa agttcagcct cgaaaggcgg ggtctgttaa   2340
gagtctacca gagatcaggc ctgtccctgc cccacgcagg aaggttaagt ctagttgtgg   2400
tgatctggcc ccgttgggcg gcaatttccc tgatagctgg gaagatttgg ctggtggctc   2460
ccttaatctc cagatcttac ctgagccggt ggcacaatcc tttgaacctg tgcctgtccc   2520
tgcaccgcgc aagactgcgc ctcgattagt gtcgtcatca ttggcgtcga cccccgtacc   2580
tacaccacga tgtgggtttc ggcagtttga gggaatgaat ttgacagctg tgaccctagc   2640
atgccaggat gagtccctca atttgtctgc atcctcgcag actgaatatg aggcttctcc   2700
tttggcattg cagcagggtg aggatgtcct tgcggtgggg ggacgagaag ccgaagaagt   2760
cctgagcgga atctcgggaa tgtcaggtgg cattagatta gcgcccgcat catcaagtag   2820
ctccttgtca agcgtggaga tcacacgccc gaagtactca gctcaagcca tcattgactc   2880
aggtggaccc tgttgcgggc accttcaaga ggtgaaagag aaataccttta atgtcatgcg   2940
tgaggcatgt gatgcgacta agctcgatga ccctgccacg caagaatggc tctctcgcat   3000
gtgggagagg gtagacatgc taacctggcg caacacgtcc atctttcaag cgccttttac   3060
cttagctgac aagtttaagt ccctcccgaa gatgatactc gaaacgccgc caccctaccc   3120
ttgcgggttt gtgatgatgc cccgcacgcc cgcaccttct gtgggtgcgg aaagcgacat   3180
caccgttggt tcagttgcta ctgaagatgt cccgcgtata ctcggggagg tgggagatgt   3240
tggcaagatg accggccagg aacccttaga atccttcgca gatgaactgg cagatgacca   3300
acctgctagg gagtcccgaa cacaagctcc tcctgcaagc acaggtagcg ctggtttagt   3360
tttggattct ggagggtcgc tggggctcac tgacctgccg ctcccaaaca atatagacgc   3420
gggcgggaaa ggaccgtttc acgcggtcaa gaaaaaagct gtagggtgct ttgaccaact   3480
gagccgccgg gtttttgaca tcgtctccca tctccctgtt ttttttcac gccttttcgc   3540
gcccggtggt ttttactctt cgggtgactg gagttttgca gcttttactt tattgtgtct   3600
ctttttatgt tacagttatc cggcctttgg ttttgctccc ctcgtgggtg tattttctgg   3660
gtcttctcgg cgcgtgcgca tgggggtttt tggctgctgg ctggcttttg ctgttggttt   3720
gttcaagcct gcacccgacc cagtcggtgc tgcttgtgag tttgactcgc cagagtgtag   3780
agacatcctt cattcttttg agctcctgca accttgggac cctgttcgca gccttgtggt   3840
gggccccgtc ggtctcggcc ttgccatttt tggcaggtta ctgggcgggg cacgctacgt   3900
ctggctgctt ttgcttaggc ttggcatcgt ttcagactgt atcctggctg gagcctatgt   3960
```

-continued

```
gctttcgcaa ggcaggtgta aaaagtgttg gggatcttgt ataagaacag cccccagtga   4020
agttgccttc aatgtgtttc cctttacacg cgcaactaga tcgtcacttg tcaacctgtg   4080
cgaccggttc tgtgcaccca agggcatgga ccccatcttc cttgccacag gatggcgcgg   4140
atgctggtcc ggccagagcc ccattgagca accctctgaa aaacccatag cgttcgccca   4200
gttggacgaa aagaaaatca cggctaggac tgtggttgcc cagccttatg accccaacca   4260
agctgtgaag tgcctgcgag tcctccaggc gggtggagcg atggtagccg aggcagttcc   4320
aaaagtagtc aaagtttctg ctgtcccgtt tcgagcccct ttttttcctg ccggagtgaa   4380
agttgaccct gaatgcaggg tcgtggttga ccctgacacc tttacaaccg ctctccggac   4440
cggctactcc accacaaacc tcattcttgg tgttggggac tttgcccagc tgaatgggtt   4500
gaagatcaga caaatttcca agtccccagg agggggccct cacctcatgg cggctttaca   4560
tgttgcttgc tcgatgactt tgcacatgct tgttgggatt tatgtcacca tggtgggttc   4620
ttgtggctct ggcactaacg atccgtggtg cactaacccg tttgccgtcc ctgtctatgg   4680
gcctggctct ctctgcacgt ccaggttgtg catttcccag cgtggcctga ccctgccctt   4740
aacagcgctt gtggcagggt ttggcgttca ggaaatcgct ttggttgttt taatctttgt   4800
ctccatcggg ggtatggccc acaggttgag ttgcaaggct gacgtgctgt gtatcctgct   4860
tgctattgtc agctatgttt ggccacccct tacctggttg ctttgtgtgt ttccttgctg   4920
gttgcgctgg ttttctttac atccccttac tattctatgg ttagtgtttt tcttgatttc   4980
tgtaaatacg ccctcgggaa tcttggcctt ggtcctgtta atctctcttt ggctccttgg   5040
tcgctatacc aatgttgccg gccttgtcac cccttatgac attcaccatt acaccaacgg   5100
ccctcgcggc gttgccgcct tggccactgc cccggatggg acctacctgg ctgctgtccg   5160
ccgtgctgcg ttgactggcc gtaccatgct gttcaccccg tcccaacttg gctcgctcct   5220
tgagggcgct tttagaaccc aaaagccttc actgaacact gtcaatgtag ttgggtcctc   5280
catgggctcc ggcggggtgt tcaccattga tgggaagatc aaatgtgtga ccgctgctca   5340
tgtcctcacg ggtaactctg ccagggtttc cggggttggc ttcaatcaaa tgttggactt   5400
tgatgttaaa ggggattttg ccatagccga ttgtccgaat tggcaaggag tcgcccccaa   5460
gtcccggttc tgcaaggatg attggactgg ccgtgcttat tggctcacgt cctccggcgt   5520
cgaacccggc gtcattgggc aaggattcgc cttttgtttc accgcgtgcg gcgattccgg   5580
gtccccagtg atcaccgagg ccggggagct tgtcggtgtc cacacgggat caaacaaaca   5640
aggaggaggc attgttacgc gcccttcagg ccggttttgt aatgtgacac ccaccaaatt   5700
aagtgaattg agtgaattct tcgctggacc tagggtcccg cttggtgacg tgaaggttgg   5760
caatcacata atcaaagata taaatgaggt gccctcagat ctctgcgcct tactcgctgc   5820
caaacccgaa ttggaaggag gcctctccac cgttcaactt ctgtgcgtgt tttttctcct   5880
atggagaatg atgggacatg cctggacacc cttggttgcc gttggttttt tcatcttgaa   5940
tgaagttctc ccagcagtcc tggtccggag tgtcttctcc tttggaatgt tcgcactgtc   6000
ttggttcacg ccgtggtctg cacaaattct aatgatcagg ctcttgacag cagccctaaa   6060
cagaaacaga tcgtcacttg ccttttacag cctgggcgca ctaaccggtt ttgttgcaga   6120
tcttgcaacc aatcaggggt atttattgca cgcggtcatg aatgtgagca cctatgcatt   6180
cctgcctcgt gcaatggccg tgacctcacc agtcccaata gttgcgtgtg gcgttgtgca   6240
cttgcttgcc atcattctgt acttgttcaa gtaccgtagc ctgcatgccg tcctggtcgg   6300
cgatggtgcg ttttccgcgg ctttcttctt gcgatacttt gcggagggaa agttgaggga   6360
```

-continued

```
aggggtgtcg cagtcttgcg gcatgaatca tgagtcacta accggtgccc tcgccatgaa   6420
actcagcgac gaagacttgg acttcctcac aaaattgact gattttaagt gctttgtttc   6480
tgcatccaac atgaggaatg cggcgggtca atttatagag gccgcctacg ccaaagcact   6540
gagggtggaa cttgcccagt tggttcaagt cgataaagtt cgaggtgtcc tggccaaact   6600
tgaagctttc gctgacaccg tggcgcctca actttcaccc ggtgacattg ttgtcgccct   6660
tggacacaca cctgtcggca gcatttttga cctgaaggtc ggcaatgtta agcacactct   6720
ccagtccatt gagaccagaa cccttgccgg gtctaaaatg actgtggcgc gcgtcgtaga   6780
cccaaccccc acacccccgc ccgcacctgt gcccatttcc ctcccaccaa aggttttgga   6840
gaacggtccc aacgcctggg gggatgagaa cggtttgaac aaaaaaaagc ggcgcaagat   6900
ggaggccgtt ggcatttacg ttatgggcgg gaaaaagtat caaaaatttt gggataagaa   6960
ttctggtgat gtgttctatg aagaagtcca cgacaacaca gacgcgtggg aatgcctcag   7020
agttgacaac cctgccgact tggatcctga gaggggaacc ttgtgtggac acaccaccat   7080
agacaacagg ccttaccatg tttatgcttc tccgtctggt aggaagtttc tagtccctgt   7140
caacccggag agcggaaaag ctcagtggga agctgctaag ctttctttag atcaggccct   7200
cagtatgatg aatgtcgacg gcgaactgac cgccaaagaa gtggaaaaat tgaagagaat   7260
aattgacaaa ctccagggcc tgactaagga gcagtgttta aactgctagc cgccagcggc   7320
ttgacccgct gtggtcgcgg cggcttggtt gttactgaga cagcggtaaa gatagtcagg   7380
ttccacaacc ggacctttac cctagggcct gtgaatttga aagtagctag cgaagttgag   7440
ttgaaggacg cggtcgagca cggccaacac ccggtcgcga taccagccga tggtggcgtc   7500
gtgctcctgc gttccgctgt tccttcgctt atagacgtcc tgatctccgg tgctgacgca   7560
tcccccaggt tgctcgcccg tcacggaccg ggaaatactg ggtcaatgg cgcgctttgg   7620
gattttgagt ctgaagctac caaagaggaa gtagcactta gtgcgcaaat aatacaggcc   7680
tgtgacatta gacgcggcga tgcacctgag attggccttc cttacaagtt gtaccctgtt   7740
aggggcaacc ctgaacgggc aagaggggtt ctaatgaaca caagatttgg agacatacct   7800
tacaagaccc ccagcgacac cgggagcccg gtgcacgcgg ccgcctgcct tacgcccaac   7860
gccactccag taactgatgg gcgctccatc ctggccacga ccatgccctc cgggtttgaa   7920
ctatatgtgc cgaccattcc agcgtctgtc cttgattacc ttgactccag accagactgt   7980
cctaaacagt tgactgagca cgggtgtgaa gatgccgcgt tgaaggacct ttctaaatat   8040
gacctgtcca cccaaggctt tgtgttacct ggagttctac gcctcgtgcg aaaatatctg   8100
tttgctcatg taggtaagtg cccgcctgtc caccggccct ctacctatcc tgccaagaac   8160
tccatggccg gaataaatgg gaacaggttc ccaaccaagg atattcaaag catccctgag   8220
atcgacgttt tgtgtgcaca agctgtgcga gaaaactggc aaactgttac accctgcact   8280
cttaagaagc agtattgcgg taaaaagaag accaggacca tacttggcac caacaacttc   8340
gttgcgctgg cccaccgggc ggcgctgagt ggtgtcaccc agggtttcat gaagaaggcg   8400
tttaactcac ccatcgccct tgggaaaaat aaatttaagg agctacagac tccagtcttg   8460
ggtaggtgtc ttgaggctga tctcgcttcc tgcgatcgat ccacgcctgc aatcgttcgc   8520
tggtttgccg ccaaccttct ttatgaactt gcctgtgctg aggagcattt accgtcgtac   8580
gtgctgaact gttgtcacga cctattggtc acgcagtccg gcgcagtgac taagagaggt   8640
ggcctgtcgt ccggtgaccc aatcacctct gtgtccaaca ccatttatag cttggtgatc   8700
tatgcacagc atatggtgct tagttacttc aaaagtggtc acccccatgg ccttctgttt   8760
ttacaagacc agctaaagtt tgaagacatg ctcaaagttc aacccctaat cgtctattcg   8820
```

-continued

```
gacgacctcg tgttgtatgc cgagtctccc accatgccaa actatcactg gtgggttgaa    8880
cacctgaatt tgatgttggg atttcagacg gacccaaaga agactgcaat aacagactca    8940
ccttcattcc taggttgtag aataataaat ggccgccagt tagtacccaa ccgtgacaga    9000
attctcgcgg cccttgccta tcacatgaag gcgagtaatg tttctgagta ctacgcctcc    9060
gcagccgcaa tactcatgga cagttgtgct tgtctagagt atgatcctga gtggtttgaa    9120
gaacttgtgg ttggaatggc gcagtgcgcc cgtaaggacg gctatagttt ccccggcccg    9180
ccgttcttct tgtccatgtg ggaaaagctc aggtcaaatt atgaggggaa gaagttgaga    9240
gtgtgtggtt attgcggagc ttcagccccg tatgctactg cctgtggcct tgacgtttgt    9300
gtttaccaca cccactttca ccagcattgt ccagtcataa tatggtgtgg ccacccggcg    9360
ggttctgggt cctgcgatga gtgcaaatcc cctacaggga agggtacaag ccctctggat    9420
gaggtcttaa gacaagtccc ttataagcct ccacggacta ttcttatgca tgtggagcag    9480
ggcctcaccc cccttgaccc aggcagatac cagacccgcc gtgggttggt tgctgtcagg    9540
cgcgggataa ggggaaatga agttgacctg ccagatggtg attatgccag tactgcccta    9600
ctccccacct gcaaagacat agacatggtt gctgtggcct ccaatgtgtt gcgcagtagg    9660
ttcatcatcg gcccacctgg cgcagggaaa acacactggc ttcttcaaca ggttcaggat    9720
agtgatgtca tttacacgcc aacccatcag accatgcttg acatgatcaa ggctttgggg    9780
acgtgccggt tcaatgtccc ggcaggcaca acgctgcaat tccctgcccc ctcccgtacc    9840
ggcccgtggg ttcgcatcct tgccggcggt tggtgtccag gtaagaattc cttcctggat    9900
gaagcagcgt attgcaatca ccttgacgtc ttgaggcttc tcagcaaaac taccctcacc    9960
tgtctggggg atttcaaaca actccacccg gtgggttttg attctcattg ctatgttttt   10020
gatatcatgc ctcagactca actgaagacc atctggaggt ttggacagaa tatctgtgac   10080
gccattcagc cagattacag ggacaaactc gtgtccatgg tcaacacaac ccgtgtaacc   10140
tatgtggaaa gacctgtcaa gtatgggcaa gtcctcaccc cctaccacag agaccgagag   10200
gatggtgcta tcactattga ctccagtcaa ggcgccacat ttgatgtggt cacattgcat   10260
ttgcccacta aagattcact caacaggcaa agagcccttg ttgctatcac cagggcaagg   10320
catgcaatct ttgtgtatga cccacacagg caactgcaga gcatgtttcg tcttcctgca   10380
aaaggcacac ctgtcaacct tgccgtgcac cgtgacgagc agctcatcgt attagataga   10440
aataacaaag agtgcacggt tgttcaggct ttaggcaatg gggacaaatt cagggccagt   10500
gacaagcgcg ttgtagattc tcttcgcgcc atttgtgcag atcttgaagg gtcgagctcc   10560
ccgctcccca aggtcgcaca caacttggga ttttatttct cacctgattt gacacagttt   10620
gctaaactcc cggcggaact tgcacccccac tggcccgtgg tgacaactca gaacaacgaa   10680
aattggccag accggctggt tgctagcctc cgccctatcc acaaatatag ccgcgcgtgc   10740
atcggagccg gctatatggt gggcccctca gtgtttctag gcactcctgg ggttgtgtca   10800
tactatctca cacaatttgt caaaggggag gctcaggtgc ttccggagac ggtcttcagc   10860
accggccgaa ttgaggtaga ttgtcgagag tatcttgatg atcgggaacg agaagttgct   10920
gagtccctcc cacatgcctt tattggcgac gtcaaaggca ctaccgttgg gggatgtcac   10980
catgtcactt ctaaatatct cccacgcttc cttcccaagg aatcagttgc ggtggttggg   11040
gtttcaagcc ccgggaaagc cgcaaaagca gtttgcacat taacagatgt gtacctccca   11100
gatcttgagg cttacctcca tccagagacc cagtctaagt gctggaaagt gatgttggac   11160
ttcaaggaag ttcgactgat ggtctggaga gataagacgg cctactttca acttgaaggc   11220
```

-continued

```
cgccatttca cctggtacca gcttgcaagt tatgcctcgt acatccgagt tcccgttaac  11280
tctacggtgt acctggaccc ctgtatgggc cctgcccttt gcaacagaag agtcgttggg  11340
tctgcacatt ggggagctga ccttgcagtt accccttatg attatggtgc caaaatcatt  11400
ctgtctagtg cgcaccatgg tgaaatgcct cctgggtaca gaattctagc gtgcgcggag  11460
ttctcgcttg atgacccagt gaggtacaaa cacacttggg ggtttgaatc ggatacagcg  11520
tatctgtacg agttcaccgg aaacggtgag gactgggagg attacaatga tgcgtttcgt  11580
gcacgccaga aagggaaaat ttataaggcc actgccacca gcatgagatt tcattttccc  11640
ccgggtcctg ccattgaacc aacattgggc ctgaactgaa atgaaatggg ggctgtgcag  11700
agccttttcg acaaaatttg ccaacttttt gtggatgctt tcacggaatt tttggtgtcc  11760
attgttgata tcatcatatt tttggccatt ttgtttggct tcaccatcgc aggctggctg  11820
gttgtcttct gtatccgact ggtttgctcc acggtactcc gtgcgcgctc taccattcac  11880
cctgagcaat tacagaagat cctatgaggc cttcctttcc cagtgccaag tggacattcc  11940
cgcctgggga actaagcatc ccttgggggt gctttggcac cacaaggtgt caactctgat  12000
tgatgaaatg gtgtcgcgtc gaatgtaccg catcatggaa aaagcaggac aggctgcctg  12060
gaaacaggtt gtgagcgaag ctacattgtc tcgcataagt ggcttggatg tggtggctca  12120
ttttcagcat cttgctgcca ttgaagccga gacttgcaaa tatttggcct ctcggctgcc  12180
catgctacac aacctagtca tgtcagggtc gaatgtaacc atagtgtata atagcacttt  12240
gggtcaagtg tttgccattt tcccaacccc tggttcccgg ccaaaacttt ctgattttca  12300
acaatggctc atagctgtgc attcttccat attttcttct gttgcggctt cttgtactct  12360
ttttgttgtg ctgtggctgc gaattccaat actacgtact gtttttggtt tccgctggtt  12420
aggggcaact ttttctttcga actcacagtg aattacacgg tgtgcccacc ctgcctcacc  12480
cggcaagcag ccgctgagat ctacgaacac agcgggtctc tttggtgcag gatagggcat  12540
gaccgatgta gccagagtga tcatgacgaa ctagggttct tggttccacc tggcctttcc  12600
agcgagggcc acttgaccag tgtttacgcc tggctggcgt tcttgtcttt cagctacaca  12660
gcccagttcc accccgagat atttggaata gggaatgtga gtagagttta tgttgacgtc  12720
actcaccaac tcatctgcgc cgaacacgac gggcagaaca ccaccctgcg tcgccatgac  12780
aatatctcag ccgtgtttca gacctattac caacatcagg tcgatggcgg caattggttt  12840
cacctagaat ggctgcgtcc cttcttttcc tcttggctgg ttttgaatgt ctcgtggttt  12900
ctcaggcgtt cgcctgcaaa ccgtgtttca gttcgagtct ttcagacatc aaaaccaaca  12960
ccaccgcagc tgcaggcttt gctgtcctcc aagacatcag ctgtcttagg catggctact  13020
cgtccattga ggcgattcgc aaaagccgtc aatgccgcac ggcgatagga acgcccgtgt  13080
acatcactgt cacggccaat gtaacagatg agaattactt gcattcctct gatctcctca  13140
tgctttcctc ttgcctcttc tatgcttctg agatgagtga aaagggattc aatgtggtct  13200
tcggcaacgt gtcaggcatt gtggctgtgt gtgtcaactt taccagctat gtccaacatg  13260
ttaaggagtt tactcagcgc tctttggtgg tcgaccacgt gcgactgctt catttcatga  13320
cacctgcgac catgaggtgg gcaacagttt tagcctgtct tttcgccatc ttgttggcga  13380
tttgaatgtt taagtatgtt ggggaaatgc ttgaccgcgg gctactgctc gcaattgctt  13440
tttttctggt gtatcgtgcc gttctgtttt gctgcgctcg tcaacgccgc cagcaacagc  13500
agctcccatt tacagttgat ttataacctg acgatatgcg agctgaatgg cacagattgg  13560
ttgaatcaaa agtttgattg ggcagtggag acttttgtca tttttcctgt gttgacccac  13620
attgtctcct acggtgccct taccaccagc catttccttg acacggccgg cctaatcact  13680
```

-continued gtgtctaccg ccggatatta ccatgggcgg tatgtgttga gtagcatcta cgccgtcttt 13740
gccctggctg cgttgatttg ttttgtcatt aggttgacaa aaaactgtat gtcctggcgc 13800
tactcatgta ccagatatac caactttctt ctggacacca aaggcaatct ctatcgttgg 13860
cggtcacccg tcgttataga gagaaggggt aaagttgagg ttggagacca cctaatcgac 13920
ctcaaaagag ttgtgcttga tggttccgcg gcaaccccta taaccaagat ttcagcggaa 13980
caatggggtc gtccctagac gacttctgca atgacagcac agctgcacaa aaggtgcttt 14040
tggcgttttc catcacctat acgccaataa tgatatatgc cctgaaggta agtcgcggcc 14100
gactgttagg gcttttgcat cttttaattt tcttgaattg tgctttcacc ttcgggtaca 14160
tgacatttgt tcattttcag agtacaaaca aggtcgcgct cactatggga gcagttgttg 14220
cactcctttg gggggtgtac tcagccatag aaacctggaa attcatcact tccagatgcc 14280
gtttgtgctt gctaggccgc aggtacattc tggcccctgc ccaccacgtt gaaagtgccg 14340
cgggctttca tccgattgcg gcaagtgata accacgcatt tgtcgtccgg cgtcccggct 14400
ccactactgt taacggcaca ttggtgcccg ggttgaaaag cctcgtgttg ggtggcagaa 14460
aagctgttaa gcggggagtg gtaaacctcg ttaaatatgc caaataacaa cggcaggcag 14520
caaaaaaata agaaggggag tggccagcca gtcaatcagc tgtgccaaat gctgggcaag 14580
atcatcgccc agcaaaatca gtccagaggc aagggaccgg gtaagaaaaa taagaagaga 14640
aacccggaga agccccattt tcctcttgcg accgaagatg acgtcaggca tcacttcacc 14700
cccagtgaac ggcaattgtg tctgtcgtcg atccagactg ccttcaacca gggcgctgga 14760
acttgcaccc tgtcagattc agggaggata agttacactg tggagtttag tttgccgacg 14820
caccacactg tgcgccttat tcgcgccaca gcatcacctc catcgtgatg ggcttacatt 14880
cttggagctc ctcagtttca caattggaag aatgtgtggt gaatggcact gattggcact 14940
gtgcctctaa gtcacctatt caattagggc gaccgtgtgg gggtttagtt taattggcga 15000
gaaccacgcg gccgaaatta aaaaaaaaaa aaaaaaaaaa aaaaaaa 15047

<210> SEQ ID NO 13
<211> LENGTH: 15047
<212> TYPE: DNA
<213> Artificial Sequence
<400> 13
atgacgtata ggtgtttgct ttatgccgcg gcatttgtat tgtcaggagc tgtgaccact 60
ggcacagccc gaaacttgct gcacagaaac acccttctgt gacagcctcc ttcaggggag 120
tttaggggtt tctccctaac gccctgcttc cggagttgca ctgctttacg gtctctccat 180
ccttttaacc atgtctggga ttcttgatcg gtgcacgtgc acccccaatg ccagggtgtt 240
tgtggcagag ggccaagtct actgcacacg atgtctcagt gcacggtccc tccttcccct 300
aaatctccaa gtttctgagc ttggggtact tggtttattc tacaggcccg aagagccatt 360
acggtggacg ttgccacacg cattccccac tgtcgagtgt gctcctgctg gcgcttgttg 420
gctttctgca atttttccaa ttgcgcgaat gaccagtgga aacctgaatt tccagcaaag 480
gctggtacgt gtcgcagccg agctttacag agccggccag ctcaccccta caagcctgaa 540
aaccttacag gtctatgaaa ggggttgccg ttggtacccc attgttggac ctgttcctgg 600
agtggccgtt tacgccaact ccctacatgt gagtgacaaa cccttcccag gagcgactca 660
cgtgctgacc aacttaccac tcccgcagag accaaaatct gaagatttct gccccttcga 720
gtgcgccacg gccgccgtct atgacatcgg ccatgacgcc gtcatgtatg taaccgagga 780
aaaggtttcc tgggctcctc gtggcgggga taaagggaaa tttgagactg ttcctgaggg 840

-continued

```
gttgaagttg actgcggaac gactctacac ctccttcccg cctcaccatg cggtggacat    900
gtccctttc atcttcacag accttgagtg cggcgcttcc atgcgggtcg aacgccaata     960
tggttgcctc tctgctggca ctgtccctga aggcaactgc tggtggagtc tgtttggctc   1020
gctttcgtta gaagctcagt ataaagaaat ccgctacgcc gcccaatttg gctatcagac   1080
caaacatggc gttactggca agtacctgca gcggaggctg caaattaatg gtctccgagc   1140
agtggttgac ccgaatgggc ctcttgtcgt acagtatttc tccgttaagg agagctggat   1200
gcgccacgtg agactggcgg aagagccagg ctatcctggg tttgaggatc tcctcaggat   1260
aagagtcgag cccaacacgt tgcctttgtc caacaaggac gagaaaatct tccgtttcgg   1320
cggttacaag tggtacggtg ctgggcggag ggcaaggaga acacgtgcaa gagcagtcac   1380
cgcagttgct agtcatgctc cgcccgctcg tggggcccag caggccgaga agcacgaagt   1440
tgctagtgcc aacaagactg agctccttac gcactactcc ccacctgctg aagggaattg   1500
cggctggcac tgcatctccg ccatcatgaa ccggatggtg cattccaagt ttgaaaccgc   1560
cctttccgaa agagtgagat ccccggaaga ctgggcgact gatgaggatc ttgtgaatac   1620
tattcaaatc ctcaggctcc ctgcggcctt agacaggaac ggcgcctgta aaaacgccaa   1680
gtacatcctt aagctggaag gtgagcactg gactgtttca gtgacccccg gaatgccccc   1740
ctcttcactt cctcttgaat gcgttcaggg ttgttgcgag cataagggca attttgactc   1800
tcaaaacgcg gtcggtttct ttgggttcga ccctgccagc cttgaccgac tcgctggggt   1860
aatgcatctg cccagcagcg ccatccctgc cgccctggcc gagttgtctg gtgaacttga   1920
ttgttcaact cccccggcca ccactgtgtg gactaccttg cagttttatg ctcgtcttgg   1980
tggggggag catcctgatc aagagtgctt gagaaaaatc atcagcctct gtgaggtgct    2040
cgggagttgc tgctgttctc agagtagggt caaccgggtc accccggaag aggtcgcagc   2100
aaagattgac ctgtatcttc gtgacgcagc gagtcttgaa gagtgcttgg ctaggcttga   2160
gaaagctcgc ccgccaagca tgctggacac ctcctttgac tgggatgttg tactccctgg   2220
tgttgggacg gctgctcggg cagcagaact accccccacc gatgagtgtc gcgctctagt   2280
cactgctgtg gcccaaaggc cttcgccgaa agttcagcct cgaaaggcgg ggtctgttaa   2340
gagtctacca gagatcaggc ctgtccctgc cccacgcagg aaggttaagt ctagttgtgg   2400
tgatctggcc ccgttgggcg gcaatttccc tgatagctgg gaagatttgg ctggtggctc   2460
ccttaatctc cagatcttac ctgagccggt ggcacaatcc tttgaacctg tgcctgtccc   2520
tgcaccgcgc aagactgcgc ctcgattagt gtcgtcatca ttggcgtcga cccccgtacc   2580
tacaccacga tgtgggtttc ggcagtttga gggaatgaat ttgacagctg tgaccctagc   2640
atgccaggat gagtccctca atttgtctgc atcctcgcag actgaatatg aggcttctcc   2700
tttggcattg cagcagggtg aggatgtcct tgcggtgggg ggacgagaag ccgaagaagt   2760
cctgagcgga atctcgggaa tgtcaggtgg cattagatta gcgcccgcat catcaagtag   2820
ctccttgtca agcgtggaga tcacacgccc gaagtactca gctcaagcca tcattgactc   2880
aggtggaccc tgttgcgggc accttcaaga ggtgaaagag aaataccctta atgtcatgcg   2940
tgaggcatgt gatgcgacta agctcgatga ccctgccacg caagaatggc tctctcgcat   3000
gtgggagagg gtagacatgc taacctggcg caacacgtcc atctttcaag cgccttttac   3060
cttagctgac aagtttaagt ccctcccgaa gatgatactc gaaacgccgc caccctaccc   3120
ttgcgggttt gtgatgatgc cccgcacgcc cgcaccttct gtgggtgcgg aaagcgacat   3180
caccgttggt tcagttgcta ctgaagatgt cccgcgtata ctcggggagg tgggagatgt   3240
tggcaagatg accggccagg aacccttaga atccttcgca gatgaactgg cagatgacca   3300
```

-continued

```
acctgctagg gagtcccgaa cacaagctcc tcctgcaagc acaggtagcg ctggtttagt   3360
tttggattct ggagggtcgc tggggctcac tgacctgccg ctcccaaaca atatagacgc   3420
gggcgggaaa ggaccgtttc acgcggtcaa gaaaaaagct gtagggtgct ttgaccaact   3480
gagccgccgg gtttttgaca tcgtctccca tctccctgtt tttttttcac gccttttcgc   3540
gcccggtggt ttttactctt cgggtgactg gagttttgca gcttttactt tattgtgtct   3600
ctttttatgt tacagttatc cggcctttgg ttttgctccc ctcgtgggtg tattttctgg   3660
gtcttctcgg cgcgtgcgca tggggggtttt tggctgctgg ctggcttttg ctgttggttt   3720
gttcaagcct gcacccgacc cagtcggtgc tgcttgtgag tttgactcgc cagagtgtag   3780
agacatcctt cattcttttg agctcctgca accttgggac cctgttcgca gccttgtggt   3840
gggccccgtc ggtctcggcc ttgccatttt tggcaggtta ctgggcgggg cacgctacgt   3900
ctggctgctt ttgcttaggc ttggcatcgt ttcagactgt atcctggctg gagcctatgt   3960
gctttcgcaa ggcaggtgta aaaagtgttg gggatcttgt ataagaacag cccccagtga   4020
agttgccttc aatgtgtttc cctttacacg cgcaactaga tcgtcacttg tcaacctgtg   4080
cgaccggttc tgtgcaccca agggcatgga ccccatcttc cttgccacag gatggcgcgg   4140
atgctggtcc ggccagagcc ccattgagca accctctgaa aaacccatag cgttcgccca   4200
gttggacgaa aagaaaatca cggctaggac tgtggttgcc cagccttatg accccaacca   4260
agctgtgaag tgcctgcgag tcctccaggc gggtggagcg atggtagccg aggcagttcc   4320
aaaagtagtc aaagtttctg ctgtcccgtt tcgagcccct ttttttcctg ccggagtgaa   4380
agttgaccct gaatgcaggg tcgtggttga ccctgacacc tttacaaccg ctctccggac   4440
cggctactcc accacaaacc tcattcttgg tgttggggac tttgcccagc tgaatgggtt   4500
gaagatcaga caaatttcca agtccccagg agggggccct cacctcatgg cggctttaca   4560
tgttgcttgc tcgatgactt tgcacatgct tgttgggatt tatgtcacca tggtgggttc   4620
ttgtggctct ggcactaacg atccgtggtg cactaacccg tttgccgtcc ctgtctatgg   4680
gcctggctct ctctgcacgt ccaggttgtg catttcccag cgtggcctga ccctgccctt   4740
aacagcgctt gtggcagggt ttggcgttca ggaaatcgct ttggttgttt taatctttgt   4800
ctccatcggg ggtatggccc acaggttgag ttgcaaggct gacgtgctgt gtatcctgct   4860
tgctattgtc agctatgttt ggccacccct tacctggttg ctttgtgtgt ttccttgctg   4920
gttgcgctgg ttttctttac atccccttac tattctatgg ttagtgtttt tcttgatttc   4980
tgtaaatacg ccctcgggaa tcttggcctt ggtcctgtta atctctcttt ggctccttgg   5040
tcgctatacc aatgttgccg gccttgtcac cccttatgac attcaccatt acaccaacgg   5100
ccctcgcggc gttgccgcct tggccactgc cccggatggg acctacctgg ctgctgtccg   5160
ccgtgctgcg ttgactggcc gtaccatgct gttcaccccg tcccaacttg gctcgctcct   5220
tgagggcgct tttagaaccc aaaagccttc actgaacact gtcaatgtag ttgggtcctc   5280
catgggctcc ggcggggtgt tcaccattga tgggaagatc aaatgtgtga ccgctgctca   5340
tgtcctcacg ggtaactctg ccagggtttc cggggttggc ttcaatcaaa tgttggactt   5400
tgatgttaaa ggggatttg ccatagccga ttgtccgaat tggcaaggag tcgcccccaa   5460
gtcccggttc tgcaaggatg attggactgg ccgtgcttat tggctcacgt cctccggcgt   5520
cgaacccggc gtcattgggc aaggattcgc cttttgtttc accgcgtgcg gcgattccgg   5580
gtccccagtg atcaccgagg ccggggagct tgtcggtgtc cacacgggat caaacaaaca   5640
aggaggaggc attgttacgc gcccttcagg ccggttttgt aatgtgacac ccaccaaatt   5700
```

-continued

```
aagtgaattg agtgaattct tcgctggacc tagggtcccg cttggtgacg tgaaggttgg   5760
caatcacata atcaaagata taaatgaggt gccctcagat ctctgcgcct tactcgctgc   5820
caaacccgaa ttggaaggag gcctctccac cgttcaactt ctgtgcgtgt tttttctcct   5880
atggagaatg atgggacatg cctggacacc cttggttgcc gttggttttt tcatcttgaa   5940
tgaagttctc ccagcagtcc tggtccggag tgtcttctcc tttggaatgt tcgcactgtc   6000
ttggttcacg ccgtggtctg cacaaattct aatgatcagg ctcttgacag cagccctaaa   6060
cagaaacaga tcgtcacttg ccttttacag cctgggcgca ctaaccggtt ttgttgcaga   6120
tcttgcaacc aatcaggggt atttattgca cgcggtcatg aatgtgagca cctatgcatt   6180
cctgcctcgt gcaatggccg tgacctcacc agtcccaata gttgcgtgtg gcgttgtgca   6240
cttgcttgcc atcattctgt acttgttcaa gtaccgtagc ctgcatgccg tcctggtcgg   6300
cgatggtgcg ttttccgcgg ctttcttctt gcgatacttt gcggagggaa agttgaggga   6360
aggggtgtcg cagtcttgcg gcatgaatca tgagtcacta accggtgccc tcgccatgaa   6420
actcagcgac gaagacttgg acttcctcac aaaattgact gattttaagt gctttgtttc   6480
tgcatccaac atgaggaatg cggcgggtca atttatagag gccgcctacg ccaaagcact   6540
gagggtggaa cttgcccagt tggttcaagt cgataaagtt cgaggtgtcc tggccaaact   6600
tgaagctttc gctgacaccg tggcgcctca actttcaccc ggtgacattg ttgtcgccct   6660
tggacacaca cctgtcggca gcatttttga cctgaaggtc ggcaatgtta agcacactct   6720
ccagtccatt gagaccagaa cccttgccgg gtctaaaatg actgtggcgc gcgtcgtaga   6780
cccaaccccc acacccccgc ccgcacctgt gcccatttcc ctcccaccaa aggttttgga   6840
gaacggtccc aacgcctggg gggatgagaa cggtttgaac aaaaaaaagc ggcgcaagat   6900
ggaggccgtt ggcatttacg ttatgggcgg gaaaaagtat caaaaatttt gggataagaa   6960
ttctggtgat gtgttctatg aagaagtcca cgacaacaca gacgcgtggg aatgcctcag   7020
agttgacaac cctgccgact tggatcctga gaggggaacc ttgtgtggac acaccaccat   7080
agacaacagg ccttaccatg tttatgcttc tccgtctggt aggaagtttc tagtccctgt   7140
caacccggag agcggaaaag ctcagtggga agctgctaag ctttctttag atcaggccct   7200
cagtatgatg aatgtcgacg gcgaactgac cgccaaagaa gtggaaaaat tgaagagaat   7260
aattgacaaa ctccagggcc tgactaagga gcagtgttta aactgctagc cgccagcggc   7320
ttgacccgct gtggtcgcgg cggcttggtt gttactgaga cagcggtaaa gatagtcagg   7380
ttccacaacc ggacctttac cctagggcct gtgaatttga aagtagctag cgaagttgag   7440
ttgaaggacg cggtcgagca cggccaacac ccggtcgcga taccagccga tggtggcgtc   7500
gtgctcctgc gttccgctgt tccttcgctt atagacgtcc tgatctccgg tgctgacgca   7560
tcccccaggt tgctcgcccg tcacggaccg ggaaatactg gggtcaatgg cgcgctttgg   7620
gattttgagt ctgaagctac caaagaggaa gtagcactta gtgcgcaaat aatacaggcc   7680
tgtgacatta gacgcggcga tgcacctgag attggccttc cttacaagtt gtaccctgtt   7740
aggggcaacc ctgaacgggc aagaggggtt ctaatgaaca caagatttgg agacatacct   7800
tacaagaccc ccagcgacac cgggagcccg gtgcacgcgg ccgcctgcct tacgcccaac   7860
gccactccag taactgatgg gcgctccatc ctggccacga ccatgccctc cgggtttgaa   7920
ctatatgtgc cgaccattcc agcgtctgtc cttgattacc ttgactccag accagactgt   7980
cctaaacagt tgactgagca cgggtgtgaa gatgccgcgt tgaaggacct ttctaaatat   8040
gacctgtcca cccaaggctt tgtgttacct ggagttctac gcctcgtgcg aaaatatctg   8100
tttgctcatg taggtaagtg cccgcctgtc caccggccct ctacctatcc tgccaagaac   8160
```

-continued

```
tccatggccg gaataaatgg gaacaggttc ccaaccaagg atattcaaag catccctgag   8220
atcgacgttt tgtgtgcaca agctgtgcga gaaaactggc aaactgttac accctgcact   8280
cttaagaagc agtattgcgg taaaaagaag accaggacca tacttggcac caacaacttc   8340
gttgcgctgg cccaccgggc ggcgctgagt ggtgtcaccc agggtttcat gaagaaggcg   8400
tttaactcac ccatcgccct tgggaaaaat aaatttaagg agctacagac tccagtcttg   8460
ggtaggtgtc ttgaggctga tctcgcttcc tgcgatcgat ccacgcctgc aatcgttcgc   8520
tggtttgccg ccaaccttct ttatgaactt gcctgtgctg aggagcattt accgtcgtac   8580
gtgctgaact gttgtcacga cctattggtc acgcagtccg gcgcagtgac taagagaggt   8640
ggcctgtcgt ccggtgaccc aatcacctct gtgtccaaca ccatttatag cttggtgatc   8700
tatgcacagc atatggtgct tagttacttc aaaagtggtc acccccatgg ccttctgttt   8760
ttacaagacc agctaaagtt tgaagacatg ctcaaagttc aacccctaat cgtctattcg   8820
gacgacctcg tgttgtatgc cgagtctccc accatgccaa actatcactg gtgggttgaa   8880
cacctgaatt tgatgttggg atttcagacg gacccaaaga agactgcaat aacagactca   8940
ccttcattcc taggttgtag aataataaat ggccgccagt tagtacccaa ccgtgacaga   9000
attctcgcgg cccttgccta tcacatgaag gcgagtaatg tttctgagta ctacgcctcc   9060
gcagccgcaa tactcatgga cagttgtgct tgtctagagt atgatcctga gtggtttgaa   9120
gaacttgtgg ttggaatggc gcagtgcgcc cgtaaggacg gctatagttt ccccggcccg   9180
ccgttcttct tgtccatgtg ggaaaagctc aggtcaaatt atgaggggaa gaagttgaga   9240
gtgtgtggtt attgcggagc ttcagccccg tatgctactg cctgtggcct tgacgtttgt   9300
gtttaccaca cccactttca ccagcattgt ccagtcataa tatggtgtgg ccacccggcg   9360
ggttctgggt cctgcgatga gtgcaaatcc cctacaggga agggtacaag ccctctggat   9420
gaggtcttaa gacaagtccc ttataagcct ccacggacta ttcttatgca tgtggagcag   9480
ggcctcaccc cccttgaccc aggcagatac cagacccgcc gtgggttggt tgctgtcagg   9540
cgcgggataa ggggaaatga agttgacctg ccagatggtg attatgccag tactgcccta   9600
ctccccacct gcaaagacat agacatggtt gctgtggcct ccaatgtgtt gcgcagtagg   9660
ttcatcatcg gcccacctgg cgcagggaaa acacactggc ttcttcaaca ggttcaggat   9720
agtgatgtca tttacacgcc aacccatcag accatgcttg acatgatcaa ggctttgggg   9780
acgtgccggt tcaatgtccc ggcaggcaca acgctgcaat tccctgcccc ctcccgtacc   9840
ggcccgtggg ttcgcatcct tgccggcggt tggtgtccag gtaagaattc cttcctggat   9900
gaagcagcgt attgcaatca ccttgacgtc ttgaggcttc tcagcaaaac taccctcacc   9960
tgtctggggg atttcaaaca actccacccg gtgggttttg attctcattg ctatgttttt  10020
gatatcatgc ctcagactca actgaagacc atctggaggt ttggacagaa tatctgtgac  10080
gccattcagc cagattacag ggacaaactc gtgtccatgg tcaacacaac ccgtgtaacc  10140
tatgtggaaa gacctgtcaa gtatgggcaa gtcctcaccc cctaccacag agaccgagag  10200
gatggtgcta tcactattga ctccagtcaa ggcgccacat ttgatgtggt cacattgcat  10260
ttgcccacta aagattcact caacaggcaa agagcccttg ttgctatcac cagggcaagg  10320
catgcaatct ttgtgtatga cccacacagg caactgcaga gcatgtttcg tcttcctgca  10380
aaaggcacac ctgtcaacct tgccgtgcac cgtgacgagc agctcatcgt attagataga  10440
aataacaaag agtgcacggt tgttcaggct ttaggcaatg gggacaaatt cagggccagt  10500
gacaagcgcg ttgtagattc tcttcgcgcc atttgtgcag atcttgaagg gtcgagctcc  10560
```

-continued

```
ccgctcccca aggtcgcaca caacttggga ttttatttct cacctgattt gacacagttt   10620
gctaaactcc cggcggaact tgcaccccac tggcccgtgg tgacaactca gaacaacgaa   10680
aattggccag accggctggt tgctagcctc cgccctatcc acaaatatag ccgcgcgtgc   10740
atcggagccg gctatatggt gggcccctca gtgtttctag gcactcctgg ggttgtgtca   10800
tactatctca cacaatttgt caaaggggag gctcaggtgc ttccggagac ggtcttcagc   10860
accggccgaa ttgaggtaga ttgtcgagag tatcttgatg atcgggaacg agaagttgct   10920
gagtccctcc cacatgcctt tattggcgac gtcaaaggca ctaccgttgg gggatgtcac   10980
catgtcactt ctaaatatct cccacgcttc cttcccaagg aatcagttgc ggtggttggg   11040
gtttcaagcc ccgggaaagc cgcaaaagca gtttgcacat taacagatgt gtacctccca   11100
gatcttgagg cttacctcca tccagagacc cagtctaagt gctggaaagt gatgttggac   11160
ttcaaggaag ttcgactgat ggtctggaga gataagacgg cctactttca acttgaaggc   11220
cgccatttca cctggtacca gcttgcaagt tatgcctcgt acatccgagt tcccgttaac   11280
tctacggtgt acctggaccc ctgtatgggc cctgcccttt gcaacagaag agtcgttggg   11340
tctgcacatt ggggagctga ccttgcagtt accccttatg attatggtgc caaaatcatt   11400
ctgtctagtg cgcaccatgg tgaaatgcct cctgggtaca gaattctagc gtgcgcggag   11460
ttctcgcttg atgacccagt gaggtacaaa cacacttggg ggtttgaatc ggatacagcg   11520
tatctgtacg agttcaccgg aaacggtgag gactgggagg attacaatga tgcgtttcgt   11580
gcacgccaga aagggaaaat ttataaggcc actgccacca gcatgagatt tcattttccc   11640
ccgggtcctg ccattgaacc aacattgggc ctgaactgaa atgaaatggg ggctgtgcag   11700
agccttttcg acaaaatttg ccaacttttt gtggatgctt tcacggaatt tttggtgtcc   11760
attgttgata tcatcatatt tttggccatt ttgtttggct tcaccatcgc aggctggctg   11820
gttgtcttct gtatccgact ggtttgctcc acggtactcc gtgcgcgctc taccattcac   11880
cctgagcaat tacagaagat cctatgaggc cttcctttcc cagtgccaag tggacattcc   11940
cgcctgggga actaagcatc ccttggggt gctttggcac cacaaggtgt caactctgat   12000
tgatgaaatg gtgtcgcgtc gaatgtaccg catcatggaa aaagcaggac aggctgcctg   12060
gaaacaggtt gtgagcgaag ctacattgtc tcgcataagt ggcttggatg tggtggctca   12120
ttttcagcat cttgctgcca ttgaagccga gacttgcaaa tatttggcct ctcggctgcc   12180
catgctacac aacctagtca tgtcagggtc gaatgtaacc atagtgtata atagcacttt   12240
gggtcaagtg tttgccattt tcccaacccc tggttcccgg ccaaaacttt ctgattttca   12300
acaatggctc atagctgtgc attcttccat attttcttct gttgcggctt cttgtactct   12360
ttttgttgtg ctgtggctgc gaattccaat actacgtact gtttttggtt tccgctggtt   12420
aggggcaact tttctttcga actcacagtg aattacacgg tgtgcccacc ctgcctcacc   12480
cggcaagcag ccgctgagat ctacgaacac agcgggtctc tttggtgcag gatagggcat   12540
gaccgatgta gccagagtga tcatgacgaa ctagggttct tggttccacc tggcctttcc   12600
agcgagggcc acttgaccag tgtttacgcc tggctggcgt tcttgtcttt cagctacaca   12660
gcccagttcc accccgagat atttggaata gggaatgtga gtagagttta tgttgacgtc   12720
actcaccaac tcatctgcgc cgaacacgac gggcagaaca ccaccctgcg tcgccatgac   12780
aatatctcag ccgtgtttca gacctattac caacatcagg tcgatggcgg caattggttt   12840
cacctagaat ggctgcgtcc cttcttttcc tcttggctgg ttttgaatgt ctcgtggttt   12900
ctcaggcgtt cgcctgcaaa ccgtgtttca gttcgagtct ttcagacatc aaaaccaaca   12960
ccaccgcagc tgcaggcttt gctgtcctcc aagacatcag ctgtcttagg catggctact   13020
```

-continued

```
cgtccattga ggcgattcgc aaaagccgtc aatgccgcac ggcgatagga acgcccgtgt   13080
acatcactgt cacggccaat gtaacagatg agaattactt gcattcctct gatctcctca   13140
tgctttcctc ttgcctcttc tatgcttctg agatgagtga aaagggattc aatgtggtct   13200
tcggcaacgt gtcaggcatt gtggctgtgt gtgtcaactt taccagctat gtccaacatg   13260
ttaaggagtt tactcagcgc tctttggtgg tcgaccacgt gcgactgctt catttcatga   13320
cacctgcgac catgaggtgg gcaacagttt tagcctgtct tttcgccatc ttgttggcga   13380
tttgaatgtt taagtatgtt ggggaaatgc ttgaccgcgg gctactgctc gcaattgctt   13440
tttttctggt gtatcgtgcc gttctgtttt gctgcgctcg tcaacgccgc cagcaacagc   13500
agctcccatt tacagttgat ttataacctg acgatatgcg agctgaatgg cacagattgg   13560
ttgaatcaaa agtttgattg ggcagtggag acttttgtca tttttcctgt gttgacccac   13620
attgtctcct acggtgccct taccaccagc catttccttg acacggccgg cctaatcact   13680
gtgtctaccg ccggatatta ccatgggcgg tatgtgttga gtagcatcta cgccgtcttt   13740
gccctggctg cgttgatttg ttttgtcatt aggttgacaa aaaactgtat gtcctggcgc   13800
tactcatgta ccagatatac caactttctt ctggacacca aggcaatctc ctatcgttgg   13860
cggtcacccg tcgttataga gagaaggggt aaagttgagg ttggagacca cctaatcgac   13920
ctcaaaagag ttgtgcttga tggttccgcg gcaaccccta taaccaagat ttcagcggaa   13980
caatggggtc gtccctagac gacttctgca atgacagcac agctgcacaa aaggtgcttt   14040
tggcgttttc catcacctat acgccaataa tgatatatgc cctgaaggta agtcgcggcc   14100
gactgttagg gcttttgcat cttttaattt tcttgaattg tgctttcacc ttcgggtaca   14160
tgacatttgt tcattttcag agtacaaaca aggtcgcgct cactatggga gcagttgttg   14220
cactcctttg gggggtgtac tcagccatag aaacctggaa attcatcact tccagatgcc   14280
gtttgtgctt gctaggccgc aggtacattc tggcccctgc ccaccacgtt gaaagtgccg   14340
cgggctttca tccgattgcg gcaagtgata accacgcatt tgtcgtccgg cgtcccggct   14400
ccactactgt taacggcaca ttggtgcccg ggttgaaaag cctcgtgttg ggtggcagaa   14460
aagctgttaa gcggggagtg gtaaacctcg ttaaatatgc caaataacaa cggcaggcag   14520
caaaaaaata agaaggggag tggccagcca gtcaatcagc tgtgccaaat gctgggcaag   14580
atcatcgccc agcaaaatca gtccagaggc aagggaccgg gtaagaaaaa taagaagaga   14640
aacccggaga agccccattt tcctcttgcg accgaagatg acgtcaggca tcacttcacc   14700
cccagtgaac ggcaattgtg tctgtcgtcg atccagactg ccttcaacca gggcgctgga   14760
acttgcaccc tgtcagattc agggaggata agttacactg tggagtttag tttgccgacg   14820
caccacactg tgcgccttat tcgcgccaca gcatcacctc catcgtgatg ggcttacatt   14880
cttggagctc ctcagtttca caattggaag aatgtgtggt gaatggcact gattggcact   14940
gtgcctctaa gtcacctatt caattagggc gaccgtgtgg gggtttagtt taattggcga   15000
gaaccacgcg gccgaaatta aaaaaaaaaa aaaaaaaaaa aaaaaaa                 15047
```

SEQUENCE LISTING

<160> NUMBER OF SEQ ID NOS: 13

<210> SEQ ID NO 1
<211> LENGTH: 15386
<212> TYPE: DNA
<213> ORGANISM: Artificial Sequence
<220> FEATURE:
<223> OTHER INFORMATION: Synthetic Construct

<400> SEQUENCE: 1
atgacgtata ggtgttggct ctatgccatg acatttgtat agtcaggagc tgcgaccatt 60
ggtacagccc aaaacttgct gcacggaaac gcccttccgt gacagccctc ttcaggggag 120
tttaggggtc tatccctagc accttgcttc cggagttgca ctgctttacg gtctctccaa 180
ccctttaacc atgtctggga tacttgatcg gtgcacgtgt acccccaatg ccagggtgtt 240
catggcggag ggccaagtct actgcacacg atgtctcagt gcacggtctc tccttcctct 300
gaatctccaa gttcccgagc ttggagtgct gggcctattt tacaggcccg aagagccgct 360
ccggtggacg ttgccacgtg cattccccac tgtcgagtgc tcccccgccg gggcttgctg 420
gctttctgcg atcttcccaa ttgcacgaat gaccagtgga aacctgaact ttcaacaaag 480
aatggtgcgg gtcgctgccg agatttacag agccggccag ctcacccctg cagtcttgaa 540
ggctctacaa gtttatgaac ggggttgccg ctggtacccc attgtcggac ctgtccctgg 600
agtggccgtt ttcgccaact ccctacatgt gagtgacaaa ccttttccgg gagcaactca 660
tgtgttaacc aatctaccgc tcccgcagag gcccaagcct gaagactttt gccctttga 720 gtgtgctatg gctgacatct atgacatcgg tcatgacgcc gtcatgtatg tggccggaga 780
gaaagtctcc tgggcccctc gtggcgggga tgaagtgaaa tttgaaaatg ttcccaagga 840
gttgaagttg attgcgaacc gactccacat ctccttcccg ccccaccacg tagtggacat 900
gtccaagttt accttcatag cccccgggag tggtgtctcc atgcgggttg agtgccaaca 960
cggctgcctc cccgctgata ctgttcctga aggaaactgc tggtggcgct tgttcgactc 1020
gctcccgccg gaagtccagc acaaagaaat tcgctatgct aaccaatttg gttatcaaac 1080
caagcatggt gtctctggca agtacctaca gcggaggctg caagttaacg gtctccgagc 1140
agtgaccgac gtacatggac ctatcgtcat acagtacttc tctgttaagg agagttggat 1200
ccgccacttc aggctggcgg aagaacctag cctccctggg ttcgaagacc tcctcagaat 1260
tagggttgag cccaatacat caccactggc tggcgaggat gggaagatct tccggtttgg 1320
cagtcacaag tggtacggtg ctggaaggag agcaaggaaa gcacgttctg gtgcgaccac 1380
catggtcgct catcgcgctt tgtccgctcg tgaaacccag caggcaaaga aggacgaggg 1440
tgccgacgct aacaaggctg agcatctcaa gcactactct ccgcccgccg aagggaactg 1500
tggttggcac tgtatttccg ccatcgccaa ccggatgata aattccaaat ttgaaactac 1560
ccttcccgaa agagtaaggc ctctggatga ctgggctact gacgaggatc ttgtgaatac 1620
catccaaatc ctcaggctcc ccgcggcctt ggataggaac ggtgcttgta gtagcgccaa 1680
gtacgtgctt aagctggaag gtgtgcattg gactgtctct gtgacccctg ggatgtcccc 1740
ttccttgctc ccccttgaat gtgttcaggg ctgttgcgag cataagggcg gttttggctc 1800
cccagatgcg gtcgaagttt ccggatttga ccctgcctgc cttgaccgac tggctgaggt 1860
aatgcacttg cctagcagtg ccatcccagc cgctctggcc gaaatgtccg gcgactccaa 1920
tcgtccggct tccccggtca acactgtgtg gactgtttcg caattctatg cccgtcatac 1980
aggaggaaat catcctgacc aggtgtgctt agagcagatc attaatctct gtcaggttat 2040
tgaggtttgt tgctgccatc aaaacaaaac caaccgggcc accccggaag aggtcgcggc 2100
aaagattgat cagtacctcc gtggtgcaac aaatcttgaa gaatgcttga ccaggcttga 2160
gagggtttgc ccgccgagcg ctgcggacac ctcctttgat tggaatgttg tgctccctgg 2220

-continued

```
ggttgaggct gcaactcaga caaccaaaca gccccacgtc aaccagtgct gcgctctggt   2280
tcctgtcgtg actcaagagc ctttggacaa agactcggtc cctctgaccg ccttctcgct   2340
gtccaattgc tactaccctg cacaaggtga agaggttcgt caccgtgaga gactaaactc   2400
cgtactctcg aagttggagg gggctgttcg tgaggaatat gggctcacgc caactgaacc   2460
tggcctgcaa cccgcactac cgaacgggct cgacgaactt aaagaccgga tggaggagga   2520
tctgctgaaa ctagtcaacg ctcaggcaac ttcagaaatg atggcctggg cagccgagca   2580
gattgattta aaagcttggg tcaaaaacta cccacggtgg acaccgccac cccctccacc   2640
aagagctcag cctcggaaaa cgaagtctgt taagagcttg ccagggaaca agcctatccc   2700
tgctccacgc aggaaggtca gatctgattt gactgttaat ggcccccttg atctttcgac   2760
accatccgag ccgatgacac ccctgagtga gcctgcactt atgcccgcgt tgcaacatat   2820
ttctaggcca gtgacatctt tgagtgagcc ggtcccagtt cctgcaccgc gtagagctgt   2880
gtcccgaccg gtgacgccct tgagtgggcc aacttttgag tttgcgccgc gacacaaatt   2940
tcagcaggtg ggagaagtga atctggcggc aacaacgctg acgcaccagg acgaacctct   3000
agatttgtct gcatcctcac agactgaata tgaggcttct cccctagtac caccgcagaa   3060
catgggtatc ctgggggtgg gggggcaaga ggctgaagaa gttctgagtg aaatctcgga   3120
tatactgagt gacattaacc ctgcacctgt gtcattaagc agctccctgt caagtgttaa   3180
gatcacacgc ccaaaatact cagctcaagc catcattgac tcgggcgggc cctgcagtgg   3240
gcatctccga agggaaaaag aagcatgcct cagcgtcatg cgtgaggctt gtgatgcggc   3300
taaacttagc gaccctgcca cgcaggaatg gctttctcgc atgtgggata gggttgacat   3360
gctgacctgg cgcaataagt ctgcttacca ggcgtttcgc atcttggatg gcaggtttga   3420
gtttctccca aagatgatac tcgagacacc gccgccctat ccgtgtgggt ttgtgatgct   3480
gcctcacacg cctgcacctt ccgtgagtgc agagagtgac cttaccattg gttcagtcgc   3540
cactgaagat gttccacgca tcctcgggaa aatagaaaac gccggcgagg tgcccaacca   3600
ggggctctcg gcatcctccg gggaagaacc gatgtatgac caacctgcca aagactcccg   3660
gatgtcgtcg cgggggtttg acgagagcat aacggctccg tccgtaggta caggtggcgc   3720
tgacttactc actgatttgc caccttcagg tggtgtggat gtggacgggg gggggccgtt   3780
acggacggta agaaagaaaa ttgaaaggct cttcgaccaa tttagccgtc aggtttttaa   3840
cctcgtctcc catctccctg ttttcttctc acacctcttc aaacctgaca gtggttattc   3900
tccgggtgat tggggtttg cagctttcac tctactttgc ctctttttgt gttatagcta   3960
cccattcttt ggcttcgctc ccctcttggg tgtattttct gggtcttctc ggagggtgcg   4020
catgggggtt tttggctgct ggttggcttt tgctgttggc ctgttcaagc ctgtgtccga   4080
cccagtcggc actgcttgtg aatttgactc gccagagtgt aggaacgtcc ttcattcttt   4140
tgagcttctc aaaccttggg accctgttcg cagccttgtt gtgggccccg caggtctcgg   4200
tcttgccatt cttggcaggt tactgggcgg ggcacgctac atctggcatt ttttgcttag   4260
gcttggcatt gttgcagatt gtgtcttggc tggagcttat gtgctttctc aaggtaggtg   4320
taaaaagtgc tggggatctt gtataagaac tgctcctaat gaaatcgcct tcaacgtgtt   4380
ccctttcacg cgtgcgacca ggtcgtcact catcgacctg tgcgaccggt ttcgtgcgcc   4440
aaaaggcatg gaccctgttt tcctcgctac tgggtggcgc gggtgctgga ccggtcaaag   4500
tcccattgag caaccctctg aaaaacccat cgcgttcgcc cagttggatg aaaagaggat   4560
cacggctaga actgtggtcg ctcagcctta tgatcctaac caagccgtaa agtgcttgcg   4620
```

```
ggtgctacag gcgggtgggg cgatggtggc cgaggcagtc ccaaaagtgg tcaaggtttc   4680
cgctattcca ttccgagccc cctttttttcc caccggagtg aaggttgatc ctgagtgcag   4740
gatcgtggtc gaccccgaca cttttactac agctctccgg tctggttact ccaccacaaa   4800
cctcgtcctt ggtgtggggg actttgccca attgaatgga ttgaaaatca ggcaaatttc   4860
caagccttcg ggaggaggcc cacacctcat tgctgccctg catgttgcgt gctctatggc   4920
gttgcacatg cttgctgggg tttatgtaac tgcagtgggg tcttgcggta ccggcaccaa   4980
cgatccgtgg tgcactaacc cattcgccgt ccctggctac ggacctggct ctctctgcac   5040
gtccagattg tgcatctccc aacatggcct caccctgccc ttgacagcac ttgtggcagg   5100
attcggtctt caggaaattg ccttagtcgt tttgattttc gtttccatcg gaggcatggc   5160
tcataggttg agttgtaagg ctgacatgct gtgcatctta cttgcaatcg ccagctatgt   5220
ttgggtaccc cttacctggt tgctctgtgt gtttccttgc tggttgcgct ggttcacttt   5280
gcaccctctc accatcctat ggttggtgtt tttcctgatt tctgtaaata tgccttcggg   5340
aatcttggcc atggtgttat tggttgctct ttggctttta ggccgttata ctaatgttgt   5400
tggtcttgtt accccctatg atattcacca ttacaccagt ggcccccgcg gtgtagccgc   5460
cttggccacc gcaccagatg ggacttactt ggccgctgtc cgccgcgctg cgttgactgg   5520
ccgcaccgtg ctgtttaccc cgtctcagct tgggtccctt cttgagggcg ctttcaggac   5580
tcgaaagccc tcattgaaca ccgtcaatgt ggtcgggtcc tccatgggct ctggcggagt   5640
gttcactatc gacgggaaaa tcaagtgcgt gactgccgca catgtcctta cgggtaattc   5700
agccagggtt tccggggtcg gcttcaatca aatgcttgac tttaatgtaa agggggactt   5760
cgccatagct gattgcccga attggcaagg ggctgctccc aagacccaat tctgcgagga   5820
tggatggact ggtcgtgcct attggctgac atcctctggt gtcgaacccg gtatcattgg   5880
gaatggattt gccttctgct tcaccgcgtg cggcgattct ggatccccag tgattaccga   5940
agccggtgag cttgtcggcg ttcacacagg atcgaacaaa caaggaggag gcattgtcac   6000
gcgcccctcg ggccagtttt gtaatgtggc gcccatcaag ctgagcgaat tgagtgaatt   6060
cttcgctgga cctaaggtcc cgctcggtga tgtgaaggtt ggcagccaca taattaaaga   6120
catatgcgag gtaccttcag acctttgcgc cttgcttgct gccaaacccg aactggaagg   6180
aggcctctct accgtccaac ttctgtgtgt gtttttcctc ctgtggagaa tgatggggca   6240
tgcctggacg cccttggttg ctgtggggtt ttttatcttg aatgaggtcc tcccagctgt   6300
cctggtccgg agtgttttct cctttggaat gtttgtgcta tcttggctca cgccatggtc   6360
tgcgcaagtt ctgatgatca ggcttctaac agcagctctt aacaggaaca gattttcact   6420
cgccttttac agccttggtg cagcgaccgg ttttgtcgca gatctggcga caactcaagg   6480
gcatccgttg caggcagtaa tgaatttaag tacctatgcc ttcctgcctc ggatgatggt   6540
tgtgacatca ccagtcccag tgattgcgtg tggtgttgtg cacctccttg ccataatttt   6600
gtacttgttc aagtaccgtt gcctgcacaa tgtccttgtt ggcgacggag cgttctctgc   6660
ggcttttttc ttgcgatact ttgccgaggg aaagttgaga gaaggggtgt cgcagtcctg   6720
cgggatgaat cacgagtcac tgactggagc cctcgctatg agactcaatg acgaggactt   6780
ggacttcctt acgaaatgga ctgattttaa gtgctttgtt tctgcttcca atatgaggaa   6840
tgcagcgggc caattcatcg aggcagccta tgctaaagca cttagaatag aacttgccca   6900
gttggtgcag gtcgacaagg ttcgaggtgt tttggccaaa cttgaagctt ttgctgatac   6960
```

-continued

```
tgtggcaccc caactctcgc ccggtgacat tgtcgttgct cttggccata cgcctgttgg   7020
tagtatcttc gacctaaagg ttggtagcac caagcatact ctccaagcca ttgagaccag   7080
agtccttgcc gggtccaaga tgaccgtggc gcgcgtcgtt gacccaaccc ccacgccccc   7140
acccgcaccc gtgcctatcc ccctcccgcc aaaaattctg gagaatggtc ccaacgcctg   7200
gggggatgag gaccgtttga ataagaagaa gaggcgcagg atggaagccg ttggcatctt   7260
tgttatgggc gggaagaagt accagaaatt ttgggacaag agctccggtg atgtgtttta   7320
cgaggaagtc catgataaca cagatgcatg ggagtgcttc agagttgaca accctgccga   7380
ctttgaccct gagaagggaa ctctgtgtgg gcataccacc attgaaaata aggcttacaa   7440
tgtctacgtc tccccatctg gcaggaagtt tctagtccct gtcaacccag agagtggaaa   7500
agcccaatgg gaagctgcaa ggctttccgt ggagcaggcc cttggcatga tgaatgtcaa   7560
cggtgaactg acagccaaag aactggagaa actgaaaaga ataattgaca aactccagga   7620
cctgactaag gagcagtgtt taaactgcta gccgccagcg gcttgacccg ctgtggtcgc   7680
ggcggcttag ttgttactga gacagcggta aaaatagtca aatttcacaa ccggaccttc   7740
accctaggac ccgtaaactt aaaagtggcc agtgaggttg agctaaaaga cgcggtcgag   7800
cataaccaac acccggttgc aagaccggtt gatggcggtg ttgtgctcct gcgctccgca   7860
gttccttcgc ttatagacgt cttgatctcc ggcgctgatg catctcctaa gttactcgcc   7920
cgccacgggc cgggaaacac tggatcgat ggcacgcttt gggactttga ggccgaggcc   7980
actagagagg aaattgcact cagtgcgcaa ataatacagg cttgtgacat taggcgcggc   8040
gacgcgcccg aaattggtct tccttataag ctgtaccctg ttaggggcaa ccctgagcgg   8100
gtaaaaggag ttttacagaa cacaaggttt ggagacatac cttacaaaac ccccagtgac   8160
actggaagcc cagtacacgc ggctgcctgc ctcacgccca atgccactcc ggtgactgat   8220
gggcgctccg tcttggctac gactatgccc tccggttttg agttgtatgt accgaccatt   8280
ccagcgtctg tccttgatta tcttgattct aggcctgact gccctaaaca gttgacagag   8340
cacggttgtg aggatgccgc attgagagac ctctccaagt atgacttgtc cacccaaggt   8400
tttgttttgc ctggagttct tcgccttgtg cggaagtacc tgtttgccca tgtgggtaag   8460
tgcccgtccg ttcatcggcc ttccacttac cctgccaaga attctatggc tggaataaat   8520
gggaacaggt ttccaaccaa ggacattcag agcgtccctg aaatcgacgt tctgtgcgca   8580
caggccgtgc gagagaactg gcaaactgtc accccttgta ccctcaagaa acagtattgt   8640
gggaagaaga agactaggac aatactcggc accaataact tcattgcgtt ggcccaccga   8700
gcagcgttga gtggtgtcac ccagggcttc atgaaaaagg cgtttaactc gcccatcgcc   8760
ctcgggaaaa acaaatttaa ggagctgcag actccggtct taggcaggtg ccttgaagct   8820
gatcttgcat cctgcgatcg atccacacca gcaattgttc gctggtttgc cgccaatctt   8880
ctttatgaac ttgcctgtgc tgaggagcat ctgccatcgt acgtgctgaa ctgctgccac   8940
gacttactgg tcacgcagtc cggcgcggtg actaagagag gtggcctgtc gtctggcgac   9000
ccgattactt ctgtgtcaaa caccatttac agcttggtga tatatgcaca gcacatggtg   9060
ctcagttact ttaaaagtgg tcaccctcat ggccttctgt ttctgcaaga ccagctgaag   9120
tttgaggaca tgctcaaggt tcaacccctg atcgtctatt cggacgacct cgtgctgtat   9180
gccgagtctc ccaccatgcc aaactaccac tggtgggtgg aacatctgaa tcttatgctg   9240
ggttttcaga cggacccaag gaagacagcc ataacagatt cgccatcatt tctaggctgt   9300
aggataataa atggacgcca actagtcccc aaccgtgaca ggatcctcgc ggccctcgct   9360
```

-continued

```
taccatatga aggcaagcaa tgtttctgaa tactacgcct cggcggctgc aatactcatg   9420
gacagctgtg cttgtttaga gtatgatcct gaatggtttg aagagctcgt ggttgggatg   9480
gcgcagtgcg cccgcaagga cggctatagt ttccctggcc cgccgttctt cttgtccatg   9540
tgggaaaaac tcaggtccaa tcatgaaggg aagaagtcca gaatgtgcgg gtactgcggg   9600
gccccggctc cgtacgccac tgcctgtggc ctcgacgtct gtgtttatca cacccacttt   9660
caccagcatt gtccagtcat aatctggtgt ggccatccgg ctggttctgg ttcttgcagt   9720
gagtgcaaac ccccccttagg gaaaggcaca agccctctag atgaggtgtt agaacaagtc   9780
ccgtacaagc ctccacggac tgtaatcatg catgtggagc agggtctcac ccctcttgac   9840
ccaggtagat accagactcg ccgcggatta gtctccgtta ggcgtggcat caggggaaat   9900
gaagttgacc taccagacgg tgattatgct agtaccgccc tgctccccac ttgtaaagag   9960
atcaacatgg tcgctgtcgc ctctaacgtg ttgcgcagca ggttcatcat cggtccgcct  10020
ggtgctggga aaacatactg gctccttcaa caggtccaag atggtgatgt catttacacg  10080
ccgactcacc agaccatgct cgacatgatt agggctttgg ggacgtgccg gttcaacgtc  10140
ccggcaggta caacgctgca attccccgcc ccctcccgta ccggcccgtg ggttcgcatc  10200
ctagccggcg gttggtgtcc tggtaagaat tccttcctgg atgaagcagc gtattgcaat  10260
caccttgatg tcttgaggct tcttagcaaa actaccctta cctgcctagg agacttcaaa  10320
caactccacc cggtgggttt tgactctcat tgctatgttt ttgacatcat gcctcagacc  10380
caactgaaga ccatctggag gtttggacag aacatctgtg atgccatcca accagattac  10440
agggacaaac ttgtatccat ggtcaacaca acccgtgtaa cctacgtgga aagacctgtc  10500
aattatgggc aagtcctcac cccttaccac agggaccgag aggacggcgc catcacaatt  10560
gactccagtc aaggcgccac atttgatgtg gttacactgc atctgcccac taaagactca  10620
ctcaacaggc aaagagccct tgttgctatc accagggcaa gacatgctat ctttgtgtat  10680
gacccacaca ggcaactgca gagcatgttt gatcttcctg cgaaaggcac acccgtcaac  10740
ctcgctgtgc accgtgacga gcagctgatc gtactagata gaaataacaa agaatgcacg  10800
gttgctcagg ctctaggcaa tggggataaa ttcagggcca cagacaagcg cgttgtagat  10860
tctctctgcg ccatttgtgc agatctggaa gggtcgagct ctccgctccc caaggtcgca  10920
cacaacttgg ggttttattt ctcacctgat ttgacacagt ttgctaaact cccggtagaa  10980
cttgcacccc actggcccgt ggtgacaacc cagaacaatg aaaagtggcc agaccggctg  11040
gttgccagtc ttcgccctgt ccataagtat agccgtgcgt gcatcggtgc cggctacatg  11100
gtgggcccct cagtgtttct aggcacccct ggggttgtgt catactatct cacaaaattt  11160
gtcaagggcg aggctcaaat gcttccggag acagttttca gcaccggccg aattgaggta  11220
gattgccggg agtatcttga tgaccgggaa cgagaaattg ctgagtccct cccccatgcc  11280
ttcattggcg acgtcaaagg cactaccgtt ggaggatgtc accatgtcac ctccaaatac  11340
cttccgcgct tccttcccaa ggaatcagtc gcggtagtcg gggtttcaag ccccgggaaa  11400
gccgcaaaag cagtttgcac attaacagat gtgtacctcc cagaccttga ggcttacctc  11460
cacccagaga cccagtccag gtgctggaaa atgatgttgg acttcaagga agttcgactg  11520
atggtctgga aagacaagac ggcctatttt caacttgaag gccgccattt cacctggtat  11580
cagcttgcga gctatgcctc gtacatccga gttcctgtta actctacggt gtatttggac  11640
ccatgcatgg gccctgccct ttgcaataga agggttgtcg ggtccaccca ttggggagct  11700
```

-continued gacctcgcag tcactcctta tgattatggt gccaagatca ttttgtctag tgcataccat 11760
ggtgaaatgc ctcctgggta caaaatccta gcgtgtgcgg agttctcgct tgatgatcca 11820
gtgaggtaca agcacacctg ggatttgaa tcggatacag cgtatctgta cgagttcacc 11880
ggaaacggtg aggactggga ggattacaat gatgcgtttc gtgcgcgcca gaaagggaaa 11940
atttataagg ccactgccac cagcatgagg tttcattttc ccccgggccc tgtcattgaa 12000
ccaactttgg gcctgaactg aaatgaaatg gggctatgc aaagcctttt ctacaaaatt 12060
ggccaacttt ttgtggatgc tttcacggag tttttggtgt ccattgttga tatcatcata 12120
tttctggcca ttttgtttgg cttcaccatc gccggctggc tggtggtctt ctgcatccga 12180
ttggtttgct ccgcggtact ccgtgcgcgc cctaccgttc accctgagca attacagaag 12240
atcttatgag gcctttcttt ctcagtgcca ggtggacatt cccacctggg gaaccaaaca 12300
tcccttgggg atgctttggc accataaggt gtcaaccctg attgatgaaa tggtgtcgcg 12360
tcgaatgtac cgcatcatgg aaaaagcagg acaggctgcc tggaaacagg tggtgagcga 12420
ggccacgctg tctcgtatta gtggtttgga tgtggtggct cattttcagc atcttgctgc 12480
cattgaagcc gagaactgta aatatttggc ctctcggctg cccatgctac acaacctgcg 12540
catgacaggg tcaaatgtaa ccttagtgta taatagcact ttgaatcagg tgttcgctat 12600
ctttccaacc cctggttccc ggccaaagct tcatgatttt cagcaatggc taatagctgt 12660
acattcctct atattttcct ccgttgcggc ttcttgtact ctttttgttg tgctgtggtt 12720
gcgaatccca attctacgta ctgtttttgg tttccactgg ttaggggcaa tttctctttc 12780
gaactcacag tgaattacac ggtgtgccca ccttgcctca cccgacaagc agccgctgag 12840
atctatgaac ccggcaggtc tctttggtgc aggataggga atgaccgatg tagtgagagc 12900
gatcatgacg aactagggtt catggttccg tctggcctct ccagcgaagg ccacttgacc 12960
agtgtttacg cttggttggc gtttctgtcc ttcagctaca cggcccagtt ccatcccgag 13020
atatttggga tagggaatgt gagtaaagtt tatgttgaca tcaagcacca attaatctgc 13080
gccgttcatg acgggcagaa caccaccttg cctcgccatg acaatatttc agccgtattt 13140
cagacctatt atcaacatca ggtcgacggc ggcaactggt ttcacctaga atggctgcgt 13200
cccttctttt cctcttggtt ggttttaaat gtttcgtggt ttctcaggcg ttcgcctgca 13260
agccatgttt cagttcgagt ctttcggaca tcaagaccaa cactaccgca gcatcaggct 13320
ttgtcgtcct ccaggacatc agctgcctta ggcatggcga ctcgtcctct cagacgattc 13380
gcaaaagctc tcagtgccgc acggcgatag ggacgcccgt gtacatcacc atgacagcca 13440
atgtcacaga tgagaattat ttgcattctt ctgatctcct catgctttct tcttgccttt 13500
tctatgcttc tgagatgagt gaaaagggat tcaaggtggt gtttggcaat gtgtcaggca 13560
tcgtggctgt gtgtgtcaac tttaccagct acgtccaaca cgtcaaggag ttcacccaac 13620
gctccttggt agtcgatcat gtgcggctgc ttcacttcat gacacctgag accatgaggt 13680
gggcaaccgt tttagcctgt ctttttgcca tcttgctggc aatttgaatg ttcaagtatg 13740
ttggggaaat gcttgaccgc gggctgttgc tcgcgattgc ctttttttgtg gtgtatcgtg 13800 ccgttctgtt ttgctgtgat cgtcgacgcc aacagcaaca gcagctctca tttccagttg 13860
atttataact tgacgttatg cgagctgaat ggcacagatt ggctggttga taaatttgat 13920
tgggcagtgg agacttttgt catttttccc gtgttgactc acattgtttc ttatggtgca 13980
ctcaccacca gccatttcct tgacacagtt ggtctggtta ctgtatccgc cgccgggttt 14040
tgtcacgggc ggtatgtctt gagtagcatc tacgcggtct gtgccctggc tgcgttggtt 14100

```
tgctttgtca tcagatttgc gaagaactgc atgtcctggc gctactcatg tactagatac  14160

accaacttcc ttctagacac taagggcaga ctctatcgtt ggcggtcgcc tgtcatcata  14220

gagaaaaggg gcaaggttga ggtcgaaggc catctgatcg acctcaaaaa agttgtgctt  14280

gatggttccg cggcaacccc tttaaccaga atttcagcgg aacaatggtg tcgtccctag  14340

acgacttttg caatgatagc acagctccac ggaaggtgct cttggcgttt tctatcacct  14400

acacgccagt gatgatatat gctctaaagg taagtcgcgg ccgactgttg gggcttctgc  14460

acctttttgat ttttctgaac tgtgccttta ccttcgggta catgacattc acgcactttc  14520

agagcacaaa tagggtcgcg ctcactatgg gagcagtagt cgcactcctt tggggggtgt  14580

actcagccat agaaacctgg aaattcatca cctccagatg ccgtttgtgc ttgctaggcc  14640

gcaagtacat tttggcccct gcccaccacg tcgaaagtgc cgcgggcttt catccgattg  14700

cggcaaatga taaccacgca tttgtcgtcc ggcgtcccgg ctccactacg gtcaacggca  14760

cattggtgcc cgggttgaaa agcctcgtgt tgggtggcag aaaagctgtt aaacagggag  14820

tggtaaacct tgtcaaatat gccaaataac aacggcaagc agcaaaagaa aaagaagggg  14880

aatggccagc cagtcaatca gctgtgccag atgctgggta agatcatcgc ccagcaaaac  14940

cagtccagag gtaagggacc ggggaagaaa aataagaaga aaaacccgga gaagccccat  15000

tttcctctag cgaccgaaga tgacgtcagg catcacttta cccctagtga gcggcaattg  15060

tgtctgtcgt cgatccagac tgcctttaac cagggcgctg gaacttgcac cctgtcagac  15120

tcagggagga taagttacac tgtggagttt agtttgccga cgcatcatac tgtgcgcctg  15180

attcgcgcca cagcatcaac ctcagcatga tgggctggca ttcttgaagc accacagtgt  15240

taggattgga agaatgtgtg gtgaatggca ctgattgaca ctgtgcctct aagtcaccta  15300

ttcaattagg gcgaccgtgt gggggtaaag tttaattggc gagaaccatg cggccgcaat  15360

taaaaaaaaa aaaaaaaaaa aaaaaa                                        15386
```

<210> SEQ ID NO 2
<211> LENGTH: 15444
<212> TYPE: DNA
<213> ORGANISM: Artificial Sequence
<220> FEATURE:
<223> OTHER INFORMATION: Synthetic Construct

<400> SEQUENCE: 2

```
tatgtacgta taggtgttgg ctctatgcct ttggcatttg tattgtcagg agctgtgacc     60

attggcacag cccaaaactt gctacacaga aacacccttc tgtgatagcc tccttcaggg    120

gagcttaggg tttgtcccta gcaccttgct tccggagttg cactgcttta cggtctctcc    180

accccttaa ccatgtctgg gatacttgat cggtgcacgt gtaccccaa tgccagggtg    240

tttatggcgg agggccaagt ctactgcaca cgatgcctca gtgcacggtc tctccttccc    300

ctgaacctcc aagtttctga gctcggggtg ctaggcctat tctacaggcc cgaagagcca    360

ctccggtgga cgttgccacg tgcattcccc actgttgagt gctcccccgc cggggcctgc    420

tggctttctg caatctttcc aatcgcacga atgaccagtg gaaacctgaa cttccaacaa    480

agaatggtac gggtcgcagc tgagctttac agagccggcc agctcacccc tgcagtcttg    540

aaggctctac aagtttatga acggggttgc cgctggtacc ccattgttgg acctgtccct    600

ggagtggccg ttttcgccaa ttccctacat gtgagtgata aacctttccc gggagcaact    660

cacgtgttga ccaacctgcc gctcccgcag agacccaagc ctgaagactt ttgccccttt    720
```

-continued

```
gagtgtgcta tggctactgt ctatgacatt ggtcatgacg ccgtcatgta tgtggccgaa    780
aggaaaatct cctgggcccc tcgtggcgag gatgaagtga aatttgaagc tgtccccggg    840
gagttgaagt tgattgcgaa ccggctccgc acctccttcc cgccccacca cacagtggac    900
atgtctaagt tcgccttcac agcccctggg tgtggtgttt ctatgcgggt cgaatgccaa    960
cacggctgcc ttcccgctga cactgtccct gaaggcaact gctggtggag cttgtttgac   1020
ttgcttccac tggaagttca gaacaaagaa attcgccatg ctaaccaatt tggctaccag   1080
accaagcatg gtgtctctgg caaataccta cagcgtaggc tgcaagttaa tggtctccga   1140
gcagtaactg acctaaacgg acctatcgtc gtacagtact tctccgttaa ggagagttgg   1200
atccgccatt tgaaactggc gggagaaccc agctactctg ggtttgagga cctcctcaga   1260
ataagggttg agcctaacac gtcgccattg gctgacaagg aagaaaaaat tttccggttt   1320
ggcagtcaca agtggtacgg cgctggaaag agagcaagaa aagcgcgctc ttgtgcgact   1380
gctacagtcg ctggccgcgc tttgtccgtt tgtgaaaccc ggcaggccaa ggagcacgag   1440
gttgccggcg ccaacaaggc tgagcacctc aaacactact ccccgcctgc cgaagggaat   1500
tgtggttggc actgcatttc cgccatcgcc aaccggatgg tgaattccaa atttgaaacc   1560
acccttcccg aaagagtgag accttcagat gactgggcta ctgacgagga tcttgtgaat   1620
gccatccaaa tcctcagact ccctgcggcc ttagacagga acggtgcttg tactagcgcc   1680
aagtacgtac ttaagctgga aggtgagcat tggactgtca ctgtgacccc tgggatgtcc   1740
ccttctttgc tccctcttga atgtgttcag ggctgttgtg ggcacaaggg cggtcttggt   1800
accccagatg cagtcgaggt ctccggattt gaccctgcct gccttgaccg gctggctgag   1860
gtgatgcacc tgcctagcag tgctatccca gccgctctgg ccgaaatgtc tggcgattcc   1920
gatcgttcgg cttctccggt caccaccgtg tggactgttt cgcagttctt tgcccgtcac   1980
agcggaggga atcaccctga ccaagtgcgc ttagggaaaa ttatcagtct ttgtcaggtg   2040
attgaggact gctgctgttc ccagaacaaa accaaccggg tcaccccgga ggaggtcgca   2100
gcaaagattg acctgtacct ccgtggtgca acaaatcttg aagaatgctt ggccaggctt   2160
gagaaagcgc gcccgccgcg cgtaatcgac accttctttg attgggatgt tgtgctccct   2220
ggggttgagg cggcaaccca gacgatcaag ctgccccagg tcaaccagtg tcgtgctctg   2280
gtccctgttg tgactcaaaa gtccttggac aacaactcgg tcccccctgac cgccttttca   2340
ctggctaact actactaccg tgcgcaaggt gacgaagttc gtcaccgtga aagactaacc   2400
gccgtgctct ccaagttgga aaaggttgtt cgagaagaat atgggctcat gccaaccgag   2460
cctggtccac ggcccacact gccacgcggg ctcgacgaac tcaaagacca gatggaggag   2520
gacttgctga aactggctaa cgcccagacg acttcggaca tgatggcctg ggcagtcgag   2580
caggttgact taaaaacttg ggtcaagaac tacccgcggt ggacaccacc accccctccg   2640
ccaaaagttc agcctcgaaa aacgaagcct gtcaagagct tgccggagag aaagcctgtc   2700
cccgccccgc gcaggaaggt tgggtccgat tgtggcagcc cggtttcatt aggcggcgat   2760
gtccctaaca gttgggaaga tttggctgtt agtagcccct ttgatctccc gacctcacct   2820
gagccggcaa caccttcaag tgagctggtg attgtgtcct caccgcaatg catcttcagg   2880
ccggcgacac ccttgagtga gccggctcca attcccgcac ctcgcggaac tgtgtctcga   2940
ccggtgacac ccttgagtga gccgatccct gtgcccgcac cgcggcgtaa gtttcagcag   3000
gtgaaaagat tgagttcggc ggcggcaatc ccaccgtacc agaacgagcc cctggatttg   3060
tctgcttcct cacagactga atatgaggcc tctcccccag caccgccgca gagcgggggc   3120
```

gttctgggag tagaggggca tgaagctgag gaaaccccga gtgaaatctc ggacatgtcg 3180
ggtaacatta aacctgcgtc cgtgtcatca agcagctcct tgtccagcgt gagaatcaca 3240
cgcccaaaat actcagctca agccatcatc gactcgggcg ggccctgcag tgggcatctc 3300
caagaggtaa aggaaacatg ccttagtgtc atgcgcgagg catgtgatgc gactaagctt 3360
gatgaccctg ctacgcagga atggctttct cgcatgtggg atcgggtgga catgctgact 3420
tggcgcaata cgtctgctta ccaggcgatt tgcaccttag atggcaggtt aaagttcctc 3480
ccaaaaatga tactcgagac accgccgccc tatccgtgtg agtttgtgat gatgcctcac 3540
acgcctgcac cttccgtagg tgcggagagc gaccttacca ttggctcagt tgctactgaa 3600
gatgttccac gcatcctcga gaaaatagaa aatgtcggcg agatggccaa ccagggaccc 3660
ttggccttct ccgaggataa accggtagat gaccaacttg tcaacgaccc ccggatatccg 3720 tcgcggaggc ctgacgagag cacatcagct ccgtccgcag gcacaggtgg cgccggctct 3780
tttaccgatt tgccgccttc agatggcgcg gatgcggacg gggggggccc gtttcggacg 3840
gtaaaaagaa aagctgaaag gctctttgac caactgagcc gtcaggtttt tgacctcgtc 3900
tcccatctcc ctgttttctt ctcacgcctt ttctaccctg gcggtggtta ttctccgggt 3960
gattggggtt ttgcagcttt tactctattg tgcctctttt tatgttacag ttacccagcc 4020
tttggtattg ctcccctctt gggtgtgttt tctgggtctt ctcggcgcgt tcgaatgggg 4080
gtttttggct gctggttggc ttttgctgtt ggtctgttca agcctgtgtc cgacccagtc 4140
ggcgctgctt gtgagtttga ctcgccagag tgtagaaaca tccttcattc ttttgagctt 4200
ctcaaacctt gggaccctgt tcgcagcctt gttgtgggcc ccgtcggtct cggtcttgcc 4260
attcttggca ggctactggg cggggcacgc tgtatctggc actttttgct taggcttggc 4320
attgttgcag actgtatctt ggctggagct tacgtgcttt ctcaaggtag gtgtaaaaag 4380
tgctggggat cttgtataag aactgctcct aatgaggtcg cttttaacgt gtttcctttc 4440
acacgtgcga ccaggtcgtc acttatcgac ctgtgcgatc ggttttgtgc accaaaagga 4500
atggacccca tttttctcgc cactgggtgg cgcgggtgct gggccggccg aagccccatt 4560
gagcaaccct ctgaaaaacc catcgcgttt gcccaattgg atgaaaagaa gattacggct 4620
aggactgtgg tcgcccagcc ttatgacccc aaccaagccg taaagtgctt gcgggtgttg 4680
caggcgggtg gggcgatggt ggctgaggcg gtcccaaaag tggtcaaggt ttccgctgtt 4740
ccattccgag ccccccttctt tcccactgga gtgaaagttg atcctgattg cagggtcgtg 4800
gttgaccctg atactttcac tgcagctctc cggtctggct actccaccac aaacctcgtc 4860
cttggtgtag gggactttgc ccagctgaat ggattaaaaa tcaggcaaat ttccaagcct 4920
tcagggggag gcccacatct catggctgcc ctgcatgttg cctgctcgat ggctctgcac 4980
atgcttgctg ggatctatgt gactgcggtg ggttcttgcg gcaccggcac caacgacccg 5040
tggtgcgcta acccgtttgc cgtccctggc tacggacctg gctctctctg cacgtccaga 5100
ttgtgcattt cccaacacgg ccttaccctg cccttgacag cacttgtggc gggattcggt 5160
attcaagaaa ttgccttagt cgttttgatt tttgtttcca tcggaggcat ggctcatagg 5220
ttgagctgta aggctgacat gctgtttgtt ttgcttgcaa tcgccagcta tgtttgggta 5280
cctcttacct ggttgctttg tgtgtttcct tgctggttgc gctgtttttc tttgcacccc 5340
ctcaccgtcc tatggttggt gtttttcttg atttctgtga atatgccttc aggaatcttg 5400
gccatggtgt tgttggtttc tctttggctt cttggtcgtt atactaatgt tgctggcctt 5460

-continued

```
gtcacccccct acgacattca ccattacacc agcggccccc gcggtgttgc cgccttggct   5520
accgctccag atgggaccta cttggccgct gtccgccgcg ctgcgttgac tggccgcacc   5580
atgctgttta ccccgtccca gcttgggtct cttcttgagg gtgctttcag aactcgaaag   5640
ccctcactga acaccgtcaa tgtgatcggg tcctccatgg gctctggcgg ggtgtttacc   5700
atcgacggga aagtcaagtg cgtaactgcc gcacatgtcc ttacgggcaa ttcagctcgg   5760
gtttccgggg tcggcttcaa tcaaatgctt gactttgacg taaagggaga ttttgctata   5820
gctgattgcc cgaattggca aggggctgcc cccaagaccc aattctgcac ggatggatgg   5880
actggccgtg cctattggct aacatcctct ggcgtcgaac ccggcgtcat tggaaaagga   5940
ttcgccttct gcttcaccgc atgtggcgat tccgggtccc cagtgatcac cgaggccggt   6000
gagcttgtcg gcgttcacac gggatcgaat aaacaagggg ggggcattgt tacgcgcccc   6060
tcaggccagt tttgtaatgt ggcacccatc aagctaagcg aattaagtga attctttgct   6120
gggcctaagg tcccgctcgg tgatgtgaag gtcggcagcc acataattat agacataagc   6180
gaggtgcctt cagatctttg tgccttgctt gctgccaaac ctgaactgga aggaggcctc   6240
tccaccgtcc aacttctttg tgtgtttttt ctcctgtgga gaatgatggg acatgcctgg   6300
acgcccttgg ttgctgtgag tttctttatt ctgaatgagg ttctccctgc cgtcctggtc   6360
cggagtgttt tctcctttgg aatgtttgtg ctatcctggc tcacgccatg gtctgcgcaa   6420
gttctgatga tcaggcttct gacagcagct cttaacagga acagatggtc acttgccttt   6480
ttcagcctcg gtgcagtgac cggttttgtc gcagatcttg cggccactca ggggcatccg   6540
ttgcaggcag tgatgaattt gagcacctat gcattcctgc ctcggatgat ggttgtgacc   6600
tcaccagtcc cagtgatcac gtgtggtgtc gtgcacctac ttgccatcat tttgtacttg   6660
tttaagtacc gtggcctgca ccatatcctt gttggcgatg gagtgttctc tgcggctttc   6720
ttcttgagat actttgccga gggaaagttg agggaagggg tgtcgcaatc ctgcggaatg   6780
aatcatgagt ctctgactgg tgccctcgct atgagactca atgacgagga cttggatttc   6840
cttatgaaat ggactgattt taagtgcttt gtttctgcgt ccaacatgag gaatgcagcg   6900
ggtcaattta tcgaggctgc ctatgctaaa gcacttagag tagaactggc ccagttggtg   6960
caggttgata aagttcgagg tactttggcc aaacttgaag cttttgctga taccgtggca   7020
cctcaactct cgcccggtga cattgttgtc gctctcggcc acacgcctgt tggcagtatc   7080
ttcgacctaa aggttggtag caccaagcat accctccaag ccattgagac cagagtcctt   7140
gctgggtcca aaatgaccgt ggcgcgcgtc gtcgacccga cccccacgcc cccgcccgca   7200
cccgtgccca tccccctccc accgaaagtt ctggagaatg gccccaacgc ttggggggat   7260
gaggaccgtt tgaataagaa gaagaggcgc aggatggaag ccctcggcat ctatgttatg   7320
ggcgggaaaa agtaccagaa attttgggac aagaattccg gtgatgtgtt ttatgaggag   7380
gtccataata acacagatga ttgggagtgt ctcagagttg gcgaccctgc cgactttgac   7440
cctgagaagg gaactctgtg tggacatgtc accattgaaa acaaggctta ccatgtttac   7500
acctccccat ctggtaagaa gttcttggtc cccgtcaacc cagagaatgg aagagttcaa   7560
tgggaagctg caaagctttc cgtggagcag gccctaggta tgatgaatgt cgacggcgaa   7620
ctgactgcca aagaactgga gaaactgaaa agaataattg acaaactcca gggcctgact   7680
aaggagcagt gtttaaactg ctagccgcta gcgacttgac ccgctgtggt cgcggcggct   7740
tggttgttac tgaaacagcg gtaaaaatag tcaaatttca caaccggacc ttcaccctgg   7800
gacctgtgaa tttaaaagtg gccagtgagg ttgagctaaa agacgcggtt gagcacaacc   7860
```

```
aacacccggt tgcgagaccg atcgatggtg gagttgtgct cctgcgttcc gcggttcctt   7920
cgcttataga cgtcttgatc tccggtgctg atgcatctcc caagttactt gcccatcacg   7980
ggccgggaaa cactgggatc gatggcacgc tctgggattt tgagtccgaa gccactaaag   8040
aggaagtcgc actcagtgcg caaataatac aggcttgtga cattaggcgc ggcgacgctc   8100
ctgaaattgg tctcccttac aagctgtacc ctgttagggg taaccctgag cgggtgaaag   8160
gagttctgca gaatacaagg tttggagaca taccttacaa aacccccagt gacactggaa   8220
gcccagtgca cgcggctgcc tgccttacgc ccaacgccac tccggtgact gatgggcgct   8280
ccgtcttggc cacgaccatg ccccccgggt ttgagttata tgtaccgacc atacctgcgt   8340
ctgtccttga ttaccttgac tctaggcctg actgccctaa acagctgaca gagcacggct   8400
gcgaagatgc cgcactgaaa gacctctcca aatatgactt gtccacccaa ggctttgttt   8460
tacctggagt tcttcgcctt gtgcggaaat acctgtttgc ccatgtaggt aagtgcccac   8520
ccgttcatcg gccttctact taccctgcta agaattctat ggctggaata aatgggaata   8580
ggttcccaac caaggacatt cagagcgtcc ctgaaatcga cgttctgtgc gcacaggctg   8640
tgcgagaaaa ctggcaaact gtcacccctt gcactcttaa gaaacagtat tgcgggaaga   8700
agaagactag gaccatactc ggcaccaata acttcatcgc actagcccac cgagcagtgt   8760
tgagtggtgt tacccagggc ttcatgaaaa aggcgtttaa ctcgcccatc gccctcggaa   8820
agaacaagtt taaggagcta cagactccgg tcctgggcag gtgccttgaa gctgatctcg   8880
catcctgcga tcgatccacg cctgcaattg tccgctggtt tgccgccaac cttctttatg   8940
aacttgcctg tgctgaagag catctaccgt cgtacgtgct gaactgctgc cacgacttac   9000
tggtcacgca gtccggcgca gtgactaaga gaggtggcct gtcgtctggc gacccgatca   9060
cctctgtgtc taacaccatt tatagtttgg tgatctatgc acagcatatg gtgcttagtt   9120
acttcaaaag tggtcacccc catggccttc tgttcttaca agaccagcta aagtttgagg   9180
acatgctcaa ggttcaaccc ctgatcgtct attcggacga cctcgtgctg tatgccgagt   9240
ctcccaccat gccaaactat cactggtggg ttgaacatct gaatttgatg ctggggtttc   9300
agacggaccc aaagaagaca gcaataacag actcgccatc atttctaggc tgtagaataa   9360
taaatgggcg ccagctagtc cccaaccgtg acaggatcct cgcggccctc gcctatcaca   9420
tgaaggcgag taatgtttct gaatactatg cctcagcggc tgcaatactc atggacagct   9480
gtgcttgttt ggagtatgat cctgaatggt ttgaagaact tgtagttgga atagcgcagt   9540
gcgcccgcaa ggacggctac agctttcccg gcacgccgtt cttcatgtcc atgtgggaaa   9600
aactcaggtc caattatgag ggggaagaagt cgagagtgtg cgggtactgc ggggccccgg   9660
ccccgtacgc tactgcctgt ggcctcgacg tctgcattta ccacacccac ttccaccagc   9720
attgtccagt cacaatctgg tgtggccatc cagcgggttc tggttcttgt agtgagtgca   9780
aatcccctgt agggaaaggc acaagccctt tagacgaggt gctggaacaa gtcccgtata   9840
agcccccacg gaccgttatc atgcatgtgg agcagggtct caccccccctt gatccaggta   9900
gataccaaac tcgccgcgga ctggtctctg tcaggcgtgg aattagggga aatgaagttg   9960
aactaccaga cggtgattat gctagcaccg ccttgctccc tacctgcaaa gagatcaaca  10020
tggtcgctgt cgcttccaat gtattgcgca gcaggttcat catcggccca cccggtgctg  10080
ggaaaacata ctggctcctt caacaggtcc aggatggtga tgttatttac acaccaactc  10140
accagaccat gcttgacatg attagggctt tggggacgtg ccggttcaac gtcccggcag  10200
```

-continued gcacaacgct gcaattcccc gtcccctccc gcaccggtcc gtgggttcgc atcctagccg 10260
gcggttggtg tcctggcaag aattccttcc tagatgaagc agcgtattgc aaccaccttg 10320
atgttttgag gcttctcagt aaaactaccc tcacctgtct aggagacttc aagcaactcc 10380
acccagtggg ttttgattct cattgctatg tttttgacat catgcctcaa actcaactga 10440
agaccatctg gaggtttgga cagaatatct gtgatgccat tcagccagat tacagggaca 10500
aactcatgtc catggtcaac acaacccgtg tgacctacgt ggaaaaacct gtcaggtatg 10560
ggcaggtcct cacccccctac cacagggacc gagaggacga cgccatcact attgactcca 10620
gtcaaggcgc cacattcgat gtggttacgt tgcatttgcc cactaaagat tcactcaaca 10680
ggcaaagagc ccttgttgcc atcaccaggg caagacacgc tatctttgcg tatgacccac 10740
acaggcagct gcagggctta tttgatcttc ctgcaaaagg cacacccgtc aacctcgcag 10800
tgcaccgcga cgggcagctg atcgtgctgg atagaaataa caaagaatgc acggttgctc 10860
aggctctagg caacggggat aaatttaggg ccacagataa gcgtgttgta gattctctcc 10920
gcgccatttg tgctgatcta gaagggtcga gctctccgct ccccaaggtc gcacacaact 10980
tgggatttta tttctcacct gatttaacac agtttgctaa actcccagta gaacttgcac 11040
ctcactggcc cgtggtgaca acccagaaca atgaaaagtg gccagatcgg ctggttgcca 11100
gccttcgccc tatccataaa tacagccgcg cgtgcatcgg tgccggctat atggtgggcc 11160
cttcggtgtt tctaggcact cctggggtcg tgtcatacta tctcacaaaa tttgttaagg 11220
gcgaggctca attgcttcca gagacggttt tcagcaccgg ccgaattgag gtagactgcc 11280
gggaatatct tgatgatcgg gagcgagaag ttgctgcgtc cctcccacac gctttcattg 11340
gcgacgtcaa aggcactacc gttggaggat gtcatcatgt cacctccaga tacctcccgc 11400
gcgtccttcc caaggaatca gttgcggtag tcggggtttc aagccccgga aaagccgcga 11460
aagcattgtg cacactgaca gatgtgtacc tcccagatct tgaagcctat ctccacccgg 11520
agacccagtc caagtgctgg aaaatgatgt tggacttcaa agaagttcga ctaatggtct 11580
ggaaagacaa aacagcctat ttccaacttg aaggtcgcta tttcacctgg tatcagcttg 11640
ccagctatgc ctcgtacatc cgtgttcctg tcaactctac ggtgtacttg gacccctgca 11700
tgggccccgc cctttgcaac aggagagtcg tcgggtccac ccattggggg gctgacctcg 11760
cggtcacccc ttatgattac ggcgctaaaa ttatcctgtc tagcgcgtac catggtgaaa 11820
tgcccccccgg atacaaaatt ctggcgtgcg cggagttctc gttggatgac ccagttaagt 11880
acaaacatac ctgggggttt gaatcggata cagcgtatct gtatgagttc accggaaacg 11940
gtgaggactg ggaggattac aatgatgcgt ttcgtgcgcg ccaggaaggg aaaatttaca 12000
aggccactgc caccagcttg aagtttcatt ttcccccggg ccctgtcatt gaaccaactt 12060
taggcctgaa ttgaaatgaa atggggtcca tgcaaagcct ttttcacaaa attggccaac 12120
tttttgtgga tgctttcacg gagttcttgg tgtccattgt tgatatcatc atatttttgg 12180
ccattttgtt tggcttcacc atcgccggtt ggctggtggt cttttgcatc agattggttt 12240
gctccgcgat actccgtacg cgctctgcca ttcactctga gcaattacag aagatcttat 12300
gaggcctttc tttcccagtg ccaagtggac attcccacct ggggaactaa acatcctttg 12360
gggattctct ggcaccataa ggtgtcaacc ctgattgatg aaatggtgtc gcgtcgaatg 12420
taccgcatca tggaaaaatc agggcaggct gcctggaaac aggtggtgag cgaggctacg 12480
ctgtctcgca ttagtagttt ggatgtggtg gctcattttc agcatctagc cgccattgaa 12540
gccgagacct gtaaatattt ggcctcccgg ctgcccatgc tacacaacct gcgcatgaca 12600

-continued ggttcaaatg taaccatagt gtataatagc actttgaatc aggtgtttgc tatttttcca 12660
acctctggtt cccggccaaa gcttcatgat tttcagcaat ggttaatagc tgtacattcc 12720
tccatatttt cctctgttgc agcttcttgt actcttttg ttgtgctgtg gttgcgtgtt 12780
ccaatactac gtactgtttt tggtttccgc tggttagggg caatttttct ttcgaactca 12840
cagtgaatta cacggtgtgt ccaccttgcc tcacccggca agcagccgca gagatctacg 12900
aacccggtag gtctctttgg tgcaggatag ggtatgaccg atgtgaggag gatgatcatg 12960
acgagctagg gtttatggta ccgcctggcc tctccagcga aggccacttg actagtgttt 13020
acgcctggtt ggcgttcttg tccttcagct acacggccca gttccatccc gagatattcg 13080
ggatagggaa tgtgagtcga gtttatgttg acatcaaaca tcaactcatc tgcgccgaac 13140
atgacgggca gaacaccacc ttgcctcgtc atgacaacat ttcagccgtg tttcagacct 13200
attaccaaca tcaagtcgat ggcggcaatt ggtttcacct agaatggctt cgtcccttct 13260
tttcctcgtg gctggtttta aatgtctctt ggtttctcag gcgttcgcct gcaaaccatg 13320
tttcagttcg agtctcgcag atattgagac caacaccacc gcagcggcaa gctttgctgt 13380
cctccaagac atcagttgcc ttaggcatcg cgactcggcc tctgaggcga ttcgcaaaat 13440
ccctcagtgc cgtacggcga tagggacacc cgtgtatatt actatcacag ccaatgtgac 13500
agatgagaat tatttacatt cttctgatct cctcatgctt tcttcttgcc ttttctatgc 13560
ttctgagatg agtgaaaagg gatttaaggt ggtatttggc aatgtgtcag gcatcgtggc 13620
tgtgtgtgtc aattttacca gctacgtcca acatgtcaag gagttcaccc aacgctccct 13680
ggtggtcgac catgtgcggt tgctccattt catgacacct gagaccatga ggtgggcaac 13740
tgttttagcc tgtcttgttg ccattctgtt ggcaatttga atgtttaagt atgttggaga 13800
aatgcttgac cgcgggctgt tgctcgcaat tgctttcttt gtggtgtatc gtgccgttct 13860
gttttgctgt gctcgccaac gccagcagcg acagcagctc ccatctacag ctgatttaca 13920
acttgacgct atgtgagctg aatggcacag attggctagc tgacaaattt gattgggcag 13980
cggagagttt tgtcatcttt cccgttttga ctcacattgt ctcctatggt gccctcacta 14040
ctagccattt ccttgacacg gtcgctttag ccactgtgtc taccgccggg tttgttcacg 14100
ggcggtatgt cctaagtagc atctacgcgg tctgtgccct ggctgcgttg acttgcttcg 14160
tcattaggtt tgcaaagaat tgcatgtcct ggcgctacgc gtgtaccaga tataccaact 14220
ttcttctgga cactaagggc agactctatc gttggcggtc gcctgtcatc atagagaaaa 14280
ggggcaaagt tgaggtcgaa ggtcatctga tcgacctcaa aagagttgtg cttgatggtt 14340
ccgtggcaac ccctataacc agagtttcag cggaacaatg ggtcgtcct tagatgactt 14400
ctgtcatgat agcacggctc cagaaaaggt gcttttggcg ttttctatta cctacacgcc 14460
agtgatgata tatgccctaa aggtgagtcg cggccgactg ctagggcttc tgcacctttt 14520
gatcttcctg aattgtgctt tcaccttcgg gtacatgact ttcgcgcact ttcagagtac 14580
aaataaggtc gcgctcacta tgggagcagt agttgcactc ctttgggggg tgtactcagc 14640
catagaaacc tggaaattca tcacctccag atgccgtttg tgcttgctag gccgcaagta 14700
cattctggcc cctgcccacc acgttgaaag tgccgcaggc tttcatccga ttgcggcaaa 14760
tgataaccac gcatttgtcg tccggcgtcc cggctccact acggtcaacg gcacattggt 14820
gcccgggtta aaaagcctcg tgttgggtgg cagaaaagct gttaaacagg gagtggtaaa 14880
ccttgtcaaa tatgccaaat aacaacggca agcagcagaa gagaaagaag gggggatggcc 14940 agccagtcaa tcagctgtgc cagatgctgg gtaagatcat cgctcagcaa aaccagtcca 15000
gaggcaaggg accgggaaag aaaaataaga agaaaaaccc ggagaagccc cattttcctc 15060
tagcgactga agatgatgtc agacatcact ttacccctag tgagcggcaa ttgtgtctgt 15120
cgtcaatcca gaccgccttt aatcaaggcg ctgggacttg caccctgtca gattcaggga 15180
ggataagtta cactgtggag tttagtttgc ctacgcatca tactgtgcgc ctgatccgcg 15240
tcacagcatc accctcagca tgatgggctg gcattcttga gacatctcag tgtttgaatt 15300
ggaagaatgt gtggtgaatg gcactgattg acattgtgcc tctaagtcac ctattcaatt 15360
agggcgaccg tgtgggggtg agatttaatt ggcgagaacc atgcggccga aattaaaaaa 15420
aaaaaaaaaa aaaaaaaaaa aaaa 15444

<210> SEQ ID NO 3
<211> LENGTH: 15013
<212> TYPE: DNA
<213> ORGANISM: Artificial Sequence
<220> FEATURE:
<223> OTHER INFORMATION: Synthetic Construct

<400> SEQUENCE: 3
atgacgtata ggtgttggct ctatgccacg gcatttgtat tgtcaggagc tgtgaccatt 60
ggcacagccc aaaacttgct gcacggaaaa cgcccttccg tgacagcctt cttcagggga 120
gcttaggggt ctgtccctaa caccttgctt ctggagttgc actgctttac ggtctctcca 180
accctttaac catgtctggg atacttgatc ggtgcacgtg cacccccaat gccagggtgt 240
ttatggcgga gggccaagtc tactgcacac gatgtctcag tgcacggtct ctccttcctc 300
tgaatctcca agtttctgag cttggagtgc tgggcctatt ttataggccc gaagagccac 360
tccggtggac gttgccacgt gcatacccca ctgtcgagtg ctcccccgcc ggggcctgct 420
ggctttctgc gatctttcca attgcacgaa tgaccagtgg gaacctgaac tttcaacaaa 480
gaatggtgcg ggtcgcagct gagatttaca gagtcggtca gctcaccccc acagtcttga 540
agaatctaca agtttatgaa cggggttgcc gctggtaccc cattgtcgga cctgtccctg 600
gagtggccgt tttcgccaat tccctacatg tgagtgacaa accttttccg ggagcaactc 660
atgtgttaac taatctaccg ctcccgcaga ggcccaagcc tgaagacttt tgtccttttg 720
agtgtgctat ggctgacatc tatgacattg gtcatgacgc cgtcatgtat gtggccggag 780
ggaaagtctc ctgggcccct cgtggcgggg atgaagggaa atttgaaact gtccccgagg 840
agttgaagtt aattgcgaac cgacttcaca tctccttccc gccccaccac gtagtggaca 900
tatctaagtt tgcctttata gcccccggga gtggtgtctc catgcgggtt gagtgccaac 960
atggctgcct ccccgctgat actgttcctg gagggaactg ctggtggcgc ttgttcgact 1020
cgctcccacc ggaagttcag aataaagaaa ttcgctatgc taaccaattt ggttatcaaa 1080
ccaagcatgg tgtctctggc aagtacctac agcggaggct gcaagttaat ggtctccgag 1140
cagtgactga tacaagtggg cctatcgtcg tacagtattt ctctgttaag gagagttgga 1200
tccgccactt aaggctggcg gaagaaccta gcctccctgg gtttgaggac ctcctcagaa 1260
taagggttga gcccaatacg tcaccattgg ttggcaagga tgtgaaaatc ttccggtttg 1320
gcaatcacaa atggtacggc gctggaaaga gagcaaggaa atcacgctct ggtgcgactg 1380
ccacggtcgc tcaccgcgct ttacccgttc gtgaaaccct gcaggctaag aggcgcgagg 1440
ttgccagcgc caacagggct gagcatatca agcactatta tccgccagcc gacggaaact 1500
gtggttggca ctgcatttcc gctattgtca accggatggt gaattctaaa tttgaaactg 1560

-continued ctcttcccga gagagcgaga ccttctgatg actgggctac tgacgaggac cttgtgaata 1620
ccatccaaat cctcagactc cctgcggcct tggacaggga cggtgcttgt gttagcgcca 1680
agtacgtgct taaactagaa ggcgagcatt ggactgtctc tgtgacccct gggatgtccc 1740
cttctttgct ccccccttgaa tgtgttcagg gctgttgtga acataagaac ggccttggtc 1800
ccccagatgc ggtcgaaagt tttggatttg accctgcctg ccttgaccga ctggctgagg 1860
taatgcactt gcctagtagt gtcatcccag ctgctctggc cgaaatgtcc ggtgacccca 1920
attgtccggc atccccggtc accactgtgt ggactgtttc acaattcttt gcccgccaca 1980
gaggaggaga gcaccctgat caggtgcgct taggaaagat catcagcctt tgtcaagttg 2040
ttgaggaatg ctgttgccat cagaataaaa ccaaccgggc caccccggaa gaggtcgcgg 2100
caaagattaa tcagtacctc catggtgcaa caagtcttga agactgcttg actaggcttg 2160
agagggcttg cccgccgagt gctgcggaca ccttctttga ttggaacgtt gtgctccctg 2220
gggttgaggc tgcaactccg ccacccccctc caccaagagt tcagcctcga aaaacaaagt 2280
ctgtcaagag cttgccggga aacaatcctg tccccgctcc acgcaggaag gttagatctg 2340
actgtggcag cccgattttg acgggcgaca atgatctttc gacgccatcc gagccgatga 2400
catctctgaa tgagcctgcg cttatgcctg cgttgcaatg tatctctagg ccagtgacat 2460
ctttgagtgt gccggcccca gttcctgcac cgcgtagagc tgtgtcccga ccggtgacgc 2520
ccttgagtga gccagttttt ttgtctgcac cgcgacacaa atttcagcag gtgaaagaag 2580
cgaatctggt ggcaacaacg ctgatgtgcc aggacgaacc tctagatttg tctgcatcct 2640
cacagactga atatgaagct tcccccccag caccactgca gaacatgggt attctggagg 2700
tggggggaca agaagctgtg gaagttctga gtgaaatctc ggatacactg aatgacacca 2760
accctgcacc tgtgtcatca agcagctccc tgtcaagtgt taagatcaca cgcccaaaat 2820
actcagctca agccatcatt gattcgggcg ggccctgcag tgggcacctc cgaaggggaa 2880
aagaagcatg cctcagcctc atgcgtgagg cttgtgatgc ggctaagctt agtgaccctg 2940
ccacgcaaga atggctttct cgcatgtggg atagggttga catgctgacc tggcgcaaca 3000
cgtctgccta ccaggcgttt cgcatcttag atggtaggtt tgagtttctc ccaaagatga 3060
tactcgagac accgccgccc tacccgtgtg ggtttgtgat gctgcctcac acgcctgcac 3120
cttccgtgag tgcagagagc gaccttacca ttggttcagt cgccactgaa gatgttccac 3180
gcattctcgg gaaaatagaa aacgccggcg agacgcccaa ccaggggctc ttggcaccct 3240
tcggggaaga accggtgtgc gaccaacctg tcaaagactc ccggatgttg tcgcgggggt 3300
ttgacgagag cacgacggct ccgtccgcag gtacaggtgg cgctgactta cccactgatt 3360
tgccaccttc agatggtgtg gatgcggacg gggtggggct gttacggacg gtaagaaaga 3420
aagctgaaag gctcttcgac caattgagcc gtcaggtttt taacctcgtc tcccatctcc 3480
ctgttttctt ctcacacctc ttcaaatctg acagtggtta ttctccgggt gattggggtt 3540
ttgcagcttt tactttattt tgcctctttt tatgttacag ctacccattc ttcggtttcg 3600
ctcccctctt gggtgtgttt tctgggtctt ctcggcgcgt gcgcatgggg gtttttggct 3660
gctggttggc ttttgctgtt ggcctgttca agcctgtgtc cgacccagtc ggcactgctt 3720
gtgagtttga ctcgccagag tgtaggaacg tccttcattc ttttgagctt ctcaaacctt 3780
gggaccctgt ccgcagcctt gttgtgggcc ccgtcggtct cggtcttgcc attcttggca 3840
ggttactggg cggggcacgc tacatctggc attttttcct taggcttggc attgttgcag 3900
attgcttctt ggctggagct tatgtgcttt ctcaaggtag gtgtaaaaaa tgctggggat 3960
cttgtgtaag aactgctcct aatgaaatcg ccttcaacgt gttccctttt acgcgtgcga 4020
ccaggtcgtc actcatcgac ctgtgcgatc ggttttgtgc gccaaaaggc atggacccca 4080
ttttcctcgc tactgggtgg cgtgggtgct ggaccggccg gagtcccatt gagcaaccct 4140
ctgaaaaacc tatcgcgttc gcccagttgg atgagaagag gattacggct agaactgtgg 4200
tcgttcagcc ttatgatcct aaccaagccg taaagtgctt gcgggtgtta caggcgggtg 4260
gggcgatggt ggccgaggca gtcccaaaag tggtcaaggt ttccgccatt ccattccgag 4320
ctcccttttt tcccaccgga gtgaaggttg atcctgagtg caggatcgtg gtcgaccccg 4380
acacttttac tacagctctc cggtctggtt actccaccac aaacctcgtc cttggtgtgg 4440
gggactttgc ccaactgaat ggattaaaaa tcaggcaaat ttccaagtct tcgggggag 4500 gcccacacct cattgctgcc ctgcatgttg cttgctcgat ggcgttgcac atgcttgctg 4560
gggtttatgt aactgcagtg gggtcttgcg gtaccggcac caatgatccg tggtgcacta 4620
acccattcgc cgtccctggc tacggacctg gctctctctg cacgtccaga ttgtgcatct 4680
cccaacatgg ccttaccctg cccttgacag cacttgtggc aggattcggt cttcaggaaa 4740
ttgccttagt cgttttgatt tttgtttcca tcggaggcat ggctcatagg ttgagttgca 4800
aggctgatat gctgtgcgtc ttacttgcaa tcgcaagcta tgtttgggta ccccttacct 4860
ggttgctctg tgtgtttcct tgctggttgc gctggttctc tttgcaccct ctcaccatcc 4920
tatggttggt gtttttctta atttccgtaa atatgccttc gggaatcttg gccgtggtgt 4980
tattggttgc tctttggctt ctaggccgtt atactaatgt tgttggtctt gttaccccct 5040
atgatattca tcatcacacc agtggccccc gcggtgttgc cgccttggct accgcaccgg 5100
atgggactta tttggccgct gtccgccgcg ctgcgttgac tggccgcacc gtgttgttta 5160
ccccgtccca gcttgggtcc ctccttgagg gcgctttcag aactcgaaag ccctcactga 5220
acaccgtcaa tgtggtcggg tcctctatgg gctctggcgg agtgttcact atcgatggga 5280
aaattaagtg cgtgactgcc gcacatgtcc ttacgggtaa ttcagctagg gtttccgggg 5340
ttggcttcaa tcaaatgctt gactttgatg taaaagggga cttcgccata gctgattgcc 5400
cgaattggca aggggctgct cctaagaccc aattctgcga ggatgggtgg actggccgtg 5460
cctattggct gacatcctct ggtgtcgaac ccggcgtcat tgggaatgga ttcgccttct 5520
gcttcaccgc gtgcggcgat tctgggtccc cagtgatcac cgaagccggt gagcttgtcg 5580
gcgttcacac aggatcaaat aaacaaggag gaggcattgt tacgcgcccc tcaggccagt 5640
tttgtaatgt ggcacccatc aagctgagcg aattaagtga gttctttgct ggacctaagg 5700
tcccgctcgg tgatgtgaag gttggcagcc acataattaa agatatatgc gaggtacctt 5760
cagacctttg cgccttgctt gccgccaaac ccgaattgga aggaggcctc tccaccgtcc 5820
aacttttatg tgtgtttttc ctcctgtgga gaatgatggg acatgcctgg acacccttgg 5880
ttgctgtggg ttttttttatc ttgaatgaag tcctcccagc tgtcctggtc cggagtgttt 5940
tctcctttgg aatgtttgtg ctatcttggc tcacaccatg gtctgcgcaa gttctgatga 6000
tcaggcttct aacagcagct ctcaacagga acagattgtc actcgccttt tacagccttg 6060
gtgcggcgac cggctttgtc gcagatctgg cggcaactca agggcatccg ttgcaagcag 6120
taatgaattt aagtacctat gccttcctgc ctcggatgat ggttgtgacc tcaccagtcc 6180
cagttattgc gtgtggtgtc gtgcacctcc ttgccataat tttgtacttg tttaagtacc 6240
gctgcctgca caatgttctt gttggcgatg gagcgttctc tgcggctttc tttttgcgat 6300

```
actttgccga ggggaaattg agggaagggg tgtcgcaatc ctgcgggatg aatcatgagt   6360
cgctgactgg tgccctcgct atgagactca atgacgagga cttggatttc cttacgaaat   6420
ggactgattt taagtgcttt gtttctgcgt ccaacatgag gaatgcggcg ggccagttca   6480
tcgaggctgc ctatgcaaaa gcacttagaa ttgaacttgc ccagttggtg caggttgata   6540
aggttcgagg tactatggcc aaacttgaag cttttgctga taccgtggca ccccaactct   6600
cgcccggtga cattgttgtt gctcttggcc atacacctgt tggcggtatc ttcgacctaa   6660
aggttggtag caccaagcac accctccaat ccattgagac cagagtcctt gccgggtcca   6720
aaatgaccgt ggcgcgtgtc gttgacccaa cccccacacc cccacccgca cccgtgccca   6780
tccccctccc accgaaagtt ctggagaatg gtcctaacgc ctggggggat gaggatcgtt   6840
tgaacaagaa gaagaggcgc aggatggaag ccgtcggcat ctttgttatg ggtggaaaga   6900
aataccagaa attttgggac aagaattccg gtgatgtgtt ttatgaggag gtccatgata   6960
acacagacgc gtgggagtgc ctcagagttg acaaccctgc cgactttgac cctgagaagg   7020
gaactctgtg tgggcatact accattgaag gtaaggctta caatgtctac gcctccccat   7080
ctggcaagaa gtttctggtc cccgtcaacc cagagagtgg aagagcccaa tgggaagctg   7140
caaagctttc cgtggagcag gcccttggca tgatgaatgt cgacggtgag ctgacagcca   7200
aagaactgga gaaactgaaa agaataattg acaaactcca gggtctgact aaggagcagt   7260
gtttaaactg ttagccgcca gcggcttgac ccgctgtggt cgcggcggct tggttgttac   7320
tgagacagcg gtaaaaatag tcaaatttca caaccggacc ttcaccctag gacctgtgaa   7380
cttaaaagtg gccagtgagg ttgagctaaa agacgcggtc gagcacaacc aacacccggt   7440
tgcaagaccg gttgatggtg gcgttgtact cctgcgcccc gcagttcctt cgcttgtaga   7500
tgtcttgatc tctggcgctg atgcatcccc taagttactc gcccgccatg ggccgggaaa   7560
cactgggatc gatggcacgc tttgggattt tgagaccgaa gccaccaaag aggaaattac   7620
acttagtgcg caaataatac aggcttgtga cattaggcgc ggcgacgcac ctgaaattgg   7680
tctcccttat aagctgcacc ctgttagggg caaccctgag cggataaaag gagttttaca   7740
gaatacaagg tttggggaca taccttacaa aacccccagt gacactggca gcccagtgca   7800
tgcggctgcc tgcctcacgc ccaatgccac tccggtgacc gatgggcgct ccgtcttggc   7860
tacgactatg ccctccggtt ttgagttgta tataccgacc attccatcgt ctgtccttga   7920
ttatcttgat tctaggcctg actgccccaa acagttaaca gagcacggct gtgaggatgc   7980
cgcattgaga gacctctcca agtatgactt gtccacccaa ggctttgttt tgcctggagt   8040
tcttcgccta gtgcgtaagt acctgtttgc tcatgtgggt aagtgcccgc ccgttcatcg   8100
gccttccact tatcctgcca agaactctat ggctggaata aatgggaaca ggtttccaac   8160
caaggacatt cagagcatcc ctgaaatcga cgttctgtgc gcacaggctg tgcgagaaaa   8220
ctggcaaact gttacccctt gcaccctcaa gaaacaatat tgtgggaaga agaagactag   8280
gacaatactc ggcaccaata acttcgttgc gttggcccac cgggcagcgt tgagtggtgt   8340
cacccagggc tttatgaaaa aggcgtttaa ctcgcccatt gccctcggga aaaacaaatt   8400
taaagagcta cagactccgg tcttaggcag gtgccttgaa gctgatcttg catcctgcga   8460
tcggtccaca cctgcaattg tccgctggtt tgccgccaat cttctttatg aacttgcctg   8520
tactgaagaa catctaccgt cgtacgtgct gaactgctgc cacgacctac tggtcacgca   8580
gtccggcgcg gtgactaaga gaggtggcct gtcgtctggc gacccgatta cctctgtgtc   8640
```

-continued

```
aaacaccatt tacagcttag tgatatatgc acagcacatg gtgctcagtt actttaaaag   8700
tggtcaccct cacggccttc tgtttctgca agaccagcta aagtttgagg acatgctcaa   8760
ggttcaaccc ctgatcgtct attcggacga cctcgtgctg tatgccgagt ctcccaccat   8820
gccaaactac cactggtggg ttgaacatct gaatcttatg ttgggttttc aaacggaccc   8880
aaggaagaca gccataacag actcaccatc ttttctaggc tgtagaataa taaatgggcg   8940
ccagctagtc ccccaccgtg acaggattct cgcggccctt gcctaccata tgaaagcaag   9000
caatgtttct gaatattacg cctcggcggc tgcaatactc atggacagct gtgcttgttt   9060
agagtatgat cctgaatggt ttgaagagct cgtggttggg atggcgcagt gcgcccgcaa   9120
ggacggctac agttttcctg gcccgccgtt cttcttgtcc atgtgggaaa aactcaggtc   9180
caaccacgag ggaaagaagt ccagaatgtg cgggtactgc ggggccccgg ctccgtacgc   9240
cactgcctgt ggcctcgatg tctgtgttta ccacacccac ttccaccagc attgtccagt   9300
cataatctgg tgtggccatc cggcgggttc tggttcttgt agtgagtgca aacccccct   9360
agggaaaggc acaagccctc tggatgaggt gttggaacaa gtcccgtaca agcctccgcg   9420
gactgtaatc atgcatgtgg agcagggtct caccctctt gacccaggta gataccaaac   9480
tcgccgcgga ttagtctccg ttaggcgtgg catcagggga aatgaagttg acctaccaga   9540
cggtgattat gccagtaccg ccctgctccc tacttgtaaa gagatcaaca tggtcgctgt   9600
cgcctctaat gtgttgcgca gcaggttcat catcggtccg cccggtgctg ggaaaacata   9660
ctggctcctt caacaggtcc aggatggtga tgtcatttac acaccaactc accagaccat   9720
gcttgacatg attagggctt tgggggcgtg ccggttcaac gtcccagcag gcacaacgct   9780
gcaattccct gccccctccc ataccggccc gtgggttcgc atcctagccg gcggttggtg   9840
tcctggtaag aattccttcc tggatgaagc agcgtattgt aatcaccttg atgtcttgag   9900
gctccttagc aaaactaccc tcacctgtct aggagatttc aaacaactcc acccagtggg   9960
ttttgattct cattgctatg tttttgacat tatgcctcag actcaactga agaccatctg  10020
gagatttgga cagaatatct gcgatgccat tcagccagat tacagggaca aacttgtatc  10080
catggtcaac acaacccgtg taacctactt ggaaaaacct gtcaagtatg ggcaagtcct  10140
cacccttac cacagggacc gagaggacgg cgccatcaca attgactcta gtcaaggcgc  10200
cacatttgat gtggttacac tgtatttgcc cactaaagat tcactcaaca ggcaaagagc  10260
ccttgttgct atcaccaggg caagacatgc tatctttgtg tatgacccac acaggcaact  10320
gcagagcatg tttgatcttc ccgcgaaagg cacacccgtc aacctcgctg tgcaccgtga  10380
cgagcagctg atcgtactag atagaaacaa caaagaatgc tcggttgctc aggctctagg  10440
caatggggat aaattcaggg ccacagacaa gcgcgttgta gattctctcc gcgccatttg  10500
tgcagatctt gaagggtcga gctccccgct tcccaaggtc gcacacaact tgggatttta  10560
tttctcgcct gatttgacac agtttgccaa actcccggta gaacttgcac cccactggcc  10620
cgtggtgaca acacagaaca atgaaaagtg gccagaccgg ttggttgcta gccttcgccc  10680
tgtccataag tatagccgcg cgtgcatcgg tgccggctac atggtgggcc cctcagtgtt  10740
tctaggcacc cctggggttg tgtcatacta tctcacaaaa tttgtcaggg gcgaggctca  10800
aatgcttccg gagacagtct tcagcaccgg ccgaattgag gtagattgcc gggagtacct  10860
tgatgaccgg gagcgagaaa ttgctgagtc cctcccccat gctttcattg gtgacgtcaa  10920
aggtactacc gttggaggat gtcaccatgt cacctccaaa taccttccgc gcttccttcc  10980
caaggaatca gtcgcggtag tcggggtttc aagccccggg aaagccgcaa aagcagtttg  11040
```

-continued

```
cacattaaca gatgtgtatc tcccagacct tgaagcttac ctccacccag agacccagtc  11100
caagtgctgg aaaatgatgt tggacttcaa ggaagttcga ctgatggtct ggaaaggcaa  11160
gacggcctat tttcaacttg aaggccgcca tttcacctgg tatcagcttg caagctacgc  11220
ctcgtacatc cgagtacctg ttaattctac ggtgtatttg gacccctgca tgggccctgc  11280
cctttgcaac agaagagttg tcgggtccac ccattgggga gccgacctcg cagtcacccc  11340
ttatgattac ggtgccaaag tcattctgtc tagtgcatac catggtgaaa tgcctcctgg  11400
gtacaaaatc ctggcgtgcg cggagttctc gcttgacgat ccagttaggt acaaacgcac  11460
ctgggggttt gaatcggata cagcgtatct gtatgagttc accggaaacg gtgaggactg  11520
ggaagactac aatgatgcgt ttcgtgcgcg ccagaaaggg aaaatttata aggccactgc  11580
caccagcatg aggtttcatt ttcccccggg ccctgttatt gaaccaactt taggcctgaa  11640
ttgagatgaa atggggtcta tgcaaagcct ctttaacaaa attggccaac tttttgtgga  11700
tgctttcacg gaatttttgg tgtccattgt tgatatcatc atatttttgg ccattttgtt  11760
tggcttcacc atcgcaggtt ggctggtggt cttctgcatc agattggttt gctccgcggt  11820
actccgtgcg cgccctgcca ttcaccctga gcaattacag aagatcctat gaggcctttc  11880
tttctcagtg ccgggtggac attcccacct ggggaactaa acatcctttg ggatattgt   11940
ggcaccataa ggtgtcaacc ctgattgatg aaatggtgtc gcgtcgaatg taccgcacca  12000
tggaaaaagc aggacaggct gcctggaaac aggtggtgag cgaggccacg ttgtctcgca  12060
ttagtggttt ggatgtggtg gctcattttc agcatcttgc cgccattgaa gccgagacct  12120
gtaaatattt ggtttctcgg ctgcccatgc tacacaacct gcgcatgaca gggtcaaatg  12180
taaccatagt gtataatagc actttaaatc aggtgtttgc catttttcca acccctggtt  12240
cccggccaag gcctcatgat tttcagcaat ggctaatagc tgtgcattcc tccatatttt  12300
cctctgttgc ggcttcttgt actctttttg ttgtgctgtg gttgcggatc ccaatgctac  12360
gtactgtttt tggtttccac tggtcagggg caatttttct ttcgaactca cggtgaatta  12420
cacggtgtgc ccaccttgcc tcacccggca agcagccgct gagatctacg aatccggcag  12480
gtctctttgg tgcaggatag ggcatgaccg atgtagtgag gacgatcacg acgaactagg  12540
gttcatggtt ccgcctggcc tctccagcga aggccactta accagtgttt atgcctggtt  12600
ggcgttcctg tctttcagct acacggccca attccatccc gagatatttg ggatagggaa  12660
tgtgagtaaa gtttatgttg acgtcaagca ccaattcatc tgcgccgttc atgacggaca  12720
aaacaccacc ttgccccgcc atgacaacat ttcagccgta tttcagacct actatcaaca  12780
tcaggtcgac ggcggcaatt ggttccacct agaatggctg cgtcccttct tttcctcttg  12840
gttagtttta aatgtttcgt ggtttctcag gcgttcgcct gcaagccatg tttcagttca  12900
agtctttcag acatcaaaac caacaccact gcagcatcag gcttcgttgt cctccaggac  12960
atcagctgcc ttaggtatgg cgactcgtcc tctccgacga ttcgcaaaag ctctcaatgc  13020
cgcacggcga tagggacacc cgtgtatatt accatcacag ccaatgtgtc agacgagaat  13080
tacttacatt cttcagatct cctcatgctt tcttcttgcc ttttctatgc ctctgagatg  13140
agtgaaaagg ggttcaaggt gatatttggc aatgtttcag gcattgtggc tgtgtgtgtc  13200
aactttacca gctacgtcca acatgttagg gagttcaccc aacgctctct ggcggtcgat  13260
catgtgcggc tgcttcattt catgacacct gagaccatga ggtgggcaac cgttttagcc  13320
tgtcttgttg ccatcctttt ggcaatttga atgtttaagt atgttgggga aatgcttgac  13380
```

cgcgggctat tgctcgcgat tgcctttttt gtggtgtatc gtgccgttct gttttgctgt 13440
gatcgtcaac gccagcagca acagcagctc tcattttcag tcgatttata acttgacgct 13500
atgtgagctg aatggcacag attggctggc tggtaaattt gattgggcag tggagacttt 13560
tgttatcttt cccgtgttga ctcacattgt ttcctatggt gcacttacca ccagccattt 13620
ccttgacaca gttggtctgg ttattgtgtc caccgccggg ttttatcatg ggcggtatgt 13680
cttgagtagc gtctacgcag tctgtgccct ggctgcgttg attcgctttg tcattagatt 13740
tgcgaagaac tgcatgtcct ggcgctactc atgtaccaga tataccaact tccttctaga 13800
taccaagggc aaactctatc gttggcggtc gcctgttatc atagagaaag gggtaaggt 13860 tgaggtcgaa ggtcacctga tcgacctcaa aagagttgtg cttgatggtt ccgtggcaac 13920
tcctttaacc agagtttcag ctgaacaatg ggtcgtccc tagacgactt ttgcaatgat 13980
agcacggctc cgcaaaaggt gcttctggcg ttttccatta cctacacgcc agtgatgata 14040
tatgctctga aggtaagtcg cggccgcctg ctagggcttc tgcacctttt aatctttctg 14100
aattgtgctt tcaccttcgg gtacatgaca ttcgcgaact ttcagagcac aaacagggtt 14160
gcgctcacta tgggagcagt agttgcactt ctttgggggg tgtactcagc catagaaacc 14220
tggaaattca tcacctccag atgccgtttg tgcttgctag gccgcaggta cattctggcc 14280
cctgcccacc acgtcgaaag tgtcgcaggc tttcatccga ttgcggcaag tgataaccac 14340
gcatttgtcg tccggcgtcc cggctccact acggttaacg gcacattggt gcccgggttg 14400
aaaagcctcg tgttgggtgg cagaaaagct gttaaacagg gagtggtaaa ccttgtcaaa 14460
tatgccaaat aacaatggca ggcagcaaaa aagaaataag gggacggcc agccagtcaa 14520 tcagctgtgt cagatgctgg gtaagatcat cgcccagcaa aatcagtcca gaggcagggg 14580
accggggaag aaaaataaaa agaaaaaccc ggagaagccc cattttcctc tagcgaccga 14640
agatgacgtc aggcatcact tcacccctag tgagcggcaa ttgtgtctgt cgtcgatcca 14700
gactgccttt aaccagggcg ctggaacttg taccctgtca gattcaggga ggataagtta 14760
cactgtggag tttagtttgc cgacgcatca cactgtgcgc ctgattcgcg ccacagcatc 14820
accctcagcg tgatgggctg gcattcttga agcacctcag tgttagaatt ggaagaatgt 14880
gtggtggatg gcactgattg acactgtgcc tctaagtcac ctattcaatt agggcgaccg 14940
tgtgggggta aagtttaatt ggcgagaacc atgcggccga aattaaaaaa aaaaaaaaaa 15000
aaaaaaaaaa aaa 15013

<210> SEQ ID NO 4
<211> LENGTH: 15444
<212> TYPE: DNA
<213> ORGANISM: Artificial Sequence
<220> FEATURE:
<223> OTHER INFORMATION: Artificial Construct

<400> SEQUENCE: 4
atgacgtata gttgttggct ctatgtcgtg acatttgtat agtcaggagc tgcgaccatt 60
ggtacagccc aaaacttgct gcgcgggaac gcccttccgt gacagccttc ttcaggggag 120
tttaggggtc tatccctagc accttgcttc cggagttgca ctgctttacg gtctctccac 180
ccctttaacc atgtctggga tacttgatcg gtgcacgtgt acccccaatg ccagggtgtt 240
tgtggcggag ggccaagtct actgcacacg atgtctcagt gcacggtctc tccttccttt 300
gaatctccaa gtttctgagc ttggggtgct gggcttattt tataggcccg aagagccgct 360
ccggtggacg ttgccacgtg cattccccac tgtcgagtgc tcccccgccg ggcctgctg 420

```
gctttctgcg atttttccaa ttgcacgaat gaccagtgga aacctgaact ttcaacaaag    480
aatagtgcgg gtcgcagctg agctctacag agccggtcag ctcacccccg tagtcttgaa    540
gaatctacag gtttatgaac ggggttgccg ttggtacccc atcgttggac ctgttcctgg    600
agtggctgtt tatgccaatt ccttacacgt gagtgacaaa cctttcccgg gagcaactca    660
tgtgttaacc aacctaccgc tcccgcagag gcccaagcct gaagactttt gcccctttga    720
gtgtgctatg gctgacgtct atgacattgg tcatgacgct gtcatgtatg tggccggagg    780
gagagtctcc tgggcccctc gtggcgggga caaaggaaaa tttgaaatag ttcccaagga    840
gttgaagttg attgcgaatc gactccacat ttccttcccg ccccaccacg cagtggacat    900
gtccaagttt gcctttataa gccctgggag tggtgtttcc atgcgggtcg agtaccaaca    960
tggctgtctc cccgctgata ctgtccctga aggaaactgt tggtggcgct tgtttgactt   1020
gcttccaccg gaagttcaga acaaagagat tcgccatgct aaccaactcg gctatcagac   1080
caagcatggt gtcgctggca agtacctaca gcggaggctg caagttaatg gactccgagc   1140
agtaactgac gcgaatggac ctatcgtcat acagtatttt tgtgataggg aaagctggat   1200
ccgccactta agactggtag aagaacctag cctccctggg tttgaggacc tcctcagaat   1260
aagagttgag cccaatacgt tgccattggt tggcgaggat gagaaaatct tccgatttgg   1320
caatcacaaa tggtacggtg ctggaaagag ggcaaggaaa gcacgctttg gtgcggctgc   1380
cacggtcgct caccgcgctt tgcccgctca cgaaacccag caggccaaga agcacgaagt   1440
taccagcgcc aacagggctg agcatctcga gcactattcc ccgcctaccg acgggaactg   1500
tggttggcac tgcgtttccg ccattgtcaa ccggattgtg aattccaaat ttgaaaccac   1560
ccttcccgag agagtgagac ctttagatga ctgggctact gacgaggatc ttgtgaatac   1620
tatccaaatc ctcaggctcc ctgcggcctt ggacaggaac ggtgcttgtg tcggcgccaa   1680
gtacgtgctc aagctggaag gtgtgcactg gacagtctct gtggcccctg ggatgacccc   1740
ttctctgctc cccccttgaat gtgttcaggg ctgttgtgag cataagagcg gtcttggtcc   1800
cccagatgtg gctgaagttt ccggatttga ccctgcctgc cttaaccgac tggctgaggt   1860
aatgcacttg cctagttgtg tcatcccagc tgctctggct gaaatgtccg acgaccccaa   1920
tcgcccggct tccccagtca ccactgtgtg gactatttcg caattctttg cccattatag   1980
aggaggagag caccctgatc aggtgtgctt agggaaaatc atcagccttt gtcaggtgat   2040
tgaggaatgc tgttgttccc agaacaaaac caaccgggcc accccggaag aggtcgcggc   2100
aaaaattgac cagtacctcc gtgatgcagc aagccttgga gaatgcttag ccaagcttga   2160
gagggctcgc ccgccgagcg cgatggacac ctcctttgat tggaatgttg tgcttcctgg   2220
ggttgaggcg gcgaaccaga cgaccaaaca gctccatgtc aaccagcacc gtgctccggt   2280
tcctgccatg actcaggagc ctttggacaa agactcggtc cctttgaccg ccttctcgct   2340
gtctaattgc tactaccctg cacaaggtga cgaggttcgt caccgtgaga ggctgatctc   2400
cgtgctctct aagttggagg aggttgttcg tgaggaatat gggctcacgc caactggatc   2460
tggcccgcga cccgcactgc cgaacgggct cgacgagctc aaagaccaga tggaagagga   2520
tctgttgaaa ctggtcaacg cccaggcaac ttcagaaatg atggcccggg cagctgagca   2580
ggttgatcta aaagtttggg tcaaaaatta cccacggtgg acaccgccac cccctccacc   2640
aagagttcag cctcgaaaaa caaagtctgc taagagcctg ccagagaaca agcctgtccc   2700
tgctccgcgc aggaaagtca gatctgattg tggcagcccg actttgaggg gcaacaatgt   2760
```

```
tcctaacggt tgggaagact tggccgttgg tggtcctctt gatctttcga caccatccga   2820
gccgatgaca cctctgagtg agcctgcact tatgcccgtg ttgcaacata tttctggacc   2880
agtgacgcct ttgagcgtgc cggcccctat tcctgcaccg cgtaaagctg tgtcccgacc   2940
gatggcgccc tcgagtgagc caatttttgt gtctgcaccg cggcaaaaat ttcagcaggt   3000
ggaagaagca aatctggcgg caacaacgct gacataccag gacgaaccta tagatctgtc   3060
agcatcctca cagactgaat atgaggctcc ttccctagca ccactgcaga acataggtac   3120
tctggaggtg ggggggcaag aagctgagga aattctgagt gaaacctcgg atataccgaa   3180
tgacatcaac cctgtgcctg tatcatcaag cagctccttg tcaagcgtta agatcacacg   3240
cccaagacac tcagctcaag ccatcatcga ctcgggcggg ccctgcagtg ggcatctcca   3300
aagggagaaa gaagcgtgcc tccgcatcat gcgtgaggct tgtgatgcga ctaagcttag   3360
tgaccctgcc acgcaggaat ggctttctcg catgtgggat agggtggaca tgctgacttg   3420
gcgcaacacg tctgctttcc aggcgtttcg catcttagac ggcaggcttg agtttcttcc   3480
aaagatgata ctcgagacgc cgccgcccta cccgtgtggg tttgtgatgc tgcctcacac   3540
ccctgcacct tccgtgagtg cagagagcga ccttaccatc ggttcagtcg ccactgaaga   3600
tattccacgc atcctcggga aaatagaaaa caccagtgag atgatcaacc agggaccctt   3660
ggcatcctct gaggaaaaac cggcatacaa ccaacccgct aaggactccc tgatatcgtc   3720
gcgggggttt gacgagagca cagcagctcc gtccgcaggt acgggtggcg ccggcttgtt   3780
tactgatttg ccaccttcag acggtgtaga tgcggacggg ggggggccgc tgcagacggt   3840
gaaaaagaac gctgaaaggc tcctcgaccg attgagccgt caggttttta acctcgtctc   3900
ccatctccct gttttcctct cacacctctt caaatctgac agtggttatt ctccgggtga   3960
ttggggtttt gcagctttta ctctattttg cctcttttta tgttacagct acccattctt   4020
tggtttcgct cccctttttgg gtgtgttttc tgggtcttct cggcgcgtgc gcatgggggt   4080
ttttggctgc tggttggctt ttgctgttgg tttgttcaag cctgtgtccg acccagtcgg   4140
cactgcttgt gagtttgatt cgccagagtg taggaatgtc cttcattctt ttgagcttct   4200
caaaccttgg gaccctgttc gcagccttgt tgtgggcccc gtcggtctcg gtcttgccat   4260
tcttggcagg ttactgggcg gggcacgcta catctggcat tttctgctta ggcttggcat   4320
tgttacagac tgtatcctgg ctggagctta tgtgctttct caaggtaggt gtaaaaagtg   4380
ctggggatct tgcataagaa cagctcctaa tgagattgcc tttaacgtgt tcccttttac   4440
acgtgcgact aggtcgtcac tcatcgacct gtgcaatcgg ttttgtgcgc caaagggcat   4500
ggaccctatt ctcctcgcca ctgggtggcg tgggtgctgg accggccgaa gccccattga   4560
acaaccctct gaaaaaccca tcgcgtttgc ccagttggac gaaaagagga ttacggccag   4620
gaccgtggtc gcccagcctt atgaccccaa ccaagccgta aagtgcttgc gggtgttaca   4680
ggcgggcggg gcgatggtgg ctgaggcagt cccaaaagtg gtcaaagttt ccgctattcc   4740
attccgagcc cccttttttc ccaccggagt gaaagttgac cctgagtgta ggatcgtggt   4800
tgaccccgac acttttacta cagccctccg gtccggctat tccaccacaa acctcgttct   4860
tggtgtgggg gactttgccc agctgaatgg attaaaaatc aggcaaattt ccaagccttc   4920
gggaggaggc ccgcacctca ttgctgccct acatgttgcc tgctcgatgg cgttgcacat   4980
gcttgctggg gtttatgtaa ctgcagtggg gtcttgcggt accggcacca acgatccgtg   5040
gtgcaccaac ccgtttgccg tccctggcta cgggcctggt actctttgca cgtccagatt   5100
gtgcatctcc caacatggcc ttaccctgcc cttgacagca cttgtggcag gattcggtct   5160
```

```
tcaggaaatt gccttggttg ttttgatttt cgtttccatc ggaggcatgg ctcacaggtt   5220
gagttgcaag gctgacatgc tgtgcgtttt acttgcaatc gccagctatg tttgggtgcc   5280
ccttacctgg tttctttgtg tgtttccttg ctggttgcgc tggttctctt tgcatcccct   5340
caccatccta tggttggtgt tttcttgat ttctgtaaat gtgccttcgg gaatcttggc   5400
tgtggtgttg ttagtttctc tttggctctt aggtcgttac actaatgttg ctggtcttgt   5460
caccccatat gacattcatc atcacaccag tggcccccga ggtgttgccg ccttggctac   5520
tgcaccggat gggacctact tggccgccgt tcgccgtgct gcgttgaccg gtcgtaccat   5580
gctgtttacc ccgtctcagc ttgggtccct tcttgagggt gctttcagaa ctcaaaagcc   5640
ctcactgaac accgtcaatg tggtcggatc ctctatgggc tccggcgggg tgttcaccat   5700
cgacgggaaa attaagtgcg taacagccgc acatgtcctt acgggtaatt cagctagggt   5760
ttccggggtc ggcttcaacc aaatgcttga ttttgatgtg aaaggggact tcgccatagc   5820
tgattgcccg aattggcaag gagctgcccc caagacccaa ttctgcgagg atggatggac   5880
tggccgtgcc tattggctga catcctctgg agtcgaaccc ggtgtcattg ggaatggatt   5940
cgccttctgc ttcaccgcgt gcggcgattc tggatccccg gtgattaccg aagccggtga   6000
gcttgtcggc gttcacacag gatcaaacaa acaaggagga ggcatagtca cacgcccctc   6060
aggccagttt tgtaatgtgg cgcccatcaa gctgagcgaa ttgagtgaat tcttcgctgg   6120
acctaaggtc ccgctcggtg atgtgaagat tggcagccac ataattaaag acgtatgcga   6180
ggtaccttca gatctttgcg ccttgctcgc tgccaaaccc gaactggaag gaggcctctc   6240
caccgtccaa cttctgtgtg tgtttttcct cctgtggaga atgatgggac atgcctggac   6300
gcccttggtt gctgtggggt tttttatctt gaatgaggtt ctcccagctg tcctggtccg   6360
gagtgtcttc tcctttggta tgtttgtgct atcttggctt acaccatggt ctgcgcaagt   6420
cctgatgatc aggcttctaa cagcagctct taacaggaac agggggtcac tcgccttcta   6480
cagcctcggt gcagtgaccg gatttatcgc agatcttgca gcaactcagg ggcatccgct   6540
gcaggcagtg atgaacttaa gcacctatgc cttcctgcct cggatgatgg ttgtgacctc   6600
accagtccca gtgcttgctt gtggtgttgt gcacctcctt gccataattt tgtacctgtt   6660
taagcaccgt tgcctgcatt atgtccttgt tggcgatgga gtgttctcta aagccttctt   6720
cttgcgatac tttgccgaag ggaagttgag ggaaggggtg tcgcagtcct gcgggatgaa   6780
tcacgagtca ctgactggtg ccctcgctat gagactcaat gacgaagact tggacttcct   6840
tacgaaatgg actgatttta agtgctttgt ttctgcgtcc aacatgagga atgcagcggg   6900
ccaattcatc gaggctgcct atgcaaaagc acttagaatt gagcttgccc agttagtaca   6960
ggttgataag gttcgaggta ctttggccaa acttgaagcc tttgctgata ccgtggcacc   7020
ccagctctcg cccggtgaca ttgttgttgc tcttggccac acgcctgttg gcagtatctt   7080
cgacctaaag gttggcagta ccaagcatac cctccaggcc attgagacca gagtccttgc   7140
cgggtccaaa atgaccgtgg cgcgtgtcgt tgatccaacc cccacgcccc cacccgcacc   7200
cgtgcccatc cccctcccac cgaaagtcct ggagaacggc cccaacgcct ggggggatga   7260
ggaccggttg aataagagga agagacgcag gatggaagcc gtcggcatct ttgttatggg   7320
tgggaagaag taccaaaaat tttgggacaa gaattccggt gatgtgtttt acgaggaggt   7380
ccatgataac acagatgcgt gggagtgcct cagagttggt gaccctgccg actttgaccc   7440
tgagaaggga actctgtgtg ggcatactac cattgaagac aaggcttata atgtctacac   7500
```

-continued

```
ctccccatct ggcaggaagt tcctggtccc cgtcaaccca gagagcggaa gagcccaatg   7560
ggaagctgca aagctttccg tagagcaggc ccttagcatg atgaatgtcg acggtgagct   7620
gacagccaaa gaactggaga aactgaaaag aataattgac aaactccagg gcctaactaa   7680
ggagcagtgt ttaaactgct agccgccagc ggcttgaccc gctgtggtcg cggcggcttg   7740
gttgttactg agacagcggt gaaaatagtt aaatttcaca accggacctt caccctagga   7800
cctgtgaatt taaaagtggc cagtgaggtt gagctaaaag acgcagtcga gcataaccaa   7860
cacccggttg caagaccggt tgatggtggt gttgtgctcc tgcgctccgc agttccttcg   7920
cttatagacg tcttgatctc tggcgctgat gcatctccta agttactcgc ccaccacggg   7980
ccgggaaaca ctgggatcga tggttcgctt tgggattttg aggccgaggc caccaaagag   8040
gaaattgcac tcagtgcgca aataatacag gcttgtgaca ttaggcgcgg cgacgcaccc   8100
gaaattggtc ttccttataa gctgcaccct gttaggggca accctgagcg ggtaaaaggg   8160
gttttacaga atacaaggtt tggagacata ccttataaaa cccccagtga cactgggagc   8220
ccagtgcacg cggctgcctg cctcacgccc aatgccactc cggtgactga cggtcgttcc   8280
gtcttggcta cgaccatgcc ctccggtttt gagttgtatg taccgaccat tccagcgtct   8340
gtccttgatt atcttgattc caggcctgat tgccccaaac agttgacaga gcacggctgt   8400
gaggatgccg cattaagaga cctctccaag tatgacttgt ccacccaagg ctttgtcttg   8460
cctggagttc ttcgccttgt gcgtaagtac ctgtttgctc atgtgggtaa gtgcccgcct   8520
attcatcggc cttccactta ccctgccaag aattccatgg ctggaataaa tgggaacagg   8580
tttccaacca aggacattca gagcgtccct gaaatcgacg ttttgtgcgc acaggccgtg   8640
cgagaaaact ggcaaactgt tactccttgt accctcaaga agcagtattg cgggaagaag   8700
aagactagga caatactcgg cactaataac ttcattgcgc tggcccaccg ggcagcattg   8760
agtggtgtca cccagggctt catgaaaaaa gcgtttaact cgcccatcgc actcgggaaa   8820
aacaaattca aggagctgca gactccggtc ttgggcagat gtcttgaagc tgaccttgca   8880
tcctgtgacc gatccacacc cgcaattgtc cgctggtttg ccgccaatct tctttatgaa   8940
cttgcctgtg ctgaggagca tataccatcg tacgtgttga actgctgcca cgacttactg   9000
gtcacgcagt ccggcgcggt gactaagaga ggtggcctat cgtctggcga cccgattact   9060
tctgtatcaa acaccattta cagcttggtg atatatgcac agcacatggt actcagttat   9120
tttaaaagtg gtcaccccca tggccttctg tttctacaag accagctaaa gtttgaggac   9180
atgctcaagg ttcagcccct gatcgtctat tcggacgacc tcgtgctgta cgccgagtct   9240
cccaccatgc caaactacca ctggtgggtt gaacatctga acctgatgct gggttttcag   9300
acggacccaa agaagacagc tataacagac tcgccatcat ttttgggttg taggataata   9360
aatggacgcc agttagtccc caaccgtgac aggatcctcg cggccctcgc ctaccatatg   9420
aaggcaaaca atgtttctga atactacgcc tcggcggctg caatactcat ggacagttgt   9480
gcttgtttgg agtacgatcc tgagtggttt gaagagctcg tggttgggat ggcgcagtgc   9540
gcccgcaagg acggctacag ttttcctggc ccgccgttct tcttgtccat gtgggaaaaa   9600
ctcaggtcca atcatgaggg gaagaagtct agaatgtgcg ggtactgtgg ggccccagct   9660
ccgtatgcca ctgcctgtgg ccttgatgtt tgtatttatc acacccactt ccaccagcat   9720
tgtccagtca taatctggtg tggccatccg gcgggttctg gctcttgtag tgagtgcaaa   9780
ccccccctag ggaaaggcac aagccctcta gatgtggtgt tagaacaagt cccgtacaag   9840
cctccacgaa ctgtaatcat gcatgtggag cagggtctca cccctcttga cccaggcaga   9900
```

```
taccagactc gccgcggatt agtctccgtt aggcgtggca tcaggggaaa cgaaatcgac   9960
ctaccagacg gtgattatgc tagtaccgcc ttgctcccca cttgtaaaga tatcaacatg  10020
gtcgctgtcg cttccaatgt gttgcgcagc aggttcatca tcggtccacc cggtgctggt  10080
aaaacatact ggctccttca acaggtccag gatggtgatg tcatttacac gccaactcat  10140
cagaccatgc ttgacatgat caaggctttg ggacgtgcc ggttcaacgc cccagcaggc   10200
acaacgctgc aattccctgc tccctcccgt accggcccgt gggttcgcat cctggccggc  10260
ggttggtgtc ctggcaagaa ttccttcctg gatgaagcag cgtattgtaa tcaccttgat  10320
gtcttgaggc ttcttagcaa aactaccctc acctgtctgg gagatttcaa acaactccac  10380
ccagtgggtt ttgattctca ttgctatgtt tttgacatca tgcctcagac tcaactgaag  10440
accatctgga ggtttggaca gaatatctgt gatgccattc agccagatta cagggacaaa  10500
cttgtgtcca tggtcaacac aacccgtgta acctacgtgg aaagacctgt caagcatggg  10560
caggtcctca ccccttacca cagggaccga gaggacggcg ccatcacaat tgactccagt  10620
caaggcgcca catttgatgt ggttacattg catttgccca ctaaagattc actcaacagg  10680
caaagagccc ttgttgctat caccagggcg agacatgcta tctttgtgta tgacccacat  10740
aggcaactgc agagcatgtt tgatcttcct gcaaaaggca cacccgtcaa ccttgccgtg  10800
caccgtgacg agcagctgat cgtactagat agaaataaca aagagtgcac ggttgctcag  10860
gctctaggca atggggacaa attcagggcc acagacaagc gcgttgtaga ttctctccgc  10920
gccatttgtg cagatcttga agggtcgagc tccccgctcc ccaaggtcgc acataacttg  10980
ggattttatt tctcacctga tttgacacag tttgctaaac tcccggcaga acttgcaccc  11040
cactggcccg tggtgacaac ccagaacaat gaaaagtggc cagacaggct ggttgccagc  11100
ctccgcccta tccataaata tagccgcgca tgcattggag ccggctatat ggtgggccct  11160
tcggtgtttc taggcacccc tggggttgtg tcatactatc tcacaaaatt tgttaagggg  11220
gaggctcagg tgcttccgga gacagtcttc agcaccggcc gaattgaggt agattgccgg  11280
gagtatcttg atgatcggga acgagaagtt gctgagtccc tcccacatgc cttcattggc  11340
gacgtcaaag gcactaccgt tgggggatgt caccatgtca cctctaaata ccttccgcgc  11400
ttccttccta aggaatcagt tgcggtggtt ggggtttcga gccccgggaa agccgcaaaa  11460
gcagtctgca cattaacaga tgtgtatctc ccagaccttg aagtttacct ccacccagag  11520
acccaatcca agtgctggaa aataatgttg gacttcaagg aagtccgact gatggtctgg  11580
aaagacaaaa cggcctattt tcaacttgaa ggccgccatt tcacctggta tcagcttgca  11640
agctatgcct cgtacatccg agttcctgtt aactctacgg tgtatttgga cccctgcatg  11700
ggccctgccc tttgcaacag aagagttgtc gggtccactc attgggggc tgacctcgca   11760
gtcacccctt atgattatgg tgccaaaatc attctgtcta gtgcatacca tggtgaaatg  11820
cctcctgggt acaaaatcct ggcgtgcgcg gagttctcgc ttgacgaccc agtgaggtac  11880
aaacacacct gggggtttga atcggacaca gcgtatctgt acgagttcac cggaaacggt  11940
gaggactggg aggattacaa tgacgcattt cgtgcgcgcc agaaagggaa aatttataag  12000
gccactgcca ccagcatgag gtttcatttt cccccgggcc ccatcattga accaacttta  12060
ggcctgaact gaaatgagat gggggctatg caaagccttt tctacaaaat tggccaactt  12120
tttgtggatg ctttcacgga atttttggtg tccattgttg atatcatcat atttttggcc  12180
attttgtttg gcttcaccat cgccggttgg ctggtggtct tctgcatccg attggtttgc  12240
```

tccgcggtac tccgtgcgcg ccctaccatt caccctgagc aattacagaa gatcctatga 12300
ggcctttctt tctcagtgcc gggtggacat tcccacctgg ggaaccaaac atcccttggg 12360
gatactttgg caccataagg tgtcaaccct gattgatgaa atggtgtcgc gtcgaatgta 12420
ccgcatcatg gaaaaatcag gacaggctgc ctggaaacag gttgtgagcg aggctacgct 12480
gtctcgcatc agtggtttgg atgtggtggc tcattttcag catcttgccg ccattgaagc 12540
cgagacctgt aaatatttgg cctctcggat gcccatgcta cacaacctgc gcatgacagg 12600
gtcaaatgta accatagtgt ataatagtac tttgaatcag gtgttagcaa tcttcccgac 12660
ctctgaatcc cggccaaagc ttcatgattt tcaacaatgg ttaataactg tacattcctc 12720
catattttcc tccgttgtgg cttcctgtac tctttttgtt gtgctgtggt tgcgaattcc 12780
aatgctacgt actgtttttg gtttccactg gttaggggca atttttcttt cgaactcaca 12840
gtgaattaca cggtgtgccc accttgcctc acccggcaag cagccgctga gatctacgaa 12900
cccggcaggt ctctttggtg caggataggg catgatcgat gtagcgagga cgatcatgac 12960
gaactagggt tcttggttcc gcctggcctc tccagcgaag gccacttgac cagtgtttac 13020
gcctggttgg cgttcctgtc cttcagctat acagcccagt tccatcccga gatatttggg 13080
atagggaatg tgagtaaaat ttatgttgac atcaagcacc aattcatctg cgccgaacac 13140
gacgggcaga acgccaccct gcctcgccat gacaacattt cagccgtgtt tcagacctac 13200
taccaacatc aggtcgatgg cggcaattgg tttcacctgg aatggctgcg ccccttcttt 13260
tcctcttggt tggttttaaa tgtttcgtgg tttctcaggc gttcgcctgc aagccatgtt 13320
tcagttcgag tctttcagac atcaaaacca acaccaccgc agcaccaaat tttgttgtcc 13380
tccaggacat cagctgcctt aggcatggcg acccgtcctc tccggcgatt cgcaaaagct 13440
ctcagtgccg cacggcgata ggaacacccg tgtatatcac catcacagcc aatgtgacag 13500
atgagaatta tttacattct tctgatctcc tcatgctttc ttcttgcctt ttctatgctt 13560
ctgagatgag tgaaaagggg ttcaaggtgg tattcggcaa tgtgtcaggc atcgtggctg 13620
tgtgtgtcaa ctttaccagt tacgtccaac atgtcaagga gtttacccaa cgctccttgg 13680
tggtcgagca tgtgcgactg cttcatttca tgacacctga aaccatgagg tgggcaaccg 13740
ttttagcctg tctttttgcc attctgttgg caatttgaat gtttaagtat gttggggaaa 13800
tgcttgaccg cgggctgttg ctcgccgttg cttttttgt ggtgtatcgt gccgtcttgc 13860
tttgttgcgc ccgtcaacgt cgacgggaac gacagctcaa agttacagct gatttacaac 13920
ttgacgctat gtgagctgaa tggcacagat tggctggctg gtagatttga ctgggcagtg 13980
gagtgttttg tcatttttcc cgtgttgact cacattgtct cctatggtgc cctcactact 14040
agccatttcc ttgacacagt cggtctggtc actgtgtctg ccgccgggtt ccttcatgaa 14100
cggtatgttt tgagtagcat ctacgcggtc tgtgccctgg ctgcgttgat ttgcttcgtc 14160
attaggcttg cgaagaactg catgtcctgg cgctactcgt gtaccagata taccaacttc 14220
cttttggaca ccaaggggag actctatcgt tggcgatcgc ccgtcatcat agagaaaaag 14280
ggtaaagttg aggttgaagg tcatttgatc gacctcaaaa gagttgtgct tgatggttcc 14340
gtggcaaccc ctataaccaa aatttcagcg gaacaatggg gtcgtcctta gatgacttct 14400
gccatgatag cacggctcca caaaaggtgc ttttggcgtt ttccattacc tatacaccag 14460
tgatgatata tgccctaaag gtaagtcgcg gccgactgct agggcttttg caccttttga 14520
tctttctgaa ctgtgctttc accttcgggt atatgacatt cacgcacttt cagagtacaa 14580
acaaggtcgc gctcactatg ggagcagtag ttgcactcct ttggggggtg tactcagcca 14640

```
tagaaacctg gaaattcatc acctccagat gccgtttgtg cttgctaggc cgcaagtaca  14700

ttctggcccc tgcccaccac gttgagagtg ccgcaggctt tcatccgatt gcggcaaatg  14760

ataaccacgc atttgtcgtc cggcgtcccg gttccactac ggtcaacggc acattggtcc  14820

ccgggttgaa aagcctcgtg ttgggtggca gaaaagctgt caaacaggga gtggtaaacc  14880

ttgttaaata tgccaagtaa caacggcagg cagcagaaaa aaagaaaggg ggatggccag  14940

ccagtcaatc agctgtgtca gatgctgggt aaaattattg cccagcaaaa tcagtccagg  15000

ggcaagggac cgggaaagaa aaataacaag aaaaaacccgg agaagcccca ttttcctcta  15060

gcgactgaag atgatgtcag acatcacttt accccgagtg agcgacaatt gtgtctgtcg  15120

tcaatccaga ctgccttcaa tcagggcgct ggaacttgta ccctgtcaga ttcaggcagg  15180

ataagttaca ctgtggagtt tagtttgccg acgcatcaca ctgtgcgcct gatccgcgct  15240

acagcatcac cctcagcatg atgagctggc attcctgggt atcccagtgt ttgaattgga  15300

agaatgtgtg gtgaatggca ctgattgaca ttgtgcttct aagtcaccta ttcaattagg  15360

gcgaccgtgt gggagtagaa tttaattggc gagaaccacg cggccgaaat taaaaaaaaa  15420

aaaaaaaaaa aaaaaaaaaa aaaa                                          15444
```

<210> SEQ ID NO 5
<211> LENGTH: 15413
<212> TYPE: DNA
<213> ORGANISM: Artificial Sequence
<220> FEATURE:
<223> OTHER INFORMATION: Artificial Construct

<400> SEQUENCE: 5

```
cgcccgggca tgtgttggct ccatgccacg acatttgtat tgtcaggagc tgtgaccact     60

ggcacagccc aaagcttgct gcacagaaac acccttctgt gacagcctcc ttcaggggag    120

tttaggggtc tgtccctaac accttgcttc cggagttgca ctgctttacg gtctctccac    180

cctttaacca tgtctgggat acttgatcgg tgcacgtgca cccccaatgc cagggtgttt    240

atggcggagg gccaagtcta ctgcacacga tgtctcagtg cacggtctct ccttcctctg    300

aatctccaag tttctgaact aggggtgcta ggcctatttt acaggcccga agagccactc    360

cggtggacgt tgccacgtgc attccccact gttgagtgct cccccgccgg ggcctgctgg    420

ctttctgcaa tttttccaat tgcacgaatg actagtggaa atctgaactt ccaacaaaga    480

atggtacggg tcgcagctga gctttacaga gccggccagc tcacccctgc agtcttaaag    540

gctctacaag tttatgaacg ggctgccgc tggtacccca ttgtaggacc tgtccctgga    600

gtggccgttt acgccaactc cttacatgtg agtgataaac ctttcccggg agcaactcac    660

gtgttaacca acctaccgct cccgcaaaga ccaaaacctg aagacttttg cccctttgag    720

tgtgccatgg ctaccgtcta tgacatcggt cgtgacgccg tcatgtatgt aaccgaggga    780

aaagtctcct gggcccctcg tggtggggat gaaacaagat ttgaaactgt ccccggtggg    840

ttgaagttga ttgcggacca actctactcc tccttcccgc cccatcacac ggtggacata    900

tctaagttcg ccctcacagc ccctgggcgc ggtgtatcca tgcgggttga acgccagtgt    960

ggctgcctcc ccgctgacac tgtccctgaa ggcaactgtt ggtggagctt attcgattca   1020

ctcccactgg aagtccagaa caaagaaatt cgccatgcta accaatttgg ctaccaaacc   1080

aagcatggcg tctccggcaa gtaccttcag cggaggctgc aagttaatgg cctccgagca   1140

gtaactgact tgaatggacc tattgtcata cagtacttct ccgttagaga gagttggatc   1200
```

-continued cgccacttga aactggcgga agaacccggc ctccctgggt ttgaggacct cctcagaata 1260
agggttgaac ccaacacatc gccattggct aacgaggatg agaaaatctt ccgatttggc 1320
agccataagt ggtacggcgc tgggaggaga gcaaggaaag cacgccacag tgcaattgct 1380
gcggtcgcag gccgcgcttc gtctgctcgt gaaatccagc aggccaagaa gcatgaggct 1440
gctgacgcca ataaggttga gcacctcaaa cgctactccc cgcccgccga agggaattgc 1500
ggttggcact gtatttctgc catcgccaat cgaatggtga attctaaatt taaaaccacc 1560
cttcccgaaa gagtgaggcc ttcagatgac tgggccactg atgaggatct tgtgaatgtc 1620
atccaaatcc tcaggctccc tgcggccttg gacaggaacg gtgcttgtgc cagcgccaag 1680
tacgtactta agctagaagg tgagcattgg actgtcactg tgacccctgg gatgtcccct 1740
tctttgctcc ctcttgaatg tgttcagggc tgttgtgagc ataagggcgg tctaggtacc 1800
ccagatgcag tcgaggtttt cggatttgac cctgcctgcc tcaactggtt ggctgaggtg 1860
atgcacctgc ctagcagtgc tatcccagcc gctctggccg aaatgtccgg tgattccggt 1920
cgttcggctt ccccggtcac caccgtgtgg accgtttcgc agttctttgc ccgccacaat 1980
ggagggagtc accctgacca agtgcgttta gggaaaatta ttagcctttg tcaggtgatt 2040
gaggactgct gctgttccca gaacaaaacc aaccgggtta ccccggagga ggtcgcagca 2100
aagattgact tgtacctccg tggagcgaca agtcttgaag aatgcttggc caggcttgag 2160
aaagctcgcc cgccacgcgt aatggacacc tcctttgatt gggatgttgt gctccctggg 2220
gttgaggcgg caactcagac gaccgaattg ccccaggtca accagtgtcg tgctttggtc 2280
cctgttgtaa ctcaaaagtc cttggacaac aactcggttc ccttgaccgc cttttcactg 2340
gctaactact actaccgtgc gcaaggtgaa gaagttcgtc accgtgaaag actaaccgcc 2400
gtgctctcca aattggaagg ggttgtccga gaggaatatg ggctcatgcc aaccgggcct 2460
ggtccacggc ccacattgcc acgcgggctc gacgaactca aagatcagat ggaagaggac 2520
ttgctgaaac tggctaacgc ccagacgact tcggagatga tggcctgggc agtcgagcag 2580
gtcgacctaa aaacttgggt caagaactac ccgcggtgga caccaccacc ccctccgcca 2640
aaagttcagc ctcgaaaaac gaagtctgcc aagagcttgc tagagagaaa gcctgtcccc 2700
gccccgcgca ggaaggttgg gaccaattgt ggcagcccga tttcattggg cgacaatatc 2760
cctaacagtt gggaagattt ggctgttggt ggcccctatg atcccccgac cccacctgag 2820
ccggcaacac cttcaggtga gctggtggtt gtgtccacac cgcaatgcat cttcaggccg 2880
gcgacaccct cgagtgagcc ggctctaatt cccgcatccc gcggggctgt gtctcgaccg 2940
gtgacaccct tgagtgagcc gatccctgtg cccgcaccgc ggcgtaagtt tcagcaggtg 3000
aaaagattga gttcggcagc ggtaaccccg ccgtaccagg acgagcccct aaatttgtct 3060
gcttcctctc aaactgaatt tgaggccccc tccctagcac cgccgcagag cgagggtgtt 3120
ttgggagtga aggggcagga agctgaggag gccctgagtg aaatctcgga catgtcgggc 3180
ggcattaaac ctgcgtccgt atcatcaagc agctccttgt ccagcgtgag agtcacacgc 3240
ccaaaatact cagctcaagc catcatagac ttgggcgggc cctgcagtgg gcatctccaa 3300
gaggtaaagg aagcatgcct cggaatcatg cgcgaggcat gtgatgcgac taagcttgat 3360
gaccctgcta cgcaggaatg gctttcccgc atgtgggacc gggtggacat gctgacttgg 3420
cgcaacacgt ctgcctacca ggcgtttcgt accttagatg gcaggttaaa gttcctccca 3480
aaaatgatac tcgagacacc gccgccctat ccgtgtgagt ttgtgatgat gcctcactcg 3540
cctgcacctt ccgtaggtgc ggagagtgac cttaccattg gctcagtcgc tactgaagat 3600
gttccacgta tcctcgagaa aatagaaaat gtcggcgaga tgaccaacca gggacccttg 3660
gccttctccg aggataaacc ggtggatgac cagcttgcca aagacccccg gatatcgtcg 3720
cagagtcctg acgagagcac atcagctccg cccacaggca caggaggcgc cggttcattt 3780
accgatttgc cgccttcaga cggcgcggat gcggacgggg gggggccgtt tcggacgata 3840
aaaagaaaag ctgaagggct ctttgaccga ctgagccgac aggtttttaa cctcgtctcc 3900
catctccctg ttttcttctc acgccttttc aacccgggcg gtagttattc tccgggtgat 3960
tggggttttg cagcttttac tctattgtgc ctccttttat gctacagtta tccagcattt 4020
ggtattgctc ccctcttggg tgtgttttct gggtcttctc ggcgcgtccg aatgggggtt 4080
tttggctgct ggttggcttt tgctgttggt ctgttcaagc ctgtgtccga cccagtcggc 4140
gctgcttgtg agtttgattc gccagagtgt agaaacatcc ttcattcttt tgagcttctc 4200
aaaccttggg accctgttcg cggccttgtt gtgggccccg tcggtctcgg tcttgccatt 4260
cttggcaggt tactgggcgg ggcacgctgc atctggcact ttttgcttag gcttggcatt 4320
gttgcagact gtgtcttggc tggagcttat gtgctttctc aaggcaggtg taaaaagtgc 4380
tggggatctt gtataagaac tgctcctagt gaggtcgctt ttaatgtgtt tccttttaca 4440
cgtgcgacca ggtcgtcgct tactgacctg tgcgatcggt tttgtgcgcc aaaaggcatg 4500
gaccccattt ttctcgccac tgggtggcgc gggtgctggg ccggccgaag ccccattgag 4560
caaccctctg aaaaacccat cgcgtttgcc cagttggatg aaaagaagat tacggctagg 4620
actgtcgtcg cccagcctta tgaccctaac caagccgtaa agtgcttgcg ggtattgcag 4680
gcgggtgggg caatggtagc tgaggcagtc ccaaaagttg tcaaggtttc cgctgtccca 4740
ttccgagccc ccttctttcc caccggagtg aaagttgacc cagaatgcag ggttgtggtt 4800
gaccccgaca ctttcaccgc agctctccgg tctggctact ccaccacaaa cctcgtcctt 4860
ggtacagggg actttgccca gctgaatgga ttgaaaatca ggcagatttc caagccttca 4920
ggaggaggcc cacacctcac ggctgccctg catgttgctt gctcgatggc tttgcacatg 4980
cttgttggga tttatgtgac tgcggtgggt tcttgcggca ccggcaccaa cgacccgtgg 5040
tgcgctaacc cgtttgccgt ccctggctac ggacctggct ctctttgcac gtccaggttg 5100
tgcatttccc aacatggcct taccctgccc ttgacagcac tcgtggcggg attcggcatt 5160
caagaaattg ccttggtcgt tttgattttt gtttccatcg gaggcatggc tcacaggtta 5220
agttgcaagg ctgacatgct gtgtgttttg cttgcaattg ccagctatgt ttgggtacct 5280
cttacctggt tgctttgtgt gtttccttgc tggttgcgct gtttttcttt gcatcccctc 5340
accatcctat ggttggtttt tttcttgatt tctgtgaata tgccttcagg aatcttggcc 5400
atggtgctgt tggtttctct ttggcttctt ggtcgttata ctaatgttgc tggtcttgtt 5460
acccccctacg acattcatca ttacactagt ggcccccgcg gtgttgccgc cttggctacc 5520
gcaccagatg ggacctactt ggccgctgtc cgccgtgctg cgttaaccgg ccgtaccatg 5580
ctgtttaccc cgtcccagct tgggtctctt cttgagggtg ctttcagaac tcgaaaaccc 5640
tcactgaaca ccgtcaatgt ggtcgggtcc tccatgggct ctggcggggt gttcaccatt 5700
gacggaaaaa ttaagtgcgt aactgccgca catgtcctta cgggcaattc agctaggatt 5760
tccggggtcg gcttcaatca aatgcttgac tttgacgtaa agggagattt cgccatagct 5820
gattgcccga attggcaagg ggttgccccc aagacccaat tctgcaagga tggatggact 5880
ggccgtgcct attggctgac atcctctggc gtcgaacccg gcgtcattgg aaaaggattc 5940

-continued

```
gccttctgct tcactgcgtg cggcgattcc gggtccccag tgatcaccga ggccggtgag   6000
cttgtcggcg ttcacacggg atcaaataaa caaggaggag gcatcgttac gcgcccctca   6060
ggccagtttt gtaatgtggc acccatcaaa ctaagcgaat taagtgaatt ctttgctggg   6120
cctaaggtcc cgctcggtga tgtaaaggtt ggcagccaca taattaaaga cataggcgag   6180
gtgccctcag atctttgtgc cttgcttgct gccaaacctg aactggaagg gggcctctcc   6240
accgtccaac ttctttgtgt gtttttcctc ctgtggagga tgatgggaca tgcctggacg   6300
cccttggttg ctgtgggttt ctttatcctg aatgaggttc tcccagccgt cctggtccgg   6360
agtgttttct cctttggaat gtttgtgcta tcctggctca cgccatggtc tgcgcaagtt   6420
ctgatgatca gacttctaac agcagccctt aacaggaaca gatggtcact tgccttttc    6480
agtcttggtg cagtgaccgg ttttgtcgca gaatttgcgg ctactcaggg gcatccgttg   6540
caggctgtga tgaatttgag cacctatgca ttcctgcctc ggatgatggt tgtgacctca   6600
ccggccccag tgatcgcgtg tggtgtcgtg cacctacttg ccatcatttt gtacttgttt   6660
aagtaccgcg gcctgcacca aatccttgtt ggcgacggag tgttctctgc ggctttcttc   6720
ttgcgatact ttgccgaggg taagttaagg gaaggggtgt cgcaatcctg tgggatggat   6780
catgagtctc tgactggtgc cctcgctatg agactcagtg acgaggactt ggatttcctt   6840
gcgaaatgga ctgattttaa gtgctttgtt tctgcgtcca acatgaggaa tgcagcgggt   6900
caatttattg aggctgccta tgctaaagca cttagaatgg agcttgccca gttggtgcag   6960
gttgacaaag ttcgaggtac tttggccaaa ctcgaagctt ttgctgatac cgtggcaccc   7020
cagctctcgc ccggtgacat tgttgttgct ctcggccata cgcctgttgg cagtatcttc   7080
gacctaaagg ttggtagcac caagcatact ctccaagcca ttgagaccag agtccttgct   7140
gggtccaaaa tgaccgtggc gcgcgtcgtc aacccgaccc ccacgccacc acccgcaccc   7200
gtgcccatcc ccctcccacc gaaagtcctg gagaatggcc ccaacgcttg gggggatgag   7260
gaccgtttga ataagaagaa gaggcgcagg atggaagccc tcggcatcta cgtcatgggc   7320
gggaaaaagt accagaaatt ctgggacaag aattccggtg atgtgtttta tgaggaggtc   7380
cataataaca tagatgagtg ggagtgtctc agagttggcg atcctgccga ctttgaccct   7440
gagaagggaa ctctgtgtgg acatgtcacc attgaagaca aggcttaccg tgtttacgcc   7500
tccccatctg gtaagaggtt cttggtcccc gtcaacccag aaaatggaag agtccaatgg   7560
gaagctgcaa agctttctgt ggagcaggcc cttggcatga tgaacgtcga cggtgagttg   7620
actgccaaag aactggagaa actaaaaaga ataattgaca aactccagag cctgactaag   7680
gagcagtgtt taaactgcta gccgccagcg gcttgacccg ctgtggtcgc ggcggcttgg   7740
ttgttactga aacagcggta aaaatagtca aatttcacaa ccggaccttc accctgggac   7800
ctgtgaattt aaaagtggcc agtgaggttg agctaaaaga cgcgattgag cacaatcaac   7860
acccggttgc gagaccggtc gatggtggtg ttgtgcttct gcgttccgcg gttccttcgc   7920
ttatagacgt cttgatctcc ggtgctgatg catctcccaa gttacttgcc caccacgggc   7980
cgggaaacac tgggatcgat ggcacgctct gggattttga gtccgaagcc actaaagagg   8040
aagtcgcact tagtgcgcaa ataatacagg cttgtgacat taggcgcggc gacgcccctg   8100
aaattggtct tccttacaag ctgtaccctg ttaggggtaa ccctgagcga gtaaaagggg   8160
ttctacaaaa tacaaggttt ggagacatac cttacaaaac cccccagtgat actggaaacc  8220
cagtgcacgc ggctgcctgc cttacgccca atgccactcc ggtgactgat gggcgctccg   8280
ttttggccac gaccatgccc tccgggtttg agttgtatgt accaaccata ccagcgtctg   8340
```

```
tccttgatta ccttgattcc agacctgact gccctaaaca gctgacagag cacggctgtg   8400
aagatgccgc actaagagac ctctccaaat atgacttgtc cacccaaggc tttgttttac   8460
ctggggttct tcgccttgta cggaaatacc tgtttgccca tgtaggtaag tgcccacccg   8520
ttcatcggcc ttccacttac cctgctaaga attctatggc tggaataaat gggaacaggt   8580
tcccaaccaa ggatattcag agcgtccctg agatcgacgt tctgtgcgca caggctgtgc   8640
gggaaaactg gcaaactgtt accccttgta ctcttaagaa acagtattgt gggaagaaga   8700
agactaggac catactcggc acaaataact tcatcgcgct agcccaccga gcagcgttga   8760
gtggtgttac ccagggcttc atgaagaagg cgtttaactc gcccatcgcc ctcggaaaaa   8820
acaagtttaa ggagctacag actccggtcc tgggcaggtg tctagaagct gatcttgcat   8880
cctgcgaccg atccacaccc gcaattgtcc gctggtttgc cgccaacctc ctttatgagc   8940
ttgcctgcgc tgaagagcat ctaccgtcgt acgtgctaaa ctgctgccac gacttactgg   9000
tcacgcagtc cggcgcagtg actaagagag gtggcctgtc gtctggcgac ccgatcacct   9060
ctgtgtctaa caccatttac agtttggtga tctacgcaca gcatatggtg ctcagttact   9120
tcaaaagtgg tcacccccat ggcctcttat tcttacagga ccagctaaag tttgaggaca   9180
tgcttaaggt tcaacccctg atcgtctatt cggacgacct cgtgctgtat gccgagtctc   9240
ccactatgcc aaactaccac tggtgggttg agcatctgaa tttgatgctg ggtttcaga    9300
cggacccaaa gaagacagcc ataacagact cgccatcatt tttgggctgt agaataataa   9360
atggacgcca gctagtcccc aaccgtgaca ggattctcgc ggccctcgcc taccacatga   9420
aggcgagtaa tgtttctgaa tactacgcct ctgcggctgc aatactcatg gacagctgtg   9480
cttgtttgga gtatgatcct gaatggttcg aagaacttgt agttggaata gcgcaatgcg   9540
cccgcaagga tggctacagc tttcccggcc cgccgttcta tatatccatg tgggaaaaac   9600
tcagatccaa ttatgagggg aagaagtcga gagtgtgcgg gtactgcggg gccccggccc   9660
cgtatgctac cgcctgtggt ctcgacgtct gcatttacca cactcacttc caccagcatt   9720
gtccagtcat aatctggtgt ggccatccag ccggttctgg ttcttgtagt gagtgcagat   9780
cccctgtggg gaaaggcaca agccctttag acgaggtgct ggaacaagtc ccgtacaagc   9840
ccccacggac cgttatcatg catgtggagc agggtcttac ccccttgac ccaggcagat    9900
atcagactcg ccgcgggtta gtctccgtca ggcgcgggat caggggaaat gaggttgagc   9960
taccagacgg tgattatgcc agtaccgcct tgctccctac ctgcaaagag atcaacatgg  10020
tcgctgtcgc ttctaatgta ttgcgcagca ggttcatcat tggtccaccc ggtgcgggga  10080
aaacatactg gctacttcaa caggtccagg atggtgatgt tatttacaca ccaactcacc  10140
agaccatgct tgacatgatt agagctttgg ggacgtgccg gttcaacgtc ccggcaggca  10200
caacgctgca attcccggtc ccctcccgca ccggtccgtg ggttcgcatc ctagccggcg  10260
gttggtgtcc tggcaagaat tccttcctgg atgaagcagc gtattgcaat caccttgatg  10320
tcttaaggct tcttagcaaa actaccctca cctgtctggg agactttaaa caactccacc  10380
cagtgggttt tgattctcat tgctatgttt ttgacatcat gcctcaaact caactgaaga  10440
ccatctggag gtttggacaa aatatctgtg atgccatcca accagattac agggacaaac  10500
tcatgtccat ggtcaacatg acccgtgtaa cctacgtgga aaaacctgtc aggtatgggc  10560
aagtcctcac cccctaccac agggaccgag aggacgacgc catcaccatt gactccagtc  10620
aaggcgccac atttgatgtg gttacactgc atttgcccac taaagattca ctcaacaggc  10680
```

aaagagccct tgttgctatc accagggcaa gacatgctat ctttgcgtat gatccacaca 10740
ggcagctgca gagcctgttt gatcttcctg caaaaggtac acccgtcaac cttgcagtgc 10800
accgcgatgg gcagctgatc gtgctagata gaaataacaa tgaatgcacg gttgctcagg 10860
ctctaggtaa cggggataaa tttagggcca cagacaagcg cgttgtagat tctctccgcg 10920
ccatttgtgc tgatctagaa ggtacgagct ctccgctccc caaggtcgca cacaacttgg 10980
gattttattt ctcacctgat ttaacacagt ttgctaaact cccagcagaa cttgcacctc 11040
actggcccgt ggtgacagcc cagaacaatg aaaagtggcc agatcggctg gttactagcc 11100
ttcgccctat ccataaatat agccgcgcgt gcatcggtgc cggctatatg gtgggcccct 11160
cggtgtttct aggcactcct ggggtcgtgt catactatct cacaaaattt gttaagggcg 11220
aggctcaagt gcttccggag acggttttca gcaccggccg aattgaggta gactgccggg 11280
aatatcttga tgaccaggag cgagaagttg ctgcgtccct cccacatgcc ttcattggcg 11340
acgtcaaagg cactaccgtt ggagggtgcc accatgtcac ttccagatac ctcccgcgct 11400
tccttcccaa ggaatcagtt gcggtagtcg gggtttcaag tcccggaaaa gccgcgaaag 11460
cattgtgcac actaacagat gtgtacctcc cagaccttga agcctatctc cacccggaga 11520
ccccgtccaa gtgctggaga atgatgttgg acttcaagga agttcgacta atggtctgga 11580
aagacaaaac agcctatttc caacttgaag gtcgctattt cacctggtat cagcttgcca 11640
gctatgcctc gtacatccgt gttcctgtca actctacggt gtacttggac ccctgcatgg 11700
gccccgccct ttgcaacagg agagtcgtcg ggtccactca ttggggggct gaccttgcgg 11760
tcacccctta tgattacggc gctaaaatca tcctgtctag cgcgtaccat ggtgaaatgc 11820
cccccggata caagattctg gcgtgcgcgg aattctcggt ggacgaccca gtcaagtaca 11880
aacatacctg gggtttgaa tcggatacag cgtatctgta tgagttcacc ggaaacggtg 11940
aggactggga ggattacaat gatgcgtttc gtgcgcgcca ggaagggaaa atttataagg 12000
ctactgccac cagcatgaag ttttattttc ccccgggccc tgtcattgaa ccaactttag 12060
gcctgaattg aaatgaaatg gggtccatgc aaagcctttt tagcaaaatt ggccaacttt 12120
ttgtggatgc tttcacggag ttcttggtgt ctattgttga tatcattata tttttggcca 12180
tcttgtttgg cttcaccatc gccggttggc tggtggtctt ttgcatcaga ttggtttgct 12240
ccgcgatact ccgtgcgcgc cctgccattc accctgagca attacagaag atcttatgag 12300
gcctttcttt cccagtgcca agtggacatt cccacctggg gaactaaaca ccctttgggg 12360
atgttttggc accataaggt gtcaaccctg attgatgaga tggtgtcgcg tcgaatgtac 12420
cgcaccatgg aaaaagcagg acaggctgcc tggaaacagg tggtgagcga ggctacgctg 12480
tctcgcatta gtagtttgga tgtggtggct cattttcagc atcttgccgc cattgaagcc 12540
gagacctgta aatatttggc ctcccggctg cccatgctac ataacctgcg catgacaggg 12600
tcaaatgtaa ccatagtgta taatagtact ttaaatcagg tgtttgctat tttcccgacc 12660
cctggttccc ggccaaagct tcatgatttt cagcaatggc taatcgctgt acactcctcc 12720
atattctcct ctgttgcagc ttcttgtact ctttttgttg tgctgtggtt gcggatgccg 12780
atgctacgta ctgtttttgg tttccgctgg ttaggggcaa cttttccttc gagctcacgg 12840
tgaattacac ggtgtgccca ccttgcctca cccggcaggc ggccgcacag gcctacgaac 12900
ccggtaggtc tctttggtgc aggatagggt acgatcggtg tggagaggac gaccatgacg 12960
agctagggtt tatggtaccg tctggcctct ccagcgaagg ccacttgacc agtgtttacg 13020
cctggttggc gttcttgtcc ttcagctaca cagcccagtt ccaccccgag atattcggga 13080

```
tagggaatgt gagtcaagtt tatgttgaca ccaaacatca actcatctgc gccaaacatg  13140
acgggcagaa caccaccttg cctcgtcatg acaatatttc agctgtgttt cagacctatt  13200
accaacatca agtcgacggc ggcaattggt ttcacctaga atggctgcgt cccttctttt  13260
cctcatggtt ggttttaaat gtctcttggt ttctcaggcg ttcgcctgca aaccatgttt  13320
cagttcgagt cttgcagaca ttaagaccaa caccaccgca gcggcaggct ttgctgtcct  13380
ccaagacatc agttgcctta ggcatcgcaa ctcggcccct gaggcgcttc gcaaaatccc  13440
tcagtgccgt acggcgatag ggacacctgt gtatattacc atcacagcca atgtgacaga  13500
tgagaattat ttacattctt ctgatctcct catgctctct tcttgccttt tctacgcttc  13560
tgagatgagt gaaaagggat ttaaggtggt ttttggcaat gtgtcaggca tcgtggctgt  13620
gtgtgtcaat tttaccagct acgtccaaca tgtcagggag tttacccaac gctccttgat  13680
ggtcgaccat gtgcggctgc tccatttcat gacacctgag accatgaggt gggcaaccgt  13740
tttagcctgt cttgttgcca ttctgttggc aatttgaatg tttaagtatg ttggggaaat  13800
gcttgaccgc gggctgttgc tcgcgattgc tttctttgtg gtgtatcgtg ccgttctgtt  13860
ccactgtgct cgtcgacgcc aacggcaaca gcagctctca tctgcaattg atttacaact  13920
tgacgctatg tgagctgaat ggcacggatt ggctagctaa tagatttgat tgggcagtgg  13980
agagctttgt catctttcct gttttgactc acatagtctc ctatgttgcc ctcaccacca  14040
gccatttcct tgacacaatt gctttagtca ctgtatctac cgccggtttt cttcacgggc  14100
ggtatgtcct gagtagcatc tacgcggtct gtgccctggc tgcgttgact tgcttcgtca  14160
ttaggtttgt aaagaattgc atgtcttggc gctactcatg taccagatat accaattttc  14220
ttctggacac taagggcaga ctctatcgtt ggcggtcgcc tgtcatcata gagaagaggg  14280
gcaaagttga ggtcgaaggt catctgatcg atctcaaaag agttgtgctt gatggttccg  14340
tggcaacccc tataaccaga gtttcagcgg aacaatgggg tcgtccttag atgacttttg  14400
tcatgatagt gcggctccac aaaaggtgct tttggcattt tctattacct acacgccagt  14460
gatgatatat gccctaaagg tgagtcgcgg ccgactgcta gggctgctgc accttttgat  14520
tttcctgaac tgtgctttca cctttgggta catgacattc acgcactttc agagtacaaa  14580
taaggtcgcg ctcactatgg gagcagtagt tgcactcctt tggggggtgt actcagccat  14640
agaaacctgg aaattcatca cctccagatg ccgtttgtgc ttgctaggcc gcaagtacat  14700
tctggcccct gcccaccacg ttgaaagtgc cgcaggcttt catccgattg cggcaaatga  14760
taaccacgca tttgtcgtcc ggcgtcccgg ctccactacg gtcaacggca cattggtgcc  14820
cgggttgaaa agcctcgtgt tgggtggcag aaaagctgtt aaacagggag tggtaaacct  14880
tgtcaaatat gccaaataac aacggcaagc agcagaagag aaagaagggg gatggccagc  14940
cagtcaatca gctgtgccag atgctgggta agatcatcgc ccagcaaaac cagtctagag  15000
gcaagggacc ggggaagaaa aataagaaga aaaacccgga gaagccccat tttcctctag  15060
ctactgaaga tgatgtcaga catcacttta cccctagtga gcggcaattg tgtctgtcgt  15120
caatccagac tgcctttaat caaggcgctg ggacttgcac cctgtcagat tcagggagga  15180
taagttacac tgtggagttt agtttgccta cgcatcatac tgtgcgcttg atccgcgtca  15240
cagcatcacc ctcagcatga tgggctggca ttctgaggca tcccagtgtt tgaattggaa  15300
gaatgtgtgg tgaatggcac tgattgacat tgtgcctcta agtcacctat tcaattaggg  15360
cgaccgtgtg gggtaatat ttaattggcg agaaccacac ggccgaaatt aaa         15413
```

<210> SEQ ID NO 6
<211> LENGTH: 15078
<212> TYPE: DNA
<213> ORGANISM: Artificial Sequence
<220> FEATURE:
<223> OTHER INFORMATION: Synthetic Construct

<400> SEQUENCE: 6
atgatgtgta gggtattccc cctacataca cgacacttct ggtgtttgtg taccttggag 60
gcgtgggtac agccccgccc cacccccttgg cccctgttct agcccaacag gtatccttct 120
ccctcggggc gagcgcgccg cctactgctc ccttgcagta ggaaggacct cccgagtatt 180
tccggagagc acctgcttta cgggatctcc accctttaac catgtctggg acgttctccc 240
ggtgcatgtg caccccggct gcccgggtat tttggaacgc cggccaagtc ttttgcacac 300
ggtgtctcag tgcgcggtct cttctctctt cagaacttca ggacactgac ctcggtgcaa 360
ttggattgtt ccacaagcct agggacaagc ttcactggaa agtccccatc ggcatccctc 420
aggtggaatg tactccatcc gggtgctgtt ggctctcagc tatattccct atagcacgta 480
tgacctctgg caatcataac ttcctccaac gacttgttaa ggttgctgat gttttgtacc 540
gcgacggttg cttggcacct cgacaccttc gtgaactcca agtttacgag cgcggctgca 600
actggtaccc gatcacgggg cccgtacccg ggatgggttt gtttgcgaac tccatgcacg 660
tatccgacca gccgttccct ggagccaccc atgtgttgac taactcgcct ctgcctcaac 720
gggcgtgccg gcaaccgttc tgtccatttg aggaagctca ttctaacgtg tataggtgga 780
ataaatttgt gattttcacg gactccactc tcaacggcca atctcgcatg atgtggacgc 840
cgggatccga tgattcagcc gccttggagg cgctaccgcc tgaattagaa cgtcaggtcg 900
gaatcctcat tcggagtttc cctgctcatc accccgttaa cctggccgac tgggagctca 960
ctgagacccc tgagaatggc ttctccttca gcacgtctca ttcttgtggt tatcttgtcc 1020
aaaaccccga tgtgtttgat agcaagtgct ggctcacttg cttttcgggc cagtcggtcg 1080
aagtgcgccg ctgtgaagaa catttagcca acgcccttgg ttaccaaacc aagtggggcg 1140
tgcacggtaa gtaccttcag cgcaggctcc aagttcgcgg cattcgtgct gtagtcgatc 1200
ctgatggccc cattcacgtt gaagcgctgt cttgctccca gtcttggatc aggcacctga 1260
ctctgaataa tggtgttacc ccaggattcg ttcgcctgac atccattcgc attgtgccga 1320
acacagagcc taccactttc cggatctttc ggtttggagc gcataagtgg tatggcgctg 1380
ctggcaaacg ggctcgtgcc aagcgtgccg ctaaaagtgg gaaagattcg gcttccactc 1440
ccaaggttgc ccagccggcc cttacctgtg gagtcaccac ctactctcca ccaacagacg 1500
ggtcttgcgg ttggcatgtc cttgccgcca taatgaaccg gatgatgaac ggtgacttca 1560
cgtccccact gcctcagtac aatagaccag aagacgattg ggcttctgat tatgatcttg 1620
ctcaggcgat tcaatgtcta caactgcctg caaccgtggt tcggaatcgt gcctgtccta 1680
acgccaagta ccttgtaaga cttaacgggg ttcactggga ggtagaggtg agatctggaa 1740
tggctccccg ctccctttct cgtgaatgtg tagttggcgt ttgctctgaa ggttgtgttg 1800
ctccgcctta tccagcggac gggcttccta aacgcgcact agaggccttg gcgtctgctt 1860
acagactacc ctccgattgt gttagctctg gcattgatga ctttcttgct aatccacccc 1920
ctcaggaatt ttggactctt gacaaaatgc tgacctcccc gtcaccagaa cggtccggct 1980
tctctagttt gtataagtta ctgttagagg ttgttccgca aaagtgtggt gccacggaag 2040
gggctttcac ctatgctgtt gagaggatgt taaaggattg tccgagctct gaacaggcca 2100
tggcccttct ggcaaaaatt aaagttccat cctcaaaggc cccgtctgtg tccctggacg 2160
ggtgtttccc tgcggatatt ccggctgatt tcgagccagc gtctcgggaa aggccccgaa 2220
gttccagcgt tgctgttgcc ctgtgttcac cggatgcaga aaggttcgag gaagtacccc 2280
cagaagaagt tcaagagaga ggctacaagg ccgtcaactc tgcactcctt gccgaaaacc 2340
ccaatgatga acaggcacag gtggttgccg gtgaacaact gaagctcggc ggttgtagtt 2400
tggcaatcgg gaatgctcag tccactccag gctccatgga agagaacatg cgcaatagcc 2460
gggaagacga accactagat ttgtccctac cagcactagc taccacgacg acccttgtga 2520
gagagcgaat actcgacaac ccaggtcctg atgccggtac cctccctgcc accgttcgag 2580
aatttgtctc gacagggcct atgctccgtc atgttgagca ttgtggcacg gagtctggcg 2640
acagcagttc acctttggat ctgtcttatg cgcaaactcc ggaccagcct ttaaatctgt 2700
ccctggccgc ttggccggtg aagaccaccg cgtctgaccc tggctgggtc cacggtaggt 2760
gcgagcctgt ctttgtaaag cctcgaaaag ctttttctga tggcgattca gcctttcagt 2820
tcggggggct ttctgagtcc agctctgtca tcgagtttga ccgaacaaaa gatgcatcgg 2880
aggttgacgc tcctgtcggc ttgacgactt cgaacgaggc cctctctgtg gtcgaccctt 2940
tcgaatttgc cgaactcaag cgcccgcgtt tctccgcaca agccttaatt gaccgaggcg 3000
gcccgcttgc cgatgtccat gcaaaaataa agcaccgggt gtatgaacaa tgccttcaag 3060
cttgtgagcc tggtagccgt gcaaccccag ccaccaagaa gtggctcgac aaaatgtggg 3120
acagggtgga catgaaaact tggcgctgca cctcgcagtt ccaagctggt cgcatccttg 3180
catccctcaa attccttcct gacatgattc aagacgcacc gcctcctgtt cccaggaaga 3240
accgagctag tgacaacgcc ggtttgaagc aactggtggc acagtgggat aggaaattga 3300
gtggaacccc cccccaaaa ccggctgggt cagtgcttga ccaggccgtc cctccaccca 3360
cggacgtcca gcaagaagat gtcactcctt ccggcgggcc actccatgcg ccggatttcc 3420
ctagtcgagt tagcacgagc gggggttgga aaagccttat actttccggg acccgtctcg 3480
cagggtctgt cagtcagcgc ctcatgacac gggtttttga agttttctcc catctcccag 3540
cttttgcgct cacacttttc tcgccgcggg gctctatggc tccaggcgat tggttgtttg 3600
caggtattgt tttacttgct ctcttgttct gtcgttttta cccgatactc ggatgccttc 3660
ccttattggg tgtcttttct gggtctgtgc ggcgtgttcg tctgggtgtt tttggttctt 3720
ggatggcttt tgctgtattt ctattctcga ctccatccaa cccagtcggt tcttcttgtg 3780
accacgattc gccggagtgt catgctgagc ttttggttct tgagcagcgc caactttggg 3840
aacctgtgcg cggccttgtg gtcggcccct cgggcctcct atgtgtcatt cttggcaagt 3900
tactcggtgg gtcacgttat ctctggcatg ttctcctacg tttatgcatg cttacagatt 3960
tggccctttc tcttgtttat gtggtgtccc aggggcgttg tcacaagtgt tggggaaagt 4020
gtataaggac ggctcctgct gaggtagcac ttaatgtatt tcctttctcg cgcgccaccc 4080
gtagctctct tgtatccttg tgtgatcggt tccaagcgcc taaaggagtt gatcctgtgc 4140
acttggcaac gggttggcac gggtgttggt gtggcgagag ccccgttcat caatcacacc 4200
aaaagccaat aacctatgcc aatttggatg aaaagaaaat atctgcccaa acggtggttg 4260
ctgtcccata cgaccccagc caggctatca aatgcctgaa agttctgcag gcgggagggg 4320
ctatcgtaga ccagcctaca cctgaagttg ttcgcgtgtc cgaggtcccc ttctcagccc 4380
catttttccc aaaagttcct gtcaacccgg attgcaggat tgtggtggat tcggacactt 4440
ttgtggctgc ggtccgctgc ggttactcga cagcacaact ggtcctgggc cggggcaatt 4500
ttgccaagct aaatcagacc cccctcagga gctctacctc caccaaaacg actggggggg 4560
cctcttacac ccttgctgta gctcaagtgt ctgcgtggac tcttgcccat ttcatcctcg 4620
gcctttggtt cacatcacct caagtgtgtg gccgagggac cgctgatcca tggtgttcaa 4680 atccctttc ataccctgcc tatggccctg gagttgtatg ctcctctcga ctttgtgtgt 4740
ctgccgatgg ggtcaccctg ccattgtttt cagctgtggc acaactctcc ggcagagagg 4800
tggggatttt tattttggtg cttgtctccc tgatagcttt ggcccatcgc ttggctctta 4860
aggcagactt gttagtggtc tttttggctt tttgtgctta cgcctggccc atgagttcct 4920
ggctaatctg cttctttcct atactcttaa agtggatcac cctccaccct ctcaccatgc 4980
tttgggtgca ctcattcttg gtgttttgcc tgccagcagc cggcgtcctc tcactaggga 5040
taactggcct tctttgggca atcggccgct ttacccaggt tgccgggatt attacacctt 5100
atgacatcca ccagtacacc tccgggccgc gtggtgcagc tgctgtggcc acagccccag 5160
aaggcactta tatggccgcc gtccggagag ctgctttaac tggcgatct ttaatattca 5220 ccccgtcagc agttggatcc ctcctcgaag gtgctttcag gactcataaa ccctgtctta 5280
atactgtgaa tgttgtgggc tcttcccttg gttccggagg cgttttcacc attgatggca 5340
gaagaactgt tgtcactgct gctcatgtgt tgaatggcga cacagctaga gttaccggcg 5400
actcctacaa ccgcatgcac actttcaaga ccaatggtga ttatgcctgg tcccatgctg 5460
atgactggca gggcattgcc cccgtggtca aggtagtgaa ggggtaccgc ggtcgtgctt 5520
attggcaaac atcaactggt gtcgaacccg gcatcattgg agaagggttt gccttctgtt 5580
tcactaattg tggtgattcg gggtcacccg tcatctcaga atccggtgat ctcatcggaa 5640
ttcacaccgg ttcaaacaaa ctcggttctg gtcttgtgac gacccctgaa ggggagacct 5700
gtaccatcaa agaaaccaag ctctccgacc tttccagaca ttttgcaggc cctagtgttc 5760
ctcttggtga cattaaatta agcccggcca tcatccctga tgtaacatct attccgagtg 5820
acttggcatc gctcctagcc tctgtccctg tggtggaagg cggcctctcg accgttcaac 5880
ttctgtgtgt ctttttcctt ctctggcgca tgatgggcca tgcctggaca cccattgttg 5940
ccgtgggctt ctttctgctg aatgaaatcc tcccagcagt tttggtccga gccgtgtttt 6000
cttttgcact ctttgtgctt gcatgggtca cccccctggtc cgcacaggtg ttgatgatta 6060
gactcctcac ggcatctctc aaccgcaaca agctctctct ggtgttctac gcactcgggg 6120
gtatcgtcgg tttggccgct gaaatcggga ctttcgctgg cagattgcct gaattgtctc 6180
aagccctttc gacctactgt ttcttgccta gggcccttgc catggccagt tgtgtcccca 6240
tcgtcattat tggcggactt catgccctcg gtgtaattct gtggttgttc aaataccggt 6300
gcctccacaa cacgctggtt ggtgatgggt gtttttcaag tgccttcttc ctgcgctatt 6360
ttgcggaggg caatctgagg aaaggtgttt cacagtcctg tggcatgaat aacgagtctc 6420
tgacggctgc tctggcttgc aagctgtcgc aggctgatct tgaatttttg tccagtttaa 6480
cgaacttcaa gtgctttgtg tctgcttcaa atatgaaaaa tgccgccggc cagtacattg 6540
aagcagctta tgccaaggcc ttgcgccaag agttggcctc tctagttcag gttgataaaa 6600
tgaaaggagt tttgtccaag ctcgaggcct ttgctgaaac agccaccccg tcccttgaca 6660
caggtgacgt ggttgttttg cttgggcagc atcctcacgg gtctatcctc gatattaatg 6720
tggggactga aaggaaaact gtgtccgtgc aagagacccg gaacctaggc ggctccaaat 6780
tcagtgtttg cactgtcgtg tccaacacac ccgtggacgc cttaaccggc atcccactcc 6840

-continued

```
ggacaccaac ccctcttttt gagaatggtc cgcgtcatcg cggtgaggaa gacgatctca   6900
aagtcgagag gatgaagaaa cactgtgtat ccctcggctt ccacaacatc aatggcaaag   6960
tctactgtaa gatctgggat aagtctaccg gtgacacctt ttacaccgac gattcccggt   7020
atacccacga ccatgctttt caggacaggt cagccgacta cagagacagg gactacgaag   7080
gtgtgcaaac cgccccccaa caaggctttg atccaaagtc tgaaacccct gttggcactg   7140
tagtgatcgg cggtatcacg tataacaggt acctgattaa aggtaaggag gtcctggtcc   7200
ccaagcctga caactgcctc gaagctgcca agctgtccct tgagcaggct ctcgctggga   7260
tgggccaaac ttgcgacctt acggctgccg aggtggaaaa gctgaagcgc atcattagtc   7320
aactccaagg tttgaccact gaacaggctt taaactgtta gccgccagcg gcttgacccg   7380
ctgtggccgc ggcggcttag tagtgactga aacggcggta aaaattgtaa aatatcacaa   7440
cagaactttc accttaggcc cttttgacct gaaagtcact accgaggcag aggtcaagaa   7500
atcagctgag cagggccacg ctgttgtggc aaatttatgt tctggtgtcg tcttgatgag   7560
acctcaccca ccgtctcttg ttgacgttct tttgaaaccc ggacttgaca caaaacccgg   7620
cattcagcca gggcatgggg ccgggaatat gggcgtggaa ggttctattt gggatttcga   7680
aaccgcacct acaaaggcag aactcgagtt atccaagcaa ataattcaag catgtgaagt   7740
taggcgcggg gacgccccga acctccaact cccttacaag ctctatcctg ttaggggggga   7800
tcctgagcgg catgagggcc gccttatcaa caccaggttt ggagatttat cttacaaaac   7860
tcctcaagac accaagtccg caatccacgc ggcttgttgc ctgcacccca acggggcccc   7920
cgtgtctgat ggtaaatcaa cactaggtac cactcttcaa catggttttg agctttacgt   7980
ccctactgtg ccttatagtg tcatggagta cctcgattca cgccctgaca cccctttttat   8040
gtgcaccaaa catggcactt ccaaggctgc tgcagaggac cttcaaaaat acgacctgtc   8100
cactcaaggc ttcgtcctgc ctggggtcct acgcctagta cgtagataca tttttggcca   8160
tattggtaag gcgccgccat tgttcctccc atcaacctat cccgccaaga actctatggc   8220
agggatcaat ggccagagat tcccaacaaa ggacgttcag agcatacctg aaattgatga   8280
aatgtgtgcc cgcgccgtca aagagaattg gcaaactgtg acaccttgta ccctcaagaa   8340
acagtattgt tccaagccca aaaccaggac catcctaggc actaacaact ttattgcctt   8400
ggctcacaga tcggcgctca gtggtgttac ccaggcattc atgaagaagg cttggaagtc   8460
cccaattgcc ttgggaaaaa acaaattcaa ggagctgcat tgcaccgtcg ccggcaggtg   8520
tcttgaggct gacttggcct cctgtgaccg cagcaccccc gccattgtga gatggttcgt   8580
cgccaacctc ctgtatgaac ttgcgggatg tgaagagtac ttgcctagct atgtacttaa   8640
ttgctgccat gaccttgtgg caacacagga tggtgccttc acaaaaacgcg gtggcctgtc   8700
gtccggggac cccgtcacca gtgtgtctaa caccgtatat tcgctggtaa tctatgccca   8760
gcacatggtg ttgtcagcct tgaaaatggg tcatgaaatc ggtcttaagt tcctcgagga   8820
acagctcaga ttcgaggacc tcctcgaaat tcagcctatg ttggtatact ctgatgacct   8880
cgttttgtac gctgaaagac ccacttttcc taattatcac tggtgggtcg agcaccttga   8940
cctaatgctg ggttttaaaa cggacccaaa gaagaccgtc ataactgata aacccagctt   9000
cctcggctgc agaattgagg cagggcggca gctggtcccc aatcgcgacc gcatcctggc   9060
tgctctcgca tatcacatga aggcgcagaa tgcctcagag tattatgcgt ctgctgccgc   9120
aatcctgatg gattcatgcg cttgcattga tcatgacccc gagtggtatg aggacctcat   9180
```

```
ctgcggtatt gcccgatgcg cccgccaaga tggttatagc ttcccaggtc cggcgttttt   9240
catgtctatg tgggagaggc tgagaagtca caatgaaggg aagaaattcc gccactgcgg   9300
catctgtgac gccaaagccg actatgcatc cgcctgtggg ctcgatctat gtttgttcca   9360
ctcgcacttt catcaacact gtcccgtcac tctgagctgc ggtcaccatg ccggttcaag   9420
ggaatgttcg cagtgtcagt cacctgttgg ggctggcaga tcccctcttg atgctgtgtt   9480
gaaacaaatt ccatacaaac ctccccgcac tgtcatcatg aaggtgagta acaaaacaac   9540
ggccctcgat ccggggaggt accagtcccg tcgaggcctc gttgcagtca agagaggtat   9600
cgccggcaat gaagttgatc tttctgatgg agactaccaa gtggtacctc ttttgccgac   9660
ttgcaaagac ataaacatgg tgaaagtggc ttgcaatgta ctactcagta agttcatagt   9720
ggggccacca ggttccggaa agaccacctg gctactagat caagtccaag acgatgatgt   9780
catttacaca ccaacccatc agactatgtt tgatatagtt agtgctctca aagtttgcag   9840
gtactctatt ccaggagcct caggactccc tttcccacca tctgccagat ccgggccgtg   9900
ggttaggctt atagccagtg ggcacgtccc tggccgcgta tcttacctcg atgaggccgg   9960
atactgtaat catctggaca ttctcagatt gctctccaaa acgccccttg tgtgtttggg  10020
tgaccttcaa cagctacacc ctgtcggctt tgattcctac tgttatgtgt ttgatcagat  10080
gccccagaag caactgaccg ttatttacag atttggccct aacatctgcg cggccattca  10140
gccttgttac agagagaagc ttgaatccaa ggctagaaac accagggtgg tttttgtcaa  10200
ccggcctgtg gcctttggtc aggtcctgac accataccat aaagatcgca tcggctctgc  10260
ggtaaccata gactcatccc agggagccac ctttgatatt gtgacactgc atctaccgtc  10320
accaaagtcc ctaaccaaat cccgagcact tgtggccatc actcgggcaa gacacgggtt  10380
gttcatttat gacccacatg accagctcca ggagtttttc aacttaatcc ctgagctcac  10440
agattgcaac cttgtgttta accgcgggga tgagctggta gttctggatt cggataatgc  10500
agtcacaact gtagcaaagg ccctagaaac aggtcaatct cgattccgag tgtcagaccc  10560
gaggtgcaag tctctcttgg ccgcttgttc ggccagtctg gaagggagct gtatgccact  10620
accgcaagta gcacataatc tggggtttta cttttcccca gacagtccag tatttgcacc  10680
tctgccaaga gagttggcgt cacattggcc agtggttacc caccagaata atcgggcgtg  10740
gcctgatcga cttgtcgcta gtatgcgccc aatcgatgcc cgctacagca agccgatggt  10800
cggtgcaggg tacgtagtcg ggccgtccac ttttcttggt actcccggtg tggtgtcata  10860
ctacctcacg ctatacatca ggggtgagcc ccaggccctg ccagaaacac tcgtttcaac  10920
ggggcgtata gcaacagatt gtcgggagta tctcgatgcg gctgaggagg aggcagcaaa  10980
agaactcccc cacgcattca ttggcgatgt caaaggtacc acggtggggg gttgtcatca  11040
catcacgtca aaatacttac ctaggtccct gcctaaagac tctgttgccg tagttggagt  11100
gagttcaccc ggcagggctg ctaaagccat gtgcaccgtc accgatgtgt atctccctga  11160
actccggccg tatctgcaac ctgagacggc atcaaagtgc tggaaactta aattagactt  11220
cagggacgtc cgactaatgg tctggaaagg agctaccgcc tatttccagt tggaagggtt  11280
tacatggtcg gcgctgcccg actatgccag gttcattcag ctgcccaagg atgccgttgt  11340
atacatcgat ccgtgtatag gaccggcaac agccaaccgc aaggtcgtgc gaaccacaga  11400
ctggcgggcc gacctggcag tgacaccgta tgactacggt gcccagacta ttttaacaac  11460
agcctggttc gaggacctcg ggccacagtg gaagattttg ggggttgcagc cctttaggcg  11520
agcacttggt ctggaaaaca ctgaggattg ggcaattctt gcacgccgta tgaatgacgg  11580
```

caaagactac actgactata actggaattg tgttcgagga cgcccacaag ccatctacgg 11640
gcgtgctcgt gaccatacgt atcatttcgc ccccggcacg gaactgcagg tagagctagg 11700
taaaccccgg ctatcgcctg agcaggtgcc gtgaatttgg agtgatgcaa tggggtcact 11760
gtggagtaaa atcagccagc tgttcgtgga tgccttcact gagttcttgg ttagtgtggt 11820
tgatattgtc atcttccttg ctatattgtt tgggttcacc gtcgcaggat ggttattggt 11880
cttccttctc agagtggttt gctccgcgtt tctccgttcg cgctctgcca ttcactctcc 11940
cgaactatcg aagatcctat gaaggcttgt tgcccaactg cagaccggat gtcccacaat 12000
ttgcattcaa gcaccctttg ggtatgttgt ggcatatgcg agtttcccac ctgattgatg 12060
agatggtctc tcgccgcatt taccagacca tggaacattc aggtcaagcg gcctggaagc 12120
aagtagttgg tgaggccact ctcacgaagc tgtcagggct cgatatagtc actcacttcc 12180
aacacctggc cgcagtggag gcggattctt gccgctttct cagctcacga ctcgtgatgc 12240
taaaaaatct tgccgttggc aatgtgagcc tacagtacaa caccacgctg gaccgcgttg 12300
agctcatttt tcccacgtca ggtacgaggc ccaagttaac cgacttcaga caatggctca 12360
tcagtgtgca cgcttccatt ttttcctctg tggcttcatc tatcaccttg tttgtagtgc 12420
tttggcttcg aattccagct ctacgctatg tttttggttt ccactggccc acggcaacac 12480
atcattcgag ctgaccatca actataccat atgcaagcct tgtcttacca gtcaagcagc 12540
tcaccaaagg cttgagcccg gtcgcaatgt gtggtgcaga atagggcatg agacgtgtga 12600
ggagcgtgac catgatgagt tgttcatgcc catcccgtcc ggatacgata acatcaaact 12660
taagggttat tatgcctggc tggctttttt gtccttttcc tacgcggccc aattccaccc 12720
ggagttgttc gggattggga atgtgtcgcg tgtctttgtg gacaaacatc accagttcat 12780
ttgtgccgag catgatggac agaattcgac cgtatctact ggacacaaca tctctgcact 12840
atatgcggca tactaccacc accaaataga cgggggtaat tggttccatt tggaatggct 12900
gcgaccactc ttttcctcct ggttggtgct caatatatca tggtttctga ggcgttcgcc 12960
tgcaagccct gtttctcgac gcatctatca gatattaaga ccaacacgac cgcggctgcc 13020
ggtttcatgg tccttcagga catcaattgt ttccaacccc acagggtccc agcaacgcaa 13080
aatggagccc ccttcaaaaa gtcgtcccaa tgccgtgaag ctgtcggcac tccccaatac 13140
atcacaataa cagctaatgt gaccgacgaa tcgtacttgt acaacgcgga cttgctgatg 13200
ctttctgcgt gccttttcta cgcttcagaa atgagtgaga aaggctttaa agtcatcttc 13260
gggaatgtct ctggcgttgt ttccgcttgt gtcaatttta cagattatgt ggcccatgtg 13320
acccaacaca cccagcagca tcacctggta attgatcaca ttcggctgct gcatttcctg 13380
acaccatctg caatgaggtg ggctacaacc attgcttgtt tgctcgccat tctcttggcg 13440
atatgagatg ttctcacaag ttggggcgtt ccttgactcc gcactcttgc ttctggtggc 13500
tttttttgct gtgtaccggc ttgtcttggt cctttgccga tggcaacggc aacaactcga 13560
cataccaata catatataat ttgacgatat gcgagttgaa tgggaccgcg tggctgtccg 13620
gccattttga ttgggcagtt gagacttttg tgctttaccc ggttgccact cacatcctct 13680
cactgggttt tctcacaaca agtcattttt ttgacgcgct cggtctcggt gttgtatcca 13740
ctgctggatt tgttggcggg cggtatgtac tcagcagcgt ctacggcgct tgtgctttcg 13800
cagcgttcgt gtgttttgcc atccgtattg cgaaaaattg catggcctgc cgctacgccc 13860
gcacccggtt taccaacttc attgtggacg accggggagg agttcatcga tggaagtccc 13920

```
caatagtggt ggaaaaattg ggcaaagccg aagtcgacgg cagccttgtc accatcaaac  13980
atgtcgtcct cgaaggggtt aaagctcaac ctttaacgag gacttcggcc gagcaatggg  14040
aggcctagat gatttttgca acgattctac cgctgcacaa aagctcgtgc tggctttcag  14100
catcacatac acacctataa tgatatatgc ccttaaggtg tcacgcggcc gactcctggg  14160
gctgttgcac atcctaatat ttctgaactg ttcctttaca ttcggataca tgacatatgt  14220
gcattttcaa tccaccaacc gtgtcgcact cactctgggg gctgtcgtcg ccctttttatg  14280
gggtgcttac agcctcacag agtcatggaa gtttatcact tccagatgca gattgtgttg  14340
ccttggccgg cgatacattc tggcccctgc ccatcacgta gaaagtgctg caggtctcca  14400
tccaatctca gcgtctggta accgagcata cgctgtgaga aagccaggac taacatcagt  14460
gaacggcact ctagtaccag gacttcggag cctcgtgctg ggcggcaaac gagctgttaa  14520
acgaggagtg gttaacctcg tcaagtatgg ccggtagaaa ccagagccag aagaaaaaga  14580
aaaacacagc tccaatgggg aatggccagc cagtcaatca actgtgccag ttgctgggtg  14640
caatgataaa gtcccagcgc cagcaaccta ggggaggaca ggccaaaaag aaaaagcctg  14700
agaagccaca ttttcccttg gctgcagaag atgacatccg gcaccacctc acccagactg  14760
aacgctccct ctgcttgcaa tcgatccaga cggctttcaa tcaaggcgcg ggaactgcgt  14820
tgctttcatc cagcgggaag gtcagttttc aagttgagtt tatgctgccg gttgctcata  14880
cagtgcgcct gattcgcgtg acttctacat ccgctagtca gggtgcaagt taatttgatg  14940
gtcaggtgaa tggtcgcgat tggcgtgtgg cctttgagtc acctattcaa ttagggcgat  15000
cacatggggg tcatacttaa tcaggcagga accatgtgac cgaaattaaa aaaaaaaaaa  15060
aaaaaaaaaa aaaaaaaa                                                15078
```

```
<210> SEQ ID NO 7
<211> LENGTH: 14885
<212> TYPE: DNA
<213> ORGANISM: Artificial Sequence
<220> FEATURE:
<223> OTHER INFORMATION: Synthetic Construct

<400> SEQUENCE: 7

tatgacgtat aggtgttggc tctatgcctt ggcatttgta ttgtcaggag ctgtgaccat     60
tggcacagcc caaaacttgc tgcacagaaa cacccttctg tgatagcctc cttcagggga    120
gcttagggtt tgtccctagc accttgcttc cggagttgca ctgctttacg gtctctccac    180
ccctttaacc atgtctggga tacttgatcg gtgcacgtgt acccccaatg ccagggtgtt    240
tatggcggag ggccaagtct actgcacacg atgcctcagt gcacggtctc tccttcccct    300
gaacctccaa gtttctgagc tcggggtgct aggcctattc tacaggcccg aagagccact    360
ccggtggacg ttgccacgtg cattccccac tgttgagtgc tcccccgccg gggcctgctg    420
gctttctgca atctttccaa tcgcacgaat gaccagtgga aacctgaact tccaacaaag    480
aatggtacgg gtcgcagctg agctttacag agccggccag ctcacccctg cagtcttgaa    540
ggctctacaa gtttatgaac ggggttgccg ctggtacccc attgttggac ctgtccctgg    600
agtggccgtt ttcgccaatt ccctacatgt gagtgataaa cctttcccgg gagctactca    660
cgtgttgacc aacctgccgc tcccgcagag acccaagcct gaagactttt gcccctttga    720
gtgtgctatg gctactgtct atgacattgg tcatgacgcc gtcatgtatg tggccgaaag    780
gaaaatctcc tgggcccctc gtggcgggga tgaagtgaaa tttgaagctg tccccgggga    840
gttgaagttg attgcgaacc agctccgcac ctccttcccg ccccaccaca cagtggacat    900
```

```
gtctaagttc gccttcacag cccctgggtg tggtgtttct atgcgggtcg aacgccaaca    960
cggctgcctt cccgctgaca ctgtccctga aggcaactgc tggtggagct tgtttgactt   1020
gcttccactg gaagttcaga acaaagaaat tcgccatgct aaccaatttg gctaccagac   1080
caagcatggt gtctctggca agtacctaca gcggaggctg caagttaatg gtctccgagc   1140
agtaactgac ctaaacggac ctatcgtcgt acagtacttc tccgttaagg agagttggat   1200
ccgccatttg aaactggcgg gagaacccag ctactctggg tttgaggacc tcctcagaat   1260
aagggttgag cctaacacgt cgccattggc tgacaaggaa gaaaaaattt tccggtttgg   1320
cagtcacaag tggtacggcg ctggaaagag agcaagaaaa gcacgctctt gtgcgactgc   1380
tacagtcgct ggccgcgcct tgtccgttcg tgaaacccgg caggccaagg agcacgaggt   1440
tgccggcgcc aacaaggctg agcacctcaa acactactcc ccgcctgccg aagggaattg   1500
tggttggcac tgcatttccg ccatcgccaa ccggatggtg aattccaaat ttgaaaccac   1560
ccttcccgaa agagtgagac cttcagatga ctgggctact gacgaggatc ttgtgaatgc   1620
catccaaatc ctcagactcc ctgcggcctt agacaggaac ggtgcttgta ctagcgccaa   1680
gtacgtactt aagctggaag gtgagcattg gactgtcact gtgacccctg ggatgtcccc   1740
ttctttgctc cctcttgaat gtgttcaggg ctgttgtggg cacaagggcg gtcttggttc   1800
cccagatgca gtcgaggtct ccgggtttga ccctgcctgc cttgaccggc tggctgaggt   1860
gatgcacctg cctagcagtg ctatcccagc cgctctggcc gaaatgtctg gcgattccga   1920
tcgttcggct tctctggtca ccaccgtgtg gactgtttcg cagttctttg cccgtcacag   1980
cggagggaat caccctgacc aagtgcgctt agggaaaatt atcagccttt gtcaggtgat   2040
tgaggactgc tgctgttccc agaacaaaac caaccgggtc accccggagg aggtcgcagc   2100
aaagattgac ctgtacctcc gtggtgcaac aaatcttgaa gaatgcttgg ccaggcttga   2160
gaaagcgcgc ccgccacgcg taatcgacac ctcctttgat tggggtgttg tgctccctgg   2220
ggttgaggcg gtaacccaga cgaccaagct gccccaggtc aaccagtgtc gtgctctggt   2280
ccctgttgtg actcaaaagt ccttggacaa caactcggtc cccctgaccg cctttttcact   2340
ggctaactac tactaccgtg cgcaaggtga cgaagttcgt caccgtgaaa gactaaccgc   2400
cgtgctctcc aagttggaaa aggttgttcg agaagaatat gggctcatgc caaccgagcc   2460
tggttcacgg cccacactgc cacgcgggct cgacgaactc aaagaccaga tggaggagga   2520
cttgctgaaa ctggctaacg cccagacgac ttcggacatg atggcctggg cggtcgagca   2580
ggttgaccta aaaacttggg tcaagaacta cccgcggtgg acaccaccac cccctccgcc   2640
aaaagttcag cctcgaaaaa cgaagcctgt caagagcttg ccggagagaa agcctgtccc   2700
cgccccgcgc aggaaggttg ggtccgattg tggcagcccg gtttcattag gcggcgatgt   2760
ccctaacagt tgggaagatt tggctgttag tagccccttt gatctcccga ccccacctga   2820
gccggcaaca ccttcaagtg agctggtgat tgtgtcctca ccgcaatgca tcttcaggcc   2880
ggcgacaccc ttgagtgagc cggctccaat tcccgcacct cgcggaactg tgtctcgacc   2940
ggtgacaccc ttgagtgagc cgatccctgt gcccgcaccg cggcgtaagt ttcagcaggt   3000
gaaaagattg agttcggcgg cggcaatccc accgtaccag aacgagcccc tggatttgtc   3060
tgcttcctca cagactgaat atgaggcctc tcccccagca ccgccgcacc agggaccctt   3120
ggccttctcc gaggataaac cggtagacga ccaacttgtc aacgactccc ggatatcgtc   3180
gcggaggcct gacgagagca catcagctcc gtccgcaggc acaggtggcg ccggctctct   3240
```

-continued taccgatttg ccgccttcag atggcgcgga tgcggacggg ggggggccgt ttcggacggt 3300
aaaaagaaaa gctgaaaggc tctttgacca actgagccgt caggtttttg acctcgtctc 3360
ccatctccct gttttcttct cacgcctttt ccaccctggc ggtggttatt ctccgggtga 3420
ttggggtttt gcagctttta ctctattgtg cctcttttta tgttacagtt acccagcctt 3480
tggtattgct cccctcttgg gtgtgttttc tgggtcttct cggcgcgttc gaatgggggt 3540
ttttggctgc tggttggctt ttgctgttgg tctgttcaaa cctgtgtccg acccagtcgg 3600
cgctgcttgt gagtttgact cgccagagtg tagaaacatc cttcattctt ttgagcttct 3660
caaaccttgg gaccctgttc gcagccttgt tgtgggcccc gtcggtctcg gtcttgccat 3720
tcttggcagg ttactgggcg gggcacgctg catctggcac tttttgctta ggcttggcat 3780
tgttgcagac tgtatcttgg ctggagctta cgtgctttct caaggtaggt gtaaaaagtg 3840
ctggggatct tgtataagaa ctgctcctaa tgaggtcgct tttaacgtgt ttcctttcac 3900
acgtgcgacc aggtcgtcac ttatcgacct gtgcgatcgg ttttgtgcgc caaaaggaat 3960
ggaccccatt tttctcgcca ctgggtggcg cgggtgctgg gccggccgaa gccccattga 4020
gcaaccctct gaaaaaccca tcgcgtttgc ccaattggat gaaaagaaga ttacggctag 4080
gactgtggtc gcccagcctt atgaccccaa ccaagccgta aagtgcttgc gggtattgca 4140
ggcgggtggg gcgatggtgg ctgaggcggt cccaaaagtg gtcaaggttt ccgctgttcc 4200
attccgagcc cccttctttc ccactggagt gaaagttgac cctgattgca gggtcgtggt 4260
tgaccctgac actttcactg cagctctccg gtctggctac tccaccacaa acctcgtcct 4320
tggtgtaggg gactttgccc agctgaatgg attaaaaatc aggcaaattt ccaagccttc 4380
agggggaggc ccacatctca tggctgccct gcatgttgcc tgctcgatgg ctctgcacat 4440
gcttgttggg atttatgtga ctgcggtggg ttcttgcggc accggcacca acgacccgtg 4500
gtgcgctaac ccgtttgccg tccctggcta cggacctggc tctctctgca cgtccagatt 4560
gtgcatttcc caacacggcc ttaccctgcc cttgacagca cttgtggcgg gattcggtat 4620
tcaagaaatt gccttggtcg ttttgatttt tgtttccatc ggaggcatgg ctcataggtt 4680
gagctgtaag gctgacatgc tgtttgtttt gcttgcaatt gccagctatg tttgggtacc 4740
tcttacctgg ttgctttgtg tgtttccttg ctggttgcgc tgtttttctt tgcacccct 4800
caccatccta tggttggtgt ttttcttgat ttctgtgaat atgccttcag gaatcttggc 4860
catggtgttg ttggtttctt tttggcttct tggtcgttat actaatgttg ctggccttgt 4920
cacccctac gacattcatc attacaccag tggcccccgc ggtgttgccg ccttggctac 4980
cgcaccagat gggacctact tggccgctgt ccgccgcgct gcgttgactg gccgcaccat 5040
gctgtttacc ccgtcccagc ttgggtctct tcttgagggt gctttcagaa ctcgaaagcc 5100
ctcactgaac accgtcaatg tgatcgggtc ctccatgggc tctggcgggg tgtttaccat 5160
cgacgggaaa gtcaagtgcg taactgccgc acatgtcctt acgggcaatt cagctcgggt 5220
ttccggggtc ggcttcaatc aaatgcttga ctttgacgta aagggagatt tcgctatagc 5280
tgattgcccg aattggcaag gggctgcccc caagacccaa ttctgcacgg atggatggac 5340
tggccgtgcc tattggctaa catcctctgg cgtcgaaccc ggcgtcattg gaaaaggatt 5400
cgccttctgc ttcaccgcat gtggcgattc cgggtcccca gtgatcaccg aggccggtga 5460
gcttgtcggc gttcacacgg gatcgaataa acaagggggg ggcattgtta cgcgcccctc 5520
aggccagttt tgtaatgtgg cacccatcaa gctaagcgaa ttaagtgaat tctttgctgg 5580
gcctaaggtc ccgctcggtg atgtgaaggt cggcagccac ataattaaag acataagcga 5640

```
ggtgccttca gatctttgtg ccttgcttgc tgccaaacct gaactggaag gaggcctctc   5700
caccgtccaa cttctttgtg tgttttttct cctgtggaga atgatgggac atgcctggac   5760
gcccttggtt gctgtgagtt tctttatttt gaatgaggtt ctcccagccg tcctggtccg   5820
gagtgttttc tcctttggaa tgtttgtgct atcctggctc acgccatggt ctgcgcaagt   5880
tctgatgatc aggcttctga cagcagctct taacaggaac agatggtcac ttgccttttt   5940
cagcctcggt gcagtgaccg gttttgtcgc agatcttgcg gccactcagg ggcatccgct   6000
gcaggcagtg atgaatttga gcacctatgc attcctgcct cggatgatgg ttgtgacctc   6060
accagtccca gtgatcacgt gtggtgtcgt gcacctactt gccatcattt tgtacttgtt   6120
taagtaccgt ggcctgcacc atatccttgt tggcgatgga gtgttctctg cggctttctt   6180
cttgagatac tttgccgagg gaaagttgag ggaaggggtg tcgcaatcct gcggaatgaa   6240
tcatgagtct ctgactggtg ccctcgctat gagactcaat gacgaggact tggatttcct   6300
tataaaatgg actgatttta agtgctttgt ttctgcgtcc aacatgagga atgcagcggg   6360
tcaatttatc gaggctgcct atgctaaagc acttagagta gaactggccc agttggtgca   6420
ggttgataaa gttcgaggta ctttggccaa acttgaagct tttgctgata ccgtggcacc   6480
tcaactctcg cccggtgaca ttgttgtcgc tctcggccac acgcctgttg gcagtatctt   6540
cgacctaaag gttggtagca ccaagcatac cctccaagcc attgagacca gagtccttgc   6600
tgggtccaaa atgaccgtgg cgcgcgtcgt cgacccgacc cccacgcccc cacccgcacc   6660
cgtgcccatc cccctcccac cgaaagttct ggagaatggc cccaacgctt ggggggatga   6720
ggaccgtttg aataagaaga agaggcgcag gatggaagcc ctcggcatct atgttatggg   6780
cgggaaaaag taccagaaat tttgggacaa gaattccggt gatgtgtttt atgaggaggt   6840
ccataataac acagatgagt gggagtgtct cagagttggc gaccctgccg actttgaccc   6900
tgagaaggga actctgtgtg gacatgtcac cattgaaaac aaggcttacc atgtttacac   6960
ctccccatct ggtaagaagt tcttggtccc cgtcaaccca gagaatggaa gagttcaatg   7020
ggaagctgca aagctttccg tggagcaggc cctaggtatg atgaatgtcg acggcgaact   7080
gactgccaaa gaactggaga aactgaaaag aataattgac aaactccagg gcctgactaa   7140
ggagcagtgt ttaaactgct agccgccagc gacttgaccc gctgtggtcg cggcggcttg   7200
gttgttactg aaacagcggt aaaaatagtc aaatttcaca accggacctt caccctggga   7260
cctgtgaatt taaaagtggc cagtgaggtt gagctaaaag acgcggttga gcacaaccaa   7320
cacccggttg cgagaccgat cgatggtgga gttgtgctcc tgcgctccgc ggttccttcg   7380
cttatagacg tcttgatctc cggtgctgat gcatctccca agttacttgc ccatcacggg   7440
ccgggaaaca ctgggatcga tggcacgctc tgggattttg agtccgaagc cactaaagag   7500
gaagtcgcac tcagtgcgca aataatacag gcttgtgaca ttaggcgcgg cgacgctcct   7560
gaaattggtc tcccttacaa gctgtaccct gttaggggta accctgagcg ggtgaaagga   7620
gttttgcaga atacaaggtt tggagacata ccttacaaaa cccccagtga cactggaagc   7680
ccagtgcacg cggctgcttg ccttacgccc aacgccactc cggtgactga tgggcgctcc   7740
gtcttggcca cgaccatgcc ccccgggttt gagttatatg taccgaccat accagcgtct   7800
gtccttgatt accttgactc taggcctgac tgccctaagc agctgacaga gcacggctgc   7860
gaagatgccg cactgaaaga cctctctaaa tatgacttgt ccacccaagg ctttgtttta   7920
cctggagttc ttcgccttgt gcggaaatac ctgtttgccc atgtaggtaa gtgcccaccc   7980
```

```
gttcatcggc cttctactta ccctgctaag aattctatgg ctggaataaa tgggaacagg   8040
ttcccaacca aggacattca gagcgtccct gaaatcgacg ttctgtgcgc acaggctgtg   8100
cgagaaaact ggcaaactgt cacccccttgt actcttaaga aacagtattg cgggaagaag   8160
aagactagga ccatactcgg caccaataac ttcatcgcac tagcccaccg agcagtgttg   8220
agtggtgtta cccagggctt catgaaaaag gcgtttaact cgcccatcgc cctcggaaag   8280
aacaagttta aggagctaca gactccggtc ctgggcaggt gccttgaagc tgatctcgca   8340
tcctgcgatc gatccacgcc tgcaattgtc cgctggtttg ccgccaacct tctttatgaa   8400
cttgcctgtg ctgaagagta tctaccgtcg tacgtgctga actgctgcca cgacttactg   8460
gtcacgcagt ccggcgcagt gactaagaga ggtggcctgt cgtctggcga cccgatcacc   8520
tctgtgtcta acaccattta tagtttggtg atctatgcac agcatatggt gcttagttac   8580
ttcaaaagtg gtcaccccca tggccttctg ttcttacaag accagctaaa gtttgaggac   8640
atgctcaagg ttcaacccct gatcgtctat tcggacgacc tcgtgctgta tgccgagtct   8700
cccaccatgc caaactatca ctggtgggtt gaacatctga atttgatgct ggggtttcag   8760
acggacccaa agaagactgc aataacagac tcgccatcat ttctaggctg tagaataata   8820
aatgggcgcc agctggtccc caaccgtgac aggatcctcg cggccctcgc ctatcacatg   8880
aaggcgagta atgtttctga atactatgcc tcagcggctg caatactcat ggacagctgt   8940
gcttgtttgg agtatgatcc tgaatggttt gaagaacttg tagttggaat agcgcagtgc   9000
gcccgcaagg acggctatag ctttcccggc acgccgttct tcatgtccat gtgggaaaaa   9060
ctcaggtcca attatgaggg gaagaagtcg agagtgtgcg ggtactgcgg ggccccggct   9120
ccgtacgcta ctgcctgtgg cctcgacgtc tgcatttacc acacccactt ccaccagcat   9180
tgtccagtca caatctggtg tggccatcca gcgggttctg gttcttgtag tgagtgcaaa   9240
tcccctgtag ggaaaggcac aagcccttta gacgaggtgc tggaacaagt cccgtataag   9300
cccccacgga ccgttatcat gcatgtggag cagggtctca cccccccttga tccaggtaga   9360
taccaaactc gccgcggact agtctctgtc aggcgtggaa ttaggggaaa tgaagttgaa   9420
ctaccagacg gtgattatgc tagcaccgcc ttgctcccta cctgcaaaga gatcaacatg   9480
gtcgctgtcg cttccaatgt attgcgcagc aggttcatca tcggcccacc cggtgctggg   9540
aaaacatact ggctccttca acaggtccag gatggtgatg ttatttacac accaactcac   9600
cagaccatgc ttgacatgat tagggctttg gggacgtgcc ggttcaacgt cccggcaggt   9660
acaacgctgc aattccccgt cccctcccgc accggtccgt gggttcgcat cctagccggc   9720
ggttggtgtc ctggcaagaa ttccttccta gatgaagcag cgtattgcaa tcaccttgat   9780
gttttgaggc ttcttagtaa aactaccctc acctgtctag gagacttcaa gcaactccac   9840
ccagtgggtt ttgattctca ttgctatgtt tttgacatca tgcctcaaac tcaactgaag   9900
accatctgga ggtttggaca gaatatctgt gatgccattc agccagatta cagggacaaa   9960
ctcatgtcca tggtcaacac aacccgtgtg acctacgtgg aaaaacctgt taggtatggg  10020
caggtcctca ccccctacca tagggaccga gaggacgacg ccatcactat tgactccagt  10080
caaggcgcca cattcgatgt ggttacattg catttgccca ctaaagattc actcaacagg  10140
caaagagccc ttgttgccat caccagggca agacacgcta tctttgcgta tgacccacac  10200
aggcagctgc agggcttgtt tgatcttcct gcaaaaggca cacccgtcaa cctcgcagtg  10260
caccgcgacg ggcagctgat cgtgctggat agaaataaca aagaatgcac ggttgctcag  10320
gctctaggca acggggataa atttagggcc acagacaagt gtgttgtaga ttctctccgc  10380
```

gccatttgtg ctgatctaga agggtcgagc tctccgctcc ccaaggtcgc acacaacttg 10440
ggattttatt tctcacctga tttaacacag tttgctaaac tcccagtaga acttgcacct 10500
cactggcccg tggtgacaac ccagaacaat gaaaagtggc cagatcggct ggttgccagc 10560
cttcgcccta tccataaata cagccgcgcg tgcatcggtg ccggctatat ggtgggccct 10620
tcggtgtttc taggcactcc tggggtcgtg tcatactatc tcacaaaatt tgttaagggc 10680
gaggctcaat tgcttccgga gacggttttc agcaccggcc gaattgaggt agactgccgg 10740
gaatatcttg atgatcggga gcgagaagtt gctgcgtccc tcccacacgc tttcattggc 10800
gacgtcaaag gcactaccgt tggaggatgt catcatgtca cctccagata cctcccgcgc 10860
gtccttccca aggaatcagt tgcggtagtc ggggtttcaa gccccggaaa agccgcaaaa 10920
gcattgtgca cactgacaga tgtgtacctc ccagatcttg aagcctatct ccacccggag 10980
acccagtcca agtgctggag aatgatgttg gacttcaaag aagttcgact aatggtctgg 11040
aaagacaaaa cagcctattt ccaacttgaa ggtcgctatt tcacctggta tcagcttgcc 11100
agctatgcct cgtacatccg tgttcctgtc aactctacgg tgtacttgga cccctgcatg 11160
ggccccgccc tttgcaacag gagagtcgtc gggtccaccc actgggggc tgacctcgcg 11220
gtcacccctt atgattacgg cgctaaaatt atcctgtcta gcgcgtacca tggtgaaatg 11280
ccccccggat acaaaattct ggcgtgcgcg gagttctcgt tggatgaccc agttaagtac 11340
aaacatacct gggggtttga atcggataca gcgtatctgt atgagttcac cggaaacggt 11400
gaggactggg aggattacaa tgatgcgttt cgtgcgcgcc aggaagggaa aatttataag 11460
gccactgcca ccagcttgaa gttttatttt cccccgggcc ctgtcattga accaacttta 11520
ggcctgaatt gaaatgaaat ggggtccatg caaagccttt tttacaaagt tggccaactt 11580
tttgtggatg ctttcacgga gttcttggtg tccattgttg atatcattat atttttggcc 11640
attttgtttg gcttcaccat cgccggttgg ctggtggtct tttgcatcag attggtttgc 11700
tccgcgatac tccgtgcgcg ccctgccatt cactctgagc aattacagaa gatcttatga 11760
ggcctttctt tcccagtgcc aagtggacat tcccacctgg ggaactaaac atcctttggg 11820
gatactttgg caccataagg tgtcaaccct gattgatgaa atggtgtcgc gtcgaatgta 11880
ccgcatcatg gaaaaagcag ggcaggctgc ctggaaacag gtggtgagcg aggctacgct 11940
gtctcgcatt agtagtttgg atgtggtggc tcattttcag catctagccg ccattgaagc 12000
cgagacctgt aaatatttgg cctcccggct gcccatgcta cacaacctgc gcatgacagg 12060
ttcaaatgta accatagtgt ataatagcac tttgaatcag gtgtttgcta tttttccaac 12120
ccctggttcc cggccaaagc gtcatgattt tcagcaatgg ttaatagctg tacattcctc 12180
catattttcc tctgttgcag cttcttgtac tctttttgtt gtgctgtggt tgcgggttcc 12240
aatactacgt actgtttttg gtttccgctg gttaggggca atttttcttt cgaactcaca 12300
gtgaattaca cggtgtgtcc accttgcctc acccggcaag cagccgcaga gatctacgaa 12360
cccggtaggt ctctttggtg caggataggg tatgaccgat gtgaggagga tgatcatgac 12420
gagctagggt ttatggtacc gcctggcctc tccagcgaag gccacttgac tagtgtttac 12480
gcctggttgg cgttcttgtc cttcagttac acggcccagt tccatcccga gatattcggg 12540
atagggaatg taagtcgagt ttatgttgac atcaaacatc aactcatctg cgccgaacat 12600
gacgggcaga acaccacctt gcctcgtcat gacaacattt cagccgtgtt tcagacctat 12660
taccaacatc aagtcgacgg cggcaattgg tttcacctag aatggcttcg tcccttcttt 12720

-continued

```
tcctcgtggt tggttttaaa tgtctcttgg tttctcaggc gttcgcctgc aaaccatgtt  12780
tcagttcgag tcttgcagac attaagacca acaccaccgc agcggcaagc tttgctgtcc  12840
tccaagacat cagttgcctt aggcatcgcg actcggcctc tgaggcgatt cgcaaaatcc  12900
ctcagtgccg tacggcgata gggacacctg tgtatgttac catcacagcc aatgtgacag  12960
atgagaatta tttacattct tctgatctcc tcatgctttc ttcttgcctt ttctatgctt  13020
ctgagatgag tgaaaaggga tttaaggtgg tatttggcaa tgtgtcaggc atcgtggctg  13080
tgtgtgtcaa ttttaccagc tacgtccaac atgtcaagga gtttacccaa cgctccctgg  13140
tggtcgacca tgtgcggttg ctccatttca tgacacctga gaccatgagg tgggcaactg  13200
ttttagcctg tctttttgcc attctgttgg caatttgaat gtttaagtat gttggagaaa  13260
tgcttgaccg cgggctgttg ctcgcaattg ctttctttgt ggtgtatcgt gccgttctgt  13320
tttgctgtgc tcgtcaacgc cagcaacgac agcagctccc atctacagct gatttacaac  13380
ttgacgctat gtgagctgaa tggcacagat tggctagcta aaaaatttga ttgggcagtg  13440
gagagttttg ttatctttcc cgttttgact cacattgtct cctatggtgc cctcactgcc  13500
agccatttct ttgacacagt cgctttagtc actgtgtcta ccgccgggtt tgttcacggg  13560
cggtatgtcc taagtagcat ctacgcggtc tgtgccctgg ctgcgttgac ttgcttcgtc  13620
attaggtttg caaagaattg catgtcctgg cgctacgcgt gtaccagata taccaacttt  13680
cttctggaca ctaagggcag actctatcgt tggcggtcgc ctgtcatcat agagaaaagg  13740
ggcaaagttg aggtcgaagg tcatctgatc gacctcaaaa gagttgtgct tgatggttcc  13800
gtggcaaccc ctataaccag agtttcagcg gaacaatggg gtcgtcctta gatgacttct  13860
gtcatgatag cacggctcca ggaaaggtgc ttttggcgtt ttctattacc tacacgccag  13920
tgatgatata tgccctaaag gtgagtcgcg gccgactgct agggcttctg caccttttga  13980
tcttcctgaa ttgtgctttc accttcgggt acatgacttt cgcgcacttt cagagtacaa  14040
ataaggtcgc gctcactatg ggagcagtag ttgcactcct ttggggggtg tactcagcca  14100
tagaaacctg gaaattcatc acctccagat gccgtttgtg cttgctaggc cgcaagtaca  14160
ttctggcccc tgcccaccac gttgaaagtg ccgcaggctt tcatccgatt gcggcaaatg  14220
ataaccacgc atttgtcgtc cggcgtcccg gctccactac ggtcaacggc acattggtgc  14280
ccgggttaaa aagcctcgtg ttgggtggca gaaaagctgt taaacaggga gtggtaaacc  14340
ttgtcaaata tgccaaataa caacggcaag cagcagaaga gaaagaaggg ggatggccag  14400
ccagtcaatc agctgtgcca gatgctgggt aagatcatcg ctcagcaaaa ccagtccaga  14460
ggcaagggac cgggaaagaa aaataagaag aaaaacccgg agaagcccca ttttcctcta  14520
gcgactgaag atgatgtcag acatcacttt acccctagtg agcggcaatt gtgtctgtcg  14580
tcaatccaga ccgcctttaa tcaaggcgct gggacttgca ccctgtcaga ttcagggagg  14640
ataagttaca ctgtggagtt tagtttgcct acgcatcata ctgtgcgcct gatccgcgtc  14700
acagcatcac cctcagcatg atgggctggc attcttgagg catctcagtg tttgaattgg  14760
aagaatgtgt ggtgaatggc actgattgac attgtgcctc taagtcacct attcaattag  14820
ggcgaccgtg tgggggtgag atttaattgg cgagaaccat gcggccgaaa ttaaaaaaaa  14880
aaaaa                                                              14885
```

<210> SEQ ID NO 8
<211> LENGTH: 15434
<212> TYPE: DNA
<213> ORGANISM: Artificial Sequence
<220> FEATURE:
<223> OTHER INFORMATION: Synthetic Construct

<400> SEQUENCE: 8
atgacgtata ggtgttggct ctatgccgtg acatttgtat agtcaggagc tgcgaccatt 60
ggtacagccc aaaacttgct gcacgggaac gcccttccgt gacagccttc ttcaggggag 120
tttagggatc tatccctagc accttgcttc cggagttgca ctgctttacg gtctctccaa 180
ccctttaacc atgtctggga tacttgatcg gtgcacgtgc acccccaatg ccagggtgtt 240
tatggcggag ggccaagtct actgcacacg atgtctcagt gcacggtctc tccttcctct 300
gaatctccaa gtccctgagc ttggggtgct gggcctattt tacaggcccg aagagccact 360
ccggtggaca ttgccgcgtg cattccccac tgtcgagtgc tcccccgccg gggcctgctg 420
gctttctgcg atcttcccaa ttgcacgaat gaccagtgga aacctgaact ttcaacaaag 480
aatggtgcgg gtcgcagctg agatttacag agccggtcag ctcactccca cagtcttgaa 540
gaatctacaa gtttatgagc ggggttgccg ttggtaccct attgtcgggc ctgtccccgg 600
agtggccgtt tacgccaact ccctacatgt gagtgacaaa ccctttccgg gagcaactca 660
tgtgttaact aatctaccgc tcccgcagag gcccaagctt gaagattttt gcccctttga 720
gtgtgctatg gctgacgtct atgatatcgg tcatgacgcc gtcatgtacg tggccaaagg 780
gaaagtctcc tgggctcctc gtggtgggga caagacaaaa tttgaaactg tccctaggga 840
gttgaagttg atcgcgaacc gactccatgt ctccttcccg ccccaccacg cagtggacat 900
gtcccagttt gcgttcataa ccttcgggag cggtgtctct atgcgggtcg agtgcccaca 960
tggctgtctc cccgccaata ccgtccctga aggcaactgc tggtggcgct tgtttgacat 1020
gcttccaccg gaggttcaga acgatgaaat tcgccgtgcc tgccaattcg gttatcaaac 1080
caagcatggt gtcgctggca agtacctaca acggaggttg caagctaatg gcctccgagc 1140
ggtgactgat acaagtgggc ctatcgttgt gcagtttttc tccgttaagg agagttggat 1200
ccgccactta aggctggcgg acgaacctag ccttcctggt tttgaggacc tcctcagaat 1260
aagggttgag cccaacacgt caccattggt tagcaaggat gtgaaaatct tccggttcgg 1320
cagtcacaaa tggtacggtg ctggaaagag ggcaaagaaa gcacgctctg gtgcggctgc 1380
cacggtcatt caccgcgctt tgcctgttcg cgaagcccag cagaccaaga cgcacaaggt 1440
tgctagcgct aacagggctg agtgtctcaa gcgctattct ccgcctgccg atgggaactg 1500
tggttggcac tgcatttccg ccatcgccaa ccggatggtg aattcgaaat ttgagaccac 1560
ccttcccgaa agagtgagac cttctgatga ttgggctacc gacgaggatc ttgtgaacgc 1620
cattcaaatc ctcaagctcc ctgcggcctt ggacaggaac ggagcttgtg gtagcgccaa 1680
gtacgtgctt aagctggaag gcgtgcattg gactgtctct gtgacccctg ggatgtcccc 1740
ctctttgctc ccccttgaat gtgttcaggg ctgttgtgag cataaggacg gttctggccc 1800
cccagatgcg gtcgaggttt ccggatttga ccctgcctgc cttgaccgac tggctggggt 1860
gatgcattta cctagcagtg ctatcccagc cgctctggct gaaatgtccg gcaactccaa 1920
tcgcccggct tccccggtca acactgtgtg gactgtttcg caattctatg cccgtcactt 1980
aggaggagtt catcctgacc aggtgtgctt agggaaaatt attagcctct gtcaagtcat 2040
tgaggattgc tgctgccatc aaaacaaaac caaccgggcc accccggaag aggtcgcggc 2100
aaagattgat cagtacctcc gtggtgcaac aagtcttgag gaatgcttga ctaggcttga 2160
aagggtttgc cctccgagcg ctgcggacac ctcctttgat tggaatgttg tgctccctgg 2220

-continued

```
ggttgaggct gcaacccaga caactaaaca gctccatgtc aaccggtgcc gcgttttggc   2280
tcctgtcgtg actcaagagc cttcggacaa agactcggtc cctctgaccg ccttctcgtt   2340
gtccaattac tactacccgg cacaaggtga cgagattcat caccgtgaga ggctgaactc   2400
cgtactctct aagttggagg gggttgttcg cgaggaatat gggctcacgc caactgaacc   2460
tggtccgcga cccgcactac cgaacgggct cgacgagctc agagaccaga tggagatgga   2520
tctgctgaga ctagtcaacg atcaggcaac ttcagaaatg atggcccggg cagctgagca   2580
ggttgatcta aaagcttggg tcaaaaacta cccacggtgg acaccgccgc ccactccacc   2640
aagagttcag cctcgaaaaa cgaggtctgt caagagcttg ccaggggata agcctgtccc   2700
ggctccgcgt aggaaggtca gatctgattg tggcagcccg attttgatgg gcgacaatgt   2760
tcctaacgat cgggaagatt tgactgttaa tgggcccctt gacctttcga caccatccga   2820
gtcgatgaca cctctgagtg agcctgcact tatgcccgcg ttgcaacatg tttctaggtc   2880
ggcgacatct ttgagtgtgc cgaccccagt tcctgtaccg cgcagagctg tgtcccgacc   2940
ggtggcaccc ttgagtgagc caacctttga gtcttcaccg cgacacaaat ttcaagaggt   3000
gaaagaagtg aatctggcgg caacaacgcc gacgcaccaa gacgaacctc tagatttgtc   3060
tgcatcctca cagactgtat gtgaggcctc tcccctagca ccgcctcaga acataggtat   3120
tctgggggtg gaggggcaag aaactgagga agtcctgagt gaagtctcgg atataccgta   3180
tgacattaac cttgcacctg tgtcatcaag cagctccctg tcaagtgtaa agatcacacg   3240
tccgaaatac tcagctcaag ccattattga ctcaggcggg ccctgcagtg ggcatcttcg   3300
aaagggaaaa gaagcatgcc tcagcatcat gcgcagggct tgtgatgcgg ctaagcttag   3360
tgaccctgcc acgcaagaat ggctttctcg tatgtgggat agggttgaca tgctgacttg   3420
gcgcaacacg tctgcttacc aggcgttgcg catcttagat ggcaggtttg ggttcctccc   3480
gaaaatgata ctcgagacac caccgcccta tccgtgtggg tttgtgatgc tgcctcacac   3540
gcctgcacct tccgtgagtg cagagagcga cattaccatt ggttcagttg cctctgaaga   3600
tgttccacgc atcctcggga aaatagaaaa cgccggcgag atgcccaacc aggggctctt   3660
ggcgtccctt gaggaaaaac cggtgcacga ccaacctgcc gaagactccc ggatgccgtt   3720
gcgggggttt gacgagagcg taacggctcc gtccgctggt acaggttgcg ctgactcacc   3780
cactgatttg tcgccttcag gtggtgtgga cgtggacggg gggggggcgt tacgggcggt   3840
aagaaagaaa gctgaaaggc tcttcgatca attgagccgc caggttttta acctcgtctc   3900
ccatctccct gttttcttct cacacctctt caaatctgac agtggttatt ctccgggtga   3960
ttggggtttt gcagctttta ctctattttg tctcttttta tgttacaact acccattttt   4020
tgggtttgct cccctcttgg gtgtgttttc tgggtcttct cggcgtgtgc gcatgggggt   4080
ttttggctgc tggttggctt ttgctgttgg cctgttcaaa cctgtgtccg acccagtcgg   4140
cactgcttgt gaatttgact cgccagagtg taggaacgtc cttcattctt ttgagcttct   4200
caaaccttgg gaccctgttc gcagccttgt tgtgggcccc gtcggtctcg gtcttgccat   4260
tcttggcagg ttactgggcg gggcacgcta catctggcat tttttgctta ggcttggcat   4320
tgttgcagat tgtgtcttgg ctggagctta tgtgctttct caaggtaggt gtaaaaagtg   4380
ctggggatct tgtgtaagaa ctgctcccaa tgaaattgcc ttcaacgtgt tccctttttac   4440
gcgtgcgacc aggtcgtcac tcatcgacct gtgcaaccgg tttcgtgcgc cgaaaggcat   4500
ggaccccatt tttctcgcta ctgggtggcg cgggtgctgg accggccaaa gtcccattga   4560
gcaaccctcc gaaaaaccca tcgcgttcgc ccagttggat gaaaagagga tcacggccag   4620
```

-continued

```
aactgtagtt gctcagcctt atgatcctaa ccaagccgta aagtgcctgc gggtgttaca   4680
ggcgggtggg gcgatggtgg ccgaggcagt cccgaaagtt gtcaaagttt ccgctatccc   4740
attccgagcc ccttttttc ccaccggagt gaaggttgat cctgagtgca ggatcgtagt   4800
cgaccccgac actttcacta ctgctcttcg gtctggttac tccaccacaa acctcgtcct   4860
tggtgtgggg gactttgccc aactgaatgg attaaaaatc aggcaaattt ccaagccttc   4920
gggaggaggc ccacacctca ttgctgccct gcatgttgct tgctcgatgg cgttgcacat   4980
gcttgctggg gtttacgtaa ctgcagtggg gtcttgcggt accggcacca acgatccgtg   5040
gtgcaccaac ccattcgccg tccctggcta cggacctggc tctctctgca cgtccaggtt   5100
gtgcatctcc caacatggcc ttaccttgcc cttgacagca cttgtggcag gcttcggtct   5160
tcaggaaatt gccttggtcg ttctgatttt tgtttccatc ggaggcatgg ctcataggtt   5220
gagttgtaag gctgatatgc tgtgcgtctt gctcgcaatc gccagctatg tttgggtacc   5280
ccttacctgg ttgctctgcg tgtttccttg ctggttgcgc tggttctctt tgcacccccct   5340
caccatccta tggttggtgt ttttcttgat ttctgtaaat atgccttcag gaaccttagc   5400
cgtggtgtta ttggtcgctc tttggcttct aggccgttac actaatgttg ttggtcttgt   5460
cacccccctac gatatccatc attacaccag cggccctcgc ggtgttgccg ccttggctac   5520
cgcaccagat ggaacttatt tggccgctgt ccgccgcgct gcgttgactg gccgtaccgt   5580
tctgtttacc ccgtctcagc ttgggtccct tcttgagggc gctttcagga ctcgaaagcc   5640
ctcattgaac accgttaatg tggtcgggtc ctccatgggc tctggcggag tgttcactat   5700
cgatgggaaa attaagtgtg tgactgccgc acatgtcctt acgggcaact cagccagggt   5760
ttccggggtc ggcttcaatc agatgcttga ctttgatgta aaaggagatt tcgccatagc   5820
tgattgcccg aattggcaag ggactgctcc taagacccaa ttctgcaagg acgggtggac   5880
tggccgtgcc tattggctaa catcttctgg tgtcgaaccc ggtgtcattg gaaatgggtt   5940
cgccttctgc ttcaccgcgt gcggtgactc cgggtctcca gtgatcaccg aagccggtga   6000
gcttgtcggc gttcacacag gatcaaacaa acaaggagga ggcattgtta cgcgcccctc   6060
aggccagttt tgtaatgtgg cacccatcaa gctgagcgaa ttaagtgagt tctttgctgg   6120
acctaaggtc ccgctcggtg atgtgaaggt tggtagccac ataattaaag acatatgcga   6180
ggtaccttca gatctttgtg ccttgcttgc tgccaaaccc gaattggaag gaggcctctc   6240
caccgtccaa cttctatgtg tatttttcct cctgtggaga atgatgggac atgcctggac   6300
acccttggtt gccgtgggtt tttttatttt gaatgagatt cttccagctg tactggtccg   6360
gagtgttttc tccttcggaa tgtttgtgtt atcttggctc acaccatggt ctgcacaagt   6420
tctgatgatc aggctcctca cagcagctct taataggaac agattgtcac tcgccttcta   6480
cagccttggt gcggcaaccg gttttgtcgc agacctagcg gcgacccaag ggcatccgtt   6540
gcacgcagta atgaatttga gtacctatgc cttcctgcct cgggtgatgg ttgtgacctc   6600
accagtccca gtaatcgcgt gtggtgttgt gcacctcctt gccataattt tgtacttgtt   6660
taggtaccgc tgcctgcatg gtgttcttgt tggcgatggg gcgttctctg cggctttttt   6720
tttgcgatac tttgctgagg ggaaattgag ggaaggggtg tcgcaatcct gcgggatgaa   6780
tcatgagtcg ctgactggtg ccctcgccat gagactcaat aacgaggatt tggatttcct   6840
cactaagtgg actgatttta agtgctttgt ttctgcttcc aacatgagga atgcagcggg   6900
ccaattcatt gaggctgcct atgccaaagc acttagaata gaacttgccc agctggtgca   6960
```

ggtcgacaag gtccgaggca ctttggccaa acttgaagct tttgccgaca ccgtggcacc 7020
ccaactctcg cccggtgaca ttgttgtcgc tcttggccat acgcctgttg gcagtgtctt 7080
cgacctgaag gttggtaaca ccaagcacac tctccaagcc attgagacca gggtccttgc 7140
tgggtccaaa atgaccgtgg cgcgcgtcgt cgacccgacc cccacgcccc cacccgcacc 7200
cgtacccatc cccctcccac cgaaggtttt ggagaacggt ccaaacgctt ggggggatga 7260
agatcgtttg aataaaaaga agaggcgcag gatggaagct gtcggcatct ttgttatggg 7320
cggaaagaaa taccagaaat tttgggacaa gaattccggt gatgtgtttt atgaggaggt 7380
ccatgacaat acagacgcgt gggagtgcct cagggttgat aactctgccg actttgatcc 7440
cgagaaggga actctgtgtg ggcatactac cattgagaat aaaacctaca atatctacgc 7500
ctccccatcc ggcaagaagt tcctggtccc tgccaactca gagggcggaa aagtccagtg 7560
ggaagctgca aagctctccg tggagcaggc ccttggcatg atgaatgtcg acggtgaact 7620
gacagccaga gaactggaga aactaaaaaa aataattgac aaactccagg acctgaccaa 7680
ggagcagtgt ttaaactgct agccgccagc ggcctgaccc gctgtggtcg cggcggctta 7740
gttgttactg agacagcggt aaaaatagtc aaatatcaca gccggacctt caccctagga 7800
cctgtaaatt taaaagtggc tagtgaggtt gagctaaaag acgcggtcga gcataaccag 7860
cacccggtcg caagaccggt tgatggtggt gttgtgcttc tgcgctccgc agttccttcg 7920
cttatagacg tcttgatctc cggcgctgat gcatctccta agttactcgc tcgccacggg 7980
ccgggaaata ctgggatcga cggcacgctt tgggattttg aggccgaggc caccaaagag 8040
gagatcgcac tcagtgcgca gataatacag gcttgtgaca ttaggcgcgg cgacgcaccc 8100
gaaattggtc tcccttataa gctgtaccct gttaggggca atcccgagcg ggtaaaagga 8160
gttttacaga atacaaggtt cggggacatt ccttataaaa cccccagtga cactggaagc 8220
ccagtgcacg cggctgcctg cctcacgccc aatgccactc cggtgactga tgggcgctcc 8280
gtcttggcta caaccatgcc ctccggtttt gagttgtacg tgccgaccat tccagcatct 8340
gtccttgatt accttgactc caggcctgac tgccctaaac agttgacaga gcacggctgt 8400
gaggatgccg cattaagaga cctttccaag tatgacttgt ccactcaagg ctttgttttg 8460
ccaggagttc ttcgccttgt gcgtaagtac ctatttgctc atgtgggcaa gtgcccgcct 8520
attcatcggc cttccaccta ccctgccaag aattctatgg ctggaataaa tgggaacagg 8580
tttccaacca aggacatcca gggcgtccct gaaatcgacg tcctgtgcgc tcaggccgtg 8640
cgggaaaact ggcagactgt caccccttgt accctcaaga aacagtattg tgggaagaag 8700
aagactagga caatactcgg caccaataat ttcattgcat tggcccaccg ggcagcgttg 8760
agtggcgtca cccagggctt tatgaaaaag gcgttcaatt cgcccatcgc cctcggaaaa 8820
aacaaattta aggagctaca aactccggtc ttaggcaggt gcctagaggc tgaccttgca 8880
tcctgcgatc gatccacacc tgcgattgtc cgctggtttg ccgccaatct tctttatgaa 8940
cttgcctgtg ctgaggaaca tctaccatcg tacgtgctga actgctgcca cgacttactg 9000
gtcacgcaat ccggcgcggt gactaagaga ggtggcctgt cgtctggcga cccgattact 9060
tctgtgtcaa acaccattta tagtttggtg atatatgcac agcacatggt gctcagttac 9120
tttaaaagtg gtcaccctca cggccttctg tttctgcaag accagctaaa gtttgaggac 9180
atgctcaagg ttcaacccct gatcgtctat tcggacgacc tcgtgttgta tgccgagtct 9240
cccactatgc caaactacca ctggtgggtt gaacatctga atcttatgtt gggttttcag 9300
acggacccaa gaaagacagc cataacagac tcaccatctt ttctaggctg tagaataata 9360
aatgggcgcc agctagtccc ccaccgtgac aggattctcg cggcccttgc ctaccatatg 9420
aaggcaagca atgtttctga atactacgct tcggcggccg cgatactcat ggacagctgt 9480
gcttgtctag agcatgatcc tgaatggttt gaagaacttg tggtcggaat ggcgcagtgt 9540
gcccgcaagg acggctacag ctttcccggc ccgccgttct tcttgtctat gtgggaaaaa 9600
ctcaggtcta attatgaggg gaagaagtcg agagcgtgcg gatactgcgg ggccccggct 9660
ccgtacgcta ccgcctgtgg cctcgacgtc tgcatttatc acacccattt ccaccagcat 9720
tgtccggtca taatctggtg tggtcatccg gcgggttctg gttcttgtag tgagtgcaaa 9780
cccccccttg ggaaaggtac aagccctcta gatgaggtgt tggaacaagt cccgtacaag 9840
cctccgcgga ccgtgatcat gcacgtagag cagggtctta ctccactcga cccaggtaga 9900
taccaaaccc gccgcggatt agtctccgtt aggcgtggca ttaggggaaa cgaagttgaa 9960
ctaccagacg gtgattatgc tagtaccgcc ttgctcccca cttgtaaaga gatcaacatg 10020
gttgctgttg cttctaacgt gttacgcagc aggttcatca tcggtccacc tggtgctggt 10080
aaaacatact ggctccttca acaggtccag gatggtgatg tcatttacac gccaactcat 10140
cagactatgc ttgacatgat taaggctttg ggacgtgcc ggttcaacgt tccagcaggc 10200
acaacgctgc aattccctgc cccctcccgc accggcccgt gggttcgcat cctggccggc 10260
ggttggtgtc ctggcaagaa ttccttcctg gatgaagcag cgtattgcaa tcatcttgac 10320
gtcttgaggc ttcttagcaa aactaccctc acctgcctgg gagatttcaa acaactccac 10380
ccggtgggtt ttgattccca ttgctatgtt tttgacatta tgcctcagac tcaactgaag 10440
accatctgga ggtttgggca gaacatctgt gacgccattc aaccagatta tagagacaaa 10500
cttgtgtcca tggtcaacac aacccgtgta acctacgtgg aaaaacctgt caagtatggg 10560
caagtcctca cccccctacca cagggaccga gaggacggcg ccgtcacaat tgactcaagt 10620
caaggcgcca catttgatgt ggttacactg catttgccca ctaaagattc actcaacagg 10680
caaagggccc ttgttgctat caccagggca agacatgcta tctttgtgta tgacccacac 10740
aggcaattgc agagcttgtt tgatcttcct gcaaaaagca cacccgtcaa tctcgcagtg 10800
caccgtgacg agcagctgac cgtgttagat agaaataaca aagagtgcac ggttgctcag 10860
gctctaggca atggggataa atttagggcc acagacaagc gcgttgtaga ttctctccgc 10920
gccgtttgtg cagacctgga agggtctagc tccccgctcc ccaaggttgc acacaacttg 10980
ggattttatt tctcgcctga tttgacacag tttgctaagc ttccggtaga acttgcacct 11040
cactggcccg tggtgacaac ccagaacaat gaaaagtggc cagaccggtt ggttgctagc 11100
cttcgccctg tccatgagta tagccgtgcg tgtgtcggtg ccggctatat ggtgggcccc 11160
tcagtgttcc taggcactcc tggggttgtg tcatactatc tcacaaaatt tgttagaggc 11220
gaggctcaaa tgcttccgga gacagtcttc agcaccggcc gaattgaggt agattgccgg 11280
gagtaccttg atgatcggga gcgagaagtt gctgagtccc tcccacacgc cttcattggc 11340
gacgtcaaag gcactaccgt tgggggatgt caccatgtca cctctaaata cctcccgcgt 11400
ttcctcccca aggaatcggt tgcggtagtt ggggtttcga gccccgggaa agccgcaaaa 11460
gcagtttgca cattgacaga tgtgtacctc ccagaccttg aagcttatct ccacccagag 11520
acccagtcta agtgctggaa aatgatgttg gacttcaagg aggttcgact gatggtctgg 11580
aaagataaga cggcctattt tcaacttgaa ggccgccatt tcacctggta ccagcttgca 11640
agctatgcct cgtacatccg agttcctgtt aattctacgg tatatctgga cccttgcatg 11700

```
ggccctgccc tttgcaacag gagggttgtc gggtccaccc attgggaagc tgacctcgca  11760
gtcacccctt atgattatgg tgccaaaatc attttgtctt gtgcatacca tggtgaaatg  11820
cctcccgggt acaagattct ggcgtgcgcg gagttctcgc ttgacgaccc agtcaggtac  11880
aaacacacct ggggatttgc atcggatata gcgtatttgt acgagttcac cggaaacggt  11940
gaggactggg aggattacaa tgatgcgttt cgtgcgcgcc agaaagggaa aatttacaaa  12000
gccactgccg ccagcatgag gttttatttt cccccgggcc ctatcgttga accaactttg  12060
ggcctagact gaaatgaaat ggggtctatg caaagcctct ttgacaaaat cggccaactt  12120
tttgtggatg ccttcacgga atttttggtg tccattgttg atatcatcat atttctggcc  12180
attttgtttg gctttaccat cgctggctgg ctggtggtct tctgcatccg actggtttgc  12240
tccgcggtac tccgtgcgcg ccctaccatt cactctgagc aattacagaa gatcctatga  12300
ggcctttctt tctcagtgcc aggtggacat tcccgcctgg ggaactaaac accccttggg  12360
gatgttttgg caccataagg tgtcgaccct gattgatgaa atggtgtcgc gtcgaatgta  12420
ccgcaccatg gaaaaagcag gacaggctgc ctggagacag gtggtaagcg aggctacgtt  12480
gtctcgcatt agtggtttgg atgtggtggc tcattttcag catcttgccg ccattgaagc  12540
tgagacctgc aaatacttgg cctctcggct tcccatgctg cacaatctgc gcatgacagg  12600
gtcaaatgta accatagtgt ataatagcac tttgaatcag gtgtttgcta tttttccaac  12660
ccctgaatcc cggccgaagc ttcatgattt tcagcaatgg ctaatagctg tgcattcctc  12720
catattttcc tccgttgcag cttcttgcac tctttttgtt gtgctgtggt tgcggattcc  12780
aacactacgt attgtttttg gtttccactg gtaaggggca atttttcctt cgagctcacg  12840
gtgaattaca cggtgtgccc gctttgcctc acccgacaag cagcctatga gatctatgaa  12900
tcacgcaggt ctttttggtg caggataggg catgaccgat gcagtgaggt cgaccacgac  12960
gagctagggt tcatggttcc gtctggcctc tccagcgaag gccacctgac cagtgtttac  13020
gcctggttgg cgttcctgtc cttcagctac acggcccagt tccatcccga gatatttggg  13080
atagggaatg tgagtcgagt ttatgttgac atcaagcacc aactcatctg cgccgttcac  13140
gacggggaga acaccacctt gcctcgtcat gacaacattt cagccgtatt tcagacctac  13200
taccagcatc aagtcgacgg cggcaattgg tttcacctag aatggctgcg tcccttcttt  13260
tcctcctggt tggttttaaa tgtctcgtgg tttctcaggc gttcgcctgc aagccatgtt  13320
tcagttcaag tctttcggac atcaaaacca acactaccgc agcatcaggc tttgttaccc  13380
tccaggacat cagctgtctt aggcatggcg actcgccctc tcagacgatt cgcaaaagcc  13440
ctccgtgccg cacggcgcta gggacacccg tgtacatcac tgttacagcc aatgtcacgg  13500
atgagaatta tttacactcc tctgatctcc tcatgctttc ttcttgcctt ttctatgctt  13560
ctgagatgag tgaaaaggga ttcaaggtga tatttggcaa tgtgtcaggc atcgtggccg  13620
tgtgtgttaa ttttaccagc tacgtccaac atgtcaaaga gttcacccaa cgctctttgg  13680
tggtcgacca tgtgcggctg ctccatttca tgacacctga aaccatgagg tgggcaaccg  13740
ttttagcctg tcttgttgcc atcttgctgg caatttgaat gtttcagtat gttggggaga  13800
tgcttgaccg cgggctgctg cttgcgattg ctttctttgt ggtgtatcgt gccgttctgg  13860
tttgctgcac tcgtcagcgc caaccagaac cacagctctc atcttcaatt gatttacaac  13920
ttgacgctat gtgagctgaa tggcacagaa tggctgggag acaaatttaa ttgggcagtg  13980
gagacctttg tcatctttcc cgtgttaact cacattgtct catatggtgc actcaccact  14040
agccatttcc ttgacacagt cggtctggtt actgtgtcta ccgccgggta ttatcacggg  14100
```

```
cggtatgttt tgagtagtat ctacgcggtc tgcgctctgg ccgcgttaat ttgcttcgtc  14160
attcggcttg cgaagaactg catgtcctgg cgctactctt gtaccagata taccaatttc  14220
cttctggaca ctaagggcag actctatcgc tggcggtcgc ccgttatcat agagaaaagg  14280
ggtaaggttg aggtcggaag tcacctgatc gatctcaaga gagttgtgct tgatggttct  14340
gcggcaaccc ctttaaccag agtttcagcg gaacaatggg gtcgtctcta gacgactttt  14400
gctatgatag cacggctcca caaaaggtgt ttttggcgtt ttccattacc tacacgccag  14460
taatgattta tgccctgaag gtaagtcgcg gccgactgtt agggcttctg caccttttga  14520
tctttctgaa ttgtgctttt accttcgggt acatgacatt tgtgcacttt gatagcacaa  14580
ataaggtcgc gctcactatg ggagcagtgg ttgcactcct ttggggggtg tactcggcca  14640
tagaaacctg gaaattcatc acctccagat gccgtttgtg cttgctaggc cgcaagtaca  14700
ttctggcccc tgcccaccac gtcgaaagtg ccgcgggctt tcatccgatt gcggcaaatg  14760
ataaccacgc atttgtcgtc cggcgtcccg gctccactac ggttaacggc acattggtgc  14820
ccgggttgaa aagcctcgtg ttgggtggca gaaaagctgt aaaacaggga gtggtaaacc  14880
ttgtcaaata tgccaaataa caacggcaag cagcaaaaga aaaaaaaggg gaatggccag  14940
ccagtcaacc agctgtgcca aatgttgggc aaaatcatcg cccagcagaa ccagtccaga  15000
ggtaagggac cgggaaagaa aattaaaaag aaaagcccgg agaagcccca ttttcctcta  15060
gcgactgagg atgacgtcag gcatcacttt acccctggtg agcggcaatt gtgtctgtcg  15120
tcaatccaga ctgcctttaa tcaaggcgct ggaacttgca ccctgtcaga ttcagggagg  15180
ataagttacg ctgtggagtt tagtttgccg acgcatcata ctgtgcgcct gattcgcgtc  15240
acagcaccac cttcagcgtg atgggctggc attcttgaga catcccggcg ttagaattgg  15300
aagaatgcgt ggtgaatggc actgattgac actgtgcctc taagtcacct attcagttag  15360
ggcgaccgtg tgggggtaga gtttaattgg cgagaaccac acggccgaaa ttaaaaaaaa  15420
aaaaaaaaaa aaaa                                                    15434
```

<210> SEQ ID NO 9
<211> LENGTH: 15047
<212> TYPE: DNA
<213> ORGANISM: Artificial Sequence
<220> FEATURE:
<223> OTHER INFORMATION: Synthetic Construct

<400> SEQUENCE: 9

```
atgacgtata ggtgtttgct ttatgccgcg gcatttgtat tgtcaggagc tgtgaccact     60
ggcacagccc gaaacttgct gcacagaaac acccttctgt gacagcctcc ttcaggggag    120
tttaggggtt tctccctaac gccctgcttc cggagttgca ctgctttacg gtctctccat    180
ccttttaacc atgtctggga ttcttgatcg gtgcacgtgc acccccaatg ccagggtgtt    240
tgtggcagag ggccaagtct actgcacacg atgtctcagt gcacggtccc tccttcccct    300
aaatctccaa gtttctgagc ttggggtact tggtttattc tacaggcccg aagagccatt    360
acggtggacg ttgccacacg cattccccac tgtcgagtgt gctcctgctg gcgcttgttg    420
gctttctgca atttttccaa ttgcgcgaat gaccagtgga aacctgaatt tccagcaaag    480
gctggtacgt gtcgcagccg agctttacag agccggccag ctcaccccta caagcctgaa    540
aaccttacag gtctatgaaa ggggttgccg ttggtacccc attgttggac ctgttcctgg    600
agtggccgtt tacgccaact ccctacatgt gagtgacaaa cccttcccag gagcgactca    660
```

```
cgtgctgacc aacttaccac tcccgcagag accaaaatct gaagatttct gccccttcga    720
gtgcgccacg gccgccgtct atgacatcgg ccatgacgcc gtcatgtatg taaccgagga    780
aaaggtttcc tgggctcctc gtggcgggga taaagggaaa tttgagactg ttcctgaggg    840
gttgaagttg actgcggaac gactctacac ctccttcccg cctcaccatg cggtggacat    900
gtccctttc atcttcacag accttgagtg cggcgcttcc atgcgggtcg aacgccaata     960
tggttgcctc tctgctggca ctgtccctga aggcaactgc tggtggagtc tgtttggctc   1020
gctttcgtta gaagctcagt ataaagaaat ccgctacgcc gcccaatttg gctatcagac   1080
caaacatggc gttactggca agtacctgca gcggaggctg caaattaatg gtctccgagc   1140
agtggttgac ccgaatgggc ctcttgtcgt acagtatttc tccgttaagg agagctggat   1200
gcgccacgtg agactggcgg aagagccagg ctatcctggg tttgaggatc tcctcaggat   1260
aagagtcgag cccaacacgt tgcctttgtc caacaaggac gagaaaatct tccgtttcgg   1320
cggttacaag tggtacggtg ctgggcggag ggcaaggaga acacgtgcaa gagcagtcac   1380
cgcagttgct agtcatgctc cgcccgctcg tggggcccag caggccgaga agcacgaagt   1440
tgctagtgcc aacaagactg agctccttac gcactactcc ccacctgctg aagggaattg   1500
cggctggcac tgcatctccg ccatcatgaa ccggatggtg cattccaagt ttgaaaccgc   1560
cctttccgaa agagtgagat ccccggaaga ctgggcgact gatgaggatc ttgtgaatac   1620
tattcaaatc ctcaggctcc ctgcggcctt agacaggaac ggcgcctgta aaaacgccaa   1680
gtacatcctt aagctggaag gtgagcactg gactgtttca gtgacccccg gaatgccccc   1740
ctcttcactt cctcttgaat gcgttcaggg ttgttgcgag cataagggca attttgactc   1800
tcaaaacgcg gtcggtttct ttgggttcga ccctgccagc cttgaccgac tcgctggggt   1860
aatgcatctg cccagcagcg ccatccctgc cgccctggcc gagttgtctg gtgaacttga   1920
ttgttcaact cccccggcca ccactgtgtg gactaccttg cagttttatg ctcgtcttgg   1980
tggggggggag catcctgatc aagagtgctt gagaaaaatc atcagcctct gtgaggtgct  2040
cgggagttgc tgctgttctc agagtagggt caaccgggtc accccggaag aggtcgcagc   2100
aaagattgac ctgtatcttc gtgacgcagc gagtcttgaa gagtgcttgg ctaggcttga   2160
gaaagctcgc ccgccaagca tgctggacac ctcctttgac tgggatgttg tactccctgg   2220
tgttgggacg gctgctcggg cagcagaact accccccacc gatgagtgtc gcgctctagt   2280
cactgctgtg gcccaaaggc cttcgccgaa agttcagcct cgaaaggcgg ggtctgttaa   2340
gagtctacca gagatcaggc ctgtccctgc cccacgcagg aaggttaagt ctagttgtgg   2400
tgatctggcc ccgttgggcg gcaatttccc tgatagctgg gaagatttgg ctggtggctc   2460
ccttaatctc cagatcttac ctgagccggt ggcacaatcc tttgaacctg tgcctgtccc   2520
tgcaccgcgc aagactgcgc ctcgattagt gtcgtcatca ttggcgtcga cccccgtacc   2580
tacaccacga tgtgggtttc ggcagtttga gggaatgaat ttgacagctg tgaccctagc   2640
atgccaggat gagtccctca atttgtctgc atcctcgcag actgaatatg aggcttctcc   2700
tttggcattg cagcagggtg aggatgtcct tgcggtgggg ggacgagaag ccgaagaagt   2760
cctgagcgga atctcgggaa tgtcaggtgg cattagatta gcgcccgcat catcaagtag   2820
ctccttgtca agcgtggaga tcacacgccc gaagtactca gctcaagcca tcattgactc   2880
aggtggaccc tgttgcgggc accttcaaga ggtgaaagag aaatacctta atgtcatgcg   2940
tgaggcatgt gatgcgacta agctcgatga ccctgccacg caagaatggc tctctcgcat   3000
gtgggagagg gtagacatgc taacctggcg caacacgtcc atctttcaag cgccttttac   3060
```

```
cttagctgac aagtttaagt ccctcccgaa gatgatactc gaaacgccgc caccctaccc   3120
ttgcgggttt gtgatgatgc cccgcacgcc cgcaccttct gtgggtgcgg aaagcgacat   3180
caccgttggt tcagttgcta ctgaagatgt cccgcgtata ctcggggagg tgggagatgt   3240
tggcaagatg accggccagg aaccccttaga atccttcgca gatgaactgg cagatgacca   3300
acctgctagg gagtcccgaa cacaagctcc tcctgcaagc acaggtagcg ctggtttagt   3360
tttggattct ggagggtcgc tggggctcac tgacctgccg ctcccaaaca atatagacgc   3420
gggcgggaaa ggaccgtttc acgcggtcaa gaaaaaagct gtagggtgct ttgaccaact   3480
gagccgccgg gtttttgaca tcgtctccca tctccctgtt tttttttcac gccttttcgc   3540
gcccggtggt ttttactctt cgggtgactg gagttttgca gcttttactt tattgtgtct   3600
ctttttatgt tacagttatc cggcctttgg ttttgctccc ctcgtgggtg tattttctgg   3660
gtcttctcgg cgcgtgcgca tgggggtttt tggctgctgg ctggcttttg ctgttggttt   3720
gttcaagcct gcacccgacc cagtcggtgc tgcttgtgag tttgactcgc cagagtgtag   3780
agacatcctt cattcttttg agctcctgca accttgggac cctgttcgca gccttgtggt   3840
gggccccgtc ggtctcggcc ttgccatttt tggcaggtta ctgggcgggg cacgctacgt   3900
ctggctgctt ttgcttaggc ttggcatcgt ttcagactgt atcctggctg gagcctatgt   3960
gctttcgcaa ggcaggtgta aaaagtgttg gggatcttgt ataagaacag cccccagtga   4020
agttgccttc aatgtgtttc cctttacacg cgcaactaga tcgtcacttg tcaacctgtg   4080
cgaccggttc tgtgcaccca agggcatgga ccccatcttc cttgccacag gatggcgcgg   4140
atgctggtcc ggccagagcc ccattgagca accctctgaa aaacccatag cgttcgccca   4200
gttggacgaa aagaaaatca cggctaggac tgtggttgcc cagccttatg accccaacca   4260
agctgtgaag tgcctgcgag tcctccaggc gggtggagcg atggtagccg aggcagttcc   4320
aaaagtagtc aaagtttctg ctgtcccgtt tcgagcccct ttttttcctg ccggagtgaa   4380
agttgaccct gaatgcaggg tcgtggttga ccctgacacc tttacaaccg ctctccggac   4440
cggctactcc accacaaacc tcattcttgg tgttggggac tttgcccagc tgaatgggtt   4500
gaagatcaga caaatttcca agtccccagg aggggggccct cacctcatgg cggctttaca   4560
tgttgcttgc tcgatgactt tgcacatgct tgttgggatt tatgtcacca tggtgggttc   4620
ttgtggctct ggcactaacg atccgtggtg cactaacccg tttgccgtcc ctgtctatgg   4680
gcctggctct ctctgcacgt ccaggttgtg catttcccag cgtggcctga ccctgccctt   4740
aacagcgctt gtggcagggt ttggcgttca ggaaatcgct ttggttgttt taatctttgt   4800
ctccatcggg ggtatggccc acaggttgag ttgcaaggct gacgtgctgt gtatcctgct   4860
tgctattgtc agctatgttt ggccacccct tacctggttg ctttgtgtgt ttccttgctg   4920
gttgcgctgg ttttctttac atccccttac tattctatgg ttagtgtttt tcttgatttc   4980
tgtaaatacg ccctcgggaa tcttggcctt ggtcctgtta atctctcttt ggctccttgg   5040
tcgctatacc aatgttgccg gccttgtcac cccttatgac attcaccatt acaccaacgg   5100
ccctcgcggc gttgccgcct tggccactgc cccggatggg acctacctgg ctgctgtccg   5160
ccgtgctgcg ttgactggcc gtaccatgct gttcaccccg tcccaacttg gctcgctcct   5220
tgagggcgct tttagaaccc aaaagccttc actgaacact gtcaatgtag ttgggtcctc   5280
catgggctcc ggcggggtgt tcaccattga tgggaagatc aaatgtgtga ccgctgctca   5340
tgtcctcacg ggtaactctg ccagggtttc cggggttggc ttcaatcaaa tgttggactt   5400
```

```
tgatgttaaa ggggattttg ccatagccga ttgtccgaat tggcaaggag tcgcccccaa   5460
gtcccggttc tgcaaggatg attggactgg ccgtgcttat tggctcacgt cctccggcgt   5520
cgaacccggc gtcattgggc aaggattcgc cttttgtttc accgcgtgcg gcgattccgg   5580
gtccccagtg atcaccgagg ccggggagct tgtcggtgtc cacacgggat caaacaaaca   5640
aggaggaggc attgttacgc gcccttcagg ccggttttgt aatgtgacac ccaccaaatt   5700
aagtgaattg agtgaattct tcgctggacc tagggtcccg cttggtgacg tgaaggttgg   5760
caatcacata atcaaagata taaatgaggt gccctcagat ctctgcgcct tactcgctgc   5820
caaacccgaa ttggaaggag gcctctccac cgttcaactt ctgtgcgtgt tttttctcct   5880
atggagaatg atgggacatg cctggacacc cttggttgcc gttggttttt tcatcttgaa   5940
tgaagttctc ccagcagtcc tggtccggag tgtcttctcc tttggaatgt tcgcactgtc   6000
ttggttcacg ccgtggtctg cacaaattct aatgatcagg ctcttgacag cagccctaaa   6060
cagaaacaga tcgtcacttg ccttttacag cctgggcgca ctaaccggtt ttgttgcaga   6120
tcttgcaacc aatcaggggt atttattgca cgcggtcatg aatgtgagca cctatgcatt   6180
cctgcctcgt gcaatggccg tgacctcacc agtcccaata gttgcgtgtg gcgttgtgca   6240
cttgcttgcc atcattctgt acttgttcaa gtaccgtagc ctgcatgccg tcctggtcgg   6300
cgatggtgcg ttttccgcgg ctttcttctt gcgatacttt gcggagggaa agttgaggga   6360
aggggtgtcg cagtcttgcg gcatgaatca tgagtcacta accggtgccc tcgccatgaa   6420
actcagcgac gaagacttgg acttcctcac aaaattgact gattttaagt gctttgtttc   6480
tgcatccaac atgaggaatg cggcgggtca atttatagag gccgcctacg ccaaagcact   6540
gagggtggaa cttgcccagt tggttcaagt cgataaagtt cgaggtgtcc tggccaaact   6600
tgaagctttc gctgacaccg tggcgcctca actttcaccc ggtgacattg ttgtcgccct   6660
tggacacaca cctgtcggca gcatttttga cctgaaggtc ggcaatgtta agcacactct   6720
ccagtccatt gagaccagaa ccccttgccgg gtctaaaatg actgtggcgc gcgtcgtaga   6780
cccaaccccc acacccccgc ccgcacctgt gcccatttcc ctcccaccaa aggttttgga   6840
gaacggtccc aacgcctggg gggatgagaa cggtttgaac aaaaaaaagc ggcgcaagat   6900
ggaggccgtt ggcatttacg ttatgggcgg gaaaaagtat caaaaatttt gggataagaa   6960
ttctggtgat gtgttctatg aagaagtcca cgacaacaca gacgcgtggg aatgcctcag   7020
agttgacaac cctgccgact tggatcctga gaggggaacc ttgtgtggac acaccaccat   7080
agacaacagg ccttaccatg tttatgcttc tccgtctggt aggaagtttc tagtccctgt   7140
caacccggag agcggaaaag ctcagtggga agctgctaag ctttctttag atcaggccct   7200
cagtatgatg aatgtcgacg gcgaactgac cgccaaagaa gtggaaaaat tgaagagaat   7260
aattgacaaa ctccagggcc tgactaagga gcagtgttta aactgctagc cgccagcggc   7320
ttgacccgct gtggtcgcgg cggcttggtt gttactgaga cagcggtaaa gatagtcagg   7380
ttccacaacc ggacctttac cctagggcct gtgaatttga aagtagctag cgaagttgag   7440
ttgaaggacg cggtcgagca cggccaacac ccggtcgcga taccagccga tggtggcgtc   7500
gtgctcctgc gttccgctgt tccttcgctt atagacgtcc tgatctccgg tgctgacgca   7560
tctcccaggt tgctcgcccg tcacggaccg ggaaatactg gggtcaatgg cgcgctttgg   7620
gattttgagt ctgaagctac caaagaggaa gtagcactta gtgcgcaaat aatacaggcc   7680
tgtgacatta gacgcggcga tgcacctgag attggccttc cttacaagtt gtaccctgtt   7740
aggggcaacc ctgaacgggc aagaggggtt ctaatgaaca caagatttgg agacatacct   7800
```

```
tacaagaccc ccagcgacac cgggagcccg gtgcacgcgg ccgcctgcct tacgcccaac   7860
gccactccag taactgatgg gcgctccatc ctggccacga ccatgccctc cgggtttgaa   7920
ctatatgtgc cgaccattcc agcgtctgtc cttgattacc ttgactccag accagactgt   7980
cctaaacagt tgactgagca cgggtgtgaa gatgccgcgt tgaaggacct ttctaaatat   8040
gacctgtcca cccaaggctt tgtgttacct ggagttctac gcctcgtgcg aaaatatctg   8100
tttgctcatg taggtaagtg cccgcctgtc caccggccct ctacctatcc tgccaagaac   8160
tccatggccg gaataaatgg gaacaggttc ccaaccaagg atattcaaag catccctgag   8220
atcgacgttt tgtgtgcaca agctgtgcga gaaaactggc aaactgttac accctgcact   8280
cttaagaagc agtattgcgg taaaaagaag accaggacca tacttggcac caacaacttc   8340
gttgcgctgg cccaccgggc ggcgctgagt ggtgtcaccc agggtttcat gaagaaggcg   8400
tttaactcac ccatcgccct tgggaaaaat aaatttaagg agctacagac tccagtcttg   8460
ggtaggtgtc ttgaggctga tctcgcttcc tgcgatcgat ccacgcctgc aatcgttcgc   8520
tggtttgccg ccaaccttct ttatgaactt gcctgtgctg aggagcattt accgtcgtac   8580
gtgctgaact gttgtcacga cctattggtc acgcagtccg gcgcagtgac taagagaggt   8640
ggcctgtcgt ccggtgaccc aatcacctct gtgtccaaca ccatttatag cttggtgatc   8700
tatgcacagc atatggtgct tagttacttc aaaagtggtc acccccatgg ccttctgttt   8760
ttacaagacc agctaaagtt tgaagacatg ctcaaagttc aacccctaat cgtctattcg   8820
gacgacctcg tgttgtatgc cgagtctccc accatgccaa actatcactg gtgggttgaa   8880
cacctgaatt tgatgttggg atttcagacg gacccaaaga agactgcaat aacagactca   8940
ccttcattcc taggttgtag aataataaat ggccgccagt tagtacccaa ccgtgacaga   9000
attctcgcgg cccttgccta tcacatgaag gcgagtaatg tttctgagta ctacgcctcc   9060
gcagccgcaa tactcatgga cagttgtgct tgtctagagt atgatcctga gtggtttgaa   9120
gaacttgtgg ttggaatggc gcagtgcgcc cgtaaggacg gctatagttt ccccggcccg   9180
ccgttcttct tgtccatgtg ggaaaagctc aggtcaaatt atgaggggaa gaagttgaga   9240
gtgtgtggtt attgcggagc ttcagccccg tatgctactg cctgtggcct tgacgtttgt   9300
gtttaccaca cccactttca ccagcattgt ccagtcataa tatggtgtgg ccacccggcg   9360
ggttctgggt cctgcgatga gtgcaaatcc cctacaggga agggtacaag ccctctggat   9420
gaggtcttaa gacaagtccc ttataagcct ccacggacta ttcttatgca tgtggagcag   9480
ggcctcaccc cccttgaccc aggcagatac cagacccgcc gtgggttggt tgctgtcagg   9540
cgcgggataa ggggaaatga agttgacctg ccagatggtg attatgccag tactgcccta   9600
ctccccacct gcaaagacat agacatggtt gctgtggcct ccaatgtgtt gcgcagtagg   9660
ttcatcatcg gcccacctgg cgcagggaaa acacactggc ttcttcaaca ggttcaggat   9720
agtgatgtca tttacacgcc aacccatcag accatgcttg acatgatcaa ggctttgggg   9780
acgtgccggt tcaatgtccc ggcaggcaca acgctgcaat tccctgcccc ctcccgtacc   9840
ggcccgtggg ttcgcatcct tgccggcggt tggtgtccag gtaagaattc cttcctggat   9900
gaagcagcgt attgcaatca ccttgacgtc ttgaggcttc tcagcaaaac taccctcacc   9960
tgtctggggg atttcaaaca actccacccg gtgggttttg attctcattg ctatgttttt  10020
gatatcatgc ctcagactca actgaagacc atctggaggt ttggacagaa tatctgtgac  10080
gccattcagc cagattacag ggacaaactc gtgtccatgg tcaacacaac ccgtgtaacc  10140
```

```
tatgtggaaa gacctgtcaa gtatgggcaa gtcctcaccc cctaccacag agaccgagag  10200
gatggtgcta tcactattga ctccagtcaa ggcgccacat ttgatgtggt cacattgcat  10260
ttgcccacta aagattcact caacaggcaa agagcccttg ttgctatcac cagggcaagg  10320
catgcaatct ttgtgtatga cccacacagg caactgcaga gcatgtttcg tcttcctgca  10380
aaaggcacac ctgtcaacct tgccgtgcac cgtgacgagc agctcatcgt attagataga  10440
aataacaaag agtgcacggt tgttcaggct ttaggcaatg gggacaaatt cagggccagt  10500
gacaagcgcg ttgtagattc tcttcgcgcc atttgtgcag atcttgaagg gtcgagctcc  10560
ccgctcccca aggtcgcaca caacttggga ttttatttct cacctgattt gacacagttt  10620
gctaaactcc cggcggaact tgcacccccac tggcccgtgg tgacaactca gaacaacgaa  10680
aattggccag accggctggt tgctagcctc cgccctatcc acaaatatag ccgcgcgtgc  10740
atcggagccg gctatatggt gggcccctca gtgtttctag gcactcctgg ggttgtgtca  10800
tactatctca cacaatttgt caaaggggag gctcaggtgc ttccggagac ggtcttcagc  10860
accggccgaa ttgaggtaga ttgtcgagag tatcttgatg atcgggaacg agaagttgct  10920
gagtccctcc cacatgcctt tattggcgac gtcaaaggca ctaccgttgg gggatgtcac  10980
catgtcactt ctaaatatct cccacgcttc cttcccaagg aatcagttgc ggtggttggg  11040
gtttcaagcc ccgggaaagc cgcaaaagca gtttgcacat taacagatgt gtacctccca  11100
gatcttgagg cttacctcca tccagagacc cagtctaagt gctggaaagt gatgttggac  11160
ttcaaggaag ttcgactgat ggtctggaga gataagacgg cctactttca acttgaaggc  11220
cgccatttca cctggtacca gcttgcaagt tatgcctcgt acatccgagt tcccgttaac  11280
tctacggtgt acctggaccc ctgtatgggc cctgcccttt gcaacagaag agtcgttggg  11340
tctgcacatt ggggagctga ccttgcagtt accccttatg attatggtgc caaaatcatt  11400
ctgtctagtg cgcaccatgg tgaaatgcct cctgggtaca gaattctagc gtgcgcggag  11460
ttctcgcttg atgacccagt gaggtacaaa cacacttggg ggtttgaatc ggatacagcg  11520
tatctgtacg agttcaccgg aaacggtgag gactgggagg attacaatga tgcgtttcgt  11580
gcacgccaga aagggaaaat ttataaggcc actgccacca gcatgagatt tcattttccc  11640
ccgggtcctg ccattgaacc aacattgggc ctgaactgaa atgaaatggg ggctgtgcag  11700
agccttttcg acaaaatttg ccaacttttt gtggatgctt tcacggaatt tttggtgtcc  11760
attgttgata tcatcatatt tttggccatt ttgtttggct tcaccatcgc aggctggctg  11820
gttgtcttct gtatccgact ggtttgctcc acggtactcc gtgcgcgctc taccattcac  11880
cctgagcaat tacagaagat cctatgaggc cttcctttcc cagtgccaag tggacattcc  11940
cgcctgggga actaagcatc ccttgggggt gctttggcac cacaaggtgt caactctgat  12000
tgatgaaatg gtgtcgcgtc gaatgtaccg catcatggaa aaagcaggac aggctgcctg  12060
gaaacaggtt gtgagcgaag ctacattgtc tcgcataagt ggcttggatg tggtggctca  12120
ttttcagcat cttgctgcca ttgaagccga gacttgcaaa tatttggcct ctcggctgcc  12180
catgctacac aacctagtca tgtcagggtc gaatgtaacc atagtgtata atagcacttt  12240
gggtcaagtg tttgccattt tcccaacccc tggttcccgg ccaaaacttt ctgattttca  12300
acaatggctc atagctgtgc attcttccat attttcttct gttgcggctt cttgtactct  12360
ttttgttgtg ctgtggctgc gaattccaat actacgtact gtttttggtt tccgctggtt  12420
aggggcaact tttctttcga actcacagtg aattacacgg tgtgcccacc ctgcctcacc  12480
cggcaagcag ccgctgagat ctacgaacac agcgggtctc tttggtgcag gatagggcat  12540
```

```
gaccgatgta gccagagtga tcatgacgaa ctagggttct tggttccacc tggcctttcc  12600
agcgagggcc acttgaccag tgtttacgcc tggctggcgt tcttgtcttt cagctacaca  12660
gcccagttcc accccgagat atttggaata gggaatgtga gtagagttta tgttgacgtc  12720
actcaccaac tcatctgcgc cgaacacgac gggcagaaca ccaccctgcg tcgccatgac  12780
aatatctcag ccgtgtttca gacctattac caacatcagg tcgatggcgg caattggttt  12840
cacctagaat ggctgcgtcc cttcttttcc tcttggctgg ttttgaatgt ctcgtggttt  12900
ctcaggcgtt cgcctgcaaa ccgtgtttca gttcgagtct ttcagacatc aaaaccaaca  12960
ccaccgcagc tgcaggcttt gctgtcctcc aagacatcag ctgtcttagg catggctact  13020
cgtccattga ggcgattcgc aaaagccgtc aatgccgcac ggcgatagga acgcccgtgt  13080
acatcactgt cacggccaat gtaacagatg agaattactt gcattcctct gatctcctca  13140
tgctttcctc ttgcctcttc tatgcttctg agatgagtga aaagggattc aatgtggtct  13200
tcggcaacgt gtcaggcatt gtggctgtgt gtgtcaactt taccagctat gtccaacatg  13260
ttaaggagtt tactcagcgc tctttggtgg tcgaccacgt gcgactgctt catttcatga  13320
cacctgcgac catgaggtgg gcaacagttt tagcctgtct tttcgccatc ttgttggcga  13380
tttgaatgtt taagtatgtt ggggaaatgc ttgaccgcgg gctactgctc gcaattgctt  13440
tttttctggt gtatcgtgcc gttctgtttt gctgcgctcg tcaacgccgc cagcaacagc  13500
agctcccatt tacagttgat ttataacctg acgatatgcg agctgaatgg cacagattgg  13560
ttgaatcaaa agtttgattg ggcagtggag acttttgtca tttttcctgt gttgacccac  13620
attgtctcct acggtgccct taccaccagc catttccttg acacggccgg cctaatcact  13680
gtgtctaccg ccggatatta ccatgggcgg tatgtgttga gtagcatcta cgccgtcttt  13740
gccctggctg cgttgatttg ttttgtcatt aggttgacaa aaaactgtat gtcctggcgc  13800
tactcatgta ccagatatac caactttctt ctggacacca aaggcaatct ctatcgttgg  13860
cggtcacccg tcgttataga gagaaggggt aaagttgagg ttggagacca cctaatcgac  13920
ctcaaaagag ttgtgcttga tggttccgcg gcaaccccta taaccaagat ttcagcggaa  13980
caatggggtc gtccctagac gacttctgca atgacagcac agctgcacaa aaggtgcttt  14040
tggcgttttc catcacctat acgccaataa tgatatatgc cctgaaggta agtcgcggcc  14100
gactgttagg gcttttgcat cttttaattt tcttgaattg tgctttcacc ttcgggtaca  14160
tgacatttgt tcattttcag agtacaaaca aggtcgcgct cactatggga gcagttgttg  14220
cactcctttg gggggtgtac tcagccatag aaacctggaa attcatcact tccagatgcc  14280
gtttgtgctt gctaggccgc aggtacattc tggcccctgc ccaccacgtt gaaagtgccg  14340
cgggctttca tccgattgcg gcaagtgata accacgcatt tgtcgtccgg cgtcccggct  14400
ccactactgt taacggcaca ttggtgcccg ggttgaaaag cctcgtgttg ggtggcagaa  14460
aagctgttaa gcggggagtg gtaaacctcg ttaaatatgc caaataacaa cggcaggcag  14520
caaaaaaata agaaggggag tggccagcca gtcaatcagc tgtgccaaat gctgggcaag  14580
atcatcgccc agcaaaatca gtccagaggc aagggaccgg gtaagaaaaa taagaagaga  14640
aacccggaga agccccattt tcctcttgcg accgaagatg acgtcaggca tcacttcacc  14700
cccagtgaac ggcaattgtg tctgtcgtcg atccagactg ccttcaacca gggcgctgga  14760
acttgcaccc tgtcagattc agggaggata agttacactg tggagtttag tttgccgacg  14820
caccacactg tgcgccttat tcgcgccaca gcatcacctc catcgtgatg ggcttacatt  14880
```

-continued cttggagctc ctcagtttca caattggaag aatgtgtggt gaatggcact gattggcact 14940
gtgcctctaa gtcacctatt caattagggc gaccgtgtgg gggtagagtt taattggcga 15000
gaaccatacg gccgaaatta aaaaaaaaaa aaaaaaaaaa aaaaaaa 15047

<210> SEQ ID NO 10
<211> LENGTH: 15444
<212> TYPE: DNA
<213> ORGANISM: Artificial Sequence
<220> FEATURE:
<223> OTHER INFORMATION: Synthetic Construct

<400> SEQUENCE: 10
atgacgtata gttgttggct ctatgtcgtg acatttgtat agtcaggagc tgcgaccatt 60
ggtacagccc aaaacttgct gcgcgggaac gcccttccgt gacagccttc ttcaggggag 120
tttaggggtc tatccctagc accttgcttc cggagttgca ctgctttacg gtctctccac 180
ccctttaacc atgtctggga tacttgatcg gtgcacgtgt acccccaatg ccagggtgtt 240
tgtggcggag ggccaagtct actgcacacg atgtctcagt gcacggtctc tccttccttt 300
gaatctccaa gtttctgagc ttggggtgct gggcttattt tataggcccg aagagccgct 360
ccggtggacg ttgccacgtg cattccccac tgtcgagtgc tcccccgccg gggcctgctg 420
gctttctgcg atttttccaa ttgcacgaat gaccagtgga aacctgaact ttcaacaaag 480
aatagtgcgg gtcgcagctg agctctacag agccggtcag ctcacccccg tagtcttgaa 540
gaatctacag gtttatgaac ggggttgccg ttggtacccc atcgttggac ctgttcctgg 600
agtggctgtt tatgccaatt ccttacacgt gagtgacaaa cctttcccgg gagcaactca 660
tgtgttaacc aacctaccgc tcccgcagag gcccaagcct gaagactttt gcccctttga 720
gtgtgctatg gctgacgtct atgacattgg tcatgacgct gtcatgtatg tggccggagg 780
gagagtctcc tgggcccctc gtggcgggga caaaggaaaa tttgaaatag ttcccaagga 840
gttgaagttg attgcgaatc gactccacat ttccttcccg ccccaccacg cagtggacat 900
gtccaagttt gcctttataa gccctgggag tggtgtttcc atgcgggtcg agtaccaaca 960
tggctgtctc cccgctgata ctgtccctga aggaaactgt tggtggcgct tgtttgactt 1020
gcttccaccg gaagttcaga acaaagagat tcgccatgct aaccaactcg gctatcagac 1080
caagcatggt gtcgctggca agtacctaca gcggaggctg caagttaatg gactccgagc 1140
agtaactgac gcgaatggac ctatcgtcat acagtatttt tgtgataggg aaagctggat 1200
ccgccactta agactggtag aagaacctag cctccctggg tttgaggacc tcctcagaat 1260
aagagttgag cccaatacgt tgccattggt tggcgaggat gagaaaatct tccgatttgg 1320
caatcacaaa tggtacggtg ctggaaagag ggcaaggaaa gcacgctttg gtgcggctgc 1380
cacggtcgct caccgcgctt tgcccgctca cgaaacccag caggccaaga agcacgaagt 1440
taccagcgcc aacagggctg agcatctcga gcactattcc ccgcctaccg acgggaactg 1500
tggttggcac tgcgtttccg ccattgtcaa ccggattgtg aattccaaat ttgaaaccac 1560
ccttcccgag agagtgagac ctttagatga ctgggctact gacgaggatc ttgtgaatac 1620
tatccaaatc ctcaggctcc ctgcggcctt ggacaggaac ggtgcttgtg tcggcgccaa 1680
gtacgtgctc aagctggaag gtgtgcactg gacagtctct gtggcccctg ggatgacccc 1740
ttctctgctc cccccttgaat gtgttcaggg ctgttgtgag cataagagcg gtcttggtcc 1800
cccagatgtg gctgaagttt ccggatttga ccctgcctgc cttaaccgac tggctgaggt 1860
aatgcacttg cctagttgtg tcatcccagc tgctctggct gaaatgtccg acgaccccaa 1920
tcgcccggct tccccagtca ccactgtgtg gactatttcg caattctttg cccattatag 1980
aggaggagag caccctgatc aggtgtgctt agggaaaatc atcagccttt gtcaggtgat 2040
tgaggaatgc tgttgttccc agaacaaaac caaccgggcc accccggaag aggtcgcggc 2100
aaaaattgac cagtacctcc gtgatgcagc aagccttgga gaatgcttag ccaagcttga 2160
gagggctcgc ccgccgagcg cgatggacac ctcctttgat tggaatgttg tgcttcctgg 2220
ggttgaggcg gcgaaccaga cgaccaaaca gctccatgtc aaccagcacc gtgcttcggt 2280
tcctgccatg actcaggagc ctttggacaa agactcggtc cctttgaccg ccttctcgct 2340
gtctaattgc tactaccctg cacaaggtga cgaggttcgt caccgtgaga ggctgatctc 2400
cgtgctctct aagttggagg aggttgttcg tgaggaatat gggctcacgc caactggatc 2460
tggcccgcga cccgcactgc cgaacgggct cgacgagctc aaagaccaga tggaagagga 2520
tctgttgaaa ctggtcaacg cccaggcaac ttcagaaatg atggcccggg cagctgagca 2580
ggttgatcta aaagtttggg tcaaaaatta cccacggtgg acaccgccac cccctccacc 2640
aagagttcag cctcgaaaaa caaagtctgc taagagcctg ccagagaaca agcctgtccc 2700
tgctccgcgc aggaaagtca gatctgattg tggcagcccg actttgaggg gcaacaatgt 2760
tcctaacggt tgggaagact tggccgttgg tggtcctctt gatctttcga caccatccga 2820
gccgatgaca cctctgagtg agcctgcact tatgcccgtg ttgcaacata tttctggacc 2880
agtgacgcct ttgagcgtgc cggcccctat tcctgcaccg cgtaaagctg tgtcccgacc 2940
gatggcgccc tcgagtgagc caatttttgt gtctgcaccg cggcaaaaat ttcagcaggt 3000
ggaagaagca aatctggcgg caacaacgct gacataccag gacgaaccta tagatctgtc 3060
agcatcctca cagactgaat atgaggctcc ttccctagca ccactgcaga acataggtac 3120
tctggaggtg ggggggcaag aagctgagga aattctgagt gaaacctcgg atataccgaa 3180
tgacatcaac cctgtgcctg tatcatcaag cagctccttg tcaagcgtta agatcacacg 3240
cccaagacac tcagctcaag ccatcatcga ctcgggcggg ccctgcagtg ggcatctcca 3300
aagggagaaa gaagcgtgcc tccgcatcat gcgtgaggct tgtgatgcga ctaagcttag 3360
tgaccctgcc acgcaggaat ggctttctcg catgtgggat agggtggaca tgctgacttg 3420
gcgcaacacg tctgctttcc aggcgtttcg catcttagac ggcaggcttg agtttcttcc 3480
aaagatgata ctcgagacgc cgccgcccta cccgtgtggg tttgtgatgc tgcctcacac 3540
ccctgcacct tccgtgagtg cagagagcga ccttaccatc ggttcagtcg ccactgaaga 3600
tattccacgc atcctcggga aaatagaaaa caccagtgag atgatcaacc agggaccctt 3660
ggcatcctct gaggaaaaac cggcatacaa ccaacccgct aaggactccc tgatatcgtc 3720
gcgggggttt gacgagagca cagcagctcc gtccgcaggt acgggtggcg ccggcttgtt 3780
tactgatttg ccaccttcag acggtgtaga tgcggacggg gggggccgc tgcagacggt 3840 gaaaaagaac gctgaaaggc tcctcgaccg attgagccgt caggttttta acctcgtctc 3900
ccatctccct gttttcctct cacacctctt caaatctgac agtggttatt ctccgggtga 3960
ttggggtttt gcagctttta ctctattttg cctcttttta tgttacagct acccattctt 4020
tggtttcgct cccctttgg gtgtgttttc tgggtcttct cggcgcgtgc gcatgggggt 4080
ttttggctgc tggttggctt ttgctgttgg tttgttcaag cctgtgtccg acccagtcgg 4140
cactgcttgt gagtttgatt cgccagagtg taggaatgtc cttcattctt ttgagcttct 4200
caaaccttgg gaccctgttc gcagccttgt tgtgggcccc gtcggtctcg gtcttgccat 4260

```
tcttggcagg ttactgggcg gggcacgcta catctggcat tttctgctta ggcttggcat   4320
tgttacagac tgtatcctgg ctggagctta tgtgctttct caaggtaggt gtaaaaagtg   4380
ctggggatct tgcataagaa cagctcctaa tgagattgcc tttaacgtgt tcccttttac   4440
acgtgcgact aggtcgtcac tcatcgacct gtgcaatcgg ttttgtgcgc caaagggcat   4500
ggaccctatt ctcctcgcca ctgggtggcg tgggtgctgg accggccgaa gccccattga   4560
acaaccctct gaaaaaccca tcgcgtttgc ccagttggac gaaaagagga ttacggccag   4620
gaccgtggtc gcccagcctt atgaccccaa ccaagccgta aagtgcttgc gggtgttaca   4680
ggcgggcggg gcgatggtgg ctgaggcagt cccaaaagtg gtcaaagttt ccgctattcc   4740
attccgagcc cccttttttc ccaccggagt gaaagttgac cctgagtgta ggatcgtggt   4800
tgaccccgac acttttacta cagccctccg gtccggctat tccaccacaa acctcgttct   4860
tggtgtgggg gactttgccc agctgaatgg attaaaaatc aggcaaattt ccaagccttc   4920
gggaggaggc ccgcacctca ttgctgccct acatgttgcc tgctcgatgg cgttgcacat   4980
gcttgctggg gtttatgtaa ctgcagtggg gtcttgcggt accggcacca acgatccgtg   5040
gtgcaccaac ccgtttgccg tccctggcta cgggcctggt actctttgca cgtccagatt   5100
gtgcatctcc caacatggcc ttaccctgcc cttgacagca cttgtggcag gattcggtct   5160
tcaggaaatt gccttggttg ttttgatttt cgtttccatc ggaggcatgg ctcacaggtt   5220
gagttgcaag gctgacatgc tgtgcgtttt acttgcaatc gccagctatg tttgggtgcc   5280
ccttacctgg tttctttgtg tgtttccttg ctggttgcgc tggttctctt tgcatcccct   5340
caccatccta tggttggtgt ttttcttgat ttctgtaaat gtgccttcgg gaatcttggc   5400
tgtggtgttg ttagtttctc tttggctctt aggtcgttac actaatgttg ctggtcttgt   5460
caccccatat gacattcatc atcacaccag tggcccccga ggtgttgccg ccttggctac   5520
tgcaccggat gggacctact tggccgccgt tcgccgtgct gcgttgaccg gtcgtaccat   5580
gctgtttacc ccgtctcagc ttgggtccct tcttgagggt gctttcagaa ctcaaaagcc   5640
ctcactgaac accgtcaatg tggtcggatc ctctatgggc tccggcgggg tgttcaccat   5700
cgacgggaaa attaagtgcg taacagccgc acatgtcctt acgggtaatt cagctagggt   5760
ttccggggtc ggcttcaacc aaatgcttga ttttgatgtg aaaggggact tcgccatagc   5820
tgattgcccg aattggcaag gagctgcccc caagacccaa ttctgcgagg atggatggac   5880
tggccgtgcc tattggctga catcctctgg agtcgaaccc ggtgtcattg ggaatggatt   5940
cgccttctgc ttcaccgcgt gcggcgattc tggatccccg gtgattaccg aagccggtga   6000
gcttgtcggc gttcacacag gatcaaacaa acaaggagga ggcatagtca cacgcccctc   6060
aggccagttt tgtaatgtgg cgcccatcaa gctgagcgaa ttgagtgaat tcttcgctgg   6120
acctaaggtc ccgctcggtg atgtgaagat tggcagccac ataattaaag acgtatgcga   6180
ggtaccttca gatctttgcg ccttgctcgc tgccaaaccc gaactggaag gaggcctctc   6240
caccgtccaa cttctgtgtg tgtttttcct cctgtggaga atgatgggac atgcctggac   6300
gcccttggtt gctgtggggt tttttatctt gaatgaggtt ctcccagctg tcctggtccg   6360
gagtgtcttc tcctttggta tgtttgtgct atcttggctt acaccatggt ctgcgcaagt   6420
cctgatgatc aggcttctaa cagcagctct taacaggaac agggggtcac tcgccttcta   6480
cagcctcggt gcagtgaccg gatttatcgc agatcttgca gcaactcagg ggcatccgct   6540
gcaggcagtg atgaacttaa gcacctatgc cttcctgcct cggatgatgg ttgtgacctc   6600
accagtccca gtgcttgctt gtggtgttgt gcacctcctt gccataattt tgtacctgtt   6660
```

-continued

```
taagcaccgt tgcctgcatt atgtccttgt tggcgatgga gtgttctcta aagccttctt   6720
cttgcgatac tttgccgaag ggaagttgag ggaaggggtg tcgcagtcct gcgggatgaa   6780
tcacgagtca ctgactggtg ccctcgctat gagactcaat gacgaagact tggacttcct   6840
tacgaaatgg actgatttta agtgctttgt ttctgcgtcc aacatgagga atgcagcggg   6900
ccaattcatc gaggctgcct atgcaaaagc acttagaatt gagcttgccc agttagtaca   6960
ggttgataag gttcgaggta ctttggccaa acttgaagcc tttgctgata ccgtggcacc   7020
ccagctctcg cccggtgaca ttgttgttgc tcttggccac acgcctgttg gcagtatctt   7080
cgacctaaag gttggcagta ccaagcatac cctccaggcc attgagacca gagtccttgc   7140
cgggtccaaa atgaccgtgg cgcgtgtcgt tgatccaacc cccacgcccc cacccgcacc   7200
cgtgcccatc cccctcccac cgaaagtcct ggagaacggc cccaacgcct gggggggatga   7260
ggaccggttg aataagagga agagacgcag gatggaagcc gtcggcatct ttgttatggg   7320
tgggaagaag taccaaaaat tttgggacaa gaattccggt gatgtgtttt acgaggaggt   7380
ccatgataac acagatgcgt gggagtgcct cagagttggt gaccctgccg actttgaccc   7440
tgagaaggga actctgtgtg ggcatactac cattgaagac aaggcttata atgtctacac   7500
ctccccatct ggcaggaagt tcctggtccc cgtcaaccca gagagcggaa gagcccaatg   7560
ggaagctgca aagctttccg tagagcaggc ccttagcatg atgaatgtcg acggtgagct   7620
gacagccaaa gaactggaga aactgaaaag aataattgac aaactccagg gcctaactaa   7680
ggagcagtgt ttaaactgct agccgccagc ggcttgaccc gctgtggtcg cggcggcttg   7740
gttgttactg agacagcggt gaaaatagtt aaatttcaca accggacctt caccctagga   7800
cctgtgaatt taaaagtggc cagtgaggtt gagctaaaag acgcagtcga gcataaccaa   7860
cacccggttg caagaccggt tgatggtggt gttgtgctcc tgcgctccgc agttccttcg   7920
cttatagacg tcttgatctc tggcgctgat gcatctccta agttactcgc ccaccacggg   7980
ccgggaaaca ctgggatcga tggttcgctt tgggattttg aggccgaggc caccaaagag   8040
gaaattgcac tcagtgcgca aataatacag gcttgtgaca ttaggcgcgg cgacgcaccc   8100
gaaattggtc ttccttataa gctgcaccct gttaggggca accctgagcg ggtaaaaggg   8160
gttttacaga atacaaggtt tggagacata ccttataaaa cccccagtga cactgggagc   8220
ccagtgcacg cggctgcctg cctcacgccc aatgccactc cggtgactga cggtcgttcc   8280
gtcttggcta cgaccatgcc ctccggtttt gagttgtatg taccgaccat tccagcgtct   8340
gtccttgatt atcttgattc caggcctgat tgccccaaac agttgacaga gcacggctgt   8400
gaggatgccg cattaagaga cctctccaag tatgacttgt ccacccaagg ctttgtcttg   8460
cctggagttc ttcgccttgt gcgtaagtac ctgtttgctc atgtgggtaa gtgcccgcct   8520
attcatcggc cttccactta ccctgccaag aattccatgg ctggaataaa tgggaacagg   8580
tttccaacca aggacattca gagcgtccct gaaatcgacg ttttgtgcgc acaggccgtg   8640
cgagaaaact ggcaaactgt tactccttgt accctcaaga agcagtattg cgggaagaag   8700
aagactagga caatactcgg cactaataac ttcattgcgc tggcccaccg ggcagcattg   8760
agtggtgtca cccagggctt catgaaaaaa gcgtttaact cgcccatcgc actcgggaaa   8820
aacaaattca aggagctgca gactccggtc ttgggcagat gtcttgaagc tgaccttgca   8880
tcctgtgacc gatccacacc cgcaattgtc cgctggtttg ccgccaatct tctttatgaa   8940
cttgcctgtg ctgaggagca tataccatcg tacgtgttga actgctgcca cgacttactg   9000
```

gtcacgcagt ccggcgcggt gactaagaga ggtggcctat cgtctggcga cccgattact 9060
tctgtatcaa acaccattta cagcttggtg atatatgcac agcacatggt actcagttat 9120
tttaaaagtg gtcaccccca tggccttctg tttctacaag accagctaaa gtttgaggac 9180
atgctcaagg ttcagcccct gatcgtctat tcggacgacc tcgtgctgta cgccgagtct 9240
cccaccatgc caaactacca ctggtgggtt gaacatctga acctgatgct gggttttcag 9300
acggacccaa agaagacagc tataacagac tcgccatcat ttttgggttg taggataata 9360
aatggacgcc agttagtccc caaccgtgac aggatcctcg cggccctcgc ctaccatatg 9420
aaggcaaaca atgtttctga atactacgcc tcggcggctg caatactcat ggacagttgt 9480
gcttgtttgg agtacgatcc tgagtggttt gaagagctcg tggttgggat ggcgcagtgc 9540
gcccgcaagg acggctacag ttttcctggc ccgccgttct tcttgtccat gtgggaaaaa 9600
ctcaggtcca atcatgaggg gaagaagtct agaatgtgcg ggtactgtgg ggccccagct 9660
ccgtatgcca ctgcctgtgg ccttgatgtt tgtatttatc acacccactt ccaccagcat 9720
tgtccagtca taatctggtg tggccatccg gcgggttctg gctcttgtag tgagtgcaaa 9780
ccccccctag ggaaaggcac aagccctcta gatgtggtgt tagaacaagt cccgtacaag 9840
cctccacgaa ctgtaatcat gcatgtggag cagggtctca cccctcttga cccaggcaga 9900
taccagactc gccgcggatt agtctccgtt aggcgtggca tcaggggaaa cgaaatcgac 9960
ctaccagacg gtgattatgc tagtaccgcc ttgctcccca cttgtaaaga tatcaacatg 10020
gtcgctgtcg cttccaatgt gttgcgcagc aggttcatca tcggtccacc cggtgctggt 10080
aaaacatact ggctccttca acaggtccag gatggtgatg tcatttacac gccaactcat 10140
cagaccatgc ttgacatgat caaggctttg gggacgtgcc ggttcaacgc cccagcaggc 10200
acaacgctgc aattccctgc tccctcccgt accggcccgt gggttcgcat cctggccggc 10260
ggttggtgtc ctggcaagaa ttccttcctg gatgaagcag cgtattgtaa tcaccttgat 10320
gtcttgaggc ttcttagcaa aactaccctc acctgtctgg gagatttcaa acaactccac 10380
ccagtgggtt ttgattctca ttgctatgtt tttgacatca tgcctcagac tcaactgaag 10440
accatctgga ggtttggaca gaatatctgt gatgccattc agccagatta cagggacaaa 10500
cttgtgtcca tggtcaacac aacccgtgta acctacgtgg aaagacctgt caagcatggg 10560
caggtcctca ccccttacca cagggaccga gaggacggcg ccatcacaat tgactccagt 10620
caaggcgcca catttgatgt ggttacattg catttgccca ctaaagattc actcaacagg 10680
caaagagccc ttgttgctat caccagggcg agacatgcta tctttgtgta tgacccacat 10740
aggcaactgc agagcatgtt tgatcttcct gcaaaaggca cacccgtcaa ccttgccgtg 10800
caccgtgacg agcagctgat cgtactagat agaaataaca aagagtgcac ggttgctcag 10860
gctctaggca atggggacaa attcagggcc acagacaagc gcgttgtaga ttctctccgc 10920
gccatttgtg cagatcttga agggtcgagc tccccgctcc ccaaggtcgc acataacttg 10980
ggattttatt tctcacctga tttgacacag tttgctaaac tcccggcaga acttgcaccc 11040
cactggcccg tggtgacaac ccagaacaat gaaaagtggc cagacaggct ggttgccagc 11100
ctccgcccta tccataaata tagccgcgca tgcattggag ccggctatat ggtgggccct 11160
tcggtgtttc taggcacccc tggggttgtg tcatactatc tcacaaaatt tgttaagggg 11220
gaggctcagg tgcttccgga gacagtcttc agcaccggcc gaattgaggt agattgccgg 11280
gagtatcttg atgatcggga acgagaagtt gctgagtccc tcccacatgc cttcattggc 11340
gacgtcaaag gcactaccgt tgggggatgt caccatgtca cctctaaata ccttccgcgc 11400
ttccttccta aggaatcagt tgcggtggtt ggggtttcga gccccgggaa agccgcaaaa 11460
gcagtctgca cattaacaga tgtgtatctc ccagaccttg aagtttacct ccacccagag 11520
acccaatcca agtgctggaa aataatgttg gacttcaagg aagtccgact gatggtctgg 11580
aaagacaaaa cggcctattt tcaacttgaa ggccgccatt tcacctggta tcagcttgca 11640
agctatgcct cgtacatccg agttcctgtt aactctacgg tgtatttgga cccctgcatg 11700
ggccctgccc tttgcaacag aagagttgtc gggtccactc attggggggc tgacctcgca 11760
gtcacccctt atgattatgg tgccaaaatc attctgtcta gtgcatacca tggtgaaatg 11820
cctcctgggt acaaaatcct ggcgtgcgcg gagttctcgc ttgacgaccc agtgaggtac 11880
aaacacacct gggggtttga atcggacaca gcgtatctgt acgagttcac cggaaacggt 11940
gaggactggg aggattacaa tgacgcattt cgtgcgcgcc agaaagggaa aatttataag 12000
gccactgcca ccagcatgag gtttcatttt cccccgggcc ccatcattga accaacttta 12060
ggcctgaact gaaatgagat gggggctatg caaagccttt tctacaaaat tggccaactt 12120
tttgtggatg ctttcacgga atttttggtg tccattgttg atatcatcat atttttggcc 12180
attttgtttg gcttcaccat cgccggttgg ctggtggtct tctgcatccg attggtttgc 12240
tccgcggtac tccgtgcgcg ccctaccatt caccctgagc aattacagaa gatcctatga 12300
ggcctttctt tctcagtgcc gggtggacat tcccacctgg ggaaccaaac atcccttggg 12360
gatactttgg caccataagg tgtcaaccct gattgatgaa atggtgtcgc gtcgaatgta 12420
ccgcatcatg gaaaaatcag gacaggctgc ctggaaacag gttgtgagcg aggctacgct 12480
gtctcgcatc agtggtttgg atgtggtggc tcattttcag catcttgccg ccattgaagc 12540
cgagacctgt aaatatttgg cctctcggat gcccatgcta cacaacctgc gcatgacagg 12600
gtcaaatgta accatagtgt ataatagtac tttgaatcag gtgttagcaa tcttcccgac 12660
ctctgaatcc cggccaaagc ttcatgattt tcaacaatgg ttaataactg tacattcctc 12720
catattttcc tccgttgtgg cttcctgtac tctttttgtt gtgctgtggt tgcgaattcc 12780
aatgctacgt actgtttttg gtttccactg gttaggggca atttttcttt cgaactcaca 12840
gtgaattaca cggtgtgccc accttgcctc acccggcaag cagccgctga gatctacgaa 12900
cccggcaggt ctctttggtg caggataggg catgatcgat gtagcgagga cgatcatgac 12960
gaactagggt tcttggttcc gcctggcctc tccagcgaag gccacttgac cagtgtttac 13020
gcctggttgg cgttcctgtc cttcagctat acagcccagt tccatcccga gatatttggg 13080
atagggaatg tgagtaaaat ttatgttgac atcaagcacc aattcatctg cgccgaacac 13140
gacgggcaga acgccaccct gcctcgccat gacaacattt cagccgtgtt tcagacctac 13200
taccaacatc aggtcgatgg cggcaattgg tttcacctgg aatggctgcg ccccttcttt 13260
tcctcttggt tggttttaaa tgtttcgtgg tttctcaggc gttcgcctgc aagccatgtt 13320
tcagttcgag tctttcagac atcaaaacca acaccaccgc agcaccaaat tttgttgtcc 13380
tccaggacat cagctgcctt aggcatggcg acccgtcctc tccggcgatt cgcaaaagct 13440
ctcagtgccg cacggcgata ggaacacccg tgtatatcac catcacagcc aatgtgacag 13500
atgagaatta tttacattct tctgatctcc tcatgctttc ttcttgcctt ttctatgctt 13560
ctgagatgag tgaaaagggg ttcaaggtgg tattcggcaa tgtgtcaggc atcgtggctg 13620
tgtgtgtcaa ctttaccagt tacgtccaac atgtcaagga gtttacccaa cgctccttgg 13680
tggtcgagca tgtgcgactg cttcatttca tgacacctga aaccatgagg tgggcaaccg 13740
ttttagcctg tctttttgcc attctgttgg caatttgaat gtttaagtat gttggggaaa 13800
tgcttgaccg cgggctgttg ctcgccgttg cttttttgt ggtgtatcgt gccgtcttgc 13860
tttgttgcgc ccgtcaacgt cgacgggaac gacagctcaa agttacagct gatttacaac 13920
ttgacgctat gtgagctgaa tggcacagat tggctggctg gtagatttga ctgggcagtg 13980
gagtgttttg tcatttttcc cgtgttgact cacattgtct cctatggtgc cctcactact 14040
agccatttcc ttgacacagt cggtctggtc actgtgtctg ccgccgggtt ccttcatgaa 14100
cggtatgttt tgagtagcat ctacgcggtc tgtgccctgg ctgcgttgat ttgcttcgtc 14160
attaggcttg cgaagaactg catgtcctgg cgctactcgt gtaccagata taccaacttc 14220
cttttggaca ccaaggggag actctatcgt tggcgatcgc ccgtcatcat agagaaaaag 14280
ggtaaagttg aggttgaagg tcatttgatc gacctcaaaa gagttgtgct tgatggttcc 14340
gtggcaaccc ctataaccaa aatttcagcg gaacaatggg gtcgtcctta gatgacttct 14400
gccatgatag cacggctcca caaaaggtgc ttttggcgtt ttccattacc tatacaccag 14460
tgatgatata tgccctaaag gtaagtcgcg gccgactgct agggcttttg caccttttga 14520
tctttctgaa ctgtgctttc accttcgggt atatgacatt cacgcacttt cagagtacaa 14580
acaaggtcgc gctcactatg ggagcagtag ttgcactcct ttggggggtg tactcagcca 14640
tagaaacctg gaaattcatc acctccagat gccgtttgtg cttgctaggc cgcaagtaca 14700
ttctggcccc tgcccaccac gttgagagtg ccgcaggctt tcatccgatt gcggcaaatg 14760
ataaccacgc atttgtcgtc cggcgtcccg gttccactac ggtcaacggc acattggtcc 14820
ccgggttgaa aagcctcgtg ttgggtggca gaaaagctgt caaacaggga gtggtaaacc 14880
ttgttaaata tgccaagtaa caacggcagg cagcagaaaa aaagaaaggg ggatggccag 14940
ccagtcaatc agctgtgtca gatgctgggt aaaattattg cccagcaaaa tcagtccagg 15000
ggcaagggac cgggaaagaa aaataacaag aaaaacccgg agaagcccca ttttcctcta 15060
gcgactgaag atgatgtcag acatcacttt accccgagtg agcgacaatt gtgtctgtcg 15120
tcaatccaga ctgccttcaa tcagggcgct ggaacttgta ccctgtcaga ttcaggcagg 15180
ataagttaca ctgtggagtt tagtttgccg acgcatcaca ctgtgcgcct gatccgcgct 15240
acagcatcac cctcagcatg atgagctggc attcctgggt atcccagtgt ttgaattgga 15300
agaatgtgtg gtgaatggca ctgattgaca ttgtgcttct aagtcaccta ttcaattagg 15360
gcgaccgtgt gggagtagaa tttaattggc gagaaccacg cggccgaaat taaaaaaaaa 15420
aaaaaaaaaa aaaaaaaaaa aaaa 15444

<210> SEQ ID NO 11
<211> LENGTH: 15444
<212> TYPE: DNA
<213> ORGANISM: Artificial Sequence
<220> FEATURE:
<223> OTHER INFORMATION: Synthetic Construct

<400> SEQUENCE: 11
atgacgtata gttgttggct ctatgtcgtg acatttgtat agtcaggagc tgcgaccatt 60
ggtacagccc aaaacttgct gcgcgggaac gcccttccgt gacagccttc ttcaggggag 120
tttaggggtc tatccctagc accttgcttc cggagttgca ctgctttacg gtctctccac 180
ccctttaacc atgtctggga tacttgatcg gtgcacgtgt acccccaatg ccagggtgtt 240
tgtggcggag ggccaagtct actgcacacg atgtctcagt gcacggtctc tccttccttt 300
gaatctccaa gtttctgagc ttggggtgct gggcttattt tataggcccg aagagccgct 360

```
ccggtggacg ttgccacgtg cattccccac tgtcgagtgc tcccccgccg gggcctgctg    420
gctttctgcg atttttccaa ttgcacgaat gaccagtgga aacctgaact ttcaacaaag    480
aatagtgcgg gtcgcagctg agctctacag agccggtcag ctcacccccg tagtcttgaa    540
gaatctacag gtttatgaac ggggttgccg ttggtacccc atcgttggac ctgttcctgg    600
agtggctgtt tatgccaatt ccttacacgt gagtgacaaa cctttcccgg gagcaactca    660
tgtgttaacc aacctaccgc tcccgcagag gcccaagcct gaagactttt gccccttga    720
gtgtgctatg gctgacgtct atgacattgg tcatgacgct gtcatgtatg tggccggagg    780
gagagtctcc tgggcccctc gtggcgggga caaaggaaaa tttgaaatag ttcccaagga    840
gttgaagttg attgcgaatc gactccacat ttccttcccg ccccaccacg cagtggacat    900
gtccaagttt gcctttataa gccctgggag tggtgtttcc atgcgggtcg agtaccaaca    960
tggctgtctc cccgctgata ctgtccctga aggaaactgt tggtggcgct tgtttgactt   1020
gcttccaccg gaagttcaga acaaagagat tcgccatgct aaccaactcg gctatcagac   1080
caagcatggt gtcgctggca agtacctaca gcggaggctg caagttaatg gactccgagc   1140
agtaactgac gcgaatggac ctatcgtcat acagtatttt tgtgataggg aaagctggat   1200
ccgccactta agactggtag aagaacctag cctccctggg tttgaggacc tcctcagaat   1260
aagagttgag cccaatacgt tgccattggt tggcgaggat gagaaaatct tccgatttgg   1320
caatcacaaa tggtacggtg ctggaaagag ggcaaggaaa gcacgctttg gtgcggctgc   1380
cacggtcgct caccgcgctt tgcccgctca cgaaacccag caggccaaga agcacgaagt   1440
taccagcgcc aacagggctg agcatctcga gcactattcc ccgcctaccg acgggaactg   1500
tggttggcac tgcgtttccg ccattgtcaa ccggattgtg aattccaaat ttgaaaccac   1560
ccttcccgag agagtgagac ctttagatga ctgggctact gacgaggatc ttgtgaatac   1620
tatccaaatc ctcaggctcc ctgcggcctt ggacaggaac ggtgcttgtg tcggcgccaa   1680
gtacgtgctc aagctggaag gtgtgcactg gacagtctct gtggcccctg ggatgacccc   1740
ttctctgctc cccttgaat gtgttcaggg ctgttgtgag cataagagcg gtcttggtcc   1800
cccagatgtg gctgaagttt ccggatttga ccctgcctgc cttaaccgac tggctgaggt   1860
aatgcacttg cctagttgtg tcatcccagc tgctctggct gaaatgtccg acgaccccaa   1920
tcgcccggct tccccagtca ccactgtgtg gactatttcg caattctttg cccattatag   1980
aggaggagag caccctgatc aggtgtgctt agggaaaatc atcagccttt gtcaggtgat   2040
tgaggaatgc tgttgttccc agaacaaaac caaccgggcc accccggaag aggtcgcggc   2100
aaaaattgac cagtacctcc gtgatgcagc aagccttgga gaatgcttag ccaagcttga   2160
gagggctcgc ccgccgagcg cgatggacac ctcctttgat tggaatgttg tgcttcctgg   2220
ggttgaggcg gcgaaccaga cgaccaaaca gctccatgtc aaccagcacc gtgcttcggt   2280
tcctgccatg actcaggagc ctttggacaa agactcggtc cctttgaccg ccttctcgct   2340
gtctaattgc tactaccctg cacaaggtga cgaggttcgt caccgtgaga ggctgatctc   2400
cgtgctctct aagttggagg aggttgttcg tgaggaatat gggctcacgc caactggatc   2460
tggcccgcga cccgcactgc cgaacgggct cgacgagctc aaagaccaga tggaagagga   2520
tctgttgaaa ctggtcaacg cccaggcaac ttcagaaatg atggcccggg cagctgagca   2580
ggttgatcta aaagtttggg tcaaaaatta cccacggtgg acaccgccac cccctccacc   2640
aagagttcag cctcgaaaaa caaagtctgc taagagcctg ccagagaaca agcctgtccc   2700
```

-continued

```
tgctccgcgc aggaaagtca gatctgattg tggcagcccg actttgaggg gcaacaatgt   2760
tcctaacggt tgggaagact tggccgttgg tggtcctctt gatctttcga caccatccga   2820
gccgatgaca cctctgagtg agcctgcact tatgcccgtg ttgcaacata tttctggacc   2880
agtgacgcct ttgagcgtgc cggcccctat tcctgcaccg cgtaaagctg tgtcccgacc   2940
gatggcgccc tcgagtgagc caatttttgt gtctgcaccg cggcaaaaat ttcagcaggt   3000
ggaagaagca aatctggcgg caacaacgct gacataccag gacgaaccta tagatctgtc   3060
agcatcctca cagactgaat atgaggctcc ttccctagca ccactgcaga acataggtac   3120
tctggaggtg ggggggcaag aagctgagga aattctgagt gaaacctcgg atataccgaa   3180
tgacatcaac cctgtgcctg tatcatcaag cagctccttg tcaagcgtta agatcacacg   3240
cccaagacac tcagctcaag ccatcatcga ctcgggcggg ccctgcagtg ggcatctcca   3300
aagggagaaa gaagcgtgcc tccgcatcat gcgtgaggct tgtgatgcga ctaagcttag   3360
tgaccctgcc acgcaggaat ggctttctcg catgtgggat agggtggaca tgctgacttg   3420
gcgcaacacg tctgctttcc aggcgtttcg catcttagac ggcaggcttg agtttcttcc   3480
aaagatgata ctcgagacgc cgccgcccta cccgtgtggg tttgtgatgc tgcctcacac   3540
ccctgcacct tccgtgagtg cagagagcga ccttaccatc ggttcagtcg ccactgaaga   3600
tattccacgc atcctcggga aaatagaaaa caccagtgag atgatcaacc agggaccctt   3660
ggcatcctct gaggaaaaac cggcatacaa ccaacccgct aaggactccc tgatatcgtc   3720
gcgggggttt gacgagagca cagcagctcc gtccgcaggt acgggtggcg ccggcttgtt   3780
tactgatttg ccaccttcag acggtgtaga tgcggacggg ggggggccgc tgcagacggt   3840
gaaaaagaac gctgaaaggc tcctcgaccg attgagccgt caggttttta acctcgtctc   3900
ccatctccct gttttcctct cacacctctt caaatctgac agtggttatt ctccgggtga   3960
ttggggtttt gcagctttta ctctattttg cctcttttta tgttacagct acccattctt   4020
tggtttcgct cccctttttgg gtgtgttttc tgggtcttct cggcgcgtgc gcatgggggt   4080
ttttggctgc tggttggctt ttgctgttgg tttgttcaag cctgtgtccg acccagtcgg   4140
cactgcttgt gagtttgatt cgccagagtg taggaatgtc cttcattctt ttgagcttct   4200
caaaccttgg gaccctgttc gcagccttgt tgtgggcccc gtcggtctcg gtcttgccat   4260
tcttggcagg ttactgggcg gggcacgcta catctggcat tttctgctta ggcttggcat   4320
tgttacagac tgtatcctgg ctggagctta tgtgctttct caaggtaggt gtaaaaagtg   4380
ctggggatct tgcataagaa cagctcctaa tgagattgcc tttaacgtgt tccctttttac   4440
acgtgcgact aggtcgtcac tcatcgacct gtgcaatcgg ttttgtgcgc caaagggcat   4500
ggaccctatt ctcctcgcca ctgggtggcg tgggtgctgg accggccgaa gccccattga   4560
acaaccctct gaaaaaccca tcgcgtttgc ccagttggac gaaaagagga ttacggccag   4620
gaccgtggtc gcccagcctt atgaccccaa ccaagccgta aagtgcttgc gggtgttaca   4680
ggcgggcggg gcgatggtgg ctgaggcagt cccaaaagtg gtcaaagttt ccgctattcc   4740
attccgagcc cccttttttc ccaccggagt gaaagttgac cctgagtgta ggatcgtggt   4800
tgaccccgac acttttacta cagccctccg gtccggctat tccaccacaa acctcgttct   4860
tggtgtgggg gactttgccc agctgaatgg attaaaaatc aggcaaattt ccaagccttc   4920
gggaggaggc ccgcacctca ttgctgccct acatgttgcc tgctcgatgg cgttgcacat   4980
gcttgctggg gtttatgtaa ctgcagtggg gtcttgcggt accggcacca acgatccgtg   5040
gtgcaccaac ccgtttgccg tccctggcta cgggcctggt actctttgca cgtccagatt   5100
```

-continued

```
gtgcatctcc caacatggcc ttaccctgcc cttgacagca cttgtggcag gattcggtct   5160
tcaggaaatt gccttggttg ttttgatttt cgtttccatc ggaggcatgg ctcacaggtt   5220
gagttgcaag gctgacatgc tgtgcgtttt acttgcaatc gccagctatg tttgggtgcc   5280
ccttacctgg tttctttgtg tgtttccttg ctggttgcgc tggttctctt tgcatcccct   5340
caccatccta tggttggtgt ttttcttgat ttctgtaaat gtgccttcgg gaatcttggc   5400
tgtggtgttg ttagtttctc tttggctctt aggtcgttac actaatgttg ctggtcttgt   5460
caccccatat gacattcatc atcacaccag tggcccccga ggtgttgccg ccttggctac   5520
tgcaccggat gggacctact tggccgccgt tcgccgtgct gcgttgaccg gtcgtaccat   5580
gctgtttacc ccgtctcagc ttgggtccct tcttgagggt gctttcagaa ctcaaaagcc   5640
ctcactgaac accgtcaatg tggtcggatc ctctatgggc tccggcgggg tgttcaccat   5700
cgacgggaaa attaagtgcg taacagccgc acatgtcctt acgggtaatt cagctagggt   5760
ttccggggtc ggcttcaacc aaatgcttga ttttgatgtg aaaggggact tcgccatagc   5820
tgattgcccg aattggcaag gagctgcccc caagacccaa ttctgcgagg atggatggac   5880
tggccgtgcc tattggctga catcctctgg agtcgaaccc ggtgtcattg ggaatggatt   5940
cgccttctgc ttcaccgcgt gcggcgattc tggatccccg gtgattaccg aagccggtga   6000
gcttgtcggc gttcacacag gatcaaacaa acaaggagga ggcatagtca cacgcccctc   6060
aggccagttt tgtaatgtgg cgcccatcaa gctgagcgaa ttgagtgaat tcttcgctgg   6120
acctaaggtc ccgctcggtg atgtgaagat tggcagccac ataattaaag acgtatgcga   6180
ggtaccttca gatctttgcg ccttgctcgc tgccaaaccc gaactggaag gaggcctctc   6240
caccgtccaa cttctgtgtg tgtttttcct cctgtggaga atgatgggac atgcctggac   6300
gcccttggtt gctgtggggt tttttatctt gaatgaggtt ctcccagctg tcctggtccg   6360
gagtgtcttc tcctttggta tgtttgtgct atcttggctt acaccatggt ctgcgcaagt   6420
cctgatgatc aggcttctaa cagcagctct taacaggaac aggggggtcac tcgccttcta   6480
cagcctcggt gcagtgaccg gatttatcgc agatcttgca gcaactcagg ggcatccgct   6540
gcaggcagtg atgaacttaa gcacctatgc cttcctgcct cggatgatgg ttgtgacctc   6600
accagtccca gtgcttgctt gtggtgttgt gcacctcctt gccataattt tgtacctgtt   6660
taagcaccgt tgcctgcatt atgtccttgt tggcgatgga gtgttctcta aagccttctt   6720
cttgcgatac tttgccgaag ggaagttgag ggaaggggtg tcgcagtcct gcgggatgaa   6780
tcacgagtca ctgactggtg ccctcgctat gagactcaat gacgaagact tggacttcct   6840
tacgaaatgg actgatttta agtgctttgt ttctgcgtcc aacatgagga atgcagcggg   6900
ccaattcatc gaggctgcct atgcaaaagc acttagaatt gagcttgccc agttagtaca   6960
ggttgataag gttcgaggta ctttggccaa acttgaagcc tttgctgata ccgtggcacc   7020
ccagctctcg cccggtgaca ttgttgttgc tcttggccac acgcctgttg gcagtatctt   7080
cgacctaaag gttggcagta ccaagcatac cctccaggcc attgagacca gagtccttgc   7140
cgggtccaaa atgaccgtgg cgcgtgtcgt tgatccaacc cccacgcccc cacccgcacc   7200
cgtgcccatc cccctcccac cgaaagtcct ggagaacggc cccaacgcct ggggggatga   7260
ggaccggttg aataagagga agagacgcag gatggaagcc gtcggcatct ttgttatggg   7320
tgggaagaag taccaaaaat tttgggacaa gaattccggt gatgtgtttt acgaggaggt   7380
ccatgataac acagatgcgt gggagtgcct cagagttggt gaccctgccg actttgaccc   7440
```

-continued

```
tgagaaggga actctgtgtg ggcatactac cattgaagac aaggcttata atgtctacac   7500
ctccccatct ggcaggaagt tcctggtccc cgtcaaccca gagagcggaa gagcccaatg   7560
ggaagctgca aagctttccg tagagcaggc ccttagcatg atgaatgtcg acggtgagct   7620
gacagccaaa gaactggaga aactgaaaag aataattgac aaactccagg gcctaactaa   7680
ggagcagtgt ttaaactgct agccgccagc ggcttgaccc gctgtggtcg cggcggcttg   7740
gttgttactg agacagcggt gaaaatagtt aaatttcaca accggacctt caccctagga   7800
cctgtgaatt taaaagtggc cagtgaggtt gagctaaaag acgcagtcga gcataaccaa   7860
cacccggttg caagaccggt tgatggtggt gttgtgctcc tgcgctccgc agttccttcg   7920
cttatagacg tcttgatctc tggcgctgat gcatctccta agttactcgc ccaccacggg   7980
ccgggaaaca ctgggatcga tggttcgctt tgggattttg aggccgaggc caccaaagag   8040
gaaattgcac tcagtgcgca aataatacag gcttgtgaca ttaggcgcgg cgacgcaccc   8100
gaaattggtc ttccttataa gctgcaccct gttaggggca accctgagcg ggtaaaaggg   8160
gttttacaga atacaaggtt tggagacata ccttataaaa cccccagtga cactgggagc   8220
ccagtgcacg cggctgcctg cctcacgccc aatgccactc cggtgactga cggtcgttcc   8280
gtcttggcta cgaccatgcc ctccggtttt gagttgtatg taccgaccat tccagcgtct   8340
gtccttgatt atcttgattc caggcctgat tgccccaaac agttgacaga gcacggctgt   8400
gaggatgccg cattaagaga cctctccaag tatgacttgt ccacccaagg ctttgtcttg   8460
cctggagttc ttcgccttgt gcgtaagtac ctgtttgctc atgtgggtaa gtgcccgcct   8520
attcatcggc cttccactta ccctgccaag aattccatgg ctggaataaa tgggaacagg   8580
tttccaacca aggacattca gagcgtccct gaaatcgacg ttttgtgcgc acaggccgtg   8640
cgagaaaact ggcaaactgt tactccttgt accctcaaga agcagtattg cgggaagaag   8700
aagactagga caatactcgg cactaataac ttcattgcgc tggcccaccg ggcagcattg   8760
agtggtgtca cccagggctt catgaaaaaa gcgtttaact cgcccatcgc actcgggaaa   8820
aacaaattca aggagctgca gactccggtc ttgggcagat gtcttgaagc tgaccttgca   8880
tcctgtgacc gatccacacc cgcaattgtc cgctggtttg ccgccaatct tctttatgaa   8940
cttgcctgtg ctgaggagca tataccatcg tacgtgttga actgctgcca cgacttactg   9000
gtcacgcagt ccggcgcggt gactaagaga ggtggcctat cgtctggcga cccgattact   9060
tctgtatcaa acaccattta cagcttggtg atatatgcac agcacatggt actcagttat   9120
tttaaaagtg gtcacccccca tggccttctg tttctacaag accagctaaa gtttgaggac   9180
atgctcaagg ttcagcccct gatcgtctat tcggacgacc tcgtgctgta cgccgagtct   9240
cccaccatgc caaactacca ctggtgggtt gaacatctga acctgatgct gggttttcag   9300
acggacccaa agaagacagc tataacagac tcgccatcat ttttgggttg taggataata   9360
aatggacgcc agttagtccc caaccgtgac aggatcctcg cggccctcgc ctaccatatg   9420
aaggcaaaca atgtttctga atactacgcc tcggcggctg caatactcat ggacagttgt   9480
gcttgtttgg agtacgatcc tgagtggttt gaagagctcg tggttgggat ggcgcagtgc   9540
gcccgcaagg acggctacag ttttcctggc ccgccgttct tcttgtccat gtgggaaaaa   9600
ctcaggtcca atcatgaggg gaagaagtct agaatgtgcg ggtactgtgg ggccccagct   9660
ccgtatgcca ctgcctgtgg ccttgatgtt tgtatttatc acacccactt ccaccagcat   9720
tgtccagtca taatctggtg tggccatccg gcgggttctg gctcttgtag tgagtgcaaa   9780
cccccccctag ggaaaggcac aagccctcta gatgtggtgt tagaacaagt cccgtacaag   9840
```

```
cctccacgaa ctgtaatcat gcatgtggag cagggtctca cccctcttga cccaggcaga   9900
taccagactc gccgcggatt agtctccgtt aggcgtggca tcaggggaaa cgaaatcgac   9960
ctaccagacg gtgattatgc tagtaccgcc ttgctcccca cttgtaaaga tatcaacatg  10020
gtcgctgtcg cttccaatgt gttgcgcagc aggttcatca tcggtccacc cggtgctggt  10080
aaaacatact ggctccttca acaggtccag gatggtgatg tcatttacac gccaactcat  10140
cagaccatgc ttgacatgat caaggctttg ggacgtgcc  ggttcaacgc cccagcaggc  10200
acaacgctgc aattccctgc tccctcccgt accggcccgt gggttcgcat cctggccggc  10260
ggttggtgtc ctggcaagaa ttccttcctg gatgaagcag cgtattgtaa tcaccttgat  10320
gtcttgaggc ttcttagcaa aactaccctc acctgtctgg gagatttcaa acaactccac  10380
ccagtgggtt ttgattctca ttgctatgtt tttgacatca tgcctcagac tcaactgaag  10440
accatctgga ggtttggaca gaatatctgt gatgccattc agccagatta cagggacaaa  10500
cttgtgtcca tggtcaacac aacccgtgta acctacgtgg aaagacctgt caagcatggg  10560
caggtcctca ccccttacca cagggaccga gaggacggcg ccatcacaat tgactccagt  10620
caaggcgcca catttgatgt ggttacattg catttgccca ctaaagattc actcaacagg  10680
caaagagccc ttgttgctat caccagggcg agacatgcta tctttgtgta tgacccacat  10740
aggcaactgc agagcatgtt tgatcttcct gcaaaaggca cacccgtcaa ccttgccgtg  10800
caccgtgacg agcagctgat cgtactagat agaaataaca aagagtgcac ggttgctcag  10860
gctctaggca atggggacaa attcagggcc acagacaagc gcgttgtaga ttctctccgc  10920
gccatttgtg cagatcttga agggtcgagc tccccgctcc ccaaggtcgc acataacttg  10980
ggattttatt tctcacctga tttgacacag tttgctaaac tcccggcaga acttgcaccc  11040
cactggcccg tggtgacaac ccagaacaat gaaaagtggc cagacaggct ggttgccagc  11100
ctccgcccta tccataaata tagccgcgca tgcattggag ccggctatat ggtgggccct  11160
tcggtgtttc taggcacccc tggggttgtg tcatactatc tcacaaaatt tgttaagggg  11220
gaggctcagg tgcttccgga gacagtcttc agcaccggcc gaattgaggt agattgccgg  11280
gagtatcttg atgatcggga acgagaagtt gctgagtccc tcccacatgc cttcattggc  11340
gacgtcaaag gcactaccgt tgggggatgt caccatgtca cctctaaata ccttccgcgc  11400
ttccttccta aggaatcagt tgcggtggtt ggggtttcga gccccgggaa agccgcaaaa  11460
gcagtctgca cattaacaga tgtgtatctc ccagaccttg aagtttacct ccacccagag  11520
acccaatcca agtgctggaa aataatgttg gacttcaagg aagtccgact gatggtctgg  11580
aaagacaaaa cggcctattt tcaacttgaa ggccgccatt tcacctggta tcagcttgca  11640
agctatgcct cgtacatccg agttcctgtt aactctacgg tgtatttgga cccctgcatg  11700
ggccctgccc tttgcaacag aagagttgtc gggtccactc attgggggc  tgacctcgca  11760
gtcacccctt atgattatgg tgccaaaatc attctgtcta gtgcatacca tggtgaaatg  11820
cctcctgggt acaaaatcct ggcgtgcgcg gagttctcgc ttgacgaccc agtgaggtac  11880
aaacacacct gggggtttga atcggacaca gcgtatctgt acgagttcac cggaaacggt  11940
gaggactggg aggattacaa tgacgcattt cgtgcgcgcc agaaagggaa aatttataag  12000
gccactgcca ccagcatgag gtttcatttt cccccgggcc ccatcattga accaacttta  12060
ggcctgaact gaaatgagat gggggctatg caaagccttt tctacaaaat tggccaactt  12120
tttgtggatg ctttcacgga atttttggtg tccattgttg atatcatcat atttttggcc  12180
```

attttgtttg gcttcaccat cgccggttgg ctggtggtct tctgcatccg attggtttgc 12240
tccgcggtac tccgtgcgcg ccctaccatt caccctgagc aattacagaa gatcctatga 12300
ggcctttctt tctcagtgcc gggtggacat tcccacctgg ggaaccaaac atcccttggg 12360
gatactttgg caccataagg tgtcaaccct gattgatgaa atggtgtcgc gtcgaatgta 12420
ccgcatcatg gaaaaatcag gacaggctgc ctggaaacag gttgtgagcg aggctacgct 12480
gtctcgcatc agtggtttgg atgtggtggc tcattttcag catcttgccg ccattgaagc 12540
cgagacctgt aaatatttgg cctctcggat gcccatgcta cacaacctgc gcatgacagg 12600
gtcaaatgta accatagtgt ataatagtac tttgaatcag gtgttagcaa tcttcccgac 12660
ctctgaatcc cggccaaagc ttcatgattt tcaacaatgg ttaataactg tacattcctc 12720
catattttcc tccgttgtgg cttcctgtac tctttttgtt gtgctgtggt tgcgaattcc 12780
aatgctacgt actgtttttg gtttccactg gttaggggca atttttcttt cgaactcaca 12840
gtgaattaca cggtgtgccc accttgcctc acccggcaag cagccgctga gatctacgaa 12900
cccggcaggt ctctttggtg caggataggg catgatcgat gtagcgagga cgatcatgac 12960
gaactagggt tcttggttcc gcctggcctc tccagcgaag gccacttgac cagtgtttac 13020
gcctggttgg cgttcctgtc cttcagctat acagcccagt tccatcccga gatatttggg 13080
atagggaatg tgagtaaaat ttatgttgac atcaagcacc aattcatctg cgccgaacac 13140
gacgggcaga acgccaccct gcctcgccat gacaacattt cagccgtgtt tcagacctac 13200
taccaacatc aggtcgatgg cggcaattgg tttcacctgg aatggctgcg cccctttctt 13260
tcctcttggt tggttttaaa tgtttcgtgg tttctcaggc gttcgcctgc aagccatgtt 13320
tcagttcgag tctttcagac atcaaaacca acaccaccgc agcaccaaat tttgttgtcc 13380
tccaggacat cagctgcctt aggcatggcg acccgtcctc tccggcgatt cgcaaaagct 13440
ctcagtgccg cacggcgata ggaacacccg tgtatatcac catcacagcc aatgtgacag 13500
atgagaatta tttacattct tctgatctcc tcatgctttc ttcttgcctt ttctatgctt 13560
ctgagatgag tgaaaagggg ttcaaggtgg tattcggcaa tgtgtcaggc atcgtggctg 13620
tgtgtgtcaa ctttaccagt tacgtccaac atgtcaagga gtttacccaa cgctccttgg 13680
tggtcgagca tgtgcgactg cttcatttca tgacacctga aaccatgagg tgggcaaccg 13740
ttttagcctg tctttttgcc attctgttgg caatttgaat gtttaagtat gttggggaaa 13800
tgcttgaccg cgggctgttg ctcgccgttg cttttttttgt ggtgtatcgt gccgtcttgc 13860
tttgttgcgc ccgtcaacgt cgacgggaac gacagctcaa agttacagct gatttacaac 13920
ttgacgctat gtgagctgaa tggcacagat tggctggctg gtagatttga ctgggcagtg 13980
gagtgttttg tcatttttcc cgtgttgact cacattgtct cctatggtgc cctcactact 14040
agccatttcc ttgacacagt cggtctggtc actgtgtctg ccgccgggtt ccttcatgaa 14100
cggtatgttt tgagtagcat ctacgcggtc tgtgccctgg ctgcgttgat ttgcttcgtc 14160
attaggcttg cgaagaactg catgtcctgg cgctactcgt gtaccagata taccaacttc 14220
cttttggaca ccaaggggag actctatcgt tggcgatcgc ccgtcatcat agagaaaaag 14280
ggtaaagttg aggttgaagg tcatttgatc gacctcaaaa gagttgtgct tgatggttcc 14340
gtggcaaccc ctataaccaa aatttcagcg gaacaatggg gtcgtcctta gatgacttct 14400
gccatgatag cacggctcca caaaaggtgc ttttggcgtt ttccattacc tatacaccag 14460
tgatgatata tgccctaaag gtaagtcgcg gccgactgct agggcttttg caccttttga 14520
tctttctgaa ctgtgctttc accttcgggt atatgacatt cacgcacttt cagagtacaa 14580
acaaggtcgc gctcactatg ggagcagtag ttgcactcct ttggggggtg tactcagcca 14640
tagaaacctg gaaattcatc acctccagat gccgtttgtg cttgctaggc cgcaagtaca 14700
ttctggcccc tgcccaccac gttgagagtg ccgcaggctt tcatccgatt gcggcaaatg 14760
ataaccacgc atttgtcgtc cggcgtcccg gttccactac ggtcaacggc acattggtcc 14820
ccgggttgaa aagcctcgtg ttgggtggca gaaaagctgt caaacaggga gtggtaaacc 14880
ttgttaaata tgccaagtaa caacggcagg cagcagaaaa aaagaaaggg ggatggccag 14940
ccagtcaatc agctgtgtca gatgctgggt aaaattattg cccagcaaaa tcagtccagg 15000
ggcaagggac cgggaaagaa aaataacaag aaaaacccgg agaagcccca ttttcctcta 15060
gcgactgaag atgatgtcag acatcacttt accccgagtg agcgacaatt gtgtctgtcg 15120
tcaatccaga ctgccttcaa tcagggcgct ggaacttgta ccctgtcaga ttcaggcagg 15180
ataagttaca ctgtggagtt tagtttgccg acgcatcaca ctgtgcgcct gatccgcgct 15240
acagcatcac cctcagcatg atgagctggc attcctgggt atcccagtgt ttgaattgga 15300
agaatgtgtg gtgaatggca ctgattgaca ttgtgcttct aagtcaccta ttcaattagg 15360
gcgaccgtgt gggagtagaa tttaattggc gagaaccacg cggccgaaat taaaaaaaaa 15420
aaaaaaaaaa aaaaaaaaaa aaaa 15444

<210> SEQ ID NO 12
<211> LENGTH: 15047
<212> TYPE: DNA
<213> ORGANISM: Artificial Sequence
<220> FEATURE:
<223> OTHER INFORMATION: Synthetic Construct

<400> SEQUENCE: 12
atgacgtata ggtgtttgct ttatgccgcg gcatttgtat tgtcaggagc tgtgaccact 60
ggcacagccc gaaacttgct gcacagaaac acccttctgt gacagcctcc ttcaggggag 120
tttaggggtt tctccctaac gccctgcttc cggagttgca ctgctttacg gtctctccat 180
ccttttaacc atgtctggga ttcttgatcg gtgcacgtgc acccccaatg ccagggtgtt 240
tgtggcagag ggccaagtct actgcacacg atgtctcagt gcacggtccc tccttcccct 300
aaatctccaa gtttctgagc ttggggtact tggtttattc tacaggcccg aagagccatt 360
acggtggacg ttgccacacg cattccccac tgtcgagtgt gctcctgctg gcgcttgttg 420
gctttctgca atttttccaa ttgcgcgaat gaccagtgga aacctgaatt tccagcaaag 480
gctggtacgt gtcgcagccg agctttacag agccggccag ctcaccccta caagcctgaa 540
aaccttacag gtctatgaaa ggggttgccg ttggtacccc attgttggac ctgttcctgg 600
agtggccgtt tacgccaact ccctacatgt gagtgacaaa cccttcccag gagcgactca 660
cgtgctgacc aacttaccac tcccgcagag accaaaatct gaagatttct gccccttcga 720
gtgcgccacg gccgccgtct atgacatcgg ccatgacgcc gtcatgtatg taaccgagga 780
aaaggtttcc tgggctcctc gtggcgggga taaagggaaa tttgagactg ttcctgaggg 840
gttgaagttg actgcggaac gactctacac ctccttcccg cctcaccatg cggtggacat 900 gtccctttc atcttcacag accttgagtg cggcgcttcc atgcgggtcg aacgccaata 960
tggttgcctc tctgctggca ctgtccctga aggcaactgc tggtggagtc tgtttggctc 1020
gctttcgtta gaagctcagt ataaagaaat ccgctacgcc gcccaatttg gctatcagac 1080
caaacatggc gttactggca agtacctgca gcggaggctg caaattaatg gtctccgagc 1140

```
agtggttgac ccgaatgggc ctcttgtcgt acagtatttc tccgttaagg agagctggat   1200
gcgccacgtg agactggcgg aagagccagg ctatcctggg tttgaggatc tcctcaggat   1260
aagagtcgag cccaacacgt tgcctttgtc caacaaggac gagaaaatct tccgtttcgg   1320
cggttacaag tggtacggtg ctgggcggag ggcaaggaga acacgtgcaa gagcagtcac   1380
cgcagttgct agtcatgctc cgcccgctcg tggggcccag caggccgaga agcacgaagt   1440
tgctagtgcc aacaagactg agctccttac gcactactcc ccacctgctg aagggaattg   1500
cggctggcac tgcatctccg ccatcatgaa ccggatggtg cattccaagt ttgaaaccgc   1560
cctttccgaa agagtgagat ccccggaaga ctgggcgact gatgaggatc ttgtgaatac   1620
tattcaaatc ctcaggctcc ctgcggcctt agacaggaac ggcgcctgta aaaacgccaa   1680
gtacatcctt aagctggaag gtgagcactg gactgtttca gtgacccccg gaatgccccc   1740
ctcttcactt cctcttgaat gcgttcaggg ttgttgcgag cataagggca attttgactc   1800
tcaaaacgcg gtcggtttct ttgggttcga ccctgccagc cttgaccgac tcgctggggt   1860
aatgcatctg cccagcagcg ccatccctgc cgccctggcc gagttgtctg gtgaacttga   1920
ttgttcaact cccccggcca ccactgtgtg gactaccttg cagttttatg ctcgtcttgg   1980
tggggggag catcctgatc aagagtgctt gagaaaaatc atcagcctct gtgaggtgct   2040
cgggagttgc tgctgttctc agagtagggt caaccgggtc accccggaag aggtcgcagc   2100
aaagattgac ctgtatcttc gtgacgcagc gagtcttgaa gagtgcttgg ctaggcttga   2160
gaaagctcgc ccgccaagca tgctggacac ctcctttgac tgggatgttg tactccctgg   2220
tgttgggacg gctgctcggg cagcagaact accccccacc gatgagtgtc gcgctctagt   2280
cactgctgtg gcccaaaggc cttcgccgaa agttcagcct cgaaaggcgg ggtctgttaa   2340
gagtctacca gagatcaggc ctgtccctgc cccacgcagg aaggttaagt ctagttgtgg   2400
tgatctggcc ccgttgggcg gcaatttccc tgatagctgg gaagatttgg ctggtggctc   2460
ccttaatctc cagatcttac ctgagccggt ggcacaatcc tttgaacctg tgcctgtccc   2520
tgcaccgcgc aagactgcgc ctcgattagt gtcgtcatca ttggcgtcga cccccgtacc   2580
tacaccacga tgtgggtttc ggcagtttga gggaatgaat ttgacagctg tgaccctagc   2640
atgccaggat gagtccctca atttgtctgc atcctcgcag actgaatatg aggcttctcc   2700
tttggcattg cagcagggtg aggatgtcct tgcggtgggg ggacgagaag ccgaagaagt   2760
cctgagcgga atctcgggaa tgtcaggtgg cattagatta gcgcccgcat catcaagtag   2820
ctccttgtca agcgtggaga tcacacgccc gaagtactca gctcaagcca tcattgactc   2880
aggtggaccc tgttgcgggc accttcaaga ggtgaaagag aaatacctta atgtcatgcg   2940
tgaggcatgt gatgcgacta agctcgatga ccctgccacg caagaatggc tctctcgcat   3000
gtgggagagg gtagacatgc taacctggcg caacacgtcc atctttcaag cgccttttac   3060
cttagctgac aagtttaagt ccctcccgaa gatgatactc gaaacgccgc caccctaccc   3120
ttgcgggttt gtgatgatgc cccgcacgcc cgcaccttct gtgggtgcgg aaagcgacat   3180
caccgttggt tcagttgcta ctgaagatgt cccgcgtata ctcggggagg tgggagatgt   3240
tggcaagatg accggccagg aacccttaga atccttcgca gatgaactgg cagatgacca   3300
acctgctagg gagtcccgaa cacaagctcc tcctgcaagc acaggtagcg ctggtttagt   3360
tttggattct ggagggtcgc tggggctcac tgacctgccg ctcccaaaca atatagacgc   3420
gggcgggaaa ggaccgtttc acgcggtcaa gaaaaaagct gtagggtgct ttgaccaact   3480
gagccgccgg gtttttgaca tcgtctccca tctccctgtt tttttttcac gccttttcgc   3540
```

gcccggtggt ttttactctt cgggtgactg gagttttgca gcttttactt tattgtgtct 3600
ctttttatgt tacagttatc cggcctttgg ttttgctccc ctcgtgggtg tattttctgg 3660
gtcttctcgg cgcgtgcgca tgggggtttt tggctgctgg ctggcttttg ctgttggttt 3720
gttcaagcct gcacccgacc cagtcggtgc tgcttgtgag tttgactcgc cagagtgtag 3780
agacatcctt cattcttttg agctcctgca accttgggac cctgttcgca gccttgtggt 3840
gggccccgtc ggtctcggcc ttgccatttt tggcaggtta ctgggcgggg cacgctacgt 3900
ctggctgctt ttgcttaggc ttggcatcgt ttcagactgt atcctggctg gagcctatgt 3960
gctttcgcaa ggcaggtgta aaaagtgttg ggatcttgt ataagaacag cccccagtga 4020
agttgccttc aatgtgtttc cctttacacg cgcaactaga tcgtcacttg tcaacctgtg 4080
cgaccggttc tgtgcaccca agggcatgga ccccatcttc cttgccacag gatggcgcgg 4140
atgctggtcc ggccagagcc ccattgagca accctctgaa aaacccatag cgttcgccca 4200
gttggacgaa aagaaaatca cggctaggac tgtggttgcc cagccttatg accccaacca 4260
agctgtgaag tgcctgcgag tcctccaggc gggtggagcg atggtagccg aggcagttcc 4320
aaaagtagtc aaagtttctg ctgtcccgtt tcgagcccct ttttttcctg ccggagtgaa 4380
agttgaccct gaatgcaggg tcgtggttga ccctgacacc tttacaaccg ctctccggac 4440
cggctactcc accacaaacc tcattcttgg tgttggggac tttgcccagc tgaatgggtt 4500
gaagatcaga caaatttcca agtccccagg agggggccct cacctcatgg cggctttaca 4560
tgttgcttgc tcgatgactt tgcacatgct tgttgggatt tatgtcacca tggtgggttc 4620
ttgtggctct ggcactaacg atccgtggtg cactaacccg tttgccgtcc ctgtctatgg 4680
gcctggctct ctctgcacgt ccaggttgtg catttcccag cgtggcctga ccctgccctt 4740
aacagcgctt gtggcagggt ttggcgttca ggaaatcgct ttggttgttt taatctttgt 4800
ctccatcggg ggtatggccc acaggttgag ttgcaaggct gacgtgctgt gtatcctgct 4860
tgctattgtc agctatgttt ggccacccct tacctggttg ctttgtgtgt ttccttgctg 4920
gttgcgctgg ttttctttac atccccttac tattctatgg ttagtgtttt tcttgatttc 4980
tgtaaatacg ccctcgggaa tcttggcctt ggtcctgtta atctctcttt ggctccttgg 5040
tcgctatacc aatgttgccg gccttgtcac cccttatgac attcaccatt acaccaacgg 5100
ccctcgcggc gttgccgcct tggccactgc cccggatggg acctacctgg ctgctgtccg 5160
ccgtgctgcg ttgactggcc gtaccatgct gttcaccccg tcccaacttg gctcgctcct 5220
tgagggcgct tttagaaccc aaaagccttc actgaacact gtcaatgtag ttgggtcctc 5280
catgggctcc ggcggggtgt tcaccattga tgggaagatc aaatgtgtga ccgctgctca 5340
tgtcctcacg ggtaactctg ccagggtttc cggggttggc ttcaatcaaa tgttggactt 5400
tgatgttaaa ggggattttg ccatagccga ttgtccgaat tggcaaggag tcgcccccaa 5460
gtcccggttc tgcaaggatg attggactgg ccgtgcttat tggctcacgt cctccggcgt 5520
cgaacccggc gtcattgggc aaggattcgc cttttgtttc accgcgtgcg gcgattccgg 5580
gtccccagtg atcaccgagg ccggggagct tgtcggtgtc cacacgggat caaacaaaca 5640
aggaggaggc attgttacgc gcccttcagg ccggttttgt aatgtgacac ccaccaaatt 5700
aagtgaattg agtgaattct tcgctggacc tagggtcccg cttggtgacg tgaaggttgg 5760
caatcacata atcaaagata taaatgaggt gccctcagat ctctgcgcct tactcgctgc 5820
caaacccgaa ttggaaggag gcctctccac cgttcaactt ctgtgcgtgt tttttctcct 5880

-continued

```
atggagaatg atgggacatg cctggacacc cttggttgcc gttggttttt tcatcttgaa   5940
tgaagttctc ccagcagtcc tggtccggag tgtcttctcc tttggaatgt tcgcactgtc   6000
ttggttcacg ccgtggtctg cacaaattct aatgatcagg ctcttgacag cagccctaaa   6060
cagaaacaga tcgtcacttg ccttttacag cctgggcgca ctaaccggtt ttgttgcaga   6120
tcttgcaacc aatcaggggt atttattgca cgcggtcatg aatgtgagca cctatgcatt   6180
cctgcctcgt gcaatggccg tgacctcacc agtcccaata gttgcgtgtg gcgttgtgca   6240
cttgcttgcc atcattctgt acttgttcaa gtaccgtagc ctgcatgccg tcctggtcgg   6300
cgatggtgcg ttttccgcgg ctttcttctt gcgatacttt gcggagggaa agttgaggga   6360
aggggtgtcg cagtcttgcg gcatgaatca tgagtcacta accggtgccc tcgccatgaa   6420
actcagcgac gaagacttgg acttcctcac aaaattgact gattttaagt gctttgtttc   6480
tgcatccaac atgaggaatg cggcgggtca atttatagag gccgcctacg ccaaagcact   6540
gagggtggaa cttgcccagt tggttcaagt cgataaagtt cgaggtgtcc tggccaaact   6600
tgaagctttc gctgacaccg tggcgcctca actttcaccc ggtgacattg ttgtcgccct   6660
tggacacaca cctgtcggca gcatttttga cctgaaggtc ggcaatgtta agcacactct   6720
ccagtccatt gagaccagaa cccttgccgg gtctaaaatg actgtggcgc gcgtcgtaga   6780
cccaaccccc acacccccgc ccgcacctgt gcccatttcc ctcccaccaa aggttttgga   6840
gaacggtccc aacgcctggg gggatgagaa cggtttgaac aaaaaaaagc ggcgcaagat   6900
ggaggccgtt ggcatttacg ttatgggcgg gaaaaagtat caaaaatttt gggataagaa   6960
ttctggtgat gtgttctatg aagaagtcca cgacaacaca gacgcgtggg aatgcctcag   7020
agttgacaac cctgccgact tggatcctga gaggggaacc ttgtgtggac acaccaccat   7080
agacaacagg ccttaccatg tttatgcttc tccgtctggt aggaagtttc tagtccctgt   7140
caacccggag agcggaaaag ctcagtggga agctgctaag ctttctttag atcaggccct   7200
cagtatgatg aatgtcgacg gcgaactgac cgccaaagaa gtggaaaaat tgaagagaat   7260
aattgacaaa ctccagggcc tgactaagga gcagtgttta aactgctagc cgccagcggc   7320
ttgacccgct gtggtcgcgg cggcttggtt gttactgaga cagcggtaaa gatagtcagg   7380
ttccacaacc ggacctttac cctagggcct gtgaatttga aagtagctag cgaagttgag   7440
ttgaaggacg cggtcgagca cggccaacac ccggtcgcga taccagccga tggtggcgtc   7500
gtgctcctgc gttccgctgt tccttcgctt atagacgtcc tgatctccgg tgctgacgca   7560
tcccccaggt tgctcgcccg tcacggaccg ggaaatactg ggtcaatggg cgcgctttgg   7620
gattttgagt ctgaagctac caaagaggaa gtagcactta gtgcgcaaat aatacaggcc   7680
tgtgacatta gacgcggcga tgcacctgag attggccttc cttacaagtt gtaccctgtt   7740
aggggcaacc ctgaacgggc aagaggggtt ctaatgaaca caagatttgg agacatacct   7800
tacaagaccc ccagcgacac cgggagcccg gtgcacgcgg ccgcctgcct tacgcccaac   7860
gccactccag taactgatgg gcgctccatc ctggccacga ccatgccctc cgggtttgaa   7920
ctatatgtgc cgaccattcc agcgtctgtc cttgattacc ttgactccag accagactgt   7980
cctaaacagt tgactgagca cgggtgtgaa gatgccgcgt tgaaggacct ttctaaatat   8040
gacctgtcca cccaaggctt tgtgttacct ggagttctac gcctcgtgcg aaaatatctg   8100
tttgctcatg taggtaagtg cccgcctgtc caccggccct ctacctatcc tgccaagaac   8160
tccatggccg gaataaatgg gaacaggttc ccaaccaagg atattcaaag catccctgag   8220
atcgacgttt tgtgtgcaca agctgtgcga gaaaactggc aaactgttac accctgcact   8280
```

```
cttaagaagc agtattgcgg taaaaagaag accaggacca tacttggcac caacaacttc   8340
gttgcgctgg cccaccgggc ggcgctgagt ggtgtcaccc agggtttcat gaagaaggcg   8400
tttaactcac ccatcgccct tgggaaaaat aaatttaagg agctacagac tccagtcttg   8460
ggtaggtgtc ttgaggctga tctcgcttcc tgcgatcgat ccacgcctgc aatcgttcgc   8520
tggtttgccg ccaaccttct ttatgaactt gcctgtgctg aggagcattt accgtcgtac   8580
gtgctgaact gttgtcacga cctattggtc acgcagtccg gcgcagtgac taagagaggt   8640
ggcctgtcgt ccggtgaccc aatcacctct gtgtccaaca ccatttatag cttggtgatc   8700
tatgcacagc atatggtgct tagttacttc aaaagtggtc acccccatgg ccttctgttt   8760
ttacaagacc agctaaagtt tgaagacatg ctcaaagttc aacccctaat cgtctattcg   8820
gacgacctcg tgttgtatgc cgagtctccc accatgccaa actatcactg gtgggttgaa   8880
cacctgaatt tgatgttggg atttcagacg gacccaaaga agactgcaat aacagactca   8940
ccttcattcc taggttgtag aataataaat ggccgccagt tagtacccaa ccgtgacaga   9000
attctcgcgg cccttgccta tcacatgaag gcgagtaatg tttctgagta ctacgcctcc   9060
gcagccgcaa tactcatgga cagttgtgct tgtctagagt atgatcctga gtggtttgaa   9120
gaacttgtgg ttggaatggc gcagtgcgcc cgtaaggacg gctatagttt ccccggcccg   9180
ccgttcttct tgtccatgtg ggaaaagctc aggtcaaatt atgaggggaa gaagttgaga   9240
gtgtgtggtt attgcggagc ttcagccccg tatgctactg cctgtggcct tgacgtttgt   9300
gtttaccaca cccactttca ccagcattgt ccagtcataa tatggtgtgg ccacccggcg   9360
ggttctgggt cctgcgatga gtgcaaatcc cctacaggga agggtacaag ccctctggat   9420
gaggtcttaa gacaagtccc ttataagcct ccacggacta ttcttatgca tgtggagcag   9480
ggcctcaccc cccttgaccc aggcagatac cagacccgcc gtgggttggt tgctgtcagg   9540
cgcgggataa ggggaaatga agttgacctg ccagatggtg attatgccag tactgcccta   9600
ctccccacct gcaaagacat agacatggtt gctgtggcct ccaatgtgtt gcgcagtagg   9660
ttcatcatcg gcccacctgg cgcagggaaa acacactggc ttcttcaaca ggttcaggat   9720
agtgatgtca tttacacgcc aacccatcag accatgcttg acatgatcaa ggctttgggg   9780
acgtgccggt tcaatgtccc ggcaggcaca acgctgcaat tccctgcccc ctcccgtacc   9840
ggcccgtggg ttcgcatcct tgccggcggt tggtgtccag gtaagaattc cttcctggat   9900
gaagcagcgt attgcaatca ccttgacgtc ttgaggcttc tcagcaaaac taccctcacc   9960
tgtctggggg atttcaaaca actccacccg gtgggttttg attctcattg ctatgttttt  10020
gatatcatgc ctcagactca actgaagacc atctggaggt ttggacagaa tatctgtgac  10080
gccattcagc cagattacag ggacaaactc gtgtccatgg tcaacacaac ccgtgtaacc  10140
tatgtggaaa gacctgtcaa gtatgggcaa gtcctcaccc cctaccacag agaccgagag  10200
gatggtgcta tcactattga ctccagtcaa ggcgccacat ttgatgtggt cacattgcat  10260
ttgcccacta aagattcact caacaggcaa agagcccttg ttgctatcac cagggcaagg  10320
catgcaatct ttgtgtatga cccacacagg caactgcaga gcatgtttcg tcttcctgca  10380
aaaggcacac ctgtcaacct tgccgtgcac cgtgacgagc agctcatcgt attagataga  10440
aataacaaag agtgcacggt tgttcaggct ttaggcaatg gggacaaatt cagggccagt  10500
gacaagcgcg ttgtagattc tcttcgcgcc atttgtgcag atcttgaagg gtcgagctcc  10560
ccgctcccca aggtcgcaca caacttggga ttttatttct cacctgattt gacacagttt  10620
```

gctaaactcc cggcggaact tgcaccccac tggcccgtgg tgacaactca gaacaacgaa 10680
aattggccag accggctggt tgctagcctc cgccctatcc acaaatatag ccgcgcgtgc 10740
atcggagccg gctatatggt gggcccctca gtgtttctag gcactcctgg ggttgtgtca 10800
tactatctca cacaatttgt caaaggggag gctcaggtgc ttccggagac ggtcttcagc 10860
accggccgaa ttgaggtaga ttgtcgagag tatcttgatg atcgggaacg agaagttgct 10920
gagtccctcc cacatgcctt tattggcgac gtcaaaggca ctaccgttgg gggatgtcac 10980
catgtcactt ctaaatatct cccacgcttc cttcccaagg aatcagttgc ggtggttggg 11040
gtttcaagcc ccgggaaagc cgcaaaagca gtttgcacat taacagatgt gtacctccca 11100
gatcttgagg cttacctcca tccagagacc cagtctaagt gctggaaagt gatgttggac 11160
ttcaaggaag ttcgactgat ggtctggaga gataagacgg cctactttca acttgaaggc 11220
cgccatttca cctggtacca gcttgcaagt tatgcctcgt acatccgagt tcccgttaac 11280
tctacggtgt acctggaccc ctgtatgggc cctgcccttt gcaacagaag agtcgttggg 11340
tctgcacatt ggggagctga ccttgcagtt accccttatg attatggtgc caaaatcatt 11400
ctgtctagtg cgcaccatgg tgaaatgcct cctgggtaca gaattctagc gtgcgcggag 11460
ttctcgcttg atgacccagt gaggtacaaa cacacttggg ggtttgaatc ggatacagcg 11520
tatctgtacg agttcaccgg aaacggtgag gactgggagg attacaatga tgcgtttcgt 11580
gcacgccaga aagggaaaat ttataaggcc actgccacca gcatgagatt tcattttccc 11640
ccgggtcctg ccattgaacc aacattgggc ctgaactgaa atgaaatggg ggctgtgcag 11700
agccttttcg acaaaatttg ccaacttttt gtggatgctt tcacggaatt tttggtgtcc 11760
attgttgata tcatcatatt tttggccatt ttgtttggct tcaccatcgc aggctggctg 11820
gttgtcttct gtatccgact ggtttgctcc acggtactcc gtgcgcgctc taccattcac 11880
cctgagcaat tacagaagat cctatgaggc cttcctttcc cagtgccaag tggacattcc 11940
cgcctgggga actaagcatc ccttgggggt gctttggcac cacaaggtgt caactctgat 12000
tgatgaaatg gtgtcgcgtc gaatgtaccg catcatggaa aaagcaggac aggctgcctg 12060
gaaacaggtt gtgagcgaag ctacattgtc tcgcataagt ggcttggatg tggtggctca 12120
ttttcagcat cttgctgcca ttgaagccga gacttgcaaa tatttggcct ctcggctgcc 12180
catgctacac aacctagtca tgtcagggtc gaatgtaacc atagtgtata atagcacttt 12240
gggtcaagtg tttgccattt tcccaacccc tggttcccgg ccaaaacttt ctgattttca 12300
acaatggctc atagctgtgc attcttccat attttcttct gttgcggctt cttgtactct 12360
ttttgttgtg ctgtggctgc gaattccaat actacgtact gtttttggtt tccgctggtt 12420
aggggcaact tttctttcga actcacagtg aattacacgg tgtgcccacc ctgcctcacc 12480
cggcaagcag ccgctgagat ctacgaacac agcgggtctc tttggtgcag gatagggcat 12540
gaccgatgta gccagagtga tcatgacgaa ctagggttct tggttccacc tggcctttcc 12600
agcgagggcc acttgaccag tgtttacgcc tggctggcgt tcttgtcttt cagctacaca 12660
gcccagttcc accccgagat atttggaata gggaatgtga gtagagttta tgttgacgtc 12720
actcaccaac tcatctgcgc cgaacacgac gggcagaaca ccaccctgcg tcgccatgac 12780
aatatctcag ccgtgtttca gacctattac caacatcagg tcgatggcgg caattggttt 12840
cacctagaat ggctgcgtcc cttcttttcc tcttggctgg ttttgaatgt ctcgtggttt 12900
ctcaggcgtt cgcctgcaaa ccgtgtttca gttcgagtct ttcagacatc aaaaccaaca 12960
ccaccgcagc tgcaggcttt gctgtcctcc aagacatcag ctgtcttagg catggctact 13020
cgtccattga ggcgattcgc aaaagccgtc aatgccgcac ggcgatagga acgcccgtgt 13080
acatcactgt cacggccaat gtaacagatg agaattactt gcattcctct gatctcctca 13140
tgctttcctc ttgcctcttc tatgcttctg agatgagtga aaagggattc aatgtggtct 13200
tcggcaacgt gtcaggcatt gtggctgtgt gtgtcaactt taccagctat gtccaacatg 13260
ttaaggagtt tactcagcgc tctttggtgg tcgaccacgt gcgactgctt catttcatga 13320
cacctgcgac catgaggtgg gcaacagttt tagcctgtct tttcgccatc ttgttggcga 13380
tttgaatgtt taagtatgtt ggggaaatgc ttgaccgcgg gctactgctc gcaattgctt 13440
tttttctggt gtatcgtgcc gttctgtttt gctgcgctcg tcaacgccgc cagcaacagc 13500
agctcccatt tacagttgat ttataacctg acgatatgcg agctgaatgg cacagattgg 13560
ttgaatcaaa agtttgattg ggcagtggag acttttgtca tttttcctgt gttgacccac 13620
attgtctcct acggtgccct taccaccagc catttccttg acacggccgg cctaatcact 13680
gtgtctaccg ccggatatta ccatgggcgg tatgtgttga gtagcatcta cgccgtcttt 13740
gccctggctg cgttgatttg ttttgtcatt aggttgacaa aaaactgtat gtcctggcgc 13800
tactcatgta ccagatatac caactttctt ctggacacca aaggcaatct ctatcgttgg 13860
cggtcacccg tcgttataga gagaaggggt aaagttgagg ttggagacca cctaatcgac 13920
ctcaaaagag ttgtgcttga tggttccgcg gcaaccccta taaccaagat ttcagcggaa 13980
caatggggtc gtccctagac gacttctgca atgacagcac agctgcacaa aaggtgcttt 14040
tggcgttttc catcacctat acgccaataa tgatatatgc cctgaaggta agtcgcggcc 14100
gactgttagg gcttttgcat cttttaattt tcttgaattg tgctttcacc ttcgggtaca 14160
tgacatttgt tcattttcag agtacaaaca aggtcgcgct cactatggga gcagttgttg 14220
cactcctttg gggggtgtac tcagccatag aaacctggaa attcatcact tccagatgcc 14280
gtttgtgctt gctaggccgc aggtacattc tggcccctgc ccaccacgtt gaaagtgccg 14340
cgggctttca tccgattgcg gcaagtgata accacgcatt tgtcgtccgg cgtcccggct 14400
ccactactgt taacggcaca ttggtgcccg ggttgaaaag cctcgtgttg ggtggcagaa 14460
aagctgttaa gcggggagtg gtaaacctcg ttaaatatgc caaataacaa cggcaggcag 14520
caaaaaaata agaaggggag tggccagcca gtcaatcagc tgtgccaaat gctgggcaag 14580
atcatcgccc agcaaaatca gtccagaggc aagggaccgg gtaagaaaaa taagaagaga 14640
aacccggaga agccccattt tcctcttgcg accgaagatg acgtcaggca tcacttcacc 14700
cccagtgaac ggcaattgtg tctgtcgtcg atccagactg ccttcaacca gggcgctgga 14760
acttgcaccc tgtcagattc agggaggata agttacactg tggagtttag tttgccgacg 14820
caccacactg tgcgccttat tcgcgccaca gcatcacctc catcgtgatg ggcttacatt 14880
cttggagctc ctcagtttca caattggaag aatgtgtggt gaatggcact gattggcact 14940
gtgcctctaa gtcacctatt caattagggc gaccgtgtgg gggtttagtt taattggcga 15000
gaaccacgcg gccgaaatta aaaaaaaaaa aaaaaaaaaa aaaaaaa 15047

<210> SEQ ID NO 13
<211> LENGTH: 15047
<212> TYPE: DNA
<213> ORGANISM: Artificial Sequence
<220> FEATURE:
<223> OTHER INFORMATION: Synthetic Construct

<400> SEQUENCE: 13

-continued

```
atgacgtata ggtgtttgct ttatgccgcg gcatttgtat tgtcaggagc tgtgaccact     60
ggcacagccc gaaacttgct gcacagaaac acccttctgt gacagcctcc ttcaggggag    120
tttaggggtt tctccctaac gccctgcttc cggagttgca ctgctttacg gtctctccat    180
ccttttaacc atgtctggga ttcttgatcg gtgcacgtgc acccccaatg ccagggtgtt    240
tgtggcagag ggccaagtct actgcacacg atgtctcagt gcacggtccc tccttcccct    300
aaatctccaa gtttctgagc ttggggtact tggtttattc tacaggcccg aagagccatt    360
acggtggacg ttgccacacg cattccccac tgtcgagtgt gctcctgctg gcgcttgttg    420
gctttctgca atttttccaa ttgcgcgaat gaccagtgga aacctgaatt tccagcaaag    480
gctggtacgt gtcgcagccg agctttacag agccggccag ctcaccccta caagcctgaa    540
aaccttacag gtctatgaaa ggggttgccg ttggtacccc attgttggac ctgttcctgg    600
agtggccgtt tacgccaact ccctacatgt gagtgacaaa cccttcccag gagcgactca    660
cgtgctgacc aacttaccac tcccgcagag accaaaatct gaagatttct gccccttcga    720
gtgcgccacg gccgccgtct atgacatcgg ccatgacgcc gtcatgtatg taaccgagga    780
aaaggtttcc tgggctcctc gtggcgggga taaagggaaa tttgagactg ttcctgaggg    840
gttgaagttg actgcggaac gactctacac ctccttcccg cctcaccatg cggtggacat    900
gtccctttttc atcttcacag accttgagtg cggcgcttcc atgcgggtcg aacgccaata    960
tggttgcctc tctgctggca ctgtccctga aggcaactgc tggtggagtc tgtttggctc   1020
gctttcgtta gaagctcagt ataaagaaat ccgctacgcc gcccaatttg gctatcagac   1080
caaacatggc gttactggca agtacctgca gcggaggctg caaattaatg gtctccgagc   1140
agtggttgac ccgaatgggc ctcttgtcgt acagtatttc tccgttaagg agagctggat   1200
gcgccacgtg agactggcgg aagagccagg ctatcctggg tttgaggatc tcctcaggat   1260
aagagtcgag cccaacacgt tgcctttgtc caacaaggac gagaaaatct tccgtttcgg   1320
cggttacaag tggtacggtg ctgggcggag ggcaaggaga acacgtgcaa gagcagtcac   1380
cgcagttgct agtcatgctc cgcccgctcg tggggcccag caggccgaga agcacgaagt   1440
tgctagtgcc aacaagactg agctccttac gcactactcc ccacctgctg aagggaattg   1500
cggctggcac tgcatctccg ccatcatgaa ccggatggtg cattccaagt ttgaaaccgc   1560
cctttccgaa agagtgagat ccccggaaga ctgggcgact gatgaggatc ttgtgaatac   1620
tattcaaatc ctcaggctcc ctgcggcctt agacaggaac ggcgcctgta aaaacgccaa   1680
gtacatcctt aagctggaag gtgagcactg gactgtttca gtgacccccg gaatgccccc   1740
ctcttcactt cctcttgaat gcgttcaggg ttgttgcgag cataagggca attttgactc   1800
tcaaaacgcg gtcggtttct ttgggttcga ccctgccagc cttgaccgac tcgctggggt   1860
aatgcatctg cccagcagcg ccatccctgc cgccctggcc gagttgtctg gtgaacttga   1920
ttgttcaact cccccggcca ccactgtgtg gactaccttg cagttttatg ctcgtcttgg   1980
tggggggggag catcctgatc aagagtgctt gagaaaaatc atcagcctct gtgaggtgct   2040
cgggagttgc tgctgttctc agagtagggt caaccgggtc accccggaag aggtcgcagc   2100
aaagattgac ctgtatcttc gtgacgcagc gagtcttgaa gagtgcttgg ctaggcttga   2160
gaaagctcgc ccgccaagca tgctggacac ctcctttgac tgggatgttg tactccctgg   2220
tgttgggacg gctgctcggg cagcagaact accccccacc gatgagtgtc gcgctctagt   2280
cactgctgtg gcccaaaggc cttcgccgaa agttcagcct cgaaaggcgg ggtctgttaa   2340
gagtctacca gagatcaggc ctgtccctgc cccacgcagg aaggttaagt ctagttgtgg   2400
```

-continued

```
tgatctggcc ccgttgggcg gcaatttccc tgatagctgg gaagatttgg ctggtggctc   2460
ccttaatctc cagatcttac ctgagccggt ggcacaatcc tttgaacctg tgcctgtccc   2520
tgcaccgcgc aagactgcgc ctcgattagt gtcgtcatca ttggcgtcga cccccgtacc   2580
tacaccacga tgtgggtttc ggcagtttga gggaatgaat ttgacagctg tgaccctagc   2640
atgccaggat gagtccctca atttgtctgc atcctcgcag actgaatatg aggcttctcc   2700
tttggcattg cagcagggtg aggatgtcct tgcggtgggg ggacgagaag ccgaagaagt   2760
cctgagcgga atctcgggaa tgtcaggtgg cattagatta gcgcccgcat catcaagtag   2820
ctccttgtca agcgtggaga tcacacgccc gaagtactca gctcaagcca tcattgactc   2880
aggtggaccc tgttgcgggc accttcaaga ggtgaaagag aaataccttta atgtcatgcg   2940
tgaggcatgt gatgcgacta agctcgatga ccctgccacg caagaatggc tctctcgcat   3000
gtgggagagg gtagacatgc taacctggcg caacacgtcc atctttcaag cgccttttac   3060
cttagctgac aagtttaagt ccctcccgaa gatgatactc gaaacgccgc caccctaccc   3120
ttgcgggttt gtgatgatgc cccgcacgcc cgcaccttct gtgggtgcgg aaagcgacat   3180
caccgttggt tcagttgcta ctgaagatgt cccgcgtata ctcggggagg tgggagatgt   3240
tggcaagatg accggccagg aacccttaga atccttcgca gatgaactgg cagatgacca   3300
acctgctagg gagtcccgaa cacaagctcc tcctgcaagc acaggtagcg ctggtttagt   3360
tttggattct ggagggtcgc tggggctcac tgacctgccg ctcccaaaca atatagacgc   3420
gggcgggaaa ggaccgtttc acgcggtcaa gaaaaaagct gtagggtgct ttgaccaact   3480
gagccgccgg gtttttgaca tcgtctccca tctccctgtt ttttttcac gccttttcgc   3540
gcccggtggt ttttactctt cgggtgactg gagttttgca gcttttactt tattgtgtct   3600
ctttttatgt tacagttatc cggcctttgg ttttgctccc ctcgtgggtg tattttctgg   3660
gtcttctcgg cgcgtgcgca tgggggtttt tggctgctgg ctggcttttg ctgttggttt   3720
gttcaagcct gcacccgacc cagtcggtgc tgcttgtgag tttgactcgc cagagtgtag   3780
agacatcctt cattcttttg agctcctgca accttgggac cctgttcgca gccttgtggt   3840
gggccccgtc ggtctcggcc ttgccatttt tggcaggtta ctgggcgggg cacgctacgt   3900
ctggctgctt ttgcttaggc ttggcatcgt ttcagactgt atcctggctg gagcctatgt   3960
gctttcgcaa ggcaggtgta aaaagtgttg ggatcttgt ataagaacag cccccagtga   4020
agttgccttc aatgtgtttc cctttacacg cgcaactaga tcgtcacttg tcaacctgtg   4080
cgaccggttc tgtgcaccca agggcatgga ccccatcttc cttgccacag gatggcgcgg   4140
atgctggtcc ggccagagcc ccattgagca accctctgaa aaacccatag cgttcgccca   4200
gttggacgaa aagaaaatca cggctaggac tgtggttgcc cagccttatg accccaacca   4260
agctgtgaag tgcctgcgag tcctccaggc gggtggagcg atggtagccg aggcagttcc   4320
aaaagtagtc aaagtttctg ctgtcccgtt tcgagcccct ttttttcctg ccggagtgaa   4380
agttgaccct gaatgcaggg tcgtggttga ccctgacacc tttacaaccg ctctccggac   4440
cggctactcc accacaaacc tcattcttgg tgttggggac tttgcccagc tgaatgggtt   4500
gaagatcaga caaatttcca agtccccagg agggggccct cacctcatgg cggctttaca   4560
tgttgcttgc tcgatgactt tgcacatgct tgttgggatt tatgtcacca tggtgggttc   4620
ttgtggctct ggcactaacg atccgtggtg cactaacccg tttgccgtcc ctgtctatgg   4680
gcctggctct ctctgcacgt ccaggttgtg catttcccag cgtggcctga ccctgccctt   4740
```

-continued

```
aacagcgctt gtggcagggt ttggcgttca ggaaatcgct ttggttgttt taatctttgt   4800
ctccatcggg ggtatggccc acaggttgag ttgcaaggct gacgtgctgt gtatcctgct   4860
tgctattgtc agctatgttt ggccacccct tacctggttg ctttgtgtgt ttccttgctg   4920
gttgcgctgg ttttctttac atccccttac tattctatgg ttagtgtttt tcttgatttc   4980
tgtaaatacg ccctcgggaa tcttggcctt ggtcctgtta atctctcttt ggctccttgg   5040
tcgctatacc aatgttgccg gccttgtcac cccttatgac attcaccatt acaccaacgg   5100
ccctcgcggc gttgccgcct tggccactgc cccggatggg acctacctgg ctgctgtccg   5160
ccgtgctgcg ttgactggcc gtaccatgct gttcaccccg tcccaacttg gctcgctcct   5220
tgagggcgct tttagaaccc aaaagccttc actgaacact gtcaatgtag ttgggtcctc   5280
catgggctcc ggcggggtgt tcaccattga tgggaagatc aaatgtgtga ccgctgctca   5340
tgtcctcacg ggtaactctg ccagggtttc cggggttggc ttcaatcaaa tgttggactt   5400
tgatgttaaa ggggattttg ccatagccga ttgtccgaat tggcaaggag tcgcccccaa   5460
gtcccggttc tgcaaggatg attggactgg ccgtgcttat tggctcacgt cctccggcgt   5520
cgaacccggc gtcattgggc aaggattcgc cttttgtttc accgcgtgcg gcgattccgg   5580
gtccccagtg atcaccgagg ccggggagct tgtcggtgtc cacacgggat caaacaaaca   5640
aggaggaggc attgttacgc gcccttcagg ccggttttgt aatgtgacac ccaccaaatt   5700
aagtgaattg agtgaattct tcgctggacc tagggtcccg cttggtgacg tgaaggttgg   5760
caatcacata atcaaagata taaatgaggt gccctcagat ctctgcgcct tactcgctgc   5820
caaacccgaa ttggaaggag gcctctccac cgttcaactt ctgtgcgtgt tttttctcct   5880
atggagaatg atgggacatg cctggacacc cttggttgcc gttggttttt tcatcttgaa   5940
tgaagttctc ccagcagtcc tggtccggag tgtcttctcc tttggaatgt tcgcactgtc   6000
ttggttcacg ccgtggtctg cacaaattct aatgatcagg ctcttgacag cagccctaaa   6060
cagaaacaga tcgtcacttg ccttttacag cctgggcgca ctaaccggtt ttgttgcaga   6120
tcttgcaacc aatcaggggt atttattgca cgcggtcatg aatgtgagca cctatgcatt   6180
cctgcctcgt gcaatggccg tgacctcacc agtcccaata gttgcgtgtg gcgttgtgca   6240
cttgcttgcc atcattctgt acttgttcaa gtaccgtagc ctgcatgccg tcctggtcgg   6300
cgatggtgcg ttttccgcgg ctttcttctt gcgatacttt gcggagggaa agttgaggga   6360
aggggtgtcg cagtcttgcg gcatgaatca tgagtcacta accggtgccc tcgccatgaa   6420
actcagcgac gaagacttgg acttcctcac aaaattgact gattttaagt gctttgtttc   6480
tgcatccaac atgaggaatg cggcgggtca atttatagag gccgcctacg ccaaagcact   6540
gagggtggaa cttgcccagt tggttcaagt cgataaagtt cgaggtgtcc tggccaaact   6600
tgaagctttc gctgacaccg tggcgcctca actttcaccc ggtgacattg ttgtcgccct   6660
tggacacaca cctgtcggca gcatttttga cctgaaggtc ggcaatgtta agcacactct   6720
ccagtccatt gagaccagaa cccttgccgg gtctaaaatg actgtggcgc gcgtcgtaga   6780
cccaaccccc acacccccgc ccgcacctgt gcccatttcc ctcccaccaa aggttttgga   6840
gaacggtccc aacgcctggg gggatgagaa cggtttgaac aaaaaaaagc ggcgcaagat   6900
ggaggccgtt ggcatttacg ttatgggcgg gaaaaagtat caaaaatttt gggataagaa   6960
ttctggtgat gtgttctatg aagaagtcca cgacaacaca gacgcgtggg aatgcctcag   7020
agttgacaac cctgccgact tggatcctga gaggggaacc ttgtgtggac acaccaccat   7080
agacaacagg ccttaccatg tttatgcttc tccgtctggt aggaagtttc tagtccctgt   7140
```

-continued

```
caacccggag agcggaaaag ctcagtggga agctgctaag ctttctttag atcaggccct   7200
cagtatgatg aatgtcgacg gcgaactgac cgccaaagaa gtggaaaaat tgaagagaat   7260
aattgacaaa ctccagggcc tgactaagga gcagtgttta aactgctagc cgccagcggc   7320
ttgacccgct gtggtcgcgg cggcttggtt gttactgaga cagcggtaaa gatagtcagg   7380
ttccacaacc ggacctttac cctagggcct gtgaatttga aagtagctag cgaagttgag   7440
ttgaaggacg cggtcgagca cggccaacac ccggtcgcga taccagccga tggtggcgtc   7500
gtgctcctgc gttccgctgt tccttcgctt atagacgtcc tgatctccgg tgctgacgca   7560
tcccccaggt tgctcgcccg tcacggaccg ggaaatactg gggtcaatgg cgcgctttgg   7620
gattttgagt ctgaagctac caaagaggaa gtagcactta gtgcgcaaat aatacaggcc   7680
tgtgacatta gacgcggcga tgcacctgag attggccttc cttacaagtt gtaccctgtt   7740
aggggcaacc ctgaacgggc aagaggggtt ctaatgaaca caagatttgg agacatacct   7800
tacaagaccc ccagcgacac cgggagcccg gtgcacgcgg ccgcctgcct tacgcccaac   7860
gccactccag taactgatgg gcgctccatc ctggccacga ccatgccctc cgggtttgaa   7920
ctatatgtgc cgaccattcc agcgtctgtc cttgattacc ttgactccag accagactgt   7980
cctaaacagt tgactgagca cgggtgtgaa gatgccgcgt tgaaggacct ttctaaatat   8040
gacctgtcca cccaaggctt tgtgttacct ggagttctac gcctcgtgcg aaaatatctg   8100
tttgctcatg taggtaagtg cccgcctgtc caccggccct ctacctatcc tgccaagaac   8160
tccatggccg gaataaatgg gaacaggttc ccaaccaagg atattcaaag catccctgag   8220
atcgacgttt tgtgtgcaca agctgtgcga gaaaactggc aaactgttac accctgcact   8280
cttaagaagc agtattgcgg taaaaagaag accaggacca tacttggcac caacaacttc   8340
gttgcgctgg cccaccgggc ggcgctgagt ggtgtcaccc agggtttcat gaagaaggcg   8400
tttaactcac ccatcgccct tgggaaaaat aaatttaagg agctacagac tccagtcttg   8460
ggtaggtgtc ttgaggctga tctcgcttcc tgcgatcgat ccacgcctgc aatcgttcgc   8520
tggtttgccg ccaaccttct ttatgaactt gcctgtgctg aggagcattt accgtcgtac   8580
gtgctgaact gttgtcacga cctattggtc acgcagtccg gcgcagtgac taagagaggt   8640
ggcctgtcgt ccggtgaccc aatcacctct gtgtccaaca ccatttatag cttggtgatc   8700
tatgcacagc atatggtgct tagttacttc aaaagtggtc acccccatgg ccttctgttt   8760
ttacaagacc agctaaagtt tgaagacatg ctcaaagttc aacccctaat cgtctattcg   8820
gacgacctcg tgttgtatgc cgagtctccc accatgccaa actatcactg gtgggttgaa   8880
cacctgaatt tgatgttggg atttcagacg gacccaaaga agactgcaat aacagactca   8940
ccttcattcc taggttgtag aataataaat ggccgccagt tagtacccaa ccgtgacaga   9000
attctcgcgg cccttgccta tcacatgaag gcgagtaatg tttctgagta ctacgcctcc   9060
gcagccgcaa tactcatgga cagttgtgct tgtctagagt atgatcctga gtggtttgaa   9120
gaacttgtgg ttggaatggc gcagtgcgcc cgtaaggacg gctatagttt ccccggcccg   9180
ccgttcttct tgtccatgtg ggaaaagctc aggtcaaatt atgaggggaa gaagttgaga   9240
gtgtgtggtt attgcggagc ttcagccccg tatgctactg cctgtggcct tgacgtttgt   9300
gtttaccaca cccactttca ccagcattgt ccagtcataa tatggtgtgg ccacccggcg   9360
ggttctgggt cctgcgatga gtgcaaatcc cctacaggga agggtacaag ccctctggat   9420
gaggtcttaa gacaagtccc ttataagcct ccacggacta ttcttatgca tgtggagcag   9480
```

ggcctcaccc cccttgaccc aggcagatac cagacccgcc gtgggttggt tgctgtcagg 9540
cgcgggataa ggggaaatga agttgacctg ccagatggtg attatgccag tactgcccta 9600
ctccccacct gcaaagacat agacatggtt gctgtggcct ccaatgtgtt gcgcagtagg 9660
ttcatcatcg gcccacctgg cgcagggaaa acacactggc ttcttcaaca ggttcaggat 9720
agtgatgtca tttacacgcc aacccatcag accatgcttg acatgatcaa ggctttgggg 9780
acgtgccggt tcaatgtccc ggcaggcaca acgctgcaat tccctgcccc ctcccgtacc 9840
ggcccgtggg ttcgcatcct tgccggcggt tggtgtccag gtaagaattc cttcctggat 9900
gaagcagcgt attgcaatca ccttgacgtc ttgaggcttc tcagcaaaac taccctcacc 9960
tgtctggggg atttcaaaca actccacccg gtgggttttg attctcattg ctatgttttt 10020
gatatcatgc ctcagactca actgaagacc atctggaggt ttggacagaa tatctgtgac 10080
gccattcagc cagattacag ggacaaactc gtgtccatgg tcaacacaac ccgtgtaacc 10140
tatgtggaaa gacctgtcaa gtatgggcaa gtcctcaccc cctaccacag agaccgagag 10200
gatggtgcta tcactattga ctccagtcaa ggcgccacat ttgatgtggt cacattgcat 10260
ttgcccacta aagattcact caacaggcaa agagcccttg ttgctatcac cagggcaagg 10320
catgcaatct ttgtgtatga cccacacagg caactgcaga gcatgtttcg tcttcctgca 10380
aaaggcacac ctgtcaacct tgccgtgcac cgtgacgagc agctcatcgt attagataga 10440
aataacaaag agtgcacggt tgttcaggct ttaggcaatg gggacaaatt cagggccagt 10500
gacaagcgcg ttgtagattc tcttcgcgcc atttgtgcag atcttgaagg gtcgagctcc 10560
ccgctcccca aggtcgcaca caacttggga ttttatttct cacctgattt gacacagttt 10620
gctaaactcc cggcggaact tgcaccccac tggcccgtgg tgacaactca gaacaacgaa 10680
aattggccag accggctggt tgctagcctc cgccctatcc acaaatatag ccgcgcgtgc 10740
atcggagccg gctatatggt gggcccctca gtgtttctag gcactcctgg ggttgtgtca 10800
tactatctca cacaatttgt caaaggggag gctcaggtgc ttccggagac ggtcttcagc 10860
accggccgaa ttgaggtaga ttgtcgagag tatcttgatg atcgggaacg agaagttgct 10920
gagtccctcc cacatgcctt tattggcgac gtcaaaggca ctaccgttgg gggatgtcac 10980
catgtcactt ctaaatatct cccacgcttc cttcccaagg aatcagttgc ggtggttggg 11040
gtttcaagcc ccgggaaagc cgcaaaaagca gtttgcacat taacagatgt gtacctccca 11100
gatcttgagg cttacctcca tccagagacc cagtctaagt gctggaaagt gatgttggac 11160
ttcaaggaag ttcgactgat ggtctggaga gataagacgg cctactttca acttgaaggc 11220
cgccatttca cctggtacca gcttgcaagt tatgcctcgt acatccgagt tcccgttaac 11280
tctacggtgt acctggaccc ctgtatgggc cctgcccttt gcaacagaag agtcgttggg 11340
tctgcacatt ggggagctga ccttgcagtt accccttatg attatggtgc caaaatcatt 11400
ctgtctagtg cgcaccatgg tgaaatgcct cctgggtaca gaattctagc gtgcgcggag 11460
ttctcgcttg atgacccagt gaggtacaaa cacacttggg ggtttgaatc ggatacagcg 11520
tatctgtacg agttcaccgg aaacggtgag gactgggagg attacaatga tgcgtttcgt 11580
gcacgccaga aagggaaaat ttataaggcc actgccacca gcatgagatt tcattttccc 11640
ccgggtcctg ccattgaacc aacattgggc ctgaactgaa atgaaatggg ggctgtgcag 11700
agccttttcg acaaaatttg ccaacttttt gtggatgctt tcacggaatt tttggtgtcc 11760
attgttgata tcatcatatt tttggccatt ttgtttggct tcaccatcgc aggctggctg 11820
gttgtcttct gtatccgact ggtttgctcc acggtactcc gtgcgcgctc taccattcac 11880
cctgagcaat tacagaagat cctatgaggc cttcctttcc cagtgccaag tggacattcc 11940
cgcctgggga actaagcatc ccttgggggt gctttggcac cacaaggtgt caactctgat 12000
tgatgaaatg gtgtcgcgtc gaatgtaccg catcatggaa aaagcaggac aggctgcctg 12060
gaaacaggtt gtgagcgaag ctacattgtc tcgcataagt ggcttggatg tggtggctca 12120
ttttcagcat cttgctgcca ttgaagccga gacttgcaaa tatttggcct ctcggctgcc 12180
catgctacac aacctagtca tgtcagggtc gaatgtaacc atagtgtata atagcacttt 12240
gggtcaagtg tttgccattt tcccaacccc tggttcccgg ccaaaacttt ctgattttca 12300
acaatggctc atagctgtgc attcttccat attttcttct gttgcggctt cttgtactct 12360
ttttgttgtg ctgtggctgc gaattccaat actacgtact gtttttggtt tccgctggtt 12420
aggggcaact tttctttcga actcacagtg aattacacgg tgtgcccacc ctgcctcacc 12480
cggcaagcag ccgctgagat ctacgaacac agcgggtctc tttggtgcag gatagggcat 12540
gaccgatgta gccagagtga tcatgacgaa ctagggttct tggttccacc tggcctttcc 12600
agcgagggcc acttgaccag tgtttacgcc tggctggcgt tcttgtcttt cagctacaca 12660
gcccagttcc accccgagat atttggaata gggaatgtga gtagagttta tgttgacgtc 12720
actcaccaac tcatctgcgc cgaacacgac gggcagaaca ccaccctgcg tcgccatgac 12780
aatatctcag ccgtgtttca gacctattac caacatcagg tcgatggcgg caattggttt 12840
cacctagaat ggctgcgtcc cttcttttcc tcttggctgg ttttgaatgt ctcgtggttt 12900
ctcaggcgtt cgcctgcaaa ccgtgtttca gttcgagtct ttcagacatc aaaaccaaca 12960
ccaccgcagc tgcaggcttt gctgtcctcc aagacatcag ctgtcttagg catggctact 13020
cgtccattga ggcgattcgc aaaagccgtc aatgccgcac ggcgatagga acgcccgtgt 13080
acatcactgt cacggccaat gtaacagatg agaattactt gcattcctct gatctcctca 13140
tgctttcctc ttgcctcttc tatgcttctg agatgagtga aaagggattc aatgtggtct 13200
tcggcaacgt gtcaggcatt gtggctgtgt gtgtcaactt taccagctat gtccaacatg 13260
ttaaggagtt tactcagcgc tctttggtgg tcgaccacgt gcgactgctt catttcatga 13320
cacctgcgac catgaggtgg gcaacagttt tagcctgtct tttcgccatc ttgttggcga 13380
tttgaatgtt taagtatgtt ggggaaatgc ttgaccgcgg gctactgctc gcaattgctt 13440
tttttctggt gtatcgtgcc gttctgtttt gctgcgctcg tcaacgccgc cagcaacagc 13500
agctcccatt tacagttgat ttataacctg acgatatgcg agctgaatgg cacagattgg 13560
ttgaatcaaa agtttgattg ggcagtggag actttttgtca tttttcctgt gttgacccac 13620
attgtctcct acggtgccct taccaccagc catttccttg acacggccgg cctaatcact 13680
gtgtctaccg ccggatatta ccatgggcgg tatgtgttga gtagcatcta cgccgtcttt 13740
gccctggctg cgttgatttg ttttgtcatt aggttgacaa aaaactgtat gtcctggcgc 13800
tactcatgta ccagatatac caactttctt ctggacacca aaggcaatct ctatcgttgg 13860
cggtcacccg tcgttataga gagaaggggt aaagttgagg ttggagacca cctaatcgac 13920
ctcaaaagag ttgtgcttga tggttccgcg gcaaccccta taaccaagat ttcagcggaa 13980
caatggggtc gtccctagac gacttctgca atgacagcac agctgcacaa aaggtgcttt 14040
tggcgttttc catcacctat acgccaataa tgatatatgc cctgaaggta agtcgcggcc 14100
gactgttagg gcttttgcat cttttaattt tcttgaattg tgctttcacc ttcgggtaca 14160
tgacatttgt tcattttcag agtacaaaca aggtcgcgct cactatggga gcagttgttg 14220

-continued

```
cactcctttg gggggtgtac tcagccatag aaacctggaa attcatcact tccagatgcc  14280

gtttgtgctt gctaggccgc aggtacattc tggcccctgc ccaccacgtt gaaagtgccg  14340

cgggctttca tccgattgcg gcaagtgata accacgcatt tgtcgtccgg cgtcccggct  14400

ccactactgt taacggcaca ttggtgcccg ggttgaaaag cctcgtgttg ggtggcagaa  14460

aagctgttaa gcggggagtg gtaaacctcg ttaaatatgc caaataacaa cggcaggcag  14520

caaaaaaata agaaggggag tggccagcca gtcaatcagc tgtgccaaat gctgggcaag  14580

atcatcgccc agcaaaatca gtccagaggc aagggaccgg gtaagaaaaa taagaagaga  14640

aacccggaga agccccattt tcctcttgcg accgaagatg acgtcaggca tcacttcacc  14700

cccagtgaac ggcaattgtg tctgtcgtcg atccagactg ccttcaacca gggcgctgga  14760

acttgcaccc tgtcagattc agggaggata agttacactg tggagtttag tttgccgacg  14820

caccacactg tgcgccttat tcgcgccaca gcatcacctc catcgtgatg ggcttacatt  14880

cttggagctc ctcagtttca caattggaag aatgtgtggt gaatggcact gattggcact  14940

gtgcctctaa gtcacctatt caattagggc gaccgtgtgg gggtttagtt taattggcga  15000

gaaccacgcg gccgaaatta aaaaaaaaaa aaaaaaaaaa aaaaaaa               15047
```

What is claimed is:

1. A modified, live Porcine Reproductive and Respiratory Syndrome (PRRS) virus strain, wherein the consensus complementary DNA sequence of said PRRS strain is at least 95% identical to a sequence selected from the group of SEQ ID NO: 4, SEQ ID NO: 10, and SEQ ID NO: 11.

2. The modified, live PRRS virus strain of claim 1, wherein the consensus complementary DNA sequence of said PRRS strain is at least 98% identical to a sequence selected from the group of SEQ ID NO: 4, SEQ ID NO: 10, and SEQ ID NO: 11.

3. The modified, live PRRS virus strain of claims 1, wherein said PRRS strain is ND 99-14.

4. The PRRS strain of claim 1, wherein said PRRS virus strain is passaged at least 80 times in tissue culture cells.

5. The PRRS strain of claim 1, wherein said PRRS virus strain is passaged 100 times in tissue culture cells.

6. An immunogenic composition comprising a modified, live PRRS virus strain having a consensus complementary DNA sequence at least 95% identical to a sequence selected from the group of SEQ ID NO: 4, SEQ ID NO: 10, and SEQ ID NO: 11; and a pharmaceutically-acceptable excipient, stabilizer, solubilizer, or diluent.

7. The immunogenic composition of claim 6, wherein the consensus complementary DNA sequence is at least 98% identical to a sequence selected from the group of SEQ ID NO: 4, SEQ ID NO: 10, and SEQ ID NO: 11.

8. The immunogenic composition of claim 6, wherein the modified, live PRRS virus strain is ND 99-14.

9. The immunogenic composition of claim 6, further comprising an adjuvant.

10. A method of treating or preventing a symptom caused by type 2 Porcine Reproductive and Respiratory Syndrome (PRRS) in a porcine animal, comprising administering to said porcine animal an immunogenic composition comprising a modified, live PRRS virus strain having a consensus complementary DNA sequence at least 98% identical to a sequence selected from the group of SEQ ID NO: 4, SEQ ID NO: 10, and SEQ ID NO: 11; and a pharmaceutically-acceptable excipient, stabilizer, solubilizer, or diluent.

11. A vaccine comprising a modified, live PRRS virus strain, wherein said PRRS virus strain is ND 99-14.

12. A method of treating or preventing a symptom caused by type 2 Porcine Reproductive and Respiratory Syndrome (PRRS) virus infection in a porcine animal, comprising administering to said porcine animal a vaccine comprising a modified, live PRRS virus strain, wherein said PRRS virus strain is ND 99-14.

13. The method of claim 12, wherein the PRRS virus infection is caused by a virulent type 2 PRRS virus heterologous to the modified, live PRRS virus strain in the vaccine.

* * * * *